US012735703B2

(12) United States Patent
Liu et al.

(10) Patent No.: US 12,735,703 B2
(45) Date of Patent: Sep. 15, 2026

(54) OLIGONUCLEOTIDE COMPOSITIONS AND METHODS OF USE THEREOF

(71) Applicant: WAVE LIFE SCIENCES LTD., Singapore (SG)

(72) Inventors: Yuanjing Liu, Boston, MA (US); Naoki Iwamoto, Boston, MA (US); Chandra Vargeese, Schwenksville, PA (US); Zhong Zhong, Hingham, MA (US); Amy Jada Andreucci, Belmont, MA (US); Susovan Mohapatra, Belmont, MA (US)

(73) Assignee: WAVE LIFE SCIENCES LTD., Singapore (SG)

( * ) Notice: Subject to any disclaimer, the term of this patent is extended or adjusted under 35 U.S.C. 154(b) by 671 days.

(21) Appl. No.: 17/766,680

(22) PCT Filed: Oct. 5, 2020

(86) PCT No.: PCT/US2020/054307

§ 371 (c)(1), (2) Date: Apr. 5, 2022

(87) PCT Pub. No.: WO2021/071788

PCT Pub. Date: Apr. 15, 2021

(65) Prior Publication Data

US 2024/0175016 A1 May 30, 2024

Related U.S. Application Data

(60) Provisional application No. 63/069,704, filed on Aug. 24, 2020, provisional application No. 62/983,736, filed on Mar. 1, 2020, provisional application No. 62/911,340, filed on Oct. 6, 2019.

(30) Foreign Application Priority Data

May 8, 2020 (WO) ................ PCT/US2020/032244

(51) Int. Cl.
*C12N 15/113* (2010.01)

(52) U.S. Cl.
CPC ........ *C12N 15/113* (2013.01); *C12N 2310/11* (2013.01); *C12N 2310/315* (2013.01); *C12N 2310/321* (2013.01); *C12N 2310/3341* (2013.01)

(58) Field of Classification Search
CPC .............. C12N 15/113; C12N 2310/11; C12N 2310/315; C12N 2310/3341; C12N 2310/3521; C12N 2310/3525; A61K 31/7088; A61P 25/28
See application file for complete search history.

(56) References Cited

U.S. PATENT DOCUMENTS

| | | | |
|---|---|---|---|
| 8,470,987 | B2 | 6/2013 | Wada et al. |
| 8,729,036 | B2 | 5/2014 | Zamore et al. |
| 8,822,671 | B2 | 9/2014 | Shimizu et al. |
| 8,859,755 | B2 | 10/2014 | Wada et al. |
| 9,394,333 | B2 | 7/2016 | Wada et al. |
| 9,476,044 | B2 | 10/2016 | Tuschl et al. |
| 9,598,458 | B2 | 3/2017 | Shimizu et al. |
| 9,605,019 | B2 | 3/2017 | Verdine et al. |
| 9,605,263 | B2 | 3/2017 | Rigo |
| 9,617,547 | B2 | 4/2017 | Gemba |
| 9,695,211 | B2 | 7/2017 | Wada et al. |
| 9,744,183 | B2 | 8/2017 | Verdine et al. |
| 9,982,257 | B2 | 5/2018 | Butler et al. |
| 10,144,933 | B2 | 12/2018 | Gemba et al. |
| 10,149,905 | B2 | 12/2018 | Gemba et al. |
| 10,160,969 | B2 | 12/2018 | Meena et al. |
| 10,167,309 | B2 | 1/2019 | Shimizu et al. |
| 10,280,192 | B2 | 5/2019 | Verdine et al. |
| 10,307,434 | B2 | 6/2019 | Verdine et al. |
| 10,322,173 | B2 | 6/2019 | Gemba et al. |
| 10,329,318 | B2 | 6/2019 | Wada et al. |
| 10,428,019 | B2 | 10/2019 | Wada et al. |
| 10,450,568 | B2 | 10/2019 | Butler et al. |
| 10,479,995 | B2 | 11/2019 | Vargeese et al. |
| 10,590,413 | B2 | 3/2020 | Butler et al. |
| 10,696,711 | B2 | 6/2020 | Shimizu et al. |
| 10,724,035 | B2 | 7/2020 | Vargeese et al. |

(Continued)

FOREIGN PATENT DOCUMENTS

| | | |
|---|---|---|
| JP | 2003-238586 A | 8/2003 |
| JP | 2011-184318 A | 9/2011 |

(Continued)

OTHER PUBLICATIONS

Jain, M. L., Bruice, P. Y., Szabó, I. E., & Bruice, T. C. (2011). Incorporation of Positively Charged Linkages into DNA and RNA Backbones: A Novel Strategy for Antigene and Antisense Agents. Chemical Reviews, 112(3), 1284-1309. https://doi.org/10.1021/cr1004265 (Year: 2011).*

National Center for Biotechnology Information (2025). PubChem Compound Summary for CID 32838, Guanidinium. Retrieved Mar. 27, 2025 from https://pubchem.ncbi.nlm.nih.gov/compound/Guanidinium. (Year: 2025).*

U.S. Appl. No. 16/624,896, filed Dec. 19, 2019, Butler et al.

U.S. Appl. No. 16/869,126, filed May 7, 2020, Vargeese et al.

U.S. Appl. No. 17/046,752, filed Oct. 9, 2020, Zhang et al.

U.S. Appl. No. 17/177,111, filed Feb. 16, 2021, Zhang et al.

(Continued)

*Primary Examiner* — J. E. Angell
*Assistant Examiner* — Sarah E Allen
(74) *Attorney, Agent, or Firm* — Choate, Hall & Stewart LLP; Xiaodong Li; Dustin K. Goncharoff

(57) ABSTRACT

Among other things, the present disclosure provides C9orf72 oligonucleotides, compositions, and methods thereof. In some embodiments, the present disclosure provides methods for treating C9orf72-associated conditions, disorders or diseases, such as amyotrophic lateral sclerosis and frontotemporal dementia.

8 Claims, 1 Drawing Sheet

Specification includes a Sequence Listing.

(56) References Cited

U.S. PATENT DOCUMENTS

| | | | |
|---|---|---|---|
| 10,815,482 | B2 | 10/2020 | Meena et al. |
| 11,013,757 | B2 | 5/2021 | Zhang et al. |
| 11,136,346 | B2 | 10/2021 | Shimizu et al. |
| 11,407,775 | B2 | 8/2022 | Butler et al. |
| 11,596,646 | B2 | 3/2023 | Zhang et al. |
| 11,597,927 | B2 | 3/2023 | Vargeese et al. |
| 11,603,532 | B2 | 3/2023 | Vargeese et al. |
| 11,608,355 | B2 | 3/2023 | Bowman et al. |
| 11,634,710 | B2 | 4/2023 | Frank-Kamenetsky et al. |
| 11,643,657 | B2 | 5/2023 | Butler et al. |
| 11,718,638 | B2 | 8/2023 | Butler et al. |
| 11,739,325 | B2 | 8/2023 | Vargeese et al. |
| 11,873,316 | B2 | 1/2024 | Butler et al. |
| 12,391,942 | B2 | 8/2025 | Zhang et al. |
| 12,428,442 | B2 | 9/2025 | Butler et al. |
| 12,435,105 | B2 | 10/2025 | Bowman et al. |
| 12,473,321 | B2 | 11/2025 | Butler et al. |
| 12,486,505 | B2 | 12/2025 | Frank-Kamenetsky et al. |
| 12,552,743 | B2 | 2/2026 | Zhang et al. |
| 2013/0178612 | A1 | 7/2013 | Wada et al. |
| 2016/0331835 | A1 | 11/2016 | Gemba et al. |
| 2016/0331836 | A1 | 11/2016 | Gemba et al. |
| 2016/0333349 | A1 | 11/2016 | Gemba et al. |
| 2017/0362270 | A1* | 12/2017 | Stetsenko .............. A61P 21/00 |
| 2019/0077817 | A1 | 3/2019 | Butler et al. |
| 2019/0127733 | A1 | 5/2019 | Butler et al. |
| 2019/0249173 | A1 | 8/2019 | Vargeese et al. |
| 2019/0264267 | A1 | 8/2019 | Yang et al. |
| 2019/0375774 | A1 | 12/2019 | Butler et al. |
| 2020/0157545 | A1 | 5/2020 | Vargeese et al. |
| 2020/0190515 | A1 | 6/2020 | Vargeese et al. |
| 2020/0231620 | A1 | 7/2020 | Bowman et al. |
| 2020/0299692 | A1 | 9/2020 | Frank-Kamenetsky et al. |
| 2020/0362337 | A1 | 11/2020 | Dodart et al. |
| 2021/0032620 | A1 | 2/2021 | Vargeese et al. |
| 2021/0115444 | A1 | 4/2021 | Meena et al. |
| 2021/0130821 | A1 | 5/2021 | Butler et al. |
| 2021/0198305 | A1 | 7/2021 | Vargeese et al. |
| 2021/0228615 | A1 | 7/2021 | Zhang et al. |
| 2021/0254062 | A1 | 8/2021 | Zhang et al. |
| 2022/0098585 | A1 | 3/2022 | Brown et al. |
| 2022/0127301 | A1 | 4/2022 | Shimizu et al. |
| 2022/0145300 | A1 | 5/2022 | Liu et al. |
| 2022/0162598 | A1 | 5/2022 | Vargeese et al. |
| 2022/0186217 | A1 | 6/2022 | Zhang et al. |
| 2022/0195429 | A1 | 6/2022 | Vargeese et al. |
| 2022/0306573 | A1 | 9/2022 | Zhang et al. |
| 2022/0307019 | A1 | 9/2022 | Yokota et al. |
| 2022/0356204 | A1 | 11/2022 | Butler et al. |
| 2022/0401467 | A1 | 12/2022 | Zhang et al. |
| 2023/0089442 | A1 | 3/2023 | Kandasamy et al. |
| 2023/0136645 | A1 | 5/2023 | Butler et al. |
| 2023/0145795 | A1 | 5/2023 | Byrne et al. |
| 2023/0203087 | A1 | 6/2023 | Kandasamy et al. |
| 2023/0220384 | A1 | 7/2023 | Monian et al. |
| 2023/0295617 | A1 | 9/2023 | Vargeese et al. |
| 2023/0295619 | A1 | 9/2023 | Maguire et al. |
| 2023/0329201 | A1 | 10/2023 | Yang et al. |
| 2023/0348524 | A1 | 11/2023 | Bowman et al. |
| 2023/0392137 | A1 | 12/2023 | Monian et al. |
| 2024/0026358 | A1 | 1/2024 | Monian et al. |
| 2024/0109931 | A1 | 4/2024 | Vargeese et al. |
| 2024/0117347 | A1 | 4/2024 | Butler et al. |
| 2024/0132894 | A1 | 4/2024 | Vargeese et al. |
| 2024/0150756 | A1 | 5/2024 | Frank-Kamenetsky et al. |
| 2024/0174710 | A1 | 5/2024 | Butler et al. |
| 2024/0175018 | A1 | 5/2024 | Vargeese et al. |
| 2024/0229026 | A1 | 7/2024 | Butler et al. |
| 2024/0368207 | A1 | 11/2024 | Butler et al. |
| 2025/0051778 | A1 | 2/2025 | Byrne et al. |
| 2025/0066775 | A1 | 2/2025 | Vargeese et al. |
| 2025/0135036 | A1 | 5/2025 | Acker et al. |
| 2025/0154190 | A1 | 5/2025 | Kandasamy et al. |
| 2025/0197857 | A1 | 6/2025 | Hu et al. |
| 2025/0262235 | A1 | 8/2025 | Lu et al. |
| 2025/0270628 | A1 | 8/2025 | Yang et al. |
| 2025/0302995 | A1 | 10/2025 | Shivalila et al. |
| 2025/0313836 | A1 | 10/2025 | Meena et al. |
| 2025/0333740 | A1 | 10/2025 | Monian et al. |
| 2026/0008806 | A1 | 1/2026 | Bowman et al. |
| 2026/0055133 | A1 | 2/2026 | Butler et al. |
| 2026/0055402 | A1 | 2/2026 | Lake et al. |

FOREIGN PATENT DOCUMENTS

| | | | | |
|---|---|---|---|---|
| WO | WO-2004/007718 | A2 | 1/2004 | |
| WO | WO-2005/014609 | A2 | 2/2005 | |
| WO | WO-2005/023828 | A1 | 3/2005 | |
| WO | WO-2005/028494 | A1 | 3/2005 | |
| WO | WO-2005/070859 | A1 | 8/2005 | |
| WO | WO-2005/085272 | A1 | 9/2005 | |
| WO | WO-2005/092909 | A1 | 10/2005 | |
| WO | WO-2010/064146 | A2 | 6/2010 | |
| WO | WO-2011/005761 | A1 | 1/2011 | |
| WO | WO-2011/034072 | A1 | 3/2011 | |
| WO | WO-2011/108682 | A1 | 9/2011 | |
| WO | WO-2012/039448 | A1 | 3/2012 | |
| WO | WO-2012/073857 | A1 | 6/2012 | |
| WO | WO-2013/012758 | A1 | 1/2013 | |
| WO | WO-2014/010250 | A1 | 1/2014 | |
| WO | WO-2014/010718 | A1 | 1/2014 | |
| WO | WO-2014/012081 | A2 | 1/2014 | |
| WO | WO-2014/062686 | A1 | 4/2014 | |
| WO | WO-2015/107425 | A2 | 7/2015 | |
| WO | WO-2015/108046 | A1 | 7/2015 | |
| WO | WO-2015/108047 | A1 | 7/2015 | |
| WO | WO-2015/108048 | A1 | 7/2015 | |
| WO | WO-2015/143078 | A1 | 9/2015 | |
| WO | WO-2016/028187 | A1 | 2/2016 | |
| WO | WO-2017/015555 | A1 | 1/2017 | |
| WO | WO-2017/015575 | A1 | 1/2017 | |
| WO | WO-2017/062862 | A2 | 4/2017 | |
| WO | WO-2017079291 | A1 * | 5/2017 | ........... C12N 15/113 |
| WO | WO-2017/109757 | A1 | 6/2017 | |
| WO | WO-2017/160741 | A1 | 9/2017 | |
| WO | WO-2017/192664 | A1 | 11/2017 | |
| WO | WO-2017/192679 | A1 | 11/2017 | |
| WO | WO-2017/210647 | A1 | 12/2017 | |
| WO | WO-2018/022473 | A1 | 2/2018 | |
| WO | WO-2018/067973 | A1 | 4/2018 | |
| WO | WO-2018/098264 | A1 | 5/2018 | |
| WO | WO-2018/223056 | A1 | 12/2018 | |
| WO | WO-2018/223073 | A1 | 12/2018 | |
| WO | WO-2018/223081 | A1 | 12/2018 | |
| WO | WO-2018/237194 | A1 | 12/2018 | |
| WO | WO-2019/032607 | A1 | 2/2019 | |
| WO | WO-2019/032612 | A1 | 2/2019 | |
| WO | WO-2019/055951 | A1 | 3/2019 | |
| WO | WO-2019/075357 | A1 | 4/2019 | |
| WO | WO-2019/200185 | A1 | 10/2019 | |
| WO | WO-2019/217784 | A1 | 11/2019 | |
| WO | WO-2020/118246 | A1 | 6/2020 | |
| WO | WO-2020/160336 | A1 | 8/2020 | |
| WO | WO-2020/191252 | A1 | 9/2020 | |
| WO | WO-2020/196662 | A1 | 10/2020 | |
| WO | WO-2020/219981 | A2 | 10/2020 | |
| WO | WO-2020/219983 | A2 | 10/2020 | |
| WO | WO-2020/227691 | A2 | 11/2020 | |
| WO | WO-2021/071788 | A2 | 4/2021 | |
| WO | WO-2021/071858 | A1 | 4/2021 | |
| WO | WO-2021/178237 | A2 | 9/2021 | |
| WO | WO-2021/234459 | A2 | 11/2021 | |
| WO | WO-2021/237223 | A1 | 11/2021 | |
| WO | WO-2022/046667 | A1 | 3/2022 | |
| WO | WO-2022/046723 | A1 | 3/2022 | |
| WO | WO-2022/099159 | A1 | 5/2022 | |
| WO | WO-2023/049475 | A1 | 3/2023 | |
| WO | WO-2023/049477 | A2 | 3/2023 | |
| WO | WO-2023/075766 | A1 | 5/2023 | |
| WO | WO-2023/076352 | A2 | 5/2023 | |
| WO | WO-2023/154528 | A1 | 8/2023 | |
| WO | WO-2023/168014 | A2 | 9/2023 | |
| WO | WO-2023/201095 | A2 | 10/2023 | |
| WO | WO-2023/220440 | A1 | 11/2023 | |

(56) References Cited

FOREIGN PATENT DOCUMENTS

WO WO-2024/035946 A1 2/2024
WO WO-2025/030155 A1 2/2025
WO WO-2025/072685 A1 4/2025
WO WO-2025/072862 A1 4/2025
WO WO-2025/072879 A1 4/2025
WO WO-2025/072881 A2 4/2025
WO WO-2025/072883 A2 4/2025
WO WO-2025/072886 A1 4/2025
WO WO-2025/151895 A1 7/2025
WO WO-2025/160090 A1 7/2025
WO WO-2025/212958 A1 10/2025
WO WO-2025/213136 A1 10/2025
WO WO-2025/213142 A2 10/2025
WO WO-2026/006477 A1 1/2026

OTHER PUBLICATIONS

U.S. Appl. No. 17/311,285, filed Jun. 4, 2021, Zhang et al.
U.S. Appl. No. 17/375,658, filed Jul. 14, 2021, Vargeese et al.
U.S. Appl. No. 17/426,511, filed Jul. 28, 2021, Brown et al.
U.S. Appl. No. 17/439,755, filed Sep. 15, 2021, Kandasamy et al.
U.S. Appl. No. 17/442,663, filed Sep. 24, 2021, Yokota et al.
U.S. Appl. No. 17/465,238, filed Feb. 9, 2021, Shimizu et al.
U.S. Appl. No. 17/605,997, filed Oct. 22, 2021, Byrne et al.
U.S. Appl. No. 17/605,998, filed Oct. 22, 2021, Byrne et al.
U.S. Appl. No. 17/609,330, filed Nov. 5, 2021, Liu et al.
U.S. Appl. No. 17/766,677, filed Apr. 5, 2022, Monlan et al.
ClinicalTrials.gov Identifier: NCT03626012, A Study to Assess the Safety, Tolerability, and Pharmacokinetics of BIIB078 in Adults With C9ORF72-Associated Amyotrophic Lateral Sclerosis, First Posted Aug. 10, 2018, Last Update Posted Jan. 14, 2022, <https://clinicaltrials.gov/ct2/show/NCT03626012?term=BIIB078&draw=2&rank=2>.
ClinicalTrials.gov Identifier: NCT04288856, A Study to Assess the Safety, Tolerability, and Pharmacokinetics, and Effect on Disease Progression of BIIB078 Administered to Previously Treated Adults C9ORF72-Associated Amyotrophic Lateral Sclerosis (ALS), First Posted Feb. 28, 2020, Last Update Posted Feb. 22, 2022, <https://clinicaltrials.gov/ct2/show/NCT04288856?term=BIIB078&draw=2&rank=1>.
ClinicalTrials.gov Identifier: NCT04931862, Study of WVE-004 in Patients With C9orf72-associated Amyotrophic Lateral Sclerosis (ALS) or Frontotemporal Dementia (FTD) (FOCUS-C9), First Posted Jun. 18, 2021, Last Update Posted Dec. 14, 2021, <https://www.clinicaltrials.gov/ct2/show/NCT04931862?term=wave+life+sciences&draw=2&rank=3>.
Fernandes, S.A. et al., Oligonucleotide-Based Therapy for FTD/ALS Caused by the C9orf72 Repeat Expansion: A Perspective, Journal of Nucleic Acids, 2013(208245):1-11 (2013).
Hu, J. et al., Recognition of c9orf72 Mutant RNA by Single-Stranded Silencing RNAs, Nucleic Acid Therapeutics, 27(2):87-94 (2017).
International Search Report for PCT/US2020/032244, 5 pages (mailed Nov. 6, 2020).
International Search Report for PCT/US2020/032244, 5 pages (mailed Oct. 6, 2020).
International Search Report for PCT/US2020/054307, 5 pages (mailed Apr. 8, 2021).
Invitation to Pay Additional Fees for PCT/US2020/032244, 3 pages (mailed Sep. 10, 2020).
Invitation to Pay Additonal Fees for PCT/US2020/054307, 3 pages (mailed Feb. 2, 2021).
Jiang, J. et al., Gain of Toxicity from ALS/FTD-Linked Repeat Expansions in C9ORF72 Is Alleviated by Antisense Oligonucleotides Targeting GGGGCC-Containing RNAs, Neuron, 1-16 (2016).
Liu, Y. et al., Preclinical evaluation of WVE-004, aninvestigational stereopure oligonucleotide for the treatment of C9orf72-associated ALS or FTD, Molecular Therapy Nucleic Acids, 28: 20 pages (2022).
Liu, Y. et al., Variant-selective stereopure oligonucleotides protect against pathologies associated with C9orf72-repeat expansion in preclinical models, Nat. Comm., 12:847, 15 pages (2021). Reporting Summary (4 pages) and Supplementary Information (22 pages).
Scoles, D.R. et al., Antisense oligonucleotides: A primer, Neurology Genetics, 5(2):1-8 (2019).
WAVE Life Sciences Press Release, WAVE Life Sciences Announces Positive Update to Ongoing Phase 1b/2a FOCUS-C9 Study Driven by Potent, Durable Reductions of Poly(GP) with Low, Single Doses of WVE-004, 3 pages (Apr. 4, 2022).
WAVE Life Sciences, Analyst & Investor Research Webcast (Aug. 2020), 64 pages.
WAVE Life Sciences, Focus-C9 clinical trial update, Presentation (Apr. 2022), 25 pages.
Wilson, K. et al., Development of a sensitive trial-ready poly(GP) CSF biomarker assay for C9orf72-associated frontotemporal dementia and amyotrophic lateral sclerosis, J. Neurol Neurosurg Psychiatry, 0: 32 pages (2022).
Written Opinion for PCT/US2020/032244, 12 pages (mailed Oct. 6, 2020).
Written Opinion for PCT/US2020/032244, 9 pages (mailed Nov. 6, 2020).
Written Opinion for PCT/US2020/054307, 9 pages (mailed Apr. 8, 2021).
U.S. Appl. No. 17/881,956, filed Aug. 5, 2022, Butler et al.
Dale, E., Enhancing the pharmacologic profiles of CNS targeting therapeutic oligonucleotides, Wave Life Sciences, presented at Tides USA, on Sep. 23, 2021.
Ejebe, K. et al., Design of an Adaptive Phase 1b/2a Randomized Controlled Trial of WVE-004 in Patients with C9orf72-ALS/FTD, Wave Life Sciences, presented at European Network to Cure ALS (ENCALES) Virtual Meeting on May 10-12, 2021.
Kandasamy, P. et al., Impact of guanidine-containing backbone linkages on stereopure antisense oligonucleotides in the CNS, Nucleic Acids Research, 50(10):5401-5423 (2022).
Kupryushkin, M. S. Phosphoryl Guanidines: A New Type of Nucleic Acid Analogues, Acta Naturae, 6(4): 116-118 (2014).
Liu, Y. et al., Impact of Nitrogen-containing Backbone Linkages on Stereopure Antisense Oligonucleotides in the CNS, Wave Life Sciences, Presented at Tides USA: Oligonucleotide & Peptide Therapeutics on Sep. 20-23, 2021 in Boston, Massachusetts.
Liu, Y. et al., Variant-selective Stereopure Oligonucleotides Protect Against Pathologies Associated with C9orf72-repeat Expansion in Preclinical Models, Wave Life Sciences, presented at Neurodegenerative Diseases: Genes, Mechanisms and Therapeutics (Keystone eSymposia) on Jun. 7-9, 2021.
Panzara, M. A. P., Targeting pathological transcriptional variants in C9orf72-associated amyotrophic lateral sclerosis (ALS) and frontotemporal dementia (FTD): Initial results from the ongoing FOCUS-C9 clinical trial, Wave Life Sciences, presented at the ENCALS Meeting, on Friday 3, 2022.
Panzara, M. A. Stereopure Oligonucleotides in Development for the Treatment of Genetically Defined Diseases, Wave Life Sciences, presented at Tides Boston Virtual Conference on Sep. 15-18, 2020.
Pavlova, A. S. et al., SDS-PAGE procedure: Application for characterization of new entirely uncharged nucleic acids analogs, Electrophor., 39:670-674 (2018).
Vergeese, C., Exploring new oligonucleotide backbone chemistries and their deployment to improve the properties of stereopure oligonucleotides, Wave Life Sciences, presented at Tides USA on Sep. 22, 2021.
Viglietta, V., A Ph1b/2a study of WVE-003, an investigational allele-selective, mHTT-lowering oligonucleotide for the treatment of early manifest Huntington's disease, and review of PRECISION-HD results, Wave Life Sciences, presented at CHDI on Apr. 27, 2021.
WAVE Life Sciences, Second Quarter 2022 Earnings Presentation, 27 pages, (2022).
WAVE Life Sciences, WAVE Life Sciences Corporate Presentation, 63 pages, May 12, 2022.
WAVE Life Sciences, Third Quarter 2022 Earnings Presentation, 24 pages, (2022).
U.S. Appl. No. 18/695,346, Monian et al.

(56) References Cited

OTHER PUBLICATIONS

U.S. Appl. No. 18/704,629, Byrne et al.
U.S. Appl. No. 18/864,860, Shivalila et al.
U.S. Appl. No. 18/864,863, Liu et al.
U.S. Appl. No. 18/953,020, Meena et al.
U.S. Appl. No. 19/008,522, Vargeese et al.
U.S. Appl. No. 19/085,460, Bowman et al.
U.S. Appl. No. 19/102,669, Lake et al.
U.S. Appl. No. 19/217,825, Vargeese et al.
U.S. Appl. No. 19/241,178, Zhang et al.
U.S. Appl. No. 19/271,472, Zhang et al.
U.S. Appl. No. 19/276,854, Zhang et al.
U.S. Appl. No. 19/281,441, Butler et al.
U.S. Appl. No. 19/281,453, Liu et al.
U.S. Appl. No. 19/284,561, Butler et al.
U.S. Appl. No. 17/956,741, filed Sep. 29, 2022, Vargeese et al.
U.S. Appl. No. 17/960,090, filed Oct. 4, 2022, Vargeese et al.
U.S. Appl. No. 18/062,422, filed Dec. 6, 2022, Butler et al.
U.S. Appl. No. 18/178,470, filed Mar. 3, 2023, Vargeese et al.
U.S. Appl. No. 18/204,895, filed Jun. 1, 2023, Vargeese et al.
U.S. Appl. No. 18/252,029, filed May 5, 2023, Monian et al.
U.S. Appl. No. 18/305,195, filed Apr. 21, 2023, Frank-Kamenetsky et al.
U.S. Appl. No. 18/316,932, filed May 12, 2023, Butler et al.
U.S. Appl. No. 18/522,146, filed Nov. 28, 2023, Butler et al.
U.S. Appl. No. 19/297,725, filed Aug. 12, 2025, Stetsenko et al.
U.S. Appl. No. 19/367,099, filed Oct. 23, 2025, Frank-Kamenetsky et al.
U.S. Appl. No. 19/434,730, filed Dec. 29, 2025, Zhang et al.
U.S. Appl. No. 19/458,525, filed Jan. 23, 2026, Shimizu et al.
U.S. Appl. No. 19/462,715, filed Jan. 28, 2026, Kandasamy et al.

* cited by examiner

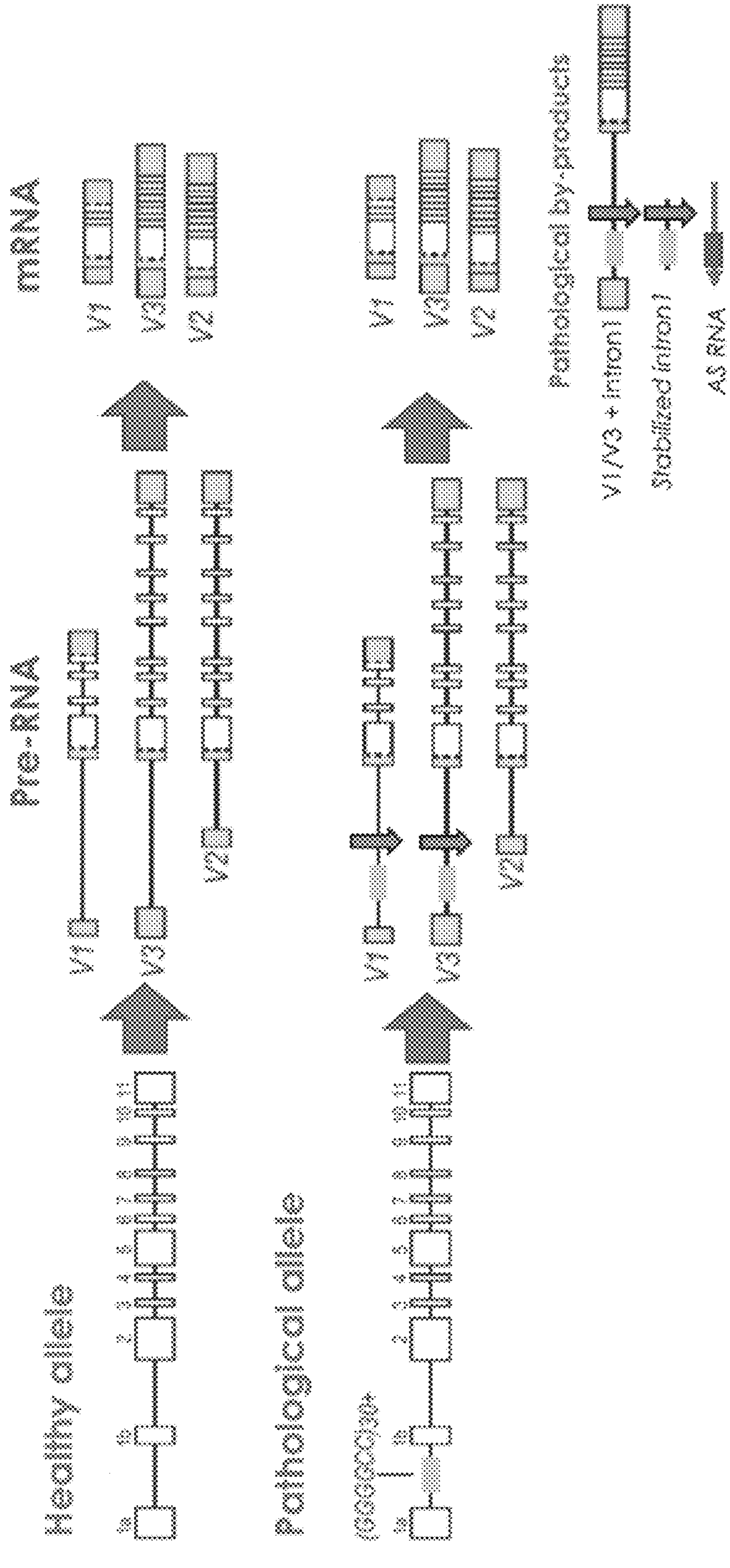
Healthy allele
Pathological allele
(GGGGCC)30+
Pre-RNA
mRNA
V1
V3
V2
Pathological by-products
V1/V3 + intron1
Stabilized intron1
AS RNA

OLIGONUCLEOTIDE COMPOSITIONS AND METHODS OF USE THEREOF

CROSS-REFERENCE TO RELATED APPLICATIONS

This application is a National Stage Entry of PCT Application No. PCT/US2020/054307, filed Oct. 5, 2020, which claims priority to United States Provisional Application Nos. 62/911,340, filed Oct. 6, 2019, 62/983,736, filed Mar. 1, 2020, and 63/069,704, filed Aug. 24, 2020, and International Application No. PCT/US2020/032244, filed May 8, 2020, the entirety of each of which is incorporated herein by reference.

SEQUENCE LISTING

The instant application contains a Sequence Listing which has been submitted electronically in ASCII format and is hereby incorporated by reference in its entirety. Said ASCII copy, created on Oct. 7, 2020, is named 2010581-1112_SL.txt and is 283,914 bytes in size.

BACKGROUND

Oligonucleotides are useful in various applications, e.g., therapeutic, diagnostic, and/or research applications, including but not limited to treatment of various conditions, disorders or diseases.

SUMMARY

The present disclosure provides oligonucleotides, and compositions thereof, that can reduce levels of C9orf72 transcripts (or products thereof). In some embodiments, provided oligonucleotides and compositions can preferentially reduce levels of disease-associated transcripts of C9orf72 (or products thereof) over non- or less-disease-associated transcripts of C9orf72 (see, e.g., FIG. 1). Example C9orf72 transcripts include transcripts from either strand of the C9orf72 gene and from various starting points. In some embodiments, at least some C9orf72 transcripts are translated into proteins; in some embodiments, at least some C9orf72 transcripts are not translated into proteins. In some embodiments, certain C9orf72 transcripts contain predominantly intronic sequences.

A hexanucleotide repeat expansion in C9orf72 (Chromosome 9, open reading frame 72) is reportedly the most frequent genetic cause of amyotrophic lateral sclerosis (ALS) and frontotemporal dementia (FTD). C9orf72 gene variants comprising the repeat expansion and/or products encoded thereof are also associated with other C9orf72-related disorders, such as corticobasal degeneration syndrome (CBD), atypical Parkinsonian syndrome, olivopontocerebellar degeneration (OPCD), primary lateral sclerosis (PLS), progressive muscular atrophy (PMA), Huntington's disease (HD) phenocopy, Alzheimer's disease (AD), bipolar disorder, schizophrenia, and other non-motor disorders. In some embodiments, the present disclosure provides compositions and methods related to oligonucleotides which target a C9orf72 target (e.g., a C9orf72 oligonucleotide) and are capable of knocking down or decreasing expression, level and/or activity of the C9orf72 target gene and/or a gene product thereof (a transcript, particularly a repeat expansion containing transcript, a protein, etc.).

In some embodiments, an oligonucleotide targets a pathological or disease-associated C9orf72 mutation or variant comprising a repeat expansion. In some embodiments, a C9orf72 gene product is a RNA (e.g., a mRNA, mature RNA or pre-mRNA) transcribed from a C9orf72 gene, a protein translated from a C9orf72 RNA transcript (e.g., a dipeptide repeat protein translated from the hexanucleotide repeat), or a focus (plural: foci) (which reportedly comprises RNA comprising the repeat expansion bound by RNA-binding proteins). In some embodiments, a C9orf72 oligonucleotide is capable of mediating preferential knockdown of a repeat expansion-containing C9orf72 RNA relative to a non-repeat expansion-containing C9orf72 RNA (a C9orf72 RNA which does not contain a repeat expansion). In some embodiments, a C9orf72 oligonucleotide decreases the expression, activity and/or level of a deleterious C9orf72 gene product (e.g., a RNA comprising a repeat expansion, a dipeptide repeat protein or a focus) without decreasing (or while decreasing to a much lower extent) the expression, activity and/or level of a wild-type or non-deleterious C9orf72 gene product. In some embodiments, a C9orf72 oligonucleotide decreases the expression, activity and/or level of a deleterious C9orf72 gene product, but does not decrease the expression, activity and/or level of a wild-type or non-deleterious C9orf72 protein enough to eliminate or significantly suppress a beneficial and/or necessary biological activity or activities of C9orf72 protein. Beneficial and/or necessary activities of C9orf72 protein are widely known and include but not limited to restricting inflammation, preventing autoimmunity and preventing premature mortality.

Among other things, the present disclosure encompasses the recognition that controlling structural elements of C9orf72 oligonucleotides can have a significant impact on oligonucleotide properties and/or activities, including knockdown of a C9orf72 target gene. In some embodiments, knockdown of a target gene is mediated by RNase H or steric hindrance affecting translation. In some embodiments, controlled structural elements of C9orf72 oligonucleotides include but are not limited to: base sequence, chemical modifications (e.g., modifications of a sugar, base and/or internucleotidic linkage) or patterns thereof, alterations in stereochemistry (e.g., stereochemistry of a backbone chiral internucleotidic linkage) or patterns thereof, wing structure, core structure, wing-core structure, wing-core-wing structure, or core-wing structure, and/or conjugation with an additional chemical moiety (e.g., a carbohydrate moiety, a targeting moiety, etc.). In some embodiments, the present disclosure provides technologies (e.g., compounds, methods, etc.) for improving C9orf72 oligonucleotide stability while maintaining or increasing oligonucleotide activity, including compositions of improved-stability oligonucleotides. In some embodiments, provided oligonucleotides target C9orf72 or products thereof. In some embodiments, a target gene is a C9orf72.

In some embodiments, the present disclosure encompasses the recognition that various optional additional chemical moieties, such as carbohydrate moieties, targeting moieties, etc., when incorporated into C9orf72 oligonucleotides, can improve one or more properties. In some embodiments, an additional chemical moiety is selected from: glucose, GluNAc (N-acetyl amine glucosamine) and anisamide moieties. These and other moieties are described in more detail herein, e.g., in Examples 1 and 2. In some embodiments, an oligonucleotide can comprise two or more additional chemical moieties, wherein the additional chemical moieties are identical or non-identical, or are of the same category (e.g., carbohydrate moiety, sugar moiety, targeting moiety, etc.) or not of the same category. In some embodiments, certain additional chemical moieties facilitate delivery of oligonucleotides to desired cells, tissues and/or organs, including but not limited to particular cells, parts or portions of the central nervous system (e.g., cerebral cortex, hippocampus, spinal cord, etc.). In some embodiments, certain additional chemical moieties facilitate internalization of oligonucleotides. In some embodiments, certain additional chemical moieties increase oligonucleotide stability. In some embodiments, the present disclosure provides technologies for incorporating various additional chemical moieties into oligonucleotides. In some embodiments, the present disclosure provides, for example, reagents and methods, for introducing additional chemical moieties through internucleotidic linkages, sugars and/or nucleobases (e.g., by covalent linkage, optionally via a linker, to a site on a sugar, a nucleobase, or an internucleotidic linkage).

In some embodiments, the present disclosure demonstrates that surprisingly high target specificity can be achieved with oligonucleotides, e.g., C9orf72 oligonucleotides, whose structures include one or more features as described herein [including, but not limited to, base sequences disclosed herein (wherein each U can be optionally and independently substituted by T and vice versa), and/or chemical modifications and/or stereochemistry and/or patterns thereof and/or combinations thereof.

In some embodiments, the present disclosure demonstrates that certain provided structural elements, technologies and/or features are particularly useful for oligonucleotides that knock down C9orf72. Regardless, however, the teachings of the present disclosure are not limited to oligonucleotides that participate in or operate via any particular biochemical mechanism. In some embodiments, the present disclosure provides oligonucleotides capable of operating via a mechanism such as double-stranded RNA interference, single-stranded RNA interference or which acts as an antisense oligonucleotide which decreases the expression, activity and/or level of a C9orf72 gene or a gene product thereof via a RNase H-mediated mechanism or steric hindrance of translation.

Further, the present disclosure pertains to any C9orf72 oligonucleotide which operates through any mechanism, and which comprises any sequence, structure or format (or portion thereof) described herein, wherein the oligonucleotide comprises at least one non-naturally-occurring modification of a base, sugar or internucleotidic linkage. In some embodiments, the present disclosure pertains to any C9orf72 oligonucleotide which comprises at least one stereocontrolled internucleotidic linkage (including but not limited to a phosphorothioate linkage in the Sp or Rp configuration). In some embodiments, the present disclosure pertains to any C9orf72 oligonucleotide which operates through any mechanism, and which comprises at least one stereocontrolled internucleotidic linkage (including but not limited to a phosphorothioate linkage in the Sp or Rp configuration). In some embodiments, the present disclosure provides a C9orf72 oligonucleotide which comprises any sequence, structure or format (or portion thereof) described herein, an optional additional chemical moiety (including but not limited to a carbohydrate moiety, and a targeting moiety), stereochemistry or patterns of stereochemistry, internucleotidic linkage or pattern of internucleotidic linkages; modification of sugar(s) or pattern of modifications of sugars; modification of base(s) or patterns of modifications of bases. In some embodiments, a modification of a sugar, nucleobase or internucleotidic linkage is a non-naturally-occurring modification.

In some embodiments, a C9orf72 disorder-associated target allele contains a hexanucleotide repeat expansion in intron 1, including but not limited to G4C2 or (GGGGCC)ng (SEQ ID NO: 1), wherein ng is 30 or more. In some embodiments, ng is 50 or more. In some embodiments, ng is 100 or more. In some embodiments, ng is 150 or more. In some embodiments, ng is 200 or more. In some embodiments, ng is 300 or more. In some embodiments, ng is 500 or more.

The C9orf72 G4C2 repeat expansion in intron 1 reportedly accounts for 1 in 10 ALS cases among European-ancestry populations. G4C2 repeats are reportedly of only about ~10% of the transcripts (e.g., transcripts V3 and V1 of the pathological allele illustrated in FIG. 1), with gain of function toxicities, at least partially mediated by the dipeptide repeat proteins and foci formation by, for example, repeat-expansion containing transcripts and/or spliced-out repeat-expansion containing introns and/or antisense transcription of the repeat-expansion containing region and various nucleic-acid binding proteins. In some embodiments, V1 is reportedly transcribed at very low levels (around 1% of the total C9orf72 transcript level) and does not contribute significantly to the levels of transcripts comprising hexanucleotide repeat expansions. Reportedly, intron nucleic acid containing repeat expansions can be retained as pre-mRNA, partially spliced RNA, and/or spliced out introns, and RNA foci comprising these nucleic acids are associated with RNA binding protein sequestration. C9orf72 RNA foci are described in, for example, Liu et al., 2017, Cell Chemical Biology 24, 1-8; Niblock et al. Acta Neuropathologica Communications (2016) 4:18. Aberrant protein products comprising dipeptide repeat proteins (DPR proteins) are reportedly produced from the repeat expansion, with toxicity to neurons. In some embodiment, the present disclosure provides oligonucleotides and compositions and methods of use thereof which target an intron sequence close to the G4C2 repeats, and can reduce levels of repeat expansion-containing transcripts, proteins encoded thereby, and/or related foci. In some embodiment, the present disclosure provides C9orf72 oligonucleotides and compositions thereof which target an intron sequence close to the G4C2 repeats, to specifically knockdown the repeat expansion-containing transcripts via RNAse-H, with minimal impact on normal C9orf 72 transcripts. In some embodiments, compared to existing data, the present disclosure demonstrates that provided technologies targeting an intron sequence (e.g., between the repeats and exon 1b) can effectively and/or preferentially reduce levels of repeat expansion-containing products.

Without wishing to be bound by any particular theory, the present disclosure notes that several possible mechanisms for the deleterious and disease-associated effects of the repeat expansion have been proposed in the literature. See for example: Edbauer et al. 2016 Curr. Opin. Neurobiol. 36: 99-106; Conlon et al. Elife. 2016 Sep. 13; 5. pii: e17820; Xi et al. 2015 Acta Neuropathol. 129: 715-727; Cohen-Hada et al. 2015 Stem Cell Rep. 7: 927-940; and Burguete et al. eLife 2015; 4:e08881. Among other things, the present disclosure provides technologies that can reduce or remove one or more or all deleterious and disease-associated C9orf72 products and/or disease-associated effects.

Without wishing to be bound by any particular theory, the present disclosure notes that a possible mechanism of a deleterious effect of repeat expansion-containing C9orf72 transcripts is the generation of foci. Reportedly, the repeat expansion results in retention of intron 1-containing C9orf72 mRNA. The majority of intron 1-retaining C9orf72 mRNA accumulates in the nucleus where it is targeted to a specific degradation pathway unable to process G4C2 RNA repeats.

The RNAs subsequently aggregate into foci, which also comprise RNA-binding proteins, sequestering them from their normal functions. Niblock Acta Neuropathol Commun. 2016; 4: 18. Reportedly antisense foci comprising antisense C9orf72 products are present at a significantly higher frequency in cerebellar Purkinje neurons and motor neurons, whereas sense foci are present at a significantly higher frequency in cerebellar granule neurons. Cooper-Knock et al. Acta Neuropathol (2015) 130:63-75. In some embodiments, the present disclosure provides technologies for reducing levels of foci. In some embodiments, provided technologies reduce levels of or remove antisense foci and/or sense foci in one or more types of neurons.

Without wishing to be bound by any particular theory, the present disclosure notes that another possible mechanism of a deleterious effect of repeat expansion-containing C9orf72 transcripts is the generation of dipeptide repeat (DPR) proteins. A small proportion of intron 1-retaining C9orf72 mRNA is exported to the cytoplasm for RAN (repeat-associated non-AUG translation) translation in all six reading frames into DPRs. Niblock Acta Neuropathol Commun. 2016; 4: 18. Cooper-Knock et al. also reported that inclusions containing sense or antisense derived dipeptide repeat proteins were present at significantly higher frequency in cerebellar granule neurons or motor neurons, respectively; and in motor neurons, which are the primary target of pathology in ALS, the presence of antisense foci but not sense foci correlated with mislocalisation of TDP-43, which is a hallmark of ALS neurodegeneration. In some embodiments, provided technologies reduce levels of one or more or all of C9orf72 DPR protein products.

In some embodiments, gain- and/or loss-of-function mechanisms lead to neurodegeneration in a C9orf72-related disorder. See, for example: Mizielinska et al. 2014 Science 345: 1192-94; Chew et al. 2015 Science 348: 1151-1154; Jiang et al. 2016 Neuron 90: 535-550; and Liu et al. 2016 Neuron 90: 521-534; Gendron et al. Cold Spring Harb. Perspect. Med. 2017 Jan. 27. pii: a024224; Haeusler et al. Nat Rev Neurosci. 2016 June; 17(6):383-95; Koppers et al. Ann. Neurol. 2015; 78:426-438; Todd et al. J. Neurochem. 2016 138 (Suppl. 1) 145-162. In some embodiments, provided technologies reduce undesired gained functions, and/or restore or enhance desired functions.

In some embodiments, provided oligonucleotides and compositions and methods of use thereof are useful for treatment of any of several C9orf72-related disorders, including but not limited to amyotrophic lateral sclerosis (ALS). In some embodiments, ALS is MIM: 612069. Amyotrophic lateral sclerosis (ALS) is a reportedly a fatal neurodegenerative disease characterized clinically by progressive paralysis leading to death, often from respiratory failure, typically within two to three years of symptom onset (Rowland and Shneider, N. Engl. J. Med., 2001, 344, 1688-1700). ALS reportedly is the third most common neurodegenerative disease in the Western world (Hirtz et al., Neurology, 2007, 68, 326-337), and there are currently no effective therapies. Approximately 10% of cases are familial in nature, whereas the bulk of patients diagnosed with the disease are classified as sporadic as they appear to occur randomly throughout the population (Chio et al., Neurology, 2008, 70, 533-537). Clinical, genetic, and epidemiological data reportedly support the hypothesis that ALS and frontotemporal dementia (FTD) represent an overlapping continuum of disease, characterized pathologically by the presence of TDP-43 positive inclusions throughout the central nervous system (Lillo and Hodges, J. Clin. Neurosci., 2009, 16, 1131-1135; Neumann et al., Science, 2006, 314, 130-133). A number of genes have been discovered as potentially causative for classical familial ALS, for example, SOD1, TARDBP, FUS, OPTN, and VCP (Johnson et al., Neuron, 2010, 68, 857-864; Kwiatkowski et al., Science, 2009, 323, 1205-1208; Maruyama et al., Nature, 2010, 465, 223-226; Rosen et al., Nature, 1993, 362, 59-62; Sreedharan et al., Science, 2008, 319, 1668-1672; Vance et al., Brain, 2009, 129, 868-876). Linkage analysis of kindreds involving multiple cases of ALS, FTD, and ALS-FTD had reportedly suggested that there was an important locus for the disease on the short arm of chromosome 9, identified as C9orf72 (Boxer et al., J. Neurol. Neurosurg. Psychiatry, 2011, 82, 196-203; Morita et al., Neurology, 2006, 66, 839-844; Pearson et al. J. Neurol., 2011, 258, 647-655; Vance et al., Brain, 2006, 129, 868-876). This mutation had been found to be the most common genetic cause of ALS and FTD. In some embodiments, ALS-FTD causing mutation is a large hexanucleotide (e.g., GGGGCC or $G_4C2$) repeat expansion in the first intron of the C9orf72 gene on chromosome 9 (Renton et al., Neuron, 2011, 72, 257-268; DeJesus-Hernandez et al., Neuron, 2011, 72, 245-256). A founder haplotype, covering the C9orf72 gene, is present in the majority of cases linked to this region (Renton et al., Neuron, 2011, 72, 257-268). This locus on chromosome 9p21 accounts for nearly half of familial ALS and nearly one-quarter of all ALS cases in a cohort of 405 Finnish patients (Laaksovirta et al, Lancet Neurol., 2010, 9, 978-985). The incidence of ALS is reportedly 1:50,000. Familial ALS reportedly represents 5-10% of all ALS cases; C9orf72 mutations reportedly can be the most common cause of ALS (40-50%). ALS is reportedly associated with degeneration of both upper and lower motor neurons in the motor cortex of the brain, the brain stem, and the spinal cord. Symptoms of ALS reportedly include: muscle weakness and/or muscle atrophy, trouble swallowing or breathing, cramping, stiffness. Respiratory failure is reportedly the main cause of death. In some embodiments, provided technologies reduces severity and/or removes one or more of symptoms related to ALS or other C9orf72 related conditions, disorders and/or diseases.

In some embodiments, provided oligonucleotides and compositions and methods of use thereof are useful for treatment of any of several C9orf72-related disorders, including but not limited to frontotemporal dementia (FTD). In some embodiments, FTD is referred to as frontotemporal lobar degeneration or FTLD, MIM: 600274. Frontotemporal dementia, reportedly the second most common form of presenile dementia, is reportedly associated with focal atrophy of the frontal or temporal lobes. Boxer et al. 2005 Alzheimer Dis. Assoc. Disord. 19 (Suppl 1):S3-S6. FTD shares extensive clinical, pathological, and molecular overlap with amyotrophic lateral sclerosis. As reported by Gijselinck, Cold Spring Harb. Perspect. Med. 2017 Jan. 27. pii: a026757, there are reportedly families and individual patients in which both diseases occur (ALS-FTD) (Lomen-Hoerth et al. 2002 Neurology 59:1077-1079), and TDP-43 inclusions (Arai et al. 2006 Biochem. Biophys. Res. Comm. 351: 602-611; Neumann et al. 2006 Science 314: 130-133) in ALS and FTLD patients can be indistinguishable (Tsuji et al. 2012 Brain 135: 3380-3391), despite the pathological distribution being different for ALS and FTLD patients. There is reportedly evidence that common disease pathways may be involved in ALS and FTLD because their clinical and pathological hallmarks overlap; hence, the pure forms of these diseases are considered the two extremes of one disease continuum (Lillo and Hodges 2009 J. Clin. Neurosci. 16: 1131-1135). Genetic studies reportedly identified mutations in the same genes in FTLD and ALS—for example, TBK1, TARDBP, FUS, VCP (Neumann et al. 2006; Kovacs et al. 2009 Mov. Disord. 24: 1843-1847; Johnson et al. 2010 Neuron 68: 857-864; Van Langenhove et al. 2010 Neurology 74: 366-371; Cirulli et al. 2015 Science 347: 1436-1441; Freischmidt et al. 2015 Nat. Neurosci. 18: 631-636; Pottier et al. 2015 Acta Neuropathol. 130: 77-92). Genetic evidence for a common disease pathomechanism was reportedly provided by the identification of the repeat expansion mutations in C9orf72 in patients with ALS, FTLD, and ALS-FTD (Gijselinck et al. 2010 Arch. Neurol. 67: 606-616; De Jesus-Hernandez et al. 2011 Neuron 72: 245-256; Renton et al. 2011 Neuron 72: 257-268).

In some embodiments, a C9orf72 target is a specific allele (e.g., one with a repeat expansion) and level, expression and/or activity of one or more products (e.g., RNA and/or protein products such as dipeptide repeat proteins or DPRs) are intended to be altered. In many embodiments, a C9orf72 target allele is one whose presence and/or expression is associated (e.g., correlated) with presence, incidence, and/or severity, of one or more diseases and/or conditions, including but not limited to ALS and FTD or other C9orf72-related disorders, or a symptom thereof. Alternatively or additionally, in some embodiments, a C9orf72 target allele is one for which alteration of expression, level and/or activity of one or more gene products correlates with improvement (e.g., delay of onset, reduction of severity, responsiveness to other therapy, etc.) in one or more aspects of a disease and/or condition, including but not limited to ALS and FTD or other C9orf72-related disorders.

In some embodiments, a neurological disease is characterized by neuronal hyperexcitability. In some embodiments, a 50% reduction in C9orf72 activity, due to and/or in the presence of the $(GGGGCC)_n$ expansion, reportedly increases neurotransmission through the glutamate receptors NMDA, AMPA, and kainite. In addition, glutamate receptors reportedly accumulate on neurons. The increased neurotransmission and accumulation of glutamate receptors reportedly leads to glutamate-induced excitotoxicity due to the neuronal hyperexcitability. Inhibiting glutamate receptors would reportedly treat the neuronal hyperexcitability. Clearance of dipeptide repeat proteins generated from the expansion reportedly is impaired, enhancing their neurotoxicity. C9orf72 reportedly promotes early endosomal trafficking through activation of RAB5, which requires phosphatidylinositol 3-phosphase (PI3P). PIKFYVE converts PI3P to phosphatidylinositol (3,5)-bisphosphate (PI(3,5)P2). Inhibiting PIKFYVE reportedly would compensate for altered RAB5 levels by increasing PI3P levels to enable early endosomal maturation, which would ultimately lead to the clearance of dipeptide repeat proteins. Neurons reportedly also use endosomal trafficking to regulate sodium and potassium ion channel localization. Inhibiting PIKFYVE reportedly may also treat neuronal hyperexcitability. In some embodiments, provided technologies reduce neuronal hyperexcitability. In some embodiments, provided technologies may be administered as part of the same treatment regime as an inhibitor of PIKFYVE.

In some embodiments, the present disclosure provides an oligonucleotide composition comprising a first plurality of oligonucleotides which share:

1) a common base sequence;
2) a common pattern of backbone linkages; and
3) a common pattern of backbone chiral centers, which composition is a substantially pure preparation of a single oligonucleotide in that a non-random or controlled level of the oligonucleotides in the composition have the common base sequence and length, the common pattern of backbone linkages, and the common pattern of backbone chiral centers.

In some embodiments, the present disclosure provides a C9orf72 oligonucleotide composition comprising a first plurality of oligonucleotides capable of directing C9orf72 knockdown, wherein oligonucleotides are of a particular oligonucleotide type characterized by:

1) a common base sequence and length;
2) a common pattern of backbone linkages; and
3) a common pattern of backbone chiral centers;

which composition is chirally controlled in that it is enriched, relative to a substantially racemic preparation of oligonucleotides having the same base sequence and length, for oligonucleotides of the particular oligonucleotide type.

In some embodiments, the present disclosure provides a chirally controlled oligonucleotide composition comprising a plurality of oligonucleotides which share the same constitution or structure, wherein the oligonucleotides comprises one or more (1, 2, 3, 4, 5, 6, 7, 8, 9, 10, 11, 12, 13, 14, 15, 16, 17, 18, 19, 20 or more) chirally controlled internucleotidic linkages. In some embodiments, base sequence of each oligonucleotide of the plurality comprises a 15, 16, 17, 18, 19, 20 or more consecutive nucleobases that are identical with or complementary to the base sequence or a portion thereof of a C9orf72 gene or a transcript thereof.

In some embodiments, when aligned with its target sequence for maximum complementarity, the base sequence of a provided oligonucleotide comprises one or more mismatches (e.g., not AT, AU or CG). In some embodiments, a mismatch is at the 3'-end. In some embodiments, no more than 1, 2, or 3 mismatches are present. As demonstrated herein, oligonucleotides whose base sequences comprise one or more mismatches when aligned with their target sequences may unexpectedly provide higher activities (e.g., when contacted with target transcripts and RNase H to reduce levels of the target transcripts), lower toxicity, etc. compared to oligonucleotides whose base sequences are fully complementary to their target sequences.

In some embodiments, a provided oligonucleotide (which can target C9orf72 or target a target other than C9orf72) comprises one or more blocks. In some embodiments, a block comprises one or more consecutive nucleosides, and/or nucleotides, and/or sugars, or bases, and/or internucleotidic linkages. In some embodiments, a provided oligonucleotide comprises three or more blocks, wherein the blocks on either end are not identical and the oligonucleotide is thus asymmetric. In some embodiments, a block is a wing or a core.

In some embodiments, a C9orf72 oligonucleotide comprises at least one wing and at least one core, wherein a wing differs structurally from a core in that a wing comprises a structure [e.g., stereochemistry, additional chemical moiety, or chemical modification at a sugar, base or internucleotidic linkage (or pattern thereof)] different than the core, or vice versa. In some embodiments, a provided oligonucleotide comprises a wing-core-wing structure. In some embodiments, a provided oligonucleotide comprises a wing-core, core-wing, or wing-core-wing structure, wherein one wing differs in structure [e.g., stereochemistry, additional chemical moiety, or chemical modification at a sugar, base or internucleotidic linkage (or pattern thereof)] from the other wing and the core (for example, an asymmetrical oligonucleotide). In some embodiments, an oligonucleotide has or comprises a wing-core, core-wing, or wing-core-wing structure, and a block is a wing or core. In some embodiments, a core is also referenced to as a gap.

In general, properties of oligonucleotide compositions as described herein can be assessed using any appropriate assay.

Those of skill in the art will be aware of and/or will readily be able to develop appropriate assays for particular oligonucleotide compositions.

BRIEF DESCRIPTION OF THE DRAWING

FIG. 1. FIG. 1 describes example C9orf72 transcripts. V3, V2 and V1 transcripts produced from a healthy and a pathological C9orf72 allele are illustrated, wherein the pathological allele contains a hexanucleotide repeat expansion [horizontal bar, indicated by $(GGGGCC)_{30}$+] (SEQ ID NO: 2). The downward-pointing arrow indicates the position of some example C9orf72 oligonucleotides targeting intron 1.

DETAILED DESCRIPTION OF CERTAIN EMBODIMENTS

Definitions

As used herein, the following definitions shall apply unless otherwise indicated. For purposes of this disclosure, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001.

As used herein in the present disclosure, unless otherwise clear from context, (i) the term "a" or "an" may be understood to mean "at least one"; (ii) the term "or" may be understood to mean "and/or"; (iii) the terms "comprising", "comprise", "including" (whether used with "not limited to" or not), and "include" (whether used with "not limited to" or not) may be understood to encompass itemized components or steps whether presented by themselves or together with one or more additional components or steps; (iv) the term "another" may be understood to mean at least an additional/second one or more; (v) the terms "about" and "approximately" may be understood to permit standard variation as would be understood by those of ordinary skill in the art; and (vi) where ranges are provided, endpoints are included.

Unless otherwise specified, description of oligonucleotides and elements thereof (e.g., base sequence, sugar modifications, internucleotidic linkages, linkage phosphorus stereochemistry, etc.) is from 5' to 3'. As those skilled in the art will appreciate, in some embodiments, oligonucleotides may be provided and/or utilized as salt forms, particularly pharmaceutically acceptable salt forms, e.g., sodium salts. As those skilled in the art will also appreciate, in some embodiments, individual oligonucleotides within a composition may be considered to be of the same constitution and/or structure even though, within such composition (e.g., a liquid composition), particular such oligonucleotides might be in different salt form(s) (and may be dissolved and the oligonucleotide chain may exist as an anion form when, e.g., in a liquid composition) at a particular moment in time. For example, those skilled in the art will appreciate that, at a given pH, individual internucleotidic linkages along an oligonucleotide chain may be in an acid (H) form, or in one of a plurality of possible salt forms (e.g., a sodium salt, or a salt of a different cation, depending on which ions might be present in the preparation or composition), and will understand that, so long as their acid forms (e.g., replacing all cations, if any, with $H^+$) are of the same constitution and/or structure, such individual oligonucleotides may properly be considered to be of the same constitution and/or structure.

Aliphatic: As used herein, "aliphatic" means a straight-chain (i.e., unbranched) or branched, substituted or unsubstituted hydrocarbon chain that is completely saturated or that contains one or more units of unsaturation, or a substituted or unsubstituted monocyclic, bicyclic, or polycyclic hydrocarbon ring that is completely saturated or that contains one or more units of unsaturation (but not aromatic), or combinations thereof. In some embodiments, aliphatic groups contain 1-50 aliphatic carbon atoms. In some embodiments, aliphatic groups contain 1-20 aliphatic carbon atoms. In other embodiments, aliphatic groups contain 1-10 aliphatic carbon atoms. In other embodiments, aliphatic groups contain 1-9 aliphatic carbon atoms. In other embodiments, aliphatic groups contain 1-8 aliphatic carbon atoms. In other embodiments, aliphatic groups contain 1-7 aliphatic carbon atoms. In other embodiments, aliphatic groups contain 1-6 aliphatic carbon atoms. In still other embodiments, aliphatic groups contain 1-5 aliphatic carbon atoms, and in yet other embodiments, aliphatic groups contain 1, 2, 3, or 4 aliphatic carbon atoms. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

Alkyl: As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some embodiments, an alkyl has 1-100 carbon atoms. In certain embodiments, a straight chain or branched chain alkyl has about 1-20 carbon atoms in its backbone (e.g., $C_1$-$C_{20}$ for straight chain, $C_2$-$C_{20}$ for branched chain), and alternatively, about 1-10. In some embodiments, cycloalkyl rings have from about 3-10 carbon atoms in their ring structure where such rings are monocyclic, bicyclic, or polycyclic, and alternatively about 5, 6 or 7 carbons in the ring structure. In some embodiments, an alkyl group may be a lower alkyl group, wherein a lower alkyl group comprises 1-4 carbon atoms (e.g., $C_1$-$C_4$ for straight chain lower alkyls).

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate and/or a pig). In some embodiments, animals include, but are not limited to, mammals, birds, reptiles, amphibians, fish and/or worms. In some embodiments, an animal may be a transgenic animal, a genetically-engineered animal and/or a clone.

Approximately: As used herein, the terms "approximately" or "about" in reference to a number are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value). In some embodiments, use of the term "about" in reference to dosages means±5 mg/kg/day.

Aryl: The term "aryl", as used herein, used alone or as part of a larger moiety as in "aralkyl," "aralkoxy," or "aryloxyalkyl," refers to monocyclic, bicyclic or polycyclic ring systems having a total of five to thirty ring members, wherein at least one ring in the system is aromatic. In some embodiments, an aryl group is a monocyclic, bicyclic or polycyclic ring system having a total of five to fourteen ring members, wherein at least one ring in the system is aromatic, and wherein each ring in the system contains 3 to 7 ring members. In some embodiments, an aryl group is a biaryl group. The term "aryl" may be used interchangeably with the term "aryl ring." In certain embodiments of the present disclosure, "aryl" refers to an aromatic ring system which includes, but not limited to, phenyl, biphenyl, naphthyl, binaphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

Comparable: The term "comparable" is used herein to describe two (or more) sets of conditions or circumstances that are sufficiently similar to one another to permit comparison of results obtained or phenomena observed. In some embodiments, comparable sets of conditions or circumstances are characterized by a plurality of substantially identical features and one or a small number of varied features. Those of ordinary skill in the art will appreciate that sets of conditions are comparable to one another when characterized by a sufficient number and type of substantially identical features to warrant a reasonable conclusion that differences in results obtained or phenomena observed under the different sets of conditions or circumstances are caused by or indicative of the variation in those features that are varied.

Cycloaliphatic: The term "cycloaliphatic," "carbocycle," "carbocyclyl," "carbocyclic radical," and "carbocyclic ring," are used interchangeably, and as used herein, refer to saturated or partially unsaturated, but non-aromatic, cyclic aliphatic monocyclic, bicyclic, or polycyclic ring systems, as described herein, having, unless otherwise specified, from 3 to 30 ring members. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, a cycloaliphatic group has 3-6 carbons. In some embodiments, a cycloaliphatic group is saturated and is cycloalkyl. The term "cycloaliphatic" may also include aliphatic rings that are fused to one or more aromatic or nonaromatic rings, such as decahydronaphthyl or tetrahydronaphthyl. In some embodiments, a cycloaliphatic group is bicyclic. In some embodiments, a cycloaliphatic group is tricyclic. In some embodiments, a cycloaliphatic group is polycyclic. In some embodiments, "cycloaliphatic" refers to $C_3$-$C_6$ monocyclic hydrocarbon, or $C_8$-$C_{10}$ bicyclic or polycyclic hydrocarbon, that is completely saturated or that contains one or more units of unsaturation, but which is not aromatic, that has a single point of attachment to the rest of the molecule, or a $C_9$-$C_{16}$ polycyclic hydrocarbon that is completely saturated or that contains one or more units of unsaturation, but which is not aromatic, that has a single point of attachment to the rest of the molecule.

Dosing regimen: As used herein, a "dosing regimen" or "therapeutic regimen" refers to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regime comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount.

Heteroaliphatic: The term "heteroaliphatic", as used herein, is given its ordinary meaning in the art and refers to aliphatic groups as described herein in which one or more carbon atoms are independently replaced with one or more heteroatoms (e.g., oxygen, nitrogen, sulfur, silicon, phosphorus, and the like). In some embodiments, one or more units selected from C, CH, $CH_2$, and $CH_3$ are independently replaced by one or more heteroatoms (including oxidized and/or substituted form thereof). In some embodiments, a heteroaliphatic group is heteroalkyl. In some embodiments, a heteroaliphatic group is heteroalkenyl.

Heteroalkyl: The term "heteroalkyl", as used herein, is given its ordinary meaning in the art and refers to alkyl groups as described herein in which one or more carbon atoms are independently replaced with one or more heteroatoms (e.g., oxygen, nitrogen, sulfur, silicon, phosphorus, and the like). Examples of heteroalkyl groups include, but are not limited to, alkoxy, poly(ethylene glycol)-, alkyl-substituted amino, tetrahydrofuranyl, piperidinyl, morpholinyl, etc.

Heteroaryl: The terms "heteroaryl" and "heteroar-", as used herein, used alone or as part of a larger moiety, e.g., "heteroaralkyl," or "heteroaralkoxy," refer to monocyclic, bicyclic or polycyclic ring systems having a total of five to thirty ring members, wherein at least one ring in the system is aromatic and at least one aromatic ring atom is a heteroatom. In some embodiments, a heteroaryl group is a group having 5 to 10 ring atoms (i.e., monocyclic, bicyclic or polycyclic), in some embodiments 5, 6, 9, or 10 ring atoms. In some embodiments, a heteroaryl group has 6, 10, or 14 $\pi$ electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, a heteroaryl is a heterobiaryl group, such as bipyridyl and the like. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be monocyclic, bicyclic or polycyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl group, wherein the alkyl and heteroaryl portions independently are optionally substituted.

Heteroatom: The term "heteroatom", as used herein, means an atom that is not carbon or hydrogen. In some embodiments, a heteroatom is boron, oxygen, sulfur, nitrogen, phosphorus, or silicon (including any oxidized form of nitrogen, sulfur, phosphorus, or silicon; the quaternized form of any basic nitrogen or a substitutable nitrogen of a heterocyclic ring (for example, N as in 3,4-dihydro-2H-pyrrolyl), NH (as in pyrrolidinyl) or NR (as in N-substituted pyrrolidinyl); etc.).

Heterocycle: As used herein, the terms "heterocycle," "heterocyclyl," "heterocyclic radical," and "heterocyclic ring", as used herein, are used interchangeably and refer to a monocyclic, bicyclic or polycyclic ring moiety (e.g., 3-30 membered) that is saturated or partially unsaturated and has one or more heteroatom ring atoms. In some embodiments, a heterocyclyl group is a stable 5- to 7-membered monocyclic or 7- to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes substituted nitrogen. As an example, in a saturated or partially unsaturated ring having 0-3 heteroatoms selected from oxygen, sulfur and nitrogen, the nitrogen may be N (as in 3,4-dihydro-2H-pyrrolyl), NH (as in pyrrolidinyl), or *NR (as in N-substituted pyrrolidinyl). A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be monocyclic, bicyclic or polycyclic. The term "heterocyclylalkyl" refers to an alkyl group substituted by a heterocyclyl, wherein the alkyl and heterocyclyl portions independently are optionally substituted.

In vitro: As used herein, the term "in vitro" refers to events that occur in an artificial environment, e.g., in a test tube or reaction vessel, in cell culture, etc., rather than within an organism (e.g., animal, plant and/or microbe).

In vivo: As used herein, the term "in vivo" refers to events that occur within an organism (e.g., animal, plant and/or microbe).

Optionally Substituted: As described herein, compounds, e.g., oligonucleotides, of the disclosure may contain optionally substituted and/or substituted moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. In some embodiments, an optionally substituted group is unsubstituted. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable atom, e.g., a suitable carbon atom, are independently halogen; $-(CH_2)_{0-4}R^\circ$; $-(CH_2)_{0-4}OR^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}Ph$, which may be substituted with R°; $-(CH_2)_{0-4}O(CH_2)_{0-1}Ph$ which may be substituted with R°; $-CH{=}CHPh$, which may be substituted with R°; $-(CH_2)_{0-4}O(CH_2)_{0-1}$-pyridyl which may be substituted with R°; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR$, $-SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-SC(S)SR^\circ$, $-(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-Si(R^\circ)_3$; $-OSi(R^\circ)_3$; $-B(R^\circ)_2$; $-OB(R^\circ)_2$; $-OB(OR^\circ)_2$; $-P(R^\circ)_2$; $-P(OR^\circ)_2$; $-OP(R^\circ)_2$; $-OP(OR^\circ)_2$; $-P(O)(R^\circ)_2$; $-P(O)(OR^\circ)_2$; $-OP(O)(R^\circ)_2$; $-OP(O)(OR^\circ)_2$; $-OP(O)(OR^\circ)(SR^\circ)$; $-SP(O)(R^\circ)_2$; $-SP(O)(OR^\circ)_2$; $-N(R^\circ)P(O)(R^\circ)_2$; $-N(R^\circ)P(O)(OR^\circ)_2$; $-P(R^\circ)_2[B(R^\circ)_3]$; $-P(OR^\circ)_2[B(R^\circ)_3]$; $-OP(R^\circ)_2[B(R^\circ)_3]$; $-OP(OR^\circ)_2[B(R^\circ)_3]$; $-(C_{1-4}$ straight or branched alkylene$)O-N(R^\circ)_2$; or $-(C_{1-4}$ straight or branched alkylene$)C(O)O-N(R^\circ)_2$, wherein each R° may be substituted as defined below and is independently hydrogen, $C_{1-20}$ aliphatic, $C_{1-20}$ heteroaliphatic having 1-5 heteroatoms independently selected from nitrogen, oxygen, sulfur, silicon and phosphorus, $-CH_2-(C_{6-14}$ aryl$)$, $-O(CH_2)_{0-1}(C_{6-14}$ aryl$)$, $-CH_2$-(5-14 membered heteroaryl ring), a 5-20 membered, monocyclic, bicyclic, or polycyclic, saturated, partially unsaturated or aryl ring having 0-5 heteroatoms independently selected from nitrogen, oxygen, sulfur, silicon and phosphorus, or, notwithstanding the definition above, two independent occurrences of R°, taken together with their intervening atom(s), form a 5-20 membered, monocyclic, bicyclic, or polycyclic, saturated, partially unsaturated or aryl ring having 0-5 heteroatoms independently selected from nitrogen, oxygen, sulfur, silicon and phosphorus, which may be substituted as defined below.

Suitable monovalent substituents on R° (or the ring formed by taking two independent occurrences of R° together with their intervening atoms), are independently halogen, —$(CH_2)_{0-2}R^●$,-(haloR^●), —$(CH_2)_{0-2}OH$, —$(CH_2)_{0-2}OR^●$, —$(CH_2)_{0-2}CH(OR^●)_2$; —O(haloR^●), —CN, —$N_3$, —$(CH_2)_{0-2}C(O)R^●$, —$(CH_2)_{0-2}C(O)OH$, —$(CH_2)_{0-2}C(O)OR^●$, —$(CH_2)_{0-2}SR^●$, —$(CH_2)_{0-2}SH$, —$(CH_2)_{0-2}NH_2$, —$(CH_2)_{0-2}NHR^●$, —$(CH_2)_{0-2}NR^●_2$, —$NO_2$, —$SiR^●_3$, —$OSiR^●_3$, —$C(O)SR^●$, —($C_{1-4}$ straight or branched alkylene)$C(O)OR^●$, or —$SSR^●$ wherein each $R^●$ is unsubstituted or where preceded by "halo" is substituted only with one or more halogens, and is independently selected from $C_{1-4}$ aliphatic, —$CH_2Ph$, —$O(CH_2)_{0-1}Ph$, and a 5-6-membered saturated, partially unsaturated, or aryl ring having 0-4 heteroatoms independently selected from nitrogen, oxygen, and sulfur. Suitable divalent substituents on a saturated carbon atom of R° include ═O and ═S.

Suitable divalent substituents, e.g., on a suitable carbon atom, are independently the following: ═O, ═S, ═$NNR^*_2$, ═$NNHC(O)R^*$, ═$NNHC(O)OR^*$, ═$NNHS(O)_2R^*$, ═$NR^*$, ═$NOR^*$, —$O(C(R^*_2))_{2-3}O$—, or —$S(C(R^*_2))_{2-3}S$—, wherein each independent occurrence of R* is selected from hydrogen, $C_{1-6}$ aliphatic which may be substituted as defined below, and an unsubstituted 5-6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: —$O(CR^*_2)_{2-3}O$—, wherein each independent occurrence of R* is selected from hydrogen, $C_{1-6}$ aliphatic which may be substituted as defined below, and an unsubstituted 5-6-membered saturated, partially unsaturated, or aryl ring having 0-4 heteroatoms independently selected from nitrogen, oxygen, and sulfur.

Suitable substituents on the aliphatic group of R* are independently halogen, —$R^●$,-(haloR^●), —OH, —OR*, —O(haloR^●), —CN, —C(O)OH, —$C(O)OR^●$, —$NH_2$, —$NHR^●$, —$NR^●_2$, or —$NO_2$, wherein each $R^●$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, and sulfur.

Oral: The phrases "oral administration" and "administered orally" as used herein have their art-understood meaning referring to administration by mouth of a compound or composition.

Parenteral: The phrases "parenteral administration" and "administered parenterally" as used herein have their art-understood meaning referring to modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal, and intrasternal injection and infusion.

Partially unsaturated: As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

Pharmaceutical composition: As used herein, the term "pharmaceutical composition" refers to an active agent, formulated together with one or more pharmaceutically acceptable carriers. In some embodiments, an active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: As used herein, the phrase "pharmaceutically acceptable" refers to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Pharmaceutically acceptable salt: The term "pharmaceutically acceptable salt", as used herein, refers to salts of such compounds that are appropriate for use in pharmaceutical contexts, i.e., salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). In some embodiments, pharmaceutically acceptable salt include, but are not limited to, nontoxic acid addition salts, which are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. In some embodiments, pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, a provided compound comprises one or more acidic groups, e.g., an oligonucleotide, and a pharmaceutically acceptable salt is an alkali, alkaline earth metal, or ammonium (e.g., an ammonium salt of $N(R)_3$, wherein each R is independently defined and described in the present disclosure) salt. Representative alkali or alkaline earth metal salts include sodium, lithium, potassium, calcium, magnesium, and the like. In some embodiments, a pharmaceutically acceptable salt is a sodium salt. In some embodiments, a pharmaceutically acceptable salt is a potassium salt. In some embodiments, a pharmaceutically acceptable salt is a calcium salt. In some embodiments, pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate. In some embodiments, a provided compound comprises more than one acid groups, for example, a provided oligonucleotide may comprise two or more acidic groups (e.g., in natural phosphate linkages and/or modified internucleotidic linkages). In some embodiments, a pharmaceutically acceptable salt, or generally a salt, of such a compound comprises two or more cations, which can be the same or different. In some embodiments, in a pharmaceutically acceptable salt (or generally, a salt), all ionizable hydrogen in the acidic groups are replaced with cations. In some embodiments, a pharmaceutically acceptable salt is a sodium salt of a provided oligonucleotide. In some embodiments, a pharmaceutically acceptable salt is a sodium salt of a provided oligonucleotide, wherein each acidic linkage group (e.g., each natural phosphate linkage, each phosphorothioate internucleotidic linkage, etc.) independently exists as a sodium salt form (all sodium salt).

Protecting group: The term "protecting group," as used herein, is well known in the art and includes those described in detail in *Protecting Groups in Organic Synthesis*, T. W. Greene and P. G. M. Wuts, 3rd edition, John Wiley & Sons, 1999, the entirety of which is incorporated herein by reference. Also included are those protecting groups specially adapted for nucleoside and nucleotide chemistry described in Current Protocols in Nucleic Acid Chemistry, edited by Serge L. Beaucage et al. 06/2012, the entirety of Chapter 2 is incorporated herein by reference. Suitable amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2, 5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N' dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), (3-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Suitably protected carboxylic acids further include, but are not limited to, silyl-, alkyl-, alkenyl-, aryl-, and arylalkyl-protected carboxylic acids. Examples of suitable silyl groups include trimethylsilyl, triethylsilyl, t-butyldimethylsilyl, t-butyldiphenylsilyl, triisopropylsilyl, and the like. Examples of suitable alkyl groups include methyl, benzyl, p-methoxybenzyl, 3,4-dimethoxybenzyl, trityl, t-butyl, tetrahydropyran-2-yl. Examples of suitable alkenyl groups include allyl. Examples of suitable aryl groups include optionally substituted phenyl, biphenyl, or naphthyl. Examples of suitable arylalkyl groups include optionally substituted benzyl (e.g., p-methoxybenzyl (MPM), 3,4-dimethoxybenzyl, O-nitrobenzyl, p-nitrobenzyl, p-halobenzyl, 2,6-dichlorobenzyl, p-cyanobenzyl), and 2- and 4-picolyl.

Suitable hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy) ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, a-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, a-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2- trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, a-methoxybenzylidene ortho ester, 1-(N,N-dimethylamino)ethylidene derivative, a-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

In some embodiments, a hydroxyl protecting group is acetyl, t-butyl, tbutoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, benzoyl, p-phenylbenzoyl, 2,6-dichlorobenzyl, diphenylmethyl, p-nitrobenzyl, triphenylmethyl (trityl), 4,4'-dimethoxytrityl, trimethylsilyl, triethylsilyl, t-butyldimethylsilyl, t-butyldiphenylsilyl, triphenylsilyl, triisopropylsilyl, benzoylformate, chloroacetyl, trichloroacetyl, trifiuoroacetyl, pivaloyl, 9-fluorenylmethyl carbonate, mesylate, tosylate, triflate, trityl, monomethoxytrityl (MMTr), 4,4'-dimethoxytrityl, (DMTr) and 4,4',4"-trimethoxytrityl (TMTr), 2-cyanoethyl (CE or Cne), 2-(trimethylsilyl)ethyl (TSE), 2-(2-nitrophenyl)ethyl, 2-(4-cyanophenyl)ethyl 2-(4-nitrophenyl)ethyl (NPE), 2-(4-nitrophenylsulfonyl)ethyl, 3,5-dichlorophenyl, 2,4-dimethylphenyl, 2-nitrophenyl, 4-nitrophenyl, 2,4,6-trimethylphenyl, 2-(2-nitrophenyl)ethyl, butylthiocarbonyl, 4,4',4"-tris(benzoyloxy)trityl, diphenylcarbamoyl, levulinyl, 2-(dibromomethyl)benzoyl (Dbmb), 2-(isopropylthiomethoxymethyl)benzoyl (Ptmt), 9-phenylxanthen-9-yl (pixyl) or 9-(p-methoxyphenyl)xanthine-9-yl (MOX). In some embodiments, each of the hydroxyl protecting groups is, independently selected from acetyl, benzyl, t-butyldimethylsilyl, t-butyldiphenylsilyl and 4,4'-dimethoxytrityl. In some embodiments, the hydroxyl protecting group is selected from the group consisting of trityl, monomethoxytrityl and 4,4'-dimethoxytrityl group. In some embodiments, a phosphorous linkage protecting group is a group attached to the phosphorous linkage (e.g., an internucleotidic linkage) throughout oligonucleotide synthesis. In some embodiments, a protecting group is attached to a sulfur atom of an phosphorothioate group. In some embodiments, a protecting group is attached to an oxygen atom of an internucleotide phosphorothioate linkage. In some embodiments, a protecting group is attached to an oxygen atom of the internucleotide phosphate linkage. In some embodiments a protecting group is 2-cyanoethyl (CE or Cne), 2-trimethylsilylethyl, 2-nitroethyl, 2-sulfonylethyl, methyl, benzyl, o-nitrobenzyl, 2-(p-nitrophenyl)ethyl (NPE or Npe), 2-phenylethyl, 3-(N-tert-butylcarboxamido)-1-propyl, 4-oxopentyl, 4-methylthio-1-butyl, 2-cyano-1,1-dimethylethyl, 4-N-methylaminobutyl, 3-(2-pyridyl)-1-propyl, 2-[N-methyl-N-(2-pyridyl)]aminoethyl, 2-(N-formyl,N-methyl)aminoethyl, or 4-[N-methyl-N-(2,2,2-trifluoroacetyl)amino]butyl.

Sample: A "sample" as used herein is a specific organism or material obtained therefrom. In some embodiments, a sample is a biological sample obtained or derived from a source of interest, as described herein. In some embodiments, a source of interest comprises an organism, such as an animal or human. In some embodiments, a biological sample comprises biological tissue or fluid. In some embodiments, a biological sample is or comprises bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions and/or excretions; and/or cells therefrom, etc. In some embodiments, a biological sample is or comprises cells obtained from an individual. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc. In some embodiments, a sample is an organism. In some embodiments, a sample is a plant. In some embodiments, a sample is an animal. In some embodiments, a sample is a human. In some embodiments, a sample is an organism other than a human.

Subject: As used herein, the term "subject" or "test subject" refers to any organism to which a provided compound or composition is administered in accordance with the present disclosure e.g., for experimental, diagnostic, prophylactic and/or therapeutic purposes. Typical subjects include animals (e.g., mammals such as mice, rats, rabbits, non-human primates, and humans; insects; worms; etc.) and plants. In some embodiments, a subject may be suffering from and/or susceptible to a disease, disorder and/or condition.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and/or chemical phenomena.

Suffering from: An individual who is "suffering from" a disease, disorder and/or condition has been diagnosed with and/or displays one or more symptoms of a disease, disorder and/or condition.

Susceptible to: An individual who is "susceptible to" a disease, disorder and/or condition is one who has a higher risk of developing the disease, disorder and/or condition than does a member of the general public. In some embodiments, an individual who is susceptible to a disease, disorder and/or condition is predisposed to have that disease, disorder and/or condition. In some embodiments, an individual who is susceptible to a disease, disorder and/or condition may not have been diagnosed with the disease, disorder and/or condition. In some embodiments, an individual who is susceptible to a disease, disorder and/or condition may exhibit symptoms of the disease, disorder and/or condition. In some embodiments, an individual who is susceptible to a disease, disorder and/or condition may not exhibit symptoms of the disease, disorder and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Systemic: The phrases "systemic administration," "administered systemically," "peripheral administration," and "administered peripherally" as used herein have their art-understood meaning referring to administration of a compound or composition such that it enters the recipient's system.

Therapeutic agent: As used herein, the phrase "therapeutic agent" refers to any agent that, when administered to a subject, has a therapeutic effect and/or elicits a desired biological and/or pharmacological effect. In some embodiments, a therapeutic agent is any substance that can be used to alleviate, ameliorate, relieve, inhibit, prevent, delay onset of, reduce severity of, and/or reduce incidence of one or more symptoms or features of a disease, disorder, and/or condition.

Therapeutically effective amount: As used herein, the term "therapeutically effective amount" means an amount of a substance (e.g., a therapeutic agent, composition, and/or formulation) that elicits a desired biological response when administered as part of a therapeutic regimen. In some embodiments, a therapeutically effective amount of a substance is an amount that is sufficient, when administered to a subject suffering from or susceptible to a disease, disorder, and/or condition, to treat, diagnose, prevent, and/or delay the onset of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. In some embodiments, a therapeutically effective amount is administered in a single dose; in some embodiments, multiple unit doses are required to deliver a therapeutically effective amount.

Treat: As used herein, the term "treat," "treatment," or "treating" refers to any method used to partially or completely alleviate, ameliorate, relieve, inhibit, prevent, delay onset of, reduce severity of, and/or reduce incidence of one or more symptoms or features of a disease, disorder, and/or condition. Treatment may be administered to a subject who does not exhibit signs of a disease, disorder, and/or condition. In some embodiments, treatment may be administered to a subject who exhibits only early signs of the disease, disorder, and/or condition, for example for the purpose of decreasing the risk of developing pathology associated with the disease, disorder, and/or condition.

Unsaturated: The term "unsaturated," as used herein, means that a moiety has one or more units of unsaturation.

Unit dose: The expression "unit dose" as used herein refers to an amount administered as a single dose and/or in a physically discrete unit of a pharmaceutical composition. In many embodiments, a unit dose contains a predetermined quantity of an active agent. In some embodiments, a unit dose contains an entire single dose of the agent. In some embodiments, more than one unit dose is administered to achieve a total single dose. In some embodiments, administration of multiple unit doses is required, or expected to be required, in order to achieve an intended effect. A unit dose may be, for example, a volume of liquid (e.g., an acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be appreciated that a unit dose may be present in a formulation that includes any of a variety of components in addition to the therapeutic agent(s). For example, acceptable carriers (e.g., pharmaceutically acceptable carriers), diluents, stabilizers, buffers, preservatives, etc., may be included as described infra. It will be appreciated by those skilled in the art, in many embodiments, a total appropriate daily dosage of a particular therapeutic agent may comprise a portion, or a plurality, of unit doses, and may be decided, for example, by the attending physician within the scope of sound medical judgment. In some embodiments, the specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts.

Wild-type: As used herein, the term "wild-type" has its art-understood meaning that refers to an entity having a structure and/or activity as found in nature in a "normal" (as contrasted with mutant, diseased, altered, etc) state or context. Those of ordinary skill in the art will appreciate that wild type genes and polypeptides often exist in multiple different forms (e.g., alleles).

Nucleic acid: The term "nucleic acid", as used herein, includes any nucleotides and polymers thereof. The term "polynucleotide", as used herein, refers to a polymeric form of nucleotides of any length, either ribonucleotides (RNA) or deoxyribonucleotides (DNA). These terms refer to the primary structure of the molecules and, thus, include double- and single-stranded DNA, and double- and single-stranded RNA. These terms include, as equivalents, analogs of either RNA or DNA made from modified nucleotides and/or modified polynucleotides, such as, though not limited to, methylated, protected and/or capped nucleotides or polynucleotides. The terms encompass poly- or oligo-ribonucleotides (RNA) and poly- or oligo-deoxyribonucleotides (DNA); RNA or DNA derived from N-glycosides or C-glycosides of nucleobases and/or modified nucleobases; nucleic acids derived from sugars and/or modified sugars; and nucleic acids derived from phosphate bridges and/or modified internucleotide linkages. The term encompasses nucleic acids containing any combinations of nucleobases, modified nucleobases, sugars, modified sugars, phosphate bridges or modified internucleotidic linkages. Examples include, and are not limited to, nucleic acids containing ribose moieties, nucleic acids containing deoxy-ribose moieties, nucleic acids containing both ribose and deoxyribose moieties, nucleic acids containing ribose and modified ribose moieties. Unless otherwise specified, the prefix poly—refers to a nucleic acid containing 2 to about 10,000 nucleotide monomer units and wherein the prefix oligo— refers to a nucleic acid containing 2 to about 200 nucleotide monomer units.

Nucleotide: The term "nucleotide" as used herein refers to a monomeric unit of a polynucleotide that consists of a nucleobase, a sugar, and one or more internucleotidic linkages. The naturally occurring bases (guanine, (G), adenine, (A), cytosine, (C), thymine, (T), and uracil (U)) are derivatives of purine or pyrimidine, though it should be understood that naturally and non-naturally occurring base analogs are also included. The naturally occurring sugar is the pentose (five-carbon sugar) deoxyribose (which forms DNA) or ribose (which forms RNA), though it should be understood that naturally and non-naturally occurring sugar analogs are also included. Nucleotides are linked via internucleotidic linkages to form nucleic acids, or polynucleotides. Many internucleotidic linkages are known in the art (such as, though not limited to, phosphate, phosphorothioates, boranophosphates and the like). Artificial nucleic acids include PNAs (peptide nucleic acids), phosphotriesters, phosphorothionates, H-phosphonates, phosphoramidates, boranophosphates, methylphosphonates, phosphonoacetates, thiophosphonoacetates and other variants of the phosphate backbone of native nucleic acids, such as those described herein. In some embodiments, a natural nucleotide comprises a naturally occurring base, sugar and internucleotidic linkage. As used herein, the term "nucleotide" also encompasses structural analogs used in lieu of natural or naturally-occurring nucleotides, such as modified nucleotides and nucleotide analogs.

Modified nucleotide: The term "modified nucleotide" includes any chemical moiety which differs structurally from a natural nucleotide but is capable of performing at least one function of a natural nucleotide. In some embodiments, a modified nucleotide comprises a modification at a sugar, base and/or internucleotidic linkage. In some embodiments, a modified nucleotide comprises a modified sugar, modified nucleobase and/or modified internucleotidic linkage. In some embodiments, a modified nucleotide is capable of at least one function of a nucleotide, e.g., forming a subunit in a polymer capable of base-pairing to a nucleic acid comprising an at least complementary sequence of bases.

Analog: The term "analog" includes any chemical moiety which differs structurally from a reference chemical moiety or class of moieties, but which is capable of performing at least one function of such a reference chemical moiety or class of moieties. As non-limiting examples, a nucleotide analog differs structurally from a nucleotide but performs at least one function of a nucleotide; a nucleobase analog differs structurally from a nucleobase but performs at least one function of a nucleobase; etc.

Nucleoside: The term "nucleoside" refers to a moiety wherein a nucleobase or a modified nucleobase is covalently bound to a sugar or a modified sugar.

Modified nucleoside: The term "modified nucleoside" refers to a moiety derived from or chemically similar to a natural nucleoside, but which comprises a chemical modification which differentiates it from a natural nucleoside. Non-limiting examples of modified nucleosides include those which comprise a modification at the base and/or the sugar. Non-limiting examples of modified nucleosides include those with a 2' modification at a sugar. Non-limiting examples of modified nucleosides also include abasic nucleosides (which lack a nucleobase). In some embodiments, a modified nucleoside is capable of at least one function of a nucleoside, e.g., forming a moiety in a polymer capable of base-pairing to a nucleic acid comprising an at least complementary sequence of bases.

Nucleoside analog: The term "nucleoside analog" refers to a chemical moiety which is chemically distinct from a natural nucleoside, but which is capable of performing at least one function of a nucleoside. In some embodiments, a nucleoside analog comprises an analog of a sugar and/or an analog of a nucleobase. In some embodiments, a modified nucleoside is capable of at least one function of a nucleoside, e.g., forming a moiety in a polymer capable of base-pairing to a nucleic acid comprising a complementary sequence of bases.

Sugar: The term "sugar" refers to a monosaccharide or polysaccharide in closed and/or open form. In some embodiments, sugars are monosaccharides. In some embodiments, sugars are polysaccharides. Sugars include, but are not limited to, ribose, deoxyribose, pentofuranose, pentopyranose, and hexopyranose moieties. As used herein, the term "sugar" also encompasses structural analogs used in lieu of conventional sugar molecules, such as glycol, polymer of which forms the backbone of the nucleic acid analog, glycol nucleic acid ("GNA"), etc. As used herein, the term "sugar" also encompasses structural analogs used in lieu of natural or naturally-occurring nucleotides, such as modified sugars and nucleotide sugars.

Modified sugar: The term "modified sugar" refers to a moiety that can replace a sugar. A modified sugar mimics the spatial arrangement, electronic properties, or some other physicochemical property of a sugar.

Nucleobase: The term "nucleobase" refers to the parts of nucleic acids that are involved in the hydrogen-bonding that binds one nucleic acid strand to another complementary strand in a sequence specific manner. The most common naturally-occurring nucleobases are adenine (A), guanine (G), uracil (U), cytosine (C), and thymine (T). In some embodiments, the naturally-occurring nucleobases are modified adenine, guanine, uracil, cytosine, or thymine. In some embodiments, the naturally-occurring nucleobases are methylated adenine, guanine, uracil, cytosine, or thymine. In some embodiments, a nucleobase is a "modified nucleobase," e.g., a nucleobase other than adenine (A), guanine (G), uracil (U), cytosine (C), and thymine (T). In some embodiments, the modified nucleobases are methylated adenine, guanine, uracil, cytosine, or thymine. In some embodiments, the modified nucleobase mimics the spatial arrangement, electronic properties, or some other physicochemical property of the nucleobase and retains the property of hydrogen-bonding that binds one nucleic acid strand to another in a sequence specific manner. In some embodiments, a modified nucleobase can pair with all of the five naturally occurring bases (uracil, thymine, adenine, cytosine, or guanine) without substantially affecting the melting behavior, recognition by intracellular enzymes or activity of the oligonucleotide duplex. As used herein, the term "nucleobase" also encompasses structural analogs used in lieu of natural or naturally-occurring nucleotides, such as modified nucleobases and nucleobase analogs.

Modified nucleobase: The terms "modified nucleobase", "modified base" and the like refer to a chemical moiety which is chemically distinct from a nucleobase, but which is capable of performing at least one function of a nucleobase. In some embodiments, a modified nucleobase is a nucleobase which comprises a modification. In some embodiments, a modified nucleobase is capable of at least one function of a nucleobase, e.g., forming a moiety in a polymer capable of base-pairing to a nucleic acid comprising an at least complementary sequence of bases.

Blocking group: The term "blocking group" refers to a group that masks the reactivity of a functional group. The functional group can be subsequently unmasked by removal of the blocking group. In some embodiments, a blocking group is a protecting group.

Moiety: The term "moiety" refers to a specific segment or functional group of a molecule. Chemical moieties are often recognized chemical entities embedded in or appended to a molecule.

Solid support: The term "solid support" refers to any support which enables synthesis of nucleic acids. In some embodiments, the term refers to a glass or a polymer, that is insoluble in the media employed in the reaction steps performed to synthesize nucleic acids, and is derivatized to comprise reactive groups. In some embodiments, the solid support is Highly Cross-linked Polystyrene (HCP) or Controlled Pore Glass (CPG). In some embodiments, the solid support is Controlled Pore Glass (CPG). In some embodiments, the solid support is hybrid support of Controlled Pore Glass (CPG) and Highly Cross-linked Polystyrene (HCP).

Homology: "Homology" or "identity" or "similarity" refers to sequence similarity between two nucleic acid molecules. Homology and identity can each be determined by comparing a position in each sequence which can be aligned for purposes of comparison. When an equivalent position in the compared sequences is occupied by the same base, then the molecules are identical at that position; when the equivalent site occupied by the same or a similar nucleic acid residue (e.g., similar in steric and/or electronic nature), then the molecules can be referred to as homologous (similar) at that position. Expression as a percentage of homology/similarity or identity refers to a function of the number of identical or similar nucleic acids at positions shared by the compared sequences. A sequence which is "unrelated" or "non-homologous" shares less than 40% identity, less than 35% identity, less than 30% identity, or less than 25% identity with a sequence described herein. In comparing two sequences, the absence of residues (amino acids or nucleic acids) or presence of extra residues also decreases the identity and homology/similarity.

In some embodiments, the term "homology" describes a mathematically based comparison of sequence similarities which is used to identify genes with similar functions or motifs. The nucleic acid sequences described herein can be used as a "query sequence" to perform a search against public databases, for example, to identify other family members, related sequences or homologs. In some embodiments, such searches can be performed using the NBLAST and XBLAST programs (version 2.0) of Altschul, et al. (1990) J. Mol. Biol. 215:403-10. In some embodiments, BLAST nucleotide searches can be performed with the NBLAST program, score=100, wordlength=12 to obtain nucleotide sequences homologous to nucleic acid molecules of the disclosure. In some embodiments, to obtain gapped alignments for comparison purposes, Gapped BLAST can be utilized as described in Altschul et al., (1997) Nucleic Acids Res. 25 (17): 3389-3402. When utilizing BLAST and Gapped BLAST programs, the default parameters of the respective programs (e.g., XBLAST and BLAST) can be used (See ncbi.nlm.nih.gov).

Identity: As used herein, "identity" means the percentage of identical nucleotide residues at corresponding positions in two or more sequences when the sequences are aligned to maximize sequence matching, i.e., taking into account gaps and insertions. Identity can be readily calculated by known methods, including but not limited to those known in the art, including but not limited to those cited in WO2017/192679.

Oligonucleotide: The term "oligonucleotide" refers to a polymer or oligomer of nucleotides, and may contain any combination of natural and non-natural nucleobases, sugars, and internucleotidic linkages.

Oligonucleotides can be single-stranded or double-stranded. A single-stranded oligonucleotide can have double-stranded regions (formed by two portions of the single-stranded oligonucleotide) and a double-stranded oligonucleotide, which comprises two oligonucleotide chains, can have single-stranded regions for example, at regions where the two oligonucleotide chains are not complementary to each other. Example oligonucleotides include, but are not limited to structural genes, genes including control and termination regions, self-replicating systems such as viral or plasmid DNA, single-stranded and double-stranded RNAi agents and other RNA interference reagents (RNAi agents or iRNA agents), shRNA, antisense oligonucleotides, ribozymes, microRNAs, microRNA mimics, supermirs, aptamers, antimirs, antagomirs, Ul adaptors, triplex-forming oligonucleotides, G-quadruplex oligonucleotides, RNA activators, immuno-stimulatory oligonucleotides, and decoy oligonucleotides.

Internucleotidic linkage: As used herein, the phrase "internucleotidic linkage" refers generally to a linkage linking nucleoside units of an oligonucleotide or a nucleic acid. In some embodiments, an internucleotidic linkage is a phosphodiester linkage, as found in naturally occurring DNA and RNA molecules (natural phosphate linkage). In some embodiments, an internucleotidic linkage includes a modified internucleotidic linkage. In some embodiments, an internucleotidic linkage is a "modified internucleotidic linkage" wherein each oxygen atom of the phosphodiester linkage is optionally and independently replaced by an organic or inorganic moiety. In some embodiments, such an organic or inorganic moiety is selected from but not limited to =S, =Se, =NR', —SR', —SeR', —$N(R')_2$, $B(R')_3$, —S—, —Se—, and —N(R')—, wherein each R' is independently as defined and described in the present disclosure. In some embodiments, an internucleotidic linkage is a phosphotriester linkage, phosphorothioate diester linkage

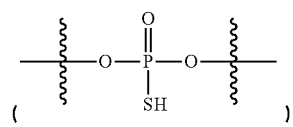

or modified phosphorothioate triester linkage. In some embodiments, an internucleotidic linkage is one of, e.g., PNA (peptide nucleic acid) or PMO (phosphorodiamidate Morpholino oligomer) linkage. It is understood by a person of ordinary skill in the art that an internucleotidic linkage may exist as an anion or cation at a given pH due to the existence of acid or base moieties in the linkage.

Non-limiting examples of modified internucleotidic linkages are modified internucleotidic linkages designated s, s1, s2, s3, s4, s5, s6, s7, s8, s9, s10, s11, s12, s13, s14, s15, s16, s17 and s18 as described in WO 2017/210647.

For instance, (Rp, Sp)-ATsCslGA has 1) a phosphorothioate internucleotidic linkage

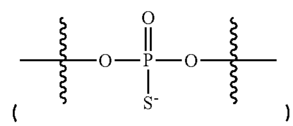

between T and C; and 2) a phosphorothioate triester internucleotidic linkage having the structure of

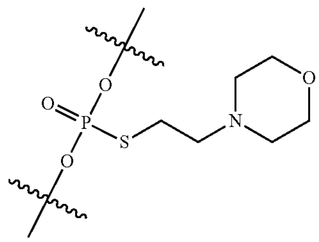 [SMILES: *OP(=O)(O*)SCCN1CCOCC1]

between C and G. Unless otherwise specified, the Rp/Sp designations preceding an oligonucleotide sequence describe the configurations of chiral linkage phosphorus atoms in the internucleotidic linkages sequentially from 5' to 3' of the oligonucleotide sequence. For instance, in (Rp, Sp)-ATsCs1GA, the phosphorus in the "s" linkage between T and C has Rp configuration and the phosphorus in "s1" linkage between C and G has Sp configuration. In some embodiments, "All-(Rp)" or "All-(Sp)" is used to indicate that all chiral linkage phosphorus atoms in oligonucleotide have the same Rp or Sp configuration, respectively.

Oligonucleotide type: As used herein, the phrase "oligonucleotide type" is used to define an oligonucleotide that has a particular base sequence, pattern of backbone linkages (i.e., pattern of internucleotidic linkage types, for example, phosphate, phosphorothioate, etc.), pattern of backbone chiral centers (i.e. pattern of linkage phosphorus stereochemistry (Rp/Sp)), and pattern of backbone phosphorus modifications. In some embodiments, oligonucleotides of a common designated "type" are structurally identical to one another.

One of skill in the art will appreciate that synthetic methods of the present disclosure provide for a degree of control during the synthesis of an oligonucleotide strand such that each nucleotide unit of the oligonucleotide strand can be designed and/or selected in advance to have a particular stereochemistry at the linkage phosphorus and/or a particular modification at the linkage phosphorus, and/or a particular base, and/or a particular sugar. In some embodiments, an oligonucleotide strand is designed and/or selected in advance to have a particular combination of stereocenters at the linkage phosphorus. In some embodiments, an oligonucleotide strand is designed and/or determined to have a particular combination of modifications at the linkage phosphorus. In some embodiments, an oligonucleotide strand is designed and/or selected to have a particular combination of bases. In some embodiments, an oligonucleotide strand is designed and/or selected to have a particular combination of one or more of the above structural characteristics. In some embodiments, the present disclosure provides compositions comprising or consisting of a plurality of oligonucleotide molecules (e.g., chirally controlled oligonucleotide compositions). In some embodiments, all such molecules are of the same type (i.e., are structurally identical to one another). In many embodiments, however, provided compositions comprise a plurality of oligonucleotides of different types, typically in pre-determined relative amounts.

Chiral control: As used herein, "chiral control" refers to control of the stereochemical designation of a chiral linkage phosphorus in a chiral internucleotidic linkage within an oligonucleotide. In some embodiments, a control is achieved through a chiral element that is absent from the sugar and base moieties of an oligonucleotide, for example, in some embodiments, a control is achieved through use of one or more chiral auxiliaries during oligonucleotide preparation as exemplified in the present disclosure, which chiral auxiliaries often are part of chiral phosphoramidites used during oligonucleotide preparation. In contrast to chiral control, a person having ordinary skill in the art appreciates that conventional oligonucleotide synthesis which does not use chiral auxiliaries cannot control stereochemistry at a chiral internucleotidic linkage if such conventional oligonucleotide synthesis is used to form the chiral internucleotidic linkage. In some embodiments, the stereochemical designation of each chiral linkage phosphorus in a chiral internucleotidic linkage within an oligonucleotide is controlled.

Chirally controlled oligonucleotide composition: The terms "chirally controlled oligonucleotide composition", "chirally controlled nucleic acid composition", and the like, as used herein, refers to a composition that comprises a plurality of oligonucleotides (or nucleic acids) which share 1) a common base sequence, 2) a common pattern of backbone linkages, and 3) a common pattern of backbone phosphorus modifications, wherein the plurality of oligonucleotides (or nucleic acids) share the same linkage phosphorus stereochemistry at one or more chiral internucleotidic linkages (chirally controlled or stereodefined internucleotidic linkages, whose chiral linkage phosphorus is Rp or Sp in the composition ("stereodefined"), not a random Rp and Sp mixture as non-chirally controlled internucleotidic linkages). Level of the plurality of oligonucleotides (or nucleic acids) in a chirally controlled oligonucleotide composition is pre-determined/controlled (e.g., through chirally controlled oligonucleotide preparation to stereoselectively form one or more chiral internucleotidic linkages). In some embodiments, about 1%-100%, (e.g., about 5%-100%, 10%-100%, 20%-100%, 30%-100%, 40%-100%, 50%-100%, 60%-100%, 70%-100%, 80-100%, 90-100%, 95-100%, 50%-90%, or about 5%, 10%, 20%, 30%, 40%, 50%, 60%, 70%, 80%, 85%, 90%, 91%, 92%, 93%, 94%, 95%, 96%, 97%, 98%, 99%, or 100%, or at least 5%, 10%, 20%, 30%, 40%, 50%, 60%, 70%, 80%, 85%, 90%, 91%, 92%, 93%, 94%, 95%, 96%, 97%, 98%, or 99%) of all oligonucleotides in a chirally controlled oligonucleotide composition are oligonucleotides of the plurality. In some embodiments, about 1%-100%, (e.g., about 5%-100%, 10%-100%, 20%-100%, 30%-100%, 40%-100%, 50%-100%, 60%-100%, 70%-100%, 80-100%, 90-100%, 95-100%, 50%-90%, or about 5%, 10%, 20%, 30%, 40%, 50%, 60%, 70%, 80%, 85%, 90%, 91%, 92%, 93%, 94%, 95%, 96%, 97%, 98%, 99%, or 100%, or at least 5%, 10%, 20%, 30%, 40%, 50%, 60%, 70%, 80%, 85%, 90%, 91%, 92%, 93%, 94%, 95%, 96%, 97%, 98%, or 99%) of all oligonucleotides in a chirally controlled oligonucleotide composition that share the common base sequence, the common pattern of backbone linkages, and the common pattern of backbone phosphorus modifications are oligonucleotides of the plurality. In some embodiments, a level is about 1%-100%, (e.g., about 5%-100%, 10%-100%, 20%-100%, 30%-100%, 40%-100%, 50%-100%, 60%-100%, 70%-100%, 80-100%, 90-100%, 95-100%, 50%-90%, or about 5%, 10%, 20%, 30%, 40%, 50%, 60%, 70%, 80%, 85%, 90%, 91%, 92%, 93%, 94%, 95%, 96%, 97%, 98%, 99%, or 100%, or at least 5%, 10%, 20%, 30%, 40%, 50%, 60%, 70%, 80%, 85%, 90%, 91%, 92%, 93%, 94%, 95%, 96%, 97%, 98%, or 99%) of all oligonucleotides in a composition, or of all oligonucleotides in a composition that share a common base sequence (e.g., of a plurality of oligonucleotide or an oligonucleotide type), or of all oligonucleotides in a composition that share a common base sequence, a common pattern of backbone linkages, and a common pattern of backbone phosphorus modifications, or of all oligonucleotides in a composition that share a common base sequence, a common patter of base modifications, a common pattern of sugar modifications, a common pattern of internucleotidic linkage types, and/or a common pattern of internucleotidic linkage modifications. In some embodiments, the plurality of oligonucleotides share the same stereochemistry at about 1-50 (e.g., about 1-10, 1-20, 5-10, 5-20, 10-15, 10-20, 10-25, 10-30, or about 1, 2, 3, 4, 5, 6, 7, 8, 9, 10, 11, 12, 13, 14, 15, 16, 17, 18, 19, or 20, or at least 1, 2, 3, 4, 5, 6, 7, 8, 9, 10, 11, 12, 13, 14, 15, 16, 17, 18, 19, or 20) chiral internucleotidic linkages. In some embodiments, the plurality of oligonucleotides share the same stereochemistry at about 1%-100% (e.g., about 5%-100%, 10%-100%, 20%-100%, 30%-100%, 40%-100%, 50%-100%, 60%-100%, 70%-100%, 80-100%, 90-100%, 95-100%, 50%-90%, about 5%, 10%, 15%, 20%, 25%, 30%, 35%, 40%, 45%, 50%, 55%, 60%, 65%, 70%, 75%, 80%, 85%, 90%, 95%, or 100%, or at least 5%, 10%, 15%, 20%, 25%, 30%, 35%, 40%, 45%, 50%, 55%, 60%, 65%, 70%, 75%, 80%, 85%, 90%, 95%, or 99%) of chiral internucleotidic linkages. In some embodiments, oligonucleotides (or nucleic acids) of a plurality are of the same constitution. In some embodiments, level of the oligonucleotides (or nucleic acids) of the plurality is about 1%-100%, (e.g., about 5%-100%, 10%-100%, 20%-100%, 30%-100%, 40%-100%, 50%-100%, 60%-100%, 70%-100%, 80-100%, 90-100%, 95-100%, 50%-90%, or about 5%, 10%, 20%, 30%, 40%, 50%, 60%, 70%, 80%, 85%, 90%, 91%, 92%, 93%, 94%, 95%, 96%, 97%, 98%, 99%, or 100%, or at least 5%, 10%, 20%, 30%, 40%, 50%, 60%, 70%, 80%, 85%, 90%, 91%, 92%, 93%, 94%, 95%, 96%, 97%, 98%, or 99%) of all oligonucleotides (or nucleic acids) in a composition that share the same constitution as the oligonucleotides (or nucleic acids) of the plurality. In some embodiments, each chiral internucleotidic linkage is a chiral controlled internucleotidic linkage, and the composition is a completely chirally controlled oligonucleotide composition. In some embodiments, oligonucleotides (or nucleic acids) of a plurality are structurally identical. In some embodiments, a chirally controlled internucleotidic linkage has a diastereopurity of at least 80%, 85%, 90%, 91%, 92%, 93%, 94%, 95%, 96%, 97%, 98%, 99% or 99.5%, typically at least 90%, 91%, 92%, 93%, 94%, 95%, 96%, 97%, 98%, 99% or 99.5%. In some embodiments, a chirally controlled internucleotidic linkage has a diastereopurity of at least 95%. In some embodiments, a chirally controlled internucleotidic linkage has a diastereopurity of at least 96%. In some embodiments, a chirally controlled internucleotidic linkage has a diastereopurity of at least 97%. In some embodiments, a chirally controlled internucleotidic linkage has a diastereopurity of at least 98%. In some embodiments, a chirally controlled internucleotidic linkage has a diastereopurity of at least 99%. In some embodiments, a percentage of a level is or is at least $(DS)^{nc}$, wherein DS is a diastereopurity as described in the present disclosure (e.g., 90%, 91%, 92%, 93%, 94%, 95%, 96%, 97%, 98%, 99% or 99.5% or more) and nc is the number of chirally controlled internucleotidic linkages as described in the present disclosure (e.g., 1-50, 1-40, 1-30, 1-25, 1-20, 5-50, 5-40, 5-30, 5-25, 5-20, 1,2,3, 4,5,6,7, 8,9, 10, 11, 12, 13, 14, 15, 16, 17, 18, 19, 20, 21, 22, 23, 24, 25 or more). In some embodiments, a percentage of a level is or is at least $(DS)^{nc}$, wherein DS is 95%-100%. For example, when DS is 99% and nc is 10, the percentage is or is at least 90% ($(99\%)^{10} \approx 0.90=90\%$). In some embodiments, level of a plurality of oligonucleotides in a composition is represented as the product of the diastereopurity of each chirally controlled internucleotidic linkage in the oligonucleotides. In some embodiments, diastereopurity of an internucleotidic linkage connecting two nucleosides in an oligonucleotide (or nucleic acid) is represented by the diastereopurity of an internucleotidic linkage of a dimer connecting the same two nucleosides, wherein the dimer is prepared using comparable conditions, in some instances, identical synthetic cycle conditions (e.g., for the linkage between Nx and Ny in an oligonucleotide . . . NxNy . . . , the dimer is NxNy). In some embodiments, not all chiral internucleotidic linkages are chiral controlled internucleotidic linkages, and the composition is a partially chirally controlled oligonucleotide composition. In some embodiments, a non-chirally controlled internucleotidic linkage has a diastereopurity of less than about 80%, 75%, 70%, 65%, 60%, 55%, or of about 50%, as typically observed in stereorandom oligonucleotide compositions (e.g., as appreciated by those skilled in the art, from traditional oligonucleotide synthesis, e.g., the phosphoramidite method). In some embodiments, oligonucleotides (or nucleic acids) of a plurality are of the same type. In some embodiments, a chirally controlled oligonucleotide composition comprises non-random or controlled levels of individual oligonucleotide or nucleic acids types. For instance, in some embodiments a chirally controlled oligonucleotide composition comprises one and no more than one oligonucleotide type. In some embodiments, a chirally controlled oligonucleotide composition comprises more than one oligonucleotide type. In some embodiments, a chirally controlled oligonucleotide composition comprises multiple oligonucleotide types. In some embodiments, a chirally controlled oligonucleotide composition is a composition of oligonucleotides of an oligonucleotide type, which composition comprises a non-random or controlled level of a plurality of oligonucleotides of the oligonucleotide type.

Chirally pure: as used herein, the phrase "chirally pure" is used to describe an oligonucleotide or compositions thereof, in which all are nearly all (the rest are impurities) of the oligonucleotide molecules exist in a single diastereomeric form with respect to the linkage phosphorus atoms.

Predetermined: By predetermined (or pre-determined) is meant deliberately selected or non-random or controlled, for example as opposed to randomly occurring, random, or achieved without control. Those of ordinary skill in the art, reading the present specification, will appreciate that the present disclosure provides technologies that permit selection of particular chemistry and/or stereochemistry features to be incorporated into oligonucleotide compositions, and further permits controlled preparation of oligonucleotide compositions having such chemistry and/or stereochemistry features. Such provided compositions are "predetermined" as described herein. Compositions that may contain certain oligonucleotides because they happen to have been generated through a process that are not controlled to intentionally generate the particular chemistry and/or stereochemistry features are not "predetermined" compositions. In some embodiments, a predetermined composition is one that can be intentionally reproduced (e.g., through repetition of a controlled process). In some embodiments, a predetermined level of a plurality of oligonucleotides in a composition means that the absolute amount, and/or the relative amount (ratio, percentage, etc.) of the plurality of oligonucleotides in the composition is controlled. In some embodiments, a predetermined level of a plurality of oligonucleotides in a composition is achieved through chirally controlled oligonucleotide preparation.

Linkage phosphorus: as defined herein, the phrase "linkage phosphorus" is used to indicate that the particular phosphorus atom being referred to is the phosphorus atom present in the internucleotidic linkage, which phosphorus atom corresponds to the phosphorus atom of a phosphodiester internucleotidic linkage as occurs in naturally occurring DNA and RNA. In some embodiments, a linkage phosphorus atom is in a modified internucleotidic linkage, wherein each oxygen atom of a phosphodiester linkage is optionally and independently replaced by an organic or inorganic moiety. In some embodiments, a linkage phosphorus atom is chiral. In some embodiments, a linkage phosphorus atom is achiral.

P-modification: as used herein, the term "P-modification" refers to any modification at the linkage phosphorus other than a stereochemical modification. In some embodiments, a P-modification comprises addition, substitution, or removal of a pendant moiety covalently attached to a linkage phosphorus. In some embodiments, the "P-modification" is —X-L-$R^1$ wherein each of X, L and $R^1$ is independently as defined and described in the present disclosure.

Blockmer: the term "blockmer," as used herein, refers to an oligonucleotide strand whose pattern of structural features characterizing each individual nucleotide unit is characterized by the presence of at least two consecutive nucleotide units sharing a common structural feature at the internucleotidic phosphorus linkage. By common structural feature is meant common stereochemistry at the linkage phosphorus or a common modification at the linkage phosphorus. In some embodiments, the at least two consecutive nucleotide units sharing a common structure feature at the internucleotidic phosphorus linkage are referred to as a "block". In some embodiments, a provided oligonucleotide is a blockmer.

In some embodiments, a blockmer is a "stereoblockmer," e.g., at least two consecutive nucleotide units have the same stereochemistry at the linkage phosphorus. Such at least two consecutive nucleotide units form a "stereoblock."

In some embodiments, a blockmer is a "P-modification blockmer," e.g., at least two consecutive nucleotide units have the same modification at the linkage phosphorus. Such at least two consecutive nucleotide units form a "P-modification block". For instance, (Rp, Sp)-ATsCsGA is a P-modification blockmer because at least two consecutive nucleotide units, the Ts and the Cs, have the same P-modification (i.e., both are a phosphorothioate diester). In the same oligonucleotide of (Rp, Sp)-ATsCsGA, TsCs forms a block, and it is a P-modification block.

In some embodiments, a blockmer is a "linkage blockmer," e.g., at least two consecutive nucleotide units have identical stereochemistry and identical modifications at the linkage phosphorus. At least two consecutive nucleotide units form a "linkage block". For instance, (Rp, Rp)-ATsCsGA is a linkage blockmer because at least two consecutive nucleotide units, the Ts and the Cs, have the same stereochemistry (both Rp) and P-modification (both phosphorothioate). In the same oligonucleotide of (Rp, Rp)-ATsCsGA, TsCs forms a block, and it is a linkage block.

In some embodiments, a blockmer comprises one or more blocks independently selected from a stereoblock, a P-modification block and a linkage block. In some embodiments, a blockmer is a stereoblockmer with respect to one block, and/or a P-modification blockmer with respect to another block, and/or a linkage blockmer with respect to yet another block.

Methods and structures described herein relating to compounds and compositions of the disclosure also apply to pharmaceutically acceptable acid or base addition salt forms unless indicated otherwise.

Description of Certain Embodiments

Oligonucleotides provide useful molecular tools in a wide variety of applications. For example, oligonucleotides (e.g., oligonucleotides which target C9orf72) are useful in therapeutic, diagnostic, and research applications, including the treatment of a variety of conditions, disorders, and diseases. The use of naturally occurring nucleic acids (e.g., unmodified DNA or RNA) is limited, for example, by their susceptibility to endo- and exo-nucleases. As such, various synthetic counterparts have been developed to circumvent these shortcomings. These include synthetic oligonucleotides that contain chemical modifications, e.g., base modifications, sugar modifications, backbone modifications, etc., which, among other things, render these molecules less susceptible to degradation and improve other properties and/or activities of oligonucleotides. From a structural point of view, modifications to internucleotidic linkages can introduce chirality, and certain properties of oligonucleotides may be affected by configurations of phosphorus atoms that form the backbone of oligonucleotides. In many embodiments, the present disclosure provides technologies (e.g., oligonucleotides, compositions, methods, etc.) comprising chirally controlled chiral internucleotidic linkages. Among other things, provided technologies can provide high activities (e.g., reduction of levels and/or activities of target nucleic acids (e.g., various transcripts) and/or products encoded thereby (e.g., various proteins)), selectivities (e.g., selective reduction of levels and/or activities of certain target nucleic acids (e.g., various transcripts) and/or products encoded thereby (e.g., various proteins) over one or more others), and/or low toxicity (e.g., low levels of undesired side effects such as low levels of undesired immune activities).

Oligonucleotides

Among other things, the present disclosure provides oligonucleotides of various designs, which may comprises various nucleobases and patterns thereof, sugars and patterns thereof, internucleotidic linkages and patterns thereof, and/or additional chemical moieties and patterns thereof as described in the present disclosure. In some embodiments, provided C9orf72 oligonucleotides can direct a decrease in the expression, level and/or activity of a C9orf72 gene and/or one or more of its products (e.g., transcripts, mRNA, proteins, etc.). In some embodiments, provided C9orf72 oligonucleotides can reduce expression, level and/or activity of C9orf72 nucleic acids (e.g., genes, transcripts, mRNA, etc., which can be or be transcribed from either strand of a C9orf72 gene) associated with various conditions, disorders or diseases and/or products (e.g., various proteins and/or peptides, etc.) encoded thereby. In some embodiments, provided C9orf72 oligonucleotides can direct a decrease in the expression, level and/or activity of a C9orf72 gene and/or one or more of its products in a cell of a subject or patient. In some embodiments, a cell normally expresses C9orf72 or produces C9orf72 protein. In some embodiments, provided C9orf72 oligonucleotides can direct a decrease in the expression, level and/or activity of a C9orf72 target gene or a gene product and has a base sequence which consists of, comprises, or comprises a portion (e.g., a span of 10, 11, 12, 13, 14, 15, 16, 17, 18, 19, 20 or more contiguous bases) of the base sequence of a C9orf72 oligonucleotide disclosed herein, wherein each T can be independently substituted with U and vice versa, and the oligonucleotide comprises at least one non-naturally-occurring modification of a base, sugar and/or internucleotidic linkage. In some embodiments, expression, level and/or activity of C9orf72 nucleic acids (e.g., genes, transcripts, mRNA, etc., which can be or be transcribed from either strand of a C9orf72 gene) associated with various conditions, disorders or diseases and/or products (e.g., various proteins and/or peptides, etc.) encoded thereby are selectively reduced over expression, level and/or activity of C9orf72 nucleic acids that are less or not associated with conditions, disorders or diseases and/or products encoded thereby. In some embodiments, v1 and/or v3 transcripts comprising expanded repeats (e.g., as shown in FIG. 1, antisense or sense) and/or products thereof are associated with various conditions, disorders or diseases. In some embodiments, v2 transcripts are not or are less associated with conditions, disorders or diseases compared to v1 and v3 transcripts comprising expanded repeats. As appreciated by those skilled in the art, two events or entities are "associated" with one another, as that term is used herein, if the presence, level and/or form of one is correlated with that of the other. For example, an entity (e.g., polypeptide, genetic signature, metabolite, microbe, transcripts, etc) is considered to be associated with a particular disease, disorder, or condition, if its presence, level and/or form correlates with incidence of and/or susceptibility to the disease, disorder, or condition (e.g., across a relevant population).

In some embodiments, C9orf72 oligonucleotides can direct a decrease in the expression, level and/or activity of a target gene, e.g., a C9orf72 target gene, or a product thereof. In some embodiments, C9orf72 oligonucleotides can direct a decrease in the expression, level and/or activity of a C9orf72 target gene or a product thereof via RNase H-mediated knockdown. In some embodiments, C9orf72 oligonucleotides can direct a decrease in the expression, level and/or activity of a C9orf72 target gene or a product thereof by sterically blocking translation after binding to a C9orf72 target gene mRNA, and/or by altering or interfering with mRNA splicing. Regardless, however, the present disclosure is not limited to any particular mechanism. In some embodiments, the present disclosure provides oligonucleotides, compositions, methods, etc., capable of operating via double-stranded RNA interference, single-stranded RNA interference, RNase H-mediated knock-down, steric hindrance of translation, or a combination of two or more such mechanisms.

In some embodiments, a C9orf72 oligonucleotide is capable of mediating a decrease in the expression, level and/or activity of C9orf72. In some embodiments, a C9orf72 oligonucleotide is capable of mediating a decrease in the expression, level and/or activity of C9orf72 via a mechanism involving mRNA degradation and/or steric hindrance of translation of C9orf72 mRNA.

In some embodiments, a C9orf72 oligonucleotide is capable of mediating a decrease in the expression, level and/or activity of more than one C9orf72 allele. In some embodiments, a C9orf72 oligonucleotide is capable of selectively mediating a decrease in the expression, level and/or activity of a C9orf72 allele associated with a condition, disorder or disease over the expression, level and/or activity of a C9orf72 allele less or not associated with a condition, disorder or disease. In some embodiments, a C9orf72 oligonucleotide is capable of selectively mediating a decrease in the expression, level and/or activity of C9orf72 transcripts associated with a condition, disorder or disease and/or a product encoded thereby over the expression, level and/or activity of C9orf72 transcripts less or not associated with a condition, disorder or disease and/or a product encoded thereby.

In some embodiments, the present disclosure pertains to a method of treatment of a C9orf72-associated disease, disorder or condition, comprising the step of administering a therapeutically effective amount of a C9orf72 oligonucleotide capable of mediating a decrease in the expression, level and/or activity of C9orf72. In some embodiments, multiple forms, e.g., alleles, of C9orf72 may exist, and provided technologies can reduce expression, level and/or activity of two or more or all of the forms and products thereof. In some embodiments, provided technologies selectively reduce expression, level and/or activity of C9orf72 transcripts and/or products encoded thereby associated with conditions, disorders or diseases over those less or not associated with conditions, disorders or diseases.

In some embodiments, the present disclosure pertains to a method of treatment of a C9orf72-associated disease, disorder or condition, comprising administering to a subject suffering therefrom a therapeutically effective amount of a provided oligonucleotide or a composition thereof.

In some embodiments, a C9orf72 oligonucleotide comprises a structural element or a portion thereof described herein, e.g., in a Table. In some embodiments, a C9orf72 oligonucleotide comprises a base sequence (or a portion thereof) described herein, wherein each T can be independently substituted with U and vice versa, a chemical modification or a pattern of chemical modifications (or a portion thereof), and/or a format or a portion thereof described herein. In some embodiments, a C9orf72 oligonucleotide has a base sequence which comprises the base sequence (or a portion thereof) wherein each T can be independently substituted with U, pattern of chemical modifications (or a portion thereof), and/or a format of an oligonucleotide disclosed herein, e.g., in a Table, or otherwise disclosed herein. In some embodiments, such oligonucleotides, e.g., C9orf72 oligonucleotides reduce expression, level and/or activity of a gene, e.g., a C9orf72 gene, or a gene product thereof.

Among other things, C9orf72 oligonucleotides may hybridize to their target nucleic acids (e.g., pre-mRNA, mature mRNA, etc.). For example, in some embodiments, a C9orf72 oligonucleotide can hybridize to a C9orf72 nucleic acid derived from a DNA strand (either strand of the C9orf72 gene). In some embodiments, a C9orf72 oligonucleotide can hybridize to a C9orf72 transcript. In some embodiments, a C9orf72 oligonucleotide can hybridize to a C9orf72 nucleic acid in any stage of RNA processing, including but not limited to a pre-mRNA or a mature mRNA. In some embodiments, a C9orf72 oligonucleotide can hybridize to any element of a C9orf72 nucleic acid or its complement, including but not limited to: a promoter region, an enhancer region, a transcriptional stop region, a translational start signal, a translation stop signal, a coding region, a non-coding region, an exon, an intron, an intron/exon or exon/intron junction, the 5' UTR, or the 3' UTR. In some embodiments, C9orf72 oligonucleotides can hybridize to their targets with no more than 2 mismatches. In some embodiments, C9orf72 oligonucleotides can hybridize to their targets with no more than one mismatch. In some embodiments, C9orf72 oligonucleotides can hybridize to their targets with no mismatches (e.g., when all C-G and/or A-T/U base paring).

In some embodiments, an oligonucleotide can hybridize to two or more variants of transcripts. In some embodiments, a C9orf72 oligonucleotide can hybridize to two or more or all variants of C9orf72 transcripts. In some embodiments, a C9orf72 oligonucleotide can hybridize to two or more or all variants of C9orf72 transcripts derived from the sense strand. In some embodiments, an oligonucleotide selectively hybridize to transcripts associated with conditions, disorders or diseases (e.g., those comprising expanded repeats).

In some embodiments, a C9orf72 target of a C9orf72 oligonucleotide is a C9orf72 RNA which is not a mRNA.

In some embodiments, oligonucleotides, e.g., C9orf72 oligonucleotides, contain increased levels of one or more isotopes. In some embodiments, oligonucleotides, e.g., C9orf72 oligonucleotides, are labeled, e.g., by one or more isotopes of one or more elements, e.g., hydrogen, carbon, nitrogen, etc. In some embodiments, oligonucleotides, e.g., C9orf72 oligonucleotides, in provided compositions, e.g., oligonucleotides of a plurality of a composition, comprise base modifications, sugar modifications, and/or internucleotidic linkage modifications, wherein the oligonucleotides contain an enriched level of deuterium. In some embodiments, oligonucleotides, e.g., C9orf72 oligonucleotides, are labeled with deuterium (replacing —$^1$H with —$^2$H) at one or more positions. In some embodiments, one or more $^1$H of an oligonucleotide chain or any moiety conjugated to the oligonucleotide chain (e.g., a targeting moiety, etc.) is substituted with $^2$H. Such oligonucleotides can be used in compositions and methods described herein.

In some embodiments, the present disclosure provides an oligonucleotide composition comprising a plurality of oligonucleotides which:

1) have a common base sequence complementary to a target sequence (e.g., a C9orf72 target sequence) in a transcript; and
2) comprise one or more modified sugar moieties and/or modified internucleotidic linkages.

In some embodiments, C9orf72 oligonucleotides having a common base sequence may have the same pattern of nucleoside modifications, e.g., sugar modifications, base modifications, etc. In some embodiments, a pattern of nucleoside modifications may be represented by a combination of locations and modifications. In some embodiments, a pattern of backbone linkages comprises locations and types (e.g., phosphate, phosphorothioate, substituted phosphorothioate, etc.) of each internucleotidic linkage.

In some embodiments, provided compositions comprise a plurality of oligonucleotides. In some embodiments, oligonucleotides of a plurality are of the same oligonucleotide type. In some embodiments, oligonucleotides of a plurality share a common base sequence. In some embodiments, oligonucleotides of a plurality share a common pattern of sugar modifications. In some embodiments, oligonucleotides of a plurality share a common pattern of base modifications. In some embodiments, oligonucleotides of a plurality share a common pattern of nucleoside modifications. In some embodiments, oligonucleotides of a plurality are of the same constitution. In some embodiments, oligonucleotides of a plurality are identical.

In some embodiments, as exemplified herein, C9orf72 oligonucleotides are chiral controlled, comprising one or more chirally controlled internucleotidic linkages. In some embodiments, C9orf72 oligonucleotides are stereochemically pure. In some embodiments, C9orf72 oligonucleotides are substantially separated from other stereoisomers.

In some embodiments, C9orf72 oligonucleotides comprise one or more modified nucleobases, one or more modified sugars, and/or one or more modified internucleotidic linkages.

In some embodiments, C9orf72 oligonucleotides comprise one or more modified sugars. In some embodiments, oligonucleotides of the present disclosure comprise one or more modified nucleobases. Various modifications can be introduced to a sugar and/or nucleobase in accordance with the present disclosure. For example, in some embodiments, a modification is a modification described in U.S. Pat. No. 9,006,198. In some embodiments, a modification is a modification described in U.S. Pat. Nos. 9,394,333, 9,744,183, 9,605,019, 9,598,458, 9,982,257, U.S. Ser. No. 10/160,969, U.S. Ser. No. 10/479,995, US 2020/0056173, US 2018/0216107, US 2019/0127733, U.S. Ser. No. 10/450,568, US 2019/0077817, US 2019/0249173, US 2019/0375774, WO 2018/223056, WO 2018/223073, WO 2018/223081, WO 2018/237194, WO 2019/032607, WO 2019/055951, WO 2019/075357, WO 2019/200185, WO 2019/217784, WO 2019/032612, and/or WO 2020/191252, the sugar, base, and internucleotidic linkage modifications of each of which are independently incorporated herein by reference.

As used in the present disclosure, in some embodiments, "one or more" is 1-200, 1-150, 1-100, 1-90, 1-80, 1-70, 1-60, 1-50, 1-40, 1-30, or 1,2, 3, 4, 5, 6, 7, 8, 9, 10, 11, 12, 13, 14, 15, 16, 17, 18, 19, 20, 21, 22, 23, 24, or 25. In some embodiments, "one or more" is one. In some embodiments, "one or more" is two. In some embodiments, "one or more" is three. In some embodiments, "one or more" is four. In some embodiments, "one or more" is five. In some embodiments, "one or more" is six. In some embodiments, "one or more" is seven. In some embodiments, "one or more" is eight. In some embodiments, "one or more" is nine. In some embodiments, "one or more" is ten. In some embodiments, "one or more" is at least one. In some embodiments, "one or more" is at least two. In some embodiments, "one or more" is at least three. In some embodiments, "one or more" is at least four. In some embodiments, "one or more" is at least five. In some embodiments, "one or more" is at least six. In some embodiments, "one or more" is at least seven. In some embodiments, "one or more" is at least eight. In some embodiments, "one or more" is at least nine. In some embodiments, "one or more" is at least ten.

As used in the present disclosure, in some embodiments, "at least one" is 1-200, 1-150, 1-100, 1-90, 1-80, 1-70, 1-60, 1-50, 1-40, 1-30, or 1,2, 3, 4, 5, 6, 7, 8, 9, 10, 11, 12, 13, 14, 15, 16, 17, 18, 19, 20, 21, 22, 23, 24, or 25. In some embodiments, "at least one" is one. In some embodiments, "at least one" is two. In some embodiments, "at least one" is three. In some embodiments, "at least one" is four. In some embodiments, "at least one" is five. In some embodiments, "at least one" is six. In some embodiments, "at least one" is seven. In some embodiments, "at least one" is eight. In some embodiments, "at least one" is nine. In some embodiments, "at least one" is ten.

In some embodiments, a C9orf72 oligonucleotide is or comprises a C9orf72 oligonucleotide described in a Table.

As demonstrated in the present disclosure, in some embodiments, a provided oligonucleotide (e.g., a C9orf72 oligonucleotide) is characterized in that, when it is contacted with the transcript in a knockdown system, knockdown of its target (e.g., a C9orf72 transcript for a C9orf72 oligonucleotide.

In some embodiments, oligonucleotides are provided as salt forms. In some embodiments, oligonucleotides are provided as salts comprising negatively-charged internucleotidic linkages (e.g., phosphorothioate internucleotidic linkages, natural phosphate linkages, etc.) existing as their salt forms. In some embodiments, oligonucleotides are provided as pharmaceutically acceptable salts. In some embodiments, oligonucleotides are provided as metal salts. In some embodiments, oligonucleotides are provided as sodium salts. In some embodiments, oligonucleotides are provided as metal salts, e.g., sodium salts, wherein each negatively-charged internucleotidic linkage is independently in a salt form (e.g., for sodium salts, —O—P(O)(SNa)—O— for a phosphorothioate internucleotidic linkage, —O—P(O)(ONa)—O— for a natural phosphate linkage, etc.).

In some embodiments, the present disclosure provides oligonucleotides that comprise one or two wings and a core, and comprise or are of a wing-core-wing, a core-wing, or a wing-core structure, wherein each wing and core independently comprises one or more nucleobases. In some embodiments, provided oligonucleotides comprise or are of a wing-core-wing structure. In some embodiments, provided oligonucleotides comprise or are of a core-wing structure. In some embodiments, provided oligonucleotides comprise or are of a wing-core structure. In some embodiments, a core of is a region of consecutive nucleotidic unit as described in the present disclosure. In some embodiments, each wing independently comprises one or more nucleobases as described in the present disclosure.

In some embodiments, a wing-core-wing motif is described as "X-Y-Z", where "X" represents the length (unless indicated otherwise, in number of nucleobases) of the 5' wing, "Y" represents the length of the core, and "Z" represents the length of the 3' wing. In some embodiments, X is 1-10, e.g., 1, 2, 3, 4, 5, 6, 7, 8, 9, 10, and Z is 1-10, e.g., 1, 2, 3, 4, 5, 6, 7, 8, 9, 10. In some embodiments, Y is 1-50, e.g., 5-50, 1, 2, 3, 4, 5, 6, 7, 8, 9, 10, 11, 12, 13, 14, 15, 16, 17, 18, 19, or 20. In some embodiments, X and Z are the same or different lengths and/or have the same or different modifications or patterns of modifications. In a preferred embodiment, Y is between 8 and 15 nucleotides. X, Y or Z can be any of 1, 2, 3, 4, 5, 6, 7, 8, 9, 10, 11, 12, 13, 14, 15, 16, 17, 18, 19, 20, 25, 30 or more nucleotides. In some embodiments, an oligonucleotide described herein has or comprises a wing-core-wing structure of, for example 5-10-5, 5-10-4, 4-10-4, 4-10-3, 3-10-3, 2-10-2, 5-9-5, 5-9-4, 4-9-5, 5-8-5, 5-8-4, 4-8-5, 5-7-5, 4-7-5, 5-7-4, or 4-7-4. In some embodiments, an oligonucleotide described herein has or comprises a wing-core or core-wing structure of, for example 5-10, 8-4, 4-12, 12-4, 3-14, 16-2, 18-1, 10-3, 2-10, 1-10, 8-2, 2-13, 5-13, 5-8, or 6-8.

In some embodiments, a wing comprises one or more sugar modifications. In some embodiments, the two wings of a wing-core-wing structure comprise the same sugar modifications. In some embodiments, the two wings of a wing-core-wing structure comprise different sugar modifications. In some embodiments, the two wings of a wing-core-wing structure comprise different patterns of sugar modifications. In some embodiments, the two wings of a wing-core-wing structure comprise different patterns of sugar modifications of the same sugar modifications. In some embodiments, the two wings of a wing-core-wing structure comprise the same patterns of sugar modifications. In some embodiments, a wing comprises two or more different sugar modifications.

In some embodiments, a sugar modification is a 2'-modification, e.g., 2'-OR wherein R is as described herein but is not —H, a bicyclic sugar modification involving 2'-carbon (e.g., in LNA sugars), etc. In some embodiments, each sugar modification in a wing is independently a 2'-modification. In some embodiments, each sugar modification in both wings of a wing-core-wing is independently a 2'-modification. In some embodiments, a wing or each wing independently comprises two or more different sugar modifications, wherein each sugar modification is independently a 2'-modification. In some embodiments, each 2'-modification is independently a 2'-OR modification, wherein R is as described herein but is not —H. In some embodiments, each 2'-modification is independently a 2'-OR modification, wherein R is optionally substituted $C_{1-6}$ alkyl. In some embodiments, each sugar modification is independently 2'-OMe or 2'-MOE.

In some embodiments, sugar modifications provide improved stability and/or hybridization compared to absence of sugar modifications. In some embodiments, certain sugar modifications, e.g., 2'-MOE, provides more stability under otherwise identical conditions than 2'-OMe.

In some embodiments, a wing comprises one or more natural phosphate linkages. In some embodiments, a wing comprises one or more consecutive natural phosphate linkages. In some embodiments, a wing comprises one or more natural phosphate linkages and one or more modified internucleotidic linkages. In some embodiments, a wing comprises no natural phosphate linkages, and each internucleotidic linkage of the wing is independently a modified internucleotidic linkage. In some embodiments, a modified internucleotidic linkage is a phosphorothioate internucleotidic linkage. In some embodiments, a modified internucleotidic linkage is a Sp phosphorothioate internucleotidic linkage. In some embodiments, a wing comprises one or more non-negatively charged internucleotidic linkages. In some embodiments, a wing comprises one or more neutral internucleotidic linkages. In some embodiments, each wing independently comprises one or more non-negatively charged internucleotidic linkages. In some embodiments, each wing independently comprises one or more neutral internucleotidic linkages. In some embodiments, a non-negatively charged internucleotidic linkage or neutral internucleotidic linkage is independently chirally controlled. In some embodiments, each non-negatively charged internucleotidic linkage or neutral internucleotidic linkage is independently chirally controlled. In some embodiments, a wing comprises 1-5, e.g., 1, 2, 3, 4, or 5 non-negatively charged internucleotidic linkages. In some embodiments, a wing comprise 1 non-negatively charged internucleotidic linkage. In some embodiments, a wing comprises 2 non-negatively charged internucleotidic linkage. In some embodiments, a wing comprises 3 non-negatively charged internucleotidic linkage. In some embodiments, a wing comprises 4 non-negatively charged internucleotidic linkage. In some embodiments, a wing comprises 5 non-negatively charged internucleotidic linkage. In some embodiments, each non-negatively charged internucleotidic linkage is independently a neutral internucleotidic linkage. In some embodiments, a non-negatively charged internucleotidic linkage or a neutral internucleotidic linkage is n001. In some embodiments, each is 001 and is optionally and independently chirally controlled. In some embodiments, each non-negatively charged internucleotidic linkage, e.g., n001, is independently chirally controlled. In some embodiments, n001 is chirally controlled and Rp. In some embodiments, n001 is chirally controlled and Sp. In some embodiments, a wing comprise one or more chirally controlled phosphorothioate internucleotidic linkages and one or more chirally controlled neutral internucleotidic linkages. In some embodiments, a wing comprise one or more chirally controlled phosphorothioate internucleotidic linkages and one or more natural phosphate linkages. In some embodiments, a wing comprises one or more chirally controlled neutral internucleotidic linkages and one or more natural phosphate linkages. In some embodiments, a wing comprise one or more chirally controlled phosphorothioate internucleotidic linkages and one or more chirally controlled neutral internucleotidic linkages and one or more natural phosphate linkages (e.g., certain 5'-wing in certain oligonucleotides in the Tables). In some embodiments, each internucleotidic linkage in a wing is independently selected from a natural phosphate linkage and a phosphorothioate internucleotidic linkage. In some embodiments, each internucleotidic linkage in a wing is independently selected from a natural phosphate linkage, a phosphorothioate internucleotidic linkage and a non-negatively charged internucleotidic linkage (e.g., neutral internucleotidic linkage such as n001). In some embodiments, each internucleotidic linkage in a wing is independently selected from a phosphorothioate internucleotidic linkage and a non-negatively charged internucleotidic linkage (e.g., neutral internucleotidic linkage such as n001). In some embodiments, one or more or each phosphorothioate internucleotidic linkage is independently chirally controlled. In some embodiments, one or more or each phosphorothioate internucleotidic linkage is independently chirally controlled and is Sp. In some embodiments, one or more or each non-negatively charged internucleotidic linkage (e.g., neutral internucleotidic linkage such as n001) is independently chirally controlled. In some embodiments, one or more or each non-negatively charged internucleotidic linkage (e.g., neutral internucleotidic linkage such as n001) is independently chirally controlled and is Rp. In some embodiments, a pattern (e.g., including types of internucleotidic linkages and linkage phosphorus stereochemistry) of a wing (e.g., a 5'-wing) is or comprises SOOO, wherein S represents a phosphorothioate internucleotidic linkage which is chirally controlled and is Sp, and O represents a natural phosphate linkage. In some embodiments, a pattern of a wing (e.g., a 3'-wing) is or comprises SSSS. In some embodiments, a pattern of a wing (e.g., a 5'-wing) is or comprises SnROnR, wherein nR represents a non-negatively charged internucleotidic linkage (e.g., a neutral internucleotidic linkage such as n001) which is chirally controlled and is Rp. In some embodiments, a pattern of a wing (e.g., a 3'-wing) is or comprises SnRSS. In some embodiments, a pattern of a wing (e.g., a 3'-wing) is or comprises SSnRS. In some embodiments, a pattern of a wing (e.g., a 3'-wing) is or comprises SSSnR. In some embodiments, a non-negatively charged internucleotidic linkage or neutral internucleotidic linkage is between two modified sugars. In some embodiments, a core may also have one or more non-negatively charged internucleotidic linkages or neutral internucleotidic linkages each of which is optionally and independently chirally controlled; in some embodiments, each is independently chirally controlled. In some embodiments, core sugars (which, in some embodiments, do not contain 2'-O—) are not bonded to neutral internucleotidic linkages.

In some embodiments, for an oligonucleotide comprising or is a wing-core-wing structure, the two wings are different in that they contain different levels and/or types of chemical modifications, backbone chiral center stereochemistry, and/or patterns thereof. In some embodiments, the two wings are different in that they contain different levels and/or types of sugar modifications, and/or internucleotidic linkages, and/or internucleotidic linkage stereochemistry, and/or patterns thereof. For example, in some embodiments, one wing comprises 2'-OR modifications wherein R is optionally substituted $C_{1-6}$ alkyl (e.g., 2-MOE), while the other wing comprises no such modifications, or lower level (e.g., by number and/or percentage) of such modifications; additionally and alternatively, one wing comprises natural phosphate linkages while the other wing comprises no natural phosphate linkages or lower level (e.g., by number and/or percentage) of natural phosphate linkages; additionally and alternatively, one wing may comprise a certain type of modified internucleotidic linkages (e.g., phosphorothioate diester internucleotidic linkage) while the other wing comprises no natural phosphate linkages or lower level (e.g., by number and/or percentage) of the type of modified internucleotidic linkages; additionally and alternatively, one wing may comprise chiral modified internucleotidic linkages comprising linkage phosphorus atoms of a particular configuration (e.g., Rp or Sp), while the other wing comprises no or lower level of chiral modified internucleotidic linkages comprising linkage phosphorus atoms of the particular configuration; alternatively or additionally, each wing may comprise a different pattern of sugar modification, internucleotidic linkages, and/or backbone chiral centers. In some embodiments, one wing comprises one or more natural phosphate linkages and one or more 2'-OR modifications wherein R is not —H or -Me, and the other wing comprises no natural phosphate linkages and no 2'-OR modifications wherein R is not —H or -Me. In some embodiments, one wing comprises one or more natural phosphate linkages and one or more 2'-MOE modifications, and each internucleotidic linkage in the other wing is a phosphorothioate linkage and each sugar unit of the other wing comprises a 2'-OMe modification. In some embodiments, one wing comprises one or more natural phosphate linkages and one or more 2'-MOE modifications, and each internucleotidic linkage in the other wing is a Sp phosphorothioate linkage and each sugar unit of the other wing comprises a 2'-OMe modification.

In some embodiments, a core comprises no sugars comprising 2'-modifications. In some embodiments, a core comprises no sugars comprising 2'-OR, wherein R is as described herein. In some embodiments, each core sugar comprises two 2'-H (e.g., as typically found in natural DNA sugars).

In some embodiments, no less than 70%, 80%, 90% or 100% of internucleotidic linkages in a core is a modified internucleotidic linkage. In some embodiments, no less than 70%, 80%, or 90% of internucleotidic linkages in a core is independently a modified internucleotidic linkage of Sp configuration, and the core also contains 1, 2, 3, 4, or 5 internucleotidic linkages selected from modified internucleotidic linkages of Rp configuration and natural phosphate linkages. In some embodiments, no less than 70%, 80%, or 90% of phosphorothioate internucleotidic linkages in a core is independently a modified internucleotidic linkage of Sp configuration, and the core also contains 1, 2, 3, 4, or 5 phosphorothioate internucleotidic linkages of Rp configuration. In some embodiments, the core also contains 1 or 2 internucleotidic linkages selected from modified internucleotidic linkages of Rp configuration and natural phosphate linkages. In some embodiments, the core also contains 1 and no more than 1 internucleotidic linkage selected from a modified internucleotidic linkage of Rp configuration and a natural phosphate linkage, and the rest internucleotidic linkages are independently modified internucleotidic linkages of Sp configuration. In some embodiments, the core also contains 2 and no more than 2 internucleotidic linkage each independently selected from a modified internucleotidic linkage of Rp configuration and a natural phosphate linkage, and the rest internucleotidic linkages are independently modified internucleotidic linkages of Sp configuration. In some embodiments, the core also contains 1 and no more than 1 natural phosphate linkage, and the rest internucleotidic linkages are independently modified internucleotidic linkages of Sp configuration. In some embodiments, the core also contains 2 and no more than 2 natural phosphate linkages, and the rest internucleotidic linkages are independently modified internucleotidic linkages of Sp configuration. In some embodiments, the core also contains 1 and no more than 1 modified internucleotidic linkage of Rp configuration, and the rest internucleotidic linkages are independently modified internucleotidic linkages of Sp configuration. In some embodiments, the core also contains 2 and no more than 2 modified internucleotidic linkages of Rp configuration, and the rest internucleotidic linkages are independently modified internucleotidic linkages of Sp configuration. In some embodiments, the two natural phosphate linkages, or the two modified internucleotidic linkages of Rp configuration, are separated by two or more modified internucleotidic linkages of Sp configuration. In some embodiments, a modified internucleotidic linkage is of formula I. In some embodiments, a modified internucleotidic linkage is a phosphorothioate internucleotidic linkage. As appreciated by those skilled in the art, an internucleotidic linkage bonded to a wing sugar and a core sugar may be considered as a core internucleotidic linkage.

Core and wings can be of various lengths. In some embodiments, a core comprises no less than 5, 6, 7, 8, 9, 10, 11, 12, 13, 14, 15, 16, 17, 18, 19, or 20 nucleobases. In some embodiments, a wing comprises no less than 1, 2, 3, 4, 5, 6, 7, 8, 9, or 10 nucleobases. In some embodiments, a wing comprises no more than 2, 3, 4, 5, 6, 7, 8, 9, or 10 nucleobases. In some embodiments, for a wing-core-wing structure, both wings are of the same length, for example, of 5 nucleobases. In some embodiments, the two wings are of different lengths. In some embodiments, a core is no less than 40%, 45%, 50%, 60%, 70%, 80%, or 90% of total oligonucleotide length as measured by percentage of nucleoside units within the core. In some embodiments, a core is no less than 50% of total oligonucleotide length.

In some embodiments, oligonucleotides may be provided in various forms including various salt forms, particularly pharmaceutically acceptable salt forms. In some embodiments, the present disclosure provides salts of oligonucleotides, and pharmaceutical compositions thereof. In some embodiments, a salt is a pharmaceutically acceptable salt. In some embodiments, each hydrogen ion that may be donated to a base (e.g., under conditions of an aqueous solution, a pharmaceutical composition, etc.) is replaced by a non-$H^+$ cation. For example, in some embodiments, a pharmaceutically acceptable salt of an oligonucleotide is an all-metal ion salt, wherein each hydrogen ion (for example, of —OH, —SH, etc.) of each internucleotidic linkage (e.g., a natural phosphate linkage, a phosphorothioate diester linkage, etc.) is replaced by a metal ion. In some embodiments, a provided salt is an all-sodium salt. In some embodiments, a provided pharmaceutically acceptable salt is an all-sodium salt. In some embodiments, a provided salt is an all-sodium salt, wherein each internucleotidic linkage which is a natural phosphate linkage (acid form —O—P(O)(OH)—O—), if any, exists as its sodium salt form (—O—P(O)(ONa)—O—), and each internucleotidic linkage which is a phosphorothioate diester linkage (acid form —O—P(O)(SH)—O—), if any, exists as its sodium salt form (—O—P(O)(SNa)—O—).

In some embodiments, a provided compound, e.g., an oligonucleotide, can modulate activities and/or functions of a C9orf72 target. In some embodiments, a C9orf72 target gene is a gene with respect to which expression and/or activity of one or more C9orf72 gene products (e.g., RNA and/or protein products) are intended to be altered. In some embodiments, a C9orf72 is associated with a condition, disorder or disease. In many embodiments, a C9orf72 target gene is intended to be inhibited. Thus, in many embodiments when a C9orf72 oligonucleotide as described herein acts on a particular C9orf72 target gene, presence and/or activity of one or more gene products of that C9orf72 gene are reduced, particularly those associated with a condition, disorder or disease, when the oligonucleotide is present as compared with when it is absent.

In some embodiments, a C9orf72 target is a specific allele (e.g., a pathological allele associated with a condition, disorder or disease) with respect to which expression and/or activity of one or more products (e.g., RNA and/or protein products) are intended to be altered. In many embodiments, a C9orf72 target allele is one whose presence and/or expression is associated (e.g., correlated) with presence, incidence, and/or severity, of one or more diseases and/or conditions, e.g., a C9orf72-related disorder. Alternatively or additionally, in some embodiments, a C9orf72 target allele is one for which alteration of level and/or activity of one or more gene products correlates with improvement (e.g., delay of onset, reduction of severity, responsiveness to other therapy, etc) in one or more aspects of a disease and/or condition. In some such embodiments, C9orf72 oligonucleotides and methods of use thereof as described herein may preferentially or specifically target the pathological allele relative to the non-pathological allele, e.g., one or more less-associated/unassociated allele(s). In some embodiments, a pathological allele of C9orf72 comprises a repeat expansion, e.g., a hexanucleotide repeat expansion (HRE), e.g., a hexanucleotide repeat expansion of greater than about 30 and up to 500 or 1000 or more. In some embodiments, transcripts from an allele may have two or more variants (e.g., from different splicing patterns). In some embodiments, provided technologies selectively reduce expression, activities and/or levels of transcripts (e.g., RNA) and/or products encoded thereby (e.g., proteins) associated with conditions, disorders or diseases compared to those less or not associated with conditions, disorders or diseases.

In some embodiments, a C9orf72 target sequence is a sequence to which an oligonucleotide as described herein binds. In many embodiments, a C9orf72 target sequence is identical to, or is an exact complement of, a sequence of a provided oligonucleotide, or of consecutive residues therein (e.g., a provided oligonucleotide includes a target-binding sequence that is identical to, or an exact complement of, a C9orf72 target sequence). In some embodiments, a small number of differences/mismatches (e.g., no more than 1, 2 or 3) is tolerated between (a relevant portion of) an oligonucleotide and its target sequence. In many embodiments, a C9orf72 target sequence is present within a C9orf72 target gene. In many embodiments, a C9orf72 target sequence is present within a transcript (e.g., an mRNA and/or a pre-mRNA) produced from a C9orf72 target gene. In some embodiments, a C9orf72 target sequence includes one or more allelic sites (i.e., positions within a C9orf72 target gene at which allelic variation occurs). In some such embodiments, a provided oligonucleotide binds to one allele preferentially or specifically relative to one or more other alleles.

In some embodiments, C9orf72 (chromosome 9 open reading frame 72) is a gene or its gene product, also designated as C90RF72, C9, ALSFTD, FTDALS, FTDALS1, DENNL72; External IDs: MGI: 1920455 HomoloGene: 10137 GeneCards: C9orf72. In some embodiments, C9orf72 may be informally designated C9. C9orf72 Orthologs: Species: Human Entrez: 203228; Ensembl: ENSG00000147894; UniProt: Q96LT7; RefSeq (mRNA): NM_145005 NM_001256054 NM_018325; RefSeq (protein): NP_001242983 NP_060795 NP_659442; Location (UCSC): Chr 9: 27.55-27.57 Mb; Species: Mouse Entrez: 73205; Ensembl: ENSMUSG00000028300; UniProt: Q6DFW0; RefSeq (mRNA): NM_001081343; RefSeq (protein): NP_00107481; Location (UCSC): Chr 4: 35.19-35.23 Mb. Nucleotides which encode C9orf72 include, without limitation, GENBANK Accession No. NM_001256054.1; GENBANK Accession No. NT_008413.18; GENBANK Accession No. BQ068108.1; GENBANK Accession No. NM_018325.3; GENBANK Accession No. DN993522.1; GENBANK Accession No. NM_145005.5; GENBANK Accession No. DB079375.1; GENBANK Accession No. BU194591.1; Sequence Identifier 4141_014_A 5; Sequence Identifier 4008_73_A; and GENBANK Accession No. NT_008413.18. C9orf72 reportedly is a 481 amino acid protein with a molecular mass of 54328 Da, which may undergo post-translational modifications of ubiquitination and phosphorylation. The expression levels of C9orf72 reportedly may be highest in the central nervous system and the protein localizes in the cytoplasm of neurons as well as in presynaptic terminals. C9orf72 reportedly plays a role in endosomal and lysosomal trafficking regulation and has been shown to interact with RAB proteins that are involved in autophagy and endocytic transport. C9orf72 reportedly activates RAB5, a GTPase that mediates early endosomal trafficking. Mutations in C9orf72 reportedly have been associated with ALS and FTD. DeJesus-Hernandez et al. 2011 Neuron 72: 245-256; Renton et al. 2011 Neuron 72: 257-268; and Itzcovich et al. 2016. Neurobiol. Aging. Volume 40, Pages 192.e13-192.e15. A hexanucleotide repeat expansion (e.g., (GGGGCC)n) in C9orf72 reportedly may be present in subjects suffering from a neurological disease, such as a C9orf72-related disorder.

In some embodiments, a C9orf72 oligonucleotide can hybridize to a C9orf72 nucleic acid derived from either DNA strand. In some embodiments, a C9orf72 oligonucleotide can hybridize to a C9orf72 antisense or sense transcript. In some embodiments, a C9orf72 oligonucleotide can hybridize to a C9orf72 nucleic acid in any stage of RNA processing, including but not limited to a pre-mRNA or a mature mRNA. In some embodiments, a C9orf72 oligonucleotide can hybridize to any element of a C9orf72 nucleic acid or its complement, including but not limited to: a promoter region, an enhancer region, a transcriptional stop region, a translational start signal, a translation stop signal, a coding region, a non-coding region, an exon, an intron, the 5' UTR, the 3' UTR, a repeat region, a hexanucleotide repeat expansion, a splice junction, intron/exon or exon/intron junction, an exon:exon splice junction, an exonic splicing silencer (ESS), an exonic splicing enhancer (ESE), exon 1a, exon 1b, exon 1c, exon 1d, exon 1e, exon 2, exon 3, exon 4, exon 5, exon 6, exon 7, exon 8, exon 9, exon 10, exon 11, intron 1, intron 2, intron 3, intron 4, intron 5, intron 6, intron 7, intron 8, intron 9, or intron 10 of a C9orf72 nucleic acid. The introns and exons alternate; intron 1 is between exon 1 (or 1a or 1b or 1c, etc.) and exon 2; intron 2 is between exon 2 and 3; etc. In some embodiments, the base sequence of an oligonucleotide is identical or complementary to a target sequence in intron 1. In some embodiments, the base sequence of an oligonucleotide is identical or complementary to a target sequence which comprises a portion from exon 1b and a portion from intron 1. In some embodiments, a C9orf72 oligonucleotide straddles the junction between exon 1b and intron 1.

In some embodiments, a C9orf72 oligonucleotide can hybridize to a portion of the C9orf72 pre-mRNA represented by GENBANK Accession No. NT_008413.18, nucleosides 27535000 to 27565000 or a complement thereof.

In some embodiments, a C9orf72 oligonucleotide can hybridize to an intron. In some embodiments, a C9orf72 oligonucleotide can hybridize to an intron comprising a hexanucleotide repeat.

In some embodiments, a C9orf72 oligonucleotide hybridizes to all variants of C9orf72 derived from the sense strand. In some embodiments, the antisense oligonucleotides described herein selectively hybridize to a variant of C9orf72 derived from the sense strand, including but not limited to that comprising a hexanucleotide repeat expansion. In some embodiments, a hexanucleotide repeat expansion comprises at least 24 repeats of any hexanucleotide. In some embodiments, a hexanucleotide repeat expansion comprises at least 30 repeats of any hexanucleotide. In some embodiments, a hexanucleotide repeat expansion comprises at least 50 repeats of any of a hexanucleotide. In some embodiments, a hexanucleotide repeat expansion comprises at least 100 repeats of any of a hexanucleotide. In some embodiments, a hexanucleotide repeat expansion comprises at least 200 repeats of any hexanucleotide. In some embodiments, a hexanucleotide repeat expansion comprises at least 500 repeats of any hexanucleotide. In some embodiments, a hexanucleotide is GGGGCC, GGGGGG, GGGGGC, GGGGCG, CCCCGG, CCCCCC, GCCCCC, and/or CGCCCC. In some embodiments, a hexanucleotide GGGGCC is designated GGGGCCexp or $(GGGGCC)_n$, or is a repeat of the hexanucleotide GGGGCC.

In some embodiments, a pattern of backbone chiral centers of a provided oligonucleotide or a region thereof (e.g., a core) comprises or is (Sp)m(Rp)n, (Rp)n(Sp)m, (Np)t[(Op)n(Sp)m]y, (Sp)t[(Op)n(Sp)m]y, (Np)t[(Rp)n(Sp)m]y, or (Sp)t[(Rp)n(Sp)m]y as described herein, wherein each of m, n, t, y is independently 1-50. In some embodiments, at least one n is 1. In some embodiments, each n is independently 1. In some embodiments, y is 1. In some embodiments, y is 2. In some embodiments, a pattern of backbone chiral centers comprises or is (Rp)n(Sp)m, (Np)t(Rp)n(Sp)m, or (Sp)t(Rp)n(Sp)m, wherein m>2. In some embodiments, a pattern of backbone chiral centers comprises or is (Rp)n(Sp)m, (Np)t(Rp)n(Sp)m, or (Sp)t(Rp)n(Sp)m, wherein n is 1, t>1, and m>2. In some embodiments, at least one n is 1, at least one t is no less than 1, and at least one m is no less than 2. In some embodiments, at least one n is 1, at least one t is no less than 2, and at least one m is no less than 3. In some embodiments, each n is 1. In some embodiments, at least one t>1. In some embodiments, at least one t>2. In some embodiments, at least one t>3. In some embodiments, at least one t>4. In some embodiments, at least one m>1. In some embodiments, at least one m>2. In some embodiments, at least one m>3. In some embodiments, at least one m>4. In some embodiments, a pattern of backbone chiral centers comprises one or more achiral natural phosphate linkages. In some embodiments, the sum of m, t, and n (or m and n if no t in a pattern) is no less than 5, 6, 7, 8, 9, 10, 11, 12, 13, 14, 15, 16, 17, 18, 19 or 20. In some embodiments, the sum is 5. In some embodiments, the sum is 6. In some embodiments, the sum is 7. In some embodiments, the sum is 8. In some embodiments, the sum is 9 In some embodiments, the sum is 10. In some embodiments, the sum is 11. In some embodiments, the sum is 12. In some embodiments, the sum is 13. In some embodiments, the sum is 14. In some embodiments, the sum is 15. In some embodiments, a Sp is configuration of a phosphorothioate internucleotidic linkage. In some embodiments, each Sp is configuration of a phosphorothioate internucleotidic linkage. In some embodiments, a Rp is configuration of a phosphorothioate internucleotidic linkage. In some embodiments, each Rp is configuration of a phosphorothioate internucleotidic linkage. In some embodiments, each Sp is configuration of a phosphorothioate internucleotidic linkage for a pattern of backbone chiral centers for a core. In some embodiments, each Rp is configuration of a phosphorothioate internucleotidic linkage for a pattern of backbone chiral centers for a core.

Base Sequences

In some embodiments, provided C9orf72 oligonucleotides are capable of directing a decrease in the expression, level and/or activity of a C9orf72 gene or its gene product. In some embodiments, a C9orf72 target gene comprises a repeat expansion. In some embodiments, provided C9orf72 oligonucleotides can comprise any base sequence described herein, or portion thereof, wherein a portion is a span of at least 15 contiguous bases, or a span of at least 15 contiguous bases with 1-5 mismatches. In some embodiments, when aligned with a base sequence of its C9orf72 target (e.g., a sequence of the same length of a C9orf72 gene or transcript), a base sequence of a provided oligonucleotide is at least 80%, 85%, 90%, 91%, 92%, 93%, 94%, 95%, 96%, 97%, 98% or 99%, or fully, complementary or identical to a target sequence. In some embodiments, there are no more than 1, 2, or 3 mismatches. In some embodiments, there are no more than 2 mismatches. In some embodiments, there is no more than 1 mismatch. In some embodiments, there are no mismatches. In some embodiments, a mismatch is in a wing. In some embodiments, a mismatch is in a 5'-wing. In some embodiments, a mismatch is in a 3'-wing. In some embodiments, a mismatch is in a core. In some embodiments, all "matches" are Watson-Crick basepairs. In some embodiments, there are one or more, e.g., 1, 2, 3, wobble basepairing. In some embodiments, there are no more than 1, 2, or 3 wobble basepairs. In some embodiments, there are no more than 2 wobble basepairs. In some embodiments, there is no more than 1 wobble basepair. In some embodiments, there are no wobble basepairs. In some embodiments, a wobble basepair in a wing. In some embodiments, a wobble basepair in a 5'-wing. In some embodiments, a wobble basepair in a 3'-wing. In some embodiments, a wobble basepair is in a core.

In some embodiments, the base sequence of a C9orf72 oligonucleotide has a sufficient length and identity to a C9orf72 transcript target to mediate target-specific knockdown. In some embodiments, the C9orf72 oligonucleotide is complementary to a portion of a transcript target sequence.

In some embodiments, the base sequence of a C9orf72 oligonucleotide is complementary to that of a C9orf72 target transcript. As used herein, "target transcript sequence," "target sequence", "target gene", and the like, refer to a contiguous portion of the nucleotide sequence of an mRNA molecule formed during the transcription of a C9orf72 gene, including mRNA that is a product of RNA processing of a primary transcription product.

The terms "complementary," "fully complementary" and "substantially complementary" herein may be used with respect to the base matching between a C9orf72 oligonucleotide and a C9orf72 target sequence, as will be understood from the context of their use. In some embodiments, the base sequence of a C9orf72 oligonucleotide is complementary to that of a C9orf72 target sequence when each base of the oligonucleotide is capable of base-pairing with a sequential base on the target strand, when maximally aligned. As a non-limiting example, if a target sequence has, for example, a base sequence of 5'-GCAUAGCGAGCGAGGGAAAAC-3' (SEQ ID NO: 3), an oligonucleotide with a base sequence of 5'GUUUUCCCUCGCUCGCUAUGC-3' (SEQ ID NO: 4) is complementary or fully complementary to such a target sequence. It is noted, of course, that substitution of T for U, or vice versa, does not alter the amount of complementarity.

As used herein, a polynucleotide that is "substantially complementary" to a C9orf72 target sequence is largely or mostly complementary but not 100% complementary. In some embodiments, a sequence (e.g., a C9orf72 oligonucleotide) which is substantially complementary has 1, 2, 3, 4 or 5 mismatches from a sequence which is 100% complementary to the target sequence.

In some embodiments, the base sequence of a C9orf72 oligonucleotide may comprise a CpG motif, which may act as an immunostimulant (e.g., when unmethylated). In some embodiments, the C or the G of a CpG motif is modified to replace the C and/or the G with another base. In some embodiments, the base sequence of a C9orf72 oligonucleotide is or comprises (or comprises a span of at least 15 contiguous bases of) the sequence of any C9orf72 oligonucleotide described herein, except that the C or the G within a CpG motif, if present, is changed to another nucleobase. In some embodiments, the base sequence of a C9orf72 oligonucleotide is or comprises (or comprises a span of at least 15 contiguous bases of) the sequence of any C9orf72 oligonucleotide described herein, except that the C within a CpG motif, if present, is changed to another nucleobase. In some embodiments, the base sequence of a C9orf72 oligonucleotide is or comprises (or comprises a span of at least 15 contiguous bases of) the sequence of any C9orf72 oligonucleotide described herein, except that the G within a CpG motif, if present, is replaced another nucleobase. As used herein, a phrase or other text related to replacing a base in an oligonucleotide with a replacement base is in reference to a situation wherein: an oligonucleotide having a base sequence which is 100% complementary to that of a target sequence (such as a mRNA) via Watson-Crick basepairing (e.g., each U or T basepairs with A, and each G basepairs with C), except that one base in the oligonucleotide (which would normally form a Watson-Crick basepair with the corresponding base in the target nucleic acid) is replaced by a replacement base (e.g., a nucleobase or nucleobase derivative) which cannot form a Watson-Crick basepair with the corresponding base of the target nucleic acid, although the replacement nucleobase may optionally be able to (but does not necessarily) form a non-Watson-Crick basepair with the corresponding base in the target nucleic acid sequence [including but not limited to: a wobble basepair, such as guanine-uracil (G-U), hypoxanthine-uracil (I-U), hypoxanthine-adenine (I-A), and hypoxanthine-cytosine (I-C)]. In some embodiments, replacement of a base in an oligonucleotide with a replacement base introduces a mismatch to the target sequence at that position. In some embodiments, a C is replaced with T (e.g., in a core, or the nucleoside C comprises no 2'-OR or no substituents at 2'-carbon). In some embodiments, a C is replaced with U (e.g., in a wing, or the nucleoside comprises a substituent at 2'-carbon). In some embodiments, one or more C are independently replaced. In some embodiments, each C in an oligonucleotide or a portion thereof (e.g., a 5'-wing, a core, a 3'-wing) is independently replaced.

In some embodiments, in a C9orf72 oligonucleotide, a G is replaced by Inosine (I). In some embodiments, the term inosine or I, as used herein, is equated with the nucleobase hypoxanthine. In some embodiments, the term inosine, as used herein, is equated with a nucleoside comprising hypoxanthine and a sugar or modified sugar. In some embodiments, a C9orf72 oligonucleotide comprises a CpI motif (e.g., a CpG motif in which the nucleobase G has been replaced by I). Non-limiting examples of such a C9orf72 oligonucleotide include but are not limited to: WV-21442 and WV-21445.

In some embodiments, in a C9orf72 oligonucleotide which has a CpG motif, the C is modified (e.g., methylated to 5 mC) to, e.g., reduce the immunogenicity of the CpG motif. In some embodiments, a modified C nucleoside, e.g., 5 mC nucleoside, comprises a 2'-MOE modification. In some embodiments, in a CpG motif in a wing the C is modified (e.g., methylated to 5 mC). In some embodiments, in a CpG motif in a 5'-wing the C is modified (e.g., methylated to 5 mC). In some embodiments, in a CpG motif in a 3'-wing the C is modified (e.g., methylated to 5 mC). In some embodiments, in a CpG motif in a core the C is modified (e.g., methylated to 5 mC). In some embodiments, each C of a CpG motif is modified (e.g., methylated to 5 mC). In some embodiments, one or more C not in CpG motif are independently modified (e.g., methylated to 5 mC). Non-limiting examples of such an oligonucleotide include: WV-21445, WV-21446, WV-23740, WV-23503, and WV-23491.

In some embodiments, a terminal base (e.g., one of the extreme 5' or 3' end) is a component in a CpG motif (e.g., the C in a CpG at the 5' end of the oligonucleotide or the G in a CpG at the 3' end). In some embodiments, a terminal base may contribute less to the hybridization of an oligonucleotide to a target nucleic acid than a base which is not a terminal base (e.g., a non-terminal base). In some embodiments, the present disclosure pertains to a CpG oligonucleotide, wherein a terminal base is a component in a CpG motif, and the terminal base is replaced by another base; and in some embodiments, a terminal base of a CpG oligonucleotide is G and is replaced by I.

In some embodiments of a base sequence under consideration for design and construction of a C9orf72 oligonucleotide, a terminal base is a component in a CpG motif and the terminal base is therefore not included in the base sequence of the oligonucleotide (e.g., the oligonucleotide is truncated by one base). Non-limiting examples of such an oligonucleotide include WV-21557, WV-23486, WV-23435, and WV-23487.

In some embodiments, in a C9orf72 oligonucleotide, a terminal base is a nucleobase A, and the base is replaced by I or G. Non-limiting examples of such an oligonucleotide include: WV-21445, WV-21446, WV-23740, WV-23503, and WV-23491.

In some embodiments, an oligonucleotide targets C9orf72 and has a base sequence which is, comprises or comprises an at least 15-base portion of the base sequence of CCCACACCTGCTCTTGCTAG (SEQ ID NO: 5), AACAGCCACCCGCCAGGATG (SEQ ID NO: 6), AACCGGGCAGCAGGGACGGC (SEQ ID NO: 7), ACAGGCTGCGGTTGTTTCCC (SEQ ID NO: 8), ACCCACACCTGCTCTTGCTA (SEQ ID NO: 9), ACCCACTCGCCACCGCCTGC (SEQ ID NO: 10), ACCCCAAACAGCCACCCGCC (SEQ ID NO: 11), ACCCCCATCTCATCCCGCAT (SEQ ID NO: 12), ACCCGAGCTGTCTCCTTCCC (SEQ ID NO: 13), ACCCGCCAGGATGCCGCCTC (SEQ ID NO: 14), ACCCGCGCCTCTTCCCGGCA (SEQ ID NO: 15), ACCCTCCGGCCTTCCCCCAG (SEQ ID NO: 16), ACCGGGCAGCAGGGACGGCT (SEQ ID NO: 17), ACCTCTCTTTCCTAGCGGGA (SEQ ID NO: 18), ACGCACCTCTCTTTCCTAGC (SEQ ID NO: 19), ACTCACCCACTCGCCACCGC (SEQ ID NO: 20), AGCAACCGGGCAGCAGGGAC (SEQ ID NO: 21), AGCCGTCCCTGCTGCCCGGT (SEQ ID NO: 22), AGCGCGCGACTCCTGAGTTC (SEQ ID NO: 23), AGCTTGCTACAGGCTGCGGT (SEQ ID NO: 24), AGGATGCCGCCTCCTCACTC (SEQ ID NO: 25), AGGCTGCGGTTGTTTCCCTC (SEQ ID NO: 26), AGGCTGTCAGCTCGGATCTC (SEQ ID NO: 27), AGGGCCACCCCTCCTGGGAA (SEQ ID NO: 28), ATCCCCTCACAGGCTCTTGT (SEQ ID NO: 29), ATGCCGCCTCCTCACTCACC (SEQ ID NO: 30), ATTGCCTGCATCCGGGCCCC (SEQ ID NO: 31), CACCCACTCGCCACCGCCTG (SEQ ID NO: 32), CACCCCCATCTCATCCCGCA (SEQ ID NO: 33), CACCCGCCAGGATGCCGCCT (SEQ ID NO: 34), CACCTCTCTTTCCTAGCGGG (SEQ ID NO: 35), CACTCACCCACTCGCCACCG (SEQ ID NO: 36), CAGGATGCCGCCTCCTCACT (SEQ ID NO: 37), CAGGCTGCGGTTGTTTCCCT (SEQ ID NO: 38), CAGGGTGGCATCTGCTTCAC (SEQ ID NO: 39), CCAAACAGCCACCCGCCAGG (SEQ ID NO: 40), CCACCCGCCAGGATGCCGCC (SEQ ID NO: 41), CCACCCTCCGGCCTTCCCCC (SEQ ID NO: 42), CCACTCGCCACCGCCTGCGC (SEQ ID NO: 43), CCAGGATGCCGCCTCCTCAC (SEQ ID NO: 44), CCCAAACAGCCACCCGCCAG (SEQ ID NO: 45), CCCACTCGCCACCGCCTGCG (SEQ ID NO: 46), CCCCAAACAGCCACCCGCCA (SEQ ID NO: 47), CCCGCCAGGATGCCGCCTCC (SEQ ID NO: 48), CCTCACTCACCCACTCGCCG (SEQ ID NO: 49), CCCGCGCCTCTTCCCGGCAG (SEQ ID NO: 50), CCCGGCAGCCGAACCCCAAA (SEQ ID NO: 51), CCGACTTGCATTGCTGCCCT (SEQ ID NO: 52), CCGCAGCCTGTAGCAAGCTC (SEQ ID NO: 53), CCGCCAGGATGCCGCCTCCT (SEQ ID NO: 54), CCGCCTCCTCACTCACCCAC (SEQ ID NO: 55), CCGCGCCTCTTCCCGGCAGC (SEQ ID NO: 56), CCGCTTCTACCCGCGCCTCT (SEQ ID NO: 57), CCGGGCAGCAGGGACGGCTG (SEQ ID NO: 58), CCTAGCGGGACACCGTAGGT (SEQ ID NO: 59), CCTCACTCACCCACTCGCCA (SEQ ID NO: 60), CCTCCGGCCTTCCCCCAGGC (SEQ ID NO: 61), CCTCCTCACTCACCCACTCG (SEQ ID NO: 62), CCTCTCTTTCCTAGCGGGAC (SEQ ID NO: 63), CCTCTGCCAAGGCCTGCCAC (SEQ ID NO: 64), CCTCTTCCCGGCAGCCGAAC (SEQ ID NO: 65), CCTGAGTTCCAGAGCTTGCT (SEQ ID NO: 66), CCTGCTCTTGCTAGACCCCG (SEQ ID NO: 67), CCTGCTGCCCGGTTGCTTCT (SEQ ID NO: 68), CCTGGTTGCTTCACAGCTCC (SEQ ID NO: 69), CCTTCCCTGAAGGTTCCTCC (SEQ ID NO: 70), CGCACCTCTCTTTCCTAGCG (SEQ ID NO: 71), CGCATAGAATCCAGTACCAT (SEQ ID NO: 72), CGCCAGGATGCCGCCTCCTC (SEQ ID NO: 73), CGCCTCCTCACTCACCCACT (SEQ ID NO: 74), CGCCTCTTCCCGGCAGCCGA (SEQ ID NO: 75), CGCGCGACTCCTGAGTTCCA (SEQ ID NO: 76), CGCTTCTACCCGCGCCTCTT (SEQ ID NO: 77), CGGGCAGCAGGGACGGCTGA (SEQ ID NO: 78), CGGTTGTTTCCCTCCTTGTT (SEQ ID NO: 79), CTACCCGCGCCTCTTCCCGG (SEQ ID NO: 80), CTCACCCACTCGCCACCGCC (SEQ ID NO: 81), CTCACTCACCCACTCGCCAC (SEQ ID NO: 82), CTCAGTACCCGAGGCTCCCT (SEQ ID NO: 83), CTCCTCACTCACCCACTCGC (SEQ ID NO: 84), CTCTTCCCGGCAGCCGAACC (SEQ ID NO: 85), CTCTTGCTAGACCCCGCCCC (SEQ ID NO: 86), CTCTTTCCTAGCGGGACACC (SEQ ID NO: 87), CTGCGGTTGTTTCCCTCCTT (SEQ ID NO: 88), CTGCTCTTGCTAGACCCCGC (SEQ ID NO: 89), CTTCCCGGCAGCCGAACCCC (SEQ ID NO: 90), CTTCCTTGCTTTCCCGCCCT (SEQ ID NO: 91), CTTCTACCCGCGCCTCTTCC (SEQ ID NO: 92), CTTGCTAGACCCCGCCCCCA (SEQ ID NO: 93), CTTGGTGTGTCAGCCGTCCC (SEQ ID NO: 94), CTTGTTCACCCTCAGCGAGT (SEQ ID NO: 95), CTTTCCTAGCGGGACACCGT (SEQ ID NO: 96), GACATCCCCTCACAGGCTCT (SEQ ID NO: 97), GAGAGCCCCCGCTTCTACCC (SEQ ID NO: 98), GAGCTGCCCAGGACCACTTC (SEQ ID NO: 99), GAGCTTGCTACAGGCTGCGG (SEQ ID NO: 100), GAGGCCAGATCCCCATCCCT (SEQ ID NO: 101), GATCCCCATTCCAGTTTCCA (SEQ ID NO: 102), GATGCCGCCTCCTCACTCAC (SEQ ID NO: 103), GCAACCGGGCAGCAGGGACG (SEQ ID NO: 104), GCACCTCTCTTTCCTAGCGG (SEQ ID NO: 105), GCAGGCGGTGGCGAGTGGGT (SEQ ID NO: 106), GCAGGCGTCTCCACACCCCC (SEQ ID NO: 107), GCAGGGACGG CTGACACACC (SEQ ID NO: 108), GCATCCGGGCCCCGGGCTTC (SEQ ID NO: 109), GCATCCTGGCGGGTGGCTGT (SEQ ID NO: 110), GCCACCCGCCAGGATGCCGC (SEQ ID NO: 111), GCCAGATCCCCATCCCTTGT (SEQ ID NO: 112), GCCAGGATGCCGCCTCCTCA (SEQ ID NO: 113), GCCCTCAGTACCCGAGCTGT (SEQ ID NO: 114), GCCGCCTCCTCACTCACCCA (SEQ ID NO: 115), GCCGGGAAGA GGCGCGGGTAG (SEQ ID NO: 116), GCCGTCCCTGCTGCCCGGTT (SEQ ID NO: 117), GCCTCCTCACTCACCCACTC (SEQ ID NO: 118), GCCTCTCAGTACCCGAGGCT (SEQ ID NO: 119), GCCTCTTCCCGGCAGCCGAA (SEQ ID NO: 120), GCGCAGGCGGTGGCGAGTG GGTGAGTGAGGAGGCGGCATC (SEQ ID NO: 121), GCGCAGGCGGTGGCGAGTGGGTGAGTGAGG (SEQ ID NO: 122), GCGCGACTCC TGAGTTCCAG (SEQ ID NO: 123), GCGCGCGACTCCTGAGTTCC (SEQ ID NO: 124), GCGGCATCCTGGCGGGTGGC (SEQ ID NO: 125), GCGGTTGCGGTGCCTGCGCC (SEQ ID NO: 126), GCGGTTGTTTCCCTCCTTGT (SEQ ID NO: 127), GCTACAGGCTGCGGTTGTTT (SEQ ID NO: 128), GCTAGACCCCGCCCCCAAAA (SEQ ID NO: 129), GCTCTGAGGAGAGCCCCCGC (SEQ ID NO: 130), GCTCTTGCTAGACCCCGCCC (SEQ ID NO: 131), GCTGCGATCCCCATTCCAGT (SEQ ID NO: 132), GCTGCGGTTGTTTCCCTCCT (SEQ ID NO: 133), GCTGGAGATGGCGGTGGGCA (SEQ ID NO: 134), GCTGGGTGTCGGGCTTTCGC (SEQ ID NO: 135), GCTGTTTGACGCACCTCTCT (SEQ ID NO: 136), GCTTCTACCCGCGCCTCTTC (SEQ ID NO: 137), GCTTGCTACAGGCTGCGGTT (SEQ ID NO: 138), GCTTGGTGTGTCAGCCGTCC (SEQ ID NO: 139), GCTTTCCCGCCCTCAGTACC (SEQ ID NO: 140), GGACCCGCTGGGAGCGCTGC (SEQ ID NO: 141), GGATGCCGCCTCCTCACTCA (SEQ ID NO: 142), GGCAGCAGGG ACGGCTGACA (SEQ ID NO: 143), GGCCTCTCAGTACCCGAGGC (SEQ ID NO: 144), GGCGGAGGCGCAGGCGGTGG (SEQ ID NO: 145), GGCGTCTCCACACCCCCATC (SEQ ID NO: 146), GGCTCCCTTTTCTCGAGCCC (SEQ ID NO: 147), GGCTGCGGTTGTTTCCCTCC (SEQ ID NO: 148), GGGAAGGCCGGAGGGTGGGC (SEQ ID NO: 149), GGGCAGCAGGGACGGCTGAC (SEQ ID NO: 150), GGGCTCTCCT CAGAGCTCGA (SEQ ID NO: 151), GGGTGTCGGGCTTTCGCCTC (SEQ ID NO: 152), GGTCCCTGCCGGCGAGGAGA (SEQ ID NO: 153), GTACCCGAGGCTCCCTTTTC (SEQ ID NO: 154), GTCAGCCGTCCCTGCTGCCC (SEQ ID NO: 155), GTCCCTGCTGCCCGGTTGCT (SEQ ID NO: 156), GTCCGTGTGCTCATTGGGTC (SEQ ID NO: 157), GTCGCTGTTTGACGCACCTC (SEQ ID NO: 158), GTCGGTGTGCTCCCCATTCT (SEQ ID NO: 159), GTGCAGGCGTCTCCACACCC (SEQ ID NO: 160), GTGCTGCGATCCCCATTCCA (SEQ ID NO: 161), GTGGCAGGCCTTGGCAGAGG (SEQ ID NO: 162), GTTCACCCTCAGCGAGTACT (SEQ ID NO: 163), GTTGCGGTGCCTGCGCCCGC (SEQ ID NO: 164), GTTGTTTCCCTCCTTGTTTT (SEQ ID NO: 165), TACAGGCTGCGGTTGTTTCC (SEQ ID NO: 166), TACCCGCGCCTCTTCCCGGC (SEQ ID NO: 167), TCACCCACTCGCCACCGCCT (SEQ ID NO: 168), TCACCCTCAGCGAGTACTGT (SEQ ID NO: 169), TCACTCACCCACTCGCCACC (SEQ ID NO: 170), TCCCCTCACAGGCTCTTGTG (SEQ ID NO: 171), TCCCGGCAGCCGAACCCCAA (SEQ ID NO: 172), TCCTCACTCACCCACTCGCC (SEQ ID NO: 173), TCCTTGCTTTCCCGCCCTCA (SEQ ID NO: 174), TCTCAGTACCCGAGGCTCCC (SEQ ID NO: 175), TCTTCCCGGCAGCCGAACCC (SEQ ID NO: 176), TCTTGCTAGACCCCGCCCCC (SEQ ID NO: 177), TGCCGCCTCCTCACTCACCC (SEQ ID NO: 178), TGCCTGCATCCGGGCCCCGG (SEQ ID NO: 179), TGCGGTTGTTTCCCTCCTTG (SEQ ID NO: 180), TGCTACAGGCTGCGGTTGTT (SEQ ID NO: 181), TGCTAGACCCCGCCCCCAAA (SEQ ID NO: 182), TGCTCTTGCTAGACCCCGCC (SEQ ID NO: 183), TGGAATGGGGATCGCAGCAC (SEQ ID NO: 184), TGGAATGGGGATCGCAGCACA (SEQ ID NO: 185), TGGCGAGTGG GTGAGTGAGGAGGCGGCATC (SEQ ID NO: 186), TGTGCTGCGATCCCCATTCC (SEQ ID NO: 187), TTCCAGAGCTTGCTACAGGC (SEQ ID NO: 188), TTCCCGGCAGCCGAACCCCA (SEQ ID NO: 189), TTCTACCCGCGCCTCTTCCC (SEQ ID NO: 190), TTGCTACAGGCTGCGGTTGT (SEQ ID NO: 191), TTGCTAGACCCCGCCCCCAA (SEQ ID NO: 192), TTTCCCCACACCACTGAGCT (SEQ ID NO: 193), ACCCACTCGCCA (SEQ ID NO: 194), ACCCACTCGCCA (SEQ ID NO: 195), ACTCACCCACTCGCCACCGC (SEQ ID NO: 196), ACTCACCCACTCGCCACCGC (SEQ ID NO: 197), ACTCACCCACTCGCCACCGC (SEQ ID NO: 198), ACTCACCCACTCGCCACCGC (SEQ ID NO: 199), ACTCACCCACTCGCCACCGC (SEQ ID NO: 200), ACTCGCCA (SEQ ID NO: 201), AUACUUACCUGG (SEQ ID NO: 202), CACTCGCCA (SEQ ID NO: 203), CCCACTCGCCA (SEQ ID NO: 204), CCCACTCGCCA (SEQ ID NO: 205), CCTCACTCACCCACTCGCC (SEQ ID NO: 206), CCTCACTCACCCACTCGCC (SEQ ID NO: 207), CCTCACTCACCCACTCGCCA (SEQ ID NO: 208), CCTCACTCACCCACTCGCCA (SEQ ID NO: 209), CCTCACTCACCCACTCGCCA (SEQ ID NO: 210), CCTCACTCACCCACTCGCCA (SEQ ID NO: 211), CCTCACTCACCCACTCGCCA (SEQ ID NO: 212), CCTCACTCACCCACTCGCCA (SEQ ID NO: 213), CCTCACTCACCCACTCGCCA (SEQ ID NO: 214), CCTCACTCACCCACTCGCCA (SEQ ID NO: 215), CCTCACTCACCCACTCGCCC (SEQ ID NO: 216), CCTCACTCACCCACTCGCCC (SEQ ID NO: 217), CCTCACTCACCCACTCGCCG (SEQ ID NO: 218), CCTCACTCACCCACTCGCCG (SEQ ID NO: 219), CCTCACTCACCCACTCGCCG (SEQ ID NO: 220), CCTCACTCACCCACTCGCCG (SEQ ID NO: 221), CCTCACTCACCCACTCGCCG (SEQ ID NO: 222), CCTCACTCACCCACTCGCCG (SEQ ID NO: 223), CCT- CACTCACCCACTCGCCI (SEQ ID NO: 224), CCTCACTCACCCACTCGCCI (SEQ ID NO: 225), CCT-CACTCACCCACTCGCCU (SEQ ID NO: 226), CCT-CACTCACCCACTCGCCU (SEQ ID NO: 227), CCT-CACTCACCCACUCGCC (SEQ ID NO: 228), CCTCACTCACCCACUCGCC (SEQ ID NO: 229), CCT-CACTCACCCACUCGCC (SEQ ID NO: 230), CCTCACT-CACCCACUCGCCA (SEQ ID NO: 231), CCTGCTGCCCGGTTGCTTCT (SEQ ID NO: 232), CCTGCTGCCCGGTTGCUUCU (SEQ ID NO: 233), CCUGCTGCCCGGTTGCTTCT (SEQ ID NO: 234), CGC-CUCCTCACTCACCCACU (SEQ ID NO: 235), CTCACT-CACCCACTCGCCAC (SEQ ID NO: 236), CUCUGGAA-CUCAGGAGUCGCGCGC (SEQ ID NO: 237), GCGCGACTCC TGAGTTCCAG (SEQ ID NO: 238), GCUACCUAUAUG (SEQ ID NO: 239), GTCCCTGCTGCCCGGTTGCT (SEQ ID NO: 240), GUCCCTGCTG CCCGGTTGCT (SEQ ID NO: 241), TCCTTGCTTTCCCGCCCTCA (SEQ ID NO: 242), TGCCGCCTCCTCACTCACCC (SEQ ID NO: 243), UCCTCACTCA CCCACUCGCC (SEQ ID NO: 244), or UCCUTGCTTTCCCGCCCTCA (SEQ ID NO: 245), wherein each nucleobase T can be independently and optionally substituted with nucleobase U, and wherein each U can be independently and optionally substituted with T, and wherein the nucleobase C and/or the nucleobase G in one or more CpG motifs, if present, is replaced by another base; and in some embodiments, the G nucleobase in a CpG motif is replaced by I.

In some embodiments, base sequence of an oligonucleotide is, comprises, or comprises an at least 15-base portion of ACTCACCCACTCGCCACCGC (SEQ ID NO: 246), wherein each nucleobase T can be independently and optionally substituted with nucleobase U, and wherein each U can be independently and optionally substituted with T, and wherein the nucleobase C and/or the nucleobase G in one or more CpG motifs, if present, is replaced by another base; and in some embodiments, the G nucleobase in a CpG motif is replaced by I. In some embodiments, base sequence of an oligonucleotide is, comprises, or comprises an at least 15-base portion of ACTCACCCACTCGCCACCGC (SEQ ID NO: 247), wherein each nucleobase T can be independently and optionally substituted with nucleobase U, and wherein each U can be independently and optionally substituted with T, and one or more G in a CpG motif are independently replaced by I. In some embodiments, base sequence of an oligonucleotide is, comprises, or comprises an at least 15-base portion of ACTCACCCACTCGC-CACCGC (SEQ ID NO: 248), wherein each nucleobase T can be independently and optionally substituted with nucleobase U, and wherein each U can be independently and optionally substituted with T. In some embodiments, base sequence of an oligonucleotide is, comprises, or comprises an at least 15-base portion of ACTCACCCACTCGC-CACCGC (SEQ ID NO: 249). As described in, oligonucleotides of the present disclosure may comprises various base, sugar and/or internucleotidic linkage modifications, e.g., in some embodiments, 5 mC are utilized as modified C.

The present disclosure presents, in Table A1 and elsewhere, various oligonucleotides, each of which has a defined base sequence. In some embodiments, the disclosure encompasses any oligonucleotide having a base sequence which is, comprises, or comprises a portion of the base sequence of any of oligonucleotide disclosed herein. In some embodiments, the disclosure encompasses any oligonucleotide having a base sequence which is, comprises, or comprises a portion of the base sequence of any oligonucleotide disclosed herein, which has any chemical modification, stereochemistry, format, structural feature (e.g., any structure or pattern of modification or portion thereof), and/or any other modification described herein (e.g., conjugation with another moiety, such as a targeting moiety, carbohydrate moiety, etc.; and/or multimerization). In some embodiments, a "portion" (e.g., of a base sequence or a pattern of modifications), is at least 5, 6, 7, 8, 9, 10, 11, 12, 13, 14, 15, 16, 17, 18, 19, or 20 long. In some embodiments, a "portion" of a base sequence is at least 5 nt long. In some embodiments, a "portion" of a base sequence is at least 10 nt long. In some embodiments, a "portion" of a base sequence is at least 15 nt long. In some embodiments, a "portion" of a base sequence is at least 20 nt long.

In some embodiments, an oligonucleotide targets C9orf72 and has a base sequence which is, comprises or comprises a portion of: CCTCACTCACCCACTCGCCA (SEQ ID NO: 250), wherein each T can be independently and optionally substituted with U.

In some embodiments, an oligonucleotide targets C9orf72 and has a base sequence which is, comprises or comprises a portion of: CCTCACTCACCCACTCGCCA (SEQ ID NO: 251), wherein each T can be independently and optionally substituted with U.

In some embodiments, an oligonucleotide targets C9orf72 and has a base sequence which is, comprises or comprises a portion of: ATACTTACCTGG (SEQ ID NO: 252), wherein each T can be independently and optionally substituted with U.

In some embodiments, an oligonucleotide targets C9orf72 and has a base sequence which is, comprises or comprises a portion of: CACTCGCCA (SEQ ID NO: 253), wherein each T can be independently and optionally substituted with U.

In some embodiments, an oligonucleotide targets C9orf72 and has a base sequence which is, comprises or comprises a portion of: ACTCGCCA (SEQ ID NO: 254), wherein each T can be independently and optionally substituted with U.

In some embodiments, an oligonucleotide targets C9orf72 and has a base sequence which is, comprises or comprises a portion of: ACCCACTCGCCA (SEQ ID NO: 255), wherein each T can be independently and optionally substituted with U.

In some embodiments, an oligonucleotide targets C9orf72 and has a base sequence which is, comprises or comprises a portion of: CCCACTCGCCA (SEQ ID NO: 256), wherein each T can be independently and optionally substituted with U.

In some embodiments, an oligonucleotide targets C9orf72 and has a base sequence which is, comprises or comprises a portion of: TGCCGCCTCCTCACTCACCC (SEQ ID NO: 257), wherein each T can be independently and optionally substituted with U.

In some embodiments, an oligonucleotide targets C9orf72 and has a base sequence which is, comprises or comprises a portion of: TGCCGCCTCCTCACTCACCC (SEQ ID NO: 258), wherein each T can be independently and optionally substituted with U.

In some embodiments, an oligonucleotide targets C9orf72 and has a base sequence which is, comprises or comprises a portion of: GCGCGACTCCTGAGTTCCAG (SEQ ID NO: 259), wherein each T can be independently and optionally substituted with U.

In some embodiments, an oligonucleotide targets C9orf72 and has a base sequence which is, comprises or comprises a portion of: TCCTTGCTTTCCCGCCCTCA (SEQ ID NO: 260), wherein each T can be independently and optionally substituted with U.

In some embodiments, an oligonucleotide targets C9orf72 and has a base sequence which is, comprises or comprises a portion of: TCCTTGCTTTCCCGCCCTCA (SEQ ID NO: 261), wherein each T can be independently and optionally substituted with U.

In some embodiments, an oligonucleotide targets C9orf72 and has a base sequence which is, comprises or comprises a portion of: TCCTTGCTTTCCCGCCCTCA (SEQ ID NO: 262), wherein each T can be independently and optionally substituted with U.

In some embodiments, an oligonucleotide targets C9orf72 and has a base sequence which is, comprises or comprises a portion of: GTCCCTGCTGCCCGGTTGCT (SEQ ID NO: 263), wherein each T can be independently and optionally substituted with U.

In some embodiments, an oligonucleotide targets C9orf72 and has a base sequence which is, comprises or comprises a portion of: GTCCCTGCTGCCCGGTTGCT (SEQ ID NO: 264), wherein each T can be independently and optionally substituted with U.

In some embodiments, an oligonucleotide targets C9orf72 and has a base sequence which is, comprises or comprises a portion of: GTCCCTGCTGCCCGGTTGCT (SEQ ID NO: 265), wherein each T can be independently and optionally substituted with U.

In some embodiments, an oligonucleotide targets C9orf72 and has a base sequence which is, comprises or comprises a portion of: CCTGCTGCCCGGTTGCTTCT (SEQ ID NO: 266), wherein each T can be independently and optionally substituted with U.

In some embodiments, an oligonucleotide targets C9orf72 and has a base sequence which is, comprises or comprises a portion of: CCTGCTGCCCGGTTGCTTCT (SEQ ID NO: 267), wherein each T can be independently and optionally substituted with U.

In some embodiments, an oligonucleotide targets C9orf72 and has a base sequence which is, comprises or comprises a portion of: CCTGCTGCCCGGTTGCTTCT (SEQ ID NO: 268), wherein each T can be independently and optionally substituted with U.

In some embodiments, an oligonucleotide targets C9orf72 and has a base sequence which is, comprises or comprises a portion of: GCTACCTATATG (SEQ ID NO: 269), wherein each T can be independently and optionally substituted with U.

In some embodiments, an oligonucleotide targets C9orf72 and has a base sequence which is, comprises or comprises a portion of: CTCTGGAACTCAGGAGTCGCGCGC (SEQ ID NO: 270), wherein each T can be independently and optionally substituted with U.

In some embodiments, an oligonucleotide targets C9orf72 and has a base sequence which is, comprises or comprises a portion of: CCTCACTCACCCACTCGCCI (SEQ ID NO: 271), wherein each T can be independently and optionally substituted with U.

In some embodiments, an oligonucleotide targets C9orf72 and has a base sequence which is, comprises or comprises a portion of: CCTCACTCACCCACTCGCCG (SEQ ID NO: 272), wherein each T can be independently and optionally substituted with U.

In some embodiments, an oligonucleotide targets C9orf72 and has a base sequence which is, comprises or comprises a portion of: TCCTCACTCACCCACTCGCC (SEQ ID NO: 273), wherein each T can be independently and optionally substituted with U.

In some embodiments, an oligonucleotide targets C9orf72 and has a base sequence which is, comprises or comprises a portion of: CTCACTCACCCACTCGCCAC (SEQ ID NO: 274), wherein each T can be independently and optionally substituted with U.

In some embodiments, an oligonucleotide targets C9orf72 and has a base sequence which is, comprises or comprises a portion of: ACTCACCCACTCGCCACCGC (SEQ ID NO: 275), wherein each T can be independently and optionally substituted with U.

In some embodiments, an oligonucleotide targets C9orf72 and has a base sequence which is, comprises or comprises a portion of: CGCCTCCTCACTCACCCACT (SEQ ID NO: 276), wherein each T can be independently and optionally substituted with U.

In some embodiments, an oligonucleotide targets C9orf72 and has a base sequence which is, comprises or comprises a portion of: CCTCACTCACCCACTCGCC (SEQ ID NO: 277), wherein each T can be independently and optionally substituted with U.

In some embodiments, an oligonucleotide targets C9orf72 and has a base sequence which is, comprises or comprises a portion of: CCTCACTCACCCACTCGCCA (SEQ ID NO: 278), wherein each T can be independently and optionally substituted with U.

In some embodiments, an oligonucleotide targets C9orf72 and has a base sequence which is, comprises or comprises a portion of: CCTCACTCACCCACTCGCC (SEQ ID NO: 279), wherein each T can be independently and optionally substituted with U.

In some embodiments, an oligonucleotide targets C9orf72 and has a base sequence which is, comprises or comprises a portion of: CCTCACTCACCCACTCGCCC (SEQ ID NO: 280), wherein each T can be independently and optionally substituted with U.

In some embodiments, an oligonucleotide targets C9orf72 and has a base sequence which is, comprises or comprises a portion of: CCTCACTCACCCACTCGCCT (SEQ ID NO: 281), wherein each T can be independently and optionally substituted with U.

In some embodiments, an oligonucleotide targets C9orf72 and has a base sequence which is, comprises or comprises a portion of: ACTCACCCACTCGCCACCGC (SEQ ID NO: 551), wherein each T can be independently and optionally substituted with U, and wherein the internucleotidic linkages of the oligonucleotide are from 5' to 3', SnROnRSSSRSSSSRSSSnRSS, wherein each S independently represents a phosphorothioate internucleotidic linkage in Sp configuration, each nR independently represents n001 in Rp configuration, O represents a natural phosphate linkage, and each R independently represents a phosphorothioate internucleotidic linkage in Rp configuration.

A pharmaceutical composition comprising an oligonucleotide which targets C9orf72 of any of the embodiments and a pharmaceutically acceptable diluent or carrier.

A pharmaceutical composition comprising an oligonucleotide which targets C9orf72 of any of the embodiments wherein the pharmaceutically acceptable diluent is a phosphate buffered saline (PBS) or artificial CFS (aCFS).

In some embodiments the pharmaceutical composition comprises an oligonucleotide which targets C9orf72 and has a base sequence which is ACTCACCCACTCGCCACCGC (SEQ ID NO: 552

In some embodiments the pharmaceutical composition comprises an oligonucleotide which targets C9orf72 and has a base sequence which is ACTCACCCACTCGCCACCGC (SEQ ID NO: 553), or a salt thereof and a pharmaceutically acceptable carrier of diluent.

In some embodiments the composition comprises an oligonucleotide which targets C9orf72 and has a base sequence which is ACTCACCCACTCGCCACCGC (SEQ ID NO: 554), wherein the salt thereof is a sodium salt.

In some embodiments, a portion of a base sequence is a span of 10, 11, 12, 13, 14, 15, 16, 17, 18, 19 or more contiguous (consecutive) bases. In some embodiments, a portion of a base sequence is a span of 15, 16, 17, 18, 19 or more contiguous (consecutive) bases. In some embodiments, abase sequence of an oligonucleotide is or comprises a base sequence, above. In some embodiments, a base sequence of an oligonucleotide is a base sequence, above.

In some embodiments, the nucleobase at the 5' end of an oligonucleotide is optionally replaced by a replacement nucleobase (as appreciated by those skilled in the art, which is different from the original 5'-end nucleobase). In some embodiments, the nucleobase at the 5' end of an oligonucleotide is replaced by a replacement nucleobase. In some embodiments, the nucleobase at the 3' end of an oligonucleotide is optionally replaced by a replacement nucleobase (as appreciated by those skilled in the art, which is different from the original 3'-end nucleobase). In some embodiments, the nucleobase at the 3' end of an oligonucleotide is replaced by a replacement nucleobase. In some embodiments, a replacement nucleobase is selected from I, A, T, U, G and C. In some embodiments, a replacement nucleobase is I. In some embodiments, a replacement nucleobase is A. In some embodiments, a replacement nucleobase is T. In some embodiments, a replacement nucleobase is U. In some embodiments, a replacement nucleobase is G. In some embodiments, a replacement nucleobase is C. In some embodiments, when aligned with a target sequence a replacement nucleobase creates a non-Watson-Crick basepair. In some embodiments, a replacement nucleobase creates a wobble basepair.

As demonstrated herein, in many embodiments replacement may provide improved properties, activities, selectivities, etc.

In some embodiments, the present disclosure provides a C9orf72 oligonucleotide of a sequence recited herein. In some embodiments, the present disclosure provides a C9orf72 oligonucleotide of a sequence recited herein, wherein the oligonucleotide is capable of directing a decrease in the expression, level and/or activity of a C9orf72 gene or its gene product. In some embodiments, a C9orf72 oligonucleotide of a recited sequence comprises any structure described herein. In various sequences, U can be replaced by T or vice versa, or a sequence can comprise a mixture of U and T. In some embodiments, a C9orf72 oligonucleotide has a length of no more than about 49, 45, 40, 30, 35, 25, 23 total nucleotides. In some embodiments, a portion is a span of at least 15, 16, 17, 18, 19, 20, 21, 22, 23, 24, or 25 total nucleotides with 0-3 mismatches. In some embodiments, a portion is a span of at least 15, 16, 17, 18, 19, 20, 21, 22, 23, 24, or 25 total nucleotides with 0-3 mismatches, wherein a span with 0 mismatches is complementary and a span with 1 or more mismatches is a non-limiting example of substantial complementarity. In some embodiments, wherein the sequence recited above starts with a U at the 5'-end, the U can be deleted and/or replaced by another base. In some embodiments, the disclosure encompasses any oligonucleotide having a base sequence which is or comprises or comprises a portion of the base sequence of any oligonucleotide disclosed herein, which has a format or a portion of a format disclosed herein.

In some embodiments, a C9orf72 oligonucleotide can comprise any base sequence described herein. In some embodiments, a C9orf72 oligonucleotide can comprise any base sequence or portion thereof, described herein. In some embodiments, a C9orf72 oligonucleotide can comprise any base sequence or portion thereof, described herein, wherein a portion is a span of 15 contiguous bases, or a span of 15 contiguous bases with 1-5 mismatches. In some embodiments, a C9orf72 oligonucleotide can comprise any base sequence or portion thereof described herein in combination with any other structural element or modification described herein. Certain examples of base sequences and useful structural elements, including modifications and patterns thereof, are described in Table A1.

Non-limiting examples of C9orf72 oligonucleotides having various base sequences and modifications are disclosed in Table A1, below.

TABLE A1

| oligonucleotides and compositions including C9orf72 and compositions. | | | | |
|---|---|---|---|---|
| ID | Description | Base Sequence | SEQ ID NO | Stereochemistry/ Internucleotidic Linkages |
| WV-8012 | mC*Sm5CeoTeom5CeomA*SC*ST*SC*RA*SC*SC*RC*SA*SC*ST*Sm C*SmG*SmC*SmC*SmA | CCTCACTCACCCA CTCGCCA | 282 | SOOOSSSRSSRSS SSSSSS |
| WV-17819 | mC * Sm5CeoTeom5CeomA * SC * ST * SC * RA * SC * SC * RC * SA * SC * ST * SmC * RmG * RmC * RmC * RmA | CCTCACTCAC CCACTCGCCA | 283 | SOOOS SSRSS RSSSS RRRR |
| WV-17820 | mC * Sm5CeoTeom5CeomA * SC * ST * SC * RA * SC * SC * RC * SA * SC * ST * Sm5Ceo * SGeo * Sm5Ceo * Sm5Ceo * SAeo | CCTCACTCAC CCACTCGCCA | 284 | SOOOS SSRSS R SSSSS SSS |
| WV-17821 | mC * Sm5CeoTeom5CeomA * SC * ST * SC * RA * SC * SC * RC * SA * SC * ST * Sm5Ceo * RGeo * Rm5Ceo * Rm5Ceo * RAeo | CCTCACTCAC CCACTCGCCA | 285 | SOOOS SSRSS RSSSS RRRR |
| WV-17822 | mC * m5CeoTeom5CeomA * C * T * C * A * C * C* C* A * C* T* m5Ceo * Geo * m5Ceo * m5Ceo * Aeo | CCTCACTCAC CCACTCGCCA | 286 | XOOOX XXXXX XXXXX XXXX |
| WV-17885 | mC * SmC * SmU * SmC * SmA * SC * ST * SC * RA * SC * SC * SC * RA * SC * ST * Sm5CeoGeom5Ceom5Ceo * RAeo | CCUCACTCACCCA C TCGCCA | 287 | SSSSS SSRSS SRSSS OOOR |
| WV-18851 | rArUrArCrUrUrArCrCrUrGrG | AUACUUACCUGG | 288 | OOOOO OOOOO O |
| WV-18852 | mC * m5CeoTeom5CeomA * C * T * C * A * C * C* C* A * C * T* mC * mG * mC * mC * mAL004 | CCTCACTCAC CCACTCGCCA | 289 | XOOOX XXXXX XXXXX XXXX |
| WV-20761 | mC * Sm5CeoTeom5CeomA * SC * ST * SC * RA * SC * SC * RC * SA * SC * ST * SmCmG * SmC * SmC * SmA | CCTCACTCAC CCACTCGCCA | 290 | SOOOS SSRSS RSSSS OSSS |
| WV-20762 | mC * Sm5CeoTeom5CeomA * SC * ST * SC * RA * SC * SC * RC * SA * SC * ST * Sm5CeomG * SmC * SmC * SmA | CCTCACTCAC CCACTCGCCA | 29 | SOOOS SSRSS RSSSS OSSS |
| WV-20763 | mC * Sm5CeoTeom5CeomA * SC * ST * SC * RA * SC * SC * RC * SA * SC * ST * Sm5Ceo * SmG * SmC * SmC * SmA | CCTCACTCAC CCACTCGCCA | 292 | SOOOS SSRSS R SSSSS SSS |
| WV-20764 | mC * Sm5CeoTeom5CeomA * SC * ST * SC * RA * SC * SC * RC * SA * SC * ST * Rm5CeomG * SmC * SmC * SmA | CCTCACTCAC CCACTCGCCA | 293 | SOOOS SSRSS RSSSROSSS |
| WV-20765 | mC * Sm5CeoTeom5CeomA * SC * ST * SC * RA * SC * SC * RC * SA * SC * ST * Rm5Ceo * SmG * SmC * SmC * SmA | CCTCACTCAC CCACTCGCCA | 294 | SOOOS SSRSS RS SSRSS SS |
| WV-20766 | mC * Sm5CeoTeom5CeomA * SC * ST * SC * RA * SC * SC * RC * SA * SC * ST * Sm5mC * SmG * SmC * SmC * SmA | CCTCACTCAC CCACTCGCCA | 295 | SOOOS SSRSS R SSSSS SSS |
| WV-20767 | C * SA * SC * ST * SmC * SmG * SmC * SmC * SmA | CACTCGCCA | 296 | SSSSS SSS |
| WV-20768 | A * SC * ST * SmC * SmG * SmC * SmC * SmA | ACTCGCCA | 297 | SSSSS SS |

TABLE A1-continued oligonucleotides and compositions including C9orf72 and compositions.

| ID | Description | Base Sequence | SEQ ID NO | Stereochemistry/ Internucleotidic Linkages |
|---|---|---|---|---|
| WV-20769 | mC * Sm5CeoTeom5CeomA * SC * ST * SC * RA * SC * SC * RC * SA * SC * ST * Sm5CeoGeomC * SmC * SmA | CCTCACTCAC CCACTCGCCA | 298 | SOOOS SSRSS RSSSS OOSS |
| WV-20770 | mC * Sm5CeoTeom5CeomA * SC * ST * SC * RA * SC * SC * RC * SA * SC * ST * Rm5CeoGeomC * SmC * SmA | CCTCACTCAC CCACTCGCCA | 299 | SOOOS SSRSS RSSSROOSS |
| WV-20771 | mC * Sm5CeoTeom5CeomA * SC * ST * SC * RA * SC * SC * RC * SA * SC * ST * Sm5mCmG * SmC * SmC * SmA | CCTCACTCAC CCACTCGCCA | 300 | SOOOS SSRSS RSSSS OSSS |
| WV-20772 | A * SC * SC * RC * SA * SC * ST * SmC * SmG * SmC * SmC * SmA | ACCCACTCGCCA | 301 | SSR SSSSS SSS |
| WV-20773 | C * SC * RC * SA * SC * ST * SmC * SmG * SmC * SmC * SmA | CCCACTCGCCA | 302 | SR SSSSS SSS |
| WV-20774 | A * SC * SC * SC * SA * SC * ST * SmC * SmG * SmC * SmC * SmA | ACCCACTCGCCA | 303 | SSSSS SSSSS S |
| WV-20775 | C * SC * SC * SA * SC * ST * SmC * SmG * SmC * SmC * SmA | CCCACTCGCCA | 304 | SSSSS SSSSS |
| WV-21145 | Teo * RGeom5Ceom5CeoGeo * RC * SC * ST * SC * RC * ST * SC * RA * SC * ST * Rm5CeoAeom5Ceom5Ceo * Rm5Ceo | TGCCGCCTCC TCACTCAC CC | 305 | ROOORS SSRSS RSSRO OOR |
| WV-21146 | Teo * RGeo * Rm5Ceo * Rm5Ceo * RGeo * RC * SC * ST * SC * RC * ST * SC * RA * SC * ST * Rm5Ceo * RAeo * Rm5Ceo * Rm5Ceo * Rm5Ceo | TGCCGCCTCC TCACTCAC CC | 306 | RRRRRS SSRSS RSSRR RRR |
| WV-21147 | Teo * RGeom5Ceom5CeoGeo * RC * SC * ST * SC * RC * ST * SC * RA * SC * ST * Rm5Ceo * RAeo * Rm5Ceo * Rm5Ceo * Rm5Ceo | TGCCGCCTCC TCACTCAC CC | 307 | ROOORS SSRSS RSSRR RRR |
| WV-21148 | Teo * RGeo * Rm5Ceo * Rm5Ceo * RGeo * RC * SC * ST * SC * RC * ST * SC * RA * SC * ST * Rm5CeoAeom5Ceom5Ceo * Rm5Ceo | TGCCGCCTCC TCACTCAC CC | 308 | RRRRRS SSRSS RSSRO OOR |
| WV-21149 | Teo * RGeom5Ceom5CeoGeo * RC * SC * ST * SC * RC * ST * SC * RA * SC * ST * Rm5Ceo * SmA * SmC * SmC * SmC | TGCCGCCTCC TCACTCAC CC | 309 | ROOORS SSRSS R SSRSS SS |
| WV-21150 | mU * SmG * SmC * SmC * SGeo * RC * SC * ST * SC * RC * ST * SC * RA * SC * ST * Rm5CeoAeom5Ceom5Ceo * Rm5Ceo | UGCCGCCTCC TCACTCAC CC | 310 | SS SSRSS SR SSRSS ROOOR |
| WV-21151 | Geo * Rm5CeoGeom5CeoGeo * RA * SC * ST * SC * RC * ST * SG * RA * SG * ST * RTeom5Ceom5CeoAeo * RGeo | GCGCGACTCC TGAGTTCCAG | 311 | ROOORS SSRSS RSSRO OOR |
| WV-21152 | Geo * Rm5Ceo * RGeo * Rm5Ceo * RGeo * RA * SC * ST * SC * RC * ST * SG * RA * SG * ST * RTeo * Rm5Ceo * Rm5Ceo * RAeo * RGeo | GCGCGACTCC TGAGTTCCAG | 312 | RRRRRS SSRSS RSSRR RRR |
| WV-21153 | Geo * Rm5CeoGeom5CeoGeo * RA * SC * ST * SC * RC * ST * SG * RA * SG * ST * RTeo * Rm5Ceo * Rm5Ceo * RAeo * RGeo | GCGCGACTCC TGAGTTCCAG | 313 | ROOORS SSRSS RSSRR RRR |
| WV-21154 | Geo * Rm5Ceo * RGeo * Rm5Ceo * RGeo * RA * SC * ST * SC * RC * ST * SG * RA * SG * ST * RTeom5Ceom5CeoAeo * RGeo | GCGCGACTCC TGAGTTCCAG | 314 | RRRRRS SSRSS RSSRO OOR |

TABLE A1-continued oligonucleotides and compositions including C9orf72 and compositions.

| ID | Description | Base Sequence | SEQ ID NO | Stereochemistry/ Internucleotidic Linkages |
|---|---|---|---|---|
| WV-21155 | Geo * Rm5CeoGeom5CeoGeo * RA * SC * ST * SC * RC * ST * SG * RA * SG * ST * RTeo * SmC * SmC * SmA * SmG | GCGCGACTCC TGAGTTCCAG | 315 | ROOORS SSRSS R SSRSS SS |
| WV-21156 | mG * SmC * SmG * SmC * SGeo * RA * SC * ST * SC * RC * ST * SG * RA * SG * ST * RTeom5Ceom5CeoAeo * RGeo | GCGCGACTCC TGAGTTCCAG | 316 | SS SSRSS SR SSRSS ROOOR |
| WV-21157 | Teo * Rm5Ceom5CeoTeoTeo * RG * SC * ST * ST * RT * SC * SC * Rm5C * SG * SC * Rm5Ceom5CeoTeom5Ceo * RAeo | TCCTTGCTTT CCCGCCCTCA | 317 | ROOORS SSRSS RSSRO OOR |
| WV-21158 | Teo * Rm5Ceo * Rm5Ceo * RTeo * RTeo * RG * SC * ST * ST * RT * SC * SC * Rm5C * SG * SC * Rm5Ceo * Rm5Ceo * RTeo * Rm5Ceo * RAeo | TCCTTGCTTT CCCGCCCTCA | 318 | RRRRRS SSRSS RSSRR RRR |
| WV-21159 | Teo * Rm5Ceom5CeoTeoTeo * RG * SC * ST * ST * RT * SC * SC * Rm5C * SG * SC * Rm5Ceo * Rm5Ceo * RTeo * Rm5Ceo * RAeo | TCCTTGCTTT CCCGCCCTCA | 319 | ROOORS SSRSS RSSRR RRR |
| WV-21160 | Teo * Rm5Ceo * Rm5Ceo * RTeo * RTeo * RG * SC * ST * ST * RT * SC * SC * Rm5C * SG * SC * Rm5Ceom5CeoTeom5Ceo * RAeo | TCCTTGCTTT CCCGCCCTCA | 320 | RRRRRS SSRSS RSSRO OOR |
| WV-21161 | Teo * Rm5Ceom5CeoTeoTeo * RG * SC * ST * ST * RT * SC * SC * Rm5C * SG * SC * Rm5Ceo * SmC * SmU * SmC * SmA | TCCTTGCTTT CCCGCCCUCA | 321 | ROOORS SSRSS R SSRSS SS |
| WV-21162 | mU * SmC * SmC * SmU * STeo * RG * SC * ST * ST * RT * SC * SC * Rm5C * SG * SC * Rm5Ceom5CeoTeom5Ceo * RAeo | UCCUTGCTTT CCCGCCCTCA | 322 | SS SSRSS SR SSRSS ROOOR |
| WV-21163 | Geo * RTeom5Ceom5Ceom5Ceo * RT * SG * SC * ST * SG * RC * SC * Sm5C * RG * SG * STeoTeoGeom5Ceo * RTeo | GTCCCTGCTG CCCGGTTGCT | 323 | ROOORSS SSRSS RSSOOOR |
| WV-21164 | Geo * RTeo * Rm5Ceo * Rm5Ceo * Rm5Ceo * RT * SG * SC * ST * SG * RC * SC * Sm5C * RG * SG * STeo * RTeo * RGeo * Rm5Ceo * RTeo | GTCCCTGCTG CCCGGTTGCT | 324 | RRRRRSS SSRSS RSSRR RR |
| WV-21165 | Geo * RTeom5Ceom5Ceom5Ceo * RT * SG * SC * ST * SG * RC * SC * Sm5C * RG * SG * STeo * RTeo * RGeo * Rm5Ceo * RTeo | GTCCCTGCTG CCCGGTTGCT | 325 | ROOORSS SSRSS RSSRR RR |
| WV-21166 | Geo * RTeo * Rm5Ceo * Rm5Ceo * Rm5Ceo * RT * SG * SC * ST * SG * RC * SC * Sm5C * RG * SG * STeoTeoGeom5Ceo * RTeo | GTCCCTGCTG CCCGGTTGCT | 326 | RRRRRSS SSRSS RSSOOOR |
| WV-21167 | Geo * RTeom5Ceom5Ceom5Ceo * RT * SG * SC * ST * SG * RC * SC * Sm5C * RG * SG * SmU * SmU * SmG * SmC * SmU | GTCCCTGCTG CCCGGUUGCU | 327 | ROOORSS SSRSS R SSSSS S |
| WV-21168 | mG * SmU * SmC * SmC * Sm5Ceo * RT * SG * SC * ST * SG * RC * SC * Sm5C * RG * SG * STeoTeoGeom5Ceo * RTeo | GUCCCTGCTG CCCGGTTGCT | 328 | SS SSRSS SSRSS RSSOOOR |
| WV-21169 | m5Ceo * Rm5CeoTeoGeom5Ceo * RT * SG * SC * SC * Rm5C * SG * SG * RT * ST * SG * Rm5CeoTeoTeom5Ceo * RTeo | CCTGCTGCCC GGTTGCTTCT | 329 | ROOORS SSRSS RSSRO OOR |

TABLE A1-continued oligonucleotides and compositions including C9orf72 and compositions.

| ID | Description | Base Sequence | SEQ ID NO | Stereochemistry/ Internucleotidic Linkages |
|---|---|---|---|---|
| WV-21170 | m5Ceo * Rm5Ceo * RTeo * RGeo * Rm5Ceo * RT * SG * SC * SC * Rm5C * SG * SG * RT * ST * SG * Rm5Ceo * RTeo * RTeo * Rm5Ceo * RTeo | CCTGCTGCCC GGTTGCTTCT | 330 | RRRRRS SSRSS RSSRR RRR |
| WV-21171 | m5Ceo * Rm5CeoTeoGeom5Ceo * RT * SG * SC * SC * Rm5C * SG * SG * RT * ST * SG * Rm5Ceo * RTeo * RTeo * Rm5Ceo * RTeo | CCTGCTGCCC GGTTGCTTCT | 331 | ROOORS SSRSS RSSRR RRR |
| WV-21172 | m5Ceo * Rm5Ceo * RTeo * RGeo * Rm5Ceo * RT * SG * SC * SC * Rm5C * SG * SG * RT * ST * SG * Rm5CeoTeoTeom5Ceo * RTeo | CCTGCTGCCC GGTTGCTTCT | 332 | RRRRRS SSRSS RSSRO OOR |
| WV-21173 | m5Ceo * Rm5CeoTeoGeom5Ceo * RT * SG * SC * SC * Rm5C * SG * SG * RT * ST * SG * Rm5Ceo * SmU * SmU * SmC * SmU | CCTGCTGCCC GGTTGCUUCU | 333 | ROOORS SSRSS R SSRSS SS |
| WV-21174 | mC * SmC * SmU * SmG * Sm5Ceo * RT * SG * SC * SC * Rm5C * SG * SG * RT * ST * SG * Rm5CeoTeoTeom5Ceo * RTeo | CCUGCTGCCC GGTTGCTTCT | 334 | SS SSRSS SR SSRSS ROOOR |
| WV-21206 | mC * Sm5CeoTeom5CeomA * SC * ST * SC * RA * SC * SC * RC * SA * SC * ST * SmCn001mG * SmC * SmC * SmA | CCTCACTCAC CCACTCGCCA | 335 | SOOOS SSRSS RSSSS nX SSS |
| WV-21207 | mC * Sm5CeoTeom5CeomA * SC * ST * SC * RA * SC * SC * SC * RA * SC * ST * SmCn001mG * SmC * SmC * SmA | CCTCACTCAC CCACTCGCCA | 336 | SOOOS SSRSS SRSSS nX SSS |
| WV-21208 | m5Ceo * Rm5CeoTeom5CeoAeo * RC * ST * SC * RA * SC * SC * RC * SA * SC * ST * SmCn001mG * SmC * SmC * SmA | CCTCACTCAC CCACTCGCCA | 337 | ROOOR SSRSS RSSSS nX SSS |
| WV-21209 | m5Ceo * Rm5CeoTeom5CeoAeo * RC * ST * SC * RA * SC * SC * SC * RA * SC * ST * SmCn001mG * SmC * SmC * SmA | CCTCACTCAC CCACTCGCCA | 338 | ROOOR SSRSS SRSSS nX SSS |
| WV-21259 | rGrCrUrArCrCrUrArUrArUrG | GCUACCUAUAUG | 339 | OOOOO OOOOO O |
| WV-21344 | rCrUrCrUrGrGrArArCrUrCrArGrGrArGrUrCrGrCrGrCrGrC | CUCUGGAACU CAGGAGUCGC GCGC | 340 | OOOOO OOOOO OOOOO OOOOO OOO |
| WV-21345 | mC * Sm5CeoTeom5CeomA * SC * ST * SC * RA * SC * SC * RC * SA * SC * ST * SmC * SmG * SmC * Sm5mC * SmA | CCTCACTCAC CCACTCGCCA | 341 | SOOOS SSRSS R SSSSS SSS |
| WV-21346 | mC * Sm5CeoTeom5CeomA * SC * ST * SC * RA * SC * SC * RC * SA * SC * ST * Sm5mC * SmG * SmC * Sm5mC * SmA | CCTCACTCAC CCACTCGCCA | 342 | SOOOS SSRSS R SSSSS SSS |
| WV-21347 | mC * Sm5CeoTeom5CeomA * SC * ST * SC * RA * SC * SC * RC * SA * SC * ST * Sm5mCmG * SmC * Sm5mC * SmA | CCTCACTCAC CCACTCGCCA | 343 | SOOOS SSRSS RSSSS OSSS |
| WV-21442 | mC * Sm5CeoTeom5CeomA * SC * ST * SC * RA * SC * SC * RC * SA * SC * ST * SmC * SmG * SmC * SmC * SmI | CCTCACTCAC CCACTCGCCI | 344 | SOOOS SSRSS R SSSSS SSS |

TABLE A1-continued oligonucleotides and compositions including C9orf72 and compositions.

| ID | Description | Base Sequence | SEQ ID NO | Stereochemistry/ Internucleotidic Linkages |
|---|---|---|---|---|
| WV-21443 | mC * Sm5CeoTeom5CeomA * SC * ST * SC * RA * SC * SC * RC * SA * SC * ST * SmC * SmG * SmC * SmC * SmG | CCTCACTCAC CCACTCGCCG | 345 | SOOOS SSRSS R SSSSS SSS |
| WV-21445 | mC * Sm5CeoTeom5CeomA * SC * ST * SC * RA * SC * SC * RC * SA * SC * ST * Sm5mC * SmG * SmC * Sm5mC * SmI | CCTCACTCAC CCACTCGCCI | 346 | SOOOS SSRSS R SSSSS SSS |
| WV-21446 | mC * Sm5CeoTeom5CeomA * SC * ST * SC * RA * SC * SC * RC * SA * SC * ST * Sm5mC * SmG * SmC * Sm5mC * SmG | CCTCACTCAC CCACTCGCCG | 347 | SOOOS SSRSS R SSSSS SSS |
| WV-21506 | mC * Sm5CeoTeom5CeomA * SC * ST * SC * RA * SC * SC * SC * RA * SC * ST * Sm5mC * SmG * SmC * Sm5mC * SmA | CCTCACTCAC CCACTCGCCA | 348 | SOOOS SSRSS SR SSSSS SS |
| WV-21507 | mC * Sm5CeoTeom5CeomA * SC * ST * SC * RA * SC * SC * RC * SA * SC * ST * SmCn001RmG * SmC * SmCn001RmA | CCTCACTCAC CCACTCGCCA | 349 | SOOOS SSRSS RSSSS nR SS nR |
| WV-21508 | mC * Sm5CeoTeom5CeomA * SC * ST * SC * RA * SC * SC * SC * RA * SC * ST * SmCn001RmG * SmC * SmCn001RmA | CCTCACTCAC CCACTCGCCA | 350 | SOOOS SSRSS SRSSS nR SS nR |
| WV-21509 | mU * Sm5Ceom5CeoTeomC * SA * SC * ST * SC * RA * SC * SC * RC * SA * SC * SmU * SmC * SmG * SmC * SmC | UCCTCACTCAC CCACUCGCC | 351 | SOOOS S SSRSS R SSSSS SS |
| WV-21510 | mU * Sm5Ceom5CeoTeomC * SA * SC * ST * SC * RA * SC * SC * SC * RA * SC * SmU * SmC * SmG * SmC * SmC | UCCTCACTCAC CCACUCGCC | 352 | SOOOS S SSRSS SR SSSSS S |
| WV-21511 | mU * Sm5Ceom5CeoTeomC * SA * SC * ST * SC * RA * SC * SC * RC * SA * SC * SmU * Sm5mC * SmG * SmC * SmC | UCCTCACTCAC CCACUCGCC | 353 | SOOOS S SSRSS R SSSSS SS |
| WV-21512 | mU * Sm5Ceom5CeoTeomC * SA * SC * ST * SC * RA * SC * SC * SC * RA * SC * SmU * Sm5mC * SmG * SmC * SmC | UCCTCACTCAC CCACUCGCC | 354 | SOOOS S SSRSS SR SSSSS S |
| WV-21513 | mU * Sm5Ceom5CeoTeomC * SA * SC * ST * SC * RA * SC * SC * RC * SA * SC * SmU * SmCn001RmG * SmC * SmC | UCCTCACTCAC CCACUCGCC | 355 | SOOOS S SSRSS RSSSS nR SS |
| WV-21514 | mU * Sm5Ceom5CeoTeomC * SA * SC * ST * SC * RA * SC * SC * SC * RA * SC * SmU * SmCn001RmG * SmC * SmC | UCCTCACTCAC CCACUCGCC | 356 | SOOOS S SSRSS SRSSS nR SS |
| WV-21515 | mC * STeom5CeoAeomC * ST * SC * RA * SC * SC * RC * SA * SC * ST * SC * SmG * SmC * SmC * SmA * SmC | CTCACTCACCCAC TCGCCAC | 357 | SOOOS SRSSR SSSSS SSSS |
| WV-21516 | mC * STeom5CeoAeomC * ST * SC * RA * SC * SC * SC * RA * SC * ST * SC * SmG * SmC * SmC * SmA * SmC | CTCACTCACCCAC TCGCCAC | 358 | SOOOS SRSSS R SSSSS SSS |
| WV-21517 | mC * STeom5CeoAeomC * ST * SC * RA * SC * SC * RC * SA * SC * ST * Sm5C * SmG * SmC * Sm5mC * SmA * SmC | CTCACTCACCCAC TCGCCAC | 359 | SOOOS SRSSR SSSSS SSSS |
| WV-21518 | mC * STeom5CeoAeomC * ST * SC * RA * SC * SC * SC * RA * SC * ST Sm5C * SmG * SmC * Sm5mC * SmA * SmC | CTCACTCACCCAC TCGCCAC | 360 | SOOOS SRSSS R SSSSS SSS |

TABLE A1-continued oligonucleotides and compositions including C9orf72 and compositions.

| ID | Description | Base Sequence | SEQ ID NO | Stereochemistry/ Internucleotidic Linkages |
|---|---|---|---|---|
| WV-21519 | mC * STeom5CeoAeomC * ST * SC * RA * SC * SC * RC * SA * SC * ST * SCn001RmG * SmC * SmCn001RmA * SmC | CTCACTCACCCAC TCGCCAC | 361 | SOOOS SR SSRSS SS nR SS nR S |
| WV-21520 | mC * STeom5CeoAeomC * ST * SC * RA * SC * SC * SC * RA * SC * ST * SCn001RmG * SmC * SmCn001RmA * SmC | CTCACTCACCCAC TCGCCAC | 362 | SOOOS SRS SSRSS S nR SS nR S |
| WV-21521 | mA * Sm5CeoTeom5CeomA * SC * SC * SC * RA * SC * ST * Sm5C * RG * SC * SC * SmA * SmC * Sm5mC * SmG * SmC | ACTCACCCAC TCGCCACCGC | 363 | SOOOS SSRSS SR SSSSS SS |
| WV-21522 | mA * Sm5CeoTeom5CeomA * SC * SC * SC * RA * SC * ST * Sm5C * RG * SC * Sm5C * SmA * SmC * Sm5mC * SmG * SmC | ACTCACCCAC TCGCCACCGC | 364 | SOOOS SSRSS SR SSSSS SS |
| WV-21523 | mA * Sm5CeoTeom5CeomA * SC * SC * SC * RA * SC * ST * Sm5C * RG * SC * SCn001RmA * SmC * SmCn001RmG * SmC | ACTCACCCAC TCGCCACCGC | 365 | SOOOS SSRSS SRSS nR SS nR S |
| WV-21524 | m5mC * SGeom5Ceom5CeomU * SC * SC * ST * SC * RA * SC * ST * SC * RA * SC * SmC * SmC * SmA * SmC * SmU | CGCCUCCTCA CTCAC CCACU | 366 | SOOOS S SSRSS SR SSSSS S |
| WV-21525 | m5mC * SGeom5Ceom5CeomU * SC * SC * ST * SC * RA * SC * ST * SC * RA * SC * SmC * Sm5mC * SmA * SmC * SmU | CGCCUCCTCA CTCAC CCACU | 367 | SOOOS S SSRSS SR SSSSS S |
| WV-21526 | mCn001RGeom5Ceom5CeomU * SC * SC * ST * SC * RA * SC * ST * SC * RA * SC * SmC * SmCn001RmA * SmC * SmU | CGCCUCCTCA CTCAC CCACU | 368 | nR OOOSS SSRSS SRSSS nR SS |
| WV-21552 | m5Ceo * Sm5CeoTeom5CeoAeo * RC * ST * SC * RA * SC * SC * RC * SA * SC * ST * Sm5mC * SmG * SmC * Sm5mC * SmA | CCTCACTCAC CCACTCGCCA | 369 | SOOOR SSRSS R SSSSS SSS |
| WV-21553 | m5Ceo * Sm5CeoTeom5CeoAeo * RC * ST * SC * RA * SC * SC * SC * RA * SC * ST * Sm5mC * SmG * SmC * Sm5mC * SmA | CCTCACTCAC CCACTCGCCA | 370 | SOOOR SSRSS SR SSSSS SS |
| WV-21554 | m5Ceo * Sm5CeoTeom5CeoAeo * RC * ST * SC * RA * SC * SC * RC * SA * SC * SmU * Sm5mC * SmG * SmC * SmC | CCTCACTCAC CCACUCGCC | 37 | SOOOR SSRSS R SSSSS SS |
| WV-21555 | m5Ceo * Sm5CeoTeom5CeoAeo * RC * ST * SC * RA * SC * SC * SC * RA * SC * SmU * Sm5mC * SmG * SmC * SmC | CCTCACTCAC CCACUCGCC | 372 | SOOOR SSRSS SR SSSSS S |
| WV-21556 | mC * Sm5CeoTeom5CeomA * SC * ST * SC * RA * SC * SC * RC * SA * SC * SmU * Sm5mC * SmG * SmC * SmC | CCTCACTCAC CCACUCGCC | 373 | SOOOS SSRSS R SSSSS SS |
| WV-21557 | mC * Sm5CeoTeom5CeomA * SC * ST * SC * RA * SC * SC * SC * RA * SC * SmU * Sm5mC * SmG * SmC * SmC | CCTCACTCAC CCACUCGCC | 374 | SOOOS SSRSS SR SSSSS S |
| WV-21558 | mC * Sm5CeoTeom5CeomA * SC * ST * SC * RA * SC * SC * RC * SA * SC * SmU * SmC * SmG * SmC * SmC * SmA | CCTCACTCAC CCACUCGCCA | 375 | SOOOS SSRSS R SSSSS SSS |

TABLE A1-continued oligonucleotides and compositions including C9orf72 and compositions.

| ID | Description | Base Sequence | SEQ ID NO | Stereochemistry/ Internucleotidic Linkages |
|---|---|---|---|---|
| WV-21559 | mC * Sm5CeoTeom5CeomA * SC * ST * SC * RA * SC * SC * RC * SA * SmC * SmU * SmC * SmG * SmC * SmC * SmA | CCTCACTCAC CCACUCGCCA | 376 | SOOOS SSRSS R SSSSS SSS |
| WV-21560 | mC * Sm5CeoTeom5CeomA * SC * ST * SC * RA * SC * SC * RC * SmA * SmC * SmU * SmC * SmG * SmC * SmC * SmA | CCTCACTCAC CCACUCGCCA | 377 | SOOOS SSRSS R SSSSS SSS |
| WV-21561 | mC * Sm5CeoTeom5CeomA * SC * ST * SC * RA * SC * SC * RmC * SmA * SmC * SmU * SmC * SmG * SmC * SmC * SmA | CCTCACTCAC CCACUCGCCA | 378 | SOOOS SSRSS R SSSSS SSS |
| WV-21562 | mC * Sm5CeoTeom5CeomA * SC * ST * SC * RA * SC * SmC * RmC * SmA * SmC * SmU * SmC * SmG * SmC * SmC * SmA | CCTCACTCAC CCACUCGCCA | 379 | SOOOS SSRSS R SSSSS SSS |
| WV-21563 | mC * Sm5CeoTeom5CeomA * SC * ST * SC * RA * SmC * SmC * RmC * SmA * SmC * SmU * SmC * SmG * SmC * SmC * SmA | CCTCACTCAC CCACUCGCCA | 380 | SOOOS SSRSS R SSSSS SSS |
| WV-21564 | mC * Sm5CeoTeom5CeoAeomC * ST * SC * RA * SC * SC * RC * SA * SC * ST * SmC * SmG * SmC * SmC * SmA | CCTCACTCAC CCACTCGCCA | 381 | SOOOO SSRSS R SSSSS SSS |
| WV-21565 | mC * Sm5CeoTeom5CeoAeomC * ST * SC * RA * SC * SC * RC * SA * SC * SmU * SmC * SmG * SmC * SmC * SmA | CCTCACTCAC CCACUCGCCA | 382 | SOOOO SSRSS R SSSSS SSS |
| WV-21566 | mC * Sm5CeoTeom5CeoAeomC * ST * SC * RA * SC * SC * RC * SA * SmC * SmU * SmC * SmG * SmC * SmC * SmA | CCTCACTCAC CCACUCGCCA | 383 | SOOOO SSRSS R SSSSS SSS |
| WV-21567 | mC * Sm5CeoTeom5CeoAeomC * ST * SC * RA * SC * SC * RC * SmA * SmC * SmU * SmC * SmG * SmC * SmC * SmA | CCTCACTCAC CCACUCGCCA | 384 | SOOOO SSRSS R SSSSS SSS |
| WV-21568 | mC * Sm5CeoTeom5CeoAeomC * ST * SC * RA * SC * SC * RmC * SmA * SmC * SmU * SmC * SmG * SmC * SmC * SmA | CCTCACTCAC CCACUCGCCA | 385 | SOOOO SSRSS R SSSSS SSS |
| WV-21569 | mC * Sm5CeoTeom5CeoAeomC * ST * SC * RA * SC * SmC * RmC * SmA * SmC * SmU * SmC * SmG * SmC * SmC * SmA | CCTCACTCAC CCACUCGCCA | 386 | SOOOO SSRSS R SSSSS SSS |
| WV-21570 | mC * Sm5CeoTeom5CeoAeomC * ST * SC * RA * SmC * SmC * RmC * SmA * SmC * SmU * SmC * SmG * SmC * SmC * SmA | CCTCACTCAC CCACUCGCCA | 387 | SOOOO SSRSS R SSSSS SSS |
| WV-23435 | mC * Sm5CeoTeom5CeomA * Sm5C * ST * Sm5C * RA * Sm5C * Sm5C * Sm5C * RA * Sm5C * SmU * Sm5mC * SmG * SmC * SmC | CCTCACTCAC CCACUCGCC | 388 | SOOOS SSRSS SR SSSSS S |
| WV-23436 | mC * Sm5Ceon001RTeom5Ceon001RmA * Sm5C * ST * Sm5C * RA * Sm5C * Sm5C * Sm5C * RA * Sm5C * SmUn001Rm5mC * SmGn001RmC * SmC | CCTCACTCAC CCACUCGCC | 389 | SnR O nR S SSRSS SRSS nR S nR S |
| WV-23437 | mC * Sm5Ceon001RTeom5Ceon001RmA * Sm5C * ST * Sm5C * RA * Sm5C * Sm5C * Sm5C * RA * Sm5C * SmUn001Rm5mCmGn001RmC * SmC | CCTCACTCAC CCACUCGCC | 390 | SnR O nR S SSRSS SRSS nR O nR S |

TABLE A1-continued oligonucleotides and compositions including C9orf72 and compositions.

| ID | Description | Base Sequence | SEQ ID NO | Stereochemistry/ Internucleotidic Linkages |
|---|---|---|---|---|
| WV-23438 | mC * Sm5Ceon001RTeom5Ceon001RmA * Sm5C * ST * Sm5C * RA * Sm5C * Sm5C * Sm5C * RA * Sm5C * SmU * SmCn001RmG * SmC * SmC | CCTCACTCAC CCACUCGCC | 391 | S nR O nR S SSRSS SRSSS nR SS |
| WV-23439 | mC * Sm5CeoTeom5CeomA * Sm5C * ST * Sm5C * RA * Sm5C * Sm5C * Sm5C * RA * Sm5C * SmU * Sm5Ceo * SmG * SmC * SmC | CCTCACTCAC CCACUCGCC | 392 | SOOOS SSRSS SR SSSSS S |
| WV-23440 | mC * Sm5CeoTeom5CeomA * Sm5C * ST * Sm5C * RA * Sm5C * Sm5C * Sm5C * RA * Sm5C * ST * Sm5mC * SmG * SmC * Sm5mC * SmA | CCTCACTCAC CCACTCGCCA | 393 | SOOOS SSRSS SR SSSSS SS |
| WV-23441 | mC * Sm5Ceon001RTeom5Ceon001RmA * Sm5C * ST * Sm5C * RA * Sm5C * Sm5C * Sm5C * RA * Sm5C * ST * SmCn001RmG * SmCn001RmC * SmA | CCTCACTCAC CCACTCGCCA | 394 | S nR O nR S SSRSS SRSSS nR S nR S |
| WV-23442 | mC * Sm5Ceon001RTeom5Ceon001RmA * Sm5C * ST * Sm5C * RA * Sm5C * Sm5C * Sm5C * RA * Sm5C * ST * SmCn001RmGmCn001RmC * SmA | CCTCACTCAC CCACTCGCCA | 395 | S nR O nR S SSRSS SRSSS nR O nR S |
| WV-23443 | mC * Sm5CeoTeom5CeomA * Sm5C * ST * Sm5C * RA * Sm5C * Sm5C * Sm5C * RA * Sm5C * ST * Sm5Ceo * SmG * SmC * Sm5Ceo * SmA | CCTCACTCAC CCACTCGCCA | 396 | SOOOS SSRSS SR SSSSS SS |
| WV-23444 | mC * Sm5Ceon001RTeom5Ceon001RmA * Sm5C * ST * Sm5C * RA * Sm5C * Sm5C * Sm5C * RA * Sm5C * ST * SmCn001RmG * SmC * SmCn001RmA | CCTCACTCAC CCACTCGCCA | 397 | S nR O nR S SSRSS SRSSS nR SS nR |
| WV-23453 | mA * Sm5CeoTeom5CeomA * Sm5C * Sm5C * Sm5C * RA * Sm5C * ST * Sm5C * RG * Sm5C * Sm5C * SmA * SmC * Sm5mC * SmG * SmC | ACTCACCCAC TCGCCACCGC | 398 | SOOOS SSRSS SR SSSSS SS |
| WV-23454 | mA * Sm5Ceon001RTeom5Ceon001RmA * Sm5C * Sm5C * Sm5C * RA * Sm5C * ST * Sm5C * RG * Sm5C * Sm5C * SmAn001RmC * SmCn001RmG * SmC | ACTCACCCAC TCGCCACCGC | 399 | SnR O nR S SSRSS SRSSS nR S nR S |
| WV-23455 | mA * Sm5Ceon001RTeom5Ceon001RmA * Sm5C * Sm5C * Sm5C * RA * Sm5C * ST * Sm5C * RG * Sm5C * Sm5C * SmAn001RmCmCn001RmG * SmC | ACTCACCCAC TCGCCACCGC | 400 | SnR O nR S SSRSS SRSSS nR O nR S |
| WV-23456 | mA * Sm5Ceon001RTeom5Ceon001RmA * Sm5C * Sm5C * Sm5C * RA * Sm5C * ST * Sm5C * RG * Sm5C * Sm5C * SmA * SmC * SmCn001RmG * SmC | ACTCACCCAC TCGCCACCGC | 401 | SnR O nR S SSRSS SR SSSSS nR S |
| WV-23457 | mA * Sm5CeoTeom5CeomA * Sm5C * Sm5C * Sm5C * RA * Sm5C * ST Sm5C * SG * Rm5C * Sm5C * SmA * SmC * Sm5mC * SmG * SmC | ACTCACCCAC TCGCCACCGC | 402 | SOOOS SSRSS SSR SSSSS S |
| WV-23458 | mA * Sm5CeoTeom5CeomA * Sm5C * Sm5C * Sm5C * RA * Sm5C * ST * Sm5C * SG * Rm5C * Sm5C * SmAn001RmC * SmCn001RmG * SmC | ACTCACCCAC TCGCCACCGC | 403 | SOOOS SSRSS SSRSS nR S nR S |

TABLE A1-continued

| ID | Description | Base Sequence | SEQ ID NO | Stereochemistry/ Internucleotidic Linkages |
|---|---|---|---|---|
| oligonucleotides and compositions including C9orf72 and compositions. | | | | |
| WV-23459 | mA * Sm5CeoTeom5CeomA * Sm5C * Sm5C * Sm5C * RA * Sm5C * ST * Sm5C * SG * Rm5C * Sm5C * SmAn001RmCmCn001RmG * SmC | ACTCACCCAC TCGCCACCGC | 40 | SOOOS SSRSS SSRSS nR O nR S |
| WV-23460 | mA * Sm5CeoTeom5CeomA * Sm5C * Sm5C * Sm5C * RA * Sm5C * ST * Sm5C * SG * Rm5C * Sm5C * SmA * SmC * SmCn001RmG * SmC | ACTCACCCAC TCGCCACCGC | 405 | SOOOS SSRSS SSRSS SS nR S |
| WV-23461 | mA * Sm5CeoTeom5CeomA * Sm5C * Sm5C * Sm5C * RA * Sm5C * ST * Sm5C * RG * Sm5C * Sm5C * SmA * SmC * Sm5Ceo * SmG * SmC | ACTCACCCAC TCGCCACCGC | 406 | SOOOS SSRSS SR SSSSS SS |
| WV-23462 | mA * Sm5CeoTeom5CeomA * Sm5C * Sm5C * Sm5C * RA * Sm5C * ST * Sm5C * SG * Rm5C * Sm5C * SmA * SmC * Sm5Ceo * SmG * SmC | ACTCACCCAC TCGCCACCGC | 407 | SOOOS SSRSS SSR SSSSS S |
| WV-23486 | mC * Sm5CeoTeom5CeomA * SC * ST * SC * RA * SC * SC * SC * RA * SC * ST * Sm5mC * SmG * SmC * SmC | CCTCACTCAC CCACTCGCC | 408 | SOOOS SSRSS SR SSSSS S |
| WV-23487 | mC * Sm5CeoTeom5CeomA * Sm5C * ST * Sm5C * RA * Sm5C * Sm5C * Sm5C * RA * Sm5C * ST * Sm5mC * SmG * SmC * SmC | CCTCACTCAC CCACTCGCC | 409 | SOOOS SSRSS SR SSSSS S |
| WV-23488 | mC * Sm5Ceon001RTeom5Ceon001RmA * Sm5C * ST * Sm5C * RA * Sm5C * Sm5C * Sm5C * RA * Sm5C * ST * Sm5mC * SmGn001RmC * SmC | CCTCACTCAC CCACTCGCC | 410 | SnR O nR S SSRSS S RSSSS nR S |
| WV-23489 | mC * Sm5Ceon001RTeom5Ceon001RmA * Sm5C * ST * Sm5C * RA * Sm5C * Sm5C * Sm5C * RA * Sm5C * ST * Sm5mCmGn001RmC * SmC | CCTCACTCAC CCACTCGCC | 411 | SnR O nR S SSRSS SRSSS O nR S |
| WV-23490 | mC * Sm5Ceon001RTeom5Ceon001RmA * Sm5C * ST * Sm5C * RA * Sm5C * Sm5C * Sm5C * RA * Sm5C * ST * SmCn001RmG * SmC * SmC | CCTCACTCAC CCACTCGCC | 412 | SnR O nR S SSRSS SRSSS nR SS |
| WV-23491 | mC * Sm5CeoTeom5CeomA * Sm5C * ST * Sm5C * RA * Sm5C * Sm5C * Sm5C * RA * Sm5C * ST * Sm5mC * SmG * SmC * Sm5mC * SmG | CCTCACTCAC CCACTCGCCG | 413 | SOOOS SSRSS SR SSSSS SS |
| WV-23492 | mC * Sm5Ceon001RTeom5Ceon001RmA * Sm5C * ST * Sm5C * RA * Sm5C * Sm5C * Sm5C * RA * Sm5C * ST * SmCn001RmG * SmCn001RmC * SmG | CCTCACTCAC CCACTCGCCG | 414 | SnR O nR S SSRSS SRSSS nR S nR S |
| WV-23493 | mC * Sm5Ceon001RTeom5Ceon001RmA * Sm5C * ST * Sm5C * RA * Sm5C * Sm5C * Sm5C * RA * Sm5C * ST * SmCn001RmGmCn001RmC * SmG | CCTCACTCAC CCACTCGCCG | 415 | S nR O nR S SSRSS SRSSS nR O nR S |
| WV-23494 | mC * Sm5Ceon001RTeom5Ceon001RmA * Sm5C * ST * Sm5C * RA * Sm5C * Sm5C * Sm5C * RA * Sm5C * ST * SmCn001RmG * SmC * SmCn001RmG | CCTCACTCAC CCACTCGCCG | 416 | S nR O nR S SSRSS SRSSS nR SS nR |
| WV-23495 | mA * Sm5Ceon001RTeom5Ceon001RmA * Sm5C * Sm5C * Sm5C * RA * Sm5C * ST * Sm5C * SG * Rm5C * Sm5C * SmAn001RmC * SmCn001RmG * SmC | ACTCACCCAC TCGCCACCGC | 417 | SnR O nR S SSRSS SSRSS nR S nR S |

TABLE A1-continued oligonucleotides and compositions including C9orf72 and compositions.

| ID | Description | Base Sequence | SEQ ID NO | Stereochemistry/ Internucleotidic Linkages |
|---|---|---|---|---|
| WV-23496 | mA * Sm5Ceon001RTeom5Ceon001RmA * Sm5C * Sm5C * Sm5C * RA * Sm5C * ST * Sm5C * SG * Rm5C * Sm5C * SmAn001RmCmCn001RmG * SmC | ACTCACCCAC TCGCCACCGC | 418 | S nR O nR S SSRSS SSRSS nR O nR S |
| WV-23497 | mA * Sm5Ceon001RTeom5Ceon001RmA * Sm5C * Sm5C * Sm5C * RA * Sm5C * ST * Sm5C * SG * Rm5C * Sm5C * SmA * SmC * SmCn001RmG * SmC | ACTCACCCAC TCGCCACCGC | 419 | SnR O nR S SSRSS SSRSS SS nR S |
| WV-23498 | mA * Sm5Ceon001RTeom5Ceon001RmA * Sm5C * Sm5C * Sm5C * RA * Sm5C * ST * Sm5C * SG * Rm5C * Sm5C * SmA * SmCmCn001RmG * SmC | ACTCACCCAC TCGCCACCGC | 420 | SnR O nR S SSRSS SSRSS SO nR S |
| WV-23503 | mC * Sm5CeoTeom5CeomA * Sm5C * ST * Sm5C * RA * Sm5C * Sm5C * Rm5C * SA * Sm5C * ST * Sm5mC * SmG * SmC * Sm5mC * SmG | CCTCACTCAC CCACTCGCCG | 42 | SOOOS SSRSS R SSSSS SSS |
| WV-23648 | mC * Sm5CeoTeom5CeomA * Sm5C * ST * Sm5C * RA * Sm5C * Sm5C * Sm5C * RA * Sm5C * ST * Sm5Ceo * SmG * SmC * SmC | CCTCACTCAC CCACTCGCC | 422 | SOOOS SSRSS SR SSSSS S |
| WV-23649 | mC * Sm5CeoTeom5CeomA * Sm5C * ST * Sm5C * RA * Sm5C * Sm5C * Sm5C * RA * Sm5C * ST * Sm5Ceo * SmG * SmC * Sm5Ceo * SmG | CCTCACTCAC CCACTCGCCG | 423 | SOOOS SSRSS SR SSSSS SS |
| WV-23650 | mC * Sm5CeoTeom5CeomA * Sm5C * ST * Sm5C * RA * Sm5C * Sm5C * Rm5C * SA * Sm5C * ST * Sm5Ceo * SmG * SmC * Sm5Ceo * SmG | CCTCACTCAC CCACTCGCCG | 424 | SOOOS SSRSS R SSSSS SSS |
| WV-23740 | mC * Sm5CeoTeom5CeomA * SC * ST * SC * RA * SC * SC * SC * RA * SC * ST * Sm5mC * SmG * SmC * Sm5mC * SmG | CCTCACTCAC CCACTCGCCG | 425 | SOOOS SSRSS SR SSSSS SS |
| WV-23741 | mA * Sm5CeoTeom5CeomA * SC * SC * SC * RA * SC * ST * Sm5C * SG * RC * SC * SmA * SmC * Sm5mC * SmG * SmC | ACTCACCCAC TCGCCACCGC | 426 | SOOOS SSRSS SSR SSSSS S |
| WV-23742 | mA * Sm5CeoTeom5CeomA * SC * SC * SC * RA * SC * ST * Sm5C * SG * RC * Sm5C * SmA * SmC * Sm5mC * SmG * SmC | ACTCACCCAC TCGCCACCGC | 427 | SOOOS SSRSS SSR SSSSS S |
| WV-26633 | mA * Sm5CeoTeom5CeomA * SC * SC * SC * RA * SC * ST * Sm5C * SG * Rm5C * SC * SmA * SmC * Sm5mC * SmG * SmC | ACTCACCCAC TCGCCACCGC | 428 | SOOOS SSRSS SSR SSSSS S |
| WV-27092 | mC * Sm5CeoTeom5CeomA * SC * ST * SC * RA * SC * SC * SC * RA * SC * ST * Sm5mC * SmG * SmC * Sm5mC * SmC | CCTCACTCAC CCACTCGCCC | 429 | SOOOS SSRSS SR SSSSS SS |
| WV-27093 | mC * Sm5CeoTeom5CeomA * SC * ST * SC * RA * SC * SC * SC * RA * SC * ST * Sm5mC * SmG * SmC * SmC * SmC | CCTCACTCAC CCACTCGCCC | 430 | SOOOS SSRSS SR SSSSS SS |
| WV-27094 | mC * Sm5CeoTeom5CeomA * SC * ST * SC * RA * SC * SC * SC * RA * SC * ST * Sm5mC * SmG * SmC * Sm5mC * SmU | CCTCACTCAC CCACTCGCCU | 431 | SOOOS SSRSS SR SSSSS SS |
| WV-27095 | mC * Sm5CeoTeom5CeomA * SC * ST * SC * RA * SC * SC * SC * RA * SC * ST * Sm5mC * SmG * SmC * SmC * SmU | CCTCACTCAC CCACTCGCCU | 432 | SOOOS SSRSS SR SSSSS SS |

TABLE A1-continued oligonucleotides and compositions including C9orf72 and compositions.

| ID | Description | Base Sequence | SEQ ID NO | Stereochemistry/ Internucleotidic Linkages |
|---|---|---|---|---|
| WV-27104 | mC * Sm5CeoTeom5CeomA * SC * ST * SC * RA * SC * SC * SC * RA * SC * ST * Sm5mC * SmG * Sm5mC * Sm5mC * SmG | CCTCACTCAC CCACTCGCCG | 433 | SOOOS SSRSS SR SSSSS SS |
| WV-27105 | mC * Sm5CeoTeom5CeomA * SC * ST * SC * RA * SC * SC * SC * RA * SC * ST * Sm5mCmG * SmC * Sm5mC * SmG | CCTCACTCAC CCACTCGCCG | 434 | SOOOS SSRSS SRSSS OSSS |
| WV-27106 | mC * Sm5CeoTeom5CeomA * SC * ST * SC * RA * SC * SC * SC * RA * SC * ST * Sm5mC * SmG * SmC * Sm5mCmG | CCTCACTCAC CCACTCGCCG | 435 | SOOOS SSRSS SR SSSSS SO |
| WV-27107 | mC * Sm5CeoTeom5CeomA * SC * ST * SC * RA * SC * SC * SC * RA * SC * ST * Sm5mCmG * SmC * Sm5mCmG | CCTCACTCAC CCACTCGCCG | 436 | SOOOS SSRSS SRSSS OSSO |
| WV-27108 | mC * Sm5CeoTeom5CeomA * SC * ST * SC * RA * SC * SC * SC * RA * SC * ST * Sm5CeomG * SmC * Sm5mC * SmG | CCTCACTCAC CCACTCGCCG | 437 | SOOOS SSRSS SRSSS OSSS |
| WV-27109 | mC * Sm5CeoTeom5CeomA * SC * ST * SC * RA * SC * SC * SC * RA * SC * ST * Sm5mC * SmG * SmC * Sm5CeomG | CCTCACTCAC CCACTCGCCG | 438 | SOOOS SSRSS SR SSSSS SO |
| WV-27110 | mC * Sm5CeoTeom5CeomA * SC * ST * SC * RA * SC * SC * SC * RA * SC * ST * Sm5CeomG * SmC * Sm5CeomG | CCTCACTCAC CCACTCGCCG | 439 | SOOOS SSRSS SRSSS OSSO |
| WV-27134 | mC * Sm5CeoTeom5CeomA * SC * ST * SC * RA * SC * SC * RC * SA * SC * ST * Sm5mC * SmG * Sm5mC * Sm5mC * SmG | CCTCACTCAC CCACTCGCCG | 440 | SOOOS SSRSS R SSSSS SSS |
| WV-27135 | mC * Sm5CeoTeom5CeomA * SC * ST * SC * RA * SC * SC * RC * SA * SC * ST * Sm5mCmG * SmC * Sm5mC * SmG | CCTCACTCAC CCACTCGCCG | 441 | SOOOS SSRSS RSSSS OSSS |
| WV-27136 | mC * Sm5CeoTeom5CeomA * SC * ST * SC * RA * SC * SC * RC * SA * SC * ST * Sm5mC * SmG * SmC * Sm5mCmG | CCTCACTCAC CCACTCGCCG | 442 | SOOOS SSRSS R SSSSS SSO |
| WV-27137 | mC * Sm5CeoTeom5CeomA * SC * ST * SC * RA * SC * SC * RC * SA * SC * ST * Sm5mCmG * SmC * Sm5mCmG | CCTCACTCAC CCACTCGCCG | 443 | SOOOS SSRSS RSSSS OSSO |
| WV-27138 | mC * Sm5CeoTeom5CeomA * SC * ST * SC * RA * SC * SC * RC * SA * SC * ST * Sm5CeomG * SmC * Sm5mC * SmG | CCTCACTCAC CCACTCGCCG | 444 | SOOOS SSRSS RSSSS OSSS |
| WV-27139 | mC * Sm5CeoTeom5CeomA * SC * ST * SC * RA * SC * SC * RC * SA * SC * ST * Sm5mC * SmG * SmC * Sm5CeomG | CCTCACTCAC CCACTCGCCG | 445 | SOOOS SSRSS R SSSSS SSO |
| WV-27140 | mC * Sm5CeoTeom5CeomA * SC * ST * SC * RA * SC * SC * RC * SA * SC * ST * Sm5CeomG * SmC * Sm5CeomG | CCTCACTCAC CCACTCGCCG | 446 | SOOOS SSRSS RSSSS OSSO |
| WV-27141 | mC * Sm5CeoTeom5CeomA * SC * ST * SC * RA * SC * SC * RC * SA * SC * ST * Sm5mC * SmG * SmC * Sm5mC * SmC | CCTCACTCAC CCACTCGCCC | 447 | SOOOS SSRSS R SSSSS SSS |

TABLE A1-continued oligonucleotides and compositions including C9orf72 and compositions.

| ID | Description | Base Sequence | SEQ ID NO | Stereochemistry/ Internucleotidic Linkages |
|---|---|---|---|---|
| WV-27142 | mC * Sm5CeoTeom5CeomA * SC * ST * SC * RA * SC * SC * RC * SA * SC * ST * Sm5mC * SmG * SmC * SmC * SmC | CCTCACTCAC CCACTCGCCC | 448 | SOOOS SSRSS R SSSSS SSS |
| WV-27143 | mC * Sm5CeoTeom5CeomA * SC * ST * SC * RA * SC * SC * RC * SA * SC * ST * Sm5mC * SmG * SmC * Sm5mC * SmU | CCTCACTCAC CCACTCGCCU | 449 | SOOOS SSRSS R SSSSS SSS |
| WV-27144 | mC * Sm5CeoTeom5CeomA * SC * ST * SC * RA * SC * SC * RC * SA * SC * ST * Sm5mC * SmG * SmC * SmC * SmU | CCTCACTCAC CCACTCGCCU | 450 | SOOOS SSRSS R SSSSS SSS |
| WV-28078 | mC * Sm5CeoTeom5CeomA * SC * ST * SC * RA * SC * SC * RC * SA * SC * ST * Sm5mC * SmG * SmC * SmU * SmG | CCTCACTCACCCAC TCGCUG | 452 | SOOOS SSRSS RSSSS SSSS |
| WV-28079 | mC * Sm5CeoTeom5CeomA * SC * ST * SC * RA * SC * SC * RC * SA * SC * ST * SmU * SmG * SmC * SmU * SmG | CCTCACTCACCCAC TUGCUG | 453 | SOOOS SSRSS RSSSS SSSS |
| WV-28080 | mC * Sm5CeoTeom5CeomA * SC * ST * SC * RA * SC * SC * SC * RA * SC * ST * SmU * SmG * SmC * SmC | CCTCACTCACCCAC TUGCC | 454 | SOOOS SSRSS SRSSS SSS |
| WV-28081 | mA * Sm5CeoTeom5CeomA * SC * SC * SC * RA * SC * ST * ST * RG * SC * SC * SmA * SmC * Sm5mC * SmG * SmC | ACTCACCCACTTGC CACCGC | 455 | SOOOS SSRSS SRSSS SSSS |
| WV-28082 | mA * Sm5CeoTeom5CeomA * SC * SC * SC * RA * SC * ST * Sm5C * RG * SC * SC * SmA * SmC * SmU * SmG * SmC | ACTCACCCACTCG CCACUGC | 456 | SOOOS SSRSS SRSSS SSSS |
| WV-28083 | mA * Sm5CeoTeom5CeomA * SC * SC * SC * RA * SC * ST * ST * RG * SC * SC * SmA * SmC * SmU * SmG * SmC | ACTCACCCACTTGC CACUGC | 457 | SOOOS SSRSS SRSSS SSSS |
| WV-28084 | mA * Sm5CeoTeom5CeomA * SC * SC * SC * RA * SC * ST * ST * RG * SC * Sm5C * SmA * SmC * Sm5mC * SmG * SmC | ACTCACCCACTTGC CACCGC | 458 | SOOOS SSRSS SRSSS SSSS |
| WV-28085 | mA * Sm5CeoTeom5CeomA * SC * SC * SC * RA * SC * ST * Sm5C * RG * SC * Sm5C * SmA * SmC * SmU * SmG * SmC | ACTCACCCACTCG CCACUGC | 459 | SOOOS SSRSS SRSSS SSSS |
| WV-28086 | mA * Sm5CeoTeom5CeomA * SC * SC * SC * RA * SC * ST * ST * RG * SC * Sm5C * SmA * SmC * SmU * SmG * SmC | ACTCACCCACTTGC CACUGC | 460 | SOOOS SSRSS SRSSS SSSS |
| WV-28087 | mA * Sm5CeoTeom5CeomA * SC * SC * SC * RA * SC * ST * ST * SG * RC * SC * SmA * SmC * Sm5mC * SmG * SmC | ACTCACCCACTTGC CACCGC | 461 | SOOOS SSRSS SSRSS SSSS |
| WV-28088 | mA * Sm5CeoTeom5CeomA * SC * SC * SC * RA * SC * ST * Sm5C * SG * RC * SC * SmA * SmC * SmU * SmG * SmC | ACTCACCCACTCG CCACUGC | 462 | SOOOS SSRSS SSRSS SSSS |
| WV-28089 | mA * Sm5CeoTeom5CeomA * SC * SC * SC * RA * SC * ST * ST * SG * RC * SC * SmA * SmC * SmU * SmG * SmC | ACTCACCCACTTGC CACUGC | 463 | SOOOS SSRSS SSRSS SSSS |
| WV-28090 | mA * Sm5CeoTeom5CeomA * SC * SC * SC * RA * SC * ST * ST * SG * Rm5C * SC * SmA * SmC * Sm5mC * SmG * SmC | ACTCACCCACTTGC CACCGC | 464 | SOOOS SSRSS SSRSS SSSS |

TABLE A1-continued oligonucleotides and compositions including C9orf72 and compositions.

| ID | Description | Base Sequence | SEQ ID NO | Stereochemistry/ Internucleotidic Linkages |
|---|---|---|---|---|
| WV-28091 | mA * Sm5CeoTeom5CeomA * SC * SC * SC * RA * SC * ST * Sm5C * SG * Rm5C * SC * SmA * SmC * SmU * SmG * SmC | ACTCACCCACTCG CCACUGC | 465 | SOOOS SSRSS SSRSS SSSS |
| WV-28092 | mA * Sm5CeoTeom5CeomA * SC * SC * SC * RA * SC * ST * ST * SG * Rm5C * SC * SmA * SmC * SmU * SmG * SmC | ACTCACCCACTTGC CACUGC | 466 | SOOOS SSRSS SSRSS SSSS |
| WV-28303 | mA * Sm5CeoTeom5CeomA * SC * SC * SC * RA * SC * ST * ST * RG * SC * SC * SmA * SmC * Sm5Ceo * SmG * SmC | ACTCACCCACTTGC CACCGC | 467 | SOOOS SSRSS SRSSS SSSS |
| WV-28304 | mA * Sm5CeoTeom5CeomA * SC * SC * SC * RA * SC * ST * ST * RG * SC * SC * SmA * SmC * Sm5CeomG * SmC | ACTCACCCACTTGC CACCGC | 468 | SOOOS SSRSS SRSSS SSOS |
| WV-28305 | mA * Sm5CeoTeom5CeomA * SC * SC * SC * RA * SC * ST * ST * RG * SC * Sm5C * SmA * SmC * Sm5Ceo * SmG * SmC | ACTCACCCACTTGC CACCGC | 469 | SOOOS SSRSS SRSSS SSSS |
| WV-28306 | mA * Sm5CeoTeom5CeomA * SC * SC * SC * RA * SC * ST * ST * RG * SC * Sm5C * SmA * SmC * Sm5CeomG * SmC | ACTCACCCACTTGC CACCGC | 470 | SOOOS SSRSS SRSSS SSOS |
| WV-28307 | mA * Sm5CeoTeom5CeomA * SC * SC * SC * RA * SC * ST * ST * SG * RC * SC * SmA * SmC * Sm5Ceo * SmG * SmC | ACTCACCCACTTGC CACCGC | 471 | SOOOS SSRSS SSRSS SSSS |
| WV-28308 | mA * Sm5CeoTeom5CeomA * SC * SC * SC * RA * SC * ST * ST * SG * RC * SC * SmA * SmC * Sm5CeomG * SmC | ACTCACCCACTTGC CACCGC | 472 | SOOOS SSRSS SSRSS SSOS |
| WV-28464 | mC * Sm5CeoTeom5CeomA * SC * ST * SC * RA * SC * SC * RC * SA * SC * ST * SmU * SmG * SmC * SmC * SmA | CCTCACTCACCCAC TUGCCA | 473 | SOOOS SSRSS RSSSS SSSS |
| WV-28465 | mC * Sm5CeoTeom5CeomA * SC * ST * SC * RA * SC * SC * RC * SA * SC * ST * SmU * SmG * SmC * Sm5mC * SmA | CCTCACTCACCCAC TUGCCA | 474 | SOOOS SSRSS RSSSS SSSS |
| WV-28466 | mC * Sm5CeoTeom5CeomA * SC * ST * SC * RA * SC * SC * RC * SA * SC * ST * Sm5mC * SmG * SmC * SmU * SmA | CCTCACTCACCCAC TCGCUA | 475 | SOOOS SSRSS RSSSS SSSS |
| WV-28467 | mC * Sm5CeoTeom5CeomA * SC * ST * SC * RA * SC * SC * RC * SA * SC * ST * SmU * SmG * SmC * SmU * SmA | CCTCACTCACCCAC TUGCUA | 476 | SOOOS SSRSS RSSSS SSSS |
| WV-28478 | mC * Sm5CeoTeom5CeomA * SC * ST * SC * RA * SC * SC * RC * SA * SC * ST * Sm5Ceo * SmG * SmC * Sm5Ceo * SmG | CCTCACTCACCCAC TCGCCG | 477 | SOOOS SSRSS RSSSS SSSS |
| WV-28479 | mC * Sm5CeoTeom5CeomA * SC * ST * SC * RA * SC * SC * SC * RA * SC * ST * Sm5Ceo * SmG * SmC * SmC | CCTCACTCACCCAC TCGCC | 478 | SOOOS SSRSS SRSSS SSS |
| WV-28480 | mC * Sm5CeoTeom5CeomA * SC * ST * SC * RA * SC * SC * SC * RA * SC * ST * Sm5CeomG * SmC * SmC | CCTCACTCACCCAC TCGCC | 479 | SOOOS SSRSS SRSSS OSS |

TABLE A1-continued oligonucleotides and compositions including C9orf72 and compositions.

| ID | Description | Base Sequence | SEQ ID NO | Stereochemistry/ Internucleotidic Linkages |
|---|---|---|---|---|
| WV-28481 | mC * Sm5CeoTeom5CeomA * SC * ST * SC * RA * SC * SC * SC * RA * SC * ST * SmU * SmG * SmC * SmU * SmG | CCTCACTCACCCAC TUGCUG | 480 | SOOOS SSRSS SRSSS SSSS |
| WV-28872 | mC * Sm5CeoTeom5CeomA * SC * ST * RC * SA * SC * SC * RC * SA * SC * ST * SmC * SmG * SmC * SmC * SmA | CCTCACTCACCCAC TCGCCA | 481 | SOOOS SRSSS RSSSS SSSS |
| WV-28873 | mC * Sm5CeoTeom5CeomA * SC * ST * RC * SA * SC * SC * RC * SA * SC * ST * Sm5mC * SmG * SmC * Sm5mC * SmG | CCTCACTCACCCAC TCGCCG | 482 | SOOOS SRSSS RSSSS SSSS |
| WV-28874 | mC * Sm5CeoTeom5CeomA * SC * ST * RC * SA * SC * SC * SC * RA * SC * ST * SmC * SmG * SmC * SmC * SmA | CCTCACTCACCCAC TCGCCA | 483 | SOOOS SRSSS SRSSS SSSS |
| WV-28875 | mC * Sm5CeoTeom5CeomA * SC * ST * RC * SA * SC * SC * SC * RA * SC * ST * Sm5mC * SmG * SmC * Sm5mC * SmG | CCTCACTCACCCAC TCGCCG | 484 | SOOOS SRSSS SRSSS SSSS |
| WV-28876 | mC * Sm5CeoTeom5CeomA * SC * ST * RC * SA * SC * RC * SC * SA * RC * ST * SmC * SmG * SmC * SmC * SmA | CCTCACTCACCCAC TCGCCA | 485 | SOOOS SRSSR SSRSS SSSS |
| WV-28877 | mC * Sm5CeoTeom5CeomA * SC * ST * RC * SA * SC * RC * SC * SA * RC * ST * Sm5mC * SmG * SmC * Sm5mC * SmG | CCTCACTCACCCAC TCGCCG | 486 | SOOOS SRSSR SSRSS SSSS |
| WV-30206 | mA * Sm5CeoTeom5CeomA * SC * SC * SC * RA * SC * ST * Sm5C * SG * Rm5C * SC * SmA * SmC * Sm5Ceo * SmG * SmC | ACTCACCCACTCG CCACCGC | 487 | SOOOS SSRSS SSRSS SSSS |
| WV-30207 | mA * Sm5Ceon001RTeon001Rm5Ceon001RmA * SC * SC * SC * RA * SC * ST * Sm5C * SG * Rm5C * SC * SmA * SmC * Sm5Ceo * SmG * SmC | ACTCACCCACTCG CCACCGC | 488 | SnRnRnRS SSRSS SSRSS SSSS |
| WV-30208 | mA * Sm5Ceon001RTeom5Ceon001RmA * SC * SC * SC * RA * SC * ST * Sm5C * SG * Rm5C * SC * SmA * SmC * Sm5Ceo * SmG * SmC | ACTCACCCACTCG CCACCGC | 489 | SnROnRS SSRSS SSRSS SSSS |
| WV-30209 | mA * Sm5Ceon001RTeom5Ceon001RmA * SC * SC * SC * RA * SC * ST * Sm5C * SG * Rm5C * SC * SmAn001RmC * Sm5Ceo * SmG * SmC | ACTCACCCACTCG CCACCGC | 490 | SnROnRS SSRSS SSRSS nRSSS |
| WV-30210 | mA * Sm5Ceon001RTeom5Ceon001RmA * SC * SC * SC * RA * SC * ST * Sm5C * SG * Rm5C * SC * SmA * SmCn001Rm5Ceo * SmG * SmC | ACTCACCCACTCG CCACCGC | 491 | SnROnRS SSRSS SSRSS SnRSS |
| WV-30211 | mA * Sm5Ceon001RTeom5Ceon001RmA * SC * SC * SC * RA * SC * ST * Sm5C * SG * Rm5C * SC * SmA * SmC * Sm5Ceon001RmG * SmC | ACTCACCCACTCG CCACCGC | 492 | SnROnRS SSRSS SSRSS SSnRS |
| WV-30212 | mA * Sm5Ceon001RTeom5Ceon001RmA * SC * SC * SC * RA * SC * ST * Sm5C * SG * Rm5C * SC * SmA * SmC * Sm5Ceo * SmGn001RmC | ACTCACCCACTCG CCACCGC | 493 | SnROnRS SSRSS SSRSS SSSnR |
| WV-30213 | mA * Sm5Ceon001RTeom5Ceon001RmA * SC * SC * SC * RA * SC * ST * Sm5C * SG * Rm5C * SC * SmA * SmC * SmU * SmG * SmC | ACTCACCCACTCG CCACUGC | 494 | SnROnRS SSRSS SSRSS SSSS |
| WV-30214 | mA * Sm5Ceon001RTeom5Ceon001RmA * SC * SC * SC * RA * SC * ST * Sm5C * SG * Rm5C * SC * SmAn001RmC * SmU * SmG * SmC | ACTCACCCACTCG CCACUGC | 495 | SnROnRS SSRSS SSRSS nRSSS |

TABLE A1-continued oligonucleotides and compositions including C9orf72 and compositions.

| ID | Description | Base Sequence | SEQ ID NO | Stereochemistry/ Internucleotidic Linkages |
|---|---|---|---|---|
| WV-30215 | mA * Sm5Ceon001RTeom5Ceon001RmA * SC * SC * SC * RA * SC * ST * Sm5C * SG * Rm5C * SC * SmA * SmCn001RmU * SmG * SmC | ACTCACCCACTCG CCACUGC | 496 | SnROnRS SSRSS SSRSS SnRSS |
| WV-30216 | mA * Sm5Ceon001RTeom5Ceon001RmA * SC * SC * SC * RA * SC * ST * Sm5C * SG * Rm5C * SC * SmA * SmC * SmUn001RmG * SmC | ACTCACCCACTCG CCACUGC | 497 | SnROnRS SSRSS SSRSS SSnRS |
| WV-30217 | mA * Sm5Ceon001RTeom5Ceon001RmA * SC * SC * SC * RA * SC * ST * Sm5C * SG * Rm5C * SC * SmA * SmC * SmU * SmGn001RmC | ACTCACCCACTCG CCACUGC | 498 | SnROnRS SSRSS SSRSS SSSnR |
| WV-30218 | mC * Sm5CeoTeom5CeomA * SC * ST * SC * RA * SC * SC * SC * RA * SC * ST * Sm5Ceo * SmG * SmC * Sm5Ceo * SmG | CCTCACTCACCCAC TCGCCG | 499 | SOOOS SSRSS SRSSS SSSS |
| WV-30219 | mC * Sm5Ceon001RTeon001Rm5Ceon001RmA * SC * ST * SC * RA * SC SC * SC * RA * SC * ST * Sm5Ceo * SmG * SmC * Sm5Ceo * SmG | CCTCACTCACCCAC TCGCCG | 500 | SnRnRnRS SSRSS SRSSS SSSS |
| WV-30220 | mC * Sm5Ceon001RTeom5Ceon001RmA * SC * ST * SC * RA * SC * SC * SC * RA * SC * ST * Sm5Ceo * SmG * SmC * Sm5Ceo * SmG | CCTCACTCACCCAC TCGCCG | 501 | SnROnRS SSRSS SRSSS SSSS |
| WV-30221 | mC * Sm5Ceon001RTeom5Ceon001RmA * SC * ST * SC * RA * SC * SC * SC * RA * SC * ST * Sm5Ceon001RmG * SmC * Sm5Ceo * SmG | CCTCACTCACCCAC TCGCCG | 502 | SnROnRS SSRSS SRSSS nRSSS |
| WV-30222 | mC * Sm5Ceon001RTeom5Ceon001RmA * SC * ST * SC * RA * SC * SC * SC * RA * SC * ST * Sm5Ceo * SmGn001RmC * Sm5Ceo * SmG | CCTCACTCACCCAC TCGCCG | 503 | SnROnRS SSRSS SRSSS SnRSS |
| WV-30223 | mC * Sm5Ceon001RTeom5Ceon001RmA * SC * ST * SC * RA * SC * SC * SC * RA * SC * ST * Sm5Ceo * SmG * SmCn001Rm5Ceo * SmG | CCTCACTCACCCAC TCGCCG | 504 | SnROnRS SSRSS SRSSS SSnRS |
| WV-30224 | mC * Sm5Ceon001RTeom5Ceon001RmA * SC * ST * SC * RA * SC * SC * SC * RA * SC * ST * Sm5Ceo * SmG * SmC * Sm5Ceon001RmG | CCTCACTCACCCAC TCGCCG | 505 | SnROnRS SSRSS SRSSS SSSnR |
| WV-30225 | m5Ceo * Sm5CeoTeom5CeoAeo * SC * ST * SC * RA * SC * SC * SC * RA SC * ST * SmU * SmG * SmC * SmU * SmG | CCTCACTCACCCAC TUGCUG | 506 | SOOOS SSRSS SRSSS SSSS |
| WV-30226 | mC * SmC * SmU * SmC * SmA * SC * ST * SC * RA * SC * SC * SC * RA * SC * ST * STeoGeom5CeoTeo * SGeo | CCUCACTCACCCA CTTGCTG | 507 | SSSSS SSRSS SRSSS OOOS |
| WV-30227 | m5Ceo * Sm5CeoTeom5CeoAeo * SC * ST * SC * RA * SC * SC * SC * RA * SC * ST * STeoGeom5CeoTeo * SGeo | CCTCACTCACCCAC TTGCTG | 508 | SOOOS SSRSS SRSSS OOOS |
| WV-30228 | m5Ceo * Sm5Ceon001RTeon001Rm5Ceon001RAeo * SC * ST * SC * RA * SC * SC * SC * RA * SC * ST * SmU * SmG * SmC * SmU * SmG | CCTCACTCACCCAC TUGCUG | 509 | SnRnRnRS SSRSS SRSSS SSSS |
| WV-30229 | mC * SmC * SmU * SmC * SmA * SC * ST * SC * RA * SC * SC * SC * RA * SC * ST * STeon001RGeon001Rm5Ceon001RTeo * SGeo | CCUCACTCACCCA CTTGCTG | 510 | SSSSS SSRSS SRSSS nRnRnRS |

TABLE A1-continued oligonucleotides and compositions including C9orf72 and compositions.

| ID | Description | Base Sequence | SEQ ID NO | Stereochemistry/ Internucleotidic Linkages |
|---|---|---|---|---|
| WV-30230 | m5Ceo * Sm5Ceon001RTeon001Rm5Ceon001RAeo * SC * ST * SC * RA * SC * SC * SC * RA * SC * ST * STeoGeom5CeoTeo * SGeo | CCTCACTCACCCAC TTGCTG | 511 | SnRnRnRS SSRSS SRSSS OOOS |
| WV-30231 | m5Ceo * Sm5CeoTeom5CeoAeo * SC * ST * SC * RA * SC * SC * SC * RA SC * ST * STeon001RGeon001Rm5Ceon001RTeo * SGeo | CCTCACTCACCCAC TTGCTG | 512 | SOOOS SSRSS SRSSS nRnRnRS |
| WV-30232 | mA * Sm5Ceon001RTeon001Rm5Ceon001RmA * SC * SC * SC * RA * SC * ST * Sm5C * SG * Rm5C * SC * SmA * SmC * SmU * SmG * SmC | ACTCACCCACTCG CCACUGC | 513 | SnRnRnRS SSRSS SSRSS SSSS |
| WV-30237 | mC * Sm5CeoTeom5CeomA * SC * ST * SC * RA * SC * SC * RC * SA * SC * ST * STeo * SmG * SmC * SmC * SmA | CCTCACTCACCCAC TTGCCA | 514 | SOOOS SSRSS RSSSS SSSS |
| WV-30238 | mC * Sm5CeoTeom5CeomA * SC * ST * SC * RA * SC * SC * SC * RA * SC * ST * STeo * SmG * SmC * SmC | CCTCACTCACCCAC TTGCC | 515 | SOOOS SSRSS SRSSS SSS |
| WV-30239 | mA * Sm5CeoTeom5CeomA * SC * SC * SC * RA * SC * ST * Sm5C * SG * RC * SC * SmA * SmC * STeo * SmG * SmC | ACTCACCCACTCG CCACTGC | 516 | SOOOS SSRSS SSRSS SSSS |
| WV-30277 | mA * Sm5CeoTeom5CeomA * SC * SC * RC * SA * SC * RT * Sm5C * SG * Rm5C * SC * SmA * SmC * Sm5Ceo * SmG * SmC | ACTCACCCACTCG CCACCGC | 517 | SOOOS SRSSR SSRSS SSSS |
| WV-30278 | mA * Sm5Ceon001RTeon001Rm5Ceon001RmA * SC * SC * RC * SA * SC * RT * Sm5C * SG * Rm5C * SC * SmA * SmC * Sm5Ceo * SmG * SmC | ACTCACCCACTCG CCACCGC | 518 | SnRnRnRS SRSSR SSRSS SSSS |
| WV-30279 | mA * Sm5Ceon001RTeom5Ceon001RmA * SC * SC * RC * SA * SC * RT * Sm5C * SG * Rm5C * SC * SmA * SmC * Sm5Ceo * SmG * SmC | ACTCACCCACTCG CCACCGC | 519 | SnROnRS SRSSR SSRSS SSSS |
| WV-30280 | mA * Sm5Ceon001RTeom5Ceon001RmA * SC * SC * RC * SA * SC * RT * Sm5C * SG * Rm5C * SC * SmAn001RmC * Sm5Ceo * SmG * SmC | ACTCACCCACTCG CCACCGC | 520 | SnROnRS SRSSR SSRSS nRSSS |
| WV-30281 | mA * Sm5Ceon001RTeom5Ceon001RmA * SC * SC * RC * SA * SC * RT * Sm5C * SG * Rm5C * SC * SmA * SmCn001Rm5Ceo * SmG * SmC | ACTCACCCACTCG CCACCGC | 521 | SnROnRS SRSSR SSRSS SnRSS |
| WV-30282 | mA * Sm5Ceon001RTeom5Ceon001RmA * SC * SC * RC * SA * SC * RT * Sm5C * SG * Rm5C * SC * SmA * SmC * Sm5Ceon001RmG * SmC | ACTCACCCACTCG CCACCGC | 522 | SnROnRS SRSSR SSRSS SSnRS |
| WV-30283 | mA * Sm5Ceon001RTeom5Ceon001RmA * SC * SC * RC * SA * SC * RT * Sm5C * SG * Rm5C * SC * SmA * SmC * Sm5Ceo * SmGn001RmC | ACTCACCCACTCG CCACCGC | 523 | SnROnRS SRSSR SSRSS SSSnR |
| WV-34205 | mAm5CeoTeom5CeomACCCACTm5CGm5CCmAmCm5CeomGmC | ACTCACCCACTCG CCACCGC | 524 | SOOOSSSRSSSSRR SSSSS |
| WV-37246 | mlm5Ceon001RTeom5Ceon001RmACCCACTm5CGm5CCmAmCn001Rm5 CeomGmC | ICTCICCCACTCGCC ACCGC | 525 | SnROnRSSSRSSSSR SSSnRSS |

TABLE A1-continued oligonucleotides and compositions including C9orf72 and compositions.

| ID | Description | Base Sequence | SEQ ID NO | Stereochemistry/ Internucleotidic Linkages |
|---|---|---|---|---|
| WV-38627 | mA*m5CeoTeom5CeomA*C*C*C*A*C*T*m5C*G*m5C*C*mA*mC*m5C eo*mG*mC | ACTCACCCACTCGC CACCGC | 555 | XOOOXXXXXXXXX XXXXXXX |
| WV-39524 | mA*m5Ceon001Teom5Ceon001mA*C*C*C*A*C*T*m5C*G*m5C*C*mA* mC*m5Ceo*mGn001mC | ACTCACCCACTCGC CACCGC | 556 | XnXOnXXXXXXXXX XXXXXXXnX |
| WV-39526 | mA*m5Ceon001Teom5Ceon001mA*C*C*C*A*C*T*m5C*G*m5C*C*mA* mC*m5Ceon001mG*mC | ACTCACCCACTCGC CACCGC | 557 | XnXOnXXXXXXXXX XXXXXXnXX |
| WV-39527 | mA*Sm5Ceon001Teom5Ceon001mA*SC*SC*SC*RA*SC*ST*Sm5C*SG*R m5C*SC*SmA*SmC*Sm5Ceo*SmGn001mC | ACTCACCCACTCGC CACCGC | 558 | SnXOnXSSSRSSSSR SSSSSnX |
| WV-39528 | mA*Sm5Ceon001Teom5Ceon001mA*SC*SC*SC*RA*SC*ST*Sm5C*SG*R m5C*SC*SmA*SmC*Sm5Ceon001mG*SmC | ACTCACCCACTCGC CACCGC | 559 | SnXOnXSSSRSSSSR SSSSnXS |
| WV-39523 | mA*Sm5Ceon001STeom5Ceon001SmA*SC*SC*SC*RA*SC*ST*Sm5C*SG *Rm5C*SC*SmA*SmC*Sm5Ceo*SmGn001SmC | ACTCACCCACTCGC CACCGC | 560 | SnSOnSSSSRSSSSR SSSSSnS |
| WV-39525 | mA*Sm5Ceon001STeom5Ceon001SmA*SC*SC*SC*RA*SC*ST*Sm5C*SG *Rm5C*SC*SmA*SmC*Sm5Ceon001SmG*SmC | ACTCACCCACTCGC CACCGC | 561 | SnSOnSSSSRSSSSR SSSSnSS |
| WV-34452 | mA*Sm5Ceon001STeom5Ceon001RmA*SC*SC*SC*RA*SC*ST*Sm5C*S G*Rm5C*SC*SmA*SmC*Sm5Ceo*SmGn001RmC | ACTCACCCACTCGC CACCGC | 562 | SnSOnRSSSRSSSSR SSSSSnR |
| WV-34453 | mA*Sm5Ceon001RTeom5Ceon001SmA*SC*SC*SC*RA*SC*ST*Sm5C*S G*Rm5C*SC*SmA*SmC*Sm5Ceo*SmGn001RmC | ACTCACCCACTCGC CACCGC | 563 | SnROnSSSSRSSSSR SSSSSnR |
| WV-34466 | mA*Sm5Ceon001RTeom5Ceon001RmA*SC*SC*SC*RA*SC*ST*Sm5C*S G*Rm5C*SC*SmA*SmC*Sm5Ceo*SmGn001SmC | ACTCACCCACTCGC CACCGC | 564 | SnROnRSSSRSSSSR SSSSSnS |
| WV-39814 | mC*Sm5Ceon001TeoTeon001mC*SC*SC*ST*RG*SA*SA*SG*SG*RT*ST *SmC*SmC*SmU*SmCn001mC | CCTTCCCTGAAGGT TCCUCC | 565 | SnXOnXSSSRSSSSR SSSSSnX |
| WV-28077 | mC * Sm5CeoTeom5CeomA * SC * ST * SC * RA * SC * SC * RC * SA * SC * ST * SmU * SmG * SmC * Sm5mC * SmG | CCTCACTCACCCAC TUGCCG | 451 | SOOOS SSRSS RSSSS SSSS |

Key to Table A1:

The present disclosure notes that some sequences, due to their length, are divided into multiple lines in Table A1; however, these sequences, as are all oligonucleotides in Table A1, are single-stranded (unless otherwise noted). As appreciated by those skilled in the art, when no internucleotidic linkage is specified between two nucleoside units, the internucleotidic linkage is a phosphodiester linkage (natural phosphate linkage), and unless indicated otherwise a sugar is a natural DNA sugar which comprises no substitution at the 2' position (two —H at 2'-carbon). Moieties and modifications listed in the Tables (or compounds used to construct oligonucleotides comprising these moieties or modifications:

- I: Inosine;
- m: 2'-OMe;
- m5: methyl at 5-position of C (nucleobase is 5-methylcytosine);
- m5Ceo: 5-methyl 2'-O-methoxyethyl C;
- m5 mC: 5-methyl 2'-OMe C;
- eo: 2'-MOE (2'-$OCH_2CH_2OCH_3$);
- r: 2'-OH;
- O, PO: phosphodiester (phosphate); can be a linkage, e.g., a linkage between linker and oligonucleotide chain, an internucleotidic linkage, etc. Phosphodiesters indicated in the Stereochemistry/Internucleotidic Linkages column may not be reproduced in the Description column; if no internucleotidic linkage is indicated in the Description column, it is a phosphodiester;
- *, PS: phosphorothioate; can be a linkage, e.g., a linkage between linker and oligonucleotide chain, an internucleotidic linkage, etc.;
- R, Rp: phosphorothioate in Rp conformation; note that *R indicates a single phosphorothioate in the Rp conformation;
- S, Sp: phosphorothioate in Sp conformation; note that *S indicates a single phosphorothioate in the Sp conformation;
- n001:

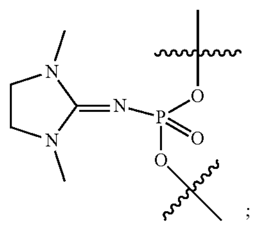 [SMILES: *OP(=O)(N=C1N(C)CCN1C)O*]

;

- nX: stereorandom n001;
- nR or n001R: n001 in Rp configuration;
- nS or n001S: n001 in Sp configuration;
- X: stereorandom phosphorothioate; and
- L004: linker having the structure of —$NH(CH_2)_4CH(CH_2OH)CH_2$—, wherein —NH— is connected to Mod (through —C(O)—) or —H, and the —$CH_2$— connecting site is connected to a linkage, e.g., phosphodiester (—O—P(O)(OH)—O—. May exist as a salt form. May be illustrated in the Table as O or PO), or phosphorothioate (—O—P(O)(SH)—O—. May exist as a salt form. May be illustrated in the Table as * if the phosphorothioate not chirally controlled; *S, S, or Sp, if chirally controlled and has an Sp configuration, and *R, R, or Rp, if chirally controlled and has an Rp configuration), at the 3'-end of an oligonucleotide chain. For example, absence of an asterisk immediately preceding L004 indicates that the linkage is a phosphodiester linkage. For example, in WV-18852, which terminates in mAL004, the linker L004 is connected (via the —$CH_2$— site) to a phosphodiester linkage at the 3' position at the 3'-terminal sugar (which is 2'-OMe and connected to the nucleobase A), and the L004 linker is connected via —NH— to —H.

For example, in some embodiments, the present disclosure provides an oligonucleotide having the structure of: mA*Sm5Ceon001RTeom5Ceon001RmA*SC*SC*SC*RA*SC*ST*Sm5C*SG*Rm5C*SC*SmA*SmCn001Rm5Ceo*SmG*SmC, or a pharmaceutically acceptable salt thereof, wherein:

m represents a 2'-OMe modification to a nucleoside (e.g., mA is 2'-OMe A);

*S represents a Sp phosphorothioate linkage;

m5Ceo represents 5-methyl 2'-O-methoxyethyl C;

n001R represents a Rp n001 linkage, wherein a n001 linkage has the structure of

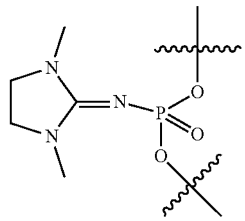

;

eo represents a 2'-$OCH_2CH_2OCH_3$ modification to a nucleoside (e.g., Teo is 2'-$OCH_2CH_2OCH_3$ T);

*R represents a Rp phosphorothioate linkage; and m5 represents a methyl at 5-position of C (e.g., in 5 mC, the nucleobase is 5-methylcytosine). In some embodiments, the present disclosure provides an oligonucleotide having the structure of: mA*Sm5Ceon001RTeom5Ceon001RmA*SC*SC*SC*RA*SC*ST*Sm5C*SG*Rm5C*SC*SmA*SmC*Sm5Ceon001RmG*SmC, or a pharmaceutically acceptable salt thereof, wherein m, *S, m5Ceo, n001R, eo, *R, m5, etc., are independently as noted herein.

In some embodiments, the present disclosure provides an oligonucleotide having the structure of: mA*Sm5Ceon001RTeom5Ceon001RmA*SC*SC*SC*RA*SC*ST*Sm5C*SG*Rm5C*SC*SmA*SmC*Sm5Ceo*SmGn001RmC, or a pharmaceutically acceptable salt thereof, wherein m, *S, m5Ceo, n001R, eo, *R, m5, etc., are independently as noted herein.

In some embodiments, the present disclosure provides an oligonucleotide having the structure of: mC*Sm5CeoTeom5CeomA*SC*ST*SC*RA*SC*SC*RC*SA*SC*ST*Sm5 mC*SmG*SmC*Sm5 mC*SmG, or a pharmaceutically acceptable salt thereof, wherein m, *S, m5Ceo, eo, *R, m5, etc., are independently as noted herein.

In some embodiments, the present disclosure provides an oligonucleotide having the structure of: mA*Sm5CeoTeom5CeomA*SC*SC*SC*RA*SC*ST*Sm5C*SG*Rm5C*SC*SmA*SmC*Sm5 mC*SmG*SmC, or a pharmaceutically acceptable salt thereof, wherein m, *S, m5Ceo, eo, *R, m5, etc., are independently as noted herein.

In some embodiments, the present disclosure provides an oligonucleotide having the structure of:

mC*Sm5CeoTeom5CeomA*SC*ST*SC*RA*SC*SC*RC*SA*SC*ST*Sm5Ceo*SmG*SmC*Sm5Ceo*SmG, or a pharmaceutically acceptable salt thereof, wherein m, *S, m5Ceo, eo, *R, m5, etc., are independently as noted herein.

In some embodiments, the present disclosure provides an oligonucleotide having the structure of:

mA*Sm5CeoTeom5CeomA*SC*SC*SC*RA*SC*ST*Sm5C*SG*Rm5C*SC*SmA*SmC*Sm5Ceo*SmG*SmC, or a pharmaceutically acceptable salt thereof, wherein m, *S, m5Ceo, eo, *R, m5, etc., are independently as noted herein.

Chirally Controlled Oligonucleotides and Chirally Controlled Oligonucleotide Compositions In some embodiments, provided C9orf72 oligonucleotides are capable of directing a decrease in the expression, level and/or activity of a C9orf72 target gene or its gene product. In some embodiments, a C9orf72 target gene comprises a repeat expansion. In some embodiments, a C9orf72 target gene comprises a hexanucleotide repeat expansion.

Among other things, the present disclosure provides chirally controlled C9orf72 oligonucleotides, and chirally controlled C9orf72 oligonucleotide compositions which are of high purity and of high diastereomeric purity. In some embodiments, the present disclosure provides chirally controlled C9orf72 oligonucleotides, and chirally controlled C9orf72 oligonucleotide compositions which are of high purity. In some embodiments, the present disclosure provides chirally controlled C9orf72 oligonucleotides, and chirally controlled C9orf72 oligonucleotide compositions which are of high diastereomeric purity.

In some embodiments, a C9orf72 oligonucleotide composition is a substantially pure preparation of a C9orf72 oligonucleotide type in that oligonucleotides in the composition that are not of the oligonucleotide type are impurities form the preparation process of said oligonucleotide type, in some case, after certain purification procedures.

In some embodiments, the present disclosure provides a chirally controlled C9orf72 oligonucleotide, wherein at least two of the individual internucleotidic linkages within the oligonucleotide have different stereochemistry and/or different P-modifications relative to one another. In certain embodiments, the present disclosure provides a chirally controlled C9orf72 oligonucleotide, wherein at least two individual internucleotidic linkages within the oligonucleotide have different P-modifications relative to one another. In certain embodiments, the present disclosure provides a chirally controlled C9orf72 oligonucleotide, wherein at least two of the individual internucleotidic linkages within the oligonucleotide have different P-modifications relative to one another, and wherein the chirally controlled C9orf72 oligonucleotide comprises at least one phosphate diester internucleotidic linkage. In certain embodiments, the present disclosure provides a chirally controlled C9orf72 oligonucleotide, wherein at least two of the individual internucleotidic linkages within the oligonucleotide have different P-modifications relative to one another, and wherein the chirally controlled C9orf72 oligonucleotide comprises at least one phosphate diester internucleotidic linkage and at least one phosphorothioate diester internucleotidic linkage. In certain embodiments, the present disclosure provides a chirally controlled C9orf72 oligonucleotide, wherein at least two of the individual internucleotidic linkages within the oligonucleotide have different P-modifications relative to one another, and wherein the chirally controlled C9orf72 oligonucleotide comprises at least one phosphorothioate triester internucleotidic linkage. In certain embodiments, the present disclosure provides a chirally controlled C9orf72 oligonucleotide, wherein at least two of the individual internucleotidic linkages within the oligonucleotide have different P-modifications relative to one another, and wherein the chirally controlled C9orf72 oligonucleotide comprises at least one phosphate diester internucleotidic linkage and at least one phosphorothioate triester internucleotidic linkage.

In some embodiments, a provided compound, e.g., a provided oligonucleotide, has a purity of 60%-100%. In some embodiments, a purity is at least 60%, 65%, 70%, 75%, 80%, 85%, 90%, 91%, 92%, 93%, 94%, 95%, 96%, 97%, 98%, or 99%. In some embodiments, a purity is at least 60%. In some embodiments, a purity is at least 70%. In some embodiments, a purity is at least 80%. In some embodiments, a purity is at least 85%. In some embodiments, a purity is at least 90%. In some embodiments, a purity is at least 91%. In some embodiments, a purity is at least 92%. In some embodiments, a purity is at least 93%. In some embodiments, a purity is at least 94%. In some embodiments, a purity is at least 95%. In some embodiments, a purity is at least 96%. In some embodiments, a purity is at least 97%. In some embodiments, a purity is at least 98%. In some embodiments, a purity is at least 99%. In some embodiments, a purity is at least 99.5%.

In some embodiments, a provided compound, e.g., a provided oligonucleotide, has a stereochemical purity of 60%-100%. In some embodiments, a provided compound, e.g., a provided oligonucleotide, has a diastereomeric purity of 60%-100%. In some embodiments, a diastereomeric purity is at least 60%, 65%, 70%, 75%, 80%, 85%, 90%, 91%, 92%, 93%, 94%, 95%, 96%, 97%, 98%, or 99%. In some embodiments, a chiral element, e.g., a chiral center (carbon, phosphorus, etc.) of a provided compound, e.g. a provided oligonucleotide, has a diastereomeric purity of 60%-100%. In some embodiments, a chiral element, e.g., a chiral center (carbon, phosphorus, etc.) has a diastereomeric purity of at least 60%, 65%, 70%, 75%, 80%, 85%, 90%, 91%, 92%, 93%, 94%, 95%, 96%, 97%, 98%, or 99%. In some embodiments, each linkage phosphorus of a chirally controlled internucleotidic linkage independently has a diastereomeric purity of 85-100%, e.g., 90-100%, or of or at least of 85%, 90%, 91%, 92%, 93%, 94%, 95%, 96%, 97%, 98%, or 99%. In some embodiments, chirally controlled internucleotidic linkages of oligonucleotides of a plurality in chirally controlled oligonucleotide compositions independently have a diastereomeric purity of 85-100%, e.g., 90-100%, or of or at least of 85%, 90%, 91%, 92%, 93%, 94%, 95%, 96%, 97%, 98%, or 99%. In some embodiments, each phosphorothioate internucleotidic linkage is independently chirally controlled. In some embodiments, a diastereomeric purity is at least 60%. In some embodiments, a diastereomeric purity is at least 70%. In some embodiments, a diastereomeric purity is at least 80%. In some embodiments, a diastereomeric purity is at least 85%. In some embodiments, a diastereomeric purity is at least 90%. In some embodiments, a diastereomeric purity is at least 91%. In some embodiments, a diastereomeric purity is at least 92%. In some embodiments, a diastereomeric purity is at least 93%. In some embodiments, a diastereomeric purity is at least 94%. In some embodiments, a diastereomeric purity is at least 95%. In some embodiments, a diastereomeric purity is at least 96%. In some embodiments, a diastereomeric purity is at least 97%. In some embodiments, a diastereomeric purity is at least 98%. In some embodiments, a diastereomeric purity is at least 99%. In some embodiments, a diastereomeric purity is at least 99.5%.

Among other things, the present disclosure provides various oligonucleotide compositions. In some embodiments, the present disclosure provides oligonucleotide compositions of oligonucleotides described herein. In some embodiments, an oligonucleotide composition, e.g., a C9orf72 oligonucleotide composition, comprises a plurality of an oligonucleotide described in the present disclosure. In some embodiments, an oligonucleotide composition, e.g., a C9orf72 oligonucleotide composition, is chirally controlled. In some embodiments, an oligonucleotide composition, e.g., a C9orf72 oligonucleotide composition, is not chirally controlled (stereorandom).

Linkage phosphorus of natural phosphate linkages is achiral. Linkage phosphorus of many modified internucleotidic linkages, e.g., phosphorothioate internucleotidic linkages, are chiral. In some embodiments, during preparation of oligonucleotide compositions (e.g., in traditional phosphoramidite oligonucleotide synthesis), configurations of chiral linkage phosphorus are not purposefully designed or controlled, creating non-chirally controlled (stereorandom) oligonucleotide compositions (substantially racemic preparations) which are complex, random mixtures of various stereoisomers (diastereoisomers)—for oligonucleotides with n chiral internucleotidic linkages (linkage phosphorus being chiral), typically $2^n$ stereoisomers (e.g., when n is 10, $2^{10}$=1,032; when n is 20, $2^{20}$=1,048,576). These stereoisomers have the same constitution, but differ with respect to the pattern of stereochemistry of their linkage phosphorus.

In some embodiments, the present disclosure encompasses technologies for designing and preparing chirally controlled oligonucleotide compositions. In some embodiments, the present disclosure provides chirally controlled oligonucleotide compositions, e.g., of many oligonucleotides in Table A1 which contain S and/or R in their stereochemistry/linkage. In some embodiments, a chirally controlled oligonucleotide composition comprises a controlled/pre-determined (not random as in stereorandom compositions) level of a plurality of oligonucleotides, wherein the oligonucleotides share the same linkage phosphorus stereochemistry at one or more chiral internucleotidic linkages (chirally controlled internucleotidic linkages). In some embodiments, the oligonucleotides share the same pattern of backbone chiral centers (stereochemistry of linkage phosphorus). In some embodiments, a pattern of backbone chiral centers is as described in the present disclosure. In some embodiments, the oligonucleotides share the same constitution. In some embodiments, the oligonucleotides are structural identical. As appreciated by those skilled in the art, various forms of an oligonucleotide, e.g., various salt forms of an oligonucleotide, may be considered to have the same constitution and/or structure unless indicated otherwise.

In some embodiments, an oligonucleotide composition is a chirally controlled oligonucleotide composition comprising a plurality of oligonucleotides, wherein the oligonucleotides share:

1) a common base sequence,
2) a common pattern of backbone linkages, and
3) the same linkage phosphorus stereochemistry at one or more (e.g., 1-50, 1-40, 1-30, 1-25, 1-20, 1-15, 1-10, 5-50, 5-40, 5-30, 5-25, 5-20, 5-15, 5-10, 1, 2, 3, 4, 5, 6, 7, 8, 9, 10, 11, 12, 13, 14, 15, 16, 17, 18, 19, 20, or more) chiral internucleotidic linkages (chirally controlled internucleotidic linkages), wherein the composition is enriched, relative to a substantially racemic preparation of oligonucleotides sharing the common base sequence and pattern of backbone linkages, for oligonucleotides of the plurality.

In some embodiments, an oligonucleotide composition is a chirally controlled oligonucleotide composition comprising a plurality of oligonucleotides, wherein the oligonucleotides share:

1) a common base sequence,
2) a common patter of backbone linkages, and
3) a common pattern of backbone chiral centers, which pattern comprises at least one Sp, wherein the composition is enriched, relative to a substantially racemic preparation of oligonucleotides sharing the common base sequence and pattern of backbone linkages, for oligonucleotides of the plurality.

In some embodiments, an oligonucleotide composition is a chirally controlled oligonucleotide composition comprising a plurality of oligonucleotides, wherein the oligonucleotides share:

1) a common base sequence,
2) a common patter of backbone linkages, and
3) a common pattern of backbone chiral centers, which pattern comprises at least one Rp, wherein the composition is enriched, relative to a substantially racemic preparation of oligonucleotides sharing the common base sequence and pattern of backbone linkages, for oligonucleotides of the plurality.

In some embodiments, oligonucleotides of a plurality are of the same constitution.

In some embodiments, the present disclosure provides a chirally controlled oligonucleotide composition comprising a plurality of oligonucleotides, wherein the oligonucleotides share:

1) a common constitution, and
2) share the same linkage phosphorus stereochemistry at one or more (e.g., 1-50, 1-40, 1-30, 1-25, 1-20, 1, 2, 3, 4, 5, 6, 7, 8, 9, 10, 11, 12, 13, 14, 15, 16, 17, 18, 19, 20, 21, 22, 23, 24, 25 or more) chiral internucleotidic linkages (chirally controlled internucleotidic linkages), wherein the composition is enriched, relative to a substantially racemic preparation of oligonucleotides of the common constitution, for oligonucleotides of the plurality.

In some embodiments, oligonucleotides of a plurality are structurally identical. In some embodiments, the present disclosure provides a chirally controlled oligonucleotide composition comprising a plurality of oligonucleotides, wherein the oligonucleotides are structurally identical, and the composition is enriched, relative to a substantially racemic preparation of oligonucleotides of the same constitution as the oligonucleotides of the plurality, for oligonucleotides of the plurality.

In some embodiments, they share the same stereochemistry independently 5-50 or more, e.g., 5, 6, 7, 8, 9, 10, 11, 12, 13, 14, 15, 16, 17, 18, 19, 20, 21, 22, 23, 24, or 25 or more chiral internucleotidic linkages. In some embodiments, oligonucleotides of the plurality share the same stereochemistry at each phosphorothioate internucleotidic linkage.

In some embodiments, an enrichment relative to a substantially racemic preparation is that at least about 5%, 10%, 20%, 30%, 40%, 50%, 60%, 70%, 80%, 85%, 90%, 91%, 92%, 93%, 94%, 95%, 96%, 97%, 98%, or 99% of all oligonucleotides in the composition are oligonucleotide of the plurality. In some embodiments, an enrichment relative to a substantially racemic preparation is that at least about 5%, 10%, 20%, 30%, 40%, 50%, 60%, 70%, 80%, 85%, 90%, 91%, 92%, 93%, 94%, 95%, 96%, 97%, 98%, or 99% of all oligonucleotides in the composition that share the common base sequence are oligonucleotides of the plurality. In some embodiments, an enrichment relative to a substantially racemic preparation is that at least about 5%, 10%, 20%, 30%, 40%, 50%, 60%, 70%, 80%, 85%, 90%, 91%, 92%, 93%, 94%, 95%, 96%, 97%, 98%, or 99% of all oligonucleotides in the composition that share the common constitution are oligonucleotides of the plurality. In some embodiments, the percentage is at least about 10%. In some embodiments, the percentage is at least about 20%. In some embodiments, the percentage is at least about 30%. In some embodiments, the percentage is at least about 40%. In some embodiments, the percentage is at least about 50%. In some embodiments, the percentage is at least about 60%. In some embodiments, the percentage is at least about 70%. In some embodiments, the percentage is at least about 75%. In some embodiments, the percentage is at least about 80%. In some embodiments, the percentage is at least about 85%. In some embodiments, the percentage is at least about 90%. In some embodiments, the percentage is at least about 91%. In some embodiments, the percentage is at least about 92%. In some embodiments, the percentage is at least about 93%. In some embodiments, the percentage is at least about 94%. In some embodiments, the percentage is at least about 95%. In some embodiments, the percentage is at least about 96%. In some embodiments, the percentage is at least about 97%. In some embodiments, the percentage is at least about 98%. In some embodiments, the percentage is at least about 99%. As appreciated by those skilled in the art, various forms of an oligonucleotide may be properly considered to have the same constitution and/or structure, and various forms of oligonucleotides sharing the same constitution may be properly considered to have the same constitution.

Levels of oligonucleotides of a plurality in chirally controlled oligonucleotide compositions are controlled. In contrast, in non-chirally controlled (or stereorandom, racemic) oligonucleotide compositions (or preparations), levels of oligonucleotides are random and not controlled. In some embodiments, a level of the oligonucleotides of a plurality in a chirally controlled oligonucleotide composition is about 1%-100%, (e.g., about 5%-100%, 10%-100%, 20%-100%, 30%-100%, 40%-100%, 50%-100%, 60%-100%, 70%-100%, 80-100%, 90-100%, 95-100%, 50%-90%, or about 5%, 10%, 20%, 30%, 40%, 50%, 60%, 70%, 80%, 85%, 90%, 91%, 92%, 93%, 94%, 95%, 96%, 97%, 98%, or 99%, or at least 5%, 10%, 20%, 30%, 40%, 50%, 60%, 70%, 80%, 85%, 90%, 91%, 92%, 93%, 94%, 95%, 96%, 97%, 98%, or 99%) of all oligonucleotides in the chirally controlled oligonucleotide composition, or of all oligonucleotides in the chirally controlled oligonucleotide composition that share the common base sequence as the oligonucleotides of the plurality, or of all oligonucleotides in the chirally controlled oligonucleotide composition that share the common base sequence and pattern of backbone linkages as the oligonucleotides of the plurality, or of all oligonucleotides in the chirally controlled oligonucleotide composition that share the common base sequence, pattern of backbone linkages as and pattern of backbone phosphorus modifications as the oligonucleotides of the plurality, or of all oligonucleotides in the chirally controlled oligonucleotide composition that share the same constitution as oligonucleotides of the plurality. In some embodiments, an enrichment relative to a substantially racemic preparation is a level described herein.

In some embodiments, a level as a percentage (e.g., a controlled level, a pre-determined level, an enrichment) is or is at least $(DS)^{nc}$, wherein DS is 90%-100%, and nc is the number of chirally controlled internucleotidic linkages as described in the present disclosure (e.g., 5, 6, 7, 8, 9, 10, 11, 12, 13, 14, 15, 16, 17, 18, 19, 20 or more). In some embodiments, each chiral internucleotidic linkage is chirally controlled, and nc is the number of chiral internucleotidic linkage. In some embodiments, DS is 90%, 91%, 92%, 93%, 94%, 95%, 96%, 97%, 98%, 99% or 99.5% or more. In some embodiments, DS is or is at least 90%. In some embodiments, DS is or is at least 91%. In some embodiments, DS is or is at least 92%. In some embodiments, DS is or is at least 93%. In some embodiments, DS is or is at least 94%. In some embodiments, DS is or is at least 95%. In some embodiments, DS is or is at least 96%. In some embodiments, DS is or is at least 97%. In some embodiments, DS is or is at least 98%. In some embodiments, DS is or is at least 99%. In some embodiments, a level (e.g., a controlled level, a pre-determined level, an enrichment) is a percentage of all oligonucleotides in a composition that share the same constitution, wherein the percentage is or is at least (DS)y°. For example, when DS is 99% and nc is 10, the percentage is or is at least 90% ($(99\%)^{10} \approx 0.90 = 90\%$). As appreciated by those skilled in the art, in a stereorandom preparation the percentage is typically about $½^{nc}$—when nc is 10, the percentage is about $½^{10}$ 0.001=0.1%.

In some embodiments, an oligonucleotide composition is a chirally controlled oligonucleotide composition comprising a plurality of oligonucleotides, wherein the oligonucleotides share:

1) a common base sequence,
2) a common pattern of backbone linkages, and
3) the same linkage phosphorus stereochemistry at one or more (e.g., 1-50, 1-40, 1-30, 1-25, 1-20, 1-15, 1-10, 5-50, 5-40, 5-30, 5-25, 5-20, 5-15, 5-10, 1, 2, 3, 4, 5, 6, 7, 8, 9, 10, 11, 12, 13, 14, 15, 16, 17, 18, 19, 20, or more) chiral internucleotidic linkages (chirally controlled internucleotidic linkages), wherein the percentage of the oligonucleotides of the plurality within all oligonucleotides in the composition that share the common base sequence and pattern of backbone linkages is at least (DS)y°, wherein DS is 90%-100%, and nc is the number of chirally controlled internucleotidic linkages.

In some embodiments, an oligonucleotide composition is a chirally controlled oligonucleotide composition comprising a plurality of oligonucleotides, wherein the oligonucleotides share:

1) a common base sequence,
2) a common patter of backbone linkages, and
3) a common pattern of backbone chiral centers, which pattern comprises at least one Sp, wherein the percentage of the oligonucleotides of the plurality within all oligonucleotides in the composition that share the common base sequence and pattern of backbone linkages is at least $(DS)^{nc}$, wherein DS is 90%-100%, and nc is the number of chirally controlled internucleotidic linkages.

In some embodiments, an oligonucleotide composition is a chirally controlled oligonucleotide composition comprising a plurality of oligonucleotides, wherein the oligonucleotides share:

1) a common base sequence,
2) a common patter of backbone linkages, and
3) a common pattern of backbone chiral centers, which pattern comprises at least one Rp, wherein the percentage of the oligonucleotides of the plurality within all oligonucleotides in the composition that share the common base sequence and pattern of backbone linkages is at least $(DS)^{nc}$, wherein DS is 90%-100%, and nc is the number of chirally controlled internucleotidic linkages.

In some embodiments, the present disclosure provides a chirally controlled oligonucleotide composition comprising a plurality of oligonucleotides, wherein the oligonucleotides are of a common constitution, and share the same linkage phosphorus stereochemistry at one or more (e.g., 1-50, 1-40, 1-30, 1-25, 1-20, 1-15, 1-10, 5-50, 5-40, 5-30, 5-25, 5-20, 5-15, 5-10, 1,2, 3,4, 5, 6, 7, 8, 9, 10, 11, 12, 13, 14, 15, 16, 17, 18, 19, 20, or more) chiral internucleotidic linkages (chirally controlled internucleotidic linkages), wherein the percentage of the oligonucleotides of the plurality within all oligonucleotides of the same constitution in the composition is at least $(DS)^{nc}$, wherein DS is 90%-100%, and nc is the number of chirally controlled internucleotidic linkages.

In some embodiments, oligonucleotides of the plurality are of different salt forms. In some embodiments, oligonucleotides of the plurality comprise one or more forms, e.g., various pharmaceutically acceptable salt forms, of a single oligonucleotide. In some embodiments, oligonucleotides of the plurality comprise one or more forms, e.g., various pharmaceutically acceptable salt forms, of two or more oligonucleotides. In some embodiments, oligonucleotides of the plurality comprise one or more forms, e.g., various pharmaceutically acceptable salt forms, of $2^{NCC}$ oligonucleotides, wherein NCC is the number of non-chirally controlled chiral internucleotidic linkages. In some embodiments, the $2^{NCC}$ oligonucleotides have relatively similar levels within a composition as, e.g., none of them are specifically enriched using chirally controlled oligonucleotide synthesis.

In some embodiments, the present disclosure provides a chirally controlled oligonucleotide composition comprising a plurality of oligonucleotides, wherein the oligonucleotides are structurally identical, and the percentage of the oligonucleotides of the plurality within all oligonucleotides of the same constitution as the oligonucleotides of the plurality in the composition is at least $(DS)^{nc}$, wherein DS is 90%-100%, and nc is the number of chirally controlled internucleotidic linkages.

In some embodiments, level of a plurality of oligonucleotides in a composition can be determined as the product of the diastereopurity of each chirally controlled internucleotidic linkage in the oligonucleotides. In some embodiments, diastereopurity of an internucleotidic linkage connecting two nucleosides in an oligonucleotide (or nucleic acid) is represented by the diastereopurity of an internucleotidic linkage of a dimer connecting the same two nucleosides, wherein the dimer is prepared using comparable conditions, in some instances, identical synthetic cycle conditions (e.g., for the linkage between Nx and Ny in an oligonucleotide . . . NxNy . . . the dimer is NxNy).

In some embodiments, all chiral internucleotidic linkages are chiral controlled, and the composition is a completely chirally controlled oligonucleotide composition. In some embodiments, not all chiral internucleotidic linkages are chiral controlled internucleotidic linkages, and the composition is a partially chirally controlled oligonucleotide composition. In some embodiments, at least 10%, 20%, 30%, 40%, 50%, 60%, 70%, 80%, 85%, 90%, 91%, 92%, 93%, 94%, 95%, 96%, 97%, 98%, or 99% of all chiral internucleotidic linkages are chirally controlled. In some embodiments, at least 50%, 60%, 70%, 80%, 85%, 90%, 91%, 92%, 93%, 94%, 95%, 96%, 97%, 98%, or 99% of all chiral internucleotidic linkages are chirally controlled. In some embodiments, each phosphorothioate internucleotidic linkage is chirally controlled.

Oligonucleotides may comprise or consist of various patterns of backbone chiral centers (patterns of stereochemistry of chiral linkage phosphorus). Certain useful patterns of backbone chiral centers are described in the present disclosure. In some embodiments, a plurality of oligonucleotides share a common pattern of backbone chiral centers, which is or comprises a pattern described in the present disclosure (e.g., as in "Linkage Phosphorus Stereochemistry and Patterns Thereof", a pattern of backbone chiral centers of a chirally controlled oligonucleotide in Table A1).

Chirally controlled oligonucleotide compositions can demonstrate a number of advantages over stereorandom oligonucleotide compositions. Among other things, chirally controlled oligonucleotide compositions are more uniform than corresponding stereorandom oligonucleotide compositions with respect to oligonucleotide structures. By controlling stereochemistry, compositions of individual stereoisomers can be prepared and assessed, so that chirally controlled oligonucleotide composition of stereoisomers with desired properties and/or activities can be developed. In some embodiments, chirally controlled oligonucleotide compositions provides better delivery, stability, clearance, activity, selectivity, and/or toxicity profiles compared to, e.g., corresponding stereorandom oligonucleotide compositions. In some embodiments, chirally controlled oligonucleotide compositions provide better efficacy, fewer side effects, and/or more convenient and effective dosage regimens. Among other things, patterns of backbone chiral centers as described herein can be utilized to provide controlled cleavage of oligonucleotide targets (e.g., transcripts such as pre-mRNA, mature mRNA, etc.; including control of cleavage sites, rate and/or extent of cleavage at cleavage sites, and/or overall rate and extent of cleavage, etc.) and greatly increased target selectivity. In some embodiments, chirally controlled oligonucleotide compositions of oligonucleotides comprising certain patterns of backbone chiral centers can differentiate sequences with nucleobase difference at very few positions, in some embodiments, at single position (e.g., at SNP site, point mutation site, etc.).

As understood by a person having ordinary skill in the art, stereorandom or (substantially) racemic preparations/non-chirally controlled oligonucleotide compositions are typically prepared without chiral control, e.g., without using chiral auxiliaries, chiral modification reagents, and/or chiral catalysts that can provide high stereoselectivity (e.g., 90%, 91%, 92%, 93%, 94%, 95%, 96%, 97%, 98%, 99% or 99.5% or more; in some embodiments, 95%, 96%, 97%, 98%, 99% or 99.5% or more; in some embodiments, 97%, 98%, 99% or 99.5% or more; in some embodiments, 98%, 99% or 99.5% or more) at linkage phosphorus during oligonucleotide synthesis. In some embodiments, in a substantially racemic (or chirally uncontrolled) preparation of oligonucleotides, coupling steps are not chirally controlled in that the coupling steps are not specifically conducted to provide enhanced stereoselectivity. An example substantially racemic preparation of oligonucleotides/non-chirally controlled oligonucleotide composition is a preparation of phosphorothioate oligonucleotides through traditional phosphoramidite oligonucleotide synthesis and sulfurization with non-chiral sulfurization reagents such as tetraethylthiuram disulfide or (TETD), 3H-1, 2-bensodithiol-3-one 1, 1-dioxide (BDTD), etc., which are well-known processes. Various methods for making stereorandom oligonucleotide compositions/substantially racemic preparations of oligonucleotides are widely known and practiced in the art and can be utilized for preparing such compositions and preparations of the present disclosure.

Certain data showing properties and/or activities of chirally controlled oligonucleotide composition, e.g., chirally controlled C9orf72 oligonucleotide compositions in decreasing the level, activity and/or expression of a C9orf72 target gene or a gene product thereof, are shown in, for example, the Examples.

In some embodiments, the present disclosure provides a chirally controlled oligonucleotide composition, e.g., a chirally controlled C9orf72 oligonucleotide composition, wherein the linkage phosphorus of at least one chirally controlled internucleotidic linkage is Sp. In some embodiments, the present disclosure provides a chirally controlled oligonucleotide composition, e.g., a chirally controlled C9orf72 oligonucleotide composition, wherein the majority of linkage phosphorus of chirally controlled internucleotidic linkages are Sp. In some embodiments, about 50%-100%, 55%-100%, 60%-100%, 65%-100%, 70%-100%, 75%-100%, 80%-100%, 85%-100%, 90%-100%, 55%-95%, 60%-95%, 65%-95%, or about 55%, 60%, 65%, 70%, 75%, 80%, 85%, 90%, 95%, 97%, 99% or more, of all chirally controlled internucleotidic linkages (or of all chiral internucleotidic linkages, or of all internucleotidic linkages) of an oligonucleotide or a portion (e.g., a 5'-wing, a 3'-wing, a core, etc.) thereof are Sp. In some embodiments, about 50%-100%, 55%-100%, 60%-100%, 65%-100%, 70%-100%, 75%-100%, 80%-100%, 85%-100%, 90%-100%, 55%-95%, 60%-95%, 65%-95%, or about 55%, 60%, 65%, 70%, 75%, 80%, 85%, 90%, 95%, 97%, 99% or more, of all chirally controlled phosphorothioate internucleotidic linkages of an oligonucleotide or a portion (e.g., a 5'-wing, a 3'-wing, a core, etc.) thereof are Sp. In some embodiments, a percentage is 60% or more. In some embodiments, a percentage is 67% or more. In some embodiments, a percentage is 70% or more. In some embodiments, a percentage is 75% or more. In some embodiments, a percentage is 80% or more. In some embodiments, a percentage is 85% or more. In some embodiments, a percentage is 90% or more. In some embodiments, a percentage is 95% or more. In some embodiments, an oligonucleotide or a portion (e.g., a 5'-wing, a 3'-wing, a core, etc.) thereof comprises one or more Rp chirally controlled internucleotidic linkages. In some embodiments, an oligonucleotide or a portion (e.g., a 5'-wing, a 3'-wing, a core, etc.) thereof comprises one or more Rp chirally controlled non-negatively charged internucleotidic linkages (e.g., neutral internucleotidic linkages such as n001). In some embodiments, an oligonucleotide or a portion (e.g., a 5'-wing, a 3'-wing, a core, etc.) thereof comprises one or more Rp chirally controlled phosphorothioate internucleotidic linkages. In some embodiments, a core comprises one or more Rp phosphorothioate internucleotidic linkages, e.g., in a pattern of backbone chiral centers comprising RpSpSp as described herein.

Stereochemistry and Patterns of Backbone Chiral Centers

In contrast to natural phosphate linkages, linkage phosphorus of chiral modified internucleotidic linkages, e.g., phosphorothioate internucleotidic linkages, are chiral. Among other things, the present disclosure provides technologies (e.g., oligonucleotides, compositions, methods, etc.) comprising control of stereochemistry of chiral linkage phosphorus in chiral internucleotidic linkages. In some embodiments, as demonstrated herein, control of stereochemistry can provide improved properties and/or activities, including desired stability, reduced toxicity, improved reduction of target nucleic acids, etc. In some embodiments, the present disclosure provides useful patterns of backbone chiral centers for oligonucleotides and/or regions thereof, which pattern is a combination of stereochemistry of each chiral linkage phosphorus (Rp or Sp) of chiral linkage phosphorus, indication of each achiral linkage phosphorus (Op, if any), etc. from 5' to 3'. In some embodiments, patterns of backbone chiral centers can control cleavage patterns of target nucleic acids when they are contacted with provided oligonucleotides or compositions thereof in a cleavage system (e.g., in vitro assay, cells, tissues, organs, organisms, subjects, etc.). In some embodiments, patterns of backbone chiral centers improve cleavage efficiency and/or selectivity of target nucleic acids when they are contacted with provided oligonucleotides or compositions thereof in a cleavage system.

In some embodiments, a pattern of backbone chiral centers of an oligonucleotide, e.g., a C9orf72 oligonucleotide, or a region thereof (e.g., a core) comprises or is (Sp)m(Rp/Op)n, (Rp/Op)n(Sp)m, (Sp)m(Rp)n, (Rp)n(Sp)m, (Np)t[(Rp/Op)n(Sp)m]y, [(Rp/Op)n(Sp)m]y(Np)t, (Np)t[(Rp)n(Sp)m]y, [(Rp)n(Sp)m]y(Np)t, [(Op)n(Sp)m]y(Rp)k, [(Op)n(Sp)m]y, (Sp)t[(Op)n(Sp)m]y, (Sp)t[(Op)n(Sp)m]y(Rp)k, [(Rp)n(Sp)m]y(Rp)k, [(Rp)n(Sp)m]y, (Sp)t[(Rp)n(Sp)m]y, or (Sp)t[(Rp)n(Sp)m]y(Rp)k, wherein each Np is independently Sp or Rp, and each of m, n, t, y, and k is independently 1-50. In some embodiments, a pattern of backbone chiral centers of an oligonucleotide, e.g., a C9orf72 oligonucleotide, or a region thereof (e.g., a core) comprises or is Rp(Sp)m. In some embodiments, a pattern of backbone chiral centers of an oligonucleotide, e.g., a C9orf72 oligonucleotide, or a region thereof (e.g., a core) comprises or is (Sp)tRp(Sp)m. In some embodiments, a pattern of backbone chiral centers of an oligonucleotide, e.g., a C9orf72 oligonucleotide, or a region thereof (e.g., a core) comprises or is [Rp(Sp)m]y. In some embodiments, a pattern of backbone chiral centers of an oligonucleotide, e.g., a C9orf72 oligonucleotide, or a region thereof (e.g., a core) comprises or is (Np)t[Rp(Sp)m]y. In some embodiments, a pattern of backbone chiral centers of an oligonucleotide, e.g., a C9orf72 oligonucleotide, or a region thereof (e.g., a core) comprises or is (Sp)t[Rp(Sp)m]y. In some embodiments, at least one n is 1. In some embodiments, each n is 1. In some embodiments, at least one m is two or more. In some embodiments, each m is independently two or more. In some embodiments, y is 1. In some embodiments, y is 2. In some embodiments, y is 3. In some embodiments, t is 1. In some embodiments, t is 2 or more. In some embodiments, t is 2 or more. In some embodiments, y is 4 or more. In some embodiments, at least one Rp/Op is Rp. In some embodiments, each of Np, Rp, Sp is independently of a phosphorothioate internucleotidic linkage. In some embodiments, Op represents a natural phosphate linkage.

In some embodiments, m is 1, 2, 3, 4, 5, 6, 7, 8, 9, 10, 11, 12, 13, 14, 15, 16, 17, 18, 19, 20, 21, 22, 23, 24, or 25. In some embodiments, in a pattern of backbone chiral centers each m is independently 2 or more. In some embodiments, each m is independently 2, 3, 4, 5, 6, 7, 8, 9, or 10. In some embodiments, each m is independently 2-3, 2-5, 2-6, or 2-10. In some embodiments, m is 2. In some embodiments, m is 3. In some embodiments, m is 4. In some embodiments, m is 5. In some embodiments, m is 6. In some embodiments, m is 7. In some embodiments, m is 8. In some embodiments, m is 9. In some embodiments, m is 10. In some embodiments, where there are two or more occurrences of m, they can be the same or different, and each of them is independently as described in the present disclosure.

In some embodiments, y is 1, 2, 3, 4, 5, 6, 7, 8, 9, 10, 11, 12, 13, 14, 15, 16, 17, 18, 19, 20, 21, 22, 23, 24, or 25. In some embodiments, y is 1, 2, 3, 4, 5, 6, 7, 8, 9, or 10. In some embodiments, y is 1. In some embodiments, y is 2. In some embodiments, y is 3. In some embodiments, y is 4. In some embodiments, y is 5. In some embodiments, y is 6. In some embodiments, y is 7. In some embodiments, y is 8. In some embodiments, y is 9. In some embodiments, y is 10.

In some embodiments, t is 1, 2, 3, 4, 5, 6, 7, 8, 9, 10, 11, 12, 13, 14, 15, 16, 17, 18, 19, 20, 21, 22, 23, 24, or 25. In some embodiments, each t is independently 1, 2, 3, 4, 5, 6, 7, 8, 9, or 10. In some embodiments, t is 2 or more. In some embodiments, t is 3 or more. In some embodiments, t is 4 or more. In some embodiments, t is 1. In some embodiments, t is 2. In some embodiments, t is 3. In some embodiments, t is 4. In some embodiments, t is 5. In some embodiments, t is 6. In some embodiments, t is 7. In some embodiments, t is 8. In some embodiments, t is 9. In some embodiments, t is 10. In some embodiments, where there are two or more occurrences of t, they can be the same or different, and each of them is independently as described in the present disclosure.

In some embodiments, n is 1, 2, 3, 4, 5, 6, 7, 8, 9, 10, 11, 12, 13, 14, 15, 16, 17, 18, 19, 20, 21, 22, 23, 24, or 25. In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10. In some embodiments, where there are two or more occurrences of n, they can be the same or different, and each of them is independently as described in the present disclosure. In many embodiments, in a pattern of backbone chiral centers, at least one occurrence of n is 1; in some cases, each n is 1.

In some embodiments, k is 1, 2, 3, 4, 5, 6, 7, 8, 9, 10, 11, 12, 13, 14, 15, 16, 17, 18, 19, 20, 21, 22, 23, 24, or 25. In some embodiments, k is 1. In some embodiments, k is 2. In some embodiments, k is 3. In some embodiments, k is 4. In some embodiments, k is 5. In some embodiments, k is 6. In some embodiments, k is 7. In some embodiments, k is 8. In some embodiments, k is 9. In some embodiments, k is 10.

In some embodiments, at least one n is 1, and at least one m is no less than 2. In some embodiments, at least one n is 1, at least one t is no less than 2, and at least one m is no less than 3. In some embodiments, each n is 1. In some embodiments, t is 1. In some embodiments, at least one $t>1$. In some embodiments, at least one $t>2$. In some embodiments, at least one $t>3$. In some embodiments, at least one $t>4$. In some embodiments, at least one $m>1$. In some embodiments, at least one $m>2$. In some embodiments, at least one $m>3$. In some embodiments, at least one $m>4$. In some embodiments, a pattern of backbone chiral centers comprises one or more achiral natural phosphate linkages. In some embodiments, the sum of m, t, and n (or m and n if no t in a pattern) is no less than 5, 6, 7, 8, 9, 10, 11, 12, 13, 14, 15, 16, 17, 18, 19 or 20. In some embodiments, the sum is 5. In some embodiments, the sum is 6. In some embodiments, the sum is 7. In some embodiments, the sum is 8. In some embodiments, the sum is 9. In some embodiments, the sum is 10. In some embodiments, the sum is 11. In some embodiments, the sum is 12. In some embodiments, the sum is 13. In some embodiments, the sum is 14. In some embodiments, the sum is 15.

In some embodiments, a number of linkage phosphorus in chirally controlled internucleotidic linkages are Sp. In some embodiments, at least 10%, 20%, 25%, 30%, 35%, 40%, 45%, 50%, 55%, 60%, 65%, 70%, 75%, 80%, 85%, 90% or 95% of chirally controlled internucleotidic linkages have Sp linkage phosphorus. In some embodiments, at least 10%, 20%, 25%, 30%, 35%, 40%, 45%, 50%, 55%, 60%, 65%, 70%, 75%, 80%, 85%, 90% or 95% of chirally controlled phosphorothioate internucleotidic linkages have Sp linkage phosphorus. In some embodiments, at least 10%, 20%, 25%, 30%, 35%, 40%, 45%, 50%, 55%, 60%, 65%, 70%, 75%, 80%, 85%, 90% or 95% of all chiral internucleotidic linkages are chirally controlled internucleotidic linkages having Sp linkage phosphorus. In some embodiments, at least 10%, 20%, 25%, 30%, 35%, 40%, 45%, 50%, 55%, 60%, 65%, 70%, 75%, 80%, 85%, 90% or 95% of all chiral internucleotidic linkages are chirally controlled phosphorothioate internucleotidic linkages having Sp linkage phosphorus. In some embodiments, at least 10%, 20%, 25%, 30%, 35%, 40%, 45%, 50%, 55%, 60%, 65%, 70%, 75%, 80%, 85%, 90% or 95% of all internucleotidic linkages are chirally controlled internucleotidic linkages having Sp linkage phosphorus. In some embodiments, the percentage is at least 20%. In some embodiments, the percentage is at least 30%. In some embodiments, the percentage is at least 40%. In some embodiments, the percentage is at least 50%. In some embodiments, the percentage is at least 60%. In some embodiments, the percentage is at least 65%. In some embodiments, the percentage is at least 70%. In some embodiments, the percentage is at least 75%. In some embodiments, the percentage is at least 80%. In some embodiments, the percentage is at least 90%. In some embodiments, the percentage is at least 95%. In some embodiments, at least 1, 2, 3, 4, 5, 6, 7, 8, 9, 10, 11, 12, 13, 14, 15, 16, 17, 18, 19, 20, 21, 22, 23, 24, or 25 internucleotidic linkages are chirally controlled internucleotidic linkages having Sp linkage phosphorus. In some embodiments, at least 5 internucleotidic linkages are chirally controlled internucleotidic linkages having Sp linkage phosphorus. In some embodiments, at least 6 internucleotidic linkages are chirally controlled internucleotidic linkages having Sp linkage phosphorus. In some embodiments, at least 7 internucleotidic linkages are chirally controlled internucleotidic linkages having Sp linkage phosphorus. In some embodiments, at least 8 internucleotidic linkages are chirally controlled internucleotidic linkages having Sp linkage phosphorus. In some embodiments, at least 9 internucleotidic linkages are chirally controlled internucleotidic linkages having Sp linkage phosphorus. In some embodiments, at least 10 internucleotidic linkages are chirally controlled internucleotidic linkages having Sp linkage phosphorus. In some embodiments, at least 11 internucleotidic linkages are chirally controlled internucleotidic linkages having Sp linkage phosphorus. In some embodiments, at least 12 internucleotidic linkages are chirally controlled internucleotidic linkages having Sp linkage phosphorus. In some embodiments, at least 13 internucleotidic linkages are chirally controlled internucleotidic linkages having Sp linkage phosphorus. In some embodiments, at least 14 internucleotidic linkages are chirally controlled internucleotidic linkages having Sp linkage phosphorus. In some embodiments, at least 15 internucleotidic linkages are chirally controlled internucleotidic linkages having Sp linkage phosphorus. In some embodiments, at least 1, 2, 3, 4, 5, 6, 7, 8, 9, 10, 11, 12, 13, 14, 15, 16, 17, 18, 19, 20, 21, 22, 23, 24, or 25 internucleotidic linkages are chirally controlled internucleotidic linkages having Rp linkage phosphorus. In some embodiments, no more than 1, 2, 3, 4, 5, 6, 7, 8, 9, 10, 11, 12, 13, 14, 15, 16, 17, 18, 19, 20, 21, 22, 23, 24, or 25 internucleotidic linkages are chirally controlled internucleotidic linkages having Rp linkage phosphorus. In some embodiments, one and no more than one internucleotidic linkage in an oligonucleotide is a chirally controlled internucleotidic linkage having Rp linkage phosphorus. In some embodiments, 2 and no more than 2 internucleotidic linkages in an oligonucleotide are chirally controlled internucleotidic linkages having Rp linkage phosphorus. In some embodiments, 3 and no more than 3 internucleotidic linkages in an oligonucleotide are chirally controlled internucleotidic linkages having Rp linkage phosphorus. In some embodiments, 4 and no more than 4 internucleotidic linkages in an oligonucleotide are chirally controlled internucleotidic linkages having Rp linkage phosphorus. In some embodiments, 5 and no more than 5 internucleotidic linkages in an oligonucleotide are chirally controlled internucleotidic linkages having Rp linkage phosphorus.

In some embodiments, all, essentially all or most of the internucleotidic linkages in an oligonucleotide are in the Sp configuration (e.g., about 50%-100%, 55%-100%, 60%-100%, 65%-100%, 70%-100%, 75%-100%, 80%-100%, 85%-100%, 90%-100%, 55%-95%, 60%-95%, 65%-95%, or about 55%, 60%, 65%, 70%, 75%, 80%, 85%, 90%, 95%, 97%, 99% or more of all chirally controlled internucleotidic linkages, or of all chiral internucleotidic linkages, or of all internucleotidic linkages in the oligonucleotide) except for one or a minority of internucleotidic linkages (e.g., 1, 2, 3, 4, or 5, and/or less than 50%, 45%, 40%, 35%, 30%, 25%, 20%, 15%, 10%, or 5% of all chirally controlled internucleotidic linkages, or of all chiral internucleotidic linkages, or of all internucleotidic linkages in the oligonucleotide) being in the Rp configuration. In some embodiments, all, essentially all or most of the internucleotidic linkages in a core are in the Sp configuration (e.g., about 50%-100%, 55%-100%, 60%-100%, 65%-100%, 70%-100%, 75%-100%, 80%-100%, 85%-100%, 90%-100%, 55%-95%, 60%-95%, 65%-95%, or about 55%, 60%, 65%, 70%, 75%, 80%, 85%, 90%, 95%, 97%, 99% or more of all chirally controlled internucleotidic linkages, or of all chiral internucleotidic linkages, or of all internucleotidic linkages, in the core) except for one or a minority of internucleotidic linkages (e.g., 1, 2, 3, 4, or 5, and/or less than 50%, 45%, 40%, 35%, 30%, 25%, 20%, 15%, 10%, or 5% of all chirally controlled internucleotidic linkages, or of all chiral internucleotidic linkages, or of all internucleotidic linkages, in the core) being in the Rp configuration. In some embodiments, all, essentially all or most of the internucleotidic linkages in the core are a phosphorothioate in the Sp configuration (e.g., about 50%-100%, 55%-100%, 60%-100%, 65%-100%, 70%-100%, 75%-100%, 80%-100%, 85%-100%, 90%-100%, 55%-95%, 60%-95%, 65%-95%, or about 55%, 60%, 65%, 70%, 75%, 80%, 85%, 90%, 95%, 97%, 99% or more of all chirally controlled internucleotidic linkages, or of all chiral internucleotidic linkages, or of all internucleotidic linkages, in the core) except for one or a minority of internucleotidic linkages (e.g., 1, 2, 3, 4, or 5, and/or less than 50%, 45%, 40%, 35%, 30%, 25%, 20%, 15%, 10%, or 5% of all chirally controlled internucleotidic linkages, or of all chiral internucleotidic linkages, or of all internucleotidic linkages, in the core) being a phosphorothioate in the Rp configuration. In some embodiments, each internucleotidic linkage in the core is a phosphorothioate in the Sp configuration except for one phosphorothioate in the Rp configuration. In some embodiments, each internucleotidic linkage in the core is a phosphorothioate in the Sp configuration except for one phosphorothioate in the Rp configuration.

In some embodiments, an oligonucleotide comprises one or more Rp internucleotidic linkages. In some embodiments, an oligonucleotide comprises one and no more than one Rp internucleotidic linkages. In some embodiments, an oligonucleotide comprises two or more Rp internucleotidic linkages. In some embodiments, an oligonucleotide comprises three or more Rp internucleotidic linkages. In some embodiments, an oligonucleotide comprises four or more Rp internucleotidic linkages. In some embodiments, an oligonucleotide comprises five or more Rp internucleotidic linkages. In some embodiments, about 5%-50% of all chirally controlled internucleotidic linkages in an oligonucleotide are Rp. In some embodiments, about 5%-40% of all chirally controlled internucleotidic linkages in an oligonucleotide are Rp. In some embodiments, about 10%-40% of all chirally controlled internucleotidic linkages in an oligonucleotide are Rp. In some embodiments, about 15%-40% of all chirally controlled internucleotidic linkages in an oligonucleotide are Rp. In some embodiments, about 20%-40% of all chirally controlled internucleotidic linkages in an oligonucleotide are Rp. In some embodiments, about 25%-40% of all chirally controlled internucleotidic linkages in an oligonucleotide are Rp. In some embodiments, about 30%-40% of all chirally controlled internucleotidic linkages in an oligonucleotide are Rp. In some embodiments, about 35%-40% of all chirally controlled internucleotidic linkages in an oligonucleotide are Rp.

In some embodiments, a base sequence comprises or is a sequence complementary to a characteristic sequence element in a target nucleic acid which characteristic sequence element can differentiate a target nucleic acid (e.g., a transcript from a particular allele or a type of transcripts from a nucleic acid (e.g., V3 in FIG. 1), which is often associated with a condition, disorder or disease) from other nucleic acids (e.g., transcripts from a different allele or different type(s) of transcripts from a nucleic acid (e.g., V2 in FIG. 1), which is often not or less associated with a condition, disorder or disease). In some embodiments, a common base sequence comprises a sequence complementary to a characteristic sequence element. In some embodiments, a common base sequence is a sequence complementary to a characteristic sequence element. In some embodiments, a common base sequence comprises or is a sequence 100% complementary to a characteristic sequence element. In some embodiments, a common base sequence comprises a sequence 100% complementary to a characteristic sequence element. In some embodiments, a common base sequence is a sequence 100% complementary to a characteristic sequence element. In some embodiments, a Rp internucleotidic linkage (e.g., a Rp phosphorothioate internucleotidic linkage) is at positions +5, +4, +3, +2, +1, −1, −2, −3, −4, or −5 relative to a characteristic sequence element. In some embodiments, such a Rp is of a RpSpSp motif in a pattern of backbone chiral centers (e.g., those comprising or consisting of (Rp)n(Sp)m, (Np)t[(Rp)n(Sp)m]y, (Sp)t[(Rp)n(Sp)m]y, Rp(Sp)m, (Sp)tRp(Sp)m, [Rp(Sp)m]y, (Np)t[Rp(Sp)m]y, or (Sp)t[Rp(Sp)m]y as described herein). Unless otherwise specified, for Rp internucleotidic linkage positioning, "−" is counting from the nucleoside at the 5'-end of the sequence that is complementary to a characteristic sequence element toward the 5'-end of an oligonucleotide with the internucleotidic linkage at the −1 position being the internucleotidic linkage bonded to the 5'-carbon of the nucleoside at the 5'-end of the sequence that is complementary to a characteristic sequence element, and "+" is counting from the nucleoside at the 3'-end of the sequence that is complementary to a characteristic sequence element toward the 3'-end of an oligonucleotide with the internucleotidic linkage at the +1 position being the internucleotidic linkage bonded to the 3'-carbon of the nucleoside at the 3'-end of the sequence that is complementary to a characteristic sequence element. In some embodiments, a characteristic sequence element comprises a single differentiating position (e.g., a point mutation). In some embodiments, a characteristic sequence element is a point mutation or a SNP. As appreciated by those skilled in the art, when a characteristic sequence element contains only one nucleoside, the nucleoside at the 5'-end of the sequence that is complementary to a characteristic sequence element and the nucleoside at the 3'-end of the sequence that is complementary to a characteristic sequence element are the same. In some embodiments, Rp is at −5. In some embodiments, Rp is at −4. In some embodiments, Rp is at −3. In some embodiments, Rp is at −2. In some embodiments, Rp is at −1. In some embodiments, Rp is at +1. In some embodiments, Rp is at +2. In some embodiments, Rp is at +3. In some embodiments, Rp is at +4. In some embodiments, Rp is at +5. In some embodiments, such an Rp is the configuration of a chirally controlled phosphorothioate internucleotidic linkage. In some embodiments, such an Rp is in a core region.

In some embodiments, an internucleotidic linkage in the Sp configuration (having a Sp linkage phosphorus) is a phosphorothioate internucleotidic linkage. In some embodiments, an achiral internucleotidic linkage is a natural phosphate linkage. In some embodiments, an internucleotidic linkage in the Rp configuration (having a Rp linkage phosphorus) is a phosphorothioate internucleotidic linkage. In some embodiments, each internucleotidic linkage in the Sp configuration is a phosphorothioate internucleotidic linkage. In some embodiments, each achiral internucleotidic linkage is a natural phosphate linkage. In some embodiments, each internucleotidic linkage in the Rp configuration is a phosphorothioate internucleotidic linkage. In some embodiments, each internucleotidic linkage in the Sp configuration is a phosphorothioate internucleotidic linkage, each achiral internucleotidic linkage is a natural phosphate linkage, and each internucleotidic linkage in the Rp configuration is a phosphorothioate internucleotidic linkage. In some embodiments, an internucleotidic linkage in the Rp configuration is a non-negatively charged internucleotidic linkage (e.g., a neutral internucleotidic linkage such as n001). In some embodiments, each chirally controlled non-negatively charged internucleotidic linkage (e.g., a neutral internucleotidic linkage such as n001) is Rp. In some embodiments, each n001 is Rp.

In some embodiments, an internucleotidic linkage bonded to a wing nucleoside and a core nucleoside is considered one of the core internucleotidic linkages, for example, when describing types, modifications, numbers, and/or patterns of core internucleotidic linkages. In some embodiments, each internucleotidic linkage bonded to a wing nucleoside and a core nucleoside is considered one of the core internucleotidic linkages, for example, when describing types, modifications, numbers, and/or patterns of core internucleotidic linkages. In some embodiments, a core internucleotidic linkage is bonded to two core nucleosides. In some embodiments, a core internucleotidic linkage is bonded to a core nucleoside and a wing nucleoside. In some embodiments, each core internucleotidic linkage is independently bonded to two core nucleosides, or a core nucleoside and a wing nucleoside. In some embodiments, each wing internucleotidic linkage is independently bonded to two wing nucleosides.

In some embodiments, provided oligonucleotides, e.g., C9orf72 oligonucleotides, in chirally controlled oligonucleotide compositions each comprise different types of internucleotidic linkages. In some embodiments, provided oligonucleotides comprise at least one natural phosphate linkage and at least one modified internucleotidic linkage. In some embodiments, provided oligonucleotides comprise at least one natural phosphate linkage and at least two modified internucleotidic linkages. In some embodiments, provided oligonucleotides comprise at least one natural phosphate linkage and at least three modified internucleotidic linkages. In some embodiments, provided oligonucleotides comprise at least one natural phosphate linkage and at least four modified internucleotidic linkages. In some embodiments, provided oligonucleotides comprise at least one natural phosphate linkage and at least five modified internucleotidic linkages. In some embodiments, provided oligonucleotides comprise at least one natural phosphate linkage and 1, 2, 3, 4, 5, 6, 7, 8, 9, 10, 11, 12, 13, 14, 15, 16, 17, 18, 19, 20, 21, 22, 23, 24, or 25 or more modified internucleotidic linkages. In some embodiments, a modified internucleotidic linkage is a phosphorothioate internucleotidic linkage. In some embodiments, each modified internucleotidic linkage is a phosphorothioate internucleotidic linkage. In some embodiments, a modified internucleotidic linkage is a non-negatively charged internucleotidic linkage. In some embodiments, a modified internucleotidic linkage is a neutral internucleotidic linkage. In some embodiments, a modified internucleotidic linkage is n001. In some embodiments, each modified internucleotidic linkage is independently phosphorothioate or a neutral internucleotidic linkage. In some embodiments, each modified internucleotidic linkage is independently phosphorothioate or n001. In some embodiments, provided oligonucleotides comprise at least one natural phosphate linkage and at least 2, 3, 4, 5, 6, 7, 8, 9, 10, 11, 12, 13, 14, 15, 16, 17, 18, 19, 20, 21, 22, 23, 24, or 25 consecutive modified internucleotidic linkages. In some embodiments, provided oligonucleotides comprise at least one natural phosphate linkage and at least 2, 3, 4, 5, 6, 7, 8, 9, 10, 11, 12, 13, 14, 15, 16, 17, 18, 19, 20, 21, 22, 23, 24, or 25 consecutive phosphorothioate internucleotidic linkages.

In some embodiments, a modified linkage comprises a chiral auxiliary, which, for example, is used to control the stereoselectivity of a reaction, e.g., a coupling reaction in an oligonucleotide synthesis cycle.

Internucleotidic Linkages

In some embodiments, oligonucleotides comprise base modifications, sugar modifications, and/or internucleotidic linkage modifications. Various internucleotidic linkages can be utilized in accordance with the present disclosure to link units comprising nucleobases, e.g., nucleosides. In some embodiments, C9orf72 oligonucleotides comprise both one or more modified internucleotidic linkages and one or more natural phosphate linkages. As widely known by those skilled in the art, natural phosphate linkages are widely found in natural DNA and RNA molecules; they have the structure of —OP(O)(OH)O—, connect sugars in the nucleosides in DNA and RNA, and may be in various salt forms, for example, at physiological pH (about 7.4), natural phosphate linkages are predominantly exist in salt forms with the anion being —OP(O)(O—)O—. A modified internucleotidic linkage, or a non-natural phosphate linkage, is an internucleotidic linkage that is not natural phosphate linkage or a salt form thereof. Modified internucleotidic linkages, depending on their structures, may also be in their salt forms. For example, as appreciated by those skilled in the art, phosphorothioate internucleotidic linkages which have the structure of —OP(O)(SH)O— may be in various salt forms, e.g., at physiological pH (about 7.4) with the anion being —OP(O)($S^-$)O—.

In some embodiments, an oligonucleotide comprises an internucleotidic linkage which is a modified internucleotidic linkage, e.g., phosphorothioate, phosphorodithioate, methylphosphonate, phosphoroamidate, thiophosphate, 3'-thiophosphate, or 5'-thiophosphate.

In some embodiments, a modified internucleotidic linkage is a chiral internucleotidic linkage which comprises a chiral linkage phosphorus. In some embodiments, a chiral internucleotidic linkage is a phosphorothioate linkage. In some embodiments, a chiral internucleotidic linkage is a non-negatively charged internucleotidic linkage. In some embodiments, a chiral internucleotidic linkage is a neutral internucleotidic linkage. In some embodiments, a chiral internucleotidic linkage is chirally controlled with respect to its chiral linkage phosphorus. In some embodiments, a chiral internucleotidic linkage is stereochemically pure with respect to its chiral linkage phosphorus. In some embodiments, a chiral internucleotidic linkage is not chirally controlled. In some embodiments, a pattern of backbone chiral centers comprises or consists of positions and linkage phosphorus configurations of chirally controlled internucleotidic linkages (Rp or Sp) and positions of achiral internucleotidic linkages (e.g., natural phosphate linkages).

In some embodiments, an oligonucleotide comprises a modified internucleotidic linkage (e.g., a modified internucleotidic linkage having the structure of Formula I, I-a, I-b, or I-c, I-n-1, I-n-2, I-n-3, I-n-4, II, II-a-1, II-a-2, II-b-1, II-b-2, II-c-1, II-c-2, II-d-1, II-d-2, etc., or a salt form thereof) as described in U.S. Pat. Nos. 9,394,333, 9,744,183, 9,605,019, 9,598,458, 9,982,257, U.S. Ser. No. 10/160,969, U.S. Ser. No. 10/479,995, US 2020/0056173, US 2018/0216107, US 2019/0127733, U.S. Ser. No. 10/450,568, US 2019/0077817, US 2019/0249173, US 2019/0375774, WO 2018/223056, WO 2018/223073, WO 2018/223081, WO 2018/237194, WO 2019/032607, WO 2019/055951, WO 2019/075357, WO 2019/200185, WO 2019/217784, WO 2019/032612, and/or WO 2020/191252 the internucleotidic linkages (e.g., those of Formula I, I-a, I-b, or I-c, I-n-1, I-n-2, I-n-3, I-n-4, II, II-a-1, II-a-2, II-b-1, II-b-2, II-c-1, II-c-2, II-d-1, II-d-2, etc.,) of each of which are independently incorporated herein by reference. In some embodiments, a modified internucleotidic linkage is a non-negatively charged internucleotidic linkage. In some embodiments, provided oligonucleotides comprise one or more non-negatively charged internucleotidic linkages. In some embodiments, a non-negatively charged internucleotidic linkage is a positively charged internucleotidic linkage. In some embodiments, a non-negatively charged internucleotidic linkage is a neutral internucleotidic linkage. In some embodiments, the present disclosure provides oligonucleotides comprising one or more neutral internucleotidic linkages. In some embodiments, a non-negatively charged internucleotidic linkage or a neutral internucleotidic linkage (e.g., one of Formula I-n-1, I-n-2, I-n-3, I-n-4, II, II-a-1, II-a-2, II-b-1, II-b-2, II-c-1, II-c-2, II-d-1, II-d-2, etc.) is as described in U.S. Pat. Nos. 9,394,333, 9,744,183, 9,605,019, 9,598,458, 9,982,257, U.S. Ser. No. 10/160,969, U.S. Ser. No. 10/479,995, US 2020/0056173, US 2018/0216107, US 2019/0127733, U.S. Ser. No. 10/450,568, US 2019/0077817, US 2019/0249173, US 2019/0375774, WO 2018/223056, WO 2018/223073, WO 2018/223081, WO 2018/237194, WO 2019/032607, WO 2019/055951, WO 2019/075357, WO 2019/200185, WO 2019/217784, WO 2019/032612, and/or WO 2020/191252. In some embodiments, a non-negatively charged internucleotidic linkage or neutral internucleotidic linkage is one of Formula I-n-1, I-n-2, I-n-3, I-n-4, II, II-a-1, II-a-2, II-b-1, II-b-2, II-c-1, II-c-2, II-d-1, II-d-2, etc. as described in WO 2018/223056, WO 2019/032607, WO 2019/075357, WO 2019/032607, WO 2019/075357, WO 2019/200185, WO 2019/217784, WO 2019/032612, and/or WO 2020/191252, such internucleotidic linkages of each of which are independently incorporated herein by reference.

In some embodiments, a non-negatively charged internucleotidic linkage can improve the delivery and/or activity (e.g., ability to decrease the level, activity and/or expression of a target gene or a gene product thereof, selectivity, etc.) of an oligonucleotide.

In some embodiments, a non-negatively charged internucleotidic linkage has the structure of —OP(=W)(—N=C(R")$_2$)—O— or —OP(=W)(—N(R")$_2$)—O—, wherein:

W is O or S;

each R" is independently R' or —N(R')$_2$;

each R' is independently —R, —C(O)R, —C(O)OR, or —S(O)$_2$R;

each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or:

two R groups are optionally and independently taken together to form a covalent bond, or:

two or more R groups on the same atom are optionally and independently taken together with the atom to form an optionally substituted, 3-30 membered monocyclic, bicyclic or polycyclic ring having, in addition to the atom, 0-10 heteroatoms, or:

two or more R groups on two or more atoms are optionally and independently taken together with their intervening atoms to form an optionally substituted, 3-30 membered monocyclic, bicyclic or polycyclic ring having, in addition to the intervening atoms, 0-10 heteroatoms.

In some embodiments, W is O. In some embodiments, W is S.

In some embodiments, R" is R'. In some embodiments, R" is —N(R')$_2$.

In some embodiments, a non-negatively charged internucleotidic linkage has the structure of —OP(=O)(—N=C(N(R')$_2$)$_2$—O—. In some embodiments, a R' group of one N(R')$_2$ is R, a R' group of the other N(R')$_2$ is R, and the two R groups are taken together with their intervening atoms to form an optionally substituted ring, e.g., a 5-membered ring as in n001. In some embodiments, each R' is independently R, wherein each R is independently optionally substituted $C_{1-6}$ aliphatic.

In some embodiments, a non-negatively charged internucleotidic linkage has the structure of —OP(=W)(—N(R')$_2$)—O—.

In some embodiments, R' is R. In some embodiments, R' is H. In some embodiments, R' is —C(O)R. In some embodiments, R' is —C(O)OR. In some embodiments, R' is —S(O)$_2$R.

In some embodiments, R" is —NHR'. In some embodiments, —N(R')$_2$ is —NHR'.

As described herein, some embodiments, R is H. In some embodiments, R is optionally substituted $C_{1-6}$ aliphatic. In some embodiments, R is optionally substituted $C_{1-6}$ alkyl. In some embodiments, R is methyl. In some embodiments, R is substituted methyl. In some embodiments, R is ethyl. In some embodiments, R is substituted ethyl.

In some embodiments, as described herein, a non-negatively charged internucleotidic linkage is a neutral internucleotidic linkage.

In some embodiments, a modified internucleotidic linkage (e.g., a non-negatively charged internucleotidic linkage) comprises optionally substituted triazolyl. In some embodiments, a modified internucleotidic linkage (e.g., a non-negatively charged internucleotidic linkage) comprises optionally substituted alkynyl. In some embodiments, a modified internucleotidic linkage comprises a triazole or alkyne moiety. In some embodiments, a triazole moiety, e.g., a triazolyl group, is optionally substituted. In some embodiments, a triazole moiety, e.g., a triazolyl group) is substituted. In some embodiments, a triazole moiety is unsubstituted. In some embodiments, a modified internucleotidic linkage comprises an optionally substituted cyclic guanidine moiety. In some embodiments, a modified internucleotidic linkage comprises an optionally substituted cyclic guanidine moiety and has the structure of:

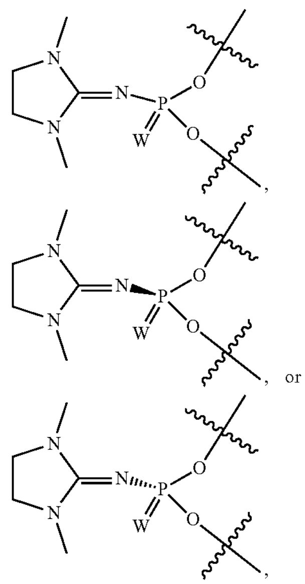

, , or , wherein W is O or S. In some embodiments, W is O. In some embodiments, W is S. In some embodiments, a non-negatively charged internucleotidic linkage is stereochemically controlled.

In some embodiments, an internucleotidic linkage, e.g., a non-negatively charged internucleotidic linkage, a neutral internucleotidic linkage, comprises a cyclic guanidine moiety. In some embodiments, an internucleotidic linkage comprising a cyclic guanidine moiety has the structure of

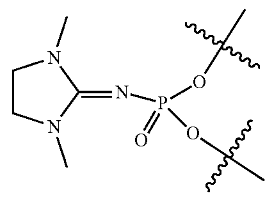

.

In some embodiments, a non-negatively charged internucleotidic linkage, or a neutral internucleotidic linkage, is or comprising a structure of

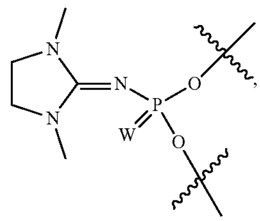

, wherein W is O or S.

In some embodiments, an internucleotidic linkage comprises a Tmg group (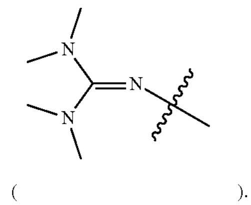).

In some embodiments, an internucleotidic linkage comprises a Tmg group and has the structure of

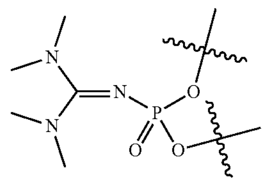 [SMILES: *OP(=O)(N=C(N(C)C)N(C)C)O*]

(the "Tmg internucleotidic linkage"). In some embodiments, neutral internucleotidic linkages include internucleotidic linkages of PNA and PMO, and an Tmg internucleotidic linkage.

In some embodiments, a non-negatively charged internucleotidic linkage comprises an optionally substituted 3-20 membered heterocyclyl or heteroaryl group having 1-10 heteroatoms. In some embodiments, a non-negatively charged internucleotidic linkage comprises an optionally substituted 3-20 membered heterocyclyl or heteroaryl group having 1-10 heteroatoms, wherein at least one heteroatom is nitrogen. In some embodiments, such a heterocyclyl or heteroaryl group is of a 5-membered ring. In some embodiments, such a heterocyclyl or heteroaryl group is of a 6-membered ring.

In some embodiments, a non-negatively charged internucleotidic linkage comprises an optionally substituted 5-20 membered heteroaryl group having 1-10 heteroatoms. In some embodiments, a non-negatively charged internucleotidic linkage comprises an optionally substituted 5-20 membered heteroaryl group having 1-10 heteroatoms, wherein at least one heteroatom is nitrogen. In some embodiments, a non-negatively charged internucleotidic linkage comprises an optionally substituted 5-6 membered heteroaryl group having 1-4 heteroatoms, wherein at least one heteroatom is nitrogen. In some embodiments, a non-negatively charged internucleotidic linkage comprises an optionally substituted 5-membered heteroaryl group having 1-4 heteroatoms, wherein at least one heteroatom is nitrogen. In some embodiments, a heteroaryl group is directly bonded to a linkage phosphorus. In some embodiments, a non-negatively charged internucleotidic linkage comprises an optionally substituted 5-20 membered heterocyclyl group having 1-10 heteroatoms. In some embodiments, a non-negatively charged internucleotidic linkage comprises an optionally substituted 5-20 membered heterocyclyl group having 1-10 heteroatoms, wherein at least one heteroatom is nitrogen. In some embodiments, a non-negatively charged internucleotidic linkage comprises an optionally substituted 5-6 membered heterocyclyl group having 1-4 heteroatoms, wherein at least one heteroatom is nitrogen. In some embodiments, a non-negatively charged internucleotidic linkage comprises an optionally substituted 5-membered heterocyclyl group having 1-4 heteroatoms, wherein at least one heteroatom is nitrogen. In some embodiments, at least two heteroatoms are nitrogen. In some embodiments, a heterocyclyl group is directly bonded to a linkage phosphorus. In some embodiments, a heterocyclyl group is bonded to a linkage phosphorus through a linker, e.g., =N— when the heterocyclyl group is part of a guanidine moiety who directed bonded to a linkage phosphorus through its =N—. In some embodiments, a non-negatively charged internucleotidic linkage comprises an optionally substituted

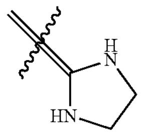 [SMILES: *=C1NCCN1]

group. In some embodiments, a non-negatively charged internucleotidic linkage comprises an substituted

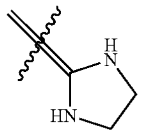 [SMILES: *=C1NCCN1]

group. In some embodiments, a non-negatively charged internucleotidic linkage comprises a

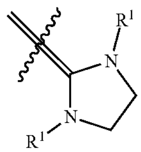

group. In some embodiments, each $R^1$ is independently optionally substituted $C_{1-6}$ alkyl. In some embodiments, each $R^1$ is independently methyl.

In some embodiments, an oligonucleotide comprises different types of internucleotidic phosphorus linkages. In some embodiments, a chirally controlled oligonucleotide comprises at least one natural phosphate linkage and at least one modified (non-natural) internucleotidic linkage. In some embodiments, an oligonucleotide comprises at least one natural phosphate linkage and at least one phosphorothioate. In some embodiments, an oligonucleotide comprises at least one non-negatively charged internucleotidic linkage. In some embodiments, an oligonucleotide comprises at least one natural phosphate linkage and at least one non-negatively charged internucleotidic linkage. In some embodiments, an oligonucleotide comprises at least one phosphorothioate internucleotidic linkage and at least one non-negatively charged internucleotidic linkage. In some embodiments, an oligonucleotide comprises at least one phosphorothioate internucleotidic linkage, at least one natural phosphate linkage, and at least one non-negatively charged internucleotidic linkage. In some embodiments, oligonucleotides comprise one or more, e.g., 1-50, 1-40, 1-30, 1-20, 1-15, 1-10, 1, 2, 3, 4, 5, 6, 7, 8, 9, 10, 11, 12, 13, 14, 15, 16, 17, 18, 19, 20 or more non-negatively charged internucleotidic linkages. In some embodiments, a non-negatively charged internucleotidic linkage is not negatively charged in that at a given pH in an aqueous solution less than 50%, 40%, 40%, 30%, 20%, 10%, 5%, or 1% of the internucleotidic linkage exists in a negatively charged salt form. In some embodiments, a pH is about pH 7.4. In some embodiments, a pH is about 4-9. In some embodiments, the percentage is less than 10%. In some embodiments, the percentage is less than 5%. In some embodiments, the percentage is less than 1%. In some embodiments, an internucleotidic linkage is a non-negatively charged internucleotidic linkage in that the neutral form of the internucleotidic linkage has no pKa that is no more than about 1, 2, 3, 4, 5, 6, or 7 in water. In some embodiments, no pKa is 7 or less. In some embodiments, no pKa is 6 or less. In some embodiments, no pKa is 5 or less. In some embodiments, no pKa is 4 or less. In some embodiments, no pKa is 3 or less. In some embodiments, no pKa is 2 or less. In some embodiments, no pKa is 1 or less. In some embodiments, pKa of the neutral form of an internucleotidic linkage can be represented by pKa of the neutral form of a compound having the structure of $CH_3$— the internucleotidic linkage-$CH_3$. For example, pKa of

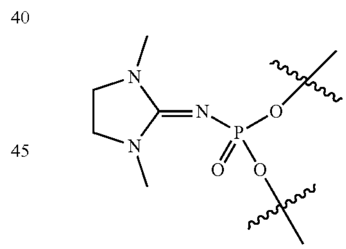

can be represented by pKa

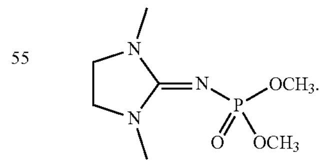

In some embodiments, a non-negatively charged internucleotidic linkage is a neutral internucleotidic linkage. In some embodiments, a non-negatively charged internucleotidic linkage is a positively-charged internucleotidic linkage. In some embodiments, a non-negatively charged internucleotidic linkage comprises a guanidine moiety. In some embodiments, a non-negatively charged internucleotidic linkage comprises a heteroaryl base moiety. In some embodiments, a non-negatively charged internucleotidic linkage comprises a triazole moiety. In some embodiments, a non-negatively charged internucleotidic linkage comprises an alkynyl moiety.

In some embodiments, an oligonucleotide comprises different types of internucleotidic phosphorus linkages. In some embodiments, a chirally controlled oligonucleotide comprises at least one natural phosphate linkage and at least one modified (non-natural) internucleotidic linkage. In some embodiments, an oligonucleotide comprises at least one natural phosphate linkage and at least one phosphorothioate. In some embodiments, an oligonucleotide comprises at least one non-negatively charged internucleotidic linkage. In some embodiments, an oligonucleotide comprises at least one natural phosphate linkage and at least one non-negatively charged internucleotidic linkage.

Without wishing to be bound by any particular theory, the present disclosure notes that a neutral internucleotidic linkage can be more hydrophobic than a phosphorothioate internucleotidic linkage (PS), which can be more hydrophobic than a natural phosphate linkage (PO). Typically, unlike a PS or PO, a neutral internucleotidic linkage bears less charge. Without wishing to be bound by any particular theory, the present disclosure notes that incorporation of one or more neutral internucleotidic linkages into an oligonucleotide may increase oligonucleotides' ability to be taken up by a cell and/or to escape from endosomes. Without wishing to be bound by any particular theory, the present disclosure notes that incorporation of one or more neutral internucleotidic linkages can be utilized to modulate melting temperature of duplexes formed between an oligonucleotide and its target nucleic acid.

Without wishing to be bound by any particular theory, the present disclosure notes that incorporation of one or more non-negatively charged internucleotidic linkages, e.g., neutral internucleotidic linkages, into an oligonucleotide may be able to increase the oligonucleotide's ability to mediate a function such as gene knockdown. In some embodiments, an oligonucleotide, e.g., a C9orf72 oligonucleotide capable of mediating knockdown of level of a nucleic acid or a product encoded thereby comprises one or more non-negatively charged internucleotidic linkages. In some embodiments, an oligonucleotide, e.g., a C9orf72 oligonucleotide capable of mediating knockdown of expression of a target gene comprises one or more non-negatively charged internucleotidic linkages.

In some embodiments, a non-negatively charged internucleotidic linkage, e.g., a neutral internucleotidic linkage is not chirally controlled. In some embodiments, a non-negatively charged internucleotidic linkage is chirally controlled. In some embodiments, a non-negatively charged internucleotidic linkage is chirally controlled and its linkage phosphorus is Rp. In some embodiments, a non-negatively charged internucleotidic linkage is chirally controlled and its linkage phosphorus is Sp.

In many embodiments, as demonstrated extensively, oligonucleotides of the present disclosure comprise two or more different internucleotidic linkages. In some embodiments, an oligonucleotide comprises a phosphorothioate internucleotidic linkage and a non-negatively charged internucleotidic linkage. In some embodiments, an oligonucleotide comprises a phosphorothioate internucleotidic linkage, a non-negatively charged internucleotidic linkage, and a natural phosphate linkage. In some embodiments, a non-negatively charged internucleotidic linkage is a neutral internucleotidic linkage. In some embodiments, a non-negatively charged internucleotidic linkage is n001. In some embodiments, each phosphorothioate internucleotidic linkage is independently chirally controlled. In some embodiments, each chiral modified internucleotidic linkage is independently chirally controlled.

In some embodiments, a non-negatively charged internucleotidic linkage, e.g., a neutral internucleotidic linkage is not chirally controlled. In some embodiments, a non-negatively charged internucleotidic linkage is chirally controlled. In some embodiments, a non-negatively charged internucleotidic linkage is chirally controlled and its linkage phosphorus is Rp. In some embodiments, a non-negatively charged internucleotidic linkage is chirally controlled and its linkage phosphorus is Sp.

A typical connection, as in natural DNA and RNA, is that an internucleotidic linkage forms bonds with two sugars (which can be either unmodified or modified as described herein). In many embodiments, as exemplified herein an internucleotidic linkage forms bonds through its oxygen atoms or heteroatoms with one optionally modified ribose or deoxyribose at its 5' carbon, and the other optionally modified ribose or deoxyribose at its 3' carbon. In some embodiments, each nucleoside units connected by an internucleotidic linkage independently comprises a nucleobase which is independently an optionally substituted A, T, C, G, or U, or an optionally substituted tautomer of A, T, C, G or U.

As appreciated by those skilled in the art, many other types of internucleotidic linkages may be utilized in accordance with the present disclosure, for example, those described in U.S. Pat. Nos. 3,687,808; 4,469,863; 4,476,301; 5,177,195; 5,023,243; 5,034,506; 5,166,315; 5,185,444; 5,188,897; 5,214,134; 5,216,141; 5,235,033; 5,264,423; 5,264,564; 5,276,019; 5,278,302; 5,286,717; 5,321,131; 5,399,676; 5,405,938; 5,405,939; 5,434,257; 5,453,496; 5,455,233; 5,466,677; 5,466,677; 5,470,967; 5,476,925; 5,489,677; 5,519,126; 5,536,821; 5,541,307; 5,541,316; 5,550,111; 5,561,225; 5,563,253; 5,571,799; 5,587,361; 5,596,086; 5,602,240; 5,608,046; 5,610,289; 5,618,704; 5,623,070; 5,625,050; 5,633,360; 5,64,562; 5,663,312; 5,677,437; 5,677,439; 6,160,109; 6,239,265; 6,028,188; 6,124,445; 6,169,170; 6,172,209; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; or RE39464. In some embodiments, a modified internucleotidic linkage is one described in U.S. Pat. Nos. 9,394,333, 9,744,183, 9,605,019, 9,598,458, 9,982,257, U.S. Ser. No. 10/160,969, U.S. Ser. No. 10/479,995, US 2020/0056173, US 2018/0216107, US 2019/0127733, U.S. Ser. No. 10/450,568, US 2019/0077817, US 2019/0249173, US 2019/0375774, WO 2018/223056, WO 2018/223073, WO 2018/223081, WO 2018/237194, WO 2019/032607, WO 2019/055951, WO 2019/075357, WO 2019/200185, WO 2019/217784, WO 2019/032612, and/or WO 2020/191252, the nucleobases, sugars, internucleotidic linkages, chiral auxiliaries/reagents, and technologies for oligonucleotide synthesis (reagents, conditions, cycles, etc.) of each of which is independently incorporated herein by reference.

Various types of internucleotidic linkages may be utilized in combination of other structural elements, e.g., sugars, to achieve desired oligonucleotide properties and/or activities. For example, the present disclosure routinely utilizes modified internucleotidic linkages and modified sugars, optionally with natural phosphate linkages and natural sugars, in designing oligonucleotides. In some embodiments, the present disclosure provides an oligonucleotide comprising one or more modified sugars. In some embodiments, the present disclosure provides an oligonucleotide comprising one or more modified sugars and one or more modified internucleotidic linkages, one or more of which are natural phosphate linkages.

Nucleobases

Various nucleobases may be utilized in provided oligonucleotides in accordance with the present disclosure. In some embodiments, a nucleobase is a natural nucleobase, the most commonly occurring ones being A, T, C, G and U. In some embodiments, a nucleobase is a modified nucleobase in that it is not A, T, C, G or U. In some embodiments, a nucleobase is optionally substituted A, T, C, G or U, or a substituted tautomer of A T, C, G or U. In some embodiments, a nucleobase is optionally substituted A, T, C, G or U, e.g., 5 mC, 5-hydroxymethyl C, etc. In some embodiments, a nucleobase is alkyl-substituted A, T, C, G or U. In some embodiments, a nucleobase is A. In some embodiments, a nucleobase is T. In some embodiments, a nucleobase is C. In some embodiments, a nucleobase is G. In some embodiments, a nucleobase is U. In some embodiments, a nucleobase is 5 mC. In some embodiments, a nucleobase is substituted A, T, C, G or U. In some embodiments, a nucleobase is a substituted tautomer of A, T, C, G or U. In some embodiments, substitution protects certain functional groups in nucleobases to minimize undesired reactions during oligonucleotide synthesis. Suitable technologies for nucleobase protection in oligonucleotide synthesis are widely known in the art and may be utilized in accordance with the present disclosure. In some embodiments, modified nucleobases improves properties and/or activities of oligonucleotides. For example, in many cases, 5 mC may be utilized in place of C to modulate certain undesired biological effects, e.g., immune responses. In some embodiments, when determining sequence identity, a substituted nucleobase having the same hydrogen-bonding pattern is treated as the same as the unsubstituted nucleobase, e.g., 5 mC may be treated the same as C [e.g., an oligonucleotide having 5 mC in place of C (e.g., AT5mCG) is considered to have the same base sequence as an oligonucleotide having C at the corresponding location(s) (e.g., ATCG)].

In some embodiments, an oligonucleotide comprises one or more A, T, C, G or U. In some embodiments, an oligonucleotide comprises one or more optionally substituted A, T, C, G or U. In some embodiments, an oligonucleotide comprises one or more 5-methylcytidine, 5-hydroxymethylcytidine, 5-formylcytosine, or 5-carboxylcytosine. In some embodiments, an oligonucleotide comprises one or more 5-methylcytidine. In some embodiments, each nucleobase in an oligonucleotide is selected from the group consisting of optionally substituted A, T, C, G and U, and optionally substituted tautomers of A, T, C, G and U. In some embodiments, each nucleobase in an oligonucleotide is optionally protected A, T, C, G and U. In some embodiments, each nucleobase in an oligonucleotide is optionally substituted A, T, C, G or U. In some embodiments, each nucleobase in an oligonucleotide is selected from the group consisting of A, T, C, G, U, and 5 mC. In some embodiments, a nucleobase is hypoxanthine.

In some embodiments, a nucleobase is optionally substituted 2AP or DAP. In some embodiments, a nucleobase is optionally substituted 2AP. In some embodiments, a nucleobase is optionally substituted DAP. In some embodiments, a nucleobase is 2AP. In some embodiments, a nucleobase is DAP.

In some embodiments, a nucleobase is a natural nucleobase or a modified nucleobase derived from a natural nucleobase. Examples include uracil, thymine, adenine, cytosine, and guanine optionally having their respective amino groups protected by acyl protecting groups, 2-fluorouracil, 2-fluorocytosine, 5-bromouracil, 5-iodouracil, 2,6-diaminopurine, azacytosine, pyrimidine analogs such as pseudoisocytosine and pseudouracil and other modified nucleobases such as 8-substituted purines, xanthine, or hypoxanthine (the latter two being the natural degradation products). Certain examples of modified nucleobases are disclosed in Chiu and Rana, R N A, 2003, 9, 1034-1048, Limbach et al. Nucleic Acids Research, 1994, 22, 2183-2196 and Revankar and Rao, Comprehensive Natural Products Chemistry, vol. 7, 313. In some embodiments, a modified nucleobase is substituted uracil, thymine, adenine, cytosine, or guanine. In some embodiments, a modified nucleobase is a functional replacement, e.g., in terms of hydrogen bonding and/or base pairing, of uracil, thymine, adenine, cytosine, or guanine. In some embodiments, a nucleobase is optionally substituted uracil, thymine, adenine, cytosine, 5-methylcytosine, or guanine. In some embodiments, a nucleobase is uracil, thymine, adenine, cytosine, 5-methylcytosine, or guanine.

In some embodiments, a provided oligonucleotide comprises one or more 5-methylcytosine. In some embodiments, the present disclosure provides an oligonucleotide whose base sequence is disclosed herein, e.g., in Table A1, wherein each T may be independently replaced with U and vice versa. In some embodiments, in provided oligonucleotides one or more C are independently modified to be 5 mC. As appreciated by those skilled in the art, in some embodiments, 5 mC may be treated as C with respect to base sequence of an oligonucleotide—such oligonucleotide comprises a nucleobase modification at the C position (e.g., see various oligonucleotides in Table A1).

In some embodiments, a nucleobase is one described in U.S. Pat. Nos. 9,394,333, 9,744,183, 9,605,019, 9,598,458, 9,982,257, U.S. Ser. No. 10/160,969, U.S. Ser. No. 10/479,995, US 2020/0056173, US 2018/0216107, US 2019/0127733, U.S. Ser. No. 10/450,568, US 2019/0077817, US 2019/0249173, US 2019/0375774, WO 2018/223056, WO 2018/223073, WO 2018/223081, WO 2018/237194, WO 2019/032607, WO 2019/055951, WO 2019/075357, WO 2019/200185, WO 2019/217784, WO 2019/032612, and/or WO 2020/191252, the nucleobases of each of which is incorporated herein by reference.

Sugars

Various sugars, including modified sugars, can be utilized in accordance with the present disclosure. In some embodiments, the present disclosure provides sugar modifications and patterns thereof optionally in combination with other structural elements (e.g., internucleotidic linkage modifications and patterns thereof, pattern of backbone chiral centers thereof, etc.) that when incorporated into oligonucleotides can provide improved properties and/or activities.

The most common naturally occurring nucleosides comprise ribose sugars (e.g., in RNA) or deoxyribose sugars (e.g., in DNA) linked to the nucleobases adenosine (A), cytosine (C), guanine (G), thymine (T) or uracil (U). In some embodiments, a sugar, e.g., various sugars in many oligonucleotides in Table A1 (unless otherwise notes), is a natural DNA sugar (in DNA nucleic acids or oligonucleotides, having the structure of

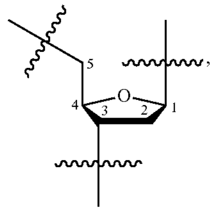

wherein a nucleobase is attached to the 1' position, and the 3' and 5' positions are connected to internucleotidic linkages (as appreciated by those skilled in the art, if at the 5'-end of an oligonucleotide, the 5' position may be connected to a 5'-end group (e.g., —OH), and if at the 3'-end of an oligonucleotide, the 3' position may be connected to a 3'-end group (e.g., —OH). In some embodiments, a sugar is a natural RNA sugar (in RNA nucleic acids or oligonucleotides, having the structure of

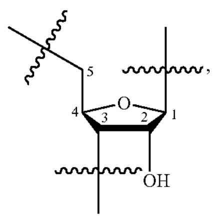

wherein a nucleobase is attached to the 1' position, and the 3' and 5' positions are connected to internucleotidic linkages (as appreciated by those skilled in the art, if at the 5'-end of an oligonucleotide, the 5' position may be connected to a 5'-end group (e.g., —OH), and if at the 3'-end of an oligonucleotide, the 3' position may be connected to a 3'-end group (e.g., —OH). In some embodiments, a sugar is a modified sugar in that it is not a natural DNA sugar or a natural RNA sugar. Among other things, modified sugars may provide improved stability. In some embodiments, modified sugars can be utilized to alter and/or optimize one or more hybridization characteristics. In some embodiments, modified sugars can be utilized to alter and/or optimize target recognition. In some embodiments, modified sugars can be utilized to optimize Tm. In some embodiments, modified sugars can be utilized to improve oligonucleotide activities.

Sugars can be bonded to internucleotidic linkages at various positions. As non-limiting examples, internucleotidic linkages can be bonded to the 2', 3', 4' or 5' positions of sugars. In some embodiments, as most commonly in natural nucleic acids, an internucleotidic linkage connects with one sugar at the 5' position and another sugar at the 3' position unless otherwise indicated.

In some embodiments, a sugar is an optionally substituted natural DNA or RNA sugar. In some embodiments, a sugar is optionally substituted

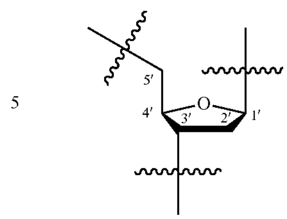

In some embodiments, the 2' position is optionally substituted. In some embodiments, a sugar is

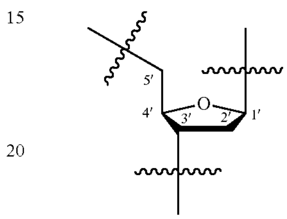

In some embodiments, a sugar has the structure of

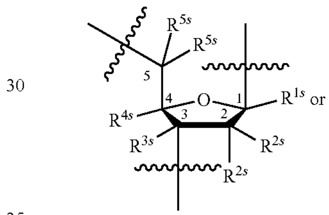

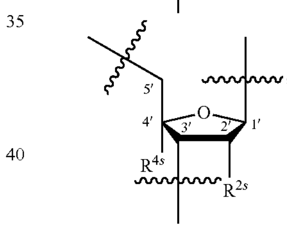

wherein each of $R^{1s}$, $R^{2s}$, $R^{3s}$, $R^{4s}$, and $R^{5s}$ is independently —H, a suitable substituent or suitable sugar modification (e.g., those described in U.S. Pat. Nos. 9,394,333, 9,744,183, 9,605,019, 9,982,257, US 20170037399, US 20180216108, US 20180216107, U.S. Pat. No. 9,598,458, WO 2017/062862, WO 2018/067973, WO 2017/160741, WO 2017/192679, WO 2017/210647, WO 2018/098264, WO 2018/022473, WO 2018/223056, WO 2018/223073, WO 2018/223081, WO 2018/237194, WO 2019/032607, WO2019/032612, WO 2019/055951, and/or WO 2019/075357, the substituents, sugar modifications, descriptions of $R^{1s}$, $R^{2s}$, $R^{3s}$, $R^{4s}$, and $R^{5s}$, and modified sugars of each of which are independently incorporated herein by reference). In some embodiments, each of $R^{1s}$, $R^{2s}$, $R^{3s}$, $R^{4s}$, and $R^{5s}$ is independently $R^s$, wherein each $R^s$ is independently —F, —Cl, —Br, —I, —CN, —$N_3$, —NO, —$NO_2$,-$L^s$-R',-$L^s$-OR',-$L^s$-SR',-$L^s$-N(R')$_2$, —O-$L^s$-OR', —O-$L^s$-SR', or —O-$L^s$-N(R')$_2$, wherein each R' is independently as described herein, and each $L^s$ is independently a covalent bond or optionally substituted bivalent $C_{1-6}$ aliphatic or heteroaliphatic having 1-4 heteroatoms; or two $R^s$ are taken together to form a bridge -$L^s$-. In some embodiments, R' is optionally substituted $C_{1-10}$ aliphatic. In some embodiments, a sugar has the structure of

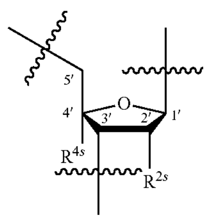

In some embodiments, $R^{4s}$ is —H. In some embodiments, a sugar has the structure of

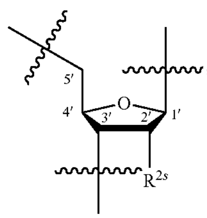

wherein $R^{2s}$ is —H, halogen, or —OR, wherein R is optionally substituted $C_{1-6}$ aliphatic. In some embodiments, $R^{2s}$ is —H. In some embodiments, $R^{2s}$ is —F. In some embodiments, $R^{2s}$ is —OMe. In some embodiments, a modified nucleoside is mA, mT, mC, m5 mC, mG, mU, etc., in which $R^{2s}$ is —OMe. In some embodiments, $R^{2s}$ is —$OCH_2CH_2OMe$. In some embodiments, a modified nucleoside is Aeo, Teo, Ceo, m5Ceo, Geo, Ueo, etc., in which $R^{2s}$ is —$OCH_2CH_2OMe$.

In some embodiments, a sugar has the structure of

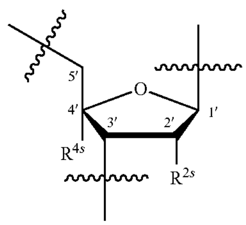

wherein $R^{2s}$ and $R^{4s}$ are taken together to form -$L^s$-, wherein $L^s$ is a covalent bond or optionally substituted bivalent $C_{1-6}$ aliphatic or heteroaliphatic having 1-4 heteroatoms. In some embodiments, each heteroatom is independently selected from nitrogen, oxygen or sulfur). In some embodiments, $L^s$ is optionally substituted C2-O—$CH_2$—C4. In some embodiments, $L^s$ is C2-O—$CH_2$—C4. In some embodiments, $L^s$ is C2-O—(R)—$CH(CH_2CH_3)$—C4. In some embodiments, $L^s$ is C2-O—(S)—$CH(CH_2CH_3)$—C4.

In some embodiments, a sugar is a bicyclic sugar, e.g., sugars wherein $R^{2s}$ and $R^{4s}$ are taken together to form a link as described in the present disclosure. In some embodiments, a sugar is selected from LNA sugars, BNA sugars, cEt sugars, etc. In some embodiments, a bridge is between the 2' and 4'-carbon atoms (corresponding to $R^{2s}$ and $R^{4s}$ taken together with their intervening atoms to form an optionally substituted ring as described herein). In some embodiments, examples of bicyclic sugars include alpha-L-methyleneoxy (4'-$CH_2$—O-2') LNA, beta-D-methyleneoxy (4'-$CH_2$—O-2') LNA, ethyleneoxy (4'-$(CH_2)_2$-O-2') LNA, aminooxy (4'-$CH_2$—O—N(R)-2') LNA, and oxyamino (4'-$CH_2$—N(R)—O-2') LNA. In some embodiments, a bicyclic sugar, e.g., a LNA or BNA sugar, is sugar having at least one bridge between two sugar carbons. In some embodiments, a bicyclic sugar in a nucleoside may have the stereochemical configurations of alpha-L-ribofuranose or beta-D-ribofuranose. In some embodiments, a sugar is a sugar described in WO 1999014226. In some embodiments, a 4'-2' bicyclic sugar or 4' to 2' bicyclic sugar is a bicyclic sugar comprising a furanose ring which comprises a bridge connecting the 2' carbon atom and the 4' carbon atom of the sugar ring. In some embodiments, a bicyclic sugar, e.g., a LNA or BNA sugar, comprises at least one bridge between two pentofuranosyl sugar carbons. In some embodiments, a LNA or BNA sugar, comprises at least one bridge between the 4' and the 2' pentofuranosyl sugar carbons.

In some embodiments, a bicyclic sugar is a sugar of alpha-L-methyleneoxy (4'-$CH_2$—O-2') BNA, beta-D-methyleneoxy (4'-$CH_2$—O-2') BNA, ethyleneoxy (4'-$(CH_2)_2$-O-2') BNA, aminooxy (4'-$CH_2$—O—N(R)-2') BNA, oxyamino (4'-$CH_2$—N(R)—O-2') BNA, methyl(methyleneoxy) (4'-$CH(CH_3)$—O-2') BNA (also referred to as constrained ethyl or cEt), methylene-thio (4'-$CH_2$—S-2') BNA, methylene-amino (4'-$CH_2$—N(R)-2') BNA, methyl carbocyclic (4'-$CH_2$—$CH(CH_3)$-2') BNA, propylene carbocyclic (4'-$(CH_2)_3$-2') BNA, or vinyl BNA.

In some embodiments, a sugar modification is 2'-OMe, 2'-MOE, 2'-LNA, 2'-F, 5'-vinyl, or S-cEt. In some embodiments, a modified sugar is a sugar of FRNA, FANA, or morpholino. In some embodiments, an oligonucleotide comprises a nucleic acid analog, e.g., GNA, LNA, PNA, TNA, F-HNA (F-THP or 3'-fluoro tetrahydropyran), MNA (mannitol nucleic acid, e.g., Leumann 2002 Bioorg. Med. Chem. 10: 841-854), ANA (anitol nucleic acid), or morpholino, or a portion thereof. In some embodiments, a sugar modification replaces a natural sugar with another cyclic or acyclic moiety. Examples of such moieties are widely known in the art, e.g., those used in morpholino, glycol nucleic acids, etc. and may be utilized in accordance with the present disclosure. As appreciated by those skilled in the art, when utilized with modified sugars, in some embodiments internucleotidic linkages may be modified, e.g., as in morpholino, PNA, etc.

In some embodiments, a sugar is a 6'-modified bicyclic sugar that have either (R) or (S)-chirality at the 6-position, e.g., those described in U.S. Pat. No. 7,399,845. In some embodiments, a sugar is a 5'-modified bicyclic sugar that has either (R) or (S)-chirality at the 5-position, e.g., those described in US 20070287831.

In some embodiments, a modified sugar contains one or more substituents at the 2' position (typically one substituent, and often at the axial position) independently selected from —F; —$CF_3$, —CN, —$N_3$, —NO, —$NO_2$, —OR', —SR', or —$N(R')_2$, wherein each R' is independently optionally substituted $C_{1-10}$ aliphatic; —O—($C_1$-$C_{10}$ alkyl), —S—($C_1$-$C_{10}$ alkyl), —NH—($C_1$-$C_{10}$ alkyl), or —N($C_1$-$C_{10}$ alkyl$)_2$; —O—($C_2$-$C_{10}$ alkenyl), —S—($C_2$-$C_{10}$ alkenyl), —NH—($C_2$-$C_{10}$ alkenyl), or —N($C_2$-$C_{10}$ alkenyl$)_2$; —O—($C_2$-$C_{10}$ alkynyl), —S—($C_2$-$C_{10}$ alkynyl), —NH—($C_2$-$C_{10}$ alkynyl), or —N($C_2$-$C_{10}$ alkynyl$)_2$; or —O—($C_1$-$C_{10}$ alkylene)-O—($C_1$-$C_{10}$ alkyl), —O—($C_1$-$C_{10}$ alkylene)-NH—($C_1$-$C_{10}$ alkyl) or —O—($C_1$-$C_{10}$ alkylene)-NH($C_1$-$C_{10}$ alkyl$)_2$, —NH—($C_1$-$C_{10}$ alkylene)-O—($C_1$-$C_{10}$ alkyl), or —N($C_1$-$C_{10}$ alkyl)-($C_1$-$C_{10}$ alkylene)-O—($C_1$-$C_{10}$ alkyl), wherein each of the alkyl, alkylene, alkenyl and alkynyl is independently and optionally substituted. In some embodiments, a substituent is —$O(CH_2)\cdot OCH_3$, —$O(CH_2)_nNH_2$, MOE, DMAOE, or DMAEOE, wherein wherein n is from 1 to about 10. In some embodiments, a modified sugar is one described in WO 2001/088198; and Martin et al., Helv. Chim. Acta, 1995, 78, 486-504. In some embodiments, a modified sugar comprises one or more groups selected from a substituted silyl group, an RNA cleaving group, a reporter group, a fluorescent label, an intercalator, a group for improving the pharmacokinetic properties of a nucleic acid, a group for improving the pharmacodynamic properties of a nucleic acid, or other substituents having similar properties. In some embodiments, modifications are made at one or more of the 2', 3', 4', or 5' positions, including the 3' position of the sugar on the 3'-terminal nucleoside or in the 5' position of the 5'-terminal nucleoside.

In some embodiments, a modified sugar is a ribose whose 2'-OH is replaced with a group (e.g., $R^{2s}$) selected from —F; —$CF_3$, —CN, —$N_3$, —NO, —$NO_2$, —OR', —SR', or —$N(R')_2$, wherein each R' is independently described in the present disclosure; —O—($C_1$-$C_{10}$ alkyl), —S—($C_1$-$C_{10}$ alkyl), —NH—($C_1$-$C_{10}$ alkyl), or —N($C_1$-$C_{10}$ alkyl)$_2$; —O—($C_2$-$C_{10}$ alkenyl), —S—($C_2$-$C_{10}$ alkenyl), —NH—($C_2$-$C_{10}$ alkenyl), or —N($C_2$-$C_{10}$ alkenyl)$_2$; —O—($C_2$-$C_{10}$ alkynyl), —S—($C_2$-$C_{10}$ alkynyl), —NH—($C_2$-$C_{10}$ alkynyl), or —N($C_2$-$C_{10}$ alkynyl)$_2$; or —O—($C_1$-$C_{10}$ alkylene)-O—($C_1$-$C_{10}$ alkyl), —O—($C_1$-$C_{10}$ alkylene)-NH—($C_1$-$C_{10}$ alkyl) or —O—($C_1$-$C_{10}$ alkylene)-NH($C_1$-$C_{10}$ alkyl)$_2$, —NH—($C_1$-$C_{10}$ alkylene)-O—($C_1$-$C_{10}$ alkyl), or —N($C_1$-$C_{10}$ alkyl)-($C_1$-$C_{10}$ alkylene)-O—($C_1$-$C_{10}$ alkyl), wherein each of the alkyl, alkylene, alkenyl and alkynyl is independently and optionally substituted. In some embodiments, the 2'-OH is replaced with —H (deoxyribose). In some embodiments, the 2'-OH is replaced with —F. In some embodiments, the 2'-OH is replaced with —OR'. In some embodiments, the 2'-OH is replaced with —OMe. In some embodiments, the 2'-OH is replaced with —$OCH_2CH_2OMe$.

In some embodiments, a sugar modification is a 2'-modification. Commonly used 2'-modifications include but are not limited to 2'-OR, wherein R is optionally substituted $C_{1-6}$ aliphatic. In some embodiments, a modification is 2'-OR, wherein R is optionally substituted $C_{1-6}$ alkyl. In some embodiments, a modification is 2'-OMe. In some embodiments, a modification is 2'-MOE. In some embodiments, a 2'-modification is S-cEt. In some embodiments, a modified sugar is an LNA sugar. In some embodiments, a 2'-modification is —F. In some embodiments, a 2'-modification is FANA. In some embodiments, a 2'-modification is FRNA. In some embodiments, a sugar modification is a 5'-modification, e.g., 5'-Me. In some embodiments, a sugar modification changes the size of the sugar ring. In some embodiments, a sugar modification is the sugar moiety in FHNA.

In some embodiments, a sugar modification replaces a sugar moiety with another cyclic or acyclic moiety. Examples of such moieties are widely known in the art, including but not limited to those used in morpholino (optionally with its phosphorodiamidate linkage), glycol nucleic acids, etc.

In some embodiments, one or more of the sugars of a C9orf72 oligonucleotide are modified. In some embodiments, each sugar of an oligonucleotide is independently modified. In some embodiments, a modified sugar comprises a 2'-modification. In some embodiments, each modified sugar independently comprises a 2'-modification. In some embodiments, a 2'-modification is 2'-OR, wherein R is optionally substituted $C_{1-6}$ aliphatic. In some embodiments, a 2'-modification is a 2'-OMe. In some embodiments, a 2'-modification is a 2'-MOE. In some embodiments, a 2'-modification is an LNA sugar modification. In some embodiments, a 2'-modification is 2'-F. In some embodiments, each sugar modification is independently a 2'-modification. In some embodiments, each sugar modification is independently 2'-OR. In some embodiments, each sugar modification is independently 2'-OR, wherein R is optionally substituted $C_{1-6}$ alkyl. In some embodiments, each sugar modification is 2'-OMe. In some embodiments, each sugar modification is 2'-MOE. In some embodiments, each sugar modification is independently 2'-OMe or 2'-MOE. In some embodiments, each sugar modification is independently 2'-OMe, 2'-MOE, or a LNA sugar.

In some embodiments, a modified sugar is an optionally substituted ENA sugar. In some embodiments, a sugar is one described in, e.g., Seth et al., J Am Chem Soc. 2010 Oct. 27; 132(42): 14942-14950. In some embodiments, a modified sugar is a sugar in XNA (xenonucleic acid), for instance, arabinose, anhydrohexitol, threose, 2'fluoroarabinose, or cyclohexene.

Modified sugars include cyclobutyl or cyclopentyl moieties in place of a pentofuranosyl sugar. Representative examples of such modified sugars include those described in U.S. Pat. Nos. 4,981,957, 5,118,800, 5,319,080, or U.S. Pat. No. 5,359,044. In some embodiments, the oxygen atom within the ribose ring is replaced by nitrogen, sulfur, selenium, or carbon. In some embodiments, —O— is replaced with —N(R')—, —S—, —Se— or —C(R')$_2$—. In some embodiments, a modified sugar is a modified ribose wherein the oxygen atom within the ribose ring is replaced with nitrogen, and wherein the nitrogen is optionally substituted with an alkyl group (e.g., methyl, ethyl, isopropyl, etc.).

In some embodiments, sugars are connected by internucleotidic linkages, in some embodiments, modified internucleotidic linkage. In some embodiments, an internucleotidic linkage does not contain a linkage phosphorus. In some embodiments, an internucleotidic linkage is -L-. In some embodiments, an internucleotidic linkage is —OP(O)(—C≡CH)O—, —OP(O)(R)O— (e.g., R is —$CH_3$), 3' —NHP(O)(OH)O-5', 3'-OP(O)($CH_3$)$OCH_2$-5', 3'-$CH_2C(O)NHCH_2$-5', 3'-$SCH_2OCH_2$-5', 3'—$OCH_2OCH_2$-5', 3'-$CH_2NR'CH_2$-5', 3'-$CH_2N(Me)OCH_2$-5', 3'-NHC(O)$CH_2CH_2$-5', 3'-NR'C(O)$CH_2CH_2$-5', 3'-$CH_2CH_2NR'$-5', 3'-$CH_2CH_2NH$-5', or 3'-$OCH_2CH_2N(R')$-5'. In some embodiments, a 5' carbon may be optionally substituted with =O.

In some embodiments, a modified sugar is an optionally substituted pentose or hexose. In some embodiments, a modified sugar is an optionally substituted pentose. In some embodiments, a modified sugar is an optionally substituted hexose. In some embodiments, a modified sugar is an optionally substituted ribose or hexitol. In some embodiments, a modified sugar is an optionally substituted ribose. In some embodiments, a modified sugar is an optionally substituted hexitol.

In some embodiments, a sugar modification is 5'-vinyl (R or S), 5'-methyl (R or S), 2'-SH, 2'-F, 2'-$OCH_3$, 2'-$OCH_2CH_3$, 2'—$OCH_2CH_2F$ or 2'-O$(CH_2)_2OCH_3$. In some embodiments, a substituent at the 2' position, e.g., a 2'-modification, is allyl, amino, azido, thio, 0-allyl, O—$C_1$-$C_{10}$ alkyl, $OCF_3$, $OCH_2F$, O$(CH_2)_2SCH_3$, O$(CH_2)_2$—O—N($R_m$)(Rn), O—$CH_2$—C(=O)—N($R_m$)(R), and O—$CH_2$—C(=O)—N($R_1$)—$(CH_2)_2$—N($R_m$)($R_n$), wherein each allyl, amino and alkyl is optionally substituted, and each of $R_1$, $R_m$ and R. is independently R' as described in the present disclosure. In some embodiments, each of $R_1$, $R_m$ and R, is independently —H or optionally substituted $C_1$-$C_{10}$ alkyl.

In some embodiments, a sugar is a tetrahydropyran or THP sugar. In some embodiments, a modified nucleoside is tetrahydropyran nucleoside or THP nucleoside which is a nucleoside having a six-membered tetrahydropyran sugar substituted for a pentofuranosyl residue in typical natural nucleosides. THP sugars and/or nucleosides include those used in hexitol nucleic acid (HNA), anitol nucleic acid (ANA), mannitol nucleic acid (MNA) (e.g., Leumann, Bioorg. Med. Chem., 2002, 10, 841-854) or fluoro HNA (F-HNA).

In some embodiments, sugars comprise rings having more than 5 atoms and/or more than one heteroatom, e.g., morpholino sugars.

As those skilled in the art will appreciate, modifications of sugars, nucleobases, internucleotidic linkages, etc. can and are often utilized in combination in oligonucleotides, e.g., see various oligonucleotides in Table A1. For example, a combination of sugar modification and nucleobase modification is 2'-F (sugar) 5-methyl (nucleobase) modified nucleosides. In some embodiments, a combination is replacement of a ribosyl ring oxygen atom with S and substitution at the 2'-position.

In some embodiments, a 2'-modified sugar is a furanosyl sugar modified at the 2' position. In some embodiments, a 2'-modification is halogen, —R' (wherein R' is not —H), —OR' (wherein R' is not —H), —SR', $—N(R')_2$, optionally substituted $—CH_2—CH{=}CH_2$, optionally substituted alkenyl, or optionally substituted alkynyl. In some embodiments, a 2'-modifications is selected from $—O[(CH_2)_nO]_mCH_3$, $—O(CH_2)_nNH_2$, $—O(CH_2)_nCH_3$, $—O(CH_2)_nF$, $—O(CH_2)_nONH_2$, $—OCH_2C({=}O)N(H)CH_3$, and $—O(CH_2)_nON[(CH_2)_nCH_3]2$, wherein each n and m is independently from 1 to about 10. In some embodiments, a 2'-modification is optionally substituted $C_1$-$C_{12}$ alkyl, optionally substituted alkenyl, optionally substituted alkynyl, optionally substituted alkaryl, optionally substituted aralkyl, optionally substituted —O-alkaryl, optionally substituted —O-aralkyl, —SH, $—SCH_3$, —OCN, —Cl, —Br, —CN, —F, $—CF_3$, $—OCF_3$, $—SOCH_3$, $—SO_2CH_3$, $—ONO_2$, $—NO_2$, $—N_3$, $—NH_2$, optionally substituted heterocycloalkyl, optionally substituted heterocycloalkaryl, optionally substituted aminoalkylamino, optionally substituted polyalkylamino, substituted silyl, a reporter group, an intercalator, a group for improving pharmacokinetic properties, a group for improving the pharmacodynamic properties, and other substituents. In some embodiments, a 2'-modification is a 2'-MOE modification.

In some embodiments, a 2'-modified or 2'-substituted sugar or nucleoside is a sugar or nucleoside comprising a substituent at the 2' position of the sugar which is other than —H (typically not considered a substituent) or —OH. In some embodiments, a 2'-modified sugar is a bicyclic sugar comprising a bridge connecting two carbon atoms of the sugar ring one of which is the 2' carbon. In some embodiments, a 2'-modification is non-bridging, e.g., allyl, amino, azido, thio, optionally substituted —O-allyl, optionally substituted —O—$C_1$-$C_{10}$ alkyl, $—OCF_3$, $—O(CH_2)_2OCH_3$, 2'-$O(CH_2)_2SCH_3$, $—O(CH_2)_2ON(R_m)(Rn)$, or $—OCH_2C({=}O)N(R_m)(Rn)$, where each $R_m$ and R. is independently —H or optionally substituted $C_1$-$C_{10}$ alkyl.

In some embodiments, a sugar is the sugar of N-methanocarba, LNA, cMOE BNA, cEt BNA, a-L-LNA or related analogs, HNA, Me-ANA, MOE-ANA, Ara-FHNA, FHNA, R-6'-Me-FHNA, S-6'-Me-FHNA, ENA, or c-ANA. In some embodiments, a modified internucleotidic linkage is C3-amide (e.g., sugar that has the amide modification attached to the C3', Mutisya et al. 2014 Nucleic Acids Res. 2014 Jun. 1; 42(10): 6542-6551), formacetal, thioformacetal, MMI [e.g., methylene(methylimino), Peoc'h et al. 2006 Nucleosides and Nucleotides 16 (7-9)], a PMO (phosphorodiamidate linked morpholino) linkage (which connects two sugars), or a PNA (peptide nucleic acid) linkage.

In some embodiments, a sugar is one described in U.S. Pat. Nos. 9,394,333, 9,744,183, 9,605,019, 9,598,458, 9,982,257, U.S. Ser. No. 10/160,969, U.S. Ser. No. 10/479,995, US 2020/0056173, US 2018/0216107, US 2019/0127733, U.S. Ser. No. 10/450,568, US 2019/0077817, US 2019/0249173, US 2019/0375774, WO 2018/223056, WO 2018/223073, WO 2018/223081, WO 2018/237194, WO 2019/032607, WO 2019/055951, WO 2019/075357, WO 2019/200185, WO 2019/217784, WO 2019/032612, and/or WO 2020/191252, the sugars of each of which is incorporated herein by reference.

Various additional sugars useful for preparing oligonucleotides or analogs thereof are known in the art and may be utilized in accordance with the present disclosure.

In some embodiments, a C9orf72 oligonucleotide can comprise any sugar described herein or known in the art. In some embodiments, a C9orf72 oligonucleotide can comprise any sugar described herein or known in the art in combination with any other structural element or modification described herein, including but not limited to, base sequence or portion thereof, base; internucleotidic linkage; stereochemistry or pattern thereof; additional chemical moiety, including but not limited to, a targeting moiety, etc.; pattern of modifications of sugars, bases or internucleotidic linkages; format or any structural element thereof, and/or any other structural element or modification described herein; and in some embodiments, the present disclosure pertains to multimers of any such oligonucleotides.

Production of Oligonucleotides and Compositions

Various methods can be utilized for production of oligonucleotides and compositions and can be utilized in accordance with the present disclosure. For example, traditional phosphoramidite chemistry (e.g., phosphoramidites comprising $—CH_2CH_2CN$ and $—N(i\text{-}Pr)_2$) can be utilized to prepare stereorandom oligonucleotides and compositions, and certain reagents and chirally controlled technologies can be utilized to prepare chirally controlled oligonucleotide compositions, e.g., as described in U.S. Pat. Nos. 9,394,333, 9,744,183, 9,605,019, 9,598,458, 9,982,257, U.S. Ser. No. 10/160,969, U.S. Ser. No. 10/479,995, US 2020/0056173, US 2018/0216107, US 2019/0127733, U.S. Ser. No. 10/450,568, US 2019/0077817, US 2019/0249173, US 2019/0375774, a WO 2018/223056, WO 2018/223073, WO 2018/223081, WO 2018/237194, WO 2019/032607, WO 2019/055951, WO 2019/075357, WO 2019/200185, WO 2019/217784, WO 2019/032612, and/or WO 2020/191252, the reagents and methods of each of which is incorporated herein by reference.

In some embodiments, chirally controlled/stereoselective preparation of oligonucleotides and compositions thereof comprise utilization of a chiral auxiliary, e.g., as part of monomeric phosphoramidites. Examples of such chiral auxiliary reagents and phosphoramidites are described in U.S. Pat. Nos. 9,394,333, 9,744,183, 9,605,019, 9,598,458, 9,982,257, U.S. Ser. No. 10/160,969, U.S. Ser. No. 10/479,995, US 2020/0056173, US 2018/0216107, US 2019/0127733, U.S. Ser. No. 10/450,568, US 2019/0077817, US 2019/0249173, US 2019/0375774, WO 2018/223056, WO 2018/223073, WO 2018/223081, WO 2018/237194, WO 2019/032607, WO 2019/055951, WO 2019/075357, WO 2019/200185, WO 2019/217784, WO 2019/032612, and/or WO 2020/191252, the chiral auxiliary reagents and phosphoramidites of each of which are independently incorporated herein by reference. In some embodiments, a chiral auxiliary is

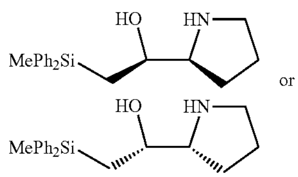

(DPSE chiral auxiliaries). In some embodiments, a chiral auxiliary is

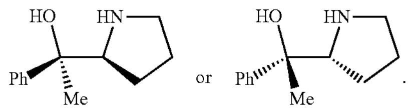 [SMILES: C[C@@](O)(c1ccccc1)[C@@H]1CCCN1 ; C[C@](O)(c1ccccc1)[C@H]1CCCN1]

In some embodiments, a chiral auxiliary is

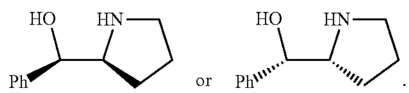

In some embodiments, a chiral auxiliary comprises —$SO_2R^{AU}$, wherein $R^{AU}$ is an optionally substituted group selected from $C_{1-20}$ aliphatic, $C_{1-20}$ heteroaliphatic having 1-10 heteroatoms, $C_{6-20}$ aryl, $C_{6-20}$ arylaliphatic, $C_{6-20}$ arylheteroaliphatic having 1-10 heteroatoms, 5-20 membered heteroaryl having 1-10 heteroatoms, and 3-20 membered heterocyclyl having 1-10 heteroatoms. In some embodiments, a chiral auxiliary is

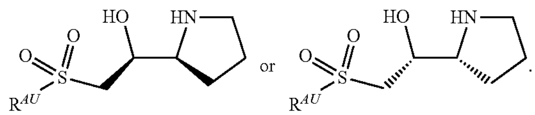

In some embodiments, $R^{AU}$ is optionally substituted aryl. In some embodiments, $R^{AU}$ is optionally substituted phenyl. In some embodiments, $R^{AU}$ is optionally substituted $C_{1-6}$ aliphatic. In some embodiments, a chiral auxiliary is

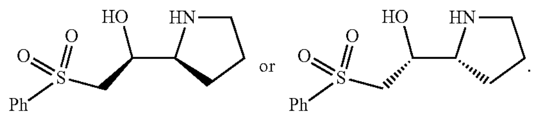 [SMILES: O=S(=O)(C[C@@H](O)[C@@H]1CCCN1)c1ccccc1 ; O=S(=O)(C[C@H](O)[C@H]1CCCN1)c1ccccc1]

(PSM chiral auxiliaries). In some embodiments, utilization of such chiral auxiliaries, e.g., preparation, phosphoramidites comprising such chiral auxiliaries, intermediate oligonucleotides comprising such auxiliaries, protection, removal, etc., is described in U.S. Pat. Nos. 9,394,333, 9,744,183, 9,605,019, 9,598,458, 9,982,257, U.S. Ser. No. 10/160,969, U.S. Ser. No. 10/479,995, US 2020/0056173, US 2018/0216107, US 2019/0127733, U.S. Ser. No. 10/450, 568, US 2019/0077817, US 2019/0249173, US 2019/0375774, WO 2018/223056, WO 2018/223073, WO 2018/223081, WO 2018/237194, WO 2019/032607, WO 2019/055951, WO 2019/075357, WO 2019/200185, WO 2019/217784, WO 2019/032612, and/or WO 2020/191252, and incorporated herein by reference.

In some embodiments, methods for preparing oligonucleotides and/or compositions comprise using a chiral auxiliary described herein, e.g., for constructing one or more chirally controlled internucleotidic linkages. In some embodiments, one or more chirally controlled internucleotidic linkages are independently constructed using a DPSE chiral auxiliary. In some embodiments, each chirally controlled phosphorothioate internucleotidic linkage is independently constructed using a DPSE chiral auxiliary. In some embodiments, one or more chirally controlled internucleotidic linkages are independently constructed using

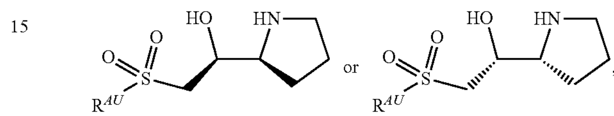

or a salt thereof, wherein $R^{AU}$ is as described herein. In some embodiments, each chirally controlled non-negatively charged internucleotidic linkage (e.g., n001) is independently constructed using

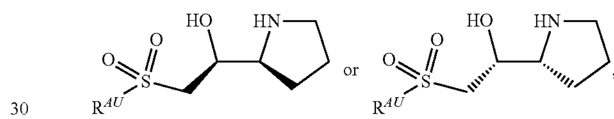

or a salt thereof. In some embodiments, each chirally controlled internucleotidic linkage is independently constructed using

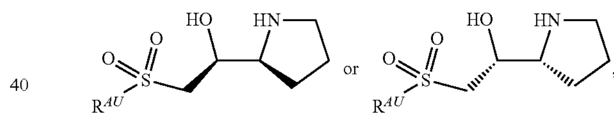

or a salt thereof. In some embodiments, $R^{AU}$ is optionally substituted $C_{1-20}$, $C_{1-10}$, $C_{1-6}$, $C_{1-5}$, or $C_{1-4}$ aliphatic. In some embodiments, $R^{AU}$ is optionally substituted $C_{1-20}$, $C_{1-10}$, $C_{1-6}$, $C_{1-5}$, or $C_{1-4}$ alkyl. In some embodiments, RAU is optionally substituted aryl. In some embodiments, $R^{AU}$ is phenyl. In some embodiments, one or more chirally controlled internucleotidic linkages are constructed using a PSM chiral auxiliary. In some embodiments, each chirally controlled non-negatively charged internucleotidic linkage (e.g., n001) is independently constructed using a PSM chiral auxiliary. In some embodiments, each chirally controlled internucleotidic linkages is independently constructed using a PSM chiral auxiliary. As appreciated by those skilled in the art, a chiral auxiliary is often utilized in a phosphoramidite (e.g.,

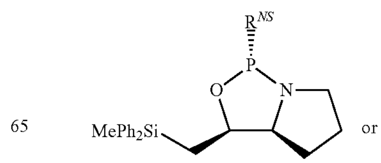

-continued

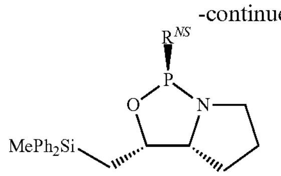

(DPSE phosphoramidites),

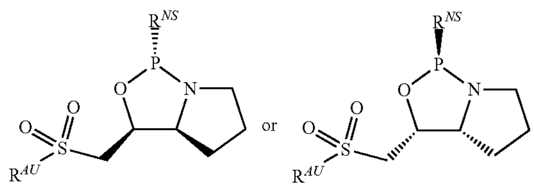

(wherein $R^{AU}$ is independently as described herein; when $R^{AU}$ is -Ph, PSM phosphoramidites), wherein $R^{NS}$ is an optionally substituted/protected nucleoside (e.g., optionally protected for oligonucleotide synthesis), or a salt thereof, etc.) for oligonucleotide preparation. In some embodiments, a method comprises providing a DPSE and/or a PSM phosphoramidite or a salt thereof. In some embodiments, a provided method comprises contacting a DPSE and/or a PSM phosphoramidite or a salt thereof with —OH (e.g., 5'-OH of a nucleoside or an oligonucleotide chain). As those skilled in the art appreciate, contacting can be performed under various suitable conditions so that a phosphorus linkage is formed. In some embodiments, preparation of each chirally controlled internucleotidic linkage independently comprises contacting a DPSE or PSM phosphoramidite or a salt thereof with —OH (e.g., 5'-OH of a nucleoside or an oligonucleotide chain). In some embodiments, preparation of each chirally controlled phosphorothioate internucleotidic linkage independently comprises contacting a DPSE phosphoramidite or a salt thereof with —OH (e.g., 5'-OH of a nucleoside or an oligonucleotide chain). In some embodiments, preparation of each chirally controlled non-negatively charged internucleotidic linkage (e.g., n001) independently comprises contacting a PSM phosphoramidite or a salt thereof with —OH (e.g., 5'-OH of a nucleoside or an oligonucleotide chain). In some embodiments, preparation of each chirally controlled internucleotidic linkage independently comprises contacting a PSM phosphoramidite or a salt thereof with —OH (e.g., 5'-OH of a nucleoside or an oligonucleotide chain). In some embodiments, contacting forms a P(III) linkage comprising a phosphorus atom bonded to two sugars and a chiral auxiliary moiety (e.g.,

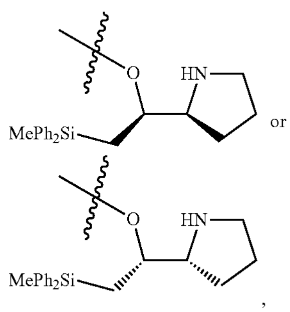

or a salt form thereof (e.g., from DPSE phosphoramidites or salts thereof),

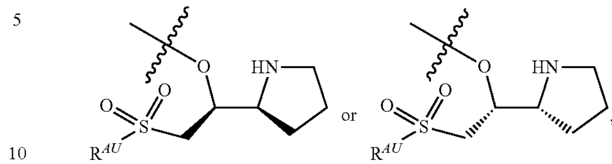

or a salt form thereof (wherein $R^{AU}$ is independently as described herein; when $R^{AU}$ is -Ph, e.g., from PSM phosphoramidites or salts thereof), etc.). In some embodiments, an oligonucleotide comprises a P(III) linkage comprising a chiral auxiliary moiety, e.g., from a DPSE or PSM phosphoramidite. In some embodiments, a P(III) linkage comprising a chiral auxiliary moiety is chirally controlled. In some embodiments, a chiral auxiliary moiety may be protected, e.g., before converting a P(III) linkage to a P(V) linkage (e.g., before sulfurization, reacting with azide, etc.). In some embodiments, a protected chiral auxiliary has the structure of

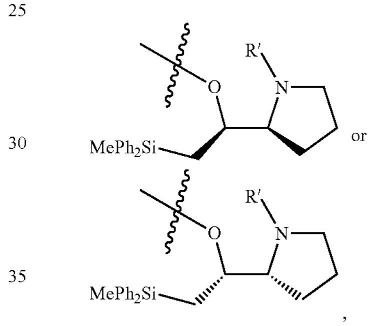

or a salt form thereof (e.g., wherein R' is independently as described herein; e.g., from DPSE phosphoramidites or salts thereof), or

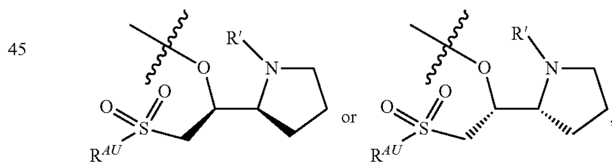

or a salt form thereof (wherein each R' and $R^{AU}$ is independently as described herein; when $R^{AU}$ is -Ph, e.g., from PSM phosphoramidites or salts thereof), wherein each R' is independently as described herein. In some embodiments, R' is —C(O)R, wherein R is as described herein. In some embodiments, R is $—CH_3$. In some embodiments, an oligonucleotide comprises a protected chiral auxiliary. In some embodiments, each chirally controlled internucleotidic linkage in an oligonucleotide independently comprises

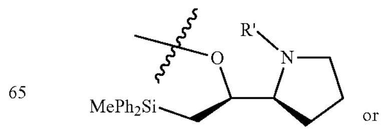

-continued

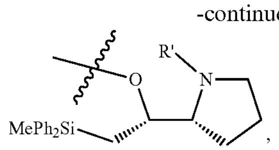

or a salt thereof, or

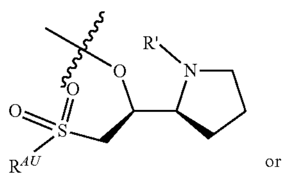

or

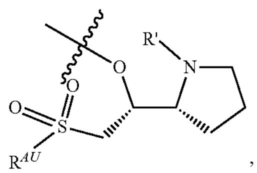

, or a salt form thereof. In some embodiments, each chirally controlled internucleotidic linkage in an oligonucleotide independently comprises

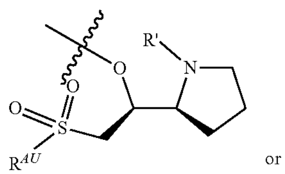

or

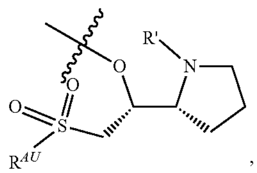

, or a salt form thereof. In some embodiments, R' is —C(O)R. In some embodiments, R' is —$C(O)CH_3$. In some embodiments, $R^{AU}$ is Ph. In some embodiments, an oligonucleotide comprises one or more

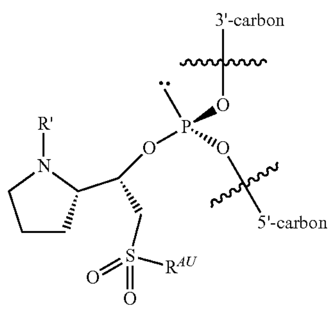

or a salt form thereof (PIII-1), wherein each variable independently as described herein. In some embodiments, an oligonucleotide comprises one or more

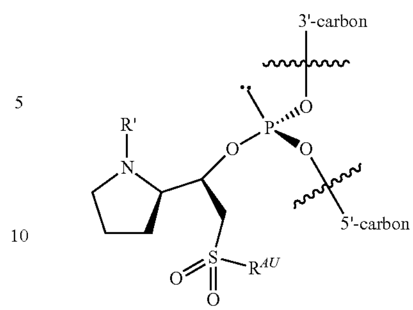

or a salt form thereof (PIII-2), wherein each variable independently as described herein. In some embodiments, an oligonucleotide comprises one or more

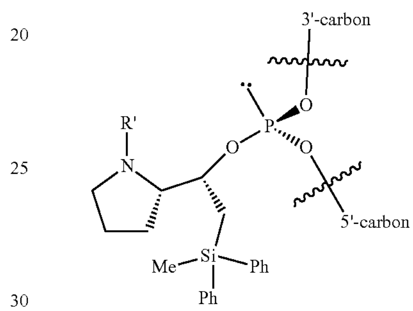

or a salt form thereof (PIII-5), wherein each variable independently as described herein. In some embodiments, an oligonucleotide comprises one or more

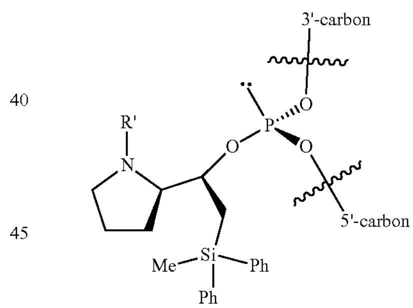

or a salt form thereof (PIII-6), wherein each variable independently as described herein. In some embodiments, a 5'-end internucleotidic linkage is PIII-1, PIII-2, PIII-5, or PIII-6. In some embodiments, a 5'-end internucleotidic linkage is PIII-1 or PIII-2. In some embodiments, R' is —H. In some embodiments, R' is —C(O)R. In some embodiments, R' is —$C(O)CH_3$. In some embodiments, $R^{AU}$ is -Ph. In some embodiments, a P(III) linkage is converted into a P(V) linkage. In some embodiments, a P(V) linkage comprises a phosphorus atom bonded to two sugars, a chiral auxiliary moiety (e.g.,

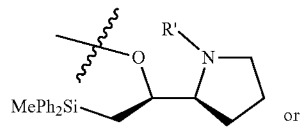

or

-continued

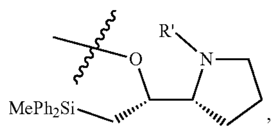

or a salt form thereof (wherein R is as described herein; e.g., from DPSE phosphoramidites or salts thereof),

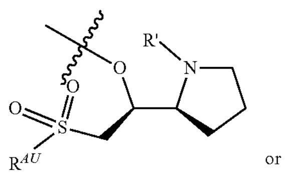

or

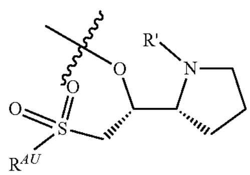

, or a salt form thereof (wherein each of R' and $R^{AU}$ is independently as described herein; when $R^{AU}$ is -Ph, e.g., from PSM phosphoramidites or salts thereof), etc.), and S or

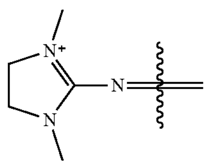

.

In some embodiments, a P(V) linkage comprises a phosphorus atom bonded to two sugars,

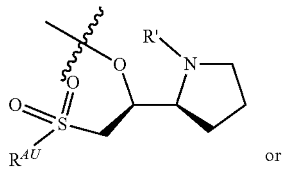

or

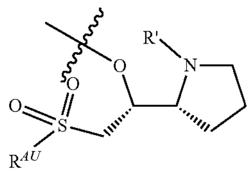

, or a salt form thereof (wherein each R' and $R^{AU}$ is independently as described herein; when $R^{AU}$ is -Ph, e.g., from PSM phosphoramidites or salts thereof), etc.), and S or

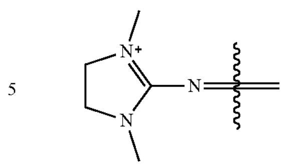

.

In some embodiments, a P(V) linkage comprises a phosphorus atom bonded to two sugars,

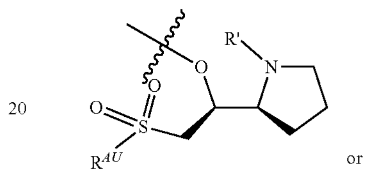

or

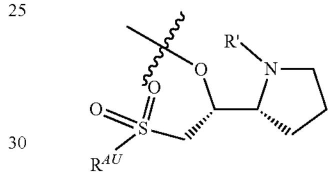

, or a salt form thereof (wherein each R' and $R^{AU}$ is independently as described herein; when $R^{AU}$ is -Ph, e.g., from PSM phosphoramidites or salts thereof), etc.), and S. In some embodiments, a P(V) linkage comprises a phosphorus atom bonded to two sugars,

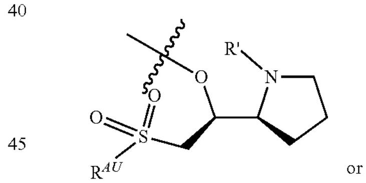

or

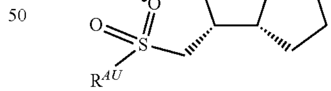

, or a salt form thereof (wherein each R' and $R^{AU}$ is independently as described herein; when $R^{AU}$ is -Ph, e.g., from PSM phosphoramidites or salts thereof), etc.), and

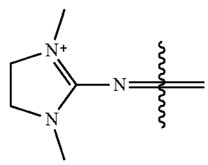

.

Those skilled in the art will appreciate that

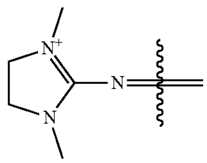 [SMILES: *=NC1=[N+](C)CCN1C]

can exist with a counterion, e.g., in some embodiments, $PF_6^-$. In some embodiments, an oligonucleotide comprises one or more

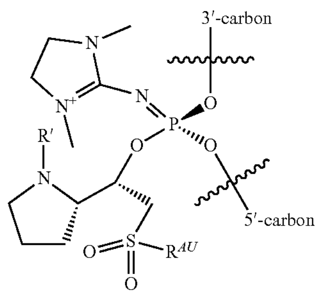

or a salt form thereof (PV-1), wherein each variable independently as described herein. In some embodiments, an oligonucleotide comprises one or more

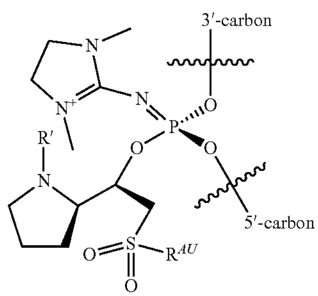

or a salt form thereof (PV-2), wherein each variable independently as described herein. In some embodiments, an oligonucleotide comprises one or more

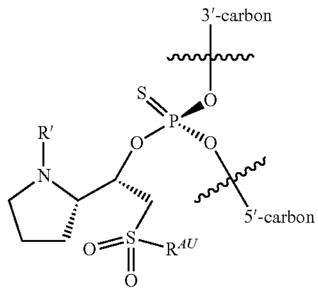

or a salt form thereof (PV-3), wherein each variable independently as described herein. In some embodiments, an oligonucleotide comprises one or more

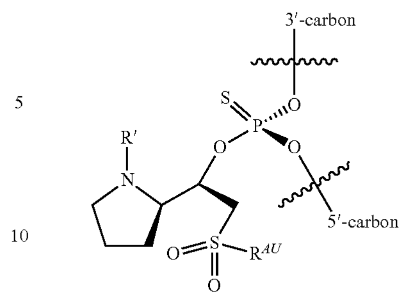

or a salt form thereof (PV-4), wherein each variable independently as described herein. In some embodiments, an oligonucleotide comprises one or more

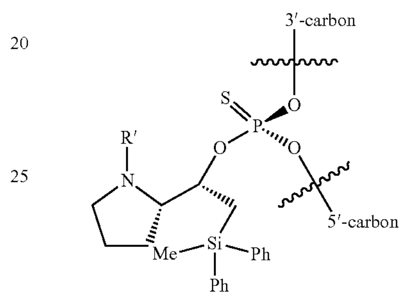

or a salt form thereof (PV-5), wherein each variable independently as described herein. In some embodiments, an oligonucleotide comprises one or more

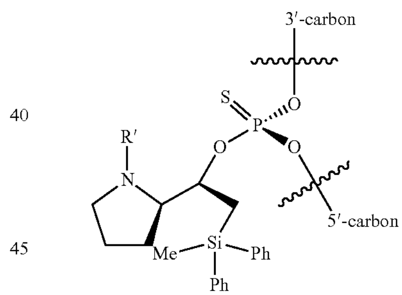

or a salt form thereof (PV-6), wherein each variable independently as described herein. In some embodiments, each chiral internucleotidic linkage, or each chirally controlled internucleotidic linkage, of an oligonucleotide is independently selected from PIII-1, P111-2, P111-5, P111-6, PV-1, PV-2, PV-3, PV-4, PV-5, and PV-6. In some embodiments, each chiral internucleotidic linkage, or each chirally controlled internucleotidic linkage, of an oligonucleotide is independently selected from PIII-1, P111-2, PV-1, PV-2, PV-3, and PV-4. In some embodiments, a linkage of PIII-1, P111-2, P111-5, or PIII-6 is typically the 5'-end internucleotidic linkage. In some embodiments, each chiral internucleotidic linkage, or each chirally controlled internucleotidic linkage, of an oligonucleotide is independently selected from PV-1, PV-2, PV-3, PV-4, PV-5, and PV-6. In some embodiments, each chiral internucleotidic linkage, or each chirally controlled internucleotidic linkage, of an oligonucleotide is independently selected from PV-1, PV-2, PV-3, or PV-4. In some embodiments, a provided oligonucleotide is an oligonucleotide as described herein, e.g., of Table A1, wherein each *S is independently replaced with PV-3 or PV-5, each *R is independently replaced with PV-4 or PV-6, each n001R is independently replaced with PV-1, and each n001S is independently replaced with PV-2. In some embodiments, a provided oligonucleotide is an oligonucleotide as described herein, e.g., of Table A1, wherein each *S is independently replaced with PV-3, each *R is independently replaced with PV-4, each n001R is independently replaced with PV-1, and each n001S is independently replaced with PV-2. In some embodiments, each natural phosphate linkage is independently replaced with a precursor, e.g.,

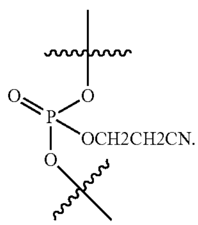

In some embodiments, R' is —H. In some embodiments, R' is —C(O)R. In some embodiments, R' is —C(O)$CH_3$. In some embodiments, $R^{AU}$ is -Ph. In some embodiments, a method comprises removal of one or more chiral auxiliary moieties so that phosphorothioate and/or non-negatively charged internucleotidic linkages (e.g., n001) are formed (e.g., from V-1, PV-2, PV-3, PV-4, PV-5, PV-6, etc.). In some embodiments, removal of a chiral auxiliary (e.g., PSM) comprises contacting an oligonucleotide with a base (e.g., $N(R)_3$ such as DEA) under anhydrous conditions.

In some embodiments, as appreciated by those skilled in the art, for preparation of a chirally controlled internucleotidic linkage, a phosphoramidite (e.g., a DPSE or PSM phosphoramidite), is typically utilized in a chirally enriched or pure form (e.g., of a purity as described herein (e.g., about or at least about 90%, 91%, 92%, 93%, 94%, 95%, 96%, 97%, 98%, or 99%, or about 100%)).

In some embodiments, chirally controlled preparation technologies, including oligonucleotide synthesis cycles, reagents and conditions are described in U.S. Pat. Nos. 9,394,333, 9,744,183, 9,605,019, 9,598,458, 9,982,257, U.S. Ser. No. 10/160,969, U.S. Ser. No. 10/479,995, US 2020/0056173, US 2018/0216107, US 2019/0127733, U.S. Ser. No. 10/450,568, US 2019/0077817, US 2019/0249173, US 2019/0375774, WO 2018/223056, WO 2018/223073, WO 2018/223081, WO 2018/237194, WO 2019/032607, WO 2019/055951, WO 2019/075357, WO 2019/200185, WO 2019/217784, WO 2019/032612, and/or WO 2020/191252, the oligonucleotide synthesis methods, cycles, reagents and conditions of each of which are independently incorporated herein by reference.

Once synthesized, oligonucleotides and compositions are typically further purified. Suitable purification technologies are widely known and practiced by those skilled in the art, including but not limited to those described in U.S. Pat. Nos. 9,394,333, 9,744,183, 9,605,019, 9,598,458, 9,982,257, U.S. Ser. No. 10/160,969, U.S. Ser. No. 10/479,995, US 2020/0056173, US 2018/0216107, US 2019/0127733, U.S. Ser. No. 10/450,568, US 2019/0077817, US 2019/0249173, US 2019/0375774, WO 2018/223056, WO 2018/223073, WO 2018/223081, WO 2018/237194, WO 2019/032607, WO 2019/055951, WO 2019/075357, WO 2019/200185, WO 2019/217784, WO 2019/032612, and/or WO 2020/191252, the purification technologies of each of which are independently incorporated herein by reference.

In some embodiments, a cycle comprises or consists of coupling, capping, modification and deblocking. In some embodiments, a cycle comprises or consists of coupling, capping, modification, capping and deblocking. These steps are typically performed in the order they are listed, but in some embodiments, as appreciated by those skilled in the art, the order of certain steps, e.g., capping and modification, may be altered. If desired, one or more steps may be repeated to improve conversion, yield and/or purity as those skilled in the art often perform in syntheses. For example, in some embodiments, coupling may be repeated; in some embodiments, modification (e.g., oxidation to install =O, sulfurization to install =S, etc.) may be repeated; in some embodiments, coupling is repeated after modification which can convert a P(III) linkage to a P(V) linkage which can be more stable under certain circumstances, and coupling is routinely followed by modification to convert newly formed P(III) linkages to P(V) linkages. In some embodiments, when steps are repeated, different conditions may be employed (e.g., concentration, temperature, reagent, time, etc.).

In some embodiments, oligonucleotides are linked to a solid support. In some embodiments, a solid support is a support for oligonucleotide synthesis. In some embodiments, a solid support comprises glass. In some embodiments, a solid support is CPG (controlled pore glass). In some embodiments, a solid support is polymer. In some embodiments, a solid support is polystyrene. In some embodiments, the solid support is Highly Crosslinked Polystyrene (HCP). In some embodiments, the solid support is hybrid support of Controlled Pore Glass (CPG) and Highly Cross-linked Polystyrene (HCP). In some embodiments, a solid support is a metal foam. In some embodiments, a solid support is a resin. In some embodiments, oligonucleotides are cleaved from a solid support.

Technologies for formulating provided oligonucleotides and/or preparing pharmaceutical compositions, e.g., for administration to subjects via various routes, are readily available in the art and can be utilized in accordance with the present disclosure, e.g., those described in U.S. Pat. Nos. 9,394,333, 9,744,183, 9,605,019, 9,598,458, 9,982,257, U.S. Ser. No. 10/160,969, U.S. Ser. No. 10/479,995, US 2020/0056173, US 2018/0216107, US 2019/0127733, U.S. Ser. No. 10/450,568, US 2019/0077817, US 2019/0249173, US 2019/0375774, WO 2018/223056, WO 2018/223073, WO 2018/223081, WO 2018/237194, WO 2019/032607, WO 2019/055951, WO 2019/075357, WO 2019/200185, WO 2019/217784, WO 2019/032612, and/or WO 2020/191252.

Biological Applications

As described herein, provided compositions and methods are capable of improving knockdown of RNA, including knockdown of C9orf72 RNA transcripts. In some embodiments, provided compositions and methods provide improved knockdown of C9orf72 transcripts (including but not limited to those comprising a repeat expansion) compared to a reference condition selected from the group consisting of absence of the composition, presence of a reference composition, and combinations thereof.

In some embodiment, a C9orf72 oligonucleotide is capable of preferentially decreasing (knocking down) the expression, level and/or activity of a mutant or repeat expansion-containing C9orf72 gene or gene product (e.g., one comprising a hexanucleotide repeat expansion) relative to that of a wild-type or non-repeat expansion-containing C9orf72 gene or gene product (e.g., one lacking a hexanucleotide repeat expansion).

In various embodiments, total transcripts include V2, V3 and V1, both normal (healthy, without repeat expansions) and mutant (pathological, comprising a repeat expansion). Various transcripts are diagrammed in FIG. 1. V1 is reportedly transcribed at very low levels (around 1% of the total C9orf72 transcripts) and does not contribute significantly to the levels of transcripts comprising hexanucleotide repeat expansions or to the levels of transcripts detected in assays for V3 transcripts.

V1, V2 and V3 are naturally produced pre-mRNA variants of the C9orf72 transcript produced by alternative pre-mRNA splicing. DeJesus-Hernandez et al. 2011. In variants 1 and 3 the expanded GGGGCC repeat is located in an intron between two alternatively spliced exons, whereas in variant 2 the repeat is located in the promoter region and thus not present in the transcript. V1 is C9orf72 Variant 1 transcript, which represents the shortest transcript and encodes the shorter C9orf72 protein (isoform b), see NM_145005.5. V2 is C9orf72 Variant 2 transcript, which differs in the 5' UTR and 3' coding region and UTR compared to variant 1. The resulting C9orf72 protein (isoform a) is longer compared to isoform 1. Variants 2 and 3 encode the same C9orf72 protein; see NM_018325.3. V3 is C9orf72 Variant 3 transcript, which differs in the 5' UTR and 3' coding region and UTR compared to variant 1. The resulting C9orf72 protein (isoform a) is longer compared to isoform 1; Variants 2 and 3 encode the same protein, see NM_001256054.1. Transcript variants 1 and 3 are predicted to encode for a 481 amino acid long protein encoded by C9orf72 exons 2-11 (NP_060795.1; isoform a), whereas variant 2 is predicted to encode a shorter 222 amino acid protein encoded by exons 2-5 (NP_659442.2; isoform b). It is noted that, according to some reports, the V1, V2 and V3 transcripts are not equally abundant; reportedly, V2 is the major transcript, representing 90% of total transcripts, V3 representing 9%, and V1 representing 1%. Therefore, without being bound by any particular theory, this disclosure suggests that a decrease in total transcripts mediated by some C9orf72 oligonucleotides includes representation of knockdown of repeat expansion-containing transcripts. The data show that many C9orf72 oligonucleotides were thus capable of mediating preferential knockdown of repeat expansion-containing C9orf72 transcripts relative to non-repeat expansion-containing C9orf72 transcripts.

In some embodiments, a C9orf72 oligonucleotide can preferentially knockdown or decrease the expression, level and/or activity of mutant (e.g., repeat expansion containing) V3 C9orf72 transcripts relative to the total C9orf72 transcripts.

In some embodiments, a C9orf72 oligonucleotide is capable of mediating a decrease in the expression, activity and/or level of a DPR protein translated from a repeat expansion.

In some embodiments, a C9orf72 oligonucleotide is capable of mediating a decrease in the expression, activity and/or level of a C9orf72 gene product. In some embodiments, a C9orf72 gene product is a protein, such as a dipeptide repeat (DPR) protein. In some embodiments, DPRs can be produced by RAN translation in any of the six reading frames of a repeat-containing C9orf72 transcript. In some embodiments, a dipeptide repeat protein is produced via RNA (repeat-associated and non-ATG-dependent translation) of either the sense or the antisense strand of a hexanucleotide repeat region. DPR proteins are described, for example, in Zu et al. 2011 Proc. Natl. Acad. Sci. USA 108: 260-265; Zu et al. Proc. Natl. Acad. Sci. USA. 2013 Dec. 17; 110(51):E4968-77; Lopez-Gonzalez et al., 2016, Neuron 92, 1-9; May et al. Acta Neuropathol (2014) 128: 485-503; and Freibaum et al. 2017 Front. Mol. Neurosci. 10, Article 35; and Westergard et al., 2016, Cell Reports 17, 645-652. In some embodiments, a C9orf72 dipeptide repeat is or comprises any of: poly-(proline-alanine) (poly-PA or) or poly-(alanine-proline) or (poly-AP); poly-(proline-arginine) (poly-PR) or poly-(arginine-proline) (poly-RP); or poly-(proline-glycine) (poly-PG) or poly-(glycine-proline (poly-GP). Poly-GA is reportedly abundantly expressed in the C9orf72 brains, followed by poly-GP and poly-GR, while poly-PA and poly-PR resulting from translation of the antisense transcript are rare. Reportedly, Poly-GA and the other DPR species are transmitted between cells and how DPR uptake affects the receiving cells. Zhou et al. detected cell-to-cell transmission of all hydrophobic DPR species and show that poly-GA boosts repeat RNA levels and DPR expression, suggesting DPR transmission may trigger a vicious cycle; treating cells with anti-GA antibodies reduced intracellular aggregation of DPRs. Zhou et al. 2017. EMBO Mol. Med. 9(5):687-702. Chang et al. reported that Glycine-Alanine Dipeptide Repeat proteins form toxic amyloids possessing cell-to-cell transmission properties. Chang et al. 2016. J. Biol. Chem. 291: 4903-4911.

In some embodiments, a DPR protein comprises poly GA. In some embodiments, a DPR protein comprises poly GP. In some embodiments, a DPR protein comprises poly GR. In some embodiments, a DPR protein is a polyGP. As non-limiting examples, the amino acid sequence of a DPR protein is or comprises any of: GAGAGAGAGAGAGAGAGAGAGAWSGRARGRARG-GAAVAVPAPA-AAEAQAVASG (SEQ ID NO: 526), GPGPGPGPGPGPGPGPGRGRGGPGGGP-GAGLRLRCLRPRRRRRRR-WRVGE (SEQ ID NO: 527), or GRGRGRGRGRGRGRGRGRGVVGAGP-GAGPGRGCGCGACARGGGGAGG-GEWVSEEAAS-WRVAVWGSAAGKRRG (SEQ ID NO: 528)(from a sense frame); or PRPRPRPRPR-PRPRPRPRPLARDS (SEQ ID NO: 529), GPGPGPGPGPGPGPGP (SEQ ID NO: 530), or PAPAPAPAPAPAPAPAPAPSARLLSS-RACYRLRLFPSLFSSG (from an antisense frame). In some embodiments (SEQ ID NO: 531), a DPR protein or a portion thereof (e.g., DPR or a portion thereof) is or comprises translation from GGGGCC repeats (or antisense frame thereof).

In some embodiments, the present disclosure provides technologies (e.g., oligonucleotides, compositions, methods, etc.) for reducing levels of a DPR protein and/or foci comprising a DPR protein in a population of cells by contacting the cells with an oligonucleotide or compositions described herein. In some embodiments, the present disclosure provides technologies (e.g., oligonucleotides, compositions, methods, etc.) for reducing levels of a DPR protein and/or foci comprising a DPR protein in a subject by administering to the subject an oligonucleotide or compositions described herein.

C9orf72 gene products also include foci, which are reported to comprise a complex of a C9orf72 RNA or a portion thereof (e.g., an excised intron) bound by multiple RNA-binding proteins. Foci are described in, for example, Mori et al. 2013 Acta Neuropath. 125: 413-423.

In some embodiments, the present disclosure provides technologies (e.g., oligonucleotides, compositions, methods, etc.) for reducing levels of foci in a population of cells by contacting the cells with an oligonucleotide or compositions described herein. In some embodiments, the present disclosure provides technologies (e.g., oligonucleotides, compositions, methods, etc.) for reducing levels of foci in a subject by administering to the subject an oligonucleotide or compositions described herein. In some embodiments, a C9orf72 oligonucleotide or composition is capable of mediating a decrease in the number of cells comprising a focus, and/or the number of foci per cell. In some embodiments, foci comprise RNA comprising GGGGCC repeats. In some embodiments, foci comprise RNA comprising expanded GGGGCC repeats. In some embodiments, foci comprise RNA comprising GGCCCC repeats. In some embodiments, foci comprise RNA comprising expanded GGCCCC repeats. In some embodiments, as described herein, expanded repeats comprises about or at least about 30, 40, 50, 60, 70, 80, 90, 100, 150, 200, 300, 400, 500, 600, 700, 800, 900, 1000, 1100, 1200, 1300, 1400, 1500, or 1600 repeats.

In some embodiments, provided technologies (e.g., oligonucleotides, compositions, methods, etc.) increase, enhance and/or restore activity levels of one or more RNA-binding proteins in a cell or subject. In some embodiments, provided technologies decrease level of, or prevents, insufficiency for C9orf72 protein and/or activity. In some embodiments, provided technologies decrease level of, or prevents, haploinsufficiency for C9orf72 protein. In some embodiments, provided technologies can improve or restore vesicular trafficking. In some embodiments, provided technologies can reduce glutamate-induced excitotoxicity. In some embodiments, provided technologies can be delivered into nucleus, reduce levels of newly transcribed RNA and/or reduce levels of RNA in foci. Among other things, as demonstrated herein, provided technologies can potently and preferentially knockdown repeat-containing C9orf72 transcripts (e.g., V1 and/or V3) and/or products encoded thereby, and/or preserves C9orf72 protein expression, level and/or activity. In some embodiments, provided technologies can decrease expression and/or levels of exon 1a-containing variants (e.g., V1 and/or V3 (e.g., mis-spliced and contain G4C2 repeats), stabilized intron 1 (or portions thereof) comprising G4C2 repeats, etc.), improve splicing efficiency, reduce levels of repeat-containing transcripts and/or reduce levels of antisense transcripts. In some embodiments, provided technologies can reduce levels of DPRs from expansion-associated sense and/or antisense transcripts. In some embodiments, provided technologies do not displace splicing machinery from the exon1b junction, or to a less extent than a reference technology. In some embodiments, provided technologies can promote neurite outgrowth (e.g., neurite length and/or neurite branching) and/or neuron (e.g., motor neuron) survival, e.g., in the presence of glutamate. In some embodiments, provided technologies can reduce levels and/or activities of transcripts and/or products encoded thereby from an allele that contain expanded G4C2 repeats and/or an allele that does not. In some embodiments, provided technologies may not increase, or may decrease, levels and/or activities of antisense transcripts and/or products encoded thereby.

As non-limiting example data, administration of C9orf72 oligonucleotides WV-7658 and WV-7659 in mouse demonstrated a 51.8% and 62.2% decrease in the number of foci counted per 100 motor neuron nuclei [compared to PBS (negative control)] in the spinal cord anterior horn (location of the lower motor neurons); and 58.3% and 70.9% decrease, respectively, in the number of cells with more than 5 foci/cell; and a 49.1% and 55.0% decrease, respectively, in the number of foci per 100 motor neurons.

Without wishing to be bound by any particular theory, the present disclosure suggests that a significant knockdown of V3 C9orf72 transcript and/or decrease in the expression, activity and/or level of a DPR protein and/or a decrease in the number of cells comprising a focus, and/or the number of foci per cell can lead to or be associated with a significant inhibition of cellular pathology, with the underlying biology rationale that the expanded hexanucleotide repeat allele leads to longer resident time of the pre-spliced C9orf72 transcripts and the spliced intron, which makes them more vulnerable to intronic targeting oligonucleotides. Without wishing to be bound by any particular theory, the present disclosure suggests that an about 50% knockdown of V3 C9orf72 transcript can lead to or be associated with an about 90% inhibition of cellular pathology.

An improvement mediated by a C9orf72 oligonucleotide can be an improvement of any desired biological functions, including but not limited to treatment and/or prevention of a C9orf72-related disorder or a symptom thereof. In some embodiments, a C9orf72-related disorder is amyotrophic lateral sclerosis (ALS), frontotemporal dementia (FTD), corticobasal degeneration syndrome (CBD), atypical Parkinsonian syndrome, olivopontocerebellar degeneration (OPCD), primary lateral sclerosis (PLS), progressive muscular atrophy (PMA), Huntington's disease (HD) phenocopy, Alzheimer's disease (AD), bipolar disorder, schizophrenia, or other non-motor disorders. In some embodiments, a symptom of a C9orf72-related disorder is selected from: agitation, anxiety, blunted emotions, changes in food preference, decreased energy and/or motivation, dementia, depression, difficulty in breathing, difficulty in swallowing, difficulty in projecting the voice, difficulty with respiration, distractibility, fasciculation and/or cramping of muscles, impaired balance, impaired motor function, inappropriate social behavior, lack of empathy, loss of memory, mood swings, muscle twitching, muscle weakness, neglect of personal hygiene, repetitive or compulsive behavior, shortness of breath, slurring of speech, unsteady gait, vision abnormality, weakness in the extremities.

In some embodiments, a symptom of a C9orf72-related disorder is semantic dementia, decrease in language comprehension, or difficulty in using correct or precise language. In some embodiments, a C9orf72-related disorder or a symptom thereof is corticobasal degeneration syndrome (CBD), shakiness, lack of coordination, muscle rigidity and/or spasm, progressive supranuclear palsy (PSP), a walking and/or balance problem, frequent falls, muscle stiffness, muscle stiffness in the neck and/or upper body, loss of physical function, and/or abnormal eye movement.

In some embodiments, FTD is behavioral variant frontotemporal dementia (bvFTD). In some embodiments, in bvFTD, reportedly, the most significant initial symptoms are associated with personality and behavior. In some embodiments, a C9orf72 oligonucleotide is capable of reducing the extent or rate at which a subject experiences disinhibition, which presents as a loss of restraint in personal relations and social life, as assessed according to methods well-known in the art.

In some embodiments, the present disclosure provides a method of treating a disease by administering a composition comprising a first plurality of oligonucleotides sharing a common base sequence comprising a common base sequence, which nucleotide sequence is complementary to a target sequence in the target C9orf72 transcript, the improvement that comprises using as the oligonucleotide composition a stereocontrolled oligonucleotide composition characterized in that, when it is contacted with the C9orf72 transcript in an oligonucleotide or a knockdown system, RNase H-mediated knockdown of the C9orf72 transcript is improved relative to that observed under a reference condition selected from the group consisting of absence of the composition, presence of a reference composition, and combinations thereof.

In some embodiments, technologies of the present disclosure provide at least 10%, 20%, 30%, 40%, 50%, 60%, 70%, 80%, 90%, 100%, 110%, 120%, 130%, 140%, 150%, 160%, 170%, 180%, or 190% more, or at least 2, 3, 4, 5, 6, 7, 8, 9, 10, 11, 12, 13, 14, 15, 16, 17, 18, 19, 20, 30, 40, 50 or more fold more, reduction of target nucleic acids (e.g., transcripts) and/or products encoded thereby (e.g., proteins) (e.g., those associated with conditions, disorders or diseases) than a reduction provided by a reference technology (e.g., a technology comprising a stereorandom oligonucleotide composition, a technology comprising a chirally controlled oligonucleotide composition of oligonucleotides of different designs, etc.) under one or more suitable conditions (e.g., one or more assays described in the Examples; at one or more concentrations, e.g., about 1, 10, 50, 100, 150, 200, 300, 400, 500, 600, 700, 800, 900, 1000, 2000, 5000, 7000, or 10000 nM).

In some embodiments, expression or level of a C9orf72 target gene or a gene product is decreased by at least about 10%, 15%, 20%, 25%, 30%, 35%, 40%, 45%, 50%, 60%, 70%, or 80% by administration of a C9orf72 oligonucleotide. In some embodiments, expression or level of a C9orf72 transcript and/or a product encoded thereby (e.g., one associated with a condition, disorder or disease) is decreased by at least about 10%, 15%, 20%, 25%, 30%, 35%, 40%, 45%, 50%, 60%, 70%, or 80% by administration of a C9orf72 oligonucleotide. In some embodiments, assessment is performed in vitro, e.g., in cells. In some embodiments, assessment is performed in vivo. As appreciated by those skilled in the art, various technologies are available for assessing properties and/or activities of provided technologies (e.g., oligonucleotides, compositions, etc.) in accordance with the present disclosure; certain such technologies are described in the Examples). In some embodiments, a reduction is achieved at certain oligonucleotide concentrations, e.g., about 1, 10, 50, 100, 150, 200, 300, 400, 500, 600, 700, 800, 900, 1000, 2000, 5000, 7000, or 10000 nM.

In some embodiments, technologies of the present disclosure can selectively reduce expression, activities and/or levels of C9orf72 nucleic acids and/or products encoded thereby that are associated with conditions, disorders or diseases over those that are not or less associated with conditions, disorders or diseases. In some embodiments, selectivity is at least 2, 3, 4, 5, 6, 7, 8, 9, 10, 11, 12, 13, 14, 15, 16, 17, 18, 19, 20, 30, 40, 50, 60, 70, 80, 90, 100, 200, 500 or 1000 fold or more. In some embodiments, selectivity is assessed by ratios of IC50 values, which can be obtained through various technologies that are suitable for assessing activities of provided technologies in accordance with the present disclosure (e.g., those described in the Examples).

In some embodiments, properties, activities, selectivities, etc., are assessed at one or more oligonucleotide concentrations, e.g., about 1, 10, 50, 100, 150, 200, 300, 400, 500, 600, 700, 800, 900, 1000, 2000, 5000, 7000, or 10000 nM.

In some embodiments, IC50 of a provided technology is about or no more than about 1, 10, 50, 100, 150, 200, 300, 400, 500, 600, 700, 800, 900, 1000, 2000, 5000, 7000, or 10000 nM. In some embodiments, it is no more than 100 nM. In some embodiments, it is no more than 200 nM. In some embodiments, it is no more than 300 nM. In some embodiments, it is no more than 400 nM. In some embodiments, it is no more than 500 nM. In some embodiments, it is no more than 1 uM. In some embodiments, it is no more than 5 uM. In some embodiments, it is no more than 10 uM. In some embodiments, IC50 is assessed using a technology described in the Examples. In some embodiments, IC50 is assessed in vitro in relevant cells. In some embodiments, IC50 is assessed an animal model.

In some embodiments, activities and/or selectivities are assessed by levels of transcripts, e.g., those associated with conditions, disorders or diseases. In some embodiments, activities and/or selectivities are assessed by levels of proteins and/or peptides, e.g., those associated with conditions, disorders or diseases. In some embodiments, activities and/or selectivities are assessed by levels of nucleic acid foci (e.g., RNA foci), e.g., those associated with conditions, disorders or diseases, in a population of cells and/or individual cells (e.g., percentage of cells having foci, and/or levels of foci in single cells).

In some embodiments, transcripts associated with conditions, disorders or diseases comprise expanded repeats, e.g., G4C2 repeats. In some embodiments, expanded G4C2 repeats are in intron 1 of C9orf72. In some embodiments, expanded repeats comprise about or at least about 30, 40, 50, 60, 70, 80, 90, 100, 150, 200, 300, 400, 500, 600, 700, 800, 900, 1000, 1100, 1200, 1300, 1400, 1500, or 1600 repeats. In some embodiments, expanded repeats comprise about or at least about 30 repeats. In some embodiments, expanded repeats comprise about or at least about 50 repeats. In some embodiments, expanded repeats comprise about or at least about 100 repeats. In some embodiments, expanded repeats comprise about or at least about 150 repeats. In some embodiments, expanded repeats comprise about or at least about 200 repeats. In some embodiments, expanded repeats comprise about or at least about 300 repeats. In some embodiments, expanded repeats comprise about or at least about 400 repeats. In some embodiments, expanded repeats comprise about or at least about 500 repeats. In some embodiments, expanded repeats comprise about or at least about 600 repeats. In some embodiments, expanded repeats comprise about or at least about 700 repeats. In some embodiments, expanded repeats comprise about or at least about 800 repeats. In some embodiments, expanded repeats comprise about or at least about 900 repeats. In some embodiments, expanded repeats comprise about or at least about 1000 repeats. In some embodiments, expanded repeats comprise about or at least about 1100 repeats. In some embodiments, expanded repeats comprise about or at least about 1200 repeats. In some embodiments, expanded repeats comprise about or at least about 1300 repeats. In some embodiments, expanded repeats comprise about or at least about 1400 repeats. In some embodiments, expanded repeats comprise about or at least about 1500 repeats. In some embodiments, expanded repeats comprise about or at least about 1600 repeats. There were reports that C9orf72 GGGGCC repeats in healthy human individuals ranged from 2-23 units or 0-15 units; and about or at least about 30-71 or 700-1600 repeats in some patients (see, e.g., Renton et al., Neuron, 2011, 72, 257-268; DeJesus-Hernandez et al., Neuron, 2011, 72, 245-256).

In some embodiments, transcripts associated with conditions, disorders or diseases are V1 and/or V3 comprising expanded repeats (e.g., those illustrated in FIG. 1). In some embodiments, provided technologies selectively reduce expression, activities and/or levels of transcripts comprising expanded repeats and/or products encoded thereby (e.g., V1 and/or V3 comprising expanded repeats as illustrated in FIG.

1) over transcripts that do not contain expanded repeats and/or products encoded thereby.

In some embodiments, the present disclosure provides technologies for reducing levels of foci. In some embodiments, foci comprise C9orf72 transcripts (from one or both strands) comprising expanded repeats and/or peptides encoded thereby). In some embodiments, provided technologies reduce the number/percentage of cells having foci, and/or reduce levels of foci in individual cells.

Characterization and Assessment

Various techniques and tools, including but not limited to many known in the art, can be used for evaluation and testing of C9orf72 oligonucleotides in accordance with the present disclosure.

In some embodiments, evaluation and testing of efficacy of C9orf72 oligonucleotides can be performed by quantifying a change or improvement in the level, activity, expression, allele-specific expression and/or intracellular distribution of a C9orf72 target nucleic acid or a corresponding gene product following delivery of a C9orf72 oligonucleotide. In some embodiments, delivery can be via a transfection agent or without a transfection agent (e.g., gymnotic).

In some embodiments, evaluation and testing of efficacy of C9orf72 oligonucleotides can be performed by quantifying a change in the level, activity, expression and/or intracellular of a C9orf72 gene product (including but not limited to a transcript, DPR or focus) following introduction of a C9orf72 oligonucleotide. C9orf72 gene products include RNA produced from a C9orf72 gene or locus.

In some embodiments, the present disclosure provides a method of identifying and/or characterizing an oligonucleotide composition, the method comprising steps of:

providing at least one composition comprising a first plurality of oligonucleotides; and assessing delivery relative to a reference composition.

In some embodiments, the present disclosure provides a method of identifying and/or characterizing an oligonucleotide composition, the method comprising steps of:

providing at least one composition comprising a first plurality of oligonucleotides; and assessing cellular uptake relative to a reference composition.

In some embodiments, properties of a provided oligonucleotide compositions are compared to a reference oligonucleotide composition.

In some embodiments, a reference oligonucleotide composition is a stereorandom oligonucleotide composition. In some embodiments, a reference oligonucleotide composition is a stereorandom composition of oligonucleotides of which all internucleotidic linkages are phosphorothioate. In some embodiments, a reference oligonucleotide composition is a DNA oligonucleotide composition with all phosphate linkages.

In some embodiments, a reference composition is a composition of oligonucleotides having the same base sequence and the same chemical modifications. In some embodiments, a reference composition is a composition of oligonucleotides having the same base sequence and the same pattern of chemical modifications. In some embodiments, a reference composition is a chirally un-controlled (or stereorandom) composition of oligonucleotides having the same base sequence and chemical modifications.

In some embodiments, a reference composition is a composition of oligonucleotides having the same base sequence but different chemical modifications, including but not limited to chemical modifications described herein. In some embodiments, a reference composition is a composition of oligonucleotides having the same base sequence but different patterns of internucleotidic linkages and/or stereochemistry of internucleotidic linkages and/or chemical modifications.

Various methods are known in the art for the detection of C9orf72 gene products, the expression, level and/or activity of which might be altered after introduction or administration of a C9orf72 oligonucleotide. As non-limiting examples: C9orf72 transcripts and their knockdown can be quantified with qPCR, C9orf72 protein levels can be determined via Western blot, RNA foci by FISH (fluorescence in situ hybridization), DPRs by Western blot, ELISA, or mass spectrometry. Commercially available C9orf72 antibodies include anti-C9orf72 antibody GT779 (1:2000; GeneTex, Irvine, California). In addition, functional assays can be performed on motor neurons (MN) expressing wild-type and/or mutant C9orf72 by Electrophysiology and NMJ formation.

In some embodiments, evaluation and testing of efficacy of C9orf72 oligonucleotides can be performed in vitro in a cell. In some embodiments, the cell is a cell which expresses C9orf72. In some embodiments, a cell is a SH-SY5Y (human neuroblastoma) cell engineered to express C9orf72. In some embodiments, a cell is a SH-SY5Y cell engineering to express C9orf72, as described in WO 2016/167780. In some embodiments, a cell is a patient-derived cell, patient-derived fibroblast, iPSC or iPSN. In some embodiments, a cell is an iPSC derived neuron or motor neuron. Various cells suitable for testing of a C9orf72 oligonucleotide include patient-derived fibroblasts, iPSCs and iPSNs and described in, for example, Donelly et al. 2013 Neuron 80, 415-428; Sareen et al. 2013 Sci. Trans. Med. 5: 208ra149; Swartz et al. STEM CELLS TRANSLATIONAL MEDICINE 2016; 5:1-12; and Almeida et al. 2013 Acta Neuropathol. 126: 385-399. In some embodiments, a cell is a BAC transgenic mouse-derived cell, including without limitation, a mouse embryonic fibroblast or cortical primary neuron. In some embodiments, evaluation and testing involves a population of cells. In some embodiments, a population of cells is a population of iCell Neurons (also referenced as iNeurons), an iPS cell-derived mixed population of human cerebral cortical neurons that exhibit native electrical and biochemical activity, commercially available from Cellular Dynamics International, Madison, Wisconsin. Additional cells, including Spinal Cord Motor Neurons, Midbrain, Dopaminergic Neurons, Glutamatergic Neurons, GABAergic Neurons, Mixed Cortical Neurons, Medium Spiny Striatal GABAergic Neurons, Parvalbumin-Enriched Cortical GABAergic Neurons, Layer V Cortical Glutamatergic Neurons, are commercially available from BrainXell, Madison, Wisconsin.

In some embodiments, evaluation of a C9orf72 oligonucleotide can be performed in an animal. In some embodiments, an animal is a mouse. C9orf72 mouse models and experimental procedures using them are described in Hukema et al. 2014 Acta Neuropath. Comm. 2: 166; Ferguson et al. 2016 J. Anat. 226: 871-891; Lagier-Tourenne et al. Proc. Natl. Acad. Sci. USA. 2013 Nov. 19; 110(47): E4530-9; Koppers et al. Ann. Neurol. 2015; 78:426-438; Kramer et al. 2016 Science 353: 708; Liu et al., 2016, Neuron 90, 521-534; Peters et al., 2015, Neuron 88, 902-909; Picher-Martel et al. Acta Neuropathologica Communications (2016) 4:70. A C9-BAC mouse model is described herein (see Example 9).

In some embodiments, target nucleic acid levels can be quantitated by any method known in the art, many of which can be accomplished with kits and materials which are commercially available, and which methods are well known and routine in the art. Such methods include, e.g., Northern blot analysis, competitive polymerase chain reaction (PCR), or quantitative real-time PCR. RNA analysis can be performed on total cellular RNA or poly(A)+ mRNA. Probes and primers are designed to hybridize to a C9orf72 nucleic acid. Methods for designing real-time PCR probes and primers are well known in the art.

In some embodiments, evaluation and testing of efficacy of C9orf72 oligonucleotides can be performed using a luciferase assay. A non-limiting example of such an assay is detailed in Example 3, below. In some embodiments, a luciferase assay employs a construct comprising the luciferase gene (or an efficacious portion thereof) linked to a portion of the sense C9orf72 transcript, such as nt 1-374 or nt 158-900 (both of which comprise a hexanucleotide repeat expansion). In some embodiments, nt 1-374 comprises exon 1a and the intron between exons 1a and 1b. In some embodiments, a luciferase assay employs a construct comprising the luciferase gene (or an efficacious portion thereof) linked to a portion of the antisense C9orf72 transcript, such as nt 900 to 1 (which comprises a hexanucleotide repeat expansion). In some embodiments, a luciferase assay is performed in a transfect COS-7 cell.

In some embodiments, a C9orf72 protein level can be evaluated or quantitated in any method known in the art, including, but not limited to, enzyme-linked immunosorbent assay (ELISA), Western blot analysis (immunoblotting), immunocytochemistry, fluorescence-activated cell sorting (FACS), immunohistochemistry, immunoprecipitation, protein activity assays (for example, caspase activity assays), and quantitative protein assays. Antibodies useful for the detection of mouse, rat, monkey, and human C9orf72 are commercially available; additional antibodies to C9orf72 can be generated via methods known in the art.

An assay for detecting levels of an oligonucleotide or other nucleic acid is described herein (e.g., in Example 4). This assay can be used to detect, as non-limiting examples, a C9orf72 oligonucleotide or any other nucleic acid of interest, including nucleic acids or other oligonucleotides which do not target C9orf72 and nucleic acids.

Evaluation and testing of efficacy of C9orf72 oligonucleotides can be performed in vitro or in vivo by determining the change in number of repeat RNA foci (or RNA foci) in cells following delivery of the C9orf72 oligonucleotide. A repeat RNA focus is a structure formed when a RNA comprising a hexanucleotide repeat sequesters RNA-binding proteins, and is a measure and/or cause of RNA-mediated toxicity. In some embodiments, a RNA focus can be a sense or an antisense RNA focus. When a C9orf72 oligonucleotide is administered in vivo to an animal, the presence and/or number of RNA foci can be determined or examined in the brain of the animal, or a portion thereof, such as, without limitation, the cerebellum, cerebral cortex, hippocampus, thalamus, medulla, or any other portion of the brain. The number of foci per cell (e.g., up to 5 or greater than 5) or average thereof and/or the number of cells comprising a focus can be determined after delivery of a C9orf72 oligonucleotide. A decrease in any or all of these numbers indicates the efficacy of a C9orf72 oligonucleotide. RNA foci can be detected by an method known in the art, including, but not limited to FISH (fluorescence in situ hybridization); a non-limiting example of FISH is presented in Example 4.

Evaluation and testing of efficacy of C9orf72 oligonucleotides can be performed in vitro by determining the change in haploinsufficiency in cells following delivery of the C9orf72 oligonucleotide. Haploinsufficiency occurs, for example, when a hexanucleotide repeat RNA acts as a negative effector on C9orf72 transcription and/or expression of a C9orf72 gene, thus decreasing the overall amount of C9orf72 transcript or gene product. A decrease in haploinsufficiency indicates the efficacy of a C9orf72 oligonucleotide.

In some embodiments, a C9orf72 oligonucleotide does not significantly decrease the expression, activity and/or level of the C9orf72 protein. In some embodiments, a C9orf72 oligonucleotide decreases the expression, activity and/or level of a C9orf72 repeat expansion or a gene product thereof, but does not significantly decrease the expression, activity and/or level of the C9orf72 protein.

In some embodiments, a C9orf72 oligonucleotide (a) decreases the expression, activity and/or level of a C9orf72 repeat expansion or a gene product thereof, and (b) does not decrease the expression, activity and/or level of C9orf72 to a degree sufficient to cause a disease condition. Various disease conditions related to insufficient production of C9orf72 include improper endosomal trafficking, a robust immune phenotype characterized by myeloid expansion, T cell activation, increased plasma cells, elevated autoantibodies, immune-mediated glomerulonephropathy, and/or an auto-immune response, as described in, for example, Farg et al. 2014 Human Mol. Gen. 23: 3579-3595; and Atanasio et al. Sci Rep. 2016 Mar. 16; 6:23204. doi: 10.1038/srep23204.

Evaluation and testing of efficacy of C9orf72 oligonucleotides can be performed in vivo. In some embodiments, C9orf72 oligonucleotides can be evaluated and/or tested in animals. In some embodiments, C9orf72 oligos can be evaluated and/or tested in humans and/or other animals to mediate a change or improvement in the level, activity, expression, allele-specific expression and/or intracellular distribution and/or to prevent, treat, ameliorate or slow the progress of a C9orf72-related disorder or at least one symptom of a C9orf72-related disorder. In some embodiments, such in vivo evaluation and/or testing can determine, after introduction of a C9orf72 oligonucleotide, phenotypic changes, such as, improved motor function and respiration. In some embodiments, a motor function can be measured by a determination of changes in any of various tests known in the art including: balance beam, grip strength, hindpaw footprint testing (e.g., in an animal), open field performance, pole climb, and rotarod. In some embodiments, respiration can measured by a determination of changes in any of various tests known in the art including: compliance measurements, invasive resistance, and whole body plethysmograph.

In some embodiments, the testing of the efficacy of a C9orf72 oligonucleotide be accomplished by contacting a motor neuron cell from a subject with a neurological disease with the C9orf72 oligonucleotide and determining whether the motor neuron cell degenerates. If the motor neuron cell does not degenerate, the C9orf72 oligonucleotide may be capable of reducing or inhibiting motor neuron degeneration. The motor neuron cell may be derived from a pluripotent stem cell. The pluripotent stem cell may have been reprogrammed from a cell from the subject. The cell from the subject may be a somatic cell, for example. The somatic cell may be a fibroblast, a lymphocyte, or a keratinocyte, for example. The assessment of whether a motor neuron cell degenerates or not may be based on a comparison to a control. In some embodiments, the control level may be a predetermined or reference value, which is employed as a benchmark against which to assess the measured and/or visual result. The predetermined or reference value may be a level in a sample (e.g. motor neuron cell) from a subject not suffering from a neurological disease or from a sample from a subject suffering from a neurological disease but wherein the motor neuron cell is not contacted with the C9orf72 oligonucleotide. The predetermined or reference value may be a level in a sample from a subject suffering from a neurological disease. In any of these screening methods, the cell from the subject having the neurological disease may comprise the (GGGGCC)n hexanucleotide expansion in C9orf72.

The efficacy of C9orf72 can also be tested in suitable test animals, such as those described in, as non-limiting examples: Peters et al. 2015 Neuron. 88(5):902-9; O'Rourke et al. 2015 Neuron. 88(5): 892-901; and Liu et al. 2016 Neuron. 90(3):521-34. In some embodiments, a test animal is a C9-BAC mouse. The efficacy of C9orf72 can also be tested in C9-BAC transgenic mice with 450 repeat expansions, which were also described in Jiang et al. 2016 Neuron 90, 1-16.

In some embodiments, in a test animal, levels of various C9orf72 transcripts can be determined, as can be C9orf72 protein level, RNA foci, and levels of DPRs (dipeptide repeat proteins). Tests can be performed on C9orf72 oligonucleotides and in comparison with reference oligonucleotides. Several C9orf72 oligonucleotides disclosed herein are capable of reducing the percentage of cells comprising RNAi foci and the average number of foci per cell. Several C9orf72 oligonucleotides disclosed herein are capable of reducing the level of DPRs such as polyGP.

In some embodiments, a C9orf72 oligonucleotide is capable of reducing the extent or rate of neurodegeneration caused by ALS, FTD or other C9orf72-related disorder. In some embodiments, in addition to an improvement, or at least reduction in the extent or rate of deterioration of any nervous system tissue, in behavioral symptoms, therapeutic efficacy of a C9orf72 oligonucleotide in a subject or other animal can also be monitored with brain scans, e.g., CAT scan, functional MRI, or PET scan, or other methods known in the art.

Various assays for analysis of C9orf72 oligonucleotides are described herein, for example in Example 9, 13, and 14, and include, inter alia, Reporter assay (Luciferase Assay), e.g., performed in an ALS neuron, and measuring, for example, analysis of V3/intron expression, activity and/or level; stability assay; TLR9 assay; Complement assay; PD (Pharmacodynamics) (C9-BAC, icv or Intracerebroventricular injection), e.g., PD and/or efficacy tested in C9orf72-BAC (C9-BAC) mouse model; in vivo procedures, including but not limited to injection into a lateral ventricle or other areas of the central nervous system (including but not limited to cortex and spinal cord) of a test animal, such as a mouse; analysis of number of foci and/or number of cells comprising foci: PolyGP (or pGP or DPR assay).

In some embodiments, selection criteria are used to evaluate the data resulting from the various assays and to select particularly desirable C9orf72 oligonucleotides. In some embodiments, at least one selection criterion is used. In some embodiments, two or more selection criteria are used. In some embodiments, selection criteria for a Luciferase assay (e.g., V3/intron knockdown) is at least partial knockdown of the V3 introns and/or at least partial knockdown of the intron transcript. In some embodiments, selection criteria for a Luciferase assay (e.g., V3/intron knockdown) is 50% KD (knockdown) of the V3 introns and 50% KD of the intron transcript. In some embodiments, selection criteria include a determination of $IC_{50}$. In some embodiments, selection criteria include an $IC_{50}$ of less than about 10 nM, less than about 5 nM or less than about 1 nM. In some embodiments, selection criteria for a stability assay is at least 50% stability [a level of at least 50% of the oligonucleotide is still remaining and/or detectable] at Day 1. In some embodiments, selection criteria for a stability assay is at least 50% stability at Day 2. In some embodiments, selection criteria for a stability assay is at least 50% stability at Day 3. In some embodiments, selection criteria for a stability assay is at least 50% stability at Day 4. In some embodiments, selection criteria for a stability assay is at least 50% stability at Day 5. In some embodiments, selection criteria for a stability assay is 80% [at least 80% of the oligonucleotide remains] at Day 5. In some embodiments, selection criteria is at least partial knockdown in number of foci and/or number of cells comprising foci. In some embodiments, selection criteria is at least 50% KD (knockdown) in number of foci and/or number of cells comprising foci. In some embodiments, selection criteria include lack of activation in a TLR9 assay. In some embodiments, selection criteria include lack of activation in a complement assay. In some embodiments, selection criteria include knockdown in a lateral ventricle or other area of the central nervous system (including but not limited to cortex and spinal cord) of a test animal, such as a mouse. In some embodiments, selection criteria include knockdown by at least 50% in a lateral ventricle or other area of the central nervous system (including but not limited to cortex and spinal cord) of a test animal, such as a mouse. In some embodiments, selection criteria include a knockdown in the expression, activity and/or level of DPR protein. In some embodiments, selection criteria include a knockdown in the expression, activity and/or level of DPR protein. In some embodiments, selection criteria include a knockdown in the expression, activity and/or level of DPR protein by at least 50%. In some embodiments, selection criteria include a knockdown in the expression, activity and/or level of the DPR protein PolyGP by at least 50%.

Oligonucleotides which have been evaluated and tested for efficacy in knocking down C9orf72 have various uses, including administration for use in treatment or prevention of a C9orf72-related disorder or a symptom thereof.

Assay for Detecting Target Nucleic Acids of Interest

In some embodiments, the present disclosure pertains to a hybridization assay for detecting and/or quantifying a target nucleic acid (e.g., a target oligonucleotide), wherein the assay utilizes a capture probe, which is at least partially complementary to the target nucleic acid, and a detection probe; wherein the detection probe or a complex comprising the capture probe, the detection probe and the target nucleic acid is capable of being detected. Such an assay can be used to detect a C9orf72 oligonucleotide (e.g., in a tissue or fluid sample), or used to detect any target nucleic acid (to any target or sequence) in any sample. In some embodiments, the capture probe comprises a primary amine, which is capable of reacting to an amino-reactive solid support, thereby immobilizing the probe on the solid support. In some embodiments, the amino-reactive solid support comprises maleic anhydride. Immobilization of the probe can be performed with click chemistry using an alkyne and an azide moiety on the probe and the solid support. For click chemistry, the alkyne or azide can be, for example, at the 5' or 3' end of the probe, and can optionally be attached via a linker. For the click chemistry, the solid support, for example, comprises an alkyne or an azide moiety. In some embodiments, click chemistry includes that described in, as a non-limiting example, Kolb et al. 2011 Angew. Chem. Int. Ed. 40: 2004-2021.

In some embodiments, a probe or complex which is capable of being detected directly or indirectly is involved in producing a detectable signal. In some embodiments, a probe or complex is (a) capable of producing a detectable signal in the absence of another chemical component (as a non-limiting example, having a moiety capable of producing a detectable signal, such as a fluorescent dye or radiolabel), or (b) comprises a ligand, label or other component which, when bound by an appropriate second moiety, is capable of producing a detectable signal. In some embodiments, a probe or complex of type (b) comprises a label such as biotin, digoxigenin, hapten, ligand, etc., which can be bound by an appropriate second chemical entity such as an antibody which, when bound to the label, is capable of producing a signal, e.g., via a radiolabel, chemiluminesce, dye, alkaline phosphatase signal, peroxidase signal, etc.

In some embodiments, the capture probe is immobilized on a solid support. In some embodiments, the capture probe is hybridized, bound or ligated to the target nucleic acid, and the detection probe is also hybridized, bound or ligated to the target nucleic acid, and the complex is capable of being detected. Many variants of hybridization assays are known in the art. In some embodiments, in a hybridization assay, the capture and the detection probe are the same probe, and a single-stranded nuclease is used to degrade probe which is not bound (or not fully bound) to a target nucleic acid.

In some embodiments, the present disclosure pertains to a hybridization assay for detecting and/or quantifying a target nucleic acid (e.g., a target oligonucleotide), wherein a probe (e.g., a capture probe) is at least partially complementary to the target nucleic acid and comprises a primary amine, wherein the primary amine is capable of reacting to an amino-reactive solid support, thereby immobilizing the probe on the solid support. The primary amine can be, for example, at the 5' or 3' end of the probe, and can optionally be attached via a linker. In some embodiments, the amino-reactive solid support comprises maleic anhydride.

The target oligonucleotide can be, for example, a C9orf72 oligonucleotide or an oligonucleotide to any target of interest.

In some embodiments, the assay is a hybridization assay, sandwich hybridization assay, competitive hybridization assay, dual ligation hybridization assay, nuclease hybridization assay, or electrochemical or electrochemical hybridization assay.

In some embodiments, the assay is a sandwich hybridization assay, wherein a capture probe is bound to a solid support and is capable of annealing to a portion of the target oligonucleotide; wherein a detection probe is capable of being detected and is capable of annealing to another portion of the target oligonucleotide; and wherein the hybridization of both the capture probe and the detection probe to the target oligonucleotide produces a complex which is capable of being detected.

In some embodiments, the assay is a nuclease hybridization assay and the capture probe is a cutting probe fully complementary to the target oligonucleotide, wherein a cutting probe which is bound by full-length target oligonucleotides is capable of being detected; and wherein a cutting probe which is free (not bound to a target oligonucleotide) or which is bound to a shortmer, metabolite or degradation product of a target oligonucleotide is degraded by S1 nuclease treatment and therefore does not produce a detectable signal.

In some embodiments, the assay is a hybridization-ligation assay, wherein the capture probe is a template probe, which is fully complementary to the target oligonucleotide and is intended to serve as a substrate for ligase-mediated ligation of the target oligonucleotide and a detection probe.

In some embodiments, the present disclosure pertains to a method of detecting and/or quantifying a target nucleic acid (e.g., a target oligonucleotide), for example, in a sample, e.g., a tissue or fluid, comprising the steps of: (1) providing a capture probe, wherein the capture probe is at least partially complementary to the target nucleic acid and comprises a primary amine, wherein the primary amine is capable of being bound by an amino-reactive solid support, thereby immobilizing the probe on the solid support; (2) immobilizing the capture probe to the solid support; (3) providing a detection probe, wherein the detection probe is at least partially complementary to the target nucleic acid (e.g., in a region of the target nucleic acid different from the region to which the capture probe binds) and is capable of directly or indirectly producing a signal; wherein steps (2) and (3) can be performed in either order; (4) bringing the tissue or fluid in contact with the capture probe and detection probe under conditions suitable for hybridization of the probes to the target nucleic acid; (5) removing detection probe not hybridized to the target nucleic acid; and (6) detecting for the signal directly or indirectly produced by the detection probe, wherein detection of the signal indicates the detection and/or quantification of the target nucleic acid.

In some embodiments, the target oligonucleotide is a C9orf72 oligonucleotide. In some embodiments, the target oligonucleotide is not a C9orf72 oligonucleotide. In some embodiments, a target nucleic acid is an oligonucleotide, an antisense oligonucleotide, a siRNA agent, a double-stranded siRNA agent, a single-stranded siRNA agent, or a nucleic acid associated with a disease (e.g., a gene or gene product which is expressed or over-expressed in a disease state, such as a transcript whose abundance is increased in cancer cells, or which nucleic acid comprises a mutation associated with a disease or disorder).

In some embodiments, the amino-reactive solid support comprises maleic anhydride.

The target oligonucleotide is reannealed to the detection probe, and then combined with the capture probe, which is attached to an amino-reactive plate via a primary amine label. Dual hybridization (e.g., sandwich hybridization) occurs between the capture probe, detection probe and the target oligonucleotide; a gap is allowable between the capture probe and detection probe, leaving a single-stranded portion of the target oligonucleotide not bound to the capture or detection probe. The solid support (e.g., a plate surface) comprises maleic anhydride (e.g., a maleic anhydride activated plate), which spontaneously reacts with the primary amine label on the end of a capture probe (e.g., at pH 8 to 9), immobilizing the probe to the solid support. In some embodiments, a solid support is a plate, tube, filter, bead, polymeric bead, gold, particle, well, or multiwell plate.

As a non-limiting example, the following conditions can be used:

Coating: 500 nM in 2.5% $Na_2CO_3$ pH9.0 50 ul/well, 37 C, 2 hr

Sample/Detection probe: 300 nM Detect probe as diluent, 4 C, O/N

Streptavidin-AP: 1:2000 in PBST 50 ul/well, RT, 1-2 hr

Substrate AttoPhos: 100 ul/well, RT, 5 min read

For example: The target nucleic acid is preannealed to the detection probe, and then combined with the capture probe, which is attached to a plate via a click chemistry using an alkyne (azide) moiety on the probe and the solid support. Dual hybridization (e.g., sandwich hybridization) occurs between the capture probe, detection probe and the target nucleic acid; a gap is allowable between the capture probe and detection probe, leaving a single-stranded portion of the target oligonucleotide not bound to the capture or detection probe. The solid support (e.g., a plate surface) comprises alkyne (or azide) moiety, which reacts with the azide (or alkyne) moiety label on the end of a capture probe with click chemistry, immobilizing the probe to the solid support. In some embodiments, a solid support is a plate, tube, filter, bead, polymeric bead, gold, particle, well, or multiwell plate.

A non-limiting example of an assay is provided below:

Hybridization ELISA assay to measure target oligonucleotide level in tissues, including animal biopsies:

The reverse complement sequence of the target oligonucleotide can be divided into 2 segments, each represented by a capture or detection probe. The 5'-sequence (of the target oligonucleotide) can be 5-15 nt; the 3' sequence can be 5-15 nt. However, the 5'-probe sequence (hybridizing to the 3'-portion of the target oligonucleotide) should not overlap the 3' probe sequence when they are both hybridized to the target oligonucleotide. A gap between 5'-probe and 3'-probe is allowable. Each probe should have a melting temperature (Tm) at least 25 C, preferably >45 C, even more preferably >50 C. To achieve high Tm, modified nucleotides can be used, such as Locked Nucleic Acids (LNA) or Peptide Nucleic Acids (PNA). Other nucleotides in the probe can be either DNA or RNA nucleotides or any other forms of modified nucleotides, such as those having a 2'-OMe, 2'-F, or 2'-MOE modification.

The 5'-probe can also be labeled with a detection moiety with a linker at the 5'-position. This probe is the Detection Probe.

The 5'-probe (hybridizing to the 3'-portion of the target oligonucleotide) can be labeled with a primary amine with a linker at the 5'-position. This probe is the Capture Probe. The linker is used to link the primary amine to the probe nucleotides. The linker can be a C6-, C12-linker, PEG, TEG or any nucleotide sequence not related to the oligonucleotide (such as oligo dT). A 5'-primary amine with a linker can be put on during synthesis or post synthesis.

The 3'-probe can also be labeled with primary amine with a linker sequences at 3'-position. This probe is the Capture Probe.

The 3'-probe (hybridizing to the 5'-portion of the target oligonucleotide) can be labeled with a detection moiety with a linker at the 3'-position. This probe is the Detection Probe. The detection moiety can be biotin, digoxigenin, HaloTag® ligand (Promega, Madison, Wisconsin), or any other hapten. The detection moiety can also be Sulfo-Tag (Meso Scale Diagnostics, Rockville, Maryland). The linker is used to link the detection moiety with the probe nucleotides. The linker can be a C6-, C12-linker, PEG, TEG or any nucleotide sequence not related to oligonucleotide (such as oligo dT). A 3'-detection moiety with a linker can be put on during synthesis or post synthesis.

The Capture Probes (with a primary amine either at the 5'- or 3'-end of probe) can be immobilized on a solid surface activated to react with a primary amine, such as Maleic Anhydride Activated Plates (Pierce; available from ThermoFisher, Waltham, Massachusetts) or N-oxysuccinimide (NOS) activated DNA-BIND plate (Corning Life Sciences, Tewksbury, Massachusetts). The plate can also be other kind of plates activated for amine conjugation, such as MSD plate (Meso Scale Diagnostics, Rockville, Maryland). The surface can be a solid support such as beads, gold particles, carboxylated polystyrene microparticles (MagPlex Microspheres, Luminex Corporation; available from ThermoFisher, Waltham, Massachusetts), or Dynabeads (Thermo Fisher Scientific, Waltham, Massachusetts), so that flow based assay platform can be used, such as Luminex or bead-array platform (BD™ Cytometric Bead Array—CBA, BD Biosciences, San Jose, California).

The biological samples containing the target oligonucleotide, such as tissue lysates or liquid biological fluids (plasma, blood, serum, CSF, urine, or other tissue or fluid), are mixed with the detection probe at a proper concentration of the oligonucleotide and detection probe, heat-denatured then put on surfaces coated with Capture Probes (plates or microparticles) to promote sequence specific hybridization either at room temperature or 4 C for a period of time (hybridization), in an appropriate hybridization buffer. Excessive detection probes are removed by washing the surfaces (plates or beads). Then the surface is incubated with reagents which recognize the detection moieties, such as avidin/streptavidin for biotin, antibodies to DIG or haptens, or HaloTag to its ligand.

The detection reagents are usually labeled with an enzyme, such as horseradish peroxidase (HRP) or alkaline phosphatase (AP), or fluorophores or Sulfo-Tag. After extensive washes, enzyme labeled detection reagents are detected by adding respective substrates, such as TMB for HRP or AttoPhos for AP, and plates are read by plate reader in absorbance mode or fluorescence mode (fluorescent substrates). In some embodiments, a label comprises Fluorescein, B-Phycoerythrin, Rhodamine, Cyanine Dye, Allophycocyanin or a variant or derivative thereof.

Fluorophore labeled detection reagents can be used for flow-based detection platform, such as Luminex or Bead-array platform.

Sulfo-Tagged detection reagents can be read by MSD reader (Meso Scale Discovery) directly.

The oligonucleotide amount can be calculated using a standard curve of serial dilution of test articles run in the same assay.

Another non-limiting example of a hybridization assay is provided in Example 4.

Various assays for utility of oligonucleotides (including but not limited to C9orf72 oligonucleotides) are described herein and/or known in the art.

Administration of Oligonucleotides and Compositions

In some embodiments, provided oligonucleotides are capable of directing a decrease in the expression and/or level of a target gene or its gene product.

In some embodiments, a target gene is a C9orf72 comprising a hexanucleotide repeat expansion.

In some embodiments, a provided oligonucleotide composition is administered at a dose and/or frequency lower than that of an otherwise comparable reference oligonucleotide composition with comparable effect in improving the knockdown of a target, including, as a non-limiting example, a C9orf72 transcript. In some embodiments, a stereocontrolled oligonucleotide composition is administered at a dose and/or frequency lower than that of an otherwise comparable stereorandom reference oligonucleotide composition with comparable effect in improving the knockdown of the target C9orf72 transcript.

In some embodiments, provided technologies provide longer durability. In some embodiments, provided technologies once administered can provide activities, e.g., reduction of target transcripts and/or products encoded thereby, at or above certain levels (e.g., levels useful and/or sufficient to provide certain biological and/or therapeutic effects) for a period of time, e.g., about or at least about 1, 2, 3,4, 5, 6, 7, 8, 9, 10, 11, 12, 13, 14, 15, 16, 17, 18, 19, 20, 21, 22, 23, 24, 25, 30, 35, 40, 45, 50, 60 or more days, about or at least about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 60 or more weeks, or about or at least about 1, 2, 3, 4, 5, 6, 7, 8, 9, or 10 months, after a last dose.

In some embodiments, the present disclosure recognizes that properties, e.g., improved knockdown activity, etc. of oligonucleotides and compositions thereof can be optimized by chemical modifications and/or stereochemistry. In some embodiments, the present disclosure provides methods for optimizing oligonucleotide properties through chemical modifications and stereochemistry.

In some embodiments, the present disclosure provides a method of administering a oligonucleotide composition comprising a first plurality of oligonucleotides and having a common nucleotide sequence, the improvement that comprises:

administering an oligonucleotide comprising a first plurality of oligonucleotides that is characterized by improved delivery relative to a reference oligonucleotide composition of the same common nucleotide sequence.

In some embodiments, provided C9orf72 oligonucleotides, compositions and methods provide improved delivery. In some embodiments, provided oligonucleotides, compositions and methods provide improved cytoplasmatic delivery. In some embodiments, improved delivery is to a population of cells. In some embodiments, improved delivery is to a tissue. In some embodiments, improved delivery is to an organ. In some embodiments, improved delivery is to the central nervous system or a portion thereof, e.g., CNS. In some embodiments, improved delivery is to an organism. Example structural elements (e.g., chemical modifications, stereochemistry, combinations thereof, etc.), oligonucleotides, compositions and methods that provide improved delivery are extensively described in this disclosure.

Various dosing regimens can be utilized to administer provided chirally controlled oligonucleotide compositions. In some embodiments, multiple unit doses are administered, separated by periods of time. In some embodiments, a given composition has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second (or subsequent) dose amount that is same as or different from the first dose (or another prior dose) amount. In some embodiments, a dosing regimen comprises administering at least one unit dose for at least one day. In some embodiments, a dosing regimen comprises administering more than one dose over a time period of at least one day, and sometimes more than one day. In some embodiments, a dosing regimen comprises administering multiple doses over a time period of at least week. In some embodiments, the time period is at least 2, 3, 4, 5, 6, 7, 8, 9, 10, 11, 12, 13, 14, 15, 16, 17, 18, 19, 20, 21, 22, 23 24, 25, 26, 27, 28, 29, 30, 31, 32, 33, 34, 35, 36, 37, 38, 39, 40 or more (e.g., about 45, 50, 55, 60, 65, 70, 75, 80, 85, 90, 95, 100 or more) weeks. In some embodiments, a dosing regimen comprises administering one dose per week f or more than one week. In some embodiments, a dosing regimen comprises administering one dose per week for 2,3,4,5,6,7, 8,9, 10, 11, 12, 13, 14, 15, 16, 17, 18, 19,20,21,22,23 24,25,26,27,28,29,30,31, 32, 33, 34, 35, 36, 37, 38, 39, 40 or more (e.g., about 45, 50, 55, 60, 65, 70, 75, 80, 85, 90, 95, 100 or more) weeks. In some embodiments, a dosing regimen comprises administering one dose every two weeks f or more than two week period. In some embodiments, a dosing regimen comprises administering one dose every two weeks over a time period of 2, 3, 4, 5, 6, 7, 8, 9, 10, 11, 12, 13, 14, 15, 16, 17, 18, 19, 20, 21, 22, 23 24, 25, 26, 27, 28, 29, 30, 31, 32, 33, 34, 35, 36, 37, 38, 39, 40 or more (e.g., about 45, 50, 55, 60, 65, 70, 75, 80, 85, 90, 95, 100 or more) weeks. In some embodiments, a dosing regimen comprises administering one dose per month for one month. In some embodiments, a dosing regimen comprises administering one dose per month f or more than one month. In some embodiments, a dosing regimen comprises administering one dose per month for 2, 3, 4, 5, 6, 7, 8, 9, 10, 11, 12, or more months. In some embodiments, a dosing regimen comprises administering one dose per week for about 10 weeks. In some embodiments, a dosing regimen comprises administering one dose per week for about 20 weeks. In some embodiments, a dosing regimen comprises administering one dose per week for about 30 weeks. In some embodiments, a dosing regimen comprises administering one dose per week for 26 weeks. In some embodiments, an oligonucleotide is administered according to a dosing regimen that differs from that utilized for a chirally uncontrolled (e.g., stereorandom) oligonucleotide composition of the same sequence, and/or of a different chirally controlled oligonucleotide composition of the same sequence. In some embodiments, an oligonucleotide is administered according to a dosing regimen that is reduced as compared with that of a chirally uncontrolled (e.g., stereorandom) oligonucleotide composition of the same sequence in that it achieves a lower level of total exposure over a given unit of time, involves one or more lower unit doses, and/or includes a smaller number of doses over a given unit of time. In some embodiments, an oligonucleotide is administered according to a dosing regimen that extends for a longer period of time than does that of a chirally uncontrolled (e.g., stereorandom) oligonucleotide composition of the same sequence Without wishing to be limited by theory, Applicant notes that in some embodiments, the shorter dosing regimen, and/or longer time periods between doses, may be due to the improved stability, bioavailability, and/or efficacy of a chirally controlled oligonucleotide composition. In some embodiments, an oligonucleotide has a longer dosing regimen compared to the corresponding chirally uncontrolled oligonucleotide composition. In some embodiments, an oligonucleotide has a shorter time period between at least two doses compared to the corresponding chirally uncontrolled oligonucleotide composition. Without wishing to be limited by theory, Applicant notes that in some embodiments longer dosing regimen, and/or shorter time periods between doses, may be due to the improved safety of a chirally controlled oligonucleotide composition.

In some embodiments, with their improved delivery (and other properties), provided compositions can be administered in lower dosages and/or with lower frequency to achieve biological effects, for example, clinical efficacy.

A single dose can contain various amounts of oligonucleotides. In some embodiments, a single dose can contain various amounts of a type of chirally controlled oligonucleotide, as desired suitable by the application. In some embodiments, a single dose contains about 1, 5, 10, 20, 30, 40, 50, 60, 70, 80, 90, 100, 110, 120, 130, 140, 150, 160, 170, 180, 190,200,210,220,230,240,250,260,270,280,290, 300 or more (e.g., about 350, 400, 450, 500, 550, 600, 650, 700, 750, 800, 850, 900, 950, 1000 or more) mg of a type of chirally controlled oligonucleotide. In some embodiments, a single dose contains about 1 mg of a type of chirally controlled oligonucleotide. In some embodiments, a single dose contains about 5 mg of a type of chirally controlled oligonucleotide. In some embodiments, a single dose contains about 10 mg of a type of chirally controlled oligonucleotide. In some embodiments, a single dose contains about 15 mg of a type of chirally controlled oligonucleotide. In some embodiments, a single dose contains about 20 mg of a type of chirally controlled oligonucleotide. In some embodiments, a single dose contains about 50 mg of a type of chirally controlled oligonucleotide. In some embodiments, a single dose contains about 100 mg of a type of chirally controlled oligonucleotide. In some embodiments, a single dose contains about 150 mg of a type of chirally controlled oligonucleotide. In some embodiments, a single dose contains about 200 mg of a type of chirally controlled oligonucleotide. In some embodiments, a single dose contains about 250 mg of a type of chirally controlled oligonucleotide. In some embodiments, a single dose contains about 300 mg of a type of chirally controlled oligonucleotide. In some embodiments, a chirally controlled oligonucleotide is administered at a lower amount in a single dose, and/or in total dose, than a chirally uncontrolled oligonucleotide. In some embodiments, a chirally controlled oligonucleotide is administered at a lower amount in a single dose, and/or in total dose, than a chirally uncontrolled oligonucleotide due to improved efficacy. In some embodiments, a chirally controlled oligonucleotide is administered at a higher amount in a single dose, and/or in total dose, than a chirally uncontrolled oligonucleotide. In some embodiments, a chirally controlled oligonucleotide is administered at a higher amount in a single dose, and/or in total dose, than a chirally uncontrolled oligonucleotide due to improved safety.

Treatment of C9orf72-Related Conditions, Disorders or Diseases

In some embodiments, provided oligonucleotides are capable of directing a decrease in the expression, level and/or activity of a C9orf72 target gene or a gene product thereof. In some embodiments, an C9orf72-related disorder is a disorder related to, caused and/or associated with abnormal or excessive activity, level and/or expression of, a deleterious mutation in, or abnormal tissue or inter- or intracellular distribution of an C9orf72 gene or a gene product thereof. In some embodiments, a C9orf72-related disorder is amyotrophic lateral sclerosis (ALS), frontotemporal dementia (FTD), corticobasal degeneration syndrome (CBD), atypical Parkinsonian syndrome, olivopontocerebellar degeneration (OPCD), primary lateral sclerosis (PLS), progressive muscular atrophy (PMA), Huntington's disease (HD) phenocopy, Alzheimer's disease (AD), bipolar disorder, schizophrenia, or other non-motor disorders. Symptoms of a C9orf72-related disorder include those described herein and known in the art.

In some embodiments, the present disclosure provides methods for treating a condition, disorder or disease, comprising administering to a subject suffering therefrom a therapeutically effective amount of a provided oligonucleotide, or a composition which comprises or delivers a therapeutically effective amount of a provided oligonucleotide. In some embodiments, the present disclosure provides methods for treating a condition, disorder or disease, comprising administering to a subject suffering therefrom a therapeutically effective amount of an oligonucleotide composition. In some embodiments, a composition is a pharmaceutical composition comprising oligonucleotides (in some embodiments, pharmaceutically acceptable salt forms thereof) and a pharmaceutically acceptable carrier. In some embodiments, a condition, disorder or disease is frontotemporal degeneration (FTD). In some embodiments, a condition, disorder or disease is amyotrophic lateral sclerosis (ALS).

Without wishing to be bound by any particular theory or terminology, the present specification notes that, with the understanding of C9orf72-related diseases constantly evolving, the exact labeling of various C9orf72-related diseases is also reportedly evolving. In some embodiments, C9orf72 oligonucleotides are useful for decreasing levels of hexanucleotide repeat-containing mutant alleles of C9orf72 (at the protein and/or mRNA level) and/or decrease the level of dipeptide repeat proteins produced from hexanucleotide-repeat-containing mutant C9orf72 mRNA, wherein the oliognucleotides are useful for treating a C9orf72 related disease.

In some embodiments, a C9orf72-related disorder is FTD. In some embodiments, FTD is an abbreviation for frontotemporal dementia or frontotemporal degeneration. In some embodiments, frontotemporal degeneration (FTD) is a disease process that affects the frontal and temporal lobes of the brain. It causes a group of disorders characterized by changes in behavior, personality, language, and/or movement. Clinical diagnoses of FTD include any one or more of: behavioral variant FTD (bvFTD), primary progressive aphasia (PPA), and the movement disorders progressive supranuclear palsy (PSP) and corticobasal degeneration (CBD). In some embodiments, a patient suffering from or susceptible to PPA, PSP or CBD does not exhibit or identify with dementia. In some embodiments, frontotemporal dementia is equivalent to or characterized by the symptoms of bvFTD.

The present disclosure pertains to methods of using oligonucleotides disclosed herein which are capable of targeting C9orf72 and useful for treating and/or manufacturing a treatment for a C9orf72-related disorder. In some embodiments, a base sequence of an oligonucleotide can comprise or consist of a base sequence which has a specified maximum number of mismatches from a specified base sequence.

In some embodiments, the present disclosure pertains to the use of a composition of comprising a C9orf72 oligonucleotide for the manufacture of a medicament for treating a neurodegenerative disease.

In some embodiments, the present disclosure pertains to a method of treating or ameliorating an C9orf72-related disorder in a patient thereof, the method comprising the step of administering to the patient a therapeutically effective amount of an oligonucleotide to C9orf72.

In some embodiments, the present disclosure pertains to a method comprising administering to an animal a composition comprising a C9orf72 oligonucleotide.

In some embodiments, the animal is a subject, e.g., a human.

In some embodiments, a subject or patient suitable for treatment of a C9orf72-related disorder, such as administration of a C9orf72 oligonucleotide, can be identified or diagnosed by a health care professional. A C9orf72-related disease is one of several neurological diseases. In some embodiments, a diagnose of a subject as having a neurological disease can be performed by the assessment of one or more symptoms, e.g., a symptom of motor neuron degeneration. In some embodiments, to diagnose a neurological disease, a physical exam may be followed by a thorough neurological exam. In some embodiments, the neurological exam may assess motor and sensory skills, nerve function, hearing and speech, vision, coordination and balance, mental status, and changes in mood or behavior. Non-limiting symptoms of a disease associated with a neurological disease may be weakness in the arms, legs, feet, or ankles; slurring of speech; difficulty lifting the front part of the foot and toes; hand weakness or clumsiness; muscle paralysis; rigid muscles; involuntary jerking or writing movements (chorea); involuntary, sustained contracture of muscles (dystonia); bradykinesia; loss of automatic movements; impaired posture and balance; lack of flexibility; tingling parts in the body; electric shock sensations that occur with movement of the head; twitching in arm, shoulders, and tongue; difficulty swallowing; difficulty breathing; difficulty chewing; partial or complete loss of vision; double vision; slow or abnormal eye movements; tremor; unsteady gait; fatigue; loss of memory; dizziness; difficulty thinking or concentrating; difficulty reading or writing; misinterpretation of spatial relationships; disorientation; depression; anxiety; difficulty making decisions and judgments; loss of impulse control; difficulty in planning and performing familiar tasks; aggressiveness; irritability; social withdrawal; mood swings; dementia; change in sleeping habits; wandering; change in appetite.

In some embodiments, the composition prevents, treats, ameliorates, or slows progression of at least one symptom of a C9orf72-related disorder.

In some embodiments, an animal or human is suffering from a symptom of a C9orf72-related disorder.

In some embodiments, the present disclosure pertains to a method for introducing an oligonucleotide that decreases C9orf72 gene expression into a cell, the method comprising: contacting the cell with an oligonucleotide or a C9orf72 oligonucleotides.

In some embodiments, the present disclosure pertains to a method for decreasing C9orf72 gene expression in a mammal in need thereof, the method comprising: administering to the mammal a nucleic acid-lipid particle comprising an oligonucleotide to C9orf72.

In some embodiments, the present disclosure pertains to a method for the in vivo delivery of an oligonucleotide that targets C9orf72 gene expression, the method comprising: administering to a mammal an oligonucleotide to C9orf72.

In some embodiments, the present disclosure pertains to a method for treating and/or ameliorating one or more symptoms associated with a C9orf72-related disorder in a mammal in need thereof, the method comprising: administering to the mammal a therapeutically effective amount of a nucleic acid-lipid particle comprising an oligonucleotide to C9orf72.

In some embodiments, the present disclosure pertains to a method of inhibiting C9orf72 expression in a cell, the method comprising: (a) contacting the cell with an oligonucleotide to C9orf72; and (b) maintaining the cell produced in step (a) for a time sufficient to obtain degradation of the mRNA transcript of an C9orf72 gene, thereby inhibiting expression of the C9orf72 gene in the cell.

In some embodiments, C9orf72 expression is inhibited by at least 30%.

In some embodiments, the present disclosure pertains to a method of treating a disorder mediated by C9orf72 expression comprising administering to a human in need of such treatment a therapeutically effective amount of an oligonucleotide to C9orf72.

In some embodiments, administration causes a decrease in the expression, activity and/or level of a C9orf72 transcript containing a repeat expansion or a gene product thereof.

In some embodiments, the present disclosure pertains to a method of treatment of a C9orf72-related disorder.

In some embodiments, the present disclosure pertains to a method comprising the steps of: providing a system comprising two or more different splicing products of the same mRNA, wherein at least one splicing product is disease-associated and at least one splicing product is non-disease-associated; introducing into a system an oligonucleotide, wherein the oligonucleotide is complementary to a sequence which is present in the at least one disease-associated splicing product, but not present in the at least one non-disease-associated splicing product, wherein the oligonucleotide is capable of reducing the expression, level and/or activity of the disease-associated splicing product relative to the expression, level and/or activity of the non-disease-associated splicing product.

In some embodiments of the method, the oligonucleotide is complementary to an intron-exon junction present on the disease-associated splicing product but not present on the non-disease-associated splicing product.

In some embodiments of the method, the oligonucleotide comprises at least one chirally controlled internucleotidic linkage.

In some embodiments of the method, the oligonucleotide is a C9orf72 oligonucleotide and the system is a subject suffering from and/or susceptible a c9orfy2-related disorder.

In some embodiments, a subject is administered a second therapeutic agent or method.

In some embodiments, a subject is administered a C9orf72 oligonucleotide and one or more second therapeutic agent or method.

In some embodiments, a second therapeutic agent or method is capable of preventing, treating, ameliorating or slowing the progress of a neurological disease.

In some embodiments, a second therapeutic agent or method is capable of preventing, treating, ameliorating or slowing the progress of a C9orf72-related disorder.

In some embodiments, a second therapeutic agent or method is capable of preventing, treating, ameliorating or slowing the progress of a neurological disease selected from: an endosomal and/or lysosomal trafficking modulator, a glutamate receptor inhibitor, a PIKFYVE kinase inhibitor, and a potassium channel activator.

In some embodiments a second therapeutic agent or method comprises an antibody to a dipeptide repeat protein or an agent (e.g., an antibody or small molecule) which disrupts the formation of or decreases the abundance or number of RNA foci.

In some embodiments, a second therapeutic agent or method indirectly decreases the expression, activity and/or level of C9orf72, as non-limiting examples, by knocking down a gene or gene product which increases the expression, activity and/or level of C9orf72. In some embodiments, a second therapeutic agent or method knocks down SUPT4H1, the human Spt4 ortholog, knockdown of which decreased production of sense and antisense C9orf72 RNA foci, as well as DPR proteins. Kramer et al. 2016 Science 353: 708. In some embodiments, a second therapeutic agent or method is a nucleic acid, small molecule, gene therapy or other agent or method described in the literature, including, as a non-limiting example, Mis et al. Mol Neurobiol. 2017 August; 54(6):4466-4476.

In some embodiments, a second therapeutic agent is physically conjugated to a C9orf72 oligonucleotide. In some embodiments, a C9orf72 oligonucleotide is physically conjugated to a second oligonucleotide which decreases (directly or indirectly) the expression, activity and/or level of C9orf72, or which is useful for treating a symptom of a C9orf72-related disorder. In some embodiments, a first C9orf72 oligonucleotide is physically conjugated to a second C9orf72 oligonucleotide, which can be identical to the first C9orf72 oligonucleotide or not identical, and which can target a different or the same or an overlapping sequence as the first C9orf72 oligonucleotide. In some embodiments, a C9orf72 oligonucleotide is conjugated or co-administered or incorporated into the same treatment regime as an oligonucleotide which knocks down SUPT4H1. In some embodiments, a C9orf72 oligonucleotide is conjugated or co-administered or incorporated into the same treatment regime as a second therapeutic agent which improves the expression, activity and/or level of another (non-C9orf72) gene or gene product which is associated with a C9orf72-related disorder such as ALS or FTD, such as: SOD1, TARDBP, FUS/TLS, MAPT, TDP-43, SUPT4H1, or FUS/TLS.

In some embodiments, improving the expression, activity and/or level of such a gene or gene product includes, inter alia: decreasing the expression, activity and/or level of such a gene or gene product is such is too high in the disease state; increasing the expression, activity and/or level or such a gene or gene product is such is too low in the disease state; and/or decreasing the expression, activity and/or level of a mutant and/or disease-associated variant of such a gene or gene product. In some embodiments, a second therapeutic agent is an oligonucleotide. In some embodiments, a second therapeutic agent is an oligonucleotide physically conjugated to a C9orf72 oligonucleotide. In some embodiments, a second therapeutic agent comprises monomethyl fumarate (MMF), which reportedly activates Nrf2, and/or an omega-3 fatty acid. In some embodiments, a second therapeutic agent comprises monomethyl fumarate (MMF) and/or the omega-3 fatty acid, docosahexaenoic acid (DHA), which reportedly inhibits NF-κB. In some embodiments, a second therapeutic agent comprises a conjugate of monomethyl fumarate (MMF) and the omega-3 fatty acid, docosahexaenoic acid (DHA). In some embodiments, a second therapeutic agent is CAT-4001 (Catabasis Pharmaceuticals, Cambridge, MA, US).

In some embodiments, a second therapeutic agent is capable of preventing, treating, ameliorating or slowing the progress of a neurological disease selected from: an endosomal and/or lysosomal trafficking modulator, a glutamate receptor inhibitor, a PIKFYVE kinase inhibitor, and a potassium channel activator described in WO2016/210372. In some embodiments, a potassium channel activator is retigabine. In some embodiments, a glutamate receptor is on a motor neuron (MN) or spinal motor neuron. In some embodiments, a glutamate receptor is NMDA, AMPA, or kainite. In some embodiments, a glutamate receptor inhibitor is AP5 ((2R)-amino-5-phosphonovaleric acid; (2R)-amino-5-phosphonopentanoate), CNQX (6-cyano-7-nitroquinoxaline-2,3-dione), orNBQX (2,3-dihydroxy-6-nitro-7-sulfamoyl-benzo[f]quinoxaline-2,3-dione).

In some embodiments, a second therapeutic agent is capable of decreasing the expression, level and/or activity of a gene (or a gene product thereof) associated with a C9orf72-related disorder, such as SOD1, TARDBP, FUS/TLS, MAPT, TDP-43, SUPT4H1, or FUS/TLS. In some embodiments, a second therapeutic agent is an agent which deceases the expression, level and/or activity of a gene (or a gene product thereof) associated with amyotrophic lateral sclerosis (ALS) or frontotemporal dementia (FTD), such as SOD1, TARDBP, FUS/TLS, MAPT, TDP-43, SUPT4H1, or FUS/TLS. In some embodiments, a second therapeutic agent is capable of controlling excessive oxidative stress. In some embodiments, a second therapeutic agent is Radicava® (edaravone). In some embodiments, a second therapeutic agent is ursodeoxycholic acid (UDCA). In some embodiments, a second therapeutic agent is capable of affecting neurons by reducing their activity through blocking Na+ entrance into the neurons, and blocking the release of the chemicals that cause the activity of the motor neurons. In some embodiments, a second therapeutic agent is riluzole. In some embodiments, a second therapeutic agent is capable of: reducing fatigue, easing muscle cramps, controlling spasticity, and/or reducing excess saliva and phlegm. In some embodiments, a second therapeutic agent is capable of reducing pain. In some embodiments, a second therapeutic agent is a nonsteroidal and/or anti-inflammatory drug and/or opioid. In some embodiments, a second therapeutic agent is capable of reducing depression, sleep disturbance, dysphagia, spasticity, difficulty swallowing saliva, and/or constipation. In some embodiments, a second therapeutic agent is baclofen or diazepam. In some embodiments, a second therapeutic agent is or comprises trihexyphenidyl, amitriptyline and/or glycopyrrolate. In some embodiments, a second therapeutic agent is a dsRNA or siRNA which comprises a strand which has a sequence which comprises at least 15 contiguous nt of the sequence of any oligonucleotide disclosed herein.

Pharmaceutical Compositions

In some embodiments, the present disclosure provides pharmaceutical compositions comprising a provided compound, e.g., a provided oligonucleotide, or a pharmaceutically acceptable salt thereof, and a pharmaceutical carrier. In some embodiments, an oligonucleotide is a C9orf72 oligonucleotide.

When used as therapeutics, a provided oligonucleotide or oligonucleotide composition described herein is administered as a pharmaceutical composition. In some embodiments, the pharmaceutical composition is suitable for administration of an oligonucleotide to an area of the body affected by a disorder, including but not limited to the central nervous system. In some embodiments, the pharmaceutical composition comprises a therapeutically effective amount of a provided oligonucleotide, or a pharmaceutically acceptable salt thereof, and at least one pharmaceutically acceptable inactive ingredient selected from pharmaceutically acceptable diluents, pharmaceutically acceptable excipients, and pharmaceutically acceptable carriers.

As appreciated by those skilled in the art, oligonucleotides of the present disclosure can be provided in their acid, base or salt forms. In some embodiments, oligonucleotides can be in acid forms, e.g., for natural phosphate linkages, in the form of —OP(O)(OH)O—; for phosphorothioate internucleotidic linkages, in the form of —OP(O)(SH)O—; etc. In some embodiments, provided oligonucleotides can be in salt forms, e.g., for natural phosphate linkages, in the form of —OP(O)(ONa)O— in sodium salts; for phosphorothioate internucleotidic linkages, in the form of —OP(O)(SNa)O— in sodium salts; etc. In some embodiments, each acidic linkages, e.g., each natural phosphate linkage and each phosphorothioate linkage, if any, independently exists in a salt form (all salt form). In some embodiments, an oligonucleotide is in a all sodium salt form. Unless otherwise noted, oligonucleotides of the present disclosure can exist in acid, base and/or salt forms.

In some embodiments, a pharmaceutical composition comprises a therapeutically effective amount of a provided oligonucleotide or a pharmaceutically acceptable salt thereof, and a pharmaceutically acceptable inactive ingredient. In some embodiments, a pharmaceutically acceptable inactive ingredient is selected from pharmaceutically acceptable diluents, pharmaceutically acceptable excipients, and pharmaceutically acceptable carriers. In some embodiments, a pharmaceutically acceptable inactive ingredient is a pharmaceutically acceptable carrier.

In some embodiments, the present disclosure provides a pharmaceutical composition comprising chirally controlled oligonucleotide or composition thereof, in admixture with a pharmaceutically acceptable inactive ingredient (e.g., a pharmaceutically acceptable excipient, a pharmaceutically acceptable carrier, etc.). One of skill in the art will recognize that the pharmaceutical compositions include pharmaceutically acceptable salts of provided oligonucleotide or compositions. In some embodiments, a pharmaceutical composition is a chirally controlled oligonucleotide composition. In some embodiments, a pharmaceutical composition is a stereopure oligonucleotide composition.

In some embodiments, the present disclosure provides salts of oligonucleotides and pharmaceutical compositions thereof. In some embodiments, a salt is a pharmaceutically acceptable salt. In some embodiments, a pharmaceutical composition comprises an oligonucleotide, optionally in its salt form, and a sodium salt. In some embodiments, a pharmaceutical composition comprises an oligonucleotide, optionally in its salt form, and sodium chloride. In some embodiments, each hydrogen ion of an oligonucleotide that may be donated to a base (e.g., under conditions of an aqueous solution, a pharmaceutical composition, etc.) is replaced by a non-$H^+$ cation. For example, in some embodiments, a pharmaceutically acceptable salt of an oligonucleotide is an all-metal ion salt, wherein each hydrogen ion (for example, of —OH, —SH, etc.) of each internucleotidic linkage (e.g., a natural phosphate linkage, a phosphorothioate internucleotidic linkage, etc.) is replaced by a metal ion. Various suitable metal salts for pharmaceutical compositions are widely known in the art and can be utilized in accordance with the present disclosure. In some embodiments, a pharmaceutically acceptable salt is a sodium salt. In some embodiments, a pharmaceutically acceptable salt is magnesium salt. In some embodiments, a pharmaceutically acceptable salt is a calcium salt. In some embodiments, a pharmaceutically acceptable salt is a potassium salt. In some embodiments, a pharmaceutically acceptable salt is an ammonium salt (cation $N(R)_4^+$). In some embodiments, a pharmaceutically acceptable salt comprises one and no more than one types of cation. In some embodiments, a pharmaceutically acceptable salt comprises two or more types of cation. In some embodiments, a cation is $Li^+$, $Na^+$, $K^+$, $Mg^{2+}$ or $Ca^{2+}$. In some embodiments, a pharmaceutically acceptable salt is an all-sodium salt. In some embodiments, a pharmaceutically acceptable salt is an all-sodium salt, wherein each internucleotidic linkage which is a natural phosphate linkage (acid form —O—P(O)(OH)—O—), if any, exists as its sodium salt form (—O—P(O)(ONa)—O—), and each internucleotidic linkage which is a phosphorothioate internucleotidic linkage linkage (acid form —O—P(O)(SH)—O—), if any, exists as its sodium salt form (—O—P(O)(SNa)—O—).

Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington, The Science and Practice of Pharmacy (20th ed. 2000). Preferred pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

Various technologies for delivering nucleic acids and/or oligonucleotides are known in the art can be utilized in accordance with the present disclosure. For example, a variety of supramolecular nanocamers can be used to deliver nucleic acids. Example nanocarriers include, but are not limited to liposomes, cationic polymer complexes and various polymeric compounds. Complexation of nucleic acids with various polycations is another approach for intracellular delivery; this includes use of PEGylated polycations, polyethyleneamine (PEI) complexes, cationic block co-polymers, and dendrimers. Several cationic nanocarriers, including PEI and polyamidoamine dendrimers help to release contents from endosomes. Other approaches include use of polymeric nanoparticles, microspheres, liposomes, dendrimers, biodegradable polymers, conjugates, prodrugs, inorganic colloids such as sulfur or iron, antibodies, implants, biodegradable implants, biodegradable microspheres, osmotically controlled implants, lipid nanoparticles, emulsions, oily solutions, aqueous solutions, biodegradable polymers, poly(lactide-coglycolic acid), poly (lactic acid), liquid depot, polymer micelles, quantum dots and lipoplexes. In some embodiments, an oligonucleotide is conjugated to another molecule.

In therapeutic and/or diagnostic applications, compounds, e.g., oligonucleotides, of the disclosure can be formulated for a variety of modes of administration, including systemic and topical or localized administration. Techniques and formulations generally may be found in Remington, The Science and Practice of Pharmacy (20th ed. 2000).

In some embodiments, a provided C9orf72 is conjugated to an additional chemical moiety suitable for use in delivery to the central nervous system, selected from: glucose, GluNAc (N-acetyl amine glucosamine) and anisamide.

In some embodiments, an additional chemical moiety conjugated to an oligonucleotide is capable of targeting the oligonucleotide to a cell in the nervous system.

In some embodiments, an additional chemical moiety conjugated to a provided oligonucleotide comprises anisamide or a derivative or analog thereof and is capable of targeting the provided oligonucleotide to a cell expressing a particular receptor, such as the sigma 1 receptor.

In some embodiments, a provided oligonucleotide is formulated for administration to a body cell and/or tissue expressing its target.

In some embodiments, an additional chemical moiety conjugated to a C9orf72 oligonucleotide is capable of targeting the C9orf72 oligonucleotide to a cell in the nervous system.

In some embodiments, an additional chemical moiety conjugated to a C9orf72 oligonucleotide comprises anisamide or a derivative or analog thereof and is capable of targeting the C9orf72 oligonucleotide to a cell expressing a particular receptor, such as the sigma 1 receptor.

In some embodiments, a provided C9orf72 oligonucleotide is formulated for administration to a body cell and/or tissue expressing C9orf72. In some embodiments, such a body cell and/or tissue is a neuron or a cell and/or tissue of the central nervous system. In some embodiments, broad distribution of oligonucleotides and compositions, described herein, within the central nervous system may be achieved with intraparenchymal administration, intrathecal administration, or intracerebroventricular administration.

In some embodiments, the pharmaceutical composition is formulated for intravenous injection, oral administration, buccal administration, inhalation, nasal administration, topical administration, ophthalmic administration or otic administration. In some embodiments, the pharmaceutical composition is a tablet, a pill, a capsule, a liquid, an inhalant, a nasal spray solution, a suppository, a suspension, a gel, a colloid, a dispersion, a suspension, a solution, an emulsion, an ointment, a lotion, an eye drop or an ear drop.

In some embodiments, the present disclosure provides a pharmaceutical composition comprising chirally controlled oligonucleotide, or composition thereof, in admixture with a pharmaceutically acceptable excipient. One of skill in the art will recognize that the pharmaceutical compositions include the pharmaceutically acceptable salts of the chirally controlled oligonucleotide, or composition thereof, described above.

A variety of supramolecular nanocarriers can be used to deliver nucleic acids. Example nanocarriers include, but are not limited to liposomes, cationic polymer complexes and various polymeric. Complexation of nucleic acids with various polycations is another approach for intracellular delivery; this includes use of PEGlyated polycations, polyethyleneamine (PEI) complexes, cationic block co-polymers, and dendrimers. Several cationic nanocarriers, including PEI and polyamidoamine dendrimers help to release contents from endosomes. Other approaches include use of polymeric nanoparticles, microspheres, liposomes, dendrimers, biodegradable polymers, conjugates, prodrugs, inorganic colloids such as sulfur or iron, antibodies, implants, biodegradable implants, biodegradable microspheres, osmotically controlled implants, lipid nanoparticles, emulsions, oily solutions, aqueous solutions, biodegradable polymers, poly(lactide-coglycolic acid), poly(lactic acid), liquid depot, polymer micelles, quantum dots and lipoplexes. In some embodiments, an oligonucleotide is conjugated to another molecular.

Additional nucleic acid delivery strategies are known in addition to the example delivery strategies described herein.

In therapeutic and/or diagnostic applications, the compounds of the disclosure can be formulated for a variety of modes of administration, including systemic and topical or localized administration. Techniques and formulations generally may be found in Remington, The Science and Practice of Pharmacy, (20th ed. 2000).

Provided oligonucleotides, and compositions thereof, are effective over a wide dosage range. For example, in the treatment of adult humans, dosages from about 0.01 to about 1000 mg, from about 0.5 to about 100 mg, from about 1 to about 50 mg per day, and from about 5 to about 100 mg per day are examples of dosages that may be used. The exact dosage will depend upon the route of administration, the form in which the compound is administered, the subject to be treated, the body weight of the subject to be treated, and the preference and experience of the attending physician.

In some embodiments, a provided C9orf72 oligonucleotides is formulated in a pharmaceutical composition described in U.S. Applications No. 61/774,759; 61/918,175, filed Dec. 19, 2013; 61/918,927; 61/918,182; 61/918941; 62/025224; 62/046487; or International Applications No. PCT/US04/042911; PCT/EP2010/070412; or PCT/I B2014/059503.

Depending on the specific conditions being treated, such agents may be formulated into liquid or solid dosage forms and administered systemically or locally. The agents may be delivered, for example, in a timed- or sustained-low release form as is known to those skilled in the art. Techniques for formulation and administration may be found in Remington, The Science and Practice of Pharmacy (20th ed. 2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articular, intra-sternal, intra-synovial, intra-hepatic, intralesional, intracranial, intraperitoneal, intranasal, or intraocular injections or other modes of delivery.

For injection, the agents of the disclosure may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection.

The compounds, e.g., oligonucleotides, can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure may also be formulated by methods known to those of skill in the art, and may include, for example, but not limited to, examples of solubilizing, diluting, or dispersing substances such as, saline, preservatives, such as benzyl alcohol, absorption promoters, and fluorocarbons.

In some embodiments, an oligonucleotide or composition is administered as a pharmaceutical composition comprising an effective amount of an oligonucleotide or composition and a pharmaceutically acceptable carrier. In some embodiments, a composition is chirally controlled. In some embodiments, a composition comprises one or more pharmaceutically acceptable salt forms of an oligonucleotide. In some embodiments, a composition is a liquid composition. In some embodiments, a liquid composition has an about neutral pH (e.g., around pH 7). In some embodiments, a liquid composition has a pH of about 7.4. In some embodiments, a liquid composition comprises a buffer.

In certain embodiments, oligonucleotides and compositions are delivered to the CNS. In certain embodiments, oligonucleotides and compositions are delivered to the cerebrospinal fluid. In certain embodiments, oligonucleotides and compositions are administered to the brain parenchyma. In certain embodiments, oligonucleotides and compositions are delivered to an animal/subject by intrathecal administration, or intracerebroventricular administration. Broad distribution of oligonucleotides and compositions, described herein, within the central nervous system may be achieved with intraparenchymal administration, intrathecal administration, or intracerebroventricular administration.

In certain embodiments, parenteral administration is by injection, by, e.g., a syringe, a pump, etc. In certain embodiments, the injection is a bolus injection. In certain embodiments, the injection is administered directly to a tissue, such as striatum, caudate, cortex, hippocampus and cerebellum.

In certain embodiments, methods of specifically localizing a pharmaceutical agent, such as by bolus injection, decreases median effective concentration (EC50) by a factor of 20, 25, 30, 35, 40, 45 or 50. In certain embodiments, the pharmaceutical agent in an antisense compound as further described herein. In certain embodiments, the targeted tissue is brain tissue. In certain embodiments the targeted tissue is striatal tissue. In certain embodiments, decreasing EC50 is desirable because it reduces the dose required to achieve a pharmacological result in a patient in need thereof.

In certain embodiments, an antisense oligonucleotide is delivered by injection or infusion once every month, every two months, every 90 days, every 3 months, every 6 months, twice a year or once a year.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of an active compound into preparations which can be used pharmaceutically. The preparations formulated for oral administration may be in the form of tablets, dragees, capsules, or solutions.

Pharmaceutical preparations for oral use can be obtained by combining an active compound, e.g., an oligonucleotide, with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

In some embodiments, dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, an active compound may be dissolved or suspended in suitable liquids, such as fatty oils, liquid paraffin, or liquid polyethylene glycols (PEGs). In addition, stabilizers may be added.

A composition can be obtained by combining an active compound, e.g., an oligonucleotide, with a lipid. In some embodiments, the lipid is conjugated to an active compound. In some embodiments, the lipid is not conjugated to an active compound. In some embodiments, a lipid comprises a $C_{10}$-$C_{40}$ linear, saturated or partially unsaturated, aliphatic chain. In some embodiments, a lipid comprises a $C_{10}$-$C_{40}$ linear, saturated or partially unsaturated, aliphatic chain, optionally substituted with one or more $C_{1-4}$ aliphatic group. In some embodiments, the lipid is selected from the group consisting of: lauric acid, myristic acid, palmitic acid, stearic acid, oleic acid, linoleic acid, alpha-linolenic acid, gamma-linolenic acid, docosahexaenoic acid (cis-DHA), turbinaric acid and dilinoleyl. In some embodiments, an active compound is any oligonucleotide or other nucleic acid described herein. In some embodiments, an active compound is a nucleic acid of a sequence comprising or consisting of any sequence of any nucleic acid listed in Table A1. In some embodiments, a composition comprises a lipid and an an active compound, and further comprises another component selected from: another lipid, and a targeting compound or moiety. In some embodiments, a lipid includes, without limitation: an amino lipid; an amphipathic lipid; an anionic lipid; an apolipoprotein; a cationic lipid; a low molecular weight cationic lipid; a cationic lipid such as CLinDMA and DLinDMA; an ionizable cationic lipid; a cloaking component; a helper lipid; a lipopeptide; a neutral lipid; a neutral zwitterionic lipid; a hydrophobic small molecule; a hydrophobic vitamin; a PEG-lipid; an uncharged lipid modified with one or more hydrophilic polymers; phospholipid; a phospholipid such as 1,2-dioleoyl-sn-glycero-3-phosphoethanolamine; a stealth lipid; a sterol; a cholesterol; and a targeting lipid; and any other lipid described herein or reported in the art. In some embodiments, a composition comprises a lipid and a portion of another lipid capable of mediating at least one function of another lipid. In some embodiments, a targeting compound or moiety is capable of targeting a compound (e.g., a composition comprising a lipid and a active compound) to a particular cell or tissue or subset of cells or tissues. In some embodiments, a targeting moiety is designed to take advantage of cell- or tissue-specific expression of particular targets, receptors, proteins, or other subcellular components; In some embodiments, a targeting moiety is a ligand (e.g., a small molecule, antibody, peptide, protein, carbohydrate, aptamer, etc.) that targets a composition to a cell or tissue, and/or binds to a target, receptor, protein, or other subcellular component.

Certain example lipids for use in preparation of a composition for delivery of an active compound allow (e.g., do not prevent or interfere with) the function of an active compound. Non-limiting example lipids include: lauric acid, myristic acid, palmitic acid, stearic acid, oleic acid, linoleic acid, alpha-linolenic acid, gamma-linolenic acid, docosahexaenoic acid (cis-DHA), turbinaric acid and dilinoleyl.

As described in the present disclosure, lipid conjugation, such as conjugation with fatty acids, may improve one or more properties of oligonucleotides.

In some embodiments, a composition for delivery of an active compound is capable of targeting an active compound to particular cells or tissues, as desired. In some embodiments, a composition for delivery of an active compound is capable of targeting an active compound to a muscle cell or tissue. In some embodiments, the present disclosure pertains to compositions and methods related to delivery of active compounds, wherein the compositions comprise an active compound a lipid. In various embodiments to a muscle cell or tissue, the lipid is selected from: lauric acid, myristic acid, palmitic acid, stearic acid, oleic acid, linoleic acid, alpha-linolenic acid, gamma-linolenic acid, docosahexaenoic acid (cis-DHA), turbinaric acid and dilinoleyl.

In some embodiments, a composition comprising an oligonucleotide is lyophilized. In some embodiments, a composition comprising an oligonucleotide is lyophilized, and the lyophilized oligonucleotide is in a vial.

Depending upon the particular disorder to be treated or prevented, additional therapeutic agents, which are normally administered to treat or prevent that condition, may be administered together with C9orf oligonucleotides of this disclosure.

In some embodiments, a second therapeutic agent administered with a first C9orf72 oligonucleotide is a second, different, C9orf72 oligonucleotide.

In some embodiments, C9orf72 oligonucleotides disclosed herein can be used for a method for the prevention and/or treatment of a C9orf72-related disorder or a symptom thereof, or for the manufacture of medicament for use in such a method.

In some embodiments, the present disclosure provides the following Example Embodiments:

1. An oligonucleotide comprising at least one modification of a sugar, base or internucleotidic linkage, wherein the base sequence of the oligonucleotide is or comprises at least 15, 16, 17, 18, 19, 20, 21, 22, 23, 24, or 25 contiguous bases of a base sequence that is at least 80% identical with or complementary to a base sequence of a C9orf72 gene or a transcript thereof, and the nucleobase on the 3' end of the oligonucleotide is optionally replaced by a replacement nucleobase selected from I, A, T, U, G and C.
2. An oligonucleotide comprising at least one modification of a sugar, base or internucleotidic linkage, wherein the base sequence of the oligonucleotide comprises at least 15, 16, 17, 18, 19, 20, 21, 22, 23, 24, or 25 contiguous bases of a base sequence that is identical with or complementary to a base sequence of a C9orf72 gene or a transcript thereof.
3. The oligonucleotide of Embodiment 1, wherein the oligonucleotide comprises at least 19 contiguous bases of a base sequence that is identical with or complementary to a base sequence of a C9orf72 gene or a transcript thereof.
4. The oligonucleotide of any one of the preceding Embodiments, wherein the base sequence of the oligonucleotide is not fully identical with or complementary to a base sequence, or any portion thereof, of a C9orf72 gene or a transcript thereof.
5. The oligonucleotide of Embodiment 4, wherein the base sequence of the oligonucleotide, when aligned for maximum complementarity, comprises a mismatch at its 3'-end which mismatch is not base-paring selected from A and T, A and U, and C and G.
6. The oligonucleotide of any one of the preceding Embodiments, wherein the 3'-end nucleoside of the oligonucleotide is inosine.
7. The oligonucleotide of Embodiment 1-3, wherein the base sequence of the oligonucleotide is fully identical with or complementary to a base sequence of a C9orf72 gene or a transcript thereof.
8. The oligonucleotide of any one of the preceding Embodiments, wherein the base sequence of the oligonucleotide is ACTCACCCACTCGCCACCGC (SEQ ID NO: 532).
9. The oligonucleotide of any one of the preceding Embodiments, wherein the oligonucleotide reduces level of a repeat expansion-containing C9orf72 transcript when administered to a system comprising the C9orf72 transcript.
10. The oligonucleotide of Embodiment 9, wherein the repeat expansion-containing C9orf72 transcript comprises at least 30, 50, 100, 150, 200, 300, 400, 500, 600, 700, 800, 900, or 1000 GGGGCC (SEQ ID NO: 533) repeats.
11. The oligonucleotide of Embodiment 10, wherein the reduction of level of the repeat-expansion-containing C9orf72 transcript as measured by percentage is at least 1.1, 1.2, 1.3, 1.4, 1.5, 1.6, 1.7, 1.8, 1.9, 2, 2.5, 3, 4, 5, 6, 7, 8, 9, or 10 fold of the reduction of level of the non-repeat-expansion-containing C9orf72 transcript as measured by percentage.
12. The oligonucleotide of any one of the preceding Embodiments, wherein the oligonucleotide hybridizes with a site in C9orf72 exon 1a, intron 1, exon 1b, or exon 2.
13. The oligonucleotide of any of the preceding Embodiments, wherein the oligonucleotide comprises at least one internucleotidic linkage wherein the linkage phosphorus is in the Sp configuration.
14. The oligonucleotide of any one of the preceding Embodiments, wherein the oligonucleotide comprises a core and at least two wings, wherein each core and each wing independently comprise one or more nucleosides.
15. The oligonucleotide of any one of the preceding Embodiments, wherein the oligonucleotide comprises or consists of a 5'-wing-core-wing-3' structure.
16. The oligonucleotide of any one of Embodiments 14-15, wherein the pattern of sugar modifications of the 5'-wing differs from the pattern of sugar modifications of the 3'-wing.
17. The oligonucleotide of any one of Embodiments 15-16, wherein each wing sugar independently comprises a 2'-modification.
18. The oligonucleotide of any one of Embodiments 15-16, wherein each wing sugar independently comprises a 2'-OR modification, wherein R is optionally substituted $C_{1-6}$ aliphatic.
19. The oligonucleotide of any one of Embodiments 15-16, wherein one wing comprises a 2'-OMe and the other wing does not.
20. The oligonucleotide of any one of Embodiments 15-16, wherein one wing comprises a 2'-MOE and the other wing does not.
21. The oligonucleotide of any one of Embodiments 15-16, wherein one wing comprises a 2'-OMe and no 2'-MOE and the other wing comprises a 2'-MOE and no 2'-OMe.

22. The oligonucleotide of any one of Embodiments 15-16, wherein the 5'-wing comprises one or more 2'-OMe modified sugars and one or more 2'-MOE modified sugars.
23. The oligonucleotide of any one of Embodiments 15-16, wherein each 5'-wing sugar is independently a 2'-OR modified sugar, wherein R is optionally substituted $C_{1-6}$ aliphatic.
24. The oligonucleotide of any one of Embodiments 15-16, wherein the 3'-wing comprises one or more 2'-OMe modified sugars and one or more 2'-MOE modified sugars.
25. The oligonucleotide of any one of Embodiments 15-16, wherein the 5'-wing comprises 2'-OMe modified sugars at its 5'-end and 3'-end, and each other sugar in the 5'-wing is independently a 2'-MOE modified sugar.
26. The oligonucleotide of any one of Embodiments 15-25, wherein the 5'-wing comprises one or more natural phosphate linkages.
27. The oligonucleotide of any one of Embodiments 15-26, wherein the 5'-wing comprises one or more one or more modified internucleotidic linkages.
28. The oligonucleotide of Embodiment 27, wherein the first internucleotidic linkage bonded to two 5'-wing nucleosides from the 5' of the 5'-wing is a modified internucleotidic linkage.
29. The oligonucleotide of any one of Embodiments 26-28, wherein each other internucleotidic linkage bonded to two 5'-wing nucleosides is a natural phosphate linkage.
30. The oligonucleotide of any one of any one of Embodiments 26-29, wherein each modified internucleotidic linkage is independently a phosphorothioate internucleotidic linkage.
31. The oligonucleotide of any one of any one of Embodiments 26-29, wherein one or more modified internucleotidic linkage are independently a phosphorothioate internucleotidic linkage.
32. The oligonucleotide of any one of any one of Embodiments 26-29 and 31, wherein one or more modified internucleotidic linkage are independently a non-negatively charged internucleotidic linkage.
33. The oligonucleotide of any one of Embodiments 30-32, wherein each phosphorothioate internucleotidic linkage is Sp.
34. The oligonucleotide of any one of Embodiments 15-33, wherein the 5'-wing comprises 1, 2, 3, 4, 5, 6, 7, 8, 9, or 10 nucleobases.
35. The oligonucleotide of any one of Embodiments 15-33, wherein the 5'-wing contains 5 and no more than 5 nucleobases.
36. The oligonucleotide of any one of Embodiments 15-35, wherein each 3'-wing sugar is independently a 2'-OR modified sugar, wherein R is optionally substituted $C_{1-6}$ aliphatic.
37. The oligonucleotide of any one of Embodiments 15-35, wherein the 3'-wing comprises one or more 2'-OMe modified sugars and one or more 2'-MOE modified sugars.
38. The oligonucleotide of any one of Embodiments 15-35, wherein each 3'-wing sugar is independently a 2'-OMe modified sugar.
39. The oligonucleotide of any one of Embodiments 15-38, wherein one or more internucleotidic linkages bonded to two 3'-wing sugar are independently a modified internucleotidic linkage.
40. The oligonucleotide of any one of Embodiments 15-39, wherein one or more internucleotidic linkages bonded to two 3'-wing sugar are a natural phosphate linkage.
41. The oligonucleotide of any one of Embodiments 15-38, wherein each internucleotidic linkage bonded to two 3'-wing sugar is independently a modified internucleotidic linkage.
42. The oligonucleotide of any one of Embodiments 39-41, wherein each modified internucleotidic linkage is independently a phosphorothioate internucleotidic linkage.
43. The oligonucleotide of any one of Embodiments 39-41, wherein one or more modified internucleotidic linkages are independently a phosphorothioate internucleotidic linkage.
44. The oligonucleotide of any one of Embodiments 39-41 and 43, wherein one or more modified internucleotidic linkages are independently a non-negatively charged internucleotidic linkage.
45. The oligonucleotide of any one of Embodiments 42-44, wherein each phosphorothioate internucleotidic linkage is Sp.
46. The oligonucleotide of any one of Embodiments 14-45, wherein the 3'-wing comprises 1, 2, 3, 4, 5, 6, 7, 8, 9, or 10 nucleobases.
47. The oligonucleotide of Embodiment 46, wherein the 3'-wing contains 5 and no more than 5 nucleobases.
48. The oligonucleotide of Embodiment 46, wherein the 3'-wing contains 4 and no more than 4 nucleobases.
49. The oligonucleotide of Embodiment 46, wherein the 3'-wing contains 3 and no more than 3 nucleobases.
50. The oligonucleotide of any one of Embodiments 14-49, wherein the core comprises no sugar comprising a 2'-OR.
51. The oligonucleotide of any one of Embodiments 14-50, wherein each core sugar independently comprises two 2'-H.
52. The oligonucleotide of any one of Embodiments 14-51, wherein the oligonucleotide or the core comprises a pattern of backbone chiral centers (linkage phosphorus) of:

*(Np)t[(Op/Rp)n(Sp)m]y,* wherein:

t is 1-50;

n is 1-10;

m is 1-50;

y is 1-10;

Np is either Rp or Sp;

Sp indicates the S configuration of a chiral linkage phosphorus of a chiral modified internucleotidic linkage;

Op indicates an achiral linkage phosphorus of a natural phosphate linkage; and

Rp indicates the S configuration of a chiral linkage phosphorus of a chiral modified internucleotidic linkage; and y is 1-10.

53. The oligonucleotide of Embodiment 52, wherein the core comprises a pattern of backbone chiral centers of (Np)t[(Op/Rp)n(Sp)m]y.
54. The oligonucleotide of Embodiment 52, wherein the pattern of backbone chiral centers of the core is (Np)t[(Op/Rp)n(Sp)m]y.
55. The oligonucleotide of any one of Embodiments 52-54, wherein each Np is Sp.

56. The oligonucleotide of any one of Embodiments 52-55, wherein the pattern comprises at least one Rp.
57. The oligonucleotide of any one of Embodiments 52-55, wherein the pattern is (Np)t[(Rp)n(Sp)m]y.
58. The oligonucleotide of any one of Embodiments 52-57, wherein at least one n is 1.
59. The oligonucleotide of any one of Embodiments 52-57, wherein each n is 1.
60. The oligonucleotide of any one of Embodiments 52-59, wherein y is 1.
61. The oligonucleotide of any one of Embodiments 52-59, wherein y is 2.
62. The oligonucleotide of any one of Embodiments 52-61, wherein t is 2 or more.
63. The oligonucleotide of any one of Embodiments 52-61, wherein t is 3 or more.
64. The oligonucleotide of any one of Embodiments 52-61, wherein t is 2-20.
65. The oligonucleotide of any one of Embodiments 52-61, wherein t is 3-20.
66. The oligonucleotide of any one of Embodiments 52-65, wherein at least one m is 2-20.
67. The oligonucleotide of any one of Embodiments 52-66, wherein at least one m is 2.
68. The oligonucleotide of any one of Embodiments 52-65, wherein at least one m is 3, 4, 5, 6, 7, 8, 9, or 10.
69. The oligonucleotide of any one of Embodiments 52-68, wherein each m is independently 2-20.
70. The oligonucleotide of any one of Embodiments 52-69, wherein the first occurrence of [(Op/Rp)n(Sp)m]y from the 5' is RpSpSp.
71. The oligonucleotide of any one of Embodiments 52-69, wherein the first occurrence of [(Op/Rp)n(Sp)m]y from the 5' is RpSpSpSp.
72. The oligonucleotide of any one of Embodiments 52-69, wherein the first occurrence of [(Op/Rp)n(Sp)m]y from the 5' is RpSpSpSpSp.
73. The oligonucleotide of any one of the preceding Embodiments, wherein the base sequence of the oligonucleotide comprises a sequence that is not identical or complementary to the GGGGCC repeats.
74. The oligonucleotide of any one of the preceding Embodiments, wherein the base sequence of the oligonucleotide comprises a sequence that is not identical or complementary to any repeats.
75. The oligonucleotide of any one of the preceding Embodiments, wherein the base sequence of the oligonucleotide is not identical or complementary to the GGGGCC repeats.
76. The oligonucleotide of any one of the preceding Embodiments, wherein the base sequence of the oligonucleotide comprises a sequence targeting a C9orf72 intro sequence.
77. The oligonucleotide of any one of the preceding Embodiments, wherein the base sequence of the oligonucleotide comprises at least 15, 16, 17, 18, 19, 20, 21, 22, 23, 24, or 25 contiguous bases of a base sequence that is identical with or complementary to a base sequence of an intron of a C9orf72 gene or a transcript thereof.
78. The oligonucleotide of any one of the preceding Embodiments, wherein the base sequence of the oligonucleotide comprises at least 15, 16, 17, 18, 19, 20, 21, 22, 23, 24, or 25 contiguous bases of a base sequence that is identical with or complementary to a characteristic base sequence of a C9orf72 gene or a transcript thereof.
79. The oligonucleotide of any one of the preceding Embodiments, wherein the oligonucleotide preferentially reduces level of a disease-associated C9orf72 product.
80. The oligonucleotide of Embodiment 79, wherein the product is a transcript comprising expanded GGGGCC repeats.
81. The oligonucleotide of Embodiment 79, wherein the product is a transcript comprising at least 30, 50, 100, 200, 300, 400, or 500 GGGGCC repeats (SEQ ID NO: 534).
82. The oligonucleotide of Embodiment 79, wherein the product is an antisense transcript comprising expanded GGGGCC repeats.
83. The oligonucleotide of Embodiment 79, wherein the product is a dipeptide repeat protein.
84. The oligonucleotide of any one of the preceding Embodiments, wherein each non-negatively charged internucleotidic linkage is n001.
85. The oligonucleotide of any one of the preceding Embodiments, comprising a linkage having the structure of PIII-1, P111-2, P111-5, PIII-6, PV-1, PV-2, PV-3, PV-4, PV-5, and PV-6.
86. The oligonucleotide of any one of the preceding Embodiments, comprising a linkage having the structure of PV-1, PV-2, PV-3, PV-4, PV-5, and PV-6.
87. The oligonucleotide of any one of the preceding Embodiments, comprising a linkage having the structure of PIII-1, PIII-2, PV-1, PV-2, PV-3, or PV-4.
88. The oligonucleotide of any one of the preceding Embodiments, comprising a linkage having the structure of PV-1, PV-2, PV-3, or PV-4.
89. The oligonucleotide of any one of Embodiments 1-142, wherein each chiral internucleotidic linkage independently has the structure of PIII-1, PIII-2, PIII-5, PIII-6, PV-1, PV-2, PV-3, PV-4, PV-5, and PV-6.
90. The oligonucleotide of any one of Embodiments 1-142, wherein each chiral internucleotidic linkage independently has the structure of PV-1, PV-2, PV-3, PV-4, PV-5, and PV-6.
91. The oligonucleotide of any one of Embodiments 1-142, wherein each chiral internucleotidic linkage independently has the structure of PIII-1, P111-2, PV-1, PV-2, PV-3, or PV-4.
92. The oligonucleotide of any one of Embodiments 1-142, wherein each chiral internucleotidic linkage independently has the structure of PV-1, PV-2, PV-3, or PV-4.
93. An oligonucleotide, wherein the oligonucleotide is WV-17819, WV-17820, WV-17821, WV-17822, WV-17885, WV-18851, WV-18852, WV-20761, WV-20762, WV-20763, WV-20764, WV-20765, WV-20766, WV-20767, WV-20768, WV-20769, WV-20770, WV-20771, WV-20772, WV-20773, WV-20774, WV-20775, WV-21145, WV-21146, WV-21147, WV-21148, WV-21149, WV-21150, WV-21151, WV-21152, WV-21153, WV-21154, WV-21155, WV-21156, WV-21157, WV-21158, WV-21159, WV-21160, WV-21161, WV-21162, WV-21163, WV-21164, WV-21165, WV-21166, WV-21167, WV-21168, WV-21169, WV-21170, WV-21171, WV-21172, WV-21173, WV-21174, WV-21206, WV-21207, WV-21208, WV-21209, WV-21259, WV-21344, WV-21345, WV-21346, WV-21347, WV-21442, WV-21443, WV-21445, WV-21446, WV-21506, WV-21507, WV-21508, WV-21509, WV-21510, WV-21511, WV-21512, WV-21513, WV-21514, WV-21515, WV-21516, WV-21517, WV-21518, WV-21519, WV-21520, WV-21521, WV-21522, WV-21523, WV-21524, WV-21525, WV-21526, WV-21552, WV-21553, WV-21554, WV-21555, WV-21556, WV-21557, WV-21558, WV-21559, WV-21560, WV-21561, WV-21562, WV-21563, WV-21564, WV-21565, WV-21566, WV-21567, WV-21568, WV-21569, WV-21570, WV-23435, WV-23436, WV-23437, WV-23438, WV-23439, WV-23440, WV-23441, WV-23442, WV-23443, WV-23444, WV-23453, WV-23454, WV-23455, WV-23456, WV-23457, WV-23458, WV-23459, WV-23460, WV-23461, WV-23462, WV-23486, WV-23487, WV-23488, WV-23489, WV-23490, WV-23491, WV-23492, WV-23493, WV-23494, WV-23495, WV-23496, WV-23497, WV-23498, WV-23503, WV-23648, WV-23649, WV-23650, WV-23740, WV-23741, WV-23742, WV-26633, WV-27092, WV-27093, WV-27094, WV-27095, WV-27104, WV-27105, WV-27106, WV-27107, WV-27108, WV-27109, WV-27110, WV-27134, WV-27135, WV-27136, WV-27137, WV-27138, WV-27139, WV-27140, WV-27141, WV-27142, WV-27143, WV-27144, WV-30206, WV-30210, WV-30211, or WV-30212.

94. The oligonucleotide of Embodiment 67, wherein the oligonucleotide is WV-23491, WV-21445, WV-23457, WV-23453, WV-23742, WV-23741, WV-21522, WV-21446, WV-23486, WV-23457, WV-21522, WV-23453, WV-23487, or WV-30206, WV-30210, WV-30211, or WV-30212.

95. The oligonucleotide of Embodiment 93, wherein the oligonucleotide is WV-23491.

96. The oligonucleotide of Embodiment 93, wherein the oligonucleotide is WV-21445.

97. The oligonucleotide of Embodiment 93, wherein the oligonucleotide is WV-23457.

98. The oligonucleotide of Embodiment 93, wherein the oligonucleotide is WV-23453.

99. The oligonucleotide of Embodiment 93, wherein the oligonucleotide is WV-23742.

100. The oligonucleotide of Embodiment 93, wherein the oligonucleotide is WV-23741.

101. The oligonucleotide of Embodiment 93, wherein the oligonucleotide is WV-21522.

102. The oligonucleotide of Embodiment 93, wherein the oligonucleotide is WV-21446.

103. The oligonucleotide of Embodiment 93, wherein the oligonucleotide is WV-23486.

104. The oligonucleotide of Embodiment 93, wherein the oligonucleotide is WV-23457.

105. The oligonucleotide of Embodiment 93, wherein the oligonucleotide is WV-21522.

106. The oligonucleotide of Embodiment 93, wherein the oligonucleotide is WV-23453.

107. The oligonucleotide of Embodiment 93, wherein the oligonucleotide is WV-23487.

108. The oligonucleotide of Embodiment 93, wherein the oligonucleotide is WV-30206.

109. The oligonucleotide of Embodiment 93, wherein the oligonucleotide is WV-30210.

110. The oligonucleotide of Embodiment 93, wherein the oligonucleotide is WV-30211.

111. The oligonucleotide of Embodiment 93, wherein the oligonucleotide is WV-30212.

112. The oligonucleotide of any one of Embodiments 93-111, wherein the oligonucleotide is in a salt form.

113. The oligonucleotide of any one of Embodiments 93-111, wherein the oligonucleotide is in a pharmaceutically acceptable salt form.

114. An oligonucleotide, wherein the oligonucleotide is an oligonucleotide of any one of Embodiments 93-113 or Table A1, wherein each Sp phosphorothioate internucleotidic linkage is independently replaced with PV-3 or PV-5.

115. The oligonucleotide of Embodiment 114, wherein the oligonucleotide is an oligonucleotide of any one of Embodiments 93-113, wherein each Sp phosphorothioate internucleotidic linkage is independently replaced with PV-3.

116. An oligonucleotide, wherein the oligonucleotide is an oligonucleotide of any one of Embodiments 93-115 or Table A1, wherein each Rp phosphorothioate internucleotidic linkage is independently replaced with PV-4 or PV-6.

117. An oligonucleotide, wherein the oligonucleotide is an oligonucleotide of any one of Embodiments 93-115 or Table A1, wherein each Rp phosphorothioate internucleotidic linkage is independently replaced with PV-4.

118. The oligonucleotide of any one of Embodiments 114-115, wherein each Rp phosphorothioate internucleotidic linkage is independently replaced with PV-4 or PV-6.

119. The oligonucleotide of any one of Embodiments 114-115, wherein each Rp phosphorothioate internucleotidic linkage is independently replaced with PV-4.

120. An oligonucleotide, wherein the oligonucleotide is an oligonucleotide of any one of Embodiments 93-115 or Table A1, wherein each Rp non-negatively charged internucleotidic linkage is independently replaced with PV-1.

121. The oligonucleotide of any one of Embodiments 114-119, wherein each Rp non-negatively charged internucleotidic linkage is independently replaced with PV-1.

122. An oligonucleotide, wherein the oligonucleotide is an oligonucleotide of any one of Embodiments 93-115 or Table A1, wherein each Sp non-negatively charged internucleotidic linkage is independently replaced with PV-2.

123. The oligonucleotide of any one of Embodiments 114-121, wherein each Sp non-negatively charged internucleotidic linkage is independently replaced with PV-2.

124. The oligonucleotide of any one of the preceding Embodiments, wherein each non-negatively charged internucleotidic linkage is independently n001.

125. The oligonucleotide of any one of Embodiments 114-124, wherein each natural phosphate linkage is independently replaced with a precursor utilized in oligonucleotide synthesis.

126. The oligonucleotide of any one of Embodiments 114-125, wherein each natural phosphate linkage is independently replaced with

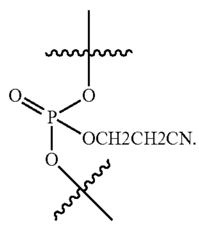

127. The oligonucleotide of any one of the preceding Embodiments, wherein one or more occurrences of $R^{AU}$ are independently optionally substituted phenyl.
128. The oligonucleotide of any one of the preceding Embodiments, wherein one or more occurrences of $R^{AU}$ are independently optionally substituted $C_{1-6}$ aliphatic.
129. The oligonucleotide of any one of Embodiments 1-127, wherein each $R^{AU}$ is -Ph.
130. The oligonucleotide of any one of the preceding Embodiments, wherein one or more occurrences of R' are independently —C(O)R.
131. The oligonucleotide of any one of the preceding Embodiments, wherein each R' is independently —C(O)R.
132. The oligonucleotide of any one of the preceding Embodiments, wherein each R' is independently —C(O)$CH_3$.
133. The oligonucleotide of Embodiment 1, wherein the oligonucleotide is an oligonucleotide of any one of Embodiments 93-132.
134. An oligonucleotide comprising at least one modification of a sugar, base or internucleotidic linkage, wherein the base sequence of the oligonucleotide comprises at least 15, 16, 17, 18, 19, 20, 21, 22, 23, 24, or 25 contiguous bases of a base sequence that is identical with or complementary to a base sequence of a target gene or a transcript thereof, wherein the nucleobase on the 3' end of the oligonucleotide is optionally replaced by a different nucleobase selected from I, A, T, U, G and C.
135. The oligonucleotide of any of Embodiments 1-134, wherein the nucleobase on the 3' end of the oligonucleotide is replaced by a replacement nucleobase selected from I, A, T, U, G and C.
136. The oligonucleotide of any of Embodiments 1-135, wherein the nucleobase on the 3' end of the oligonucleotide is replaced by a replacement nucleobase selected from I, A, T, U, G and C, wherein the replacement introduces a mismatch between the oligonucleotide and the target nucleic acid at that position.
137. The oligonucleotide of any of Embodiments 1-135, wherein the nucleobase on the 3' end of the oligonucleotide is replaced by a replacement nucleobase selected from I, A, T, U, G and C, wherein the replacement introduces a wobble base pair between the oligonucleotide and the target nucleic acid at that position.
138. The oligonucleotide of any of Embodiments 1-135, wherein the nucleobase on the 3' end of the oligonucleotide is replaced by a replacement nucleobase selected from I, A, T, U, G and C, wherein the replacement increases the activity of the oligonucleotide.
139. The oligonucleotide of any of Embodiments 1-138, wherein the nucleobase on the 3' end of the oligonucleotide is replaced by a replacement nucleobase selected from I, A, T, U, G and C, wherein the replacement increases the activity of the oligonucleotide by at least 25%.
140. The oligonucleotide of any of Embodiments 1-138, wherein the nucleobase on the 3' end of the oligonucleotide is replaced by a replacement nucleobase selected from I, A, T, U, G and C, wherein the replacement increases the activity of the oligonucleotide by at least 50%.
141. The oligonucleotide of any of Embodiments 1-138, wherein the nucleobase on the 3' end of the oligonucleotide is replaced by a replacement nucleobase selected from I, A, T, U, G and C, wherein the replacement increases the activity of the oligonucleotide by at least 100%.
142. The oligonucleotide of any of Embodiments 1-138, wherein the nucleobase on the 3' end of the oligonucleotide is replaced by a replacement nucleobase selected from I, A, T, U, G and C, wherein the replacement increases the activity of the oligonucleotide by at least 1, 2, 3, 4, 5, 6, 7, 8, 9, 10 or more fold.
143. The oligonucleotide of any one of the preceding Embodiments, wherein each phosphorothioate internucleotidic linkage in the oligonucleotide independently has a diastereomeric purity of at least 90%, 95%, 96%, 97%, 98%, or 99%.
144. The oligonucleotide of any one of the preceding Embodiments, wherein each chiral internucleotidic linkage in the oligonucleotide independently has a diastereomeric purity of at least 90%, 95%, 96%, 97%, 98%, or 99%.
145. The oligonucleotide of any one of the preceding Embodiments, having a diastereomeric purity of at least 50%, 60%, 70%, 80%, 85%, 90%, 95%, 96%, 97%, 98%, or 99%.
146. A composition comprising an oligonucleotide of any one of the preceding Embodiments or a salt form thereof.
147. A pharmaceutical composition which comprises or delivers an oligonucleotide of any one of Embodiments 1-145 or a pharmaceutically acceptable salt form thereof.
148. The composition of Embodiment 147, further comprising a pharmaceutically acceptable carrier.
149. The composition of any one of Embodiments 146-148, wherein the salt form is a sodium salt of the oligonucleotide.
150. The composition of any one of Embodiments 146-149, wherein the composition is chirally controlled.
151. A composition comprising oligonucleotides of a particular oligonucleotide type characterized by:
    a) a common base sequence;
    b) a common pattern of backbone linkages;
    c) a common pattern of backbone chiral centers;
    wherein composition is enriched, relative to a substantially racemic preparation of oligonucleotides having the same common base sequence, for oligonucleotides of the particular oligonucleotide type; and
    wherein the oligonucleotide targets C9orf72.
152. An oligonucleotide composition comprising oligonucleotides of a particular oligonucleotide type characterized by:
    a) a common base sequence;
    b) a common pattern of backbone linkages;
    c) a common pattern of backbone chiral centers;
    wherein the composition is enriched, relative to a substantially racemic preparation of oligonucleotides having the same common base sequence, for oligonucleotides of the particular oligonucleotide type; and wherein each oligonucleotide of the particular oligonucleotide type is independently an oligonucleotide of any of Embodiments 1-145 or a salt form thereof.

153. An oligonucleotide composition comprising a plurality of oligonucleotides, wherein:

oligonucleotides of the plurality are of the same constitution;

oligonucleotides of the plurality share the same linkage phosphorus stereochemistry at one or more (1, 2, 3, 4, 5, 6, 7, 8, 9, 10, 11, 12, 13, 14, 15, 16, 17, 18, 19, or 20 or more) chirally controlled internucleotidic linkages;

wherein the composition is enriched, relative to a substantially racemic preparation of oligonucleotides having the same common base sequence, for oligonucleotides of the particular oligonucleotide type; and oligonucleotides of the plurality are each independently an oligonucleotide of any of Embodiments 1-145 or a salt form thereof.

154. An oligonucleotide composition comprising a plurality of oligonucleotides which have:

a) a common base sequence;

b) a common pattern of backbone linkages;

c) a common pattern of backbone chiral centers;

wherein level of the plurality of oligonucleotides in the composition is not random; and wherein each oligonucleotide of the plurality is independently an oligonucleotide of any of Embodiments 1-145 or a salt form thereof.

155. An oligonucleotide composition comprising a plurality of oligonucleotides, wherein:

oligonucleotides of the plurality are each independently an oligonucleotide of any of Embodiments 1-145 or a salt form thereof;

oligonucleotides of the plurality share the same linkage phosphorus stereochemistry at one or more (1, 2, 3, 4, 5, 6, 7, 8, 9, 10, 11, 12, 13, 14, 15, 16, 17, 18, 19, or 20 or more) chirally controlled internucleotidic linkages, and one or more (1, 2, 3, 4, 5, 6, 7, 8, 9, 10, 11, 12, 13, 14, 15, 16, 17, 18, 19, or 20 or more) or each of the chirally controlled internucleotidic linkages independently has a diastereomeric purity of about or at least about at least 90%, 95%, 96%, 97%, 98%, or 99% in the composition.

156. The composition of Embodiment 155, wherein oligonucleotides of the plurality share the same linkage phosphorus stereochemistry at 5 or more internucleotidic linkage, each of which independently has a diastereomeric purity of about or at least about at least 90%, 95%, 96%, 97%, 98%, or 99% in the composition.

157. The composition of Embodiment 155, wherein oligonucleotides of the plurality share the same linkage phosphorus stereochemistry at each phosphorothioate internucleotidic linkage, each of which independently has a diastereomeric purity of about or at least about at least 90%, 95%, 96%, 97%, 98%, or 99% in the composition.

158. The composition of Embodiment 155, wherein oligonucleotides of the plurality share the same linkage phosphorus stereochemistry at each chiral internucleotidic linkage, each of which independently has a diastereomeric purity of about or at least about at least 90%, 95%, 96%, 97%, 98%, or 99% in the composition.

159. The composition of any one of Embodiments 151-158, wherein the composition is enriched such that 1-100% (e.g., about 5%-100%, 10%-100%, 20%-100%, 30%-100%, 40%-100%, 50%-100%, 60%-100%, 70%-100%, 80-100%, 90-100%, 95-100%, 50%-90%, or about 5%, 10%, 20%, 30%, 40%, 50%, 60%, 70%, 80%, 85%, 90%, 91%, 92%, 93%, 94%, 95%, 96%, 97%, 98%, 99%, or 100%, or at least 5%, 10%, 20%, 30%, 40%, 50%, 60%, 70%, 80%, 85%, 90%, 91%, 92%, 93%, 94%, 95%, 96%, 97%, 98%, or 99%) of all oligonucleotide in the composition that share the same base sequence as oligonucleotides of the particular type or oligonucleotides of the plurality are oligonucleotides of the particular type or oligonucleotides of the plurality.

160. An oligonucleotide composition comprising a plurality of oligonucleotides, wherein:

oligonucleotides of the plurality are of the same constitution;

oligonucleotides of the plurality share the same linkage phosphorus stereochemistry at one or more (1, 2, 3, 4, 5, 6, 7, 8, 9, 10, 11, 12, 13, 14, 15, 16, 17, 18, 19, or 20 or more) chirally controlled internucleotidic linkages;

at each chirally controlled internucleotidic linkage, at least 90%, 95%, 96%, 97%, 98%, or 99% of all oligonucleotides in the composition that share same constitution share the same linkage phosphorus stereochemistry; and oligonucleotides of the plurality are each independently an oligonucleotide of any of Embodiments 1-145 or a salt form thereof.

161. The composition of any one of Embodiments 153-160, wherein oligonucleotides of the plurality share the same linkage phosphorus stereochemistry at at least 5 internucleotidic linkages.

162. The composition of any one of Embodiments 153-161, wherein oligonucleotides of the plurality share the same linkage phosphorus stereochemistry independently at each phosphorothioate internucleotidic linkage.

163. The composition of any one of Embodiments 153-162, wherein oligonucleotides of the plurality share the same linkage phosphorus stereochemistry independently at one or more non-negatively charged internucleotidic linkages.

164. The composition of any one of Embodiments 153-162, wherein oligonucleotides of the plurality share the same linkage phosphorus stereochemistry independently at each non-negatively charged internucleotidic linkage.

165. The composition of any one of Embodiments 153-162, wherein oligonucleotides of the plurality share the same linkage phosphorus stereochemistry independently at each chiral internucleotidic linkage.

166. The composition of any one of Embodiments 151-165, wherein oligonucleotides of the plurality or type share the same structure.

167. The composition of any one of Embodiments 151-166, wherein oligonucleotides of the plurality are each independently an oligonucleotide having the structure of:

mA *S m5Ceo n001R Teo m5Ceo n001RmA *S C *S C *S C *RA *S C *S T *S m5C *S G *R m5C *S C *S mA *S mC n001R m5Ceo *S mG *S mC, or a pharmaceutically acceptable salt thereof, wherein:

m represents a 2'-OMe modification to a nucleoside;

S represents a Sp phosphorothioate linkage;

m5Ceo represents 5-methyl 2'-O-methoxyethyl C;

n001R represents a Rp n001 linkage, wherein a n001 linkage has the structure of

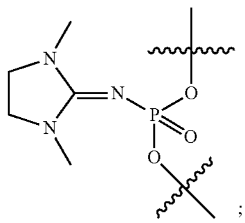 [SMILES: *OP(=O)(N=C1N(C)CCN1C)O*]

eo represents a 2'-$OCH_2CH_2OCH_3$ modification to a nucleoside;

R represents a Rp phosphorothioate linkage; and m5 represents a methyl at 5-position of C.

168. The composition of any one of Embodiments 151-166, wherein oligonucleotides of the plurality are each independently an oligonucleotide having the structure of:

mA *S m5Ceo n001RTeo m5Ceo n001RmA *S C *S C *S C *RA *S C *S T *S m5C *S G *R m5C *S C *S mA *S mC *S m5Ceo n001R mG *S mC, or a pharmaceutically acceptable salt thereof, wherein:

m represents a 2'-OMe modification to a nucleoside;

S represents a Sp phosphorothioate linkage;

m5Ceo represents 5-methyl 2'-O-methoxyethyl C;

n001R represents a Rp n001 linkage, wherein a n001 linkage has the structure of

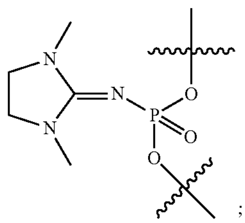 [SMILES: *OP(=O)(N=C1N(C)CCN1C)O*]

eo represents a 2'-$OCH_2CH_2OCH_3$ modification to a nucleoside;

R represents a Rp phosphorothioate linkage; and m5 represents a methyl at 5-position of C.

169. The composition of any one of Embodiments 151-166, wherein oligonucleotides of the plurality are each independently an oligonucleotide having the structure of:

mA *S m5Ceo n001R Teo m5Ceo n001RmA *S C *S C *S C *RA *S C *S T *S m5C *S G *R m5C *S C *S mA *S mC *S m5Ceo *S mG n001R mC, or a pharmaceutically acceptable salt thereof, wherein:

m represents a 2'-OMe modification to a nucleoside;

S represents a Sp phosphorothioate linkage;

m5Ceo represents 5-methyl 2'-O-methoxyethyl C;

n001R represents a Rp n001 linkage, wherein a n001 linkage has the structure of

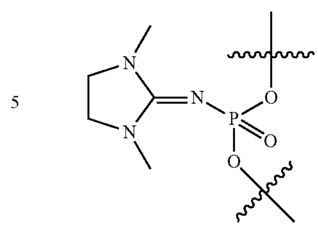

eo represents a 2'-$OCH_2CH_2OCH_3$ modification to a nucleoside;

R represents a Rp phosphorothioate linkage; and m5 represents a methyl at 5-position of C.

170. The composition of any one of Embodiments 151-166, wherein oligonucleotides of the plurality are each independently an oligonucleotide having the structure of:

mC *S m5Ceo Teo m5Ceo mA *S C *S T *S C *R A *S C *S C *R C *S A *S C *S T *S m5 mC*S mG*S mC*S m5 mC*S mG, or a pharmaceutically acceptable salt thereof, wherein:

m represents a 2'-OMe modification to a nucleoside;

S represents a Sp phosphorothioate linkage;

m5Ceo represents 5-methyl 2'-O-methoxyethyl C;

eo represents a 2'-$OCH_2CH_2OCH_3$ modification to a nucleoside;

R represents a Rp phosphorothioate linkage; and m5 represents a methyl at 5-position of C.

171. The composition of any one of Embodiments 151-166, wherein oligonucleotides of the plurality are each independently an oligonucleotide having the structure of:

mA *S m5Ceo Teo m5Ceo mA *S C *S C *S C *R A *S C *S T *S m5C *S G *R m5C *S C *S mA *S mC *S m5 mC *S mG *S mC, or a pharmaceutically acceptable salt thereof, wherein:

m represents a 2'-OMe modification to a nucleoside;

S represents a Sp phosphorothioate linkage;

m5Ceo represents 5-methyl 2'-O-methoxyethyl C;

eo represents a 2'-$OCH_2CH_2OCH_3$ modification to a nucleoside;

R represents a Rp phosphorothioate linkage; and m5 represents a methyl at 5-position of C.

172. The composition of any one of Embodiments 151-166, wherein oligonucleotides of the plurality are each independently an oligonucleotide having the structure of:

mC *S m5Ceo Teo m5Ceo mA *S C *S T *S C *R A *S C *S C *R C *S A *S C *S T *S m5Ceo *S mG *S mC *S m5Ceo *S mG, or a pharmaceutically acceptable salt thereof, wherein:

m represents a 2'-OMe modification to a nucleoside;

S represents a Sp phosphorothioate linkage;

m5Ceo represents 5-methyl 2'-O-methoxyethyl C;

eo represents a 2'-$OCH_2CH_2OCH_3$ modification to a nucleoside;

R represents a Rp phosphorothioate linkage; and m5 represents a methyl at 5-position of C.

173. The composition of any one of Embodiments 151-166, wherein oligonucleotides of the plurality are each independently an oligonucleotide having the structure of:

mA *S m5Ceo Teo m5Ceo mA *S C *S C *S C *R A *S C *S T *S m5C *S G *R m5C *S C *S mA *S mC *S m5Ceo *S mG *S mC, or a pharmaceutically acceptable salt thereof, wherein:

m represents a 2'-OMe modification to a nucleoside;

S represents a Sp phosphorothioate linkage;

m5Ceo represents 5-methyl 2'-O-methoxyethyl C;

eo represents a 2'-$OCH_2CH_2OCH_3$ modification to a nucleoside;

R represents a Rp phosphorothioate linkage; and m5 represents a methyl at 5-position of C.

174. The composition of any one of Embodiments 151-173, wherein each oligonucleotide is independently in a salt form.

175. The composition of any one of Embodiments 151-173, wherein each oligonucleotide is independently in a pharmaceutically acceptable salt form.

176. The composition of any one of Embodiment 174, wherein the salt form is a sodium form.

177. A pharmaceutical composition which comprises or delivers a composition of any one of Embodiments 151-176.

178. The composition of Embodiment 177, further comprising a pharmaceutically acceptable carrier.

179. A method, comprising administering to a subject suffering from or susceptible to a condition, disorder, and/or disease related to C9orf72 expanded repeats an effective amount of an oligonucleotide or a composition of any one of the preceding Embodiments.

180. The method of Embodiment 179, wherein the condition, disorder, and/or disease is amyotrophic lateral sclerosis (ALS), frontotemporal dementia (FTD), corticobasal degeneration syndrome (CBD), atypical Parkinsonian syndrome, olivopontocerebellar degeneration (OPCD), or Alzheimer's disease.

181. The method of Embodiment 179, wherein the condition, disorder, and/or disease is amyotrophic lateral sclerosis (ALS).

182. The method of Embodiment 179, wherein the condition, disorder, and/or disease is frontotemporal dementia (FTD).

183. A method for preventing or treating amyotrophic lateral sclerosis (ALS) in a subject, comprising administering to a subject susceptible thereto or suffering therefrom an oligonucleotide or composition of any one of the preceding Embodiments.

184. A method for preventing or treating frontotemporal dementia (FTD) in a subject, comprising administering to a subject susceptible thereto or suffering therefrom an oligonucleotide or composition of any one of the preceding Embodiments.

185. The method of any one of Embodiments 183-184, wherein the subject comprises expanded GGGGCC repeats in C9orf72.

186. A method of decreasing the activity, expression and/or level of a C9orf72 target gene or its gene product in a cell, comprising introducing into the cell an oligonucleotide or a composition of any of preceding Embodiments.

187. A method for reducing foci in a population of cells, comprising contacting the cells with an oligonucleotide or a composition of any of preceding Embodiments.

188. A method for reducing level of a dipeptide repeat (DPR) protein in a population of cells, comprising contacting the cells with an oligonucleotide or a composition of any of preceding Embodiments.

189. A method of decreasing the activity, expression and/or level of a C9orf72 target gene or its gene product in a subject, comprising administering to the subject an oligonucleotide or a composition of any of preceding Embodiments.

190. A method for reducing foci in a subject, comprising administering to the subject an oligonucleotide or a composition of any of preceding Embodiments.

191. A method for reducing levels of dipeptide repeat (DPR) protein in a subject, comprising administering to the subject an oligonucleotide or a composition of any of preceding Embodiments.

192. The method of any one of Embodiments 179-191, wherein the percentage of cells with foci is reduced.

193. The method of any one of Embodiments 179-192, wherein the number of foci per cell is reduced.

194. The method of any one of Embodiments 179-193, wherein foci comprise RNA comprising GGGGCC repeats.

195. The method of any one of Embodiments 179-194, wherein level of a DPR protein encoded by a GGGGCC repeat sequence is reduced.

196. The method of any one of Embodiments 179-195, wherein level of a DPR protein comprising poly-GP is reduced.

197. The method of any one of Embodiments 179-196, wherein level of a DPR protein comprising poly-GA is reduced.

198. The method of any one of Embodiments 179-197, wherein level of a DPR protein comprising poly-GR is reduced.

199. The method of any one of Embodiments 179-198, wherein GGGGCC repeats are expanded GGGGCC (SEQ ID NO: 566) repeats (e.g., about or at least about 30, 40, 50, 60, 70, 80, 90, 100, 150, 200, 300, 400, 500, 600, 700, 800, 900, 1000, 1100, 1200, 1300, 1400, 1500, or 1600 repeats).

200. The method of any one of Embodiments 179-199, wherein foci in a population of cells in a subject is reduced.

201. The method of any one of Embodiments 179-200, wherein level of a DPR protein in a population of cells in a subject is reduced.

202. The method of any one of Embodiments 179-201, wherein the subject is a human who comprises expanded GGGGCC repeats in C9orf72.

203. A method for preferential knockdown of a repeat expansion-containing C9orf72 RNA transcript relative to a non-repeat expansion-containing C9orf72 RNA transcript in a cell, comprising contacting a cell comprising the repeat expansion-containing C9orf72 RNA transcript and the non-repeat expansion-containing C9orf72 RNA transcript with an oligonucleotide or composition of any one of the preceding Embodiments, wherein the oligonucleotide comprises a sequence present in or complementary to a sequence in the repeat expansion-containing C9orf72 RNA transcript, wherein the oligonucleotide directs preferential knockdown of a repeat expansion-containing C9orf72 RNA transcript relative to a non-repeat expansion-containing C9orf72 RNA transcript in a cell.

204. The oligonucleotide, composition or method of any one of the preceding Embodiments, wherein an expanded GGGGCC (SEQ ID NO: 567) repeats comprises about or at least about 30 repeats.

205. The oligonucleotide, composition or method of any one of the preceding Embodiments, wherein an expanded GGGGCC (SEQ ID NO: 568) repeats comprises about or at least about 50 repeats.

206. The oligonucleotide, composition or method of any one of the preceding Embodiments, wherein an expanded GGGGCC (SEQ ID NO: 569) repeats comprises about or at least about 100 repeats.

207. The oligonucleotide, composition or method of any one of the preceding Embodiments, wherein an expanded GGGGCC (SEQ ID NO: 570) repeats comprises about or at least about 150 repeats.

208. The oligonucleotide, composition or method of any one of the preceding Embodiments, wherein an expanded GGGGCC (SEQ ID NO: 571) repeats comprises about or at least about 200 repeats.

209. The oligonucleotide, composition or method of any one of the preceding Embodiments, wherein an expanded GGGGCC (SEQ ID NO: 572) repeats comprises about or at least about 300 repeats.

210. The oligonucleotide, composition or method of any one of the preceding Embodiments, wherein an expanded GGGGCC (SEQ ID NO: 573) repeats comprises about or at least about 500 repeats.

211. The oligonucleotide, composition or method of any one of the preceding Embodiments, wherein an expanded GGGGCC (SEQ ID NO: 574) repeats comprises about or at least about 1000 repeats.

212. The oligonucleotide, composition or method of any one of the preceding Embodiments, wherein an expanded GGGGCC (SEQ ID NO: 575) repeats comprises about or at least about 1500 repeats.

213. A method for preparing an oligonucleotide or composition of any one of the preceding Embodiments, comprising contacting a phosphoramidite having the structure of

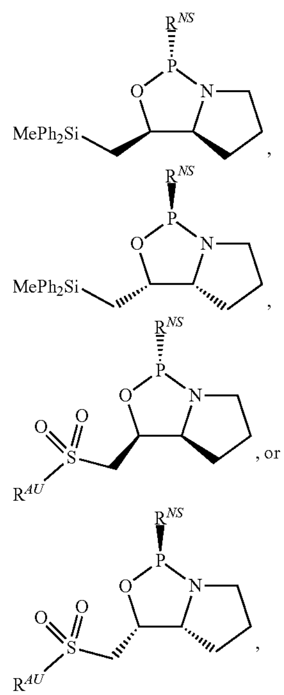

or a salt thereof, with a —OH of a nucleoside or an oligonucleotide, wherein $R^{AU}$ is an optionally substituted group selected from $C_{1-20}$ aliphatic, $C_{1-20}$ heteroaliphatic having 1-10 heteroatoms, $C_{6-20}$ aryl, $C_{6-20}$ arylaliphatic, $C_{6-20}$ arylheteroaliphatic having 1-10 heteroatoms, 5-20 membered heteroaryl having 1-10 heteroatoms, and 3-20 membered heterocyclyl having 1-10 heteroatoms, and $R^{NS}$ is an optionally substituted or protected nucleoside.

214. The method of Embodiment 213, wherein a phosphoramidite has the structure of

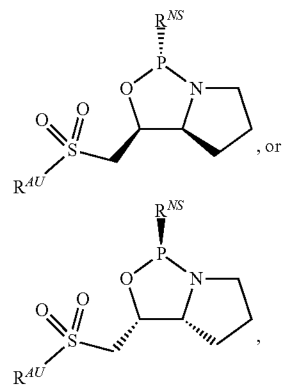

or a salt thereof, with —OH of a nucleoside or an oligonucleotide.

215. The method of any one of Embodiments 213-214, wherein $R^{AU}$ is -Ph.

216. The method of any one of Embodiments 213-215, wherein $R^{NS}$ is A, T, C, or G optionally protected for oligonucleotide synthesis.

217. The method of any one of Embodiments 213-216, wherein —OH is 5'-OH.

218. A compound, oligonucleotide, composition, or method described in the specification.

EXEMPLIFICATION

Various technologies for preparing oligonucleotides and oligonucleotide compositions (both stereorandom and chirally controlled) are known and can be utilized in accordance with the present disclosure, including, for example, those in U.S. Pat. Nos. 9,394,333, 9,744,183, 9,605,019, 9,598,458, 9,982,257, U.S. Ser. No. 10/160,969, U.S. Ser. No. 10/479,995, US 2020/0056173, US 2018/0216107, US 2019/0127733, U.S. Ser. No. 10/450,568, US 2019/0077817, US 2019/0249173, US 2019/0375774, WO 2018/223056, WO 2018/223073, WO 2018/223081, WO 2018/237194, WO 2019/032607, WO 2019/055951, WO 2019/075357, WO 2019/200185, WO 2019/217784, WO 2019/032612, and/or WO 2020/191252, the methods and reagents of each of which are incorporated herein by reference.

In some embodiments, oligonucleotides were prepared using suitable chiral auxiliaries, e.g., DPSE and PSM chiral auxiliaries. Various oligonucleotides, e.g., those in Table A1, and compositions thereof, were prepared in accordance with the present disclosure.

Example 1. C9orf72 Oligonucleotide Compositions are Active and Selective in Various Assays Among other things, as demonstrated herein the present disclosure provides technologies that can effectively and/or selectively reduce expression, activities and/or levels of C9orf72 transcripts and/or products encoded thereby associated with conditions, disorders or diseases and comprising expanded repeats. In the following Tables: Shown are residual levels of various C9orf72 transcripts (e.g., all V transcripts, only V3 transcripts, etc.) relative to HPRT1, after treatment with C9orf72 oligonucleotides, wherein 1.000 would represent 100% relative transcript level (no knockdown) and 0.000 would represent 0% relative transcript level (e.g., 100% knockdown). Results from replicate experiments are shown. WV-12890 is a non-targeting control. Experiments were conducted in ALS motor neurons. Additional assay conditions are described herein and/or in WO 2019/032607.

This Table shows data of various C9orf72 oligonucleotides in knocking down C9orf72 transcripts in ALS motor neurons (only V3 transcripts). As in other "only V3 transcripts" assessments, relative-fold change of V3 in C9orf72/HPRT1 is shown. WV-9491 is a control, which is a stereorandom oligonucleotide composition (description: mC*m5CeoTeoTeomC*C*C*T*G*A*A*G*G*T*T*mC*mC*mU*mC*mC, base sequence: CCTTCCCTGAAGGTTCCUCC (SEQ ID NO: 535), Stereochemistry/Internucleotidic Linkages: XOOOXXXXXXXXXXXXXXX, see Key to Table A1).

TABLE 1A

Activity of C9orf72 oligonucleotides

| Dose (uM) | WV-8012 | | | WV-30206 | | | WV-30210 | | |
|---|---|---|---|---|---|---|---|---|---|
| 0.0032 | 1.057 | 1.087 | 1.028 | 1.133 | 1.043 | 1.072 | 1.189 | 1.094 | 1.050 |
| 0.016 | 0.933 | 0.986 | 1.079 | 0.908 | 0.889 | 0.966 | 1.000 | 1.021 | 0.993 |
| 0.08 | 0.779 | 0.758 | 0.712 | 0.747 | 0.763 | 0.853 | 0.796 | 0.847 | 0.841 |
| 0.4 | 0.274 | 0.283 | 0.252 | 0.387 | 0.406 | 0.412 | 0.356 | 0.321 | 0.361 |
| 2 | 0.107 | 0.098 | 0.093 | 0.170 | 0.178 | 0.173 | 0.097 | 0.093 | 0.089 |
| 10 | 0.036 | 0.036 | 0.034 | 0.075 | 0.063 | 0.069 | 0.019 | 0.022 | 0.015 |
| **Dose (uM)** | **WV-30211** | | | **WV-30212** | | | **WV-9491** | | |
| 0.0032 | 1.141 | 1.165 | 1.094 | 1.141 | 1.189 | 1.165 | | | |
| 0.016 | 1.014 | 1.064 | 1.057 | 0.940 | 0.824 | 1.000 | 1.395 | 0.829 | 0.824 |
| 0.08 | 0.697 | 0.732 | 0.824 | 0.737 | 0.655 | 0.655 | 0.889 | 1.275 | 0.953 |
| 0.4 | 0.392 | 0.304 | 0.304 | 0.281 | 0.255 | 0.243 | 1.173 | 0.847 | 1.189 |
| 2 | 0.128 | 0.128 | 0.099 | 0.095 | 0.090 | 0.067 | 0.986 | 1.125 | 1.064 |
| 10 | 0.033 | 0.031 | 0.031 | | 0.027 | 0.027 | 1.007 | 0.993 | 0.993 |

TABLE 1B

Activity of C9orf72 oligonucleotides

| Dose (uM) | WV-8012 | | | WV-30206 | | | WV-30210 | | |
|---|---|---|---|---|---|---|---|---|---|
| 0.0032 | 0.954 | 0.987 | 1.058 | 1.008 | 0.954 | 1.095 | 0.980 | 0.859 | 0.994 |
| 0.016 | | 0.921 | 0.947 | 1.058 | 0.928 | 1.015 | 0.890 | 0.848 | 0.775 |
| 0.08 | 0.688 | 0.708 | 0.733 | 0.748 | 0.813 | 0.665 | 0.775 | 0.890 | 0.819 |
| 0.4 | 0.583 | 0.670 | 0.651 | 0.660 | 0.743 | 0.780 | 0.563 | 0.608 | 0.670 |
| 2 | 0.467 | 0.529 | 0.490 | 0.708 | 0.591 | 0.625 | 0.500 | 0.579 | 0.567 |
| 10 | 0.321 | 0.332 | 0.473 | 0.379 | 0.427 | 0.461 | | 0.377 | 0.310 |
| **Dose (uM)** | **WV-30211** | | | **WV-30212** | | | **WV-9491** | | |
| 0.0032 | 0.921 | 0.987 | 0.902 | 0.994 | 0.819 | 1.065 | | | |
| 0.016 | 0.796 | 0.947 | 0.853 | 0.842 | 0.865 | 0.902 | 0.987 | 0.954 | 1.008 |
| 0.08 | 0.791 | 0.884 | 0.987 | 0.819 | 0.733 | 0.902 | 0.908 | 1.073 | 0.877 |
| 0.4 | 0.670 | 0.629 | 0.642 | 0.522 | 0.708 | 0.733 | 1.058 | 0.785 | 1.349 |
| 2 | 0.461 | 0.540 | 0.385 | 0.567 | 0.511 | 0.525 | 1.001 | 1.088 | 0.871 |
| 10 | 0.401 | 0.349 | 0.306 | | 0.433 | 0.407 | | 0.954 | 1.029 |

This Table shows data of various C9orf72 oligonucleotides in knocking down C9orf72 transcripts in ALS motor neurons (All V transcripts). Relative fold-change in C9orf72/HPRT1 is shown.

As demonstrated, various oligonucleotide compositions can effectively and selectively reduce targeted transcripts, e.g., transcripts that can contain expanded repeats and be associated with various conditions, disorders or diseases (e.g., V3 transcripts).

TABLE 2A

Activity of C9orf72 oligonucleotides

| Conc. | WV-8012 | | | WV-23486 | | | WV-28080 | | |
|---|---|---|---|---|---|---|---|---|---|
| 0.2 uM | 0.38 | 0.59 | 0.49 | 0.26 | 0.34 | 0.43 | 0.68 | 0.73 | 0.74 |
| 1 uM | 0.33 | 0.34 | 0.27 | 0.27 | 0.25 | 0.29 | 0.34 | 0.44 | 0.47 |
| 5 uM | 0.16 | 0.11 | 0.21 | 0.11 | 0.15 | 0.14 | 0.26 | 0.27 | 0.32 |

| Conc. | WV-28479 | | | WV-23741 | | |
|---|---|---|---|---|---|---|
| 0.2 uM | 0.68 | 0.64 | 0.79 | 0.53 | 0.63 | 0.65 |
| 1 uM | 0.30 | 0.22 | 0.29 | 0.38 | 0.29 | 0.38 |
| 5 uM | 0.13 | 0.13 | 0.15 | 0.14 | 0.16 | 0.22 |

| Conc. | WV-28086 | | | WV-28305 | | | WV-28089 | | |
|---|---|---|---|---|---|---|---|---|---|
| 0.2 uM | 0.96 | 0.89 | 1.10 | 1.02 | 1.06 | 0.98 | 0.89 | 0.87 | 0.92 |
| 1 uM | 0.87 | 1.00 | 0.89 | 0.99 | 0.82 | 0.98 | 0.77 | 1.00 | 1.11 |
| 5 uM | 0.75 | 0.54 | 0.94 | 0.74 | 0.70 | 0.82 | 0.75 | 0.74 | 0.81 |

| Conc. | WV-28307 | | | WV-9491 | | |
|---|---|---|---|---|---|---|
| 0.2 uM | 0.83 | 0.90 | 0.96 | 1.04 | 0.90 | 0.87 |
| 1 uM | 0.78 | 0.68 | 0.79 | 1.02 | 1.11 | 1.07 |
| 5 uM | 0.62 | 0.65 | 0.81 | 0.99 | 0.92 | 1.07 |

This Table shows data of various C9orf72 oligonucleotides in knocking down C9orf72 transcripts in ALS motor neurons (only V3 transcripts). As in other "only V3 transcripts" assessments, relative-fold change of V3 in C9orf72/HPRT1 is shown.

TABLE 2B

Activity of C9orf72 oligonucleotides

| Conc. | WV-8012 | | | WV-23486 | | | WV-28080 | | |
|---|---|---|---|---|---|---|---|---|---|
| 0.2 uM | 0.63 | 0.82 | 0.66 | 0.48 | 0.64 | 0.65 | 0.96 | 0.98 | 0.94 |
| 1 uM | 0.77 | 0.77 | 0.96 | 0.84 | 0.79 | 0.84 | 0.74 | 0.83 | 0.96 |
| 5 uM | 0.60 | 0.42 | 0.67 | 0.63 | 0.72 | 0.69 | 0.67 | 0.76 | 0.83 |

| Conc. | WV-28479 | | | WV-23741 | | |
|---|---|---|---|---|---|---|
| 0.2 uM | 0.87 | 0.89 | 0.91 | 0.94 | 0.91 | 0.88 |
| 1 uM | 0.83 | 0.77 | 0.76 | 0.76 | 0.69 | 0.78 |
| 5 uM | 0.68 | 0.68 | 0.70 | 0.70 | 0.67 | 0.79 |

| Conc. | WV-28086 | | | WV-28305 | | | WV-28089 | | |
|---|---|---|---|---|---|---|---|---|---|
| 0.2 uM | 0.82 | 0.92 | 0.98 | 1.10 | 1.07 | 1.05 | 0.78 | 0.86 | 0.90 |
| 1 uM | 0.87 | 1.11 | 0.87 | 1.14 | 0.96 | 0.94 | 0.94 | 0.95 | 0.90 |
| 5 uM | 0.86 | 0.69 | 1.09 | 0.90 | 1.05 | 1.06 | 0.89 | 0.93 | 0.89 |

| Conc. | WV-28307 | | | WV-9491 | | |
|---|---|---|---|---|---|---|
| 0.2 uM | 0.70 | 0.92 | 0.97 | 1.05 | 0.96 | 0.84 |
| 1 uM | 0.92 | 0.91 | 0.83 | 0.99 | 1.05 | 1.02 |
| 5 uM | 0.77 | 0.84 | 0.84 | 1.10 | 0.86 | 1.07 |

This Table shows data of various C9orf72 oligonucleotides in knocking down C9orf72 transcripts in ALS motor neurons (All V transcripts). Relative-fold change in C9orf72/HPRT1 is shown.

As demonstrated, at multiple oligonucleotide concentrations various oligonucleotide compositions can effectively and selectively reduce targeted transcripts, e.g., transcripts that can contain expanded repeats and be associated with various conditions, disorders or diseases (e.g., V3 transcripts).

TABLE 3A

| Activity of C9orf72 oligonucleotides | | | | | | | | | | | | |
|---|---|---|---|---|---|---|---|---|---|---|---|---|
| WV-8012 | WV-21446 | WV-28077 | WV-28078 | WV-28079 | WV-28478 | WV-27140 | WV-28481 | WV-28464 | WV-28465 | WV-28466 | WV-28467 | WV-9491 |
| 0.33 | 0.17 | 0.58 | 0.29 | 0.71 | 0.24 | 0.46 | 0.53 | 0.60 | 0.63 | 0.42 | 0.75 | 1.02 |
| 0.34 | 0.17 | 0.65 | 0.26 | 0.70 | 0.22 | 0.53 | 0.46 | 0.59 | 0.64 | 0.39 | 0.66 | 1.11 |
| 0.27 | 0.18 | 0.57 | 0.35 | 0.74 | 0.23 | 0.53 | 0.53 | 0.63 | 0.65 | 0.43 | 0.86 | 1.07 |

This Table shows data of various C9orf72 oligonucleotides (1 uM) in knocking down C9orf72 transcripts in ALS motor neurons (only V3 transcripts). As in other “only V3 transcripts”

TABLE 3B

| Activity of C9orf72 oligonucleotides | | | | | |
|---|---|---|---|---|---|
| WV-8012 | WV-23486 | WV-28080 | WV-28479 | WV-28480 | WV-9491 |
| 0.33 | 0.27 | 0.34 | 0.30 | 0.44 | 1.02 |
| 0.34 | 0.25 | 0.44 | 0.22 | 0.40 | 1.11 |
| 0.27 | 0.29 | 0.47 | 0.29 | 0.42 | 1.07 |

This Table shows data of various C9orf72 oligonucleotides (1 uM) in knocking down C9orf72 transcripts in ALS motor neurons (only V3 transcripts). As in other “only V3 transcripts” assessments, relative-fold change of V3 in C9orf72/HPRT1 is shown.

TABLE 3C

| Activity of C9orf72 oligonucleotides | | | | | | | | | | | | |
|---|---|---|---|---|---|---|---|---|---|---|---|---|
| WV-8012 | WV-21446 | WV-28077 | WV-28078 | WV-28079 | WV-28478 | WV-27140 | WV-28481 | WV-28464 | WV-28465 | WV-28466 | WV-28467 | WV-9491 |
| 0.77 | 0.84 | 0.92 | 0.84 | 0.89 | 0.75 | 0.83 | 0.87 | 0.82 | 0.98 | 0.87 | 0.99 | 0.99 |
| 0.77 | 0.75 | 0.94 | 0.67 | 0.94 | 0.79 | 0.94 | 0.84 | 0.95 | 1.04 | 0.89 | 0.78 | 1.05 |
| 0.96 | 0.83 | 0.93 | 0.79 | 0.91 | 0.72 | 0.87 | 0.89 | 0.96 | 0.99 | 0.86 | 0.97 | 1.02 |

This Table shows data of various C9orf72 oligonucleotides (1 uM) in knocking down C9orf72 transcripts in ALS motor neurons (All V transcripts). Relative-fold change in C9orf72/HPRT1 is shown.

TABLE 3D

| Activity of C9orf72 oligonucleotides | | | | | |
|---|---|---|---|---|---|
| WV-8012 | WV-23486 | WV-28080 | WV-28479 | WV-28480 | WV-9491 |
| 0.77 | 0.84 | 0.74 | 0.83 | 0.84 | 0.99 |
| 0.77 | 0.79 | 0.83 | 0.77 | 0.75 | 1.05 |
| 0.96 | 0.84 | 0.96 | 0.76 | 0.81 | 1.02 |

This Table shows data of various C9orf72 oligonucleotides (1 uM) in knocking down C9orf72 transcripts in ALS motor neurons (All V transcripts). Relative-fold change in C9orf72/HPRT1 is shown.

As demonstrated, various oligonucleotide compositions can effectively and selectively reduce targeted transcripts, e.g., transcripts that can contain expanded repeats and be associated with various conditions, disorders or diseases (e.g., V3 transcripts).

TABLE 4A

Activity of C9orf72 oligonucleotides

| WV-8012 | WV-23741 | WV-28081 | WV-28082 | WV-28083 | WV-28084 | WV-28085 | WV-28086 | WV-28087 |
|---|---|---|---|---|---|---|---|---|
| 0.33 | 0.38 | 0.88 | 0.73 | 0.98 | 0.98 | 0.64 | 0.87 | 0.72 |
| 0.34 | 0.29 | 0.86 | 0.70 | 1.18 | 1.00 | 0.73 | 1.00 | 0.74 |
| 0.27 | 0.38 | 0.85 | 0.68 | 1.05 | 1.11 | 0.68 | 0.89 | 1.00 |

| WV-28088 | WV-28089 | WV-28303 | WV-28304 | WV-28305 | WV-28306 | WV-28307 | WV-28308 | WV-9491 |
|---|---|---|---|---|---|---|---|---|
| 0.50 | 0.77 | 0.45 | 0.79 | 0.99 | 0.92 | 0.78 | 0.89 | 1.02 |
| 0.45 | 1.00 | 0.87 | 0.77 | 0.82 | 0.98 | 0.68 | 0.81 | 1.11 |
| 0.54 | 1.11 | 0.91 | 0.87 | 0.98 | 0.83 | 0.79 | 0.81 | 1.07 |

This Table shows data of various C9orf72 oligonucleotides (1 uM) in knocking down C9orf72 transcripts in ALS motor neurons (only V3 transcripts). As in other "only V3 transcripts" assessments, relative-fold change of V3 in C9orf72/HPRT1 is shown.

TABLE 4B

Activity of C9orf72 oligonucleotides

| WV-8012 | WV-23741 | WV-28081 | WV-28082 | WV-28083 | WV-28084 | WV-28085 | WV-28086 | WV-28087 |
|---|---|---|---|---|---|---|---|---|
| 0.77 | 0.76 | 0.98 | 0.89 | 1.05 | 1.05 | 0.93 | 0.87 | 0.91 |
| 0.77 | 0.69 | 0.87 | 0.92 | 1.19 | 1.15 | 0.96 | 1.11 | 0.96 |
| 0.96 | 0.78 | 0.92 | 0.81 | 1.15 | 1.09 | 0.96 | 0.87 | 0.98 |

| WV-28088 | WV-28089 | WV-28303 | WV-28304 | WV-28305 | WV-28306 | WV-28307 | WV-28308 | WV-9491 |
|---|---|---|---|---|---|---|---|---|
| 0.94 | 0.94 | 2.40 | 0.99 | 1.14 | 1.03 | 0.92 | 0.92 | 0.99 |
| 0.84 | 0.95 | 0.93 | 0.86 | 0.96 | 0.91 | 0.91 | 0.96 | 1.05 |
| 0.87 | 0.90 | 0.95 | 1.04 | 0.94 | 0.86 | 0.83 | 0.88 | 1.02 |

This Table shows data of various C9orf72 oligonucleotides (1 uM) in knocking down C9orf72 transcripts in ALS motor neurons (All V transcripts). Relative-fold change in C9orf72/HPRT1 is shown.

As demonstrated, various oligonucleotide compositions can effectively and selectively reduce targeted transcripts, e.g., transcripts that can contain expanded repeats and be associated with various conditions, disorders or diseases (e.g., V3 transcripts).

TABLE 5A

Activity of C9orf72 oligonucleotides

| Conc(uM) | WV-8012 | | | WV-28478 | | | WV-26633 | | |
|---|---|---|---|---|---|---|---|---|---|
| 0.0032 | 0.97 | 0.93 | 0.96 | 1.09 | 1.00 | | 1.08 | 1.04 | 1.15 |
| 0.016 | 0.84 | 0.88 | 0.90 | 1.12 | 0.86 | 0.61 | 0.99 | 0.92 | 0.94 |
| 0.08 | 0.71 | 0.69 | 0.72 | 0.76 | 0.62 | 0.61 | 0.74 | 0.79 | 0.76 |
| 0.4 | 0.29 | 0.29 | 0.28 | 0.22 | 0.27 | 0.23 | 0.37 | 0.37 | 0.39 |

TABLE 5A-continued

| Activity of C9orf72 oligonucleotides | | | | | | | | | |
|---|---|---|---|---|---|---|---|---|---|
| 2 | 0.11 | 0.10 | 0.09 | 0.06 | 0.08 | 0.06 | 0.19 | 0.17 | 0.18 |
| 10 | 0.03 | 0.03 | 0.03 | 0.02 | 0.01 | 0.02 | 0.07 | 0.08 | 0.07 |

| Conc(uM) | WV-30206 | | | WV-30277 | | |
|---|---|---|---|---|---|---|
| 0.0032 | 1.08 | 0.90 | 0.94 | 1.08 | 0.88 | 1.08 |
| 0.016 | 0.79 | 0.82 | 0.98 | 1.06 | 1.06 | 1.03 |
| 0.08 | 0.75 | 0.82 | 0.76 | 1.00 | 0.96 | 0.92 |
| 0.4 | 0.35 | 0.33 | 0.35 | 0.71 | 0.66 | 0.71 |
| 2 | 0.12 | 0.14 | 0.13 | 0.44 | 0.48 | 0.43 |
| 10 | 0.06 | 0.06 | 0.05 | 0.33 | 0.34 | 0.35 |

This Table shows data of various C9orf72 oligonucleotides (1 uM) in knocking down C9orf72 transcripts in ALS motor neurons (V3 transcripts). Relative-fold change in C9orf72/HPRT1 is shown.

TABLE 5B

| Activity of C9orf72 oligonucleotides | | | | | | | | | |
|---|---|---|---|---|---|---|---|---|---|
| Conc(uM) | WV-8012 | | | WV-28478 | | | WV-26633 | | |
| 0.0032 | 0.97 | 0.89 | 0.98 | 0.95 | 1.01 | | 1.01 | 1.00 | 0.97 |
| 0.016 | 0.94 | 0.91 | 0.92 | 0.97 | 1.09 | 1.22 | 0.94 | 0.94 | 1.10 |
| 0.08 | 0.87 | 0.85 | 0.94 | 0.93 | 0.89 | 0.82 | 0.89 | 0.88 | 0.97 |
| 0.4 | 0.79 | 0.76 | 0.76 | 0.71 | 0.80 | 0.83 | 0.82 | 0.84 | 0.80 |
| 2 | 0.64 | 0.52 | 0.59 | 0.61 | 0.55 | 0.60 | 0.58 | 0.62 | 0.68 |
| 10 | 0.40 | 0.42 | 0.46 | 0.47 | 0.48 | 0.49 | 0.53 | 0.50 | 0.54 |

| Conc(uM) | WV-30206 | | | WV-30277 | | |
|---|---|---|---|---|---|---|
| 0.0032 | 0.98 | 0.91 | 0.96 | 0.99 | 1.42 | 0.98 |
| 0.016 | 0.79 | 0.95 | 0.95 | 1.01 | 0.95 | 0.97 |
| 0.08 | 0.93 | 0.88 | 0.92 | 0.97 | 0.96 | 1.01 |
| 0.4 | 0.82 | 0.72 | 0.77 | 0.79 | 1.01 | 0.99 |
| 2 | 0.52 | 0.54 | 0.57 | 0.75 | 0.87 | 0.78 |
| 10 | 0.49 | 0.45 | 0.50 | 0.73 | 0.73 | 0.77 |

This Table shows data of various C9orf72 oligonucleotides (1 uM) in knocking down C9orf72 transcripts in ALS motor neurons (All V transcripts). Relative-fold change in C9orf72/HPRT1 is shown.

TABLE 5C

| Activity of certain oligonucleotides. | |
|---|---|
| ID | IC50 |
| WV-8012 | 184.9 nM |
| WV-28478 | 130.3 nM |
| WV-26633 | 171.3 nM |
| WV-30206 | 232.7 nM |
| WV-30277 | 459.0 nM |

Various C9orf72 oligonucleotides were tested for their efficacy in knocking down C9orf72 transcripts in ALS motor neurons (V3 transcripts). Data from a set of results are presented below.

As demonstrated, at multiple oligonucleotide concentrations various oligonucleotide compositions can effectively and selectively reduce targeted transcripts, e.g., transcripts that can contain expanded repeats and be associated with various conditions, disorders or diseases (e.g., V3 transcripts).

TABLE 6

| Activity of C9orf72 oligonucleotides | | | |
|---|---|---|---|
| WV-8012 | 0.22 | 0.21 | 0.26 |
| WV-26633 | | 0.29 | 0.42 |
| WV-30206 | 0.25 | 0.27 | 0.32 |
| WV-30207 | 0.29 | 0.38 | 0.32 |
| WV-30208 | 0.22 | 0.24 | 0.26 |
| WV-30209 | 0.31 | 0.23 | 0.23 |
| WV-30210 | 0.21 | 0.21 | 0.23 |
| WV-30211 | 0.24 | 0.22 | 0.22 |
| WV-30212 | 0.16 | 0.21 | 0.17 |
| WV-28091 | 0.54 | 0.50 | 0.56 |
| WV-30232 | 0.56 | 0.52 | 0.61 |
| WV-30213 | 0.51 | 0.45 | 0.39 |
| WV-30214 | 0.20 | 0.32 | 0.37 |
| WV-30215 | 0.47 | 0.47 | 0.38 |
| WV-30216 | 0.45 | 0.43 | 0.51 |
| WV-30217 | 0.38 | 0.45 | 0.45 |
| WV-30277 | 0.73 | 0.88 | 0.71 |
| WV-30278 | 0.81 | 0.74 | 0.75 |
| WV-30279 | 0.55 | 0.67 | 0.51 |
| WV-30280 | 0.60 | 0.59 | 0.61 |
| WV-30281 | 0.53 | 0.68 | 0.71 |
| WV-30282 | 0.77 | 0.74 | 0.81 |
| WV-30283 | 0.78 | 0.72 | 0.70 |

TABLE 7

| Activity of C9orf72 oligonucleotides | | | |
|---|---|---|---|
| WV-8012 | 0.62 | 0.67 | 0.69 |
| WV-26633 | | 0.66 | 0.70 |
| WV-30206 | 0.69 | 0.67 | 0.65 |
| WV-30207 | 0.77 | 0.69 | 0.66 |
| WV-30208 | 0.72 | 0.74 | 0.72 |
| WV-30209 | 0.69 | 0.64 | 0.68 |
| WV-30210 | 0.61 | 0.59 | 0.70 |
| WV-30211 | 0.67 | 0.72 | 0.68 |
| WV-30212 | 0.65 | 0.58 | 0.60 |
| WV-28091 | 0.84 | 0.76 | 0.87 |
| WV-30232 | 0.86 | 0.86 | 0.85 |
| WV-30213 | 0.84 | 0.84 | 0.76 |
| WV-30214 | 0.49 | 0.79 | 0.80 |
| WV-30215 | 0.68 | 0.73 | 0.80 |
| WV-30216 | 0.73 | 0.76 | 0.79 |
| WV-30217 | 0.82 | 0.83 | 0.80 |
| WV-30277 | 0.98 | 0.86 | 0.98 |
| WV-30278 | 1.03 | 0.90 | 1.02 |
| WV-30279 | 0.83 | 0.87 | 0.87 |
| WV-30280 | 1.00 | 0.75 | 0.92 |
| WV-30281 | 0.89 | 0.92 | 0.82 |
| WV-30282 | 0.90 | 0.95 | 1.06 |
| WV-30283 | 1.05 | 0.97 | 1.00 |

This Table shows data of various C9orf72 oligonucleotides (1 uM) in knocking down C9orf72 transcripts in ALS motor neurons (V3 transcripts). Relative-fold change in C9orf72/HPRT1 is shown.

This Table shows data of various C9orf72 oligonucleotides (1 uM) in knocking down C9orf72 transcripts in ALS motor neurons (All V transcripts). Relative-fold change in C9orf72/HPRT1 is shown.

As demonstrated, various oligonucleotide compositions can effectively and selectively reduce targeted transcripts, e.g., transcripts that can contain expanded repeats and be associated with various conditions, disorders or diseases (e.g., V3 transcripts).

TABLE 8A

| Activity of C9orf72 oligonucleotides | | | |
|---|---|---|---|
| WV-8012 | 0.22 | 0.21 | 0.26 |
| WV-28478 | 0.19 | 0.16 | 0.19 |
| WV-30219 | 0.07 | 0.07 | 0.07 |
| WV-30220 | 0.08 | 0.07 | 0.07 |
| WV-30221 | 0.24 | 0.18 | 0.23 |
| WV-30222 | 0.14 | 0.15 | 0.16 |
| WV-30223 | 0.12 | 0.13 | 0.16 |
| WV-30224 | 0.21 | 0.21 | 0.19 |
| WV-30225 | 0.43 | 0.40 | 0.50 |
| WV-30226 | 0.95 | 0.59 | 0.74 |

TABLE 8A-continued

| Activity of C9orf72 oligonucleotides | | | |
|---|---|---|---|
| WV-30227 | 0.61 | 0.29 | 0.61 |
| WV-30228 | 0.40 | 0.45 | 0.46 |
| WV-30229 | 0.74 | 0.86 | 0.83 |
| WV-30230 | 0.88 | 0.88 | 0.85 |
| WV-30231 | 0.46 | 0.53 | 0.49 |
| WV-30237 | 0.52 | 0.62 | 0.55 |
| WV-30238 | 0.39 | 0.50 | 0.50 |
| WV-30239 | 0.50 | 0.49 | 0.49 |
| WV-9491 | 1.13 | 1.04 | 1.04 |
| WV-17820 | 0.41 | 0.35 | 0.33 |

This Table shows data of various C9orf72 oligonucleotides (1 uM) in knocking down C9orf72 transcripts in ALS motor neurons (V3 transcripts). Relative-fold change in C9orf72/HPRT1 is shown.

TABLE 8B

| Activity of C9orf72 oligonucleotides | | | |
|---|---|---|---|
| WV-8012 | 0.62 | 0.67 | 0.69 |
| WV-28478 | 0.70 | 0.72 | 0.74 |
| WV-30219 | 0.58 | 0.62 | 0.61 |
| WV-30220 | 0.65 | 0.67 | 0.64 |
| WV-30221 | 0.69 | 0.73 | 0.73 |
| WV-30222 | 0.73 | 0.70 | 0.69 |
| WV-30223 | 0.68 | 0.69 | 0.70 |
| WV-30224 | 0.70 | 0.75 | 0.71 |
| WV-30225 | 0.79 | 0.87 | 0.83 |
| WV-30226 | 1.07 | 0.82 | 1.09 |
| WV-30227 | 0.92 | 0.63 | 0.87 |
| WV-30228 | 0.81 | 0.86 | 0.79 |
| WV-30229 | 0.91 | 1.00 | 1.08 |
| WV-30230 | 1.11 | 1.05 | 1.00 |
| WV-30231 | 0.81 | 0.89 | 0.92 |
| WV-30237 | 0.70 | 0.91 | 0.89 |
| WV-30238 | 0.84 | 0.77 | 0.86 |
| WV-30239 | 0.82 | 0.87 | 0.99 |
| WV-9491 | 1.15 | 1.05 | 1.15 |
| WV-17820 | 0.73 | 0.78 | 0.85 |

This Table shows data of various C9orf72 oligonucleotides (1 uM) in knocking down C9orf72 transcripts in ALS motor neurons (All V transcripts). Relative-fold change in C9orf72/HPRT1 is shown.

As demonstrated, various oligonucleotide compositions can effectively and selectively reduce targeted transcripts, e.g., transcripts that can contain expanded repeats and be associated with various conditions, disorders or diseases (e.g., V3 transcripts), including those of oligonucleotides comprising 3'-end replacement nucleobases and/or mismatches/wobbles.

TABLE 9A

| Activity of C9orf72 oligonucleotides | | | | | | | | | |
|---|---|---|---|---|---|---|---|---|---|
| Dose (uM) | WV-8012 | | | WV-30206 | | | WV-30208 | | |
| 0.0032 | 1.06 | 1.09 | 1.03 | 1.13 | 1.04 | 1.07 | 1.06 | 1.04 | 1.04 |
| 0.016 | 0.93 | 0.99 | 1.08 | 0.91 | 0.89 | 0.97 | 0.91 | 0.82 | 0.93 |
| 0.08 | 0.78 | 0.76 | 0.71 | 0.75 | 0.76 | 0.85 | 0.67 | 0.62 | 0.70 |
| 0.4 | 0.27 | 0.28 | 0.25 | 0.39 | 0.41 | 0.41 | 0.31 | 0.24 | 0.26 |
| 2 | 0.11 | 0.10 | 0.09 | 0.17 | 0.18 | 0.17 | 0.08 | 0.09 | 0.10 |
| 10 | 0.04 | 0.04 | 0.03 | 0.08 | 0.06 | 0.07 | 0.03 | 0.03 | 0.03 |
| Dose (uM) | WV-30209 | | | WV-30210 | | | WV-30211 | | |
| 0.0032 | 1.20 | 1.09 | 0.91 | 1.19 | 1.09 | 1.05 | 1.14 | 1.16 | 1.09 |
| 0.016 | 1.01 | 1.01 | 1.09 | 1.00 | 1.02 | 0.99 | 1.01 | 1.06 | 1.06 |
| 0.08 | 0.57 | 0.27 | 0.54 | 0.80 | 0.85 | 0.84 | 0.70 | 0.73 | 0.82 |
| 0.4 | 0.34 | 0.30 | 0.23 | 0.36 | 0.32 | 0.36 | 0.39 | 0.30 | 0.30 |

TABLE 9A-continued

| Activity of C9orf72 oligonucleotides | | | | | | | | | |
|---|---|---|---|---|---|---|---|---|---|
| 2 | 0.09 | 0.10 | 0.09 | 0.10 | 0.09 | 0.09 | 0.13 | 0.13 | 0.10 |
| 10 | 0.01 | 0.01 | 0.02 | 0.02 | 0.02 | 0.01 | 0.03 | 0.03 | 0.03 |
| Dose (uM) | WV-30212 | | | WV-30220 | | | WV-9491 | | |
| 0.0032 | 1.14 | 1.19 | 1.16 | 1.15 | 0.98 | 1.09 | | | |
| 0.016 | 0.94 | 0.82 | 1.00 | 1.03 | 0.93 | 0.97 | 1.39 | 0.83 | 0.82 |
| 0.08 | 0.74 | 0.66 | 0.66 | 0.56 | 0.62 | 0.61 | 0.89 | 1.27 | 0.95 |
| 0.4 | 0.28 | 0.26 | 0.24 | | 0.15 | 0.14 | 1.17 | 0.85 | 1.19 |
| 2 | 0.10 | 0.09 | 0.07 | 0.02 | 0.02 | 0.02 | 0.99 | 1.13 | 1.06 |
| 10 | | 0.03 | 0.03 | 0.01 | 0.01 | 0.01 | 1.01 | 0.99 | 0.99 |

This Table shows data of various C9orf72 oligonucleotides in knocking down C9orf72 transcripts in ALS motor neurons (only V3 transcripts). As in other "only V3 transcripts" assessments, relative-fold change of V3 in C9orf72/HPRT1 is shown.

TABLE 9B

| Activity of C9orf72 oligonucleotides | | | | | | | | | |
|---|---|---|---|---|---|---|---|---|---|
| Dose (uM) | WV-8012 | | | WV-30206 | | | WV-30208 | | |
| 0.0032 | 0.95 | 0.99 | 1.06 | 1.01 | 0.95 | 1.10 | 0.82 | 0.90 | 0.80 |
| 0.016 | | 0.92 | 0.95 | 1.06 | 0.93 | 1.01 | 0.65 | 0.67 | 0.72 |
| 0.08 | 0.69 | 0.71 | 0.73 | 0.75 | 0.81 | 0.66 | 0.60 | 0.77 | 0.96 |
| 0.4 | 0.58 | 0.67 | 0.65 | 0.66 | 0.74 | 0.78 | 0.44 | 0.64 | 0.66 |
| 2 | 0.47 | 0.53 | 0.49 | 0.71 | 0.59 | 0.62 | 0.54 | 0.46 | 0.41 |
| 10 | 0.32 | 0.33 | 0.47 | 0.38 | 0.43 | 0.46 | 0.34 | 0.31 | 0.43 |
| Dose (uM) | WV-30209 | | | WV-30210 | | | WV-30211 | | |
| 0.0032 | 0.87 | 0.83 | 0.80 | 0.98 | 0.86 | 0.99 | 0.92 | 0.99 | 0.90 |
| 0.016 | 0.71 | 0.79 | 0.79 | 0.89 | 0.85 | 0.77 | 0.80 | 0.95 | 0.85 |
| 0.08 | 0.55 | 0.48 | 0.65 | 0.77 | 0.89 | 0.82 | 0.79 | 0.88 | 0.99 |
| 0.4 | 0.51 | 0.69 | 0.50 | 0.56 | 0.61 | 0.67 | 0.67 | 0.63 | 0.64 |
| 2 | 0.39 | 0.44 | 0.44 | 0.50 | 0.58 | 0.57 | 0.46 | 0.54 | 0.38 |
| 10 | 0.18 | 0.27 | 0.24 | | 0.38 | 0.31 | 0.40 | 0.35 | 0.31 |
| Dose (uM) | WV-30212 | | | WV-30220 | | | WV-9491 | | |
| 0.0032 | 0.99 | 0.82 | 1.07 | 1.01 | 1.04 | 1.10 | | | |
| 0.016 | 0.84 | 0.87 | 0.90 | 1.06 | 0.94 | 0.95 | 0.99 | 0.95 | 1.01 |
| 0.08 | 0.82 | 0.73 | 0.90 | 0.66 | 0.99 | 1.10 | 0.91 | 1.07 | 0.88 |
| 0.4 | 0.52 | 0.71 | 0.73 | | 0.68 | 0.84 | 1.06 | 0.79 | 1.35 |
| 2 | 0.57 | 0.51 | 0.53 | 0.51 | 0.58 | 0.64 | 1.00 | 1.09 | 0.87 |
| 10 | | 0.43 | 0.41 | 0.36 | 0.41 | 0.41 | | 0.95 | 1.03 |

This Table shows data of various C9orf72 oligonucleotides in knocking down C9orf72 transcripts in ALS motor neurons (All V transcripts). Relative-fold change in C9orf72/HPRT1 is shown.

TABLE 9C

| Activity of certain oligonucleotides. | |
|---|---|
| ID | IC50 (nM) |
| WV-8012 | 151.4 |
| WV-30206 | 207.4 |
| WV-30208 | 123 |
| WV-30209 | 65.24 |
| WV-30210 | 201.7 |
| WV-30211 | 145.9 |
| WV-30212 | 90.17 |
| WV-30220 | 92.28 |
| WV-9491 | No significant reduction observed |

Various C9orf72 oligonucleotides were tested for their efficacy in knocking down C9orf72 transcripts in ALS motor neurons (V3 transcripts). Data from a set of results are presented below.

As demonstrated, at multiple oligonucleotide concentrations various oligonucleotide compositions can effectively and selectively reduce targeted transcripts, e.g., transcripts that can contain expanded repeats and be associated with various conditions, disorders or diseases (e.g., V3 transcripts).

TABLE 10A

| Activity of C9orf72 oligonucleotides | | | | | | |
|---|---|---|---|---|---|---|
| Concentration | WV-30210 | | | WV-37246 | | |
| 0.0032 | 1.19 | 0.98 | 1.03 | 1.17 | 1.16 | 0.84 |
| 0.016 | 0.84 | 0.72 | 1.08 | 1.02 | 1.33 | 0.85 |
| 0.08 | 0.75 | 0.99 | 0.94 | 0.70 | 0.78 | 0.77 |
| 0.4 | 0.45 | 0.38 | 0.39 | 0.79 | 0.76 | 0.66 |
| 2 | 0.07 | 0.07 | 0.10 | 0.22 | 0.19 | 0.23 |
| 10 | 0.01 | 0.01 | 0.02 | 0.05 | 0.05 | 0.05 |

This Table shows data of various C9orf72 oligonucleotides in knocking down C9orf72 transcripts in ALS motor neurons (only V3 transcripts). As in other "only V3 transcripts" assessments, relative-fold change of V3 in C9orf72/HPRT1 is shown.

TABLE 10B

Activity of C9orf72 oligonucleotides

| Concentration | WV-30210 | | | WV-37246 | | |
|---|---|---|---|---|---|---|
| 0.0032 | 1.21 | 1.03 | 0.98 | 1.07 | 1.04 | 1.02 |
| 0.016 | 0.96 | 0.94 | 1.03 | 0.98 | 0.97 | 1.05 |
| 0.08 | 0.84 | 0.89 | 0.86 | 1.14 | 0.87 | 1.13 |
| 0.4 | 0.82 | 0.82 | 0.75 | 0.88 | 0.94 | 0.84 |
| 2 | 0.80 | 0.50 | 0.66 | 0.74 | 0.83 | 0.64 |
| 10 | 0.34 | 0.33 | 0.50 | 0.51 | 0.39 | 0.62 |

This Table shows data of various C9orf72 oligonucleotides in knocking down C9orf72 transcripts in ALS motor neurons (All V transcripts). Relative-fold change in C9orf72/HPRT1 is shown.

TABLE 10C

Activity of certain oligonucleotides.

| ID | IC50 |
|---|---|
| WV-30210 | 318.2 nM |
| WV-37246 | 736.3 nM |

Various C9orf72 oligonucleotides were tested for their efficacy in knocking down C9orf72 transcripts in ALS motor neurons (V3 transcripts). Data from a set of results are presented below.

As demonstrated, at multiple oligonucleotide concentrations various oligonucleotide compositions can effectively and selectively reduce targeted transcripts, e.g., transcripts that can contain expanded repeats and be associated with various conditions, disorders or diseases (e.g., V3 transcripts).

Example 2. Certain In Vitro Screening Protocols

Various technologies can be utilized to assess properties and/or activities of provided technologies in accordance with the present disclosure. This example describes an in vitro screening protocol for C9orf72 oligonucleotides.

Oligonucleotides were delivered gymnotically to ALS neurons for 48 hours in 24-well plates.

RNA Extraction

RNA extraction with RNeasy Plus 96 kit (Qiagen, Waltham, Mass.) following protocol: Purification of Total RNA from Cells Using Vacuum/Spin Technology (gDNA removal is critical). For each well, total RNA was eluted in 60 ul of RNase-free water.

Reverse Transcription

Reverse transcription with High-Capacity RNA-to-cDNA™ Kit (Applied Biosystems; available from Thermofisher, Waltham, Mass.)

| | |
|---|---|
| 2X RT Buffer Mix | 9 ul |
| RNA sample | 13.5 ul |

Heat denaturation at 72° C. for 5 mins, Cool down the plate on ice for at least 2 mins.

To each well of heat denatured RNA, add:

| | |
|---|---|
| 2X RT Buffer Mix | 6 |
| 20X RT Enzyme Mix | 1.5 ul |

The final volume of the cDNA is 30 ul.

Real-Time PCR

Taqman Probes:

C9orf72 all variants: Hs00376619_m1 (FAM), Catalog #4351368 (ThermoFisher, Waltham, Mass.)

C9orf72 V3: Hs00948764_m1(FAM), Catalog #4351368 (ThermoFisher, Waltham, Mass.)

C9orf72 Exon 1a:

```
                                          (SEQ ID NO: 536)
Forward primer AGATGACGCTTGGTGTGTC

                                          (SEQ ID NO: 537)
Reverse primer TAAACCCACACCTGCTCTTG

                                          (SEQ ID NO: 538)
probe          CTGCTGCCCGGTTGCTTCTCTTT
```

C9orf72 antisense RNA/intron:

```
                                          (SEQ ID NO: 539)
Forward primer GGTCAGAGAAATGAGAGGGAAAG

                                          (SEQ ID NO: 540)
Reverse primer CGAGTGGGTGAGTGAGGA

                                          (SEQ ID NO: 541)
probe          AAATGCGTCGAGCTCTGAGGAGAG
```

Internal control: Human HPRT1 (VIC) Hs02800695_m1, Catalog #4448486 (ThermoFisher, Waltham, Mass.)

PCR Reaction:

| | |
|---|---|
| Lightcycler 480 master mix | 10 ul |
| C9 probe (FAM) | 0.5 ul |
| HPRT 1 (VIC) | 0.5 ul |
| cDNA * | up to 9 ul |
| Nuclease-free H2O | to 20 ul |

* 2 ul of cDNA for all variants probe. 9 ul of cDNA for other C9 probes.

Real-Time PCR Using Bio-Rad CFX96 Touch

Run Information:

| | |
|---|---|
| 1 | 95.0 C. for 3:00 |
| 2 | 95.0 C. for 0:10 |
| 3 | 60.0 C. for 0:30 |
| | + Plate Read |
| 4 | GOTO 2, 39 more times |
| | END |

Example 3. C9orf72 Oligonucleotide Compositions are Active and Selective in Various Assays Provided oligonucleotides and compositions were assessed in various assays to demonstrate, among other things, activities and/or selectivities.

Brief description of various assays performed:

Reporter:

Luciferase assay, as described herein. For some oligonucleotides, two numbers are given (e.g., 1.32/2.63 for WV-6408); these indicate replicate experiments.

Als Neurons:

Neuronal differentiation of iPSCs: iPSCs derived from fibroblasts from a C9orf72-associated ALS patient (female, 64 years old) were obtained from RUCDR Infinite Biologics. iPSCs were maintained as colonies on Corning Matrigel matrix (Sigma-Aldrich, St. Louis, MO) in mTeSR1 medium (STEMCELL Technologies, Vancouver, BC). Neural progenitors were produced using the STEMdiff Neural System (STEMCELL Technologies, Vancouver, BC). iPSCs were suspended in an AggreWell800 plate and grown as embryoid bodies in STEMdiff Neural Induction Medium for 5 days, with daily 75% medium changes. Embryoid bodies were harvested with a 37 μm cell strainer and plated onto Matrigel-coated plates in STEMdiff Neural Induction Medium. Medium was changed daily for 7 days, with 85-95% of embryoid bodies exhibiting neural rosettes 2 days post-plating. Rosettes were picked manually and transferred to plates coated with poly-L-ornithine and laminin in STEMdiff Neural Induction Medium (STEMCELL Technologies, Vancouver, BC). Medium was changed daily for 7 days, until cells reached 90% confluence and were considered neural progenitor cells (NPCs). NPCs were dissociated with TrypLE (Gibco, available through ThermoFisher, Waltham, Massachusetts) and passaged at a ratio of 1:2 or 1:3 on poly-L-ornithine/laminin plates in a neural maintenance medium (NMM, 70% DMEM, 30% Ham's F12, 1× B27 supplement) supplemented with growth factors (20 ng/ml FGF2, 20 ng/ml EGF, 5 μg/ml heparin). For maturation into neurons, NPCs were maintained and expanded for fewer than five passages, and at>90% confluence were passaged 1:4 onto poly-L-orinithine/laminin-coated plates in NMM supplemented with growth factors. The next day, Day 0 of differentiation, medium was changed to fresh NMM without growth factors. Differentiating neurons were maintained in NMM for 4 or more weeks, with twice weekly 50% medium changes. Cells were re-plated with TrypLE at a density of 125,000 cells/$cm^2$ as needed.

V3/intron: Knockdown (KD) of V3 RNA transcript and intron RNA transcript were measured in ALS neurons. V3 transcripts knocked down are both wild-type and repeat-containing (indicated as "Healthy allele" V3 and "Pathological allele" V3 in FIG. 1 of WO2019/032607). Note, however, that, while the present disclosure is not bound by any particular theory, the repeat-containing transcript may have a longer retention time in the nucleus and thus may be preferentially knocked down. Intron transcript is indicated by the backwards AS arrow in FIG. 1 of WO2019/032607. Two numbers indicate the V3 and intron knockdown; for example, for WV-6408, V3 was knocked down by 59% and intron by 65%.

Stability:

Stability was assayed in vitro using Mouse (Ms) brain homogenates.

TLR9:

TLR9 Reporter Assay Protocol: Induction of NF-κB (NF-κB inducible SEAP) activity was analyzed using a human TLR9 or mouse TLR9 reporter assay (HEK-Blue™ TLR9 cells, InvivoGen, San Diego, California). Oligonucleotides at a concentration of 50 μM (330 μg/mL) and 2-fold serial dilution were plated into 96-well-plates in the final volume of 20 μL in water. HEK-Blue™ TLR9 cells were added to each well at a density of $7.2\times10^4$ cells in a volume of 180 μL of HEK Blue™ detection medium. Final working concentration of oligonucleotides in the wells was 5, 2.5, 1.25, 0.625, 0.312, 0.156, 0.078, and 0.0375 μM. HEK-Blue™ TLR9 cells were incubated with oligonucleotides for 16 hours at 37° C. and 5% $CO_2$. At the end of the incubation, absorbance at 655 nM was measured by Spectramax. Water was a negative control. Positive controls were WV-2021 and ODN 2359, a CpG oligonucleotide. The results are expressed as fold change in NF-κB activation over vehicle control-treated cells. Reference: Human TLR9 Agonist Kit (InvivoGen, San Diego, California). In this assay, an oligonucleotide is considered "Clean" if no or essential no activity was detected. In some experiments, WV-8005, WV-8006, WV-8007, WV-8008, WV-8009, WV-8010, WV-8011, WV-8012 and WV-8321 showed no appreciable hTLR9 activity, though some showed small activity in mTRL9.

Complement:

In some embodiments, complement is assessed in a cynomolgus monkey serum complement activation ex vivo assay. The effects of oligonucleotides on complement activation were measured in cynomolgus monkey serum ex vivo. Serum samples from 3 individual male cynomolgus monkeys were pooled and the pool was used for the studies.

The time course of C3a production was measured by incubating oligonucleotides at a final concentration of 330 μg/mL or the water control at 37° C. in freshly thawed cynomolgus monkey serum (1:30 ratio, v/v). Specifically, 9.24 μL of 10 mg/mL stock of oligonucleotide in vehicle or vehicle alone was added to 270.76 μL of pooled serum, and the resulting mixtures were incubated at 37° C. At 0, 5, 10, and 30 minutes, 20-μL aliquots were collected and the reaction was terminated immediately by addition of 2.2 μL of 18 mg/mL EDTA.

C3a concentrations were measured using MicroVue C3a Plus Enzyme Immunoassays at a 1:3000 dilution. The results were presented as the complement split product concentration increase upon the treatment of pooled serum with oligonucleotides compared with the treatment with the vehicle control.

PD (Pharmacodynamics) (C9-BAC, icv or Intracerebroventricular injection):

PD and Efficacy were tested in: C9orf72-BAC (C9-BAC) mouse model:

The transgenic mice used for in vivo pharmacological studies have been described in O'Rourke et al. 2015 Neuron. 88(5): 892-901. Briefly, the transgenic construct was designed using a bacterial artificial chromosome (BAC) clone derived from fibroblasts of a patient with amyotrophic lateral sclerosis (ALS), carrying the human chromosome 9 open reading frame 72 gene (C9orf72) with a hexanucleotide repeat expansion (GGGGCC) in the intron between the alternatively-spliced non-coding first exons 1a and 1b (variant 3). The BAC isolated a -166 kbp sequence (~36 kbp human C9orf72 genomic sequence, with -1 10 kbp upstream and -20 kbp downstream sequences). Upon amplification of different BAC subclones, one subclone with a limited contraction to 100-1000 GGGGCC (SEQ ID NO: 542) repeats was used. The Tg(C9orf72_3) line 112 mice (JAX Stock No. 023099, Jackson Laboratories, Bar Harbor, Maine) have several tandem copies of the C9orf72_3 transgene, with each copy having between 100-1000 repeats ([GGGGCC] 100-1000)(SEQ ID NO: 542). However, only mice expressing 500 or more repeats were selected for in vivo studies used herein.

In Vivo Procedures:

For injections of oligonucleotides into the lateral ventricle, mice were anesthetized and placed on a rodent stereotaxic apparatus; they were then implanted with a stainless-steel guide cannula in one of their lateral ventricles (coordinates: −0.3 mm posterior, +1.0 mm lateral and −2.2 mm vertically from bregma), which was secured in place using dental cement. Mice were allowed a one-week recovery period prior to the injection of compounds. Typical pharmacological studies involved the injection of up to 50 g oligonucleotide in a volume of 2.5 μl on day 1, which was followed by another injection of the same amount and volume on day 8. Euthanasia was performed on day 15; the mice were deeply anesthetized with avertin and transcardially perfused with saline. Brains were rapidly removed from the skull, one hemisphere was processed for histological analyses, the other hemisphere dissected and frozen on dry ice for biochemical analyses. Similarly, spinal cord was dissected and frozen on dry ice (lumbar) or processed for histological analyses (cervical/thoracic).

Efficacy (C9-BAC): Foci:

Tissue Preparation and Histological Analyses

Hemibrains and spinal cord were drop-fixed in 4% paraformaldehyde for 24 hours, then transferred to 30% sucrose for 24-48 hours and frozen in liquid nitrogen. Serial sagittal 20-μm thick sections were cut at −18° C. in a cryostat and placed on Superfrost slides.

Efficacy (C9-BAC): PolyGP (DPR assay):

Tissue preparation for protein and PolyGP quantification:

Brain and spinal cord samples were processed using a 2-step extraction procedure; each step was followed by centrifugation at 10,000 rpm for 10 minutes at 4° C. The first step consisted of homogenizing samples in RIPA (50 mM Tris, 150 mM NaCl, 0.5% DOC, 1% NP40, 0.1% SDS and Complete™, pH 8.0). The second step consisted of re-suspension of the pellet in 5M guanidine-HCl.

PolyGP's were quantified in each pool using a Mesoscale-based assay. Briefly, the polyclonal antibody AB1358 (Millipore, available from Millipore Sigma, Billerica, Ma.) was used as both capture and detection antibody. MULTI-ARRAY 96 Sm Spot Plate Pack, SECTOR Plate was coated with 1 μl of 10 ug/ml purified anti-polyGP antibody (Millipore, AB1358, available from Millipore Sigma, Billerica, Ma.) in PBS directly on small spot overnight at 4 C. After washing 3 times with PBST (0.05% Tween-20 in PBS), the plates were blocked with MSD Blocker A Kit (R93AA-2) or 10% FBS/PBS, at room temperature for 1 hour. Poly-GP purified from HEK-293 cells (by anti-FLAG affinity purification after plasmids transfection, Genescript custom made) were serial diluted with 10% FBS/PBS and used as standard. 25 μl of standard poly-GP and samples (diluted or non-diluted) were added to each well, incubated at room temperature for 1-2 hours. After 3 washes with PBST, sulfo-tagged anti-GP (AB1358) were added 25 μl per well, and incubated at room temperature for another hour. The plates were then washed 3 times, 150 μl/well of MSD Read Buffer T (1×) (R92TC-2, MSD) was added to each well and read by MSD (MESO QUICKPLEX SQ 120) according to manufacturer's default setting.

Expression of C9orf72 protein was determined by western blotting. Briefly, proteins from RIPA extracts were size fractionated by 4-12% SDS-PAGE (Criterion gel, Bio-Rad) and transferred onto PVDF membrane. To detect C9orf72, the membrane was immunoblotted using the mouse monoclonal anti-C9orf72 antibody GT779 (1:2000; GeneTex, Irvine, California), followed by secondary DyLight conjugated antibody. Visualization was conducted using the Odyssey/Li-Cor imaging system.

Some additional abbreviations:

Cx: Cortex

HP: Hippocampus

KD: knockdown

SC: Spinal Cord

Str: Striatum

Example 4. Certain Additional Protocols

Those skilled in the art will appreciate that various technologies are available for assessing provided technologies in accordance with the present disclosure. Certain additional useful protocols for experiments are presented below.

A non-limiting example of a hybridization assay for detecting a target nucleic acid is described herein. Such an assay can be used for detecting and/or quantifying a C9orf72 oligonucleotide, or any other nucleic acid or oligonucleotide to any target, including targets which are not C9orf72.

Pharmacokinetics Studies:

Tissue preparation for oligonucleotide quantification and transcript quantification: Tissues were dissected and fresh-frozen in the pre-weighted Eppendorf tubes. Tissue weight were calculated by re-weight the tubes. 4 volume of Trizol or lysis buffer (4 M Guanidine; 0.33% N-Lauryl Sarcosine; 25 mM Sodium Citrate; 10 mM DTT) were added to one unit weight (4 μl of buffer for 1 mg tissue). Tissue lysis were done by Precellys Evolution tissue homogenizer (Bertin Technologies, Montigny-le-Bretonneux, France) until all the tissue pieces were dissolved at 4 C. 30-50 μl of tissue lysates were saved in 96 well plate for PK measurement, and rest of lysates were stored at −80 C (if it is in lysis buffer) or continue with RNA extraction (if it is in Trizol buffer).

Transcript quantification:

Hybridization Probes (IDT-DNA)

```
Capture probe:
                                   (SEQ ID NO: 543)
"C9-Intron-Cap" /5AmMC12/TGGCGAGTGG

Detection probe:
                                   (SEQ ID NO: 544)
"C9-Intron-Det": GTGAGTGAGG/3BioTEG/
```

5AmC12 is a 5'-amine with $C_{12}$ linker.

3BioTEG is a Biotinylated probe.

Maleic anhydride activated 96 well plate (Pierce 15110) was coated with 50 μl of capture probe at 500 nM in 2.5% $NaHCO_3$(Gibco, 25080-094) for 2 hours at 37 C. The plate then washed 3 times with PBST (PBS+0.1% Tween-20), blocked with 5% fat free milk-PBST at 37 C for 1 hour. Payload oligonucleotide was serial diluted into matrix. This standard together with original samples were diluted with lysis buffer (4 M Guanidine; 0.33% N-Lauryl Sarcosine; 25 mM Sodium Citrate; 10 mM DTT) so that oligonucleotide amount in all samples is less than 50 ng/ml. 20 μl of diluted samples were mixed with 180 μl of 333 nM detection probe diluted in PBST, then denatured in PCR machine (65 C, 10 min, 95 C, 15 min, 4 C ∞). 50 μl of denatured samples were distributed in blocked ELISA plate in triplicates, and incubated overnight at 4 C. After 3 washes of PBST, 1:2000 streptavidin-AP (SouthernBiotech, 7100-04) in PBST was added, 50 μl per well and incubated at room temperature for 1 hour. After extensive wash with PBST, 100 μl of AttoPhos (Promega S1000) was added, incubated at room temperature in dark for 10 min and read on plate reader (Molecular Device, M5) fluorescence channel: Ex435 nm, Em555 nm. The oligonucleotide in samples were calculated according to standard curve by 4-parameter regression.

FISH protocol for GGGGCC and GGCCCC RNA foci

Fixation:

The slides were dried at room temperature for 30 mins then fixed in 4% PFA for 20 mins. After fixation, the slides were washed for 3 times in PBS then stored at 4° C. in 70% prechilled ethanol for at least 30 min.

Pre-Hybridization:

The slides were rehydrated in FISH washing buffer (40% formamide, 2×SSC in DEPC water) for 10 min. Hybridization buffer (40% Formamide, 2×SSC, 0.1 mg/ml BSA, 0.1 g/ml dextran sulfate, 1% Vanadyl sulfate complex, 0.25 mg/ml tRNA in DEPC water) was added on slides and incubated at 55° C. for 30 min.

Preparation of the Probe:

Cy3-(GGCCCC)3 (SEQ ID NO: 545)(detecting sense repeat expansion) and Cy3-(GGGGCC)3 (SEQ ID NO: 576) (detecting antisense repeat expansion) probes were denatured at 95° C. for 10 mins. After cooling down on ice, the probes were diluted to 200 ng/ml with cold hybridization buffer.

Hybridization:

The slides were briefly washed with FISH washing buffer and diluted probes were added on the slides. The slides were incubated at 55° C. for 3 hours in a hybridization oven. After hybridization, slides were washed 3 times at 55° C. with FISH washing buffer, 15 min per wash. Then slides were briefly washed once with 1×PBS.

Neuronal nuclei immunofluorescence staining:

The slides were blocked with blocking solution (2% normal goat serum in PBS) for 1 hour. Anti-NeuN antibody (MAB377, Millipore) was diluted 1:500 in blocking solution and applied to the slides at 4° C. over night. The slides were then washed 3 times with PBS and incubate with 1:500 diluted goat anti-mouse secondary antibody with Alexa Fluor 488(Life technology) at room temperature for 1 hour. Then the slides were washed 3 times with PBS. Finally, the sides were mounted with DAPI for imaging.

Imaging and Foci Quantification:

The images were taken with RPI spinning disk confocal microscope (Zeiss) at 40× magnification. 488, CY3 and DAPI channels were collected. RNA foci were quantified with ImageJ software (NIH).

Various technologies (reagents, methods, constructions, etc.) are suitable and were used for manufacturing, characterizing, testing, etc., of various oligonucleotides. Certain such technologies are described below.

Experimenters obtained synthesis of certain phosphodiester-based and stereorandom PS-modified oligonucleotides from third party providers; such oligonucleotides may also be prepared using standard solid-phase oligonucleotide synthesis protocols. Experimenters prepared various chemically modified, chirally controlled oligonucleotides and compositions as described, and sometimes with certain modifications from preparations to preparations. Certain technologies that can be useful for chirally controlled oligonucleotide synthesis include those described in Iwamoto, N. et al. Control of phosphorothioate stereochemistry substantially increases the efficacy of antisense oligonucleotides. *Nat Biotechnol* 35, 845-851, doi:10.1038/nbt.3948 (2017); Butler, D. C. D. et al. Compounds, Compositions and Methods for Synthesis. WO2018237194 (2018); and Butler, D., Iwamoto, N., Meena, M., Svrzikapa, N., Verdine, G. L., Zlatev, I. Chiral Control. WO2014012081 (2014).

In some embodiments, NMR spectra ($^{1}$H NMR, $^{13}$C NMR and $^{31}$P NMR) were recorded with the appropriate reference on a Varian MERCURY 300, 400 or 500 NMR spectrometer or Brukar BioSpin GmbH NMR Spectrometer. ESI high-resolution mass spectra were recorded on Agilent 6230 ESI TOF.

In some embodiments, useful technologies for analyzing/characterizing certain oligonucleotides and compositions are LC-HRMS and HPLC. Certain procedures are described below as examples; those skilled in the art will appreciate that certain or all parameters may be adjusted.

Reversed-phase HPLC. 10 μL of a 5 μM solution of each oligomer was injected onto an analytical HPLC column (Poroshell 120 EC—C18, 2.7 μm, 2.1×50 mm, Agilent) using Buffer A (200 mM hexafluoroisopropanol and 8 mM triethylamine in water) and Buffer B (methanol) as eluents with a gradient of Buffer B from 5%-30% at 60° C. UV absorbance was recorded at 254 nm and 280 nm.

DNA constructs. For luciferase reporter assays, in some embodiments, experimenters introduced C9orf72 sequences into the NotI site of the psiCHECK-2 vector (Promega), which is in the middle of the 3'-UTR of the hRluc gene. C9orf72 sequences encompassed~1 Kb of DNA surrounding intron 1, including exons 1a and 1b and downstream regions of the gene.

Animals. Various animal experiments were performed in compliance with appropriate animal care and use guidelines for care and use of animals. For in vivo studies, experimenters used C9BAC transgenic mice [O'Rourke, J. G. et al. C9orf72 BAC Transgenic Mice Display Typical Pathologic Features of ALS/FTD. *Neuron* 88, 892-901, doi:10.1016/j.neuron.2015.10.027 (2015)] Tg(C9orf72_3) No. 023099, Jackson Laboratories), which have several tandem copies of the C9orf72 transgene, with each copy having between 100-1,000 repeats. For studies herein, experimenters selected mice expressing ≥500 repeats that were 10-12 weeks old. Experimenters utilized both male and female mice. For intracerebroventricular (ICV) cannulation under stereotaxic surgery, experimenters anesthetized mice (avertin) and placed them on a rodent stereotaxic apparatus; they were then implanted with a stainless-steel guide cannula in one of their lateral ventricles (coordinates: −0.3 mm posterior, +1.0 mm lateral and −2.2 mm vertically from bregma), which experimenters secured in place using dental cement. Mice were allowed a one-week recovery period.

In a dose-escalation study, experimenters administered 8 μg, 20 μg, or 50 μg of ASO in 2.5 μL on days 1 and 8, and mice were necropsied 2 weeks after the first injection. For the 2-week multi-dose study, experimenters administered 50 μg oligonucleotide in 2.5 μL on days 1 and 8, and mice were necropsied as above. For the duration of action study, experimenters assessed mice at three time points (2, 4 and 8 weeks, n=5-8 per group per timepoint) after dosing. For the single-dose duration study, experimenters injected 100 μg oligonucleotide in 2.5 μL on day 1 and assessed mice 48 hours (n=6 per group), 1 week (n=6), 2 weeks (n=6), 8 weeks (n=6) and 12 weeks (n=6) after dosing. At necropsy, mice were transcardially perfused with saline under avertin anesthesia. Experimenters rapidly removed brains from the skull; experimenters processed one hemisphere for histological analyses (drop-fixed in 10% formalin) and the other, experimenters dissected into cortex, hippocampus, striatum and cerebellum and froze on dry ice for biochemical analyses. Similarly, experimenters dissected spinal cord and froze it on dry ice or processed it for histological analyses.

Cellular models. In some embodiments, oligonucleotides and/or compositions were assessed using cellular models. Experimenters obtained Cos-7 cells from ATCC. iPSCs derived from patient fibroblasts came from a C9orf72-associated female patient with ALS (64 years old, RUCDR Infinite Biologics). Experimenters maintained iPSCs as colonies on Corning Matrigel matrix (Millipore Sigma) in mTeSR1 medium (STEMCELL Technologies). Neural progenitors were produced in STEMdiff Neural System (STEMCELL Technologies). iPSCs were suspended in an AggreWell800 plate and allowed to grow as embryoid bodies in STEMdiff Neural Induction Medium for 5 days, with daily 75% medium changes. Experimenters harvested embryoid bodies with a 37 μm cell strainer and plated them onto Matrigel-coated plates in STEMdiff Neural Induction Medium, which was changed daily for 7 days, with 85-95% of embryoid bodies exhibiting neural rosettes 2-days post-plating. Rosettes were manually selected and transferred to plates coated with poly-L-ornithine and laminin in STEMdiff Neural Induction Medium (STEMCELL Technologies). Experimenters changed the medium daily until cells reached 90% confluence (7 days) and were considered neural progenitor cells (NPCs). Experimenters dissociated NPCs with TrypLE (ThermoFisher) and passaged them at a ratio of 1:2 or 1:3 on poly-L-ornithine/laminin plates in a neural maintenance medium (NMM; 70% DMEM, 30% Ham's F12, 1×B27 supplement) supplemented with growth factors (20 ng/mL FGF2, 20 ng/mL EGF, 5 μg/mL heparin). For maturation into neurons, experimenters maintained NPCs and expanded them for <5 passages, and at>90% confluence experimenters passaged them 1:4 onto poly-L-orinithine/laminin-coated plates in NMM supplemented with growth factors. The next day, Day 0 of differentiation, experimenters changed the medium to fresh NMM without growth factors. Differentiating neurons were maintained in NMM for ≥4 weeks, with twice weekly 50%-medium changes. Cells were re-plated with TrypLE at a density of 125,000 cells/$cm^2$ as needed. Motor neurons derived from the same patient iPSC line were differentiated by BrainXell and seeded with their standard protocol. C9-ALS primary fibroblasts were generated from skin biopsies from two unrelated C9 carriers, each carrying more than 1,000 repeats. Briefly, experimenters cut the biopsied skin into small pieces, which were then cultured with DMEM supplemented with 15% FBS to allow fibroblast expansion. Experimenters generated primary cortical neurons from E15.5 C9-BAC transgenic embryos. O'Rourke, J. G. et al. C9orf72 BAC Transgenic Mice Display Typical Pathologic Features of ALS/FTD. Neuron 88, 892-901, doi:10.1016/j.neuron.2015.10.027 (2015). Experimenters dissected cortical tissue from each embryo on ice-cold Hank's Balanced Salt Solution (ThermoScientific). Pooled tissue was minced and digested with 0.05% Trypsin-EDTA (Life Technology) at 37° C. for 12 min. Digestion was halted by addition of 10% FBS/DMEM. Cells were triturated, resuspended in neurobasal media supplemented with Glutamax (ThermoScientific), 2% penicillin/streptomyocin and B27 supplement (ThermoScientific) and seeded at $0.5\times10^6$ cells/well in 6-well plates pre-coated with poly-ornithine (Sigma). iCell Neurons (iNeurons) are commercially available from Cellular Dynamics International. iPSC-derived motor neurons are commercially available from BrainXell. Experimenters calculated $IC_{50}$s in full dose-response assays (10, 2.5, 0.625, 0.16, 0.04 and 0.001 μM) in ALS motor neurons. Briefly, experimenters delivered oligonucleotides gymnotically and evaluated transcript levels as described above after 1 week. Experimenters fit data using non-linear regression for variable slope (4 parameters) using GraphPad software.

Southern blot. Genomic DNA was isolated from ALS iPSCs, ALS motor neurons and C9 BAC transgenic mice using Gentra Puregene Tissue kits (Qiagen). 10 μg DNA was digested overnight with AluI and DdeI at 37° C. and then separated by electrophoresis on a 0.6% agarose gel, transferred to positively charged nylon membrane (Roche Applied Science), cross-linked by exposure to UV light, and hybridized overnight at 55° C. with digoxigenin-labeled $(G_2C_4)_5$ DNA probe in hybridization buffer (EasyHyb, Roche). The probe was detected using anti-digoxigenin antibody (Catalog No. 11093274910, Roche) and CDP-Star reagent as recommended by the manufacturer.

Thermal denaturation (Tm). Equimolar amounts of surrogate RNA (5'-GGUGGCGAGUGGGUGAGUGAGGAG) (SEQ ID NO: 546), U1 mimic (5'-AUACUUACCUGG) (SEQ ID NO: 547) or ASO were dissolved in 1×PBS to obtain a final concentration of 1 μM of each strand. Duplex samples were then annealed by heating at 90° C., followed by slow cooling to 4° C. and storage at 4° C. UV absorbance at 254 nm was recorded at intervals of 30 see as the temperature was raised from 5 or 15° C. to 95° C. at a rate of +0.5° C. per min, using a Cary Series UV-Vis spectrophotometer (Agilent Technologies). Absorbance was plotted against the temperature and the Tm values were calculated by taking the first derivative of each curve.

RNase H assays. For certain RNase H assays, experimenters incubated heteroduplexes with human RNase HC (prepared as described in Iwamoto, N. et al. Control of phosphorothioate stereochemistry substantially increases the efficacy of antisense oligonucleotides. Nat Biotechnol 35, 845-851, doi: 10.1038/nbt.3948 (2017)) at 37° C. Experimenters prepared duplexes by mixing equimolar (20 μM each) solutions of ASO and/or U1 mimic and RNA. Each reaction contained 5.6 μM ASO-RNA, U1 mimic-RNA, or ASO-U1 mimic-RNA heterocomplexes in RNase H buffer (75 mM KCl, 50 mM Tris-HCl, 3 mM $MgCl_2$, 10 mM dithiothreitol, pH=8.3) in a reaction volume of 90 μL. The pre-mixtures were incubated at 37° C. for 10 minutes prior to the addition of enzyme+U1 mimic, enzyme+ASO, or enzyme alone with final concentration ratios 2,000:1, 1,000:1, or 500:1 substrate: RNase HC. Experimenters quenched the reactions at 5, 10, 15, 30, 45 and 60 min using 7.0 μL of 500 mM EDTA disodium solution in water. For the 0 min-time point, experimenters added EDTA to the reaction mixture before enzyme. Experimenters recorded UV absorbance at 254 nm and 280 nm of each reaction after injection onto an Agilent Poroshell 120 EC-C18 column (2.7 μm, 2.1×50 mm) at 70° C. using a gradient of Buffer A (200 mM HFIP and 8 mM triethylamine) and Buffer B (A+methanol, 50:50, v/v). Experimenters integrated the peak areas from the chromatograms, corresponding to full-length RNA oligomer, normalized them compared to the antisense strand. Experimenters plotted the percentage RNA remaining, with the 0 min-time point defined as 100%, to show relative rates of RNA cleavage (n=3). Experimenters analyzed the data with 2-way ANOVA. Error bars indicate s.d.

Duplex analysis for RNase H assays. In some embodiments, experimenters mixed equimolar solutions of ASO, RNA and/or U1 to prepare duplexes at a final concentration of 20 μM. Experimenters prepared three complexes: ASO+RNA, RNA+U1, and ASO+RNA+U1. The mixtures were heated to 90° C. for 2 min and allowed to cool slowly to room temperature for more than 4 h. The D1000 ladder and sample buffer (7 mM KCl, 20 mL Phosphate buffer, 20 mM Guanidine-HCl, 80 mM NaCl, 20 mM acetate) were equilibrated at room temperature for 30 min. Samples for analysis were prepared by mixing 1:1 with D1000 sample buffer. The samples and ladder were mixed thoroughly using the IKA vortex at 2,000 rpm for 1 min. Samples were centrifuged to ensure the full volume settled to the bottom of the tube. Experimenters analyzed duplexes on 4200 Agilent TapeStation using High Sensitivity D1000 screentape (sizing range 35-1,000 bp) according to manufacturer's protocol.

Thermal denaturation (Tm). Equimolar amounts of RNA and each ASO were dissolved in 1×PBS to obtain a final concentration of 1 μM of each strand. Duplex samples were then annealed by heating at 90° C., followed by slow cooling to 4° C. and storage at 4° C. UV absorbance at 254 nm was recorded at intervals of 30 see as the temperature was raised from 15° C. to 95° C. at a rate of +0.5° C. per min, using a Cary Series UV-Vis spectrophotometer (Agilent Technologies). Absorbance was plotted against the temperature and the Tm values were calculated by taking the first derivative of each curve.

Luciferase screening assay. Experimenters generated a luciferase construct containing sequences from the human C9orf72 gene (158-900 base pairs) in the 3'-UTR of the renilla luciferase gene in psiCHECK2 vector. An ASO targeting this sequence should decrease renilla luciferase signal without affecting the firefly luciferase signal. Experimenters normalized renilla to firefly luciferase signals to compare the relative activity of ASOs versus a non-targeting control ASO (WV-993). Experimenters delivered ASOs (15 or 30 nM) and the luciferase reporter constructs (20 ng) by transfection with Lipofectamine 2000 into Cos-7 cells. The firefly and renilla luciferase signals were quantified with a plate reader (Molecular Devices Spectramax M5) 48-hours post-transfection. Experimenters performed three biological replicates per experiment.

ASO delivery to cellular models. Human ALS cortical neurons were maintained in NMM for at least 4 weeks in 24-well plates (250,000 cells per well) and treated with 1 μM of the indicated ASO gymnotically (with no transfection reagent) for one week. Primary neurons from C9-BAC transgenic mice were treated with ASO gymnotically at the indicated dose 5 days after culture and collected 15 days after treatment. Human ALS motor neurons were seeded in 12-well plates (280,000 cells per well) from frozen stocks and treated gymnotically on day 7 and harvested on day 14. 50 μL of a growth factor cocktail containing 10 ng BDNF, 10 ng of GDNF, and 1 ng of TGF-β1 were added on day 10 without changing the medium. C9-patient derived fibroblasts were plated in 10 cm dishes, and the ASOs were transfected using Lipofectamine RNAiMax Reagent (ThermoScientific). The cells were harvested 72 hours after treatment.

C9orf72 transcript quantification assays. In human C9-ALS cortical neurons and motor neurons, total RNA was extracted using Trizol (Invitrogen) according to manufacturer's protocol. For each sample, total RNA was eluted in 29.5 μL of RNase-free water followed by the addition of 2 μL (4U) of DNase I (New England Biolabs, M0303L) and 3.5 μL of 10× reaction buffer. Samples were incubated at 37° C. for 15 min for gDNA removal. EDTA was added to 5 mM final concentration, and DNase I was heat inactivated at 75° C. for 10 min. RNA was reverse transcribed with High-Capacity RNA-to-cDNA™ Kit (Applied Biosystems) according to manufacturer instructions. Experimenters used the following Tagman probes: Hs00376619_m1 (FAM) (Catalog #4351368, ThermoFisher) for C9orf72 All Transcripts (common on V1, V2 and V3); Hs00948764_m1 (FAM) (Catalog #4351368, ThermoFisher) for C9orf72 V3 transcripts; Hs02800695_ml for human HPRT1 transcripts (Catalog #4448486, ThermoFisher). qPCR reaction: 3 min at 95° C., 40 cycles of 10 sec at 95° C. and 30 sec at 60° C. In C9-patient-derived fibroblasts and C9-BAC primary cell lines, total RNA was isolated using Trizol (ThermoScientific) and subsequently treated with DNase I (Qiagen). One μg of total RNA was reverse transcribed into cDNA using random hexamers and MultiScribe reverse transcriptase (ThermoScientific) following the manufacturer's instructions. Quantitative PCR was performed on a StepOnePlus Real-Time PCR (qRT-PCR) system using SYBR Green Master Mix (Applied Biosystems) and 0.2 μM of forward and reverse primers as described. Tran, H. et al. Differential Toxicity of Nuclear RNA Foci versus Dipeptide Repeat Proteins in a *Drosophila* Model of C90RF72 FTD/ALS. Neuron 87, 1207-1214, doi:10.1016/j.neuron.2015.09.015 (2015). For Hprt detection, experimenters used the following primers: forward 5'-CAAACTTTGCTTTCCCTGGTT (SEQ ID NO: 548), reverse 5'-TGGCCTGTATCCAACACTTC (SEQ ID NO: 549). Ct values for each sample and transcript were normalized to Hprt. The 2exp (−ΔΔCt) method was used to determine the relative expression of each transcript.

Tissue processing for transcript analyses by PCR and ASO quantification by hybridization ELISA. Experimenters dissected and fresh-froze tissues in pre-weighed Eppendorf tubes. Experimenters calculated tissue weight by re-weighing. For lysis, experimenters added four volumes of Trizol or lysis buffer (4 M Guanidine; 0.33% N-Lauryl Sarcosine; 25 mM Sodium Citrate; 10 mM DTT) to 1-unit weight (4 μL of buffer for 1 mg tissue) and homogenized tissue at 4° C. using Precellys until all the tissue pieces were dissolved. 30-50 μL of tissue lysates were saved in 96-well plates for pharmacokinetic (PK) measurement. The remaining lysates were either stored at −80° C. (when in lysis buffer) or used for RNA extraction (when in Trizol).

Experimenters utilized the following probes to selectively quantify the ASOs used in this study by hybridization ELISA: Capture probe: "C9-Intron-Cap"/5AmMC12/TGGCGAGTGG (SEQ ID NO: 543); Detection probe: "C9-Intron-Det": GTGAGTGAGG/3BioTEG/(SEQ ID NO: 544). Experimenters coated maleic anhydride-activated 96-well plate (Pierce 15110) with 50 μL of capture probe at 500 nM in 2.5% $NaHCO_3$ (Gibco, 25080-094) for 2 hours at 370 C. The plate was then washed 3 times with PBST (PBS+0.1% Tween-20), blocked with 5% fat free milk-PBST at 370 C for 1 hour. Payload ASO was serially diluted into matrix. This standard together with original samples were diluted with lysis buffer (4 M Guanidine; 0.33% N-Lauryl Sarcosine; 25 mM Sodium Citrate; 10 mM DTT) so that the ASO amount in all samples was less than 50 ng/mL. 20 μL of diluted samples were mixed with 180 μL of 333 nM detection probe diluted in PBST, then denatured (650 C, 10 min, 950 C, 15 min, 4° C. ∞). 50 μL of the denatured samples were distributed in blocked ELISA plates in triplicates, and incubated overnight at 4° C. After 3 washes with PBST, 50 μL of 1:2,000 streptavidin-AP (SouthernBiotech, 7100-04) in PBST was added, 50 μL per well and incubated at room temperature for 1 hour. After extensive washes with PBST, 100 μL of AttoPhos (Promega S1000) was added, incubated at room temperature in the dark for 10 min and read on the plate reader (Molecular Device, M5) fluorescence channel: Ex435 nm, Em555 nm. The ASO in samples were calculated according to standard curve by 4-parameter regression. The lower limit of detection was 1.25 μg ASO per gram of tissue.

Stability in mouse brain homogenate. Experimenters determined the stability of the ASOs in mouse brain homogenate by adding 5 μL of each oligo solution (200 μM) to 45 μL of mouse brain homogenate (prepared in-house, 20 mg/mL). Experimenters incubated each reaction at 37° C. while shaking at 400 rpm. Experimenters used a 20-mer DNA sequence as a positive control to assess the performance of the assay. Because it does not incorporate chemical modifications to protect against nuclease degradation, DNA degrades rapidly. Experimenters terminated reactions, which experimenters performed in triplicate, at each time point (0-5 days) by adding 50 μL of Stop buffer (2.5% IGEPAL, 0.5 M NaCl, 10 mM EDTA, 50 mM Tris, pH=8.0) followed by vortexing. Experimenters than added 20 μL of internal standard (50 μM: 5'-GCGTTTGCTCTTCTTC-UUGCGTTTTUU-3')(SEQ ID NO: 550), 250 μL of 2% ammonium hydroxide and 100 μL of phenol:chloroform: isoamyl alcohol (25:24:1) to each tube. After vortexing, experimenters spun each reaction at 17,000 rpm at room temperature for 30 minutes and repeated the above extraction protocol with the aqueous layer using 150 μL of chloroform. After transferring the new aqueous layer to a new tube, experimenters dried and then reconstituted each sample with water in a volume of 100 μL. 2 μL of the mixture was injected to Q Exactive mass spectrometer (Thermo Fisher Scientific) using Agilent Poroshell column (120, EC-C18 2.7 μm, 2.1×50 mm) and mobile Phase A (400 mM HFIP, 15 mM TEA in water) and Mobile Phase B (Methanol). Experimenters used Xcalibur™ (version 4.0.27.10, Thermo Fisher Scientific) for data capture and to calculate peak areas and peak area ratios of analytes to the internal standard. Reduction in analyte amount was used to evaluate the extent of in vitro stability. Experimenters calculated mean and standard deviation from three technical replicates.

Fluorescence in situ hybridization (FISH) detection of RNA foci. Experimenters performed FISH as previously described. Tran, H. et al. Differential Toxicity of Nuclear RNA Foci versus Dipeptide Repeat Proteins in a *Drosophila* Model of C90RF72 FTD/ALS. Neuron 87, 1207-1214, doi:10.1016/j.neuron.2015.09.015 (2015). Experimenters used a 5'-end, Cy3-conjugated $(G_2C4)_{3.4}$ probe to detect sense-repeat expansions and a Cy3-conjugated $(G_4C2)_3$ probe to detecting antisense repeat expansions (probes from Integrated DNA Technologies). Probes were hybridized at 55° C. in hybridization buffer containing 40% formamide, 2×SSC, 0.1% Tween-20 and salmon sperm DNA. Samples were then washed twice in pre-warmed buffer and in stringency wash buffer (0.2×SSC, 0.1% Tween20) at 55° C. Samples were then mounted in Prolong Gold Antifade reagent with DAPI (ThermoFisher). Confocal images were taken with a Leica TCS SP5 II laser scanning confocal microscope and processed with Leica LAS AF software. Experimenters used 1:500 dilution of primary antibody (Anti-NeuN antibody, MAB377, Millipore) and 1:500 diluted goat anti-mouse secondary antibody with Alexa Fluor 488 (Life Technologies). Experimenters used an RPI spinning disk confocal microscope (Zeiss) at 40× magnification and collected images at 488 nm, Cy3 and DAPI channels. The stacked images from red (Cy3), green (488) and blue (DAPI) were merged using Z Project function. DAPI channel was used to make Nuclei mask with Convert to Mask function with a set threshold (set for each experiment, constant between samples).

Quantification of RNA foci. Nuclei are identified with the mask and the area of each nucleus is measured. The green channel is stained with NeuN as a marker of neurons. Based on the observation that NeuN stains bigger nuclei in anterior horn region, cells with nuclei bigger than 78 $\mu m^2$ are identified as motor neurons for high-throughput foci counting. The Cy3 channel was used to identify foci, Find Maximum function was used to identify single points with a set noise tolerance (30 to 90, set for each experiment, constant between samples). Within each nucleus, the integrated density was recorded and divided by 255 as the number of foci in this nucleus. A probabilistic model was used to calculate the posterior of foci/cell; foci count and cell count were modeled with the poisson distribution using the function rpois in the R::Stats package. Posterior samples were obtained using a Monte Carlo method. Inference was performed on the posteriors by subtracting the PBS (i.e., control) posterior from the posterior for each treatment, including itself. If the 95% highest posterior density for the compound treatments did not cover zero, then these treatments were considered credibly different from PBS at the 95% confidence level.

PolyGP quantification using the MSD platform. Brain and spinal cord samples were homogenized in 4 volumes RIPA (50 mM Tris, 150 mM NaCl, 0.5% DOC, 1% NP40, 0.1% SDS and Complete protease inhibitor, pH 8.0) by shaking in a Precellys instrument with 1.4 mm zirconium oxide beads. Samples were centrifuged at 10,000 rpm for 10 min at 4° C., and total protein concentration of clarified lysate was determined with 600 nm Protein Assay Reagent (Pierce). MSD Small-Spot plates were coated with 1 μL of a 10 μg/mL solution of a polyclonal capture antibody (rabbit anti-polyGP; AB1358, Millipore) and incubated at 4° C. overnight. The next day, plates were washed with PBST, blocked with a 10% FBS/PBST solution for 1 hr at room temperature, and then washed with PBST and incubated with 50-120 μg of brain lysate (diluted 1:4 or 1:5 into 10% FBS/PBST) for 2-4 hrs. Plates were washed with PBST and incubated with Sulfo-tag-conjugated detection antibody (rabbit anti-polyGP; AB1358, Millipore) for 1 hr at room temperature. Plates were washed with PBST and incubated with 150 μL of MSD Read Buffer T 1× and read in an MSD QuickPlex SQ 120 plate reader. A standard curve of recombinant purified polyGPx30 was prepared in a matrix of wild-type mouse cortex or spinal cord homogenate. After subtracting the background signal measured from empty-wells, a linear best-fit regression line for the standard curve was used to interpolate the concentration of polyGP per microgram of tissue.

Western blots. Experimenters quantified the expression of C9orf72 protein by western blotting. Briefly, proteins from RIPA extracts were size fractionated with precast 4-12% SDS-PAGE (Criterion gels, Bio-Rad) and transferred onto PVDF membrane. To detect C9orf72, experimenters used the mouse monoclonal anti-C9orf72 antibody GT779 (1:2, 000, GeneTex Inc.) and the secondary DyLight-conjugated antibody. Experimenters visualized and quantified blots using the Odyssey imaging system (LI-COR Biosciences). Full-sized blots for 2-week data and for 8-week data were analyzed.

Tissue preparation. Brain and spinal cord samples were processed using a 2-step extraction procedure; each step was followed by centrifugation at 10,000 rpm for 10 min at 4° C. Experimenters first homogenized samples in RIPA (50 mM Tris, 150 mM NaCl, 0.5% DOC, 1% NP40, 0.1% SDS and Complete, pH 8.0) buffer, and then re-suspended the pellet in 5M guanidine-HCl. Experimenters quantified polyGPs in each pool with Meso Scale Discovery assay using MSD Blocker A Kit (R93AA-2) (Meso Scale Diagnostics) with Sulfo-tag-conjugated anti-polyGP. Experimenters used the polyclonal anti-GP antibody AB1358 (Millipore Sigma) as both the capture and detection antibody. Assays were read by MSD (MESO QUICKPLEX SQ 120) according to manufacturer instructions (Meso Scale Diagnostics). Experimenters quantified polyGP in comparison to a standard curve based on affinity-purified Flag-polyGP (GenScript) diluted into wild-type mouse brain RIPA lysate.

Pharmacokinetic (PK) Analysis. The mean tissue concentration-time profiles of C9orf72-631 were modeled using a one-compartment model with a first-order absorption rate and a first-order elimination rate. The tissue concentration was described by:

$$C_t=\text{Dose}*Ka/V*(Ka-Ke)*(\exp(-Ka*t)-\exp(-Ke*t)$$

where $C_t$ represents the tissue concentration, Dose represents administered amount, Ka represents absorption rate, V represents volume distribution, Ke represents elimination rate, and t represents time post-dose. The terminal half-life in tissues was derived as ln2/Ke. A 2-compartment model was also tested but appeared to be over-parameterized. All below the limit of quantification values were set to zero for the analysis. The model parameters were estimated using Phoenix@ WinNonlin® 8.1 software program (Certara, Princeton, NJ, USA).

ViewRNA ISH Assay.

Experimenters adapted ViewRNA ISH Tissue 1-Plex Assay (ThermoFisher Scientific, Cat #QVT0051) for detection of ASOs in situ. Briefly, after cessation of the mouse, the hemibrain and spinal cord biopsies were fixed in 10% neutral buffered formalin overnight at 2 to 8° C., processed and embedded in paraffin. Paraffin sections (5 μm thickness) were prepared and stored at room temperature until use. After baking slides at 60° C. for at least 1 h, dewaxing was performed by incubation of sections in xylene (VWR Chemicals) for 10 min and rinsed in 100% ethanol (ThermoFisher Scientific). After air drying slides for at least 30 min at room temperature, a hydrophobic barrier was created and dried before continuing with ViewRNA ISH standard protocol. Rehydrated slides with pre-heated target retrieval reagent for heat pretreatment for 10 min at 95° C., temperature as determined, followed by protease digestion (Protease QF 1:100 in 1×PBS, pre-warmed) at 37° C. for 15 min. Treated slides were rinsed in 1×PBS with agitation and then treated with QuantiGene ViewRNA miRNA probe sets for WVE-3972-01, Peptidylprolyl Isomerase B (PPiB) (positive control), and/or dihydrodipicolinate reductase (dapB) (negative control) (ThermoFisher Scientific) diluted to 12.5 nM in pre-warmed Probe Set Diluent QT (300 μL per section) for 2 h at 40° C. Rinsed slides could be stored at room temperature for up to 24 h. For signal amplification and detection, slides were incubated in working PreAmp1 QF solution diluted at 1:200 in prewarmed Amplifier Diluent QF for 30 minutes at 40° C.; and rinsed in wash buffer with agitation, followed by incubation in working Amp1 QF solution diluted at 1:200 in prewarmed Amplifier Diluent QF for 20 minutes at 40° C. and rinsed in wash buffer with agitation, which was followed by incubation in Label Probe-AP working solution (diluted 1:1000 in Label Probe Diluent QF) for 20 min at 40° C. and rinsed in wash buffer with agitation. AP-Enhancer Solution was added and incubated for 5 minutes at room temperature before adding Fast Red Substrate, which was incubated for 30 minutes at 40° C. to develop red color deposit. Afterwards, the nucleic acid DNA was counterstained with Hematoxylin and/or Hoechst 33342 dye. The slides were mounted with ProLong Gold Antifade mounting medium and covered with a thin glass coverslip. For each hemibrain/spinal cord cross-section, the representative digital images were generated using a Zeiss Axio Observer microscope (Zeiss, Thornwood, NY, USA) under brightfield or fluorescent field.

In vivo visualization was performed and distribution of oligonucleotides in the Brain and Spinal Cord tissues was assessed using ViewRNA probes designed to detect WV-30210 on tissue sections of 8 weeks treatment group. It was confirmed that WV-30210 can be broadly distributed throughout the tissues and enriched in neurons.

Statistical analyses. Unless otherwise indicated, in vivo data were analyzed by a one-way analysis of variance (ANOVA) followed by Student-Newman-Keuls post-hoc analyses using SigmaPlot 13.0.

Quantitation of C9orf72 Protein Expression using a Capillary Western Immunoassay (Wes).

An assessment using Was is described below as an example. Materials:

- RIPA lysis and extraction buffer (Thermo Scientific, Cat #89901)
- Pierce Protease Inhibitor Mini Tablets (Life technologies, Cat #A32953)
- Bertin Technologies Precellys Evolution Tissue Homogenizer
- Pierce BCA Reagent A and B (Fisher Scientific, Cat #PI23228 and Cat #PI23224)
- Pierce Bovine Serum Albumin standards (Thermo Scientific, Cat #23208)
- Wes system (ProteinSimple, Cat #004-600)
- Jess/Wes Separation Kit 12-230 kDa (ProteinSimple, Cat #SM-W004)
- Anti-C9orf72 antibody, mouse (GeneTex, Cat #GTX632041)
- Anti-HPRT antibody, rabbit (Novus Biologicals, Cat #NBPI-33527)
- Anti-Rabbit Detection Module (ProteinSimple, Cat #DM-001)
- Anti-Mouse Detection Module (ProteinSimple, Cat #DM-002)

Method:

Protein lysates from spinal cord and cortex tissue were prepared by adding 10× weight in volume of RIPA buffer with tablets and a scoop of lysis beads. The samples were then homogenized for 2-4 cycles (3×20 seconds; 6800 rpm) on the Precellys Evolution Tissue Homogenizer and spun down for 10 min at 14000 rpm at 4 degrees. The supernatants were carefully transferred into new tubes. To measure total protein concentration, 20 μl of a 15× dilution of the lysates was quantified using the Pierce BCA protein assay kit with BSA standards according to the manufacturer's protocol. Lysates were normalized to 0.5 ug/uL in 0.1× sample buffer. C9orf72 quantitation was performed on a Wes system, according to the manufacturer's instructions using a 12-230 kDa Separation Module, the Anti-Rabbit Detection Module and the Anti-Mouse Detection Module. Lysates were mixed with Fluorescent Master Mix and denatured at 95° C. for 5 minutes. The samples, blocking reagent (antibody diluent), primary antibodies (1:100 Anti-C9orf72, 1:250 Anti-HPRT in antibody diluent), HRP-conjugated secondary antibodies (ready to use anti-mouse combined with ready to use anti-rabbit in 1:1 ratio) plus chemiluminescent substrate were pipetted into the plate. Instrument default settings were used: stacking and separation at 475 V for 30 min; blocking reagent for 5 min, primary and secondary antibody both for 30 min; Luminol/peroxide chemiluminescence detection for ~15 min (exposures of 1-2-4-8-16-32-64-128-512s). The chemiluminescence produced is automatically quantified (area under the curve or "AUC" of detected peaks) by the Compass software and is displayed as an electropherogram or as a virtual blot-like image. The calculated concentrations were analyzed by dividing the AUC of the C9orf72 peak by the AUC of the HPRT peak. Then the PBS-treated group of animals was averaged, and all data points were divided by this value.

Example 5. C9orf72 Oligonucleotide Compositions are Active In Vivo

Various technologies including animal models are available for assessing provided technologies in accordance with the present disclosure. In some embodiments, provided technologies are assessed in mouse models. For example, a pharmacodynamics study was performed to assess certain C9orf72 oligonucleotide compositions on knockdown of C9orf72 products.

C9orf72 oligonucleotides tested were: WV-8012, WV-23741, WV-26633, WV-30206, and WV-28478. Negative controls were PBS (phosphate-buffered saline).

Animals used: Male and Female C9-BAC mice, 2-3 month-old, 6 groups, 38 mice. Table 11A illustrates dosing design.

TABLE 11A

Design of in vivo study

| Group | Test Article | Dose | Dosing Regimen | Dose Volume | Total # mice per group* | Necropsy Timepoint |
|---|---|---|---|---|---|---|
| 1 | PBS | NA | ICV, day 0, day 7 | 2.5 uL | 5 | 2 weeks |
| 2 | WV-8012 | 50/50 ug | ICV, day 0, day 7 | 2.5 uL | 5 | 2 weeks |
| 3 | WV-23741 | 50/50 ug | ICV, day 0, day 7 | 2.5 uL | 7 | 2 weeks |
| 4 | WV-26633 | 50/50 ug | ICV, day 0, day 7 | 2.5 uL | 7 | 2 weeks |
| 5 | WV-30206 | 50/50 ug | ICV, day 0, day 7 | 2.5 uL | 7 | 2 weeks |
| 6 | WV-28478 | 50/50 ug | ICV, day 0, day 7 | 2.5 uL | 7 | 2 weeks |

ICV cannulation was performed. ICV injection of PBS or 50 ug of oligonucleotide on Day 1 in awake animals. 2nd dose of PBS or 50 ug of oligonucleotide on Day 7. Dose volume, 2.5 uL. Necropsy 2 weeks after first injection.

Necropsy:

Timepoints:2 weeks

Tissues:

One hemibrain in formalin (Histology, Paraffin).

Cortex (CX), hippocampus, cerebellum, and upper half of the lumbar spinal cord (SC) flash freeze, in weighed tubes (PK/PD).

Lower half of the lumbar spinal cord, flash freeze in unweighted tubes (DPR).

Cervical and thoracic spinal cord, formalin (RNA Foci quantification, OCT frozen blocks)

Results are shown in Tables 11B-111.

Transcripts were analyzed from the spinal cord (SC) (All transcripts Table 11B, V3 Table 11C) and cerebral cortex (CX) (All transcripts Table 11D, V3 Table 11E). Poly GP levels in all dose groups were analyzed from cerebral cortex (CX) (Table 11F), and spinal cord (SC) (Table 11G). C9orf72 protein were analyzed from spinal cord (SC) (Table 11H), and cerebral cortex (CX) (Table 11I). The protocol of C9orf72 protein analysis is disclosed in Example 4 (Quantitation of C9orf72 Protein Expression using the Capillary Western Immunoassay (Wes)).

TABLE 11B

Transcripts analysis, spinal cord (SC), all transcripts

| PBS | WV-8012 | WV-23741 | WV-26633 | WV-30206 | WV-28478 |
|---|---|---|---|---|---|
| 1.1263 | 1.022 | 0.743 | 0.656 | | 0.830 |
| 1.3581 | 0.934 | 0.689 | 0.525 | | 0.748 |
| 0.9604 | 0.629 | 0.748 | | 0.583 | 0.994 |
| 0.7587 | 0.825 | 0.442 | 0.738 | 0.477 | 1.396 |
| 0.7964 | 0.536 | 0.647 | 0.764 | 0.515 | 0.718 |
| | | 0.436 | 0.515 | 0.504 | 1.015 |
| | | 0.759 | 0.522 | 0.454 | 0.775 |

TABLE 11C

Transcripts analysis, spinal cord (SC), V3

| PBS | WV-8012 | WV-23741 | WV-26633 | WV-30206 | WV-28478 |
|---|---|---|---|---|---|
| 0.999 | 0.287 | 0.297 | 0.466 | | 0.248 |
| 1.172 | 0.308 | 0.349 | 0.334 | | 0.607 |
| 0.959 | 0.233 | 0.182 | | 0.255 | 0.212 |
| 0.870 | 0.323 | 0.138 | 0.299 | 0.303 | 0.230 |
| 0.999 | 0.291 | 0.262 | 0.507 | 0.240 | 0.525 |

TABLE 11C-continued

Transcripts analysis, spinal cord (SC), V3

| PBS | WV-8012 | WV-23741 | WV-26633 | WV-30206 | WV-28478 |
|---|---|---|---|---|---|
| | | 0.216 | 0.361 | 0.374 | 0.301 |
| | | 0.312 | 0.236 | 0.182 | 0.260 |

TABLE 11D

Transcripts analysis, cerebral cortex (CX), all transcripts

| PBS | WV-8012 | WV-23741 | WV-26633 | WV-30206 | WV-28478 |
|---|---|---|---|---|---|
| 0.8727 | 0.604 | 0.776 | 0.922 | 0.648 | 0.776 |
| 0.9289 | 0.776 | 0.671 | 0.948 | 0.942 | 0.680 |
| 1.1436 | 0.639 | 0.675 | 0.809 | 0.484 | 0.621 |
| 1.0523 | 0.685 | 0.803 | 0.588 | 0.694 | 0.714 |
| 1.0025 | 0.661 | 0.699 | 0.724 | 0.680 | 0.699 |
| | | 0.739 | 0.714 | 0.666 | 0.760 |
| | | 0.584 | 0.661 | 0.481 | 0.704 |

TABLE 11E

Transcripts analysis, cerebral cortex (CX), V3

| PBS | WV-8012 | WV-23741 | WV-26633 | WV-30206 | WV-28478 |
|---|---|---|---|---|---|
| 1.063 | 0.582 | 0.806 | 0.876 | 0.659 | 0.547 |
| 1.034 | 0.711 | 0.641 | 1.034 | 0.711 | 1.063 |
| 1.155 | 0.641 | 0.570 | 0.706 | 0.558 | 0.637 |
| 0.789 | 0.637 | 0.778 | 0.752 | 0.852 | 0.594 |
| 0.958 | 0.532 | 0.811 | 0.664 | 0.716 | 0.562 |
| | | 0.768 | 0.870 | 0.602 | 0.692 |
| | | 0.687 | 0.882 | 0.414 | 0.650 |

TABLE 11F

| Poly GP levels (in all doses), cerebral cortex (CX) | | | | | |
|---|---|---|---|---|---|
| PBS | WV-8012 | WV-23741 | WV-26633 | WV-30206 | WV-28748 |
| 2.1830 | 0.680 | 1.239 | 1.119 | 1.387 | 0.690 |
| 2.3560 | 0.735 | 1.179 | 1.188 | 0.499 | 1.250 |
| 3.8870 | 0.894 | 0.882 | 1.344 | 0.703 | 0.481 |
| 0.9520 | 1.007 | 0.927 | 0.180 | 1.420 | 0.458 |
| 1.1490 | 0.662 | 0.789 | 0.910 | 0.518 | 0.622 |
| | | 0.913 | 0.896 | 0.543 | 0.889 |
| | | 1.162 | 1.641 | 1.134 | 1.220 |

TABLE 11G

| Poly GP levels (in all doses), spinal cord (SC) | | | | | |
|---|---|---|---|---|---|
| PBS | WV-8012 | WV-23741 | WV-26633 | WV-30206 | WV-28748 |
| 0.968 | 0.000 | 0.000 | 0.284 | 0.482 | 0.454 |
| 2.868 | 0.000 | 0.198 | 0.502 | 0.000 | 0.361 |
| 1.445 | 0.000 | 0.645 | 1.117 | 0.000 | 0.000 |
| 2.165 | 0.130 | 0.416 | 0.088 | 0.000 | 0.000 |
| 1.345 | 0.210 | 0.193 | 0.382 | 0.000 | 0.100 |
| | | 0.173 | 0.373 | 0.287 | 0.469 |
| | | 0.000 | 0.181 | 0.121 | 0.262 |

TABLE 11H

| C9orf72 protein analysis spinal cord (SC) | | | | | |
|---|---|---|---|---|---|
| PBS | WV-8012 | WV-23741 | WV-26633 | WV-30206 | WV-28478 |
| 1.1419 | 1.158 | 0.973 | 0.793 | 0.536 | 0.966 |
| 0.6477 | 1.178 | 0.945 | 0.988 | 0.617 | 1.058 |
| 0.9952 | 1.013 | 0.584 | 0.764 | 0.932 | 1.353 |
| 1.0976 | 0.756 | 0.846 | 0.865 | 0.812 | 1.287 |
| 1.1176 | 0.975 | 1.007 | 0.642 | 0.555 | 0.699 |
| | | 0.686 | 0.712 | 0.418 | 0.806 |
| | | 1.051 | 0.539 | 0.867 | 1.208 |

TABLE 11I

| C9orf72 protein analysis cerebral cortex (CX) | | | | | |
|---|---|---|---|---|---|
| PBS | WV-8012 | WV-23741 | WV-26633 | WV-30206 | WV-28478 |
| 0.983 | 1.041 | 0.944 | 0.957 | 0.829 | 1.148 |
| 0.959 | 1.023 | 1.071 | 1.082 | 0.996 | 1.055 |
| 1.088 | 1.138 | 1.002 | 0.946 | 0.879 | 1.095 |
| 0.894 | 1.089 | 1.007 | 0.984 | 0.972 | 1.022 |
| 1.077 | 1.148 | 1.092 | 1.096 | 0.701 | 1.062 |
| | | 0.982 | 1.020 | 0.989 | 1.062 |
| | | 1.008 | 0.822 | 1.064 | 0.964 |

As demonstrated herein, multiple C9orf72 oligonucleotide compositions can knock down C9orf72 products associated with conditions, disorders or diseases.

Example 6. C9orf72 Oligonucleotide Compositions are Active In Vivo

In another example, a pharmacodynamics study was performed to assess certain C9orf72 oligonucleotide compositions on knockdown of C9orf72 products.

C9orf72 oligonucleotides tested were: WV-30206, WV-30210, WV-30211, and WV-30212. Negative controls were PBS (phosphate-buffered saline).

Animals used: Male and Female C9-BAC mice, 2-4 month-old, 15 groups, 102 mice. Table 12A illustrates dosing design.

TABLE 12A

| Design of in vivo study | | | | | | |
|---|---|---|---|---|---|---|
| Group | Test Article | Dose | Dosing Regimen | Dose Volume | Total # mice per group* | Necropsy Timepoint |
| 1 | PBS | NA | ICV, day 0, day 7 | 2.5 ul | 6 | 8 weeks |
| 2 | WV-30206 | 50/50 ug | ICV, day 0, day 7 | 2.5 ul | 7 | 8 weeks |
| 3 | WV-30210 | 50/50 ug | ICV, day 0, day 7 | 2.5 ul | 7 | 8 weeks |
| 4 | WV-30211 | 50/50 ug | ICV, day 0, day 7 | 2.5 ul | 7 | 8 weeks |
| 5 | WV-30212 | 50/50 ug | ICV, day 0, day 7 | 2.5 ul | 7 | 8 weeks |
| 6 | PBS | NA | ICV, day 0, day 7 | 2.5 ul | 6 | 4 weeks |
| 7 | WV-30206 | 50/50 ug | ICV, day 0, day 7 | 2.5 ul | 7 | 4 weeks |
| 8 | WV-30210 | 50/50 ug | ICV, day 0, day 7 | 2.5 ul | 7 | 4 weeks |
| 9 | WV-30211 | 50/50 ug | ICV, day 0, day 7 | 2.5 ul | 7 | 4 weeks |
| 10 | WV-30212 | 50/50 ug | ICV, day 0, day 7 | 2.5 ul | 7 | 4 weeks |
| 11 | PBS | NA | ICV, day 0, day 7 | 2.5 ul | 6 | 2 weeks |
| 12 | WV-30206 | 50/50 ug | ICV, day 0, day 7 | 2.5 ul | 7 | 2 weeks |
| 13 | WV-30210 | 50/50 ug | ICV, day 0, day 7 | 2.5 ul | 7 | 2 weeks |
| 14 | WV-30211 | 50/50 ug | ICV, day 0, day 7 | 2.5 ul | 7 | 2 weeks |
| 15 | WV-30212 | 50/50 ug | ICV, day 0, day 7 | 2.5 ul | 7 | 2 weeks |

ICV cannulation was performed. ICV injection of PBS or 50 ug of oligonucleotide on Day 1 in awake animals. 2nd dose of PBS or 50 ug of oligonucleotide on Day 7. Dose volume, 2.5 uL. Necropsy 2 weeks, 4 weeks and 8 weeks after first injection.

Necropsy:

Timepoints:2 weeks, 4 weeks and 8 weeks

Tissues:

One hemibrain in formalin (Histology, Paraffin).

Cortex (CX), hippocampus, cerebellum, liver, kidney and upper half of the lumbar spinal cord (SC) flash freeze, in weighted tubes (PK/PD).

Lower half of the lumbar spinal cord, flash freeze in unweighted tubes (DPR).

Cervical and thoracic spinal cord, formalin (RNA Foci quantification, OCT frozen blocks).

Results are shown in Tables 12B-121.

Transcripts were analyzed from the spinal cord (SC) (All transcripts Table 12B, V3 Table 12C) and cerebral cortex (CX) (All transcripts Table 12D, V3 Table 12E). Poly GP levels in all dose groups were analyzed from cerebral cortex (CX) (Table 12F), and spinal cord (SC) (Table 12G). C9orf72 protein were analyzed from spinal cord (SC) (Table 12H), and cerebral cortex (CX) (Table 12I). The protocol of C9orf72 protein analysis is disclosed in Example 4 (Quantitation of C9orf72 Protein Expression using the Capillary Western Immunoassay (Wes)).

TABLE 12B

Transcripts analysis, spinal cord (SC), all transcripts

| PBS 2 wk | WV-30206 2 wk | WV-30210 2 wk | WV-30211 2 wk | WV-30212 2 wk | PBS 4 wk | WV-30206 4 wk | WV-30210 4 wk | WV-30211 4 wk | WV-30212 4 wk |
|---|---|---|---|---|---|---|---|---|---|
| 0.90 | 0.64 | 0.56 | 0.58 | 0.51 | 0.98 | 0.63 | 0.58 | 0.51 | 0.56 |
| 1.17 | 0.71 | 0.49 | 0.41 | 0.58 | 0.93 | 0.98 | 0.65 | 0.59 | 0.51 |
| 1.05 | 0.70 | 0.53 | 0.55 | 0.53 | 1.06 | 0.59 | 0.42 | 0.62 | 0.53 |
| 0.94 | 0.83 | 0.65 | 0.46 | 0.50 | 0.98 | | 0.57 | 0.78 | 0.57 |
| 0.90 | 0.72 | 0.52 | 0.50 | 0.47 | 1.09 | 0.79 | 0.43 | 0.62 | 0.72 |
| 1.04 | 0.83 | 0.49 | 0.50 | 0.50 | 0.96 | 0.39 | 0.42 | 0.54 | 0.51 |
| | 0.74 | 0.69 | 0.51 | 0.62 | | 0.87 | 0.81 | 0.49 | 0.54 |

| PBS 8 wk | WV-30206 8 wk | WV-30210 8 wk | WV-30211 8 wk | WV-30212 8 wk |
|---|---|---|---|---|
| 0.97 | 0.84 | 0.68 | 0.56 | 0.37 |
| 1.11 | 1.03 | 0.55 | 0.49 | 0.50 |
| 0.91 | 0.88 | 0.41 | 0.42 | 0.58 |
| 1.01 | 1.09 | 0.63 | 0.57 | 0.51 |
| 1.06 | 0.98 | 0.45 | 0.65 | 0.47 |
| 0.93 | 1.01 | 0.47 | 0.72 | 0.71 |
| | 1.00 | 0.39 | 0.51 | 0.43 |

TABLE 12C

Transcripts analysis, spinal cord (SC), V3

| PBS 2 wk | WV-30206 2 wk | WV-30210 2 wk | WV-30211 2 wk | WV-30212 2 wk | PBS 4 wk | WV-30206 4 wk | WV-30210 4 wk | WV-30211 4 wk | WV-30212 4 wk |
|---|---|---|---|---|---|---|---|---|---|
| 0.86 | 0.73 | 0.60 | 0.63 | 0.47 | 0.86 | 0.59 | 0.42 | 0.47 | 0.53 |
| 1.24 | 0.76 | 0.47 | 0.19 | 0.53 | 1.11 | 0.91 | 0.60 | 0.55 | 0.41 |
| 0.84 | 0.71 | 0.47 | 0.59 | 0.47 | 0.95 | 0.64 | 0.34 | 0.59 | 0.41 |
| 0.99 | 0.82 | 0.71 | 0.39 | 0.45 | 1.03 | | 0.45 | 0.67 | 0.47 |
| 0.90 | 0.68 | 0.48 | 0.52 | 0.58 | 0.99 | 0.88 | 0.17 | 0.73 | 0.75 |
| 1.17 | 0.99 | 0.44 | 0.57 | 0.50 | 1.06 | 0.27 | 0.27 | 0.37 | 0.43 |
| | 0.90 | 0.66 | 0.43 | 0.74 | | 0.78 | 0.76 | 0.52 | 0.39 |

| PBS 8 wk | WV-30206 8 wk | WV-30210 8 wk | WV-30211 8 wk | WV-30212 8 wk |
|---|---|---|---|---|
| 0.94 | 0.72 | 0.47 | 0.47 | 0.09 |
| 1.07 | 0.92 | 0.41 | 0.33 | 0.28 |
| 1.01 | 0.80 | 0.13 | 0.16 | 0.33 |
| 0.91 | 0.96 | 0.46 | 0.42 | 0.31 |
| 1.22 | 1.00 | 0.32 | 0.34 | 0.33 |
| 0.86 | 0.83 | 0.19 | 0.59 | 0.63 |
| | 0.94 | 0.09 | 0.26 | 0.13 |

TABLE 12D

| Transcripts analysis, cerebral cortex (CX), all transcripts | | | | | | | | | |
|---|---|---|---|---|---|---|---|---|---|
| PBS 2 wk | WV-30206 2 wk | WV-30210 2 wk | WV-30211 2 wk | WV-30212 2 wk | PBS 4 wk | WV-30206 4 wk | WV-30210 4 wk | WV-30211 4 wk | WV-30212 4 wk |
| 0.90 | 0.64 | 0.56 | 0.58 | 0.51 | 0.98 | 0.63 | 0.58 | 0.51 | 0.56 |
| 1.17 | 0.71 | 0.49 | 0.41 | 0.58 | 0.93 | 0.98 | 0.65 | 0.59 | 0.51 |
| 1.05 | 0.70 | 0.53 | 0.55 | 0.53 | 1.06 | 0.59 | 0.42 | 0.62 | 0.53 |
| 0.94 | 0.83 | 0.65 | 0.46 | 0.50 | 0.98 | | 0.57 | 0.78 | 0.57 |
| 0.90 | 0.72 | 0.52 | 0.50 | 0.47 | 1.09 | 0.79 | 0.43 | 0.62 | 0.72 |
| 1.04 | 0.83 | 0.49 | 0.50 | 0.50 | 0.96 | 0.39 | 0.42 | 0.54 | 0.51 |
| | 0.74 | 0.69 | 0.51 | 0.62 | | 0.87 | 0.81 | 0.49 | 0.54 |

| PBS 8 wk | WV-30206 8 wk | WV-30210 8 wk | WV-30211 8 wk | WV-30212 8 wk |
|---|---|---|---|---|
| 0.97 | 0.84 | 0.68 | 0.56 | 0.37 |
| 1.11 | 1.03 | 0.55 | 0.49 | 0.50 |
| 0.91 | 0.88 | 0.41 | 0.42 | 0.58 |
| 1.01 | 1.09 | 0.63 | 0.57 | 0.51 |
| 1.06 | 0.98 | 0.45 | 0.65 | 0.47 |
| 0.93 | 1.01 | 0.47 | 0.72 | 0.71 |
| | 1.00 | 0.39 | 0.51 | 0.43 |

TABLE 12E

| Transcripts analysis, cerebral cortex (CX), V3 | | | | | | | | | |
|---|---|---|---|---|---|---|---|---|---|
| PBS 2 wk | WV-30206 2 wk | WV-30210 2 wk | WV-30211 2 wk | WV-30212 2 wk | PBS 4 wk | WV-30206 4 wk | WV-30210 4 wk | WV-30211 4 wk | WV-30212 4 wk |
| 0.86 | 0.73 | 0.60 | 0.63 | 0.47 | 0.86 | 0.59 | 0.42 | 0.47 | 0.53 |
| 1.24 | 0.76 | 0.47 | 0.19 | 0.53 | 1.11 | 0.91 | 0.60 | 0.55 | 0.41 |
| 0.84 | 0.71 | 0.47 | 0.59 | 0.47 | 0.95 | 0.64 | 0.34 | 0.59 | 0.41 |
| 0.99 | 0.82 | 0.71 | 0.39 | 0.45 | 1.03 | | 0.45 | 0.67 | 0.47 |
| 0.90 | 0.68 | 0.48 | 0.52 | 0.58 | 0.99 | 0.88 | 0.17 | 0.73 | 0.75 |
| 1.17 | 0.99 | 0.44 | 0.57 | 0.50 | 1.06 | 0.27 | 0.27 | 0.37 | 0.43 |
| | 0.90 | 0.66 | 0.43 | 0.74 | | 0.78 | 0.76 | 0.52 | 0.39 |

| PBS 8 wk | WV-30206 8 wk | WV-30210 8 wk | WV-30211 8 wk | WV-30212 8 wk |
|---|---|---|---|---|
| 0.94 | 0.72 | 0.47 | 0.47 | 0.09 |
| 1.07 | 0.92 | 0.41 | 0.33 | 0.28 |
| 1.01 | 0.80 | 0.13 | 0.16 | 0.33 |
| 0.91 | 0.96 | 0.46 | 0.42 | 0.31 |
| 1.22 | 1.00 | 0.32 | 0.34 | 0.33 |
| 0.86 | 0.83 | 0.19 | 0.59 | 0.63 |
| | 0.94 | 0.09 | 0.26 | 0.13 |

TABLE 12F

| Poly GP levels (in all doses), cerebral cortex (CX) | | | | | | | | |
|---|---|---|---|---|---|---|---|---|
| PBS 2 wk | PBS 4 wk | PBS 8 wk | WV-30206 2 wk | WV-30206 4 wk | WV-30206 8 wk | WV-30210 2 wk | WV-30210 4 wk | WV-30210 8 wk |
| 1.10 | | 0.66 | 0.52 | | 0.44 | 0.25 | | 0.10 |
| | 0.22 | 0.71 | 0.27 | 0.18 | 0.63 | 0.09 | 0.42 | 0.00 |
| 1.08 | 0.57 | 0.91 | 0.60 | 0.09 | 0.68 | 0.00 | 0.00 | 0.25 |
| 0.89 | 2.06 | 1.16 | 0.73 | 0.17 | 0.46 | 0.18 | 0.10 | 0.00 |
| 0.97 | 1.05 | 0.59 | 0.93 | 0.41 | 0.34 | 0.09 | 0.00 | 0.00 |
| 0.96 | 1.10 | 1.98 | 0.69 | 0.46 | 0.48 | 0.10 | 0.00 | 0.00 |
| | | | 0.45 | 0.34 | 0.69 | 0.50 | 0.29 | 0.00 |

TABLE 12F-continued

| Poly GP levels (in all doses), cerebral cortex (CX) | | | | | | | | |
|---|---|---|---|---|---|---|---|---|
| PBS 2 wk | PBS 4 wk | PBS 8 wk | WV-30211 2 wk | WV-30211 4 wk | WV-30211 8 wk | WV-30212 2 wk | WV-30212 4 wk | WV-30212 8 wk |
| 1.10 | | 0.66 | 0.57 | | 0.00 | 0.28 | | 0.00 |
| | 0.22 | 0.71 | 0.16 | 0.00 | 0.09 | 0.24 | 0.00 | 0.05 |
| 1.08 | 0.57 | 0.91 | 0.36 | 0.77 | 0.00 | 0.26 | 0.09 | 0.05 |
| 0.89 | 2.06 | 1.16 | 2.25 | 0.57 | 0.10 | 0.26 | 0.00 | 0.06 |
| 0.97 | 1.05 | 0.59 | 0.27 | 0.80 | 0.19 | 0.27 | 0.35 | 0.00 |
| 0.96 | 1.10 | 1.98 | 0.38 | 0.16 | 0.47 | 0.42 | 0.34 | 0.08 |
| | | | 0.11 | 0.24 | 0.00 | 0.45 | 0.13 | 0.00 |

TABLE 12G

| Poly GP levels (in all doses), spinal cord (SC) | | | | | | | | |
|---|---|---|---|---|---|---|---|---|
| PBS 2 wk | PBS 4 wk | PBS 8 wk | WV-30206 2 wk | WV-30206 4 wk | WV-30206 8 wk | WV-30210 2 wk | WV-30210 4 wk | WV-30210 8 wk |
| 1.10 | 0.81 | | 0.00 | 0.00 | 0.00 | 0.00 | 0.00 | 0.00 |
| 0.57 | 0.94 | 0.88 | 0.00 | | 0.13 | 0.00 | 0.23 | 0.00 |
| 1.22 | 1.79 | 1.40 | 0.00 | 0.00 | 0.00 | 0.00 | 0.00 | 0.00 |
| 1.12 | 0.67 | 0.84 | 0.24 | 0.00 | 0.00 | 0.00 | 0.00 | 0.00 |
| 1.08 | 1.11 | 1.00 | 0.00 | 0.00 | 0.26 | 0.00 | 0.00 | 0.00 |
| 0.90 | 0.68 | 0.89 | 0.23 | 0.00 | 0.00 | 0.00 | 0.00 | 0.00 |
| | | | 0.00 | 0.00 | 0.00 | 0.00 | 0.20 | 0.00 |
| PBS 2 wk | PBS 4 wk | PBS 8 wk | WV-30211 2 wk | WV-30211 4 wk | WV-30211 8 wk | WV-30212 2 wk | WV-30212 4 wk | WV-30212 8 wk |
| 1.10 | 0.81 | | 0.23 | 0.00 | 0.00 | 0.00 | 0.00 | 0.00 |
| 0.57 | 0.94 | 0.88 | 0.00 | 0.00 | 0.00 | 0.00 | 0.00 | 0.00 |
| 1.22 | 1.79 | 1.40 | 0.00 | 1.06 | | 0.00 | 0.00 | 0.00 |
| 1.12 | 0.67 | 0.84 | 1.79 | 0.24 | 0.00 | 0.00 | 0.00 | 0.00 |
| 1.08 | 1.11 | 1.00 | 0.30 | 0.23 | 0.13 | 0.00 | 0.00 | 0.00 |
| 0.90 | 0.68 | 0.89 | 0.35 | | 0.00 | 0.30 | 0.00 | 0.00 |
| | | | 0.00 | 0.00 | 0.00 | 0.23 | 0.00 | 0.00 |

TABLE 12H

| C9orf72 protein analysis spinal cord (SC) | | | | |
|---|---|---|---|---|
| PBS | WV-30206 | WV-30210 | WV-30211 | WV-30212 |
| 0.77 | 1.02 | 0.90 | 1.18 | 1.01 |
| 1.07 | 1.02 | 0.95 | 1.05 | 1.14 |
| 1.09 | 0.77 | 1.03 | | 0.89 |
| 1.02 | 1.03 | 0.73 | 1.04 | 1.15 |
| 1.13 | 1.07 | 1.05 | 0.92 | 0.99 |
| 0.92 | 1.00 | 1.06 | 0.99 | 1.16 |
| | 0.85 | 0.89 | 1.08 | 0.88 |

TABLE 12I

| C9orf72 protein analysis cerebral cortex (CX) | | | | |
|---|---|---|---|---|
| PBS | WV-30206 | WV-30210 | WV-30211 | WV-30212 |
| 1.01 | 0.95 | 1.11 | 1.02 | 0.93 |
| 1.13 | 1.12 | 0.97 | 1.14 | 0.97 |
| 0.85 | 1.04 | 0.93 | 0.91 | 1.10 |
| 0.78 | 1.05 | 1.00 | 0.98 | 0.93 |
| 1.08 | 0.88 | 0.87 | 0.96 | 0.99 |

TABLE 12I-continued

| C9orf72 protein analysis cerebral cortex (CX) | | | | |
|---|---|---|---|---|
| PBS | WV-30206 | WV-30210 | WV-30211 | WV-30212 |
| 1.15 | 1.08 | 0.74 | 1.11 | 1.06 |
| | 1.08 | 0.90 | 0.96 | 0.97 |

As demonstrated herein, multiple C9orf72 oligonucleotide compositions can knock down C9orf72 products associated with conditions, disorders or diseases.

Example 7. C9orf72 Oligonucleotide Compositions are Active In Vivo

In another example, a pharmacodynamics study was performed to assess certain C9orf72 oligonucleotide compositions on knockdown of C9orf72 products.

C9orf72 oligonucleotides tested were WV-8012 and WV-21446. Negative controls were PBS (phosphate-buffered saline).

Animals used: Male and Female C9-BAC mice, 2 month-old. Table 13A illustrates dosing design.

TABLE 13A

| Design of in vivo study | | | | | | |
|---|---|---|---|---|---|---|
| Group | Test Article | Dose | Dosing Regimen | Dose Volume | Total # mice per group* | Necropsy Timepoint |
| 1 | PBS | NA | ICV, day 0 | 2.5 ml | 5 | 2 weeks |
| 2 | WV-8012 | 25 µg | ICV, day 0 | 2.5 ml | 4 | 2 weeks |
| 3 | WV-8012 | 50 µg | ICV, day 0 | 2.5 ml | 5 | 2 weeks |
| 4 | WV-8012 | 100 µg | ICV, day 0 | 2.5 ml | 5 | 2 weeks |
| 5 | WV-21446 | 25 µg | ICV, day 0 | 2.5 ml | 7 | 2 weeks |
| 6 | WV-21446 | 50 µg | ICV, day 0 | 2.5 ml | 7 | 2 weeks |
| 7 | WV-21446 | 100 µg | ICV, day 0 | 2.5 ml | 7 | 2 weeks |
| 8 | NA | NA | NA | NA | 4 | 2 weeks |

Necropsy:

Timepoints:2 weeks

Tissues:

One hemibrain in formalin (Histology, Paraffin).

Cortex, hippocampus, cerebellum, and half of the lumbar spinal cord flash freeze, in weighted tubes (PK/PD).

The other half of the lumbar spinal cord, flash freeze in unweighted tubes (DPR).

Cervical and theoretic spinal cord, formialin (RNA Foci quantification, OCT frozen blocks). Results are shown in Tables 13B3-13G.

Transcripts were analyzed from the cerebral cortex (CX) (All transcripts Table 13B, V3 Table 13C) and spinal cord (SC) (All transcripts Table 13D, V3 Table 13E).

TABLE 13B

| Transcripts analysis, cerebral cortex (CX), all transcripts | | | | | | |
|---|---|---|---|---|---|---|
| PBS | WV-8012 (25 ug) | WV-8012 (50 ug) | WV-8012 (100 ug) | WV-21446 (25 ug) | WV-21446 (50 ug) | WV-21446 (100 ug) |
| 1.04 | 1.02 | 0.87 | 0.89 | 0.79 | 0.85 | 0.68 |
| 1.07 | 0.86 | 0.81 | 0.77 | 0.91 | 0.81 | 0.76 |
| 0.87 | 0.89 | 1.00 | 0.83 | 0.89 | 0.96 | 0.78 |
| 1.02 | 0.89 | 0.97 | 0.93 | 0.86 | 0.91 | |
| | | | 0.75 | 1.17 | 0.77 | 0.76 |
| | | | | 0.92 | 0.61 | 0.66 |
| | | | | 1.06 | 0.56 | 0.69 |

TABLE 13C

| Transcripts analysis, cerebral cortex (CX), V3 | | | | | | |
|---|---|---|---|---|---|---|
| PBS | WV-8012 (25 ug) | WV-8012 (50 ug) | WV-8012 (100 ug) | WV-21446 (25 ug) | WV-21446 (50 ug) | WV-21446 (100 ug) |
| 0.97 | 0.89 | 0.91 | 0.74 | 0.59 | 0.47 | 0.39 |
| 0.94 | 0.96 | 0.85 | 0.80 | 1.12 | 0.85 | 0.77 |
| 0.97 | 1.10 | 1.05 | 0.93 | 1.05 | 0.98 | 0.90 |
| 1.11 | 0.92 | 1.05 | 0.87 | 0.95 | 0.89 | |
| | | | 0.73 | 1.18 | 0.72 | 0.47 |
| | | | | 1.03 | 0.64 | 0.44 |
| | | | | 0.98 | 0.46 | 0.61 |

TABLE 13D

| Transcripts analysis, spinal cord (SC), all transcripts | | | | | | |
|---|---|---|---|---|---|---|
| PBS | WV-8012 (25 ug) | WV-8012 (50 ug) | WV-8012 (100 ug) | WV-21446 (25 ug) | WV-21446 (50 ug) | WV-21446 (100 ug) |
| 1.05 | 0.66 | 1.07 | 0.99 | 0.83 | 0.93 | 1.11 |
| 1.07 | 0.73 | 1.05 | 0.76 | 0.79 | 1.03 | 0.90 |
| 0.79 | 0.76 | 0.86 | 1.26 | 1.28 | 0.75 | 0.83 |
| 1.10 | 0.83 | 0.72 | 0.74 | 0.68 | 0.91 | |
| | | | 0.93 | 0.79 | 0.79 | 0.94 |
| | | | | 0.58 | 0.79 | 0.83 |
| | | | | 0.61 | 0.70 | 0.86 |

TABLE 13E

| Transcripts analysis, spinal cord (SC), V3 transcripts | | | | | | |
|---|---|---|---|---|---|---|
| PBS | WV-8012 (25 ug) | WV-8012 (50 ug) | WV-8012 (100 ug) | WV-21446 (25 ug) | WV-21446 (50 ug) | WV-21446 (100 ug) |
| 1.08 | 0.54 | 1.23 | 1.04 | 0.22 | 0.90 | 0.16 |
| 1.16 | 0.60 | 0.45 | 0.33 | 0.24 | 0.20 | 0.13 |
| 0.71 | 0.52 | 0.90 | 1.20 | 1.33 | 0.59 | 0.22 |
| 1.05 | 0.68 | 0.35 | 0.45 | 0.39 | 0.50 | |
| | | | 0.36 | 0.96 | 0.13 | 0.16 |
| | | | | 0.27 | 0.13 | 0.15 |
| | | | | 0.24 | 0.14 | 0.14 |

CNS tissue exposure of WV-8012 and WV-21446 were assessed. Dose dependent increase were observed in brain and spinal cord tissues (2 week necropsy). Mean tissue concentrations: WV-8012: Brain (0.4-2.1 µg/g), Spinal Cord: (1.5-2.7 µg/g); and WV-21446: Brain (0.4-2.9 µg/g), Spinal Cord: (1.8-6.3 µg/g).

TABLE 13F

| Tissue Exposure, brain (ug oligonucleotide/g tissue) | | | | |
|---|---|---|---|---|
| PBS | WT | WV-8012 25 µg | WV-8012 50 µg | WV-8012 100 µg |
| 0.00 | 0.00 | 0.40 | 1.11 | 2.97 |
| 0.40 | 0.67 | 0.95 | 2.16 | 1.41 |
| 0.00 | 0.40 | 0.74 | 0.42 | 0.61 |
| 0.36 | 0.35 | 0.64 | 1.15 | 0.72 |
| | | | | 4.77 |
| PBS | WT | WV-21446 25 µg | WV-21446 50 µg | WV-21446 100 µg |
| 0.00 | 0.00 | 0.64 | 10.76 | 6.29 |
| 0.00 | 0.40 | 0.00 | 0.46 | 0.78 |
| 0.00 | 0.00 | 0.00 | 0.32 | 0.39 |

TABLE 13F-continued

| Tissue Exposure, brain (ug oligonucleotide/g tissue) | | | | |
|---|---|---|---|---|
| 0.00 | 0.00 | 0.38 | 0.44 | 0.00 |
| | | 0.00 | 1.16 | 3.92 |
| | | 0.00 | 1.15 | 7.33 |
| | | 0.00 | 3.04 | 1.41 |

TABLE 13G

| Tissue Exposure, spinal cord (ug oligonucleotide/g tissue) | | | | |
|---|---|---|---|---|
| PBS | WT | WV-8012 25 μg | WV-8012 50 μg | WV-8012 100 μg |
| 0.00 | 0.32 | 2.42 | 0.39 | 0.55 |
| 0.00 | 0.00 | 0.70 | 5.42 | 5.32 |
| 0.00 | 0.00 | 1.21 | 0.74 | 0.81 |
| 0.00 | 0.00 | 1.78 | 2.99 | 2.57 |
| | | | | 4.26 |
| PBS | WT | WV-21446 25 μg | WV-21446 50 μg | WV-21446 100 μg |
| 0.00 | 0.00 | 1.72 | 0.34 | 13.34 |
| 0.00 | 0.00 | 4.48 | 4.16 | 6.44 |

TABLE 13G-continued

| Tissue Exposure, spinal cord (ug oligonucleotide/g tissue) | | | | |
|---|---|---|---|---|
| 0.00 | 0.00 | 0.00 | 0.68 | 2.64 |
| 0.00 | 0.00 | 2.04 | 0.66 | 0.12 |
| | | 0.32 | 1.92 | 8.58 |
| | | 1.54 | 5.12 | 6.30 |
| | | 2.20 | 2.00 | 6.40 |

As demonstrated herein, C9orf72 oligonucleotide compositions can be delivered and can knock down C9orf72 products associated with conditions, disorders or diseases.

Example 8. C9orf72 Oligonucleotide Compositions are Active In Vivo

In another example, a pharmacodynamics study was performed to assess certain C9orf72 oligonucleotide compositions on knockdown of C9orf72 products.

C9orf72 oligonucleotides tested were WV-30210 and WV-30212. Negative controls were PBS (phosphate-buffered saline).

Animals used: Male and Female C9-BAC mice, 2-4 month-old. Table 14A illustrates dosing design.

TABLE 14A

| Design of in vivo study | | | | | | |
|---|---|---|---|---|---|---|
| Group | Test Article | Dose | Dosing Regimen | Dose Volume | Total # mice per group* | Necropsy Timepoint |
| 1 | PBS | NA | ICV, day 0, day 7 | 2.5 ml | 8 | 6 weeks |
| 2 | WV-30210 | 50/50 ug | ICV, day 0, day 7 | 2.5 ml | 8 | 6 weeks |
| 3 | WV-30210 | 15/15 ug | ICV, day 0, day 7 | 2.5 ml | 8 | 6 weeks |
| 4 | WV-30210 | 5/5 ug | ICV, day 0, day 7 | 2.5 ml | 8 | 6 weeks |
| 5 | WV-30210 | 1.5/1.5 ug | ICV, day 0, day 7 | 2.5 ml | 8 | 6 weeks |
| 6 | WV-30212 | 50/50 ug | ICV, day 0, day 7 | 2.5 ml | 8 | 6 weeks |
| 7 | WV-30212 | 15/15 ug | ICV, day 0, day 7 | 2.5 ml | 8 | 6 weeks |
| 8 | WV-30212 | 5/5 ug | ICV, day 0, day 7 | 2.5 ml | 8 | 6 weeks |
| 9 | WV-30212 | 1.5/1.5 ug | ICV, day 0, day 7 | 2.5 ml | 8 | 6 weeks |

Timepoints:6 weeks.

Tissues from each animal:

Cortex: combine cortex from two hemibrains flash freeze into one weighted tube.

Spinal cord: separate upper and lower lumbar spinal cord flash freeze into two tubes, upper lumbar in weighted tubes (RNAPD and Trizol PK), lower for in unweighted tubes (DPR). Cervical+theoretic spinal cord, flash freeze in weighted tubes (Proteinase K PK).

Hippocampus and Cerebellum: separate hippocampus and cerebellum from two hemibrains flash freeze into two unweighted tubes.

Results are shown in Tables 14B-14G.

Transcripts were analyzed from the cerebral cortex (CX) (All transcripts Table 14B, V3 Table 14C, tissue exposure Table 14D) and spinal cord (SC) (All transcripts Table 14E, V3 Table 14F, tissue exposure Table 14G).

TABLE 14B

| Transcripts analysis, cerebral cortex (CX), all transcripts | | | | | | | | |
|---|---|---|---|---|---|---|---|---|
| PBS | WV-30210 50, 50 | WV-30210 15, 15 | WV-30210 5, 5 | WV-30210 1.5, 1.5 | WV-30212 50, 50 | WV-30212 15, 15 | WV-30212 5, 5 | WV-30212 1.5, 1.5 |
| 0.68 | 0.45 | 0.77 | 0.86 | 1.08 | 0.44 | 0.55 | 0.80 | 0.71 |
| 0.90 | 0.49 | 0.81 | 1.14 | 1.04 | 0.69 | 0.83 | 0.64 | 0.49 |

TABLE 14B-continued

| Transcripts analysis, cerebral cortex (CX), all transcripts | | | | | | | | |
|---|---|---|---|---|---|---|---|---|
| PBS | WV-30210 50, 50 | WV-30210 15, 15 | WV-30210 5, 5 | WV-30210 1.5, 1.5 | WV-30212 50, 50 | WV-30212 15, 15 | WV-30212 5, 5 | WV-30212 1.5, 1.5 |
| 1.22 | | 0.59 | 1.00 | 1.20 | 0.57 | 0.62 | 0.67 | 0.65 |
| 1.16 | 0.52 | 0.86 | 1.16 | 1.27 | 0.93 | 0.74 | 0.73 | 0.85 |
| 0.99 | 0.53 | 0.86 | 0.59 | 1.31 | 0.63 | 0.71 | 0.56 | 0.91 |
| 0.99 | 0.73 | 1.18 | 0.94 | 1.24 | 0.67 | 1.02 | 0.69 | 1.07 |
| 1.09 | 0.45 | 0.31 | 1.09 | 1.09 | 0.58 | 0.73 | 1.08 | 0.87 |
| 0.96 | 1.32 | 0.89 | 1.01 | 1.36 | 0.55 | 1.06 | 1.04 | 1.15 |

TABLE 14C

| Transcripts analysis, cerebral cortex (CX), V3 transcripts | | | | | | | | |
|---|---|---|---|---|---|---|---|---|
| PBS | WV-30210 50, 50 | WV-30210 15, 15 | WV-30210 5, 5 | WV-30210 1.5, 1.5 | WV-30212 50, 50 | WV-30212 15, 15 | WV-30212 5, 5 | WV-30212 1.5, 1.5 |
| 0.89 | 0.30 | 0.75 | 0.76 | 0.91 | 0.23 | 0.61 | 0.69 | 0.63 |
| 0.90 | 0.49 | 0.83 | 0.98 | 0.94 | 0.57 | 0.81 | 0.78 | 0.47 |
| 0.98 | | 0.70 | 0.82 | 0.91 | 0.55 | 0.51 | 0.73 | 0.50 |
| 0.90 | 0.26 | 0.78 | 0.84 | 0.94 | 0.69 | 0.48 | 0.66 | 0.64 |
| 1.04 | 0.37 | 0.77 | 0.56 | 0.98 | 0.66 | 0.70 | 0.66 | 0.82 |
| 1.18 | 0.60 | 0.90 | 0.92 | 1.14 | 0.62 | 0.92 | 0.71 | 1.03 |
| 1.06 | 0.42 | 0.19 | 0.93 | 1.10 | 0.39 | 0.79 | 0.92 | 0.76 |
| 1.05 | 1.19 | 0.93 | 1.02 | 1.09 | 0.52 | 0.93 | 0.89 | 1.11 |

TABLE 14D

| Tissue exposure, cerebral cortex (CX) ( ug oligonucleotide / g tissue) | | | | | | | | |
|---|---|---|---|---|---|---|---|---|
| PBS | WV-30210 50/50 ug | WV-30210 15/15 ug | WV-30210 5/5 ug | WV-30210 1.5/1.5 ug | WV-30212 50/50 ug | WV-30212 15/15 ug | WV-30212 5/5 ug | WV-30212 1.5/1.5 ug |
| 0.00 | 15.38 | 1.42 | 0.20 | 0.04 | 21.97 | 1.48 | 0.21 | 0.04 |
| 0.00 | 4.04 | 0.67 | 0.09 | 0.04 | 2.20 | 1.03 | 0.24 | 0.05 |
| 0.00 | | | 0.29 | 0.18 | 2.15 | 1.90 | 0.21 | 0.07 |
| 0.00 | 7.71 | 0.46 | 0.38 | 0.03 | 0.92 | 2.61 | 0.35 | 0.06 |
| 0.00 | 4.37 | 0.62 | 1.69 | 0.04 | 1.52 | 0.54 | 0.97 | 0.06 |
| 0.00 | 1.47 | 0.46 | 0.27 | 0.01 | 3.54 | 0.36 | 0.13 | 0.07 |
| | 4.00 | 0.91 | 0.34 | 0.11 | 3.38 | 0.46 | 0.15 | 0.05 |
| 0.00 | 1.26 | 0.36 | 0.06 | 0.01 | 4.39 | 0.45 | 0.23 | 0.08 |

TABLE 14E

| Transcripts analysis, spinal cord (SC), all transcripts | | | | | | | | |
|---|---|---|---|---|---|---|---|---|
| PBS | WV-30210 50/50 ug | WV-30210 15/15 ug | WV-30210 5/5 ug | WV-30210 1.5/1.5 ug | WV-30212 50/50 ug | WV-30212 15/15 ug | WV-30212 5/5 ug | WV-30212 1.5/1.5 ug |
| 1.44 | 0.38 | 0.51 | 0.72 | 1.05 | 0.45 | 0.25 | 0.34 | 0.65 |
| 0.82 | 0.41 | 0.45 | 1.25 | 0.87 | 0.25 | 0.64 | 0.99 | 0.83 |
| 0.79 | | 0.41 | 0.64 | 1.32 | 0.37 | 0.38 | 0.92 | 0.73 |
| 0.82 | 0.36 | 0.76 | 0.71 | 1.15 | 0.50 | 0.48 | 1.01 | 1.06 |
| 1.00 | 0.30 | 0.39 | 0.92 | 1.03 | 0.69 | 0.57 | 0.65 | 0.91 |
| 1.10 | 0.52 | 0.14 | 0.90 | 1.12 | 0.33 | 0.52 | 1.10 | 1.01 |
| 1.01 | 0.31 | 0.40 | 0.67 | 1.03 | 0.24 | 0.26 | 1.09 | 0.71 |
| 1.02 | 0.74 | 0.50 | 0.74 | 0.94 | 0.40 | 0.87 | 0.98 | 0.94 |

TABLE 14F

| Transcripts analysis, spinal cord (SC), V3 transcripts | | | | | | | | |
|---|---|---|---|---|---|---|---|---|
| PBS | WV-30210 50, 50 | WV-30210 15, 15 | WV-30210 5, 5 | WV-30210 1.5, 1.5 | WV-30212 50, 50 | WV-30212 15, 15 | WV-30212 5, 5 | WV-30212 1.5, 1.5 |
| 1.42 | 0.30 | 0.57 | 0.78 | 1.19 | 0.48 | 0.15 | 0.62 | 0.88 |
| 0.84 | 0.13 | 0.37 | 1.14 | 0.84 | 0.13 | 0.76 | 0.97 | 0.93 |
| 0.81 | | 0.35 | 0.71 | 1.28 | 0.27 | 0.24 | 1.23 | 0.90 |
| 0.88 | 0.09 | 0.73 | 0.67 | 1.23 | 0.42 | 0.30 | 1.18 | 1.25 |
| 1.11 | 0.10 | 0.37 | 0.94 | 1.04 | 0.86 | 0.66 | 0.65 | 0.96 |
| 1.04 | 0.11 | 0.16 | 0.95 | 1.25 | 0.16 | 0.49 | 1.31 | 1.12 |
| 0.88 | 0.08 | 0.42 | 0.70 | 1.36 | 0.10 | 0.39 | 1.26 | 0.80 |
| 1.02 | 0.29 | 0.32 | 0.71 | 1.02 | 0.08 | 0.77 | 0.99 | 1.21 |

TABLE 14G

| Tissue exposure, spinal cord (SC) (ug oligonucleotide/g tissue) | | | | | | | | |
|---|---|---|---|---|---|---|---|---|
| PBS | WV-30210 50/50 ug | WV-30210 15/15 ug | WV-30210 5/5 ug | WV-30210 1.5/1.5 ug | WV-30212 50/50 ug | WV-30212 15/15 ug | WV-30212 5/5 ug | WV-30212 1.5/1.5 ug |
| 0.00 | 2.36 | 1.41 | 0.29 | 0.11 | 2.82 | 3.00 | 0.71 | 0.05 |
| 0.00 | 3.30 | 2.04 | 0.15 | 0.19 | 4.24 | 0.73 | 0.72 | 0.14 |
| 0.00 | | 2.59 | 0.55 | 0.04 | 3.30 | 3.68 | 0.48 | 0.13 |
| 0.00 | 8.13 | 0.68 | 0.72 | 0.13 | 2.05 | 2.94 | 0.48 | 0.03 |
| 0.00 | 6.97 | 2.54 | 0.63 | 0.23 | 1.99 | 2.16 | 1.61 | 0.07 |
| 0.00 | 3.50 | 2.20 | 0.35 | 0.11 | 4.92 | 1.93 | 0.48 | 0.10 |
| 0.00 | 10.59 | 1.38 | 0.71 | 0.11 | 7.97 | 2.15 | 0.46 | 0.08 |
| 0.00 | 3.62 | 3.19 | 0.66 | 0.07 | 6.65 | 1.69 | 1.50 | 0.11 |

TABLE 14H

| Poly GP Protein Measurement, cortex (CX) | | | | | | | | |
|---|---|---|---|---|---|---|---|---|
| PBS | WV-30210 50/50 ug | WV-30210 15/15 ug | WV-30210 5/5 ug | WV-30210 1.5/1.5 ug | WV-30212 50/50 ug | WV-30212 15/15 ug | WV-30212 5/5 ug | WV-30212 1.5/1.5 ug |
| 0.69 | 0.05 | 0.56 | 1.45 | 1.14 | 0.12 | 0.48 | 0.88 | 2.01 |
| 0.55 | 0.13 | 0.68 | 1.09 | 1.07 | 0.16 | 0.76 | 0.80 | 0.96 |
| 1.15 | | 0.32 | 0.64 | 0.71 | 0.12 | 0.60 | 0.89 | 1.01 |
| 1.17 | 0.00 | 0.98 | 0.31 | 0.54 | 0.27 | 0.18 | 1.07 | 0.91 |
| 0.89 | 0.07 | 1.09 | 0.21 | 1.74 | 0.47 | 0.26 | 0.66 | 1.38 |
| 1.08 | 0.46 | 0.10 | 0.80 | 1.50 | 0.09 | 0.80 | 0.51 | 0.40 |
| 1.41 | 0.10 | 0.37 | 0.83 | 0.96 | 0.08 | 0.27 | 1.76 | 0.22 |
| 1.08 | 0.59 | 0.31 | 1.33 | 0.30 | 0.09 | 1.40 | 1.67 | 0.50 |

TABLE 14I

| Poly GP Protein Measurement, Spinal Cord (SC) | | | | | | | | |
|---|---|---|---|---|---|---|---|---|
| PBS | WV-30210 50/50 ug | WV-30210 15/15 ug | WV-30210 5/5 ug | WV-30210 1.5/1.5 ug | WV-30212 50/50 ug | WV-30212 15/15 ug | WV-30212 5/5 ug | WV-30212 1.5/1.5 ug |
| 1.13 | 0.18 | 0.00 | 0.88 | 1.62 | 0.00 | 0.00 | 0.27 | 0.46 |
| 0.61 | 0.00 | 0.00 | 0.59 | 0.89 | 0.00 | 0.29 | 0.14 | 0.24 |
| 1.40 | | 0.00 | 0.34 | 0.57 | 0.09 | 0.09 | 0.35 | 1.19 |
| 0.64 | 0.00 | 0.21 | 0.22 | 0.48 | 0.00 | 0.00 | 0.45 | 3.11 |
| 0.51 | 0.08 | 0.12 | 0.48 | 1.29 | 0.21 | 0.13 | 0.35 | 2.41 |
| | 0.00 | 0.00 | 0.24 | 0.78 | 0.00 | 0.11 | 1.07 | 2.26 |
| 1.79 | 0.00 | 0.10 | 0.26 | 0.85 | 0.00 | 0.00 | 1.04 | 0.74 |
| 0.92 | 0.00 | 0.00 | 0.10 | 1.01 | 0.00 | 0.21 | 0.31 | 0.95 |

As demonstrated herein, C9orf72 oligonucleotide compositions can be delivered and can knock down C9orf72 products associated with conditions, disorders or diseases.

Example 9. WV-30210 Provides In Vivo Activity at Least 24 Weeks Post Administration In some embodiments, a pharmacodynamics study was performed to assess a C9orf72 oligonucleotide composition, WV-30210, on knockdown of C9orf72 products. It confirmed that WV-30210 can reduce levels of C9orf72 transcripts and products encoded thereby at least 4, 12, 18 and 24 weeks post administration (at least 23 weeks post last dose). Those skilled in the art appreciate that reduction can last even longer beyond 24 weeks. PBS (phosphate-buffered saline) was utilized as a negative control.

Animals used: Male and Female C9-BAC mice, 2-4 month-old, 8 groups, 64 mice. Table 15A illustrates dosing design.

TABLE 15A

Design of an in vivo study.

| Group | Test Article | Dose | Dosing Regimen | Dose Volume | Total # mice per group | Necropsy Timepoint |
|---|---|---|---|---|---|---|
| 1 | PBS | NA | ICV, day 0, day 7 | 2.5 ul | 8 | 4 weeks |
| 2 | WV-30210 | 50/50 μg | ICV, day 0, day 7 | 2.5 ul | 8 | 4 weeks |
| 3 | PBS | NA | ICV, day 0, day 7 | 2.5 ul | 8 | 12 weeks |
| 4 | WV-30210 | 50/50 μg | ICV, day 0, day 7 | 2.5 ul | 8 | 12 weeks |
| 5 | PBS | NA | ICV, day 0, day 7 | 2.5 ul | 8 | 18 weeks |
| 6 | WV-30210 | 50/50 μg | ICV, day 0, day 7 | 2.5 ul | 8 | 18 weeks |
| 7 | PBS | NA | ICV, day 0, day 7 | 2.5 ul | 8 | 24 weeks |
| 8 | WV-30210 | 50/50 μg | ICV, day 0, day 7 | 2.5 ul | 8 | 24 weeks |

ICV cannulation was performed. ICV injection of PBS or 50 ug of oligonucleotide on Day 0 in awake animals. 2nd dose of PBS or 50 ug of oligonucleotide on Day 7. Dose volume, 2.5 uL. Necropsy 4 weeks, 12 weeks, 18 weeks and 24 weeks after first injection.

Tissues:

Cortex (CX): combine cortex from two hemibrains flash freeze into one weighted tube.

Spinal Cord (SC): separate upper and lower lumbar spinal cord flash freeze into two tubes, upper lumbar in weighted tubes (RNAPD and Trizol PK), lower for in unweighted tubes (DPR). Cervical +theoretic spinal cord, flash freeze in weighted tubes (Proteinase K PK).

Hippocampus and cerebellum: separate hippocampus and cerebellum from two hemibrains flash freeze into two unweighted tubes.

Certain results are shown in Tables 15B-15I.

Transcripts were analyzed from the spinal cord (SC) (All transcripts Table 15B, V3 Table 15C) and cerebral cortex (CX) (All transcripts Table 15D, V3 Table 15E). Poly GP levels in all dose groups were analyzed from cerebral cortex (CX) (Table 15F), and spinal cord (SC) (Table 15G). Tissue exposures were analyzed from spinal cord (SC) (Table 15H), and cerebral cortex (CX) (Table 15I). Total C9orf72 protein was analyzed in cerebral cortex (CX) (Table 15J) and spinal cord (SC) (Table 15K). The protocol of C9orf72 protein analysis is disclosed in Example 4 (Quantitation of C9orf72 Protein Expression using the Capillary Western Immunoassay (Wes)).

TABLE 15B

Transcripts analysis, spinal cord (SC), all transcripts

| PBS 4 wk | WV-30210 4 wk | PBS 12 wk | WV-30210 12 wk | PBS 18 wk | WV-30210 18 wk | PBS 24 wk | WV-30210 24 wk |
|---|---|---|---|---|---|---|---|
| 1.34 | 0.49 | 1.03 | 0.52 | 1.07 | 0.69 | 1.18 | 0.50 |
| 0.95 | | 1.03 | 0.53 | 0.95 | 0.57 | 0.76 | 0.51 |
| 0.87 | 0.43 | 0.96 | 0.50 | 0.84 | 0.54 | 1.36 | 0.47 |
| 0.93 | 0.43 | 0.92 | 0.57 | 1.17 | | 0.92 | 0.50 |
| 0.98 | 0.55 | 1.07 | 0.54 | 1.02 | 0.58 | 0.89 | 0.46 |
| 1.21 | 0.45 | 0.91 | 0.55 | 0.94 | 0.55 | 0.93 | 0.67 |
| 0.89 | 0.64 | 0.97 | 0.54 | 0.99 | 0.80 | 0.96 | |
| 0.82 | 0.45 | 1.11 | 0.51 | 1.02 | 0.61 | 1.00 | 0.43 |

TABLE 15C

Transcripts analysis, spinal cord (SC), V3

| PBS 4 wk | WV-30210 4 wk | PBS 12 wk | WV-30210 12 wk | PBS 18 wk | WV-30210 18 wk | PBS 24 wk | WV-30210 24 wk |
|---|---|---|---|---|---|---|---|
| 1.09 | 0.17 | 1.07 | 0.11 | 1.13 | 0.49 | 1.01 | 0.28 |
| 0.97 | | 1.01 | 0.16 | 0.86 | 0.17 | 0.83 | 0.23 |
| 0.97 | 0.09 | 0.98 | 0.10 | 1.05 | 0.19 | 1.48 | 0.21 |
| 1.03 | 0.09 | 0.99 | 0.15 | 1.01 | | 0.82 | 0.37 |
| 0.95 | 0.18 | 1.00 | 0.09 | 1.01 | 0.37 | 0.88 | 0.25 |
| 1.17 | 0.09 | 0.91 | 0.22 | 1.05 | 0.26 | 1.01 | 0.54 |
| 0.99 | 0.43 | 0.94 | 0.10 | 0.97 | 0.69 | 0.95 | |
| 0.82 | 0.10 | 1.10 | 0.14 | 0.93 | 0.21 | 1.01 | 0.32 |

TABLE 15D

Transcripts analysis, cerebral cortex (CX), all transcripts

| PBS 4 wk | WV-30210 4 wk | PBS 12 wk | WV-30210 12 wk | PBS 18 wk | WV-30210 18 wk | PBS 24 wk | WV-30210 24 wk |
|---|---|---|---|---|---|---|---|
| 0.99 | 0.54 | 0.90 | 0.53 | 1.10 | 0.82 | 0.89 | 0.64 |
| 1.07 | | 0.91 | 0.65 | 1.00 | 0.52 | 0.88 | 0.56 |
| 0.91 | 0.54 | 0.87 | 0.54 | 0.98 | 0.58 | 1.23 | 0.61 |
| 1.07 | 0.54 | 1.00 | 0.53 | 0.99 | | 1.11 | 0.77 |
| 0.85 | 0.56 | 1.16 | 0.52 | 1.00 | 0.73 | 0.91 | 0.64 |
| 1.03 | 0.51 | 1.04 | 0.48 | 0.96 | 0.61 | 0.95 | 0.62 |
| 0.88 | 0.65 | 1.06 | 0.80 | 1.01 | 0.83 | 1.14 | |
| 1.22 | 0.54 | 1.07 | 0.61 | 0.96 | 0.62 | 0.89 | 0.73 |

TABLE 15E

Transcripts analysis, cerebral cortex (CX), V3

| PBS 4 wk | WV-30210 4 wk | PBS 12 wk | WV-30210 12 wk | PBS 18 wk | WV-30210 18 wk | PBS 24 wk | WV-30210 24 wk |
|---|---|---|---|---|---|---|---|
| 1.00 | 0.58 | 0.90 | 0.44 | 0.92 | 0.79 | 0.81 | 0.52 |
| 1.09 | | 1.06 | 0.58 | 1.02 | 0.38 | 0.91 | 0.62 |
| 0.96 | 0.58 | 0.90 | 0.51 | 1.02 | 0.64 | 1.38 | 0.46 |
| 0.92 | 0.46 | 0.87 | 0.53 | 1.05 | | 1.02 | 0.77 |
| 1.03 | 0.56 | 1.03 | 0.45 | 0.95 | 0.72 | 0.89 | 0.56 |
| 1.07 | 0.47 | 1.07 | 0.28 | 0.94 | 0.64 | 0.97 | 0.47 |
| 0.87 | 0.77 | 1.02 | 0.64 | 1.12 | 0.83 | 0.95 | |
| 1.06 | 0.48 | 1.14 | 0.66 | 0.98 | 0.56 | 1.07 | 0.63 |

TABLE 15F

Poly GP levels (in all doses), cerebral cortex (CX)

| PBS 4 wk | WV-30210 4 wk | PBS 12 wk | WV-30210 12 wk | PBS 18 wk | WV-30210 18 wk | PBS 24 wk | WV-30210 24 wk |
|---|---|---|---|---|---|---|---|
| 0.45 | 0.09 | 0.76 | 0.05 | 0.69 | 0.21 | 0.92 | 0.06 |
| 0.97 | | 0.97 | 0.08 | 0.33 | 0.06 | 1.2 | 0.08 |
| 0.93 | 0.14 | 1.28 | 0.03 | 1.33 | 0.08 | | 0.08 |
| 1.22 | 0.03 | 0.5 | 0.05 | 1.33 | | 0.53 | 0.17 |
| 0.86 | 0.1 | 1.34 | 0.12 | 1.3 | 0.18 | 0.91 | 0.16 |
| 0.74 | 0.15 | 0.99 | 0.04 | 0.96 | 0.13 | 0.88 | 0.17 |
| 1.32 | 0.2 | 0.54 | 0.04 | 1.03 | 0.29 | 1.32 | |
| 1.5 | 0.15 | 1.61 | 0.09 | 1.02 | 0.16 | 1.23 | 0.18 |

TABLE 15G

Poly GP levels (in all doses), spinal cord (SC)

| PBS 4 wk | WV-30210 4 wk | PBS 12 wk | WV-30210 12 wk | PBS 18 wk | WV-30210 18 wk | PBS 24 wk | WV-30210 24 wk |
|---|---|---|---|---|---|---|---|
| | | 1.07 | 0 | 0.87 | 0 | 1.09 | 0.01 |
| | | | 0 | 1.33 | 0 | 0.44 | 0 |
| 1.64 | 0 | 2.17 | 0 | 1.48 | 0 | 2.22 | 0.01 |
| | 0 | 0.7 | 0 | 0.44 | | 0.62 | |
| 1.37 | | 0.7 | 0 | 1.4 | 0 | 1.07 | |
| 0.35 | 0 | 0.46 | 0.01 | 0.6 | 0.02 | 0.47 | 0.25 |
| 0.64 | 0 | 1.31 | 0 | 0.81 | 0.08 | 1.56 | |
| | 0 | 0.6 | 0 | 1.07 | 0 | 0.53 | 0.02 |

TABLE 15H

Tissue exposure in spinal cord (SC) (ug oligonucleotide/g tissue)

| PBS 4 wk | WV-30210 4 wk | PBS 12 wk | WV-30210 12 wk | PBS 18 wk | WV-30210 18 wk | PBS 24 wk | WV-30210 24 wk |
|---|---|---|---|---|---|---|---|
| 0.00 | 3.25 | 0.00 | 1.32 | 0.00 | 0.64 | 0.00 | 0.86 |
| 0.00 | 2.67 | 0.00 | 1.88 | 0.00 | 3.54 | 0.00 | 2.03 |
| 0.00 | 9.96 | 0.00 | 3.70 | 0.00 | 3.69 | 0.00 | 1.69 |
| 0.00 | 9.27 | 0.00 | 3.07 | 0.00 | | 0.00 | 0.42 |
| 0.00 | 3.24 | 0.00 | 5.01 | 0.00 | 1.82 | 0.00 | 0.80 |
| 0.00 | 7.02 | 0.00 | 1.16 | 0.00 | 1.74 | 0.00 | 0.14 |
| 0.00 | 1.61 | 0.00 | 2.60 | 0.00 | 0.56 | 0.00 | 0.82 |
| 0.00 | 5.66 | 0.00 | 1.88 | 0.00 | 1.46 | 0.00 | 0.35 |

TABLE 15I

Tissue exposure in cerebral cortex (CX) (ug oligonucleotide/g tissue)

| PBS 4 wk | WV-30210 4 wk | PBS 12 wk | WV-30210 12 wk | PBS 18 wk | WV-30210 18 wk | PBS 24 wk | WV-30210 24 wk |
|---|---|---|---|---|---|---|---|
| 0.00 | 1.71 | 0.00 | 1.87 | 0.07 | 0.40 | 0.00 | 1.36 |
| 0.00 | 4.56 | 0.00 | 1.29 | 0.00 | 1.83 | 0.00 | 0.63 |
| 0.00 | 2.64 | 0.00 | 2.90 | 0.00 | 1.44 | 0.00 | 0.95 |
| 0.00 | 5.08 | 0.00 | 2.57 | 0.00 | | 0.00 | 0.30 |
| 0.00 | 2.29 | 0.00 | 1.48 | 0.00 | 0.90 | 0.00 | 0.52 |
| 0.00 | 3.38 | 0.00 | 0.85 | 0.00 | 0.69 | 0.00 | 1.24 |
| 0.00 | 1.15 | 0.00 | 0.70 | 0.00 | 0.33 | 0.00 | 0.91 |
| 0.00 | 2.47 | 0.00 | 0.67 | 0.00 | 0.48 | 0.00 | 0.42 |

TABLE 15J

C9orf72 protein analysis in cerebral cortex (CX) at 24 weeks

| PBS | WV-30210 |
|---|---|
| 1.0173 | 0.9617 |
| 0.9275 | 0.981 |
| 0.9412 | 0.8581 |
| 1.0999 | 1.0275 |
| 1.036 | 0.9953 |
| 0.9894 | 0.9102 |
| 0.9887 | 0.918 |

TABLE 15K

C9or72 protein analysis in spinal cord (SC) at 24 weeks

| PBS | WV-30210 |
|---|---|
| 1.1115 | 0.88 |
| 0.9836 | 0.8175 |
| 1.0792 | 0.6414 |
| 0.9599 | 0.8703 |
| 0.9427 | 1.1028 |
| 0.9101 | 1.0617 |
| 1.013 | 0.8591 |

As demonstrated herein, WV-30210 can provide lasting reduction of C9orf72 transcripts and products encoded thereby which can be associated with various conditions, disorders or diseases.

Example 10. C9orf72 Oligonucleotide Compositions are Active and/or Selective in Various Assays Among other things, as demonstrated herein the present disclosure provides technologies that can effectively and/or selectively reduce expression, activities and/or levels of C9orf72 transcripts and/or products encoded thereby associated with conditions, disorders or diseases and comprising expanded repeats. Shown in the the following Tables are certain residual levels of various C9orf72 transcripts (e.g., all V transcripts, only V3 transcripts, etc.) relative to HPRT1, aftertreatment with C9orf72 oligonucleotide compositions, wherein 1.000 would represent 100% relative transcript level (no knockdown) and 0.000 would represent 0% o relative transcript level (e.g., 100% o knockdown). Certain results from replicate experiments are shown. Experiments were conducted in ALS motor neurons. Additional assay conditions are described herein and/or in WO 2019/032607.

TABLE 16A

Activity of certain C9orf72 oligonucleotide compositions.

| Dose (uM) | WV-38627 | WV-39524 | WV-39526 | WV-30206 | WV-39527 | WV-39528 | WV-30212 |
|---|---|---|---|---|---|---|---|
| 0.08 | 0.89 | 0.94 | 0.96 | 0.75 | 0.45 | 0.55 | 0.57 |
| | 0.81 | 0.88 | 0.85 | 0.76 | 0.45 | 0.52 | 0.56 |
| | 0.82 | 0.88 | 0.81 | 0.85 | 0.45 | 0.55 | 0.49 |
| 0.4 | 0.66 | 0.67 | 0.56 | 0.39 | 0.15 | 0.20 | 0.26 |
| | 0.66 | 0.61 | 0.66 | 0.41 | 0.13 | 0.25 | 0.27 |
| | 0.71 | 0.60 | 0.61 | 0.41 | 0.14 | 0.21 | 0.24 |
| 2 | 0.44 | 0.32 | 0.30 | 0.17 | 0.03 | 0.05 | 0.07 |
| | 0.43 | 0.36 | 0.32 | 0.18 | 0.03 | 0.05 | 0.07 |
| | 0.43 | 0.30 | 0.32 | 0.17 | 0.03 | 0.06 | 0.09 |
| **Dose (uM)** | **WV-30211** | **WV-39523** | **WV-39525** | **WV-34452** | **WV-34453** | **WV-34466** | **WV-39814** |
| 0.08 | 0.65 | 0.37 | 0.53 | 0.34 | 0.47 | 0.54 | 0.96 |
| | 0.59 | 0.34 | 0.53 | 0.33 | 0.49 | 0.50 | 0.91 |
| | 0.61 | 0.35 | 0.48 | 0.38 | 0.45 | 0.52 | 1.02 |
| 0.4 | 0.27 | 0.09 | 0.18 | 0.09 | 0.15 | 0.19 | 0.91 |
| | 0.25 | 0.08 | 0.16 | 0.08 | 0.14 | 0.17 | 1.01 |
| | 0.24 | 0.09 | 0.17 | 0.09 | 0.14 | 0.17 | 0.91 |
| 2 | 0.08 | 0.01 | 0.04 | 0.02 | 0.04 | 0.05 | 0.87 |
| | 0.08 | 0.02 | 0.03 | 0.02 | 0.03 | 0.04 | 1.01 |
| | 0.07 | 0.02 | 0.04 | 0.02 | 0.04 | 0.05 | 0.89 |

This Table shows certain data of various C9orf72 oligonucleotide compositions in knocking down C9orf72 transcripts in ALS motor neurons (only V3 transcripts). As in other "only V3 transcripts" assessments, relative-fold change of V3 in C9orf72/HPRT1 is shown.

This Table shows data of various C9orf72 oligonucleotide compositions in knocking down C9orf72 transcripts in ALS motor neurons (All V transcripts). Relative fold-change in C9orf72/HPRT1 is shown.

TABLE 16B

Activity of certain C9orf72 oligonucleotide compositions.

| Dose (uM) | WV-38627 | WV-39524 | WV-39526 | WV-30206 | WV-39527 | WV-39528 | WV-30212 |
|---|---|---|---|---|---|---|---|
| 0.08 | 0.94 | 0.96 | 0.85 | 0.75 | 0.84 | 0.86 | 0.81 |
| | 0.90 | 0.94 | 0.91 | 0.81 | 0.83 | 0.83 | 0.79 |
| | 0.86 | 0.92 | 0.88 | 0.66 | 0.78 | 0.77 | 0.78 |
| 0.4 | 0.95 | 0.83 | 0.84 | 0.66 | 0.69 | 0.63 | 0.71 |
| | 0.88 | 0.92 | 0.79 | 0.74 | 0.65 | 0.68 | 0.74 |
| | 0.83 | 0.88 | 0.92 | 0.78 | 0.67 | 0.68 | 0.64 |
| 2 | 0.65 | 0.66 | 0.68 | 0.71 | 0.41 | 0.51 | 0.56 |
| | 0.77 | 0.65 | 0.60 | 0.59 | 0.47 | 0.48 | 0.50 |
| | 0.70 | 0.64 | 0.76 | 0.62 | 0.47 | 0.47 | 0.57 |
| **Dose (uM)** | **WV-30211** | **WV-39523** | **WV-39525** | **WV-34452** | **WV-34453** | **WV-34466** | **WV-39814** |
| 0.08 | 0.96 | 0.77 | 0.85 | 0.82 | 0.79 | 0.84 | 0.95 |
| | 0.89 | 0.79 | 0.76 | 0.75 | 0.83 | 0.82 | 0.92 |
| | 0.89 | 0.82 | 0.82 | 0.79 | 0.87 | 0.83 | 1.05 |

TABLE 16B-continued

Activity of certain C9orf72 oligonucleotide compositions.

| Dose (uM) | WV-30211 | WV-39523 | WV-39525 | WV-34452 | WV-34453 | WV-34466 | WV-39814 |
|---|---|---|---|---|---|---|---|
| 0.4 | 0.76 | 0.63 | 0.69 | 0.69 | 0.72 | 0.70 | 1.00 |
| | 0.72 | 0.62 | 0.59 | 0.66 | 0.73 | 0.69 | 1.04 |
| | 0.75 | 0.62 | 0.63 | 0.67 | 0.63 | 0.70 | 0.90 |
| 2 | 0.52 | 0.37 | 0.38 | 0.42 | 0.48 | 0.45 | 1.09 |
| | 0.58 | 0.37 | 0.39 | 0.42 | 0.52 | 0.46 | 1.00 |
| | 0.57 | 0.37 | 0.46 | 0.44 | 0.55 | 0.41 | 1.23 |

As demonstrated, various oligonucleotide compositions can effectively and selectively reduce targeted transcripts, e.g., transcripts that can contain expanded repeats and be associated with various conditions, disorders or diseases (e.g., V3 transcripts).

Unless otherwise noted, in various experiments, cells and animals used in experiments were used in conditions typical for those cells or animals. Unless otherwise noted, in in vitro experiments, various cells were grown under standard conditions (e.g., the most common conditions used for a particular cell type, cell line or a similar cell type or line), e.g., with ordinary growth medium, normal temperature (37° C.), and gravity and atmospheric pressure typical of Cambridge, MA. Animals were kept under standard laboratory conditions, generally at room temperature, or a few degrees cooler, with normal conditions of feeding, cage size, gravity and atmospheric pressure typical of Massachusetts, etc. Neither cells nor animals, unless otherwise noted, were subjected to extremes of temperature (e.g., cold shock or heat shock), pressure, gravity, ambient sound, food or nutrient deprivation, etc.

While various embodiments have been described and illustrated herein, those of ordinary skill in the art will readily envision a variety of other means and/or structures for performing the functions and/or obtaining the results and/or one or more of the advantages described in the present disclosure, and each of such variations and/or modifications is deemed to be included. More generally, those skilled in the art will readily appreciate that all parameters, dimensions, materials, and configurations described herein are meant to be example and that the actual parameters, dimensions, materials, and/or configurations will depend upon the specific application or applications for which the teachings of the present disclosure is/are used. Those skilled in the art will recognize, or be able to ascertain using no more than routine experimentation, many equivalents to the specific embodiments of the disclosure described in the present disclosure. It is, therefore, to be understood that the foregoing embodiments are presented by way of example only and that, within the scope of the appended claims and equivalents thereto, claimed technologies may be practiced otherwise than as specifically described and claimed. In addition, any combination of two or more features, systems, articles, materials, kits, and/or methods, if such features, systems, articles, materials, kits, and/or methods are not mutually inconsistent, is included within the scope of the present disclosure.

The invention claimed is:

1. An oligonucleotide, wherein the oligonucleotide is mA Sm5Ceon001RTeom5Ceon001RmA * SC * SC * SC * RA * SC * ST * Sm5C * SG * Rm5C SC * SmA * SmC * Sm5Ceo * SmGn001RmC (SEQ ID NO: 493) or a salt thereof, wherein:

m represents a 2'-OMe modified nucleoside;

eo represents a 2'-MOE modified nucleoside;

m5C represents 5-methylcytosine;

* S represents a phosphorothioate in the Sp configuration;

* R represents a phosphorothioate in the Rp configuration; and n001R is

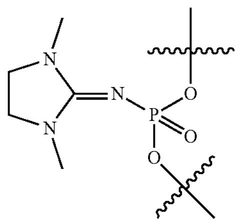 [SMILES: *OP(=O)(N=C1N(C)CCN1C)O*]

wherein the phosphorus is of the Rp configuration.

2. The oligonucleotide of claim 1, wherein the oligonucleotide is a pharmaceutically acceptable salt.

3. The oligonucleotide of claim 1, wherein the oligonucleotide is a sodium salt.

4. The oligonucleotide of claim 1, wherein each phosphorothioate internucleotidic linkage in the oligonucleotide independently has a diastereomeric purity of at least 90%.

5. An oligonucleotide composition comprising an oligonucleotide, wherein the oligonucleotide is mA * Sm5Ceon001RTeom5Ceon001RmA * SC * SC * SC * RA * SC * ST * Sm5C * SG * Rm5C * SC * SmA * SmC * Sm5Ceo SmGn001RmC (SEQ ID NO: 493) or a salt thereof, wherein:

m represents a 2'-OMe modified nucleoside;

eo represents a 2'-MOE modified nucleoside;

m5C represents 5-methylcytosine;

S represents a phosphorothioate in the Sp configuration;

* R represents a phosphorothioate in the Rp configuration; and n001R is

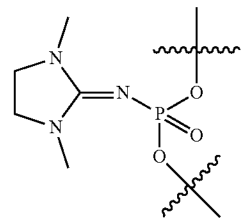 [SMILES: *OP(=O)(N=C1N(C)CCN1C)O*]

wherein the phosphorus is of the Rp configuration; and wherein the composition is chirally controlled in that it is enriched, relative to a substantially racemic preparation of the oligonucleotide, for the oligonucleotide.

6. The composition of claim 5, wherein the oligonucleotide is a pharmaceutically acceptable salt.

7. The composition of claim 5, wherein the oligonucleotide is a sodium salt.

8. A pharmaceutical composition which comprises an oligonucleotide of claim 1 and a pharmaceutically acceptable carrier.

* * * * *

SEQUENCE LISTING

```
<160> NUMBER OF SEQ ID NOS: 576

<210> SEQ ID NO 1
<211> LENGTH: 3000
<212> TYPE: DNA
<213> ORGANISM: Artificial Sequence
<220> FEATURE:
<223> OTHER INFORMATION: Synthetic
<220> FEATURE:
```

-continued

<221> NAME/KEY: misc_feature
<223> OTHER INFORMATION: In some embodiments, "GGGGCC" repeats 30 times or more. The remaining "GGGGCC" may or may not be present.
<220> FEATURE:
<221> NAME/KEY: misc_feature
<223> OTHER INFORMATION: In some embodiments, "GGGGCC" repeats 50 times or more. The remaining "GGGGCC" may or may not be present.
<220> FEATURE:
<221> NAME/KEY: misc_feature
<223> OTHER INFORMATION: In some embodiments, "GGGGCC" repeats 100 times or more. The remaining "GGGGCC" may or may not be present.
<220> FEATURE:
<221> NAME/KEY: misc_feature
<223> OTHER INFORMATION: In some embodiments, "GGGGCC" repeats 150 times or more. The remaining "GGGGCC" may or may not be present.
<220> FEATURE:
<221> NAME/KEY: misc_feature
<223> OTHER INFORMATION: In some embodiments, "GGGGCC" repeats 200 times or more. The remaining "GGGGCC" may or may not be present.
<220> FEATURE:
<221> NAME/KEY: misc_feature
<223> OTHER INFORMATION: In some embodiments, "GGGGCC" repeats 300 times or more. The remaining "GGGGCC" may or may not be present.
<220> FEATURE:
<221> NAME/KEY: misc_feature
<223> OTHER INFORMATION: In some embodiments, "GGGGCC" repeats 500 times or more.

<400> SEQUENCE: 1

```
ggggccgggg ccggggccgg ggccggggcc ggggccgggg ccggggccgg ggccggggcc     60
ggggccgggg ccggggccgg ggccggggcc ggggccgggg ccggggccgg ggccggggcc    120
ggggccgggg ccggggccgg ggccggggcc ggggccgggg ccggggccgg ggccggggcc    180
ggggccgggg ccggggccgg ggccggggcc ggggccgggg ccggggccgg ggccggggcc    240
ggggccgggg ccggggccgg ggccggggcc ggggccgggg ccggggccgg ggccggggcc    300
ggggccgggg ccggggccgg ggccggggcc ggggccgggg ccggggccgg ggccggggcc    360
ggggccgggg ccggggccgg ggccggggcc ggggccgggg ccggggccgg ggccggggcc    420
ggggccgggg ccggggccgg ggccggggcc ggggccgggg ccggggccgg ggccggggcc    480
ggggccgggg ccggggccgg ggccggggcc ggggccgggg ccggggccgg ggccggggcc    540
ggggccgggg ccggggccgg ggccggggcc ggggccgggg ccggggccgg ggccggggcc    600
ggggccgggg ccggggccgg ggccggggcc ggggccgggg ccggggccgg ggccggggcc    660
ggggccgggg ccggggccgg ggccggggcc ggggccgggg ccggggccgg ggccggggcc    720
ggggccgggg ccggggccgg ggccggggcc ggggccgggg ccggggccgg ggccggggcc    780
ggggccgggg ccggggccgg ggccggggcc ggggccgggg ccggggccgg ggccggggcc    840
ggggccgggg ccggggccgg ggccggggcc ggggccgggg ccggggccgg ggccggggcc    900
ggggccgggg ccggggccgg ggccggggcc ggggccgggg ccggggccgg ggccggggcc    960
ggggccgggg ccggggccgg ggccggggcc ggggccgggg ccggggccgg ggccggggcc   1020
ggggccgggg ccggggccgg ggccggggcc ggggccgggg ccggggccgg ggccggggcc   1080
ggggccgggg ccggggccgg ggccggggcc ggggccgggg ccggggccgg ggccggggcc   1140
ggggccgggg ccggggccgg ggccggggcc ggggccgggg ccggggccgg ggccggggcc   1200
ggggccgggg ccggggccgg ggccggggcc ggggccgggg ccggggccgg ggccggggcc   1260
ggggccgggg ccggggccgg ggccggggcc ggggccgggg ccggggccgg ggccggggcc   1320
ggggccgggg ccggggccgg ggccggggcc ggggccgggg ccggggccgg ggccggggcc   1380
ggggccgggg ccggggccgg ggccggggcc ggggccgggg ccggggccgg ggccggggcc   1440
ggggccgggg ccggggccgg ggccggggcc ggggccgggg ccggggccgg ggccggggcc   1500
```

-continued gggccgggg ccggggccgg ggccggggcc ggggccgggg ccggggccgg ggccggggcc 1560
ggggccgggg ccggggccgg ggccggggcc ggggccgggg ccggggccgg ggccggggcc 1620
ggggccgggg ccggggccgg ggccggggcc ggggccgggg ccggggccgg ggccggggcc 1680
ggggccgggg ccggggccgg ggccggggcc ggggccgggg ccggggccgg ggccggggcc 1740
ggggccgggg ccggggccgg ggccggggcc ggggccgggg ccggggccgg ggccggggcc 1800
ggggccgggg ccggggccgg ggccggggcc ggggccgggg ccggggccgg ggccggggcc 1860
ggggccgggg ccggggccgg ggccggggcc ggggccgggg ccggggccgg ggccggggcc 1920
ggggccgggg ccggggccgg ggccggggcc ggggccgggg ccggggccgg ggccggggcc 1980
ggggccgggg ccggggccgg ggccggggcc ggggccgggg ccggggccgg ggccggggcc 2040
ggggccgggg ccggggccgg ggccggggcc ggggccgggg ccggggccgg ggccggggcc 2100
ggggccgggg ccggggccgg ggccggggcc ggggccgggg ccggggccgg ggccggggcc 2160
ggggccgggg ccggggccgg ggccggggcc ggggccgggg ccggggccgg ggccggggcc 2220
ggggccgggg ccggggccgg ggccggggcc ggggccgggg ccggggccgg ggccggggcc 2280
ggggccgggg ccggggccgg ggccggggcc ggggccgggg ccggggccgg ggccggggcc 2340
ggggccgggg ccggggccgg ggccggggcc ggggccgggg ccggggccgg ggccggggcc 2400
ggggccgggg ccggggccgg ggccggggcc ggggccgggg ccggggccgg ggccggggcc 2460
ggggccgggg ccggggccgg ggccggggcc ggggccgggg ccggggccgg ggccggggcc 2520
ggggccgggg ccggggccgg ggccggggcc ggggccgggg ccggggccgg ggccggggcc 2580
ggggccgggg ccggggccgg ggccggggcc ggggccgggg ccggggccgg ggccggggcc 2640
ggggccgggg ccggggccgg ggccggggcc ggggccgggg ccggggccgg ggccggggcc 2700
ggggccgggg ccggggccgg ggccggggcc ggggccgggg ccggggccgg ggccggggcc 2760
ggggccgggg ccggggccgg ggccggggcc ggggccgggg ccggggccgg ggccggggcc 2820
ggggccgggg ccggggccgg ggccggggcc ggggccgggg ccggggccgg ggccggggcc 2880
ggggccgggg ccggggccgg ggccggggcc ggggccgggg ccggggccgg ggccggggcc 2940
ggggccgggg ccggggccgg ggccggggcc ggggccgggg ccggggccgg ggccggggcc 3000

<210> SEQ ID NO 2
<211> LENGTH: 180
<212> TYPE: DNA
<213> ORGANISM: Artificial Sequence
<220> FEATURE:
<223> OTHER INFORMATION: Synthetic

<400> SEQUENCE: 2
ggggccgggg ccggggccgg ggccggggcc ggggccgggg ccggggccgg ggccggggcc 60
ggggccgggg ccggggccgg ggccggggcc ggggccgggg ccggggccgg ggccggggcc 120
ggggccgggg ccggggccgg ggccggggcc ggggccgggg ccggggccgg ggccggggcc 180

<210> SEQ ID NO 3
<211> LENGTH: 21
<212> TYPE: RNA
<213> ORGANISM: Artificial Sequence
<220> FEATURE:
<223> OTHER INFORMATION: Synthetic

<400> SEQUENCE: 3
gcauagcgag cgagggaaaa c 21

<210> SEQ ID NO 4
<211> LENGTH: 21
<212> TYPE: RNA
<213> ORGANISM: Artificial Sequence
<220> FEATURE:
<223> OTHER INFORMATION: Synthetic

<400> SEQUENCE: 4
guuuucccuc gcucgcuaug c 21

<210> SEQ ID NO 5
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 5
cccacacctg ctcttgctag 20

<210> SEQ ID NO 6
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 6
aacagccacc cgccaggatg 20

<210> SEQ ID NO 7
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 7
aaccgggcag cagggacggc 20

<210> SEQ ID NO 8
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 8
acaggctgcg gttgtttccc 20

<210> SEQ ID NO 9
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 9
acccacacct gctcttgcta 20

<210> SEQ ID NO 10
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 10
acccactcgc caccgcctgc 20

<210> SEQ ID NO 11
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature

```
<223> OTHER INFORMATION: any C and/or G in one or more CpG motifs, if
      present, is replaced by another base; and in some embodiments, the
      G nucleobase in a CpG motif is replaced by I

<400> SEQUENCE: 11

accccaaaca gccacccgcc                                                  20


<210> SEQ ID NO 12
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and
      optionally substituted with U; and any U, if present, can be
      independently and optionally substituted with T
<220> FEATURE:
<221> NAME/KEY: misc_feature
<223> OTHER INFORMATION: any C and/or G in one or more CpG motifs, if
      present, is replaced by another base; and in some embodiments, the
      G nucleobase in a CpG motif is replaced by I

<400> SEQUENCE: 12

acccccatct catcccgcat                                                  20


<210> SEQ ID NO 13
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and
      optionally substituted with U; and any U, if present, can be
      independently and optionally substituted with T
<220> FEATURE:
<221> NAME/KEY: misc_feature
<223> OTHER INFORMATION: any C and/or G in one or more CpG motifs, if
      present, is replaced by another base; and in some embodiments, the
      G nucleobase in a CpG motif is replaced by I

<400> SEQUENCE: 13

acccgagctg tctccttccc                                                  20


<210> SEQ ID NO 14
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and
      optionally substituted with U; and any U, if present, can be
      independently and optionally substituted with T
<220> FEATURE:
<221> NAME/KEY: misc_feature
<223> OTHER INFORMATION: any C and/or G in one or more CpG motifs, if
      present, is replaced by another base; and in some embodiments, the
      G nucleobase in a CpG motif is replaced by I

<400> SEQUENCE: 14

acccgccagg atgccgcctc                                                  20


<210> SEQ ID NO 15
<211> LENGTH: 20
<212> TYPE: DNA
<213> ORGANISM: Artificial Sequence
```

<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 15
acccgcgcct cttcccggca 20

<210> SEQ ID NO 16
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 16
accctccggc cttcccccag 20

<210> SEQ ID NO 17
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 17
accgggcagc agggacggct 20

<210> SEQ ID NO 18
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 18
acctctcttt cctagcggga 20

<210> SEQ ID NO 19
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 19
acgcacctct ctttcctagc 20

<210> SEQ ID NO 20
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 20
actcacccac tcgccaccgc 20

<210> SEQ ID NO 21
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 21
agcaaccggg cagcagggac 20

<210> SEQ ID NO 22
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 22
agccgtccct gctgcccggt 20

<210> SEQ ID NO 23
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 23
agcgcgcgac tcctgagttc 20

<210> SEQ ID NO 24
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 24
agcttgctac aggctgcggt 20

<210> SEQ ID NO 25
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 25
aggatgccgc ctcctcactc 20

<210> SEQ ID NO 26
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 26
aggctgcggt tgtttccctc 20

<210> SEQ ID NO 27
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 27
aggctgtcag ctcggatctc 20

<210> SEQ ID NO 28
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 28
agggccaccc ctcctgggaa 20

<210> SEQ ID NO 29
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:

<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 29
atcccctcac aggctcttgt 20

<210> SEQ ID NO 30
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 30
atgccgcctc ctcactcacc 20

<210> SEQ ID NO 31
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 31
attgcctgca tccgggcccc 20

<210> SEQ ID NO 32
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 32
cacccactcg ccaccgcctg 20

<210> SEQ ID NO 33
<211> LENGTH: 20
<212> TYPE: DNA

-continued

<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 33
cacccccatc tcatcccgca 20

<210> SEQ ID NO 34
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 34
cacccgccag gatgccgcct 20

<210> SEQ ID NO 35
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 35
cacctctctt tcctagcggg 20

<210> SEQ ID NO 36
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 36
cactcaccca ctcgccaccg 20

<210> SEQ ID NO 37
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 37
caggatgccg cctcctcact 20

<210> SEQ ID NO 38
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 38
caggctgcgg ttgtttccct 20

<210> SEQ ID NO 39
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 39
cagggtggca tctgcttcac 20

<210> SEQ ID NO 40
<211> LENGTH: 20
<212> TYPE: DNA
<213> ORGANISM: Artificial Sequence
<220> FEATURE:
<223> OTHER INFORMATION: Synthetic
<220> FEATURE:

<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 40
ccaaacagcc acccgccagg 20

<210> SEQ ID NO 41
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 41
ccacccgcca ggatgccgcc 20

<210> SEQ ID NO 42
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 42
ccaccctccg gccttccccc 20

<210> SEQ ID NO 43
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 43
ccactcgcca ccgcctgcgc 20

<210> SEQ ID NO 44
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 44
ccaggatgcc gcctcctcac 20

<210> SEQ ID NO 45
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 45
cccaaacagc cacccgccag 20

<210> SEQ ID NO 46
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 46
cccactcgcc accgcctgcg 20

<210> SEQ ID NO 47
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 47
ccccaaacag ccacccgcca 20

<210> SEQ ID NO 48
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 48
cccgccagga tgccgcctcc 20

<210> SEQ ID NO 49
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 49
cctcactcac ccactcgccg 20

<210> SEQ ID NO 50
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 50
cccgcgcctc ttcccggcag 20

<210> SEQ ID NO 51
<211> LENGTH: 20

<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 51
cccggcagcc gaaccccaaa 20

<210> SEQ ID NO 52
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 52
ccgacttgca ttgctgccct 20

<210> SEQ ID NO 53
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 53
ccgcagcctg tagcaagctc 20

<210> SEQ ID NO 54
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 54
ccgccaggat gccgcctcct 20

<210> SEQ ID NO 55
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 55
ccgcctcctc actcacccac 20

<210> SEQ ID NO 56
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 56
ccgcgcctct tcccggcagc 20

<210> SEQ ID NO 57
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 57
ccgcttctac ccgcgcctct 20

<210> SEQ ID NO 58
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 58
ccgggcagca gggacggctg 20

<210> SEQ ID NO 59
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 59
cctagcggga caccgtaggt 20

<210> SEQ ID NO 60
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 60
cctcactcac ccactcgcca 20

<210> SEQ ID NO 61
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 61

```
cctccggcct tcccccaggc                                                20


<210> SEQ ID NO 62
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and
      optionally substituted with U; and any U, if present, can be
      independently and optionally substituted with T
<220> FEATURE:
<221> NAME/KEY: misc_feature
<223> OTHER INFORMATION: any C and/or G in one or more CpG motifs, if
      present, is replaced by another base; and in some embodiments, the
      G nucleobase in a CpG motif is replaced by I

<400> SEQUENCE: 62

cctcctcact cacccactcg                                                20


<210> SEQ ID NO 63
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and
      optionally substituted with U; and any U, if present, can be
      independently and optionally substituted with T
<220> FEATURE:
<221> NAME/KEY: misc_feature
<223> OTHER INFORMATION: any C and/or G in one or more CpG motifs, if
      present, is replaced by another base; and in some embodiments, the
      G nucleobase in a CpG motif is replaced by I

<400> SEQUENCE: 63

cctctctttc ctagcgggac                                                20


<210> SEQ ID NO 64
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and
      optionally substituted with U; and any U, if present, can be
      independently and optionally substituted with T
<220> FEATURE:
<221> NAME/KEY: misc_feature
<223> OTHER INFORMATION: any C and/or G in one or more CpG motifs, if
      present, is replaced by another base; and in some embodiments, the
      G nucleobase in a CpG motif is replaced by I

<400> SEQUENCE: 64

cctctgccaa ggcctgccac                                                20


<210> SEQ ID NO 65
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and
      optionally substituted with U; and any U, if present, can be
```

-continued independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 65
cctcttcccg gcagccgaac 20

<210> SEQ ID NO 66
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 66
cctgagttcc agagcttgct 20

<210> SEQ ID NO 67
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 67
cctgctcttg ctagaccccg 20

<210> SEQ ID NO 68
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 68
cctgctgccc ggttgcttct 20

<210> SEQ ID NO 69

<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 69
cctggttgct tcacagctcc 20

<210> SEQ ID NO 70
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 70
ccttccctga aggttcctcc 20

<210> SEQ ID NO 71
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 71
cgcacctctc tttcctagcg 20

<210> SEQ ID NO 72
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 72
cgcatagaat ccagtaccat 20

<210> SEQ ID NO 73
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 73
cgccaggatg ccgcctcctc 20

<210> SEQ ID NO 74
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 74
cgcctcctca ctcacccact 20

<210> SEQ ID NO 75
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 75
cgcctcttcc cggcagccga 20

<210> SEQ ID NO 76
<211> LENGTH: 20
<212> TYPE: DNA
<213> ORGANISM: Artificial Sequence
<220> FEATURE:

<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 76
cgcgcgactc ctgagttcca 20

<210> SEQ ID NO 77
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 77
cgcttctacc cgcgcctctt 20

<210> SEQ ID NO 78
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 78
cgggcagcag ggacggctga 20

<210> SEQ ID NO 79
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 79
cggttgtttc cctccttgtt 20

<210> SEQ ID NO 80
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 80
ctacccgcgc ctcttcccgg 20

<210> SEQ ID NO 81
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 81
ctcacccact cgccaccgcc 20

<210> SEQ ID NO 82
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 82
ctcactcacc cactcgccac 20

<210> SEQ ID NO 83
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 83
ctcagtaccc gaggctccct 20

<210> SEQ ID NO 84
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 84
ctcctcactc acccactcgc 20

<210> SEQ ID NO 85
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 85
ctcttcccgg cagccgaacc 20

<210> SEQ ID NO 86
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 86
ctcttgctag accccgcccc 20

-continued

<210> SEQ ID NO 87
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 87
ctctttccta gcgggacacc 20

<210> SEQ ID NO 88
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 88
ctgcggttgt ttccctcctt 20

<210> SEQ ID NO 89
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 89
ctgctcttgc tagaccccgc 20

<210> SEQ ID NO 90
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 90
cttcccggca gccgaacccc 20

<210> SEQ ID NO 91
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 91
cttccttgct ttcccgccct 20

<210> SEQ ID NO 92
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 92
cttctacccg cgcctcttcc 20

<210> SEQ ID NO 93
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 93
cttgctagac cccgccccca 20

<210> SEQ ID NO 94
<211> LENGTH: 20
<212> TYPE: DNA
<213> ORGANISM: Artificial Sequence -continued
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 94
cttggtgtgt cagccgtccc 20

<210> SEQ ID NO 95
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 95
cttgttcacc ctcagcgagt 20

<210> SEQ ID NO 96
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 96
ctttcctagc gggacaccgt 20

<210> SEQ ID NO 97
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 97
gacatcccct cacaggctct 20

<210> SEQ ID NO 98
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 98
gagagccccc gcttctaccc 20

<210> SEQ ID NO 99
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 99
gagctgccca ggaccacttc 20

<210> SEQ ID NO 100
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 100
gagcttgcta caggctgcgg 20

<210> SEQ ID NO 101
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 101
gaggccagat ccccatccct 20

<210> SEQ ID NO 102
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 102
gatccccatt ccagtttcca 20

<210> SEQ ID NO 103
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 103
gatgccgcct cctcactcac 20

<210> SEQ ID NO 104
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 104
gcaaccgggc agcagggacg 20

<210> SEQ ID NO 105
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 105
gcacctctct ttcctagcgg 20

<210> SEQ ID NO 106
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 106
gcaggcggtg gcgagtgggt 20

<210> SEQ ID NO 107
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 107
gcaggcgtct ccacaccccc 20

<210> SEQ ID NO 108
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:

<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 108
gcagggacgg ctgacacacc 20

<210> SEQ ID NO 109
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 109
gcatccgggc cccgggcttc 20

<210> SEQ ID NO 110
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 110
gcatcctggc gggtggctgt 20

<210> SEQ ID NO 111
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 111
gccacccgcc aggatgccgc 20

<210> SEQ ID NO 112
<211> LENGTH: 20
<212> TYPE: DNA

<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 112
gccagatccc catcccttgt 20

<210> SEQ ID NO 113
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 113
gccaggatgc cgcctcctca 20

<210> SEQ ID NO 114
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 114
gccctcagta cccgagctgt 20

<210> SEQ ID NO 115
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 115
gccgcctcct cactcaccca 20

<210> SEQ ID NO 116
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 116
gccgggaaga ggcgcgggta g 21

<210> SEQ ID NO 117
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 117
gccgtccctg ctgcccggtt 20

<210> SEQ ID NO 118
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 118
gcctcctcac tcacccactc 20

<210> SEQ ID NO 119
<211> LENGTH: 20
<212> TYPE: DNA
<213> ORGANISM: Artificial Sequence
<220> FEATURE:
<223> OTHER INFORMATION: Synthetic
<220> FEATURE:

<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 119
gcctctcagt acccgaggct 20

<210> SEQ ID NO 120
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 120
gcctcttccc ggcagccgaa 20

<210> SEQ ID NO 121
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 121
gcgcaggcgg tggcgagtgg gtgagtgagg aggcggcatc 40

<210> SEQ ID NO 122
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 122
gcgcaggcgg tggcgagtgg gtgagtgagg 30

<210> SEQ ID NO 123
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 123
gcgcgactcc tgagttccag 20

<210> SEQ ID NO 124
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 124
gcgcgcgact cctgagttcc 20

<210> SEQ ID NO 125
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 125
gcggcatcct ggcgggtggc 20

<210> SEQ ID NO 126
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 126
gcggttgcgg tgcctgcgcc 20

<210> SEQ ID NO 127
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 127
gcggttgttt ccctccttgt 20

<210> SEQ ID NO 128
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 128
gctacaggct gcggttgttt 20

<210> SEQ ID NO 129
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 129
gctagacccc gcccccaaaa 20

<210> SEQ ID NO 130
<211> LENGTH: 20

<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 130
gctctgagga gagcccccgc 20

<210> SEQ ID NO 131
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 131
gctcttgcta gaccccgccc 20

<210> SEQ ID NO 132
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 132
gctgcgatcc ccattccagt 20

<210> SEQ ID NO 133
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 133
gctgcggttg tttccctcct 20

<210> SEQ ID NO 134
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 134
gctggagatg gcggtgggca 20

<210> SEQ ID NO 135
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 135
gctgggtgtc gggctttcgc 20

<210> SEQ ID NO 136
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 136
gctgtttgac gcacctctct 20

<210> SEQ ID NO 137
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 137
gcttctaccc gcgcctcttc 20

<210> SEQ ID NO 138
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 138
gcttgctaca ggctgcggtt 20

<210> SEQ ID NO 139
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 139
gcttggtgtg tcagccgtcc 20

<210> SEQ ID NO 140
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 140
gctttcccgc cctcagtacc 20

<210> SEQ ID NO 141
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 141
ggacccgctg ggagcgctgc 20

<210> SEQ ID NO 142
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 142
ggatgccgcc tcctcactca 20

<210> SEQ ID NO 143
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 143
ggcagcaggg acggctgaca 20

<210> SEQ ID NO 144
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 144
ggcctctcag tacccgaggc 20

<210> SEQ ID NO 145
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 145
ggcggaggcg caggcggtgg 20

<210> SEQ ID NO 146
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 146
ggcgtctcca cacccccatc 20

<210> SEQ ID NO 147
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 147
ggctcccttt tctcgagccc 20

<210> SEQ ID NO 148

<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 148
ggctgcggtt gtttccctcc 20

<210> SEQ ID NO 149
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 149
gggaaggccg gagggtgggc 20

<210> SEQ ID NO 150
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 150
gggcagcagg gacggctgac 20

<210> SEQ ID NO 151
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 151
gggctctcct cagagctcga 20

<210> SEQ ID NO 152
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 152
gggtgtcggg ctttcgcctc 20

<210> SEQ ID NO 153
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 153
ggtccctgcc ggcgaggaga 20

<210> SEQ ID NO 154
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 154
gtacccgagg ctcccttttc 20

<210> SEQ ID NO 155
<211> LENGTH: 20
<212> TYPE: DNA
<213> ORGANISM: Artificial Sequence
<220> FEATURE:

<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 155
gtcagccgtc cctgctgccc 20

<210> SEQ ID NO 156
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 156
gtccctgctg cccggttgct 20

<210> SEQ ID NO 157
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 157
gtccgtgtgc tcattgggtc 20

<210> SEQ ID NO 158
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 158
gtcgctgttt gacgcacctc 20

<210> SEQ ID NO 159
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 159
gtcggtgtgc tccccattct 20

<210> SEQ ID NO 160
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 160
gtgcaggcgt ctccacaccc 20

<210> SEQ ID NO 161
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 161
gtgctgcgat ccccattcca 20

<210> SEQ ID NO 162
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 162
gtggcaggcc ttggcagagg 20

<210> SEQ ID NO 163
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 163
gttcaccctc agcgagtact 20

<210> SEQ ID NO 164
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 164
gttgcggtgc ctgcgcccgc 20

<210> SEQ ID NO 165
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 165
gttgtttccc tccttgtttt 20

```
<210> SEQ ID NO 166
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and
      optionally substituted with U; and any U, if present, can be
      independently and optionally substituted with T
<220> FEATURE:
<221> NAME/KEY: misc_feature
<223> OTHER INFORMATION: any C and/or G in one or more CpG motifs, if
      present, is replaced by another base; and in some embodiments, the
      G nucleobase in a CpG motif is replaced by I

<400> SEQUENCE: 166

tacaggctgc ggttgtttcc                                                  20


<210> SEQ ID NO 167
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and
      optionally substituted with U; and any U, if present, can be
      independently and optionally substituted with T
<220> FEATURE:
<221> NAME/KEY: misc_feature
<223> OTHER INFORMATION: any C and/or G in one or more CpG motifs, if
      present, is replaced by another base; and in some embodiments, the
      G nucleobase in a CpG motif is replaced by I

<400> SEQUENCE: 167

tacccgcgcc tcttcccggc                                                  20


<210> SEQ ID NO 168
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and
      optionally substituted with U; and any U, if present, can be
      independently and optionally substituted with T
<220> FEATURE:
<221> NAME/KEY: misc_feature
<223> OTHER INFORMATION: any C and/or G in one or more CpG motifs, if
      present, is replaced by another base; and in some embodiments, the
      G nucleobase in a CpG motif is replaced by I

<400> SEQUENCE: 168

tcacccactc gccaccgcct                                                  20


<210> SEQ ID NO 169
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and
      optionally substituted with U; and any U, if present, can be
      independently and optionally substituted with T
<220> FEATURE:
<221> NAME/KEY: misc_feature
```

<223> OTHER INFORMATION: any C and/or G in one or more CpG motifs, if present, is replaced by another base; and in some embodiments, the G nucleobase in a CpG motif is replaced by I

<400> SEQUENCE: 169
tcaccctcag cgagtactgt 20

<210> SEQ ID NO 170
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 170
tcactcaccc actcgccacc 20

<210> SEQ ID NO 171
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 171
tcccctcaca ggctcttgtg 20

<210> SEQ ID NO 172
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 172
tcccggcagc cgaaccccaa 20

<210> SEQ ID NO 173
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 173
tcctcactca cccactcgcc 20

<210> SEQ ID NO 174
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 174
tccttgcttt cccgccctca 20

<210> SEQ ID NO 175
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 175
tctcagtacc cgaggctccc 20

<210> SEQ ID NO 176
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 176
tcttcccggc agccgaaccc 20

<210> SEQ ID NO 177
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 177
tcttgctaga ccccgccccc 20

<210> SEQ ID NO 178
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 178
tgccgcctcc tcactcaccc 20

<210> SEQ ID NO 179
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 179
tgcctgcatc cgggccccgg 20

<210> SEQ ID NO 180
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 180
tgcggttgtt tccctccttg 20

<210> SEQ ID NO 181
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 181
tgctacaggc tgcggttgtt 20

<210> SEQ ID NO 182
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 182
tgctagaccc cgcccccaaa 20

<210> SEQ ID NO 183
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 183
tgctcttgct agaccccgcc 20

<210> SEQ ID NO 184
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 184
tggaatgggg atcgcagcac 20

<210> SEQ ID NO 185
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 185
tggaatgggg atcgcagcac a 21

<210> SEQ ID NO 186
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 186
tggcgagtgg gtgagtgagg aggcggcatc 30

<210> SEQ ID NO 187
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:

```
<221> NAME/KEY: misc_feature
<223> OTHER INFORMATION: any C and/or G in one or more CpG motifs, if
      present, is replaced by another base; and in some embodiments, the
      G nucleobase in a CpG motif is replaced by I

<400> SEQUENCE: 187

tgtgctgcga tccccattcc                                               20


<210> SEQ ID NO 188
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and
      optionally substituted with U; and any U, if present, can be
      independently and optionally substituted with T
<220> FEATURE:
<221> NAME/KEY: misc_feature
<223> OTHER INFORMATION: any C and/or G in one or more CpG motifs, if
      present, is replaced by another base; and in some embodiments, the
      G nucleobase in a CpG motif is replaced by I

<400> SEQUENCE: 188

ttccagagct tgctacaggc                                               20


<210> SEQ ID NO 189
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and
      optionally substituted with U; and any U, if present, can be
      independently and optionally substituted with T
<220> FEATURE:
<221> NAME/KEY: misc_feature
<223> OTHER INFORMATION: any C and/or G in one or more CpG motifs, if
      present, is replaced by another base; and in some embodiments, the
      G nucleobase in a CpG motif is replaced by I

<400> SEQUENCE: 189

ttcccggcag ccgaacccca                                               20


<210> SEQ ID NO 190
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and
      optionally substituted with U; and any U, if present, can be
      independently and optionally substituted with T
<220> FEATURE:
<221> NAME/KEY: misc_feature
<223> OTHER INFORMATION: any C and/or G in one or more CpG motifs, if
      present, is replaced by another base; and in some embodiments, the
      G nucleobase in a CpG motif is replaced by I

<400> SEQUENCE: 190

ttctacccgc gcctcttccc                                               20


<210> SEQ ID NO 191
<211> LENGTH: 20
<212> TYPE: DNA
```

<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 191
ttgctacagg ctgcggttgt 20

<210> SEQ ID NO 192
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 192
ttgctagacc ccgcccccaa 20

<210> SEQ ID NO 193
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 193
tttccccaca ccactgagct 20

<210> SEQ ID NO 194
<211> LENGTH: 12
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 194
acccactcgc ca 12

<210> SEQ ID NO 195
<211> LENGTH: 12
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 195
acccactcgc ca 12

<210> SEQ ID NO 196
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 196
actcacccac tcgccaccgc 20

<210> SEQ ID NO 197
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 197
actcacccac tcgccaccgc 20

<210> SEQ ID NO 198
<211> LENGTH: 20
<212> TYPE: DNA
<213> ORGANISM: Artificial Sequence
<220> FEATURE:
<223> OTHER INFORMATION: Synthetic
<220> FEATURE:

<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 198
actcacccac tcgccaccgc 20

<210> SEQ ID NO 199
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 199
actcacccac tcgccaccgc 20

<210> SEQ ID NO 200
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 200
actcacccac tcgccaccgc 20

<210> SEQ ID NO 201
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 201 actcgcca 8

<210> SEQ ID NO 202
<211> LENGTH: 12
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 202
auacuuaccu gg 12

<210> SEQ ID NO 203
<211> LENGTH: 9
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 203 cactcgcca 9

<210> SEQ ID NO 204
<211> LENGTH: 11
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 204
cccactcgcc a 11

<210> SEQ ID NO 205
<211> LENGTH: 11
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 205
cccactcgcc a 11

<210> SEQ ID NO 206
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 206
cctcactcac ccactcgcc 19

<210> SEQ ID NO 207
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 207
cctcactcac ccactcgcc 19

<210> SEQ ID NO 208
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 208
cctcactcac ccactcgcca 20

<210> SEQ ID NO 209
<211> LENGTH: 20

<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 209
cctcactcac ccactcgcca 20

<210> SEQ ID NO 210
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 210
cctcactcac ccactcgcca 20

<210> SEQ ID NO 211
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 211
cctcactcac ccactcgcca 20

<210> SEQ ID NO 212
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 212
cctcactcac ccactcgcca 20

<210> SEQ ID NO 213
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 213
cctcactcac ccactcgcca 20

<210> SEQ ID NO 214
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 214
cctcactcac ccactcgcca 20

<210> SEQ ID NO 215
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 215
cctcactcac ccactcgcca 20

<210> SEQ ID NO 216
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 216
cctcactcac ccactcgccc 20

<210> SEQ ID NO 217
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 217
cctcactcac ccactcgccc 20

<210> SEQ ID NO 218
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 218
cctcactcac ccactcgccg 20

<210> SEQ ID NO 219
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 219
cctcactcac ccactcgccg 20

<210> SEQ ID NO 220
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 220
cctcactcac ccactcgccg 20

<210> SEQ ID NO 221
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 221
cctcactcac ccactcgccg 20

<210> SEQ ID NO 222
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 222
cctcactcac ccactcgccg 20

<210> SEQ ID NO 223
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 223
cctcactcac ccactcgccg 20

<210> SEQ ID NO 224
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I
<220> FEATURE:
<221> NAME/KEY: misc_feature
<222> LOCATION: (20)..(20)
<223> OTHER INFORMATION: n is inosine

<400> SEQUENCE: 224
cctcactcac ccactcgccn 20

<210> SEQ ID NO 225
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I
<220> FEATURE:
<221> NAME/KEY: misc_feature
<222> LOCATION: (20)..(20)
<223> OTHER INFORMATION: n is inosine

<400> SEQUENCE: 225
cctcactcac ccactcgccn 20

<210> SEQ ID NO 226
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 226
cctcactcac ccactcgccu 20

<210> SEQ ID NO 227
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 227
cctcactcac ccactcgccu 20

<210> SEQ ID NO 228
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 228
cctcactcac ccacucgcc 19

<210> SEQ ID NO 229
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 229
cctcactcac ccacucgcc 19

<210> SEQ ID NO 230
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 230
cctcactcac ccacucgcc 19

<210> SEQ ID NO 231
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 231
cctcactcac ccacucgcca 20

<210> SEQ ID NO 232
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 232
cctgctgccc ggttgcttct 20

<210> SEQ ID NO 233
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 233
cctgctgccc ggttgcuucu 20

<210> SEQ ID NO 234
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 234
ccugctgccc ggttgcttct 20

<210> SEQ ID NO 235
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 235
cgccucctca ctcacccacu 20

<210> SEQ ID NO 236
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 236
ctcactcacc cactcgccac 20

<210> SEQ ID NO 237
<211> LENGTH: 24
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 237
cucuggaacu caggagucgc gcgc 24

<210> SEQ ID NO 238
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 238
gcgcgactcc tgagttccag 20

<210> SEQ ID NO 239
<211> LENGTH: 12
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 239
gcuaccuaua ug 12

<210> SEQ ID NO 240
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 240
gtccctgctg cccggttgct 20

<210> SEQ ID NO 241

<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 241
guccctgctg cccggttgct 20

<210> SEQ ID NO 242
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 242
tccttgcttt cccgccctca 20

<210> SEQ ID NO 243
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the G nucleobase in a CpG motif is replaced by I

<400> SEQUENCE: 243
tgccgcctcc tcactcaccc 20

<210> SEQ ID NO 244
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U; and any U, if present, can be independently and optionally substituted with T
<220> FEATURE:
<221> NAME/KEY: misc_feature
<223> OTHER INFORMATION: any C and/or G in one or more CpG motifs, if present, is replaced by another base; and in some embodiments, the
G nucleobase in a CpG motif is replaced by I

<400> SEQUENCE: 244
ucctcactca cccacucgcc 20

<210> SEQ ID NO 245
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and
optionally substituted with U; and any U, if present, can be
independently and optionally substituted with T
<220> FEATURE:
<221> NAME/KEY: misc_feature
<223> OTHER INFORMATION: any C and/or G in one or more CpG motifs, if
present, is replaced by another base; and in some embodiments, the
G nucleobase in a CpG motif is replaced by I

<400> SEQUENCE: 245
uccutgcttt cccgccctca 20

<210> SEQ ID NO 246
<211> LENGTH: 20
<212> TYPE: DNA
<213> ORGANISM: Artificial Sequence
<220> FEATURE:
<223> OTHER INFORMATION: Synthetic

<400> SEQUENCE: 246
actcacccac tcgccaccgc 20

<210> SEQ ID NO 247
<211> LENGTH: 20
<212> TYPE: DNA
<213> ORGANISM: Artificial Sequence
<220> FEATURE:
<223> OTHER INFORMATION: Synthetic

<400> SEQUENCE: 247
actcacccac tcgccaccgc 20

<210> SEQ ID NO 248
<211> LENGTH: 20
<212> TYPE: DNA
<213> ORGANISM: Artificial Sequence
<220> FEATURE:
<223> OTHER INFORMATION: Synthetic

<400> SEQUENCE: 248
actcacccac tcgccaccgc 20

<210> SEQ ID NO 249
<211> LENGTH: 20
<212> TYPE: DNA
<213> ORGANISM: Artificial Sequence
<220> FEATURE:
<223> OTHER INFORMATION: Synthetic

<400> SEQUENCE: 249
actcacccac tcgccaccgc 20

<210> SEQ ID NO 250

<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U

<400> SEQUENCE: 250
cctcactcac ccactcgcca 20

<210> SEQ ID NO 251
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U

<400> SEQUENCE: 251
cctcactcac ccactcgcca 20

<210> SEQ ID NO 252
<211> LENGTH: 12
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U

<400> SEQUENCE: 252
atacttacct gg 12

<210> SEQ ID NO 253
<211> LENGTH: 9
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U

<400> SEQUENCE: 253 cactcgcca 9

<210> SEQ ID NO 254
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U

<400> SEQUENCE: 254 actcgcca 8

```
<210> SEQ ID NO 255
<211> LENGTH: 12
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and
      optionally substituted with U

<400> SEQUENCE: 255

acccactcgc ca                                                          12


<210> SEQ ID NO 256
<211> LENGTH: 11
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and
      optionally substituted with U

<400> SEQUENCE: 256

cccactcgcc a                                                           11


<210> SEQ ID NO 257
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and
      optionally substituted with U

<400> SEQUENCE: 257

tgccgcctcc tcactcaccc                                                  20


<210> SEQ ID NO 258
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and
      optionally substituted with U

<400> SEQUENCE: 258

tgccgcctcc tcactcaccc                                                  20


<210> SEQ ID NO 259
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and
      optionally substituted with U

<400> SEQUENCE: 259

gcgcgactcc tgagttccag                                                  20
```

<210> SEQ ID NO 260
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U

<400> SEQUENCE: 260
tccttgcttt cccgccctca 20

<210> SEQ ID NO 261
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U

<400> SEQUENCE: 261
tccttgcttt cccgccctca 20

<210> SEQ ID NO 262
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U

<400> SEQUENCE: 262
tccttgcttt cccgccctca 20

<210> SEQ ID NO 263
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U

<400> SEQUENCE: 263
gtccctgctg cccggttgct 20

<210> SEQ ID NO 264
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U

<400> SEQUENCE: 264
gtccctgctg cccggttgct 20

<210> SEQ ID NO 265
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U

<400> SEQUENCE: 265
gtccctgctg cccggttgct 20

<210> SEQ ID NO 266
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U

<400> SEQUENCE: 266
cctgctgccc ggttgcttct 20

<210> SEQ ID NO 267
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U

<400> SEQUENCE: 267
cctgctgccc ggttgcttct 20

<210> SEQ ID NO 268
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U

<400> SEQUENCE: 268
cctgctgccc ggttgcttct 20

<210> SEQ ID NO 269
<211> LENGTH: 12
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U

<400> SEQUENCE: 269
gctacctata tg 12

<210> SEQ ID NO 270
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U

<400> SEQUENCE: 270
ctctggaact caggagtcgc gcgc 24

<210> SEQ ID NO 271
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U
<220> FEATURE:
<221> NAME/KEY: misc_feature
<222> LOCATION: (20)..(20)
<223> OTHER INFORMATION: n is inosine

<400> SEQUENCE: 271
cctcactcac ccactcgccn 20

<210> SEQ ID NO 272
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U

<400> SEQUENCE: 272
cctcactcac ccactcgccg 20

<210> SEQ ID NO 273
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U

<400> SEQUENCE: 273
tcctcactca cccactcgcc 20

<210> SEQ ID NO 274
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U

<400> SEQUENCE: 274
ctcactcacc cactcgccac 20

<210> SEQ ID NO 275
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U

<400> SEQUENCE: 275
actcacccac tcgccaccgc 20

<210> SEQ ID NO 276
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U

<400> SEQUENCE: 276
cgcctcctca ctcacccact 20

<210> SEQ ID NO 277
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U

<400> SEQUENCE: 277
cctcactcac ccactcgcc 19

<210> SEQ ID NO 278
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and optionally substituted with U

<400> SEQUENCE: 278
cctcactcac ccactcgcca 20

<210> SEQ ID NO 279
<211> LENGTH: 19
<212> TYPE: DNA
<213> ORGANISM: Artificial Sequence
<220> FEATURE:
<223> OTHER INFORMATION: Synthetic
<220> FEATURE:

```
<221> NAME/KEY: misc_feature
<223> OTHER INFORMATION: any T, if present, can be independently and
      optionally substituted with U

<400> SEQUENCE: 279

cctcactcac ccactcgcc                                              19


<210> SEQ ID NO 280
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and
      optionally substituted with U

<400> SEQUENCE: 280

cctcactcac ccactcgccc                                             20


<210> SEQ ID NO 281
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: any T, if present, can be independently and
      optionally substituted with U

<400> SEQUENCE: 281

cctcactcac ccactcgcct                                             20


<210> SEQ ID NO 282
<211> LENGTH: 20
<212> TYPE: DNA
<213> ORGANISM: Artificial Sequence
<220> FEATURE:
<223> OTHER INFORMATION: Synthetic

<400> SEQUENCE: 282

cctcactcac ccactcgcca                                             20


<210> SEQ ID NO 283
<211> LENGTH: 20
<212> TYPE: DNA
<213> ORGANISM: Artificial Sequence
<220> FEATURE:
<223> OTHER INFORMATION: Synthetic

<400> SEQUENCE: 283

cctcactcac ccactcgcca                                             20


<210> SEQ ID NO 284
<211> LENGTH: 20
<212> TYPE: DNA
<213> ORGANISM: Artificial Sequence
<220> FEATURE:
<223> OTHER INFORMATION: Synthetic

<400> SEQUENCE: 284

cctcactcac ccactcgcca                                             20


<210> SEQ ID NO 285
<211> LENGTH: 20
```

<212> TYPE: DNA
<213> ORGANISM: Artificial Sequence
<220> FEATURE:
<223> OTHER INFORMATION: Synthetic

<400> SEQUENCE: 285
cctcactcac ccactcgcca 20

<210> SEQ ID NO 286
<211> LENGTH: 20
<212> TYPE: DNA
<213> ORGANISM: Artificial Sequence
<220> FEATURE:
<223> OTHER INFORMATION: Synthetic

<400> SEQUENCE: 286
cctcactcac ccactcgcca 20

<210> SEQ ID NO 287
<211> LENGTH: 20
<212> TYPE: DNA
<213> ORGANISM: Artificial Sequence
<220> FEATURE:
<223> OTHER INFORMATION: Synthetic

<400> SEQUENCE: 287
ccucactcac ccactcgcca 20

<210> SEQ ID NO 288
<211> LENGTH: 12
<212> TYPE: RNA
<213> ORGANISM: Artificial Sequence
<220> FEATURE:
<223> OTHER INFORMATION: Synthetic

<400> SEQUENCE: 288
auacuuaccu gg 12

<210> SEQ ID NO 289
<211> LENGTH: 20
<212> TYPE: DNA
<213> ORGANISM: Artificial Sequence
<220> FEATURE:
<223> OTHER INFORMATION: Synthetic

<400> SEQUENCE: 289
cctcactcac ccactcgcca 20

<210> SEQ ID NO 290
<211> LENGTH: 20
<212> TYPE: DNA
<213> ORGANISM: Artificial Sequence
<220> FEATURE:
<223> OTHER INFORMATION: Synthetic

<400> SEQUENCE: 290
cctcactcac ccactcgcca 20

<210> SEQ ID NO 291
<211> LENGTH: 20
<212> TYPE: DNA
<213> ORGANISM: Artificial Sequence
<220> FEATURE:
<223> OTHER INFORMATION: Synthetic

<400> SEQUENCE: 291
cctcactcac ccactcgcca 20

<210> SEQ ID NO 292
<211> LENGTH: 20
<212> TYPE: DNA
<213> ORGANISM: Artificial Sequence
<220> FEATURE:
<223> OTHER INFORMATION: Synthetic

<400> SEQUENCE: 292
cctcactcac ccactcgcca 20

<210> SEQ ID NO 293
<211> LENGTH: 20
<212> TYPE: DNA
<213> ORGANISM: Artificial Sequence
<220> FEATURE:
<223> OTHER INFORMATION: Synthetic

<400> SEQUENCE: 293
cctcactcac ccactcgcca 20

<210> SEQ ID NO 294
<211> LENGTH: 20
<212> TYPE: DNA
<213> ORGANISM: Artificial Sequence
<220> FEATURE:
<223> OTHER INFORMATION: Synthetic

<400> SEQUENCE: 294
cctcactcac ccactcgcca 20

<210> SEQ ID NO 295
<211> LENGTH: 20
<212> TYPE: DNA
<213> ORGANISM: Artificial Sequence
<220> FEATURE:
<223> OTHER INFORMATION: Synthetic

<400> SEQUENCE: 295
cctcactcac ccactcgcca 20

<210> SEQ ID NO 296
<211> LENGTH: 9
<212> TYPE: DNA
<213> ORGANISM: Artificial Sequence
<220> FEATURE:
<223> OTHER INFORMATION: Synthetic

<400> SEQUENCE: 296 cactcgcca 9

<210> SEQ ID NO 297
<211> LENGTH: 8
<212> TYPE: DNA
<213> ORGANISM: Artificial Sequence
<220> FEATURE:
<223> OTHER INFORMATION: Synthetic

<400> SEQUENCE: 297 actcgcca 8

<210> SEQ ID NO 298
<211> LENGTH: 20
<212> TYPE: DNA
<213> ORGANISM: Artificial Sequence
<220> FEATURE:
<223> OTHER INFORMATION: Synthetic

<400> SEQUENCE: 298
cctcactcac ccactcgcca 20

<210> SEQ ID NO 299
<211> LENGTH: 20
<212> TYPE: DNA
<213> ORGANISM: Artificial Sequence
<220> FEATURE:
<223> OTHER INFORMATION: Synthetic

<400> SEQUENCE: 299
cctcactcac ccactcgcca 20

<210> SEQ ID NO 300
<211> LENGTH: 20
<212> TYPE: DNA
<213> ORGANISM: Artificial Sequence
<220> FEATURE:
<223> OTHER INFORMATION: Synthetic

<400> SEQUENCE: 300
cctcactcac ccactcgcca 20

<210> SEQ ID NO 301
<211> LENGTH: 12
<212> TYPE: DNA
<213> ORGANISM: Artificial Sequence
<220> FEATURE:
<223> OTHER INFORMATION: Synthetic

<400> SEQUENCE: 301
acccactcgc ca 12

<210> SEQ ID NO 302
<211> LENGTH: 11
<212> TYPE: DNA
<213> ORGANISM: Artificial Sequence
<220> FEATURE:
<223> OTHER INFORMATION: Synthetic

<400> SEQUENCE: 302
cccactcgcc a 11

<210> SEQ ID NO 303
<211> LENGTH: 12
<212> TYPE: DNA
<213> ORGANISM: Artificial Sequence
<220> FEATURE:
<223> OTHER INFORMATION: Synthetic

<400> SEQUENCE: 303
acccactcgc ca 12

<210> SEQ ID NO 304
<211> LENGTH: 11
<212> TYPE: DNA
<213> ORGANISM: Artificial Sequence
<220> FEATURE:
<223> OTHER INFORMATION: Synthetic

<400> SEQUENCE: 304
cccactcgcc a 11

<210> SEQ ID NO 305
<211> LENGTH: 20
<212> TYPE: DNA
<213> ORGANISM: Artificial Sequence
<220> FEATURE:
<223> OTHER INFORMATION: Synthetic

<400> SEQUENCE: 305
tgccgcctcc tcactcaccc 20

<210> SEQ ID NO 306
<211> LENGTH: 20
<212> TYPE: DNA
<213> ORGANISM: Artificial Sequence
<220> FEATURE:
<223> OTHER INFORMATION: Synthetic

<400> SEQUENCE: 306
tgccgcctcc tcactcaccc 20

<210> SEQ ID NO 307
<211> LENGTH: 20
<212> TYPE: DNA
<213> ORGANISM: Artificial Sequence
<220> FEATURE:
<223> OTHER INFORMATION: Synthetic

<400> SEQUENCE: 307
tgccgcctcc tcactcaccc 20

<210> SEQ ID NO 308
<211> LENGTH: 20
<212> TYPE: DNA
<213> ORGANISM: Artificial Sequence
<220> FEATURE:
<223> OTHER INFORMATION: Synthetic

<400> SEQUENCE: 308
tgccgcctcc tcactcaccc 20

<210> SEQ ID NO 309
<211> LENGTH: 20
<212> TYPE: DNA
<213> ORGANISM: Artificial Sequence
<220> FEATURE:
<223> OTHER INFORMATION: Synthetic

<400> SEQUENCE: 309
tgccgcctcc tcactcaccc 20

<210> SEQ ID NO 310
<211> LENGTH: 20
<212> TYPE: DNA
<213> ORGANISM: Artificial Sequence
<220> FEATURE:
<223> OTHER INFORMATION: Synthetic

<400> SEQUENCE: 310
ugccgcctcc tcactcaccc 20

<210> SEQ ID NO 311
<211> LENGTH: 20
<212> TYPE: DNA
<213> ORGANISM: Artificial Sequence
<220> FEATURE:
<223> OTHER INFORMATION: Synthetic

<400> SEQUENCE: 311
gcgcgactcc tgagttccag 20

<210> SEQ ID NO 312
<211> LENGTH: 20
<212> TYPE: DNA
<213> ORGANISM: Artificial Sequence
<220> FEATURE:
<223> OTHER INFORMATION: Synthetic

<400> SEQUENCE: 312
gcgcgactcc tgagttccag 20

<210> SEQ ID NO 313
<211> LENGTH: 20
<212> TYPE: DNA
<213> ORGANISM: Artificial Sequence
<220> FEATURE:
<223> OTHER INFORMATION: Synthetic

<400> SEQUENCE: 313
gcgcgactcc tgagttccag 20

<210> SEQ ID NO 314
<211> LENGTH: 20
<212> TYPE: DNA
<213> ORGANISM: Artificial Sequence
<220> FEATURE:
<223> OTHER INFORMATION: Synthetic

<400> SEQUENCE: 314
gcgcgactcc tgagttccag 20

<210> SEQ ID NO 315
<211> LENGTH: 20
<212> TYPE: DNA
<213> ORGANISM: Artificial Sequence
<220> FEATURE:
<223> OTHER INFORMATION: Synthetic

<400> SEQUENCE: 315
gcgcgactcc tgagttccag 20

<210> SEQ ID NO 316
<211> LENGTH: 20
<212> TYPE: DNA
<213> ORGANISM: Artificial Sequence
<220> FEATURE:
<223> OTHER INFORMATION: Synthetic

<400> SEQUENCE: 316
gcgcgactcc tgagttccag 20

<210> SEQ ID NO 317
<211> LENGTH: 20
<212> TYPE: DNA
<213> ORGANISM: Artificial Sequence
<220> FEATURE:
<223> OTHER INFORMATION: Synthetic

<400> SEQUENCE: 317
tccttgcttt cccgccctca 20

<210> SEQ ID NO 318

<211> LENGTH: 20
<212> TYPE: DNA
<213> ORGANISM: Artificial Sequence
<220> FEATURE:
<223> OTHER INFORMATION: Synthetic

<400> SEQUENCE: 318
tccttgcttt cccgccctca 20

<210> SEQ ID NO 319
<211> LENGTH: 20
<212> TYPE: DNA
<213> ORGANISM: Artificial Sequence
<220> FEATURE:
<223> OTHER INFORMATION: Synthetic

<400> SEQUENCE: 319
tccttgcttt cccgccctca 20

<210> SEQ ID NO 320
<211> LENGTH: 20
<212> TYPE: DNA
<213> ORGANISM: Artificial Sequence
<220> FEATURE:
<223> OTHER INFORMATION: Synthetic

<400> SEQUENCE: 320
tccttgcttt cccgccctca 20

<210> SEQ ID NO 321
<211> LENGTH: 20
<212> TYPE: DNA
<213> ORGANISM: Artificial Sequence
<220> FEATURE:
<223> OTHER INFORMATION: Synthetic

<400> SEQUENCE: 321
tccttgcttt cccgcccuca 20

<210> SEQ ID NO 322
<211> LENGTH: 20
<212> TYPE: DNA
<213> ORGANISM: Artificial Sequence
<220> FEATURE:
<223> OTHER INFORMATION: Synthetic

<400> SEQUENCE: 322
uccutgcttt cccgccctca 20

<210> SEQ ID NO 323
<211> LENGTH: 20
<212> TYPE: DNA
<213> ORGANISM: Artificial Sequence
<220> FEATURE:
<223> OTHER INFORMATION: Synthetic

<400> SEQUENCE: 323
gtccctgctg cccggttgct 20

<210> SEQ ID NO 324
<211> LENGTH: 20
<212> TYPE: DNA
<213> ORGANISM: Artificial Sequence
<220> FEATURE:
<223> OTHER INFORMATION: Synthetic

<400> SEQUENCE: 324
gtccctgctg cccggttgct 20

<210> SEQ ID NO 325
<211> LENGTH: 20
<212> TYPE: DNA
<213> ORGANISM: Artificial Sequence
<220> FEATURE:
<223> OTHER INFORMATION: Synthetic

<400> SEQUENCE: 325
gtccctgctg cccggttgct 20

<210> SEQ ID NO 326
<211> LENGTH: 20
<212> TYPE: DNA
<213> ORGANISM: Artificial Sequence
<220> FEATURE:
<223> OTHER INFORMATION: Synthetic

<400> SEQUENCE: 326
gtccctgctg cccggttgct 20

<210> SEQ ID NO 327
<211> LENGTH: 20
<212> TYPE: DNA
<213> ORGANISM: Artificial Sequence
<220> FEATURE:
<223> OTHER INFORMATION: Synthetic

<400> SEQUENCE: 327
gtccctgctg cccgguugcu 20

<210> SEQ ID NO 328
<211> LENGTH: 20
<212> TYPE: DNA
<213> ORGANISM: Artificial Sequence
<220> FEATURE:
<223> OTHER INFORMATION: Synthetic

<400> SEQUENCE: 328
guccctgctg cccggttgct 20

<210> SEQ ID NO 329
<211> LENGTH: 20
<212> TYPE: DNA
<213> ORGANISM: Artificial Sequence
<220> FEATURE:
<223> OTHER INFORMATION: Synthetic

<400> SEQUENCE: 329
cctgctgccc ggttgcttct 20

<210> SEQ ID NO 330
<211> LENGTH: 20
<212> TYPE: DNA
<213> ORGANISM: Artificial Sequence
<220> FEATURE:
<223> OTHER INFORMATION: Synthetic

<400> SEQUENCE: 330
cctgctgccc ggttgcttct 20

<210> SEQ ID NO 331
<211> LENGTH: 20
<212> TYPE: DNA

<213> ORGANISM: Artificial Sequence
<220> FEATURE:
<223> OTHER INFORMATION: Synthetic

<400> SEQUENCE: 331
cctgctgccc ggttgcttct 20

<210> SEQ ID NO 332
<211> LENGTH: 20
<212> TYPE: DNA
<213> ORGANISM: Artificial Sequence
<220> FEATURE:
<223> OTHER INFORMATION: Synthetic

<400> SEQUENCE: 332
cctgctgccc ggttgcttct 20

<210> SEQ ID NO 333
<211> LENGTH: 20
<212> TYPE: DNA
<213> ORGANISM: Artificial Sequence
<220> FEATURE:
<223> OTHER INFORMATION: Synthetic

<400> SEQUENCE: 333
cctgctgccc ggttgcuucu 20

<210> SEQ ID NO 334
<211> LENGTH: 20
<212> TYPE: DNA
<213> ORGANISM: Artificial Sequence
<220> FEATURE:
<223> OTHER INFORMATION: Synthetic

<400> SEQUENCE: 334
ccugctgccc ggttgcttct 20

<210> SEQ ID NO 335
<211> LENGTH: 20
<212> TYPE: DNA
<213> ORGANISM: Artificial Sequence
<220> FEATURE:
<223> OTHER INFORMATION: Synthetic

<400> SEQUENCE: 335
cctcactcac ccactcgcca 20

<210> SEQ ID NO 336
<211> LENGTH: 20
<212> TYPE: DNA
<213> ORGANISM: Artificial Sequence
<220> FEATURE:
<223> OTHER INFORMATION: Synthetic

<400> SEQUENCE: 336
cctcactcac ccactcgcca 20

<210> SEQ ID NO 337
<211> LENGTH: 20
<212> TYPE: DNA
<213> ORGANISM: Artificial Sequence
<220> FEATURE:
<223> OTHER INFORMATION: Synthetic

<400> SEQUENCE: 337
cctcactcac ccactcgcca 20

<210> SEQ ID NO 338
<211> LENGTH: 20
<212> TYPE: DNA
<213> ORGANISM: Artificial Sequence
<220> FEATURE:
<223> OTHER INFORMATION: Synthetic

<400> SEQUENCE: 338
cctcactcac ccactcgcca 20

<210> SEQ ID NO 339
<211> LENGTH: 12
<212> TYPE: RNA
<213> ORGANISM: Artificial Sequence
<220> FEATURE:
<223> OTHER INFORMATION: Synthetic

<400> SEQUENCE: 339
gcuaccuaua ug 12

<210> SEQ ID NO 340
<211> LENGTH: 24
<212> TYPE: RNA
<213> ORGANISM: Artificial Sequence
<220> FEATURE:
<223> OTHER INFORMATION: Synthetic

<400> SEQUENCE: 340
cucuggaacu caggagucgc gcgc 24

<210> SEQ ID NO 341
<211> LENGTH: 20
<212> TYPE: DNA
<213> ORGANISM: Artificial Sequence
<220> FEATURE:
<223> OTHER INFORMATION: Synthetic

<400> SEQUENCE: 341
cctcactcac ccactcgcca 20

<210> SEQ ID NO 342
<211> LENGTH: 20
<212> TYPE: DNA
<213> ORGANISM: Artificial Sequence
<220> FEATURE:
<223> OTHER INFORMATION: Synthetic

<400> SEQUENCE: 342
cctcactcac ccactcgcca 20

<210> SEQ ID NO 343
<211> LENGTH: 20
<212> TYPE: DNA
<213> ORGANISM: Artificial Sequence
<220> FEATURE:
<223> OTHER INFORMATION: Synthetic

<400> SEQUENCE: 343
cctcactcac ccactcgcca 20

<210> SEQ ID NO 344
<211> LENGTH: 20
<212> TYPE: DNA
<213> ORGANISM: Artificial Sequence
<220> FEATURE:

<223> OTHER INFORMATION: Synthetic
<220> FEATURE:
<221> NAME/KEY: misc_feature
<222> LOCATION: (20)..(20)
<223> OTHER INFORMATION: n is inosine

<400> SEQUENCE: 344
cctcactcac ccactcgccn 20

<210> SEQ ID NO 345
<211> LENGTH: 20
<212> TYPE: DNA
<213> ORGANISM: Artificial Sequence
<220> FEATURE:
<223> OTHER INFORMATION: Synthetic

<400> SEQUENCE: 345
cctcactcac ccactcgccg 20

<210> SEQ ID NO 346
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(20)
<223> OTHER INFORMATION: n is inosine

<400> SEQUENCE: 346
cctcactcac ccactcgccn 20

<210> SEQ ID NO 347
<211> LENGTH: 20
<212> TYPE: DNA
<213> ORGANISM: Artificial Sequence
<220> FEATURE:
<223> OTHER INFORMATION: Synthetic

<400> SEQUENCE: 347
cctcactcac ccactcgccg 20

<210> SEQ ID NO 348
<211> LENGTH: 20
<212> TYPE: DNA
<213> ORGANISM: Artificial Sequence
<220> FEATURE:
<223> OTHER INFORMATION: Synthetic

<400> SEQUENCE: 348
cctcactcac ccactcgcca 20

<210> SEQ ID NO 349
<211> LENGTH: 20
<212> TYPE: DNA
<213> ORGANISM: Artificial Sequence
<220> FEATURE:
<223> OTHER INFORMATION: Synthetic

<400> SEQUENCE: 349
cctcactcac ccactcgcca 20

<210> SEQ ID NO 350
<211> LENGTH: 20
<212> TYPE: DNA
<213> ORGANISM: Artificial Sequence
<220> FEATURE:
<223> OTHER INFORMATION: Synthetic

<400> SEQUENCE: 350
cctcactcac ccactcgcca 20

<210> SEQ ID NO 351
<211> LENGTH: 20
<212> TYPE: DNA
<213> ORGANISM: Artificial Sequence
<220> FEATURE:
<223> OTHER INFORMATION: Synthetic

<400> SEQUENCE: 351
ucctcactca cccacucgcc 20

<210> SEQ ID NO 352
<211> LENGTH: 20
<212> TYPE: DNA
<213> ORGANISM: Artificial Sequence
<220> FEATURE:
<223> OTHER INFORMATION: Synthetic

<400> SEQUENCE: 352
ucctcactca cccacucgcc 20

<210> SEQ ID NO 353
<211> LENGTH: 20
<212> TYPE: DNA
<213> ORGANISM: Artificial Sequence
<220> FEATURE:
<223> OTHER INFORMATION: Synthetic

<400> SEQUENCE: 353
ucctcactca cccacucgcc 20

<210> SEQ ID NO 354
<211> LENGTH: 20
<212> TYPE: DNA
<213> ORGANISM: Artificial Sequence
<220> FEATURE:
<223> OTHER INFORMATION: Synthetic

<400> SEQUENCE: 354
ucctcactca cccacucgcc 20

<210> SEQ ID NO 355
<211> LENGTH: 20
<212> TYPE: DNA
<213> ORGANISM: Artificial Sequence
<220> FEATURE:
<223> OTHER INFORMATION: Synthetic

<400> SEQUENCE: 355
ucctcactca cccacucgcc 20

<210> SEQ ID NO 356
<211> LENGTH: 20
<212> TYPE: DNA
<213> ORGANISM: Artificial Sequence
<220> FEATURE:
<223> OTHER INFORMATION: Synthetic

<400> SEQUENCE: 356
ucctcactca cccacucgcc 20

<210> SEQ ID NO 357
<211> LENGTH: 20
<212> TYPE: DNA
<213> ORGANISM: Artificial Sequence
<220> FEATURE:
<223> OTHER INFORMATION: Synthetic

<400> SEQUENCE: 357
ctcactcacc cactcgccac 20

<210> SEQ ID NO 358
<211> LENGTH: 20
<212> TYPE: DNA
<213> ORGANISM: Artificial Sequence
<220> FEATURE:
<223> OTHER INFORMATION: Synthetic

<400> SEQUENCE: 358
ctcactcacc cactcgccac 20

<210> SEQ ID NO 359
<211> LENGTH: 20
<212> TYPE: DNA
<213> ORGANISM: Artificial Sequence
<220> FEATURE:
<223> OTHER INFORMATION: Synthetic

<400> SEQUENCE: 359
ctcactcacc cactcgccac 20

<210> SEQ ID NO 360
<211> LENGTH: 20
<212> TYPE: DNA
<213> ORGANISM: Artificial Sequence
<220> FEATURE:
<223> OTHER INFORMATION: Synthetic

<400> SEQUENCE: 360
ctcactcacc cactcgccac 20

<210> SEQ ID NO 361
<211> LENGTH: 20
<212> TYPE: DNA
<213> ORGANISM: Artificial Sequence
<220> FEATURE:
<223> OTHER INFORMATION: Synthetic

<400> SEQUENCE: 361
ctcactcacc cactcgccac 20

<210> SEQ ID NO 362
<211> LENGTH: 20
<212> TYPE: DNA
<213> ORGANISM: Artificial Sequence
<220> FEATURE:
<223> OTHER INFORMATION: Synthetic

<400> SEQUENCE: 362
ctcactcacc cactcgccac 20

<210> SEQ ID NO 363
<211> LENGTH: 20
<212> TYPE: DNA
<213> ORGANISM: Artificial Sequence
<220> FEATURE:
<223> OTHER INFORMATION: Synthetic

<400> SEQUENCE: 363
actcacccac tcgccaccgc 20

<210> SEQ ID NO 364
<211> LENGTH: 20
<212> TYPE: DNA
<213> ORGANISM: Artificial Sequence
<220> FEATURE:
<223> OTHER INFORMATION: Synthetic

<400> SEQUENCE: 364
actcacccac tcgccaccgc 20

<210> SEQ ID NO 365
<211> LENGTH: 20
<212> TYPE: DNA
<213> ORGANISM: Artificial Sequence
<220> FEATURE:
<223> OTHER INFORMATION: Synthetic

<400> SEQUENCE: 365
actcacccac tcgccaccgc 20

<210> SEQ ID NO 366
<211> LENGTH: 20
<212> TYPE: DNA
<213> ORGANISM: Artificial Sequence
<220> FEATURE:
<223> OTHER INFORMATION: Synthetic

<400> SEQUENCE: 366
cgccucctca ctcacccacu 20

<210> SEQ ID NO 367
<211> LENGTH: 20
<212> TYPE: DNA
<213> ORGANISM: Artificial Sequence
<220> FEATURE:
<223> OTHER INFORMATION: Synthetic

<400> SEQUENCE: 367
cgccucctca ctcacccacu 20

<210> SEQ ID NO 368
<211> LENGTH: 20
<212> TYPE: DNA
<213> ORGANISM: Artificial Sequence
<220> FEATURE:
<223> OTHER INFORMATION: Synthetic

<400> SEQUENCE: 368
cgccucctca ctcacccacu 20

<210> SEQ ID NO 369
<211> LENGTH: 20
<212> TYPE: DNA
<213> ORGANISM: Artificial Sequence
<220> FEATURE:
<223> OTHER INFORMATION: Synthetic

<400> SEQUENCE: 369
cctcactcac ccactcgcca 20

<210> SEQ ID NO 370

<211> LENGTH: 20
<212> TYPE: DNA
<213> ORGANISM: Artificial Sequence
<220> FEATURE:
<223> OTHER INFORMATION: Synthetic

<400> SEQUENCE: 370
cctcactcac ccactcgcca 20

<210> SEQ ID NO 371
<211> LENGTH: 19
<212> TYPE: DNA
<213> ORGANISM: Artificial Sequence
<220> FEATURE:
<223> OTHER INFORMATION: Synthetic

<400> SEQUENCE: 371
cctcactcac ccacucgcc 19

<210> SEQ ID NO 372
<211> LENGTH: 19
<212> TYPE: DNA
<213> ORGANISM: Artificial Sequence
<220> FEATURE:
<223> OTHER INFORMATION: Synthetic

<400> SEQUENCE: 372
cctcactcac ccacucgcc 19

<210> SEQ ID NO 373
<211> LENGTH: 19
<212> TYPE: DNA
<213> ORGANISM: Artificial Sequence
<220> FEATURE:
<223> OTHER INFORMATION: Synthetic

<400> SEQUENCE: 373
cctcactcac ccacucgcc 19

<210> SEQ ID NO 374
<211> LENGTH: 19
<212> TYPE: DNA
<213> ORGANISM: Artificial Sequence
<220> FEATURE:
<223> OTHER INFORMATION: Synthetic

<400> SEQUENCE: 374
cctcactcac ccacucgcc 19

<210> SEQ ID NO 375
<211> LENGTH: 20
<212> TYPE: DNA
<213> ORGANISM: Artificial Sequence
<220> FEATURE:
<223> OTHER INFORMATION: Synthetic

<400> SEQUENCE: 375
cctcactcac ccacucgcca 20

<210> SEQ ID NO 376
<211> LENGTH: 20
<212> TYPE: DNA
<213> ORGANISM: Artificial Sequence
<220> FEATURE:
<223> OTHER INFORMATION: Synthetic

<400> SEQUENCE: 376
cctcactcac ccacucgcca 20

<210> SEQ ID NO 377
<211> LENGTH: 20
<212> TYPE: DNA
<213> ORGANISM: Artificial Sequence
<220> FEATURE:
<223> OTHER INFORMATION: Synthetic

<400> SEQUENCE: 377
cctcactcac ccacucgcca 20

<210> SEQ ID NO 378
<211> LENGTH: 20
<212> TYPE: DNA
<213> ORGANISM: Artificial Sequence
<220> FEATURE:
<223> OTHER INFORMATION: Synthetic

<400> SEQUENCE: 378
cctcactcac ccacucgcca 20

<210> SEQ ID NO 379
<211> LENGTH: 20
<212> TYPE: DNA
<213> ORGANISM: Artificial Sequence
<220> FEATURE:
<223> OTHER INFORMATION: Synthetic

<400> SEQUENCE: 379
cctcactcac ccacucgcca 20

<210> SEQ ID NO 380
<211> LENGTH: 20
<212> TYPE: DNA
<213> ORGANISM: Artificial Sequence
<220> FEATURE:
<223> OTHER INFORMATION: Synthetic

<400> SEQUENCE: 380
cctcactcac ccacucgcca 20

<210> SEQ ID NO 381
<211> LENGTH: 20
<212> TYPE: DNA
<213> ORGANISM: Artificial Sequence
<220> FEATURE:
<223> OTHER INFORMATION: Synthetic

<400> SEQUENCE: 381
cctcactcac ccactcgcca 20

<210> SEQ ID NO 382
<211> LENGTH: 20
<212> TYPE: DNA
<213> ORGANISM: Artificial Sequence
<220> FEATURE:
<223> OTHER INFORMATION: Synthetic

<400> SEQUENCE: 382
cctcactcac ccacucgcca 20

<210> SEQ ID NO 383
<211> LENGTH: 20
<212> TYPE: DNA

<213> ORGANISM: Artificial Sequence
<220> FEATURE:
<223> OTHER INFORMATION: Synthetic

<400> SEQUENCE: 383
cctcactcac ccacucgcca 20

<210> SEQ ID NO 384
<211> LENGTH: 20
<212> TYPE: DNA
<213> ORGANISM: Artificial Sequence
<220> FEATURE:
<223> OTHER INFORMATION: Synthetic

<400> SEQUENCE: 384
cctcactcac ccacucgcca 20

<210> SEQ ID NO 385
<211> LENGTH: 20
<212> TYPE: DNA
<213> ORGANISM: Artificial Sequence
<220> FEATURE:
<223> OTHER INFORMATION: Synthetic

<400> SEQUENCE: 385
cctcactcac ccacucgcca 20

<210> SEQ ID NO 386
<211> LENGTH: 20
<212> TYPE: DNA
<213> ORGANISM: Artificial Sequence
<220> FEATURE:
<223> OTHER INFORMATION: Synthetic

<400> SEQUENCE: 386
cctcactcac ccacucgcca 20

<210> SEQ ID NO 387
<211> LENGTH: 20
<212> TYPE: DNA
<213> ORGANISM: Artificial Sequence
<220> FEATURE:
<223> OTHER INFORMATION: Synthetic

<400> SEQUENCE: 387
cctcactcac ccacucgcca 20

<210> SEQ ID NO 388
<211> LENGTH: 19
<212> TYPE: DNA
<213> ORGANISM: Artificial Sequence
<220> FEATURE:
<223> OTHER INFORMATION: Synthetic

<400> SEQUENCE: 388
cctcactcac ccacucgcc 19

<210> SEQ ID NO 389
<211> LENGTH: 19
<212> TYPE: DNA
<213> ORGANISM: Artificial Sequence
<220> FEATURE:
<223> OTHER INFORMATION: Synthetic

<400> SEQUENCE: 389
cctcactcac ccacucgcc 19

<210> SEQ ID NO 390
<211> LENGTH: 19
<212> TYPE: DNA
<213> ORGANISM: Artificial Sequence
<220> FEATURE:
<223> OTHER INFORMATION: Synthetic

<400> SEQUENCE: 390
cctcactcac ccacucgcc 19

<210> SEQ ID NO 391
<211> LENGTH: 19
<212> TYPE: DNA
<213> ORGANISM: Artificial Sequence
<220> FEATURE:
<223> OTHER INFORMATION: Synthetic

<400> SEQUENCE: 391
cctcactcac ccacucgcc 19

<210> SEQ ID NO 392
<211> LENGTH: 19
<212> TYPE: DNA
<213> ORGANISM: Artificial Sequence
<220> FEATURE:
<223> OTHER INFORMATION: Synthetic

<400> SEQUENCE: 392
cctcactcac ccacucgcc 19

<210> SEQ ID NO 393
<211> LENGTH: 20
<212> TYPE: DNA
<213> ORGANISM: Artificial Sequence
<220> FEATURE:
<223> OTHER INFORMATION: Synthetic

<400> SEQUENCE: 393
cctcactcac ccactcgcca 20

<210> SEQ ID NO 394
<211> LENGTH: 20
<212> TYPE: DNA
<213> ORGANISM: Artificial Sequence
<220> FEATURE:
<223> OTHER INFORMATION: Synthetic

<400> SEQUENCE: 394
cctcactcac ccactcgcca 20

<210> SEQ ID NO 395
<211> LENGTH: 20
<212> TYPE: DNA
<213> ORGANISM: Artificial Sequence
<220> FEATURE:
<223> OTHER INFORMATION: Synthetic

<400> SEQUENCE: 395
cctcactcac ccactcgcca 20

<210> SEQ ID NO 396
<211> LENGTH: 20
<212> TYPE: DNA
<213> ORGANISM: Artificial Sequence
<220> FEATURE:

<223> OTHER INFORMATION: Synthetic

<400> SEQUENCE: 396
cctcactcac ccactcgcca 20

<210> SEQ ID NO 397
<211> LENGTH: 20
<212> TYPE: DNA
<213> ORGANISM: Artificial Sequence
<220> FEATURE:
<223> OTHER INFORMATION: Synthetic

<400> SEQUENCE: 397
cctcactcac ccactcgcca 20

<210> SEQ ID NO 398
<211> LENGTH: 20
<212> TYPE: DNA
<213> ORGANISM: Artificial Sequence
<220> FEATURE:
<223> OTHER INFORMATION: Synthetic

<400> SEQUENCE: 398
actcacccac tcgccaccgc 20

<210> SEQ ID NO 399
<211> LENGTH: 20
<212> TYPE: DNA
<213> ORGANISM: Artificial Sequence
<220> FEATURE:
<223> OTHER INFORMATION: Synthetic

<400> SEQUENCE: 399
actcacccac tcgccaccgc 20

<210> SEQ ID NO 400
<211> LENGTH: 20
<212> TYPE: DNA
<213> ORGANISM: Artificial Sequence
<220> FEATURE:
<223> OTHER INFORMATION: Synthetic

<400> SEQUENCE: 400
actcacccac tcgccaccgc 20

<210> SEQ ID NO 401
<211> LENGTH: 20
<212> TYPE: DNA
<213> ORGANISM: Artificial Sequence
<220> FEATURE:
<223> OTHER INFORMATION: Synthetic

<400> SEQUENCE: 401
actcacccac tcgccaccgc 20

<210> SEQ ID NO 402
<211> LENGTH: 20
<212> TYPE: DNA
<213> ORGANISM: Artificial Sequence
<220> FEATURE:
<223> OTHER INFORMATION: Synthetic

<400> SEQUENCE: 402
actcacccac tcgccaccgc 20

<210> SEQ ID NO 403
<211> LENGTH: 20
<212> TYPE: DNA
<213> ORGANISM: Artificial Sequence
<220> FEATURE:
<223> OTHER INFORMATION: Synthetic

<400> SEQUENCE: 403
actcacccac tcgccaccgc 20

<210> SEQ ID NO 404
<211> LENGTH: 20
<212> TYPE: DNA
<213> ORGANISM: Artificial Sequence
<220> FEATURE:
<223> OTHER INFORMATION: Synthetic

<400> SEQUENCE: 404
actcacccac tcgccaccgc 20

<210> SEQ ID NO 405
<211> LENGTH: 20
<212> TYPE: DNA
<213> ORGANISM: Artificial Sequence
<220> FEATURE:
<223> OTHER INFORMATION: Synthetic

<400> SEQUENCE: 405
actcacccac tcgccaccgc 20

<210> SEQ ID NO 406
<211> LENGTH: 20
<212> TYPE: DNA
<213> ORGANISM: Artificial Sequence
<220> FEATURE:
<223> OTHER INFORMATION: Synthetic

<400> SEQUENCE: 406
actcacccac tcgccaccgc 20

<210> SEQ ID NO 407
<211> LENGTH: 20
<212> TYPE: DNA
<213> ORGANISM: Artificial Sequence
<220> FEATURE:
<223> OTHER INFORMATION: Synthetic

<400> SEQUENCE: 407
actcacccac tcgccaccgc 20

<210> SEQ ID NO 408
<211> LENGTH: 19
<212> TYPE: DNA
<213> ORGANISM: Artificial Sequence
<220> FEATURE:
<223> OTHER INFORMATION: Synthetic

<400> SEQUENCE: 408
cctcactcac ccactcgcc 19

<210> SEQ ID NO 409
<211> LENGTH: 19
<212> TYPE: DNA
<213> ORGANISM: Artificial Sequence
<220> FEATURE:
<223> OTHER INFORMATION: Synthetic

<400> SEQUENCE: 409
cctcactcac ccactcgcc 19

<210> SEQ ID NO 410
<211> LENGTH: 19
<212> TYPE: DNA
<213> ORGANISM: Artificial Sequence
<220> FEATURE:
<223> OTHER INFORMATION: Synthetic

<400> SEQUENCE: 410
cctcactcac ccactcgcc 19

<210> SEQ ID NO 411
<211> LENGTH: 19
<212> TYPE: DNA
<213> ORGANISM: Artificial Sequence
<220> FEATURE:
<223> OTHER INFORMATION: Synthetic

<400> SEQUENCE: 411
cctcactcac ccactcgcc 19

<210> SEQ ID NO 412
<211> LENGTH: 19
<212> TYPE: DNA
<213> ORGANISM: Artificial Sequence
<220> FEATURE:
<223> OTHER INFORMATION: Synthetic

<400> SEQUENCE: 412
cctcactcac ccactcgcc 19

<210> SEQ ID NO 413
<211> LENGTH: 20
<212> TYPE: DNA
<213> ORGANISM: Artificial Sequence
<220> FEATURE:
<223> OTHER INFORMATION: Synthetic

<400> SEQUENCE: 413
cctcactcac ccactcgccg 20

<210> SEQ ID NO 414
<211> LENGTH: 20
<212> TYPE: DNA
<213> ORGANISM: Artificial Sequence
<220> FEATURE:
<223> OTHER INFORMATION: Synthetic

<400> SEQUENCE: 414
cctcactcac ccactcgccg 20

<210> SEQ ID NO 415
<211> LENGTH: 20
<212> TYPE: DNA
<213> ORGANISM: Artificial Sequence
<220> FEATURE:
<223> OTHER INFORMATION: Synthetic

<400> SEQUENCE: 415
cctcactcac ccactcgccg 20

<210> SEQ ID NO 416
<211> LENGTH: 20

<212> TYPE: DNA
<213> ORGANISM: Artificial Sequence
<220> FEATURE:
<223> OTHER INFORMATION: Synthetic

<400> SEQUENCE: 416
cctcactcac ccactcgccg 20

<210> SEQ ID NO 417
<211> LENGTH: 20
<212> TYPE: DNA
<213> ORGANISM: Artificial Sequence
<220> FEATURE:
<223> OTHER INFORMATION: Synthetic

<400> SEQUENCE: 417
actcacccac tcgccaccgc 20

<210> SEQ ID NO 418
<211> LENGTH: 20
<212> TYPE: DNA
<213> ORGANISM: Artificial Sequence
<220> FEATURE:
<223> OTHER INFORMATION: Synthetic

<400> SEQUENCE: 418
actcacccac tcgccaccgc 20

<210> SEQ ID NO 419
<211> LENGTH: 20
<212> TYPE: DNA
<213> ORGANISM: Artificial Sequence
<220> FEATURE:
<223> OTHER INFORMATION: Synthetic

<400> SEQUENCE: 419
actcacccac tcgccaccgc 20

<210> SEQ ID NO 420
<211> LENGTH: 20
<212> TYPE: DNA
<213> ORGANISM: Artificial Sequence
<220> FEATURE:
<223> OTHER INFORMATION: Synthetic

<400> SEQUENCE: 420
actcacccac tcgccaccgc 20

<210> SEQ ID NO 421
<211> LENGTH: 20
<212> TYPE: DNA
<213> ORGANISM: Artificial Sequence
<220> FEATURE:
<223> OTHER INFORMATION: Synthetic

<400> SEQUENCE: 421
cctcactcac ccactcgccg 20

<210> SEQ ID NO 422
<211> LENGTH: 19
<212> TYPE: DNA
<213> ORGANISM: Artificial Sequence
<220> FEATURE:
<223> OTHER INFORMATION: Synthetic

<400> SEQUENCE: 422
cctcactcac ccactcgcc 19

<210> SEQ ID NO 423
<211> LENGTH: 20
<212> TYPE: DNA
<213> ORGANISM: Artificial Sequence
<220> FEATURE:
<223> OTHER INFORMATION: Synthetic

<400> SEQUENCE: 423
cctcactcac ccactcgccg 20

<210> SEQ ID NO 424
<211> LENGTH: 20
<212> TYPE: DNA
<213> ORGANISM: Artificial Sequence
<220> FEATURE:
<223> OTHER INFORMATION: Synthetic

<400> SEQUENCE: 424
cctcactcac ccactcgccg 20

<210> SEQ ID NO 425
<211> LENGTH: 20
<212> TYPE: DNA
<213> ORGANISM: Artificial Sequence
<220> FEATURE:
<223> OTHER INFORMATION: Synthetic

<400> SEQUENCE: 425
cctcactcac ccactcgccg 20

<210> SEQ ID NO 426
<211> LENGTH: 20
<212> TYPE: DNA
<213> ORGANISM: Artificial Sequence
<220> FEATURE:
<223> OTHER INFORMATION: Synthetic

<400> SEQUENCE: 426
actcacccac tcgccaccgc 20

<210> SEQ ID NO 427
<211> LENGTH: 20
<212> TYPE: DNA
<213> ORGANISM: Artificial Sequence
<220> FEATURE:
<223> OTHER INFORMATION: Synthetic

<400> SEQUENCE: 427
actcacccac tcgccaccgc 20

<210> SEQ ID NO 428
<211> LENGTH: 20
<212> TYPE: DNA
<213> ORGANISM: Artificial Sequence
<220> FEATURE:
<223> OTHER INFORMATION: Synthetic

<400> SEQUENCE: 428
actcacccac tcgccaccgc 20

<210> SEQ ID NO 429
<211> LENGTH: 20
<212> TYPE: DNA
<213> ORGANISM: Artificial Sequence
<220> FEATURE:
<223> OTHER INFORMATION: Synthetic

<400> SEQUENCE: 429
cctcactcac ccactcgccc 20

<210> SEQ ID NO 430
<211> LENGTH: 20
<212> TYPE: DNA
<213> ORGANISM: Artificial Sequence
<220> FEATURE:
<223> OTHER INFORMATION: Synthetic

<400> SEQUENCE: 430
cctcactcac ccactcgccc 20

<210> SEQ ID NO 431
<211> LENGTH: 20
<212> TYPE: DNA
<213> ORGANISM: Artificial Sequence
<220> FEATURE:
<223> OTHER INFORMATION: Synthetic

<400> SEQUENCE: 431
cctcactcac ccactcgccu 20

<210> SEQ ID NO 432
<211> LENGTH: 20
<212> TYPE: DNA
<213> ORGANISM: Artificial Sequence
<220> FEATURE:
<223> OTHER INFORMATION: Synthetic

<400> SEQUENCE: 432
cctcactcac ccactcgccu 20

<210> SEQ ID NO 433
<211> LENGTH: 20
<212> TYPE: DNA
<213> ORGANISM: Artificial Sequence
<220> FEATURE:
<223> OTHER INFORMATION: Synthetic

<400> SEQUENCE: 433
cctcactcac ccactcgccg 20

<210> SEQ ID NO 434
<211> LENGTH: 20
<212> TYPE: DNA
<213> ORGANISM: Artificial Sequence
<220> FEATURE:
<223> OTHER INFORMATION: Synthetic

<400> SEQUENCE: 434
cctcactcac ccactcgccg 20

<210> SEQ ID NO 435
<211> LENGTH: 20
<212> TYPE: DNA
<213> ORGANISM: Artificial Sequence
<220> FEATURE:
<223> OTHER INFORMATION: Synthetic

<400> SEQUENCE: 435
cctcactcac ccactcgccg 20

<210> SEQ ID NO 436
<211> LENGTH: 20
<212> TYPE: DNA
<213> ORGANISM: Artificial Sequence
<220> FEATURE:
<223> OTHER INFORMATION: Synthetic

<400> SEQUENCE: 436
cctcactcac ccactcgccg 20

<210> SEQ ID NO 437
<211> LENGTH: 20
<212> TYPE: DNA
<213> ORGANISM: Artificial Sequence
<220> FEATURE:
<223> OTHER INFORMATION: Synthetic

<400> SEQUENCE: 437
cctcactcac ccactcgccg 20

<210> SEQ ID NO 438
<211> LENGTH: 20
<212> TYPE: DNA
<213> ORGANISM: Artificial Sequence
<220> FEATURE:
<223> OTHER INFORMATION: Synthetic

<400> SEQUENCE: 438
cctcactcac ccactcgccg 20

<210> SEQ ID NO 439
<211> LENGTH: 20
<212> TYPE: DNA
<213> ORGANISM: Artificial Sequence
<220> FEATURE:
<223> OTHER INFORMATION: Synthetic

<400> SEQUENCE: 439
cctcactcac ccactcgccg 20

<210> SEQ ID NO 440
<211> LENGTH: 20
<212> TYPE: DNA
<213> ORGANISM: Artificial Sequence
<220> FEATURE:
<223> OTHER INFORMATION: Synthetic

<400> SEQUENCE: 440
cctcactcac ccactcgccg 20

<210> SEQ ID NO 441
<211> LENGTH: 20
<212> TYPE: DNA
<213> ORGANISM: Artificial Sequence
<220> FEATURE:
<223> OTHER INFORMATION: Synthetic

<400> SEQUENCE: 441
cctcactcac ccactcgccg 20

<210> SEQ ID NO 442
<211> LENGTH: 20
<212> TYPE: DNA
<213> ORGANISM: Artificial Sequence
<220> FEATURE:
<223> OTHER INFORMATION: Synthetic

<400> SEQUENCE: 442
cctcactcac ccactcgccg 20

<210> SEQ ID NO 443
<211> LENGTH: 20
<212> TYPE: DNA
<213> ORGANISM: Artificial Sequence
<220> FEATURE:
<223> OTHER INFORMATION: Synthetic

<400> SEQUENCE: 443
cctcactcac ccactcgccg 20

<210> SEQ ID NO 444
<211> LENGTH: 20
<212> TYPE: DNA
<213> ORGANISM: Artificial Sequence
<220> FEATURE:
<223> OTHER INFORMATION: Synthetic

<400> SEQUENCE: 444
cctcactcac ccactcgccg 20

<210> SEQ ID NO 445
<211> LENGTH: 20
<212> TYPE: DNA
<213> ORGANISM: Artificial Sequence
<220> FEATURE:
<223> OTHER INFORMATION: Synthetic

<400> SEQUENCE: 445
cctcactcac ccactcgccg 20

<210> SEQ ID NO 446
<211> LENGTH: 20
<212> TYPE: DNA
<213> ORGANISM: Artificial Sequence
<220> FEATURE:
<223> OTHER INFORMATION: Synthetic

<400> SEQUENCE: 446
cctcactcac ccactcgccg 20

<210> SEQ ID NO 447
<211> LENGTH: 20
<212> TYPE: DNA
<213> ORGANISM: Artificial Sequence
<220> FEATURE:
<223> OTHER INFORMATION: Synthetic

<400> SEQUENCE: 447
cctcactcac ccactcgccc 20

<210> SEQ ID NO 448
<211> LENGTH: 20
<212> TYPE: DNA
<213> ORGANISM: Artificial Sequence
<220> FEATURE:
<223> OTHER INFORMATION: Synthetic

<400> SEQUENCE: 448
cctcactcac ccactcgccc 20

<210> SEQ ID NO 449

<211> LENGTH: 20
<212> TYPE: DNA
<213> ORGANISM: Artificial Sequence
<220> FEATURE:
<223> OTHER INFORMATION: Synthetic

<400> SEQUENCE: 449
cctcactcac ccactcgccu 20

<210> SEQ ID NO 450
<211> LENGTH: 20
<212> TYPE: DNA
<213> ORGANISM: Artificial Sequence
<220> FEATURE:
<223> OTHER INFORMATION: Synthetic

<400> SEQUENCE: 450
cctcactcac ccactcgccu 20

<210> SEQ ID NO 451
<211> LENGTH: 20
<212> TYPE: DNA
<213> ORGANISM: Artificial Sequence
<220> FEATURE:
<223> OTHER INFORMATION: Synthetic

<400> SEQUENCE: 451
cctcactcac ccactugccg 20

<210> SEQ ID NO 452
<211> LENGTH: 20
<212> TYPE: DNA
<213> ORGANISM: Artificial Sequence
<220> FEATURE:
<223> OTHER INFORMATION: Synthetic

<400> SEQUENCE: 452
cctcactcac ccactcgcug 20

<210> SEQ ID NO 453
<211> LENGTH: 20
<212> TYPE: DNA
<213> ORGANISM: Artificial Sequence
<220> FEATURE:
<223> OTHER INFORMATION: Synthetic

<400> SEQUENCE: 453
cctcactcac ccactugcug 20

<210> SEQ ID NO 454
<211> LENGTH: 19
<212> TYPE: DNA
<213> ORGANISM: Artificial Sequence
<220> FEATURE:
<223> OTHER INFORMATION: Synthetic

<400> SEQUENCE: 454
cctcactcac ccactugcc 19

<210> SEQ ID NO 455
<211> LENGTH: 20
<212> TYPE: DNA
<213> ORGANISM: Artificial Sequence
<220> FEATURE:
<223> OTHER INFORMATION: Synthetic

<400> SEQUENCE: 455
actcacccac ttgccaccgc 20

<210> SEQ ID NO 456
<211> LENGTH: 20
<212> TYPE: DNA
<213> ORGANISM: Artificial Sequence
<220> FEATURE:
<223> OTHER INFORMATION: Synthetic

<400> SEQUENCE: 456
actcacccac tcgccacugc 20

<210> SEQ ID NO 457
<211> LENGTH: 20
<212> TYPE: DNA
<213> ORGANISM: Artificial Sequence
<220> FEATURE:
<223> OTHER INFORMATION: Synthetic

<400> SEQUENCE: 457
actcacccac ttgccacugc 20

<210> SEQ ID NO 458
<211> LENGTH: 20
<212> TYPE: DNA
<213> ORGANISM: Artificial Sequence
<220> FEATURE:
<223> OTHER INFORMATION: Synthetic

<400> SEQUENCE: 458
actcacccac ttgccaccgc 20

<210> SEQ ID NO 459
<211> LENGTH: 20
<212> TYPE: DNA
<213> ORGANISM: Artificial Sequence
<220> FEATURE:
<223> OTHER INFORMATION: Synthetic

<400> SEQUENCE: 459
actcacccac tcgccacugc 20

<210> SEQ ID NO 460
<211> LENGTH: 20
<212> TYPE: DNA
<213> ORGANISM: Artificial Sequence
<220> FEATURE:
<223> OTHER INFORMATION: Synthetic

<400> SEQUENCE: 460
actcacccac ttgccacugc 20

<210> SEQ ID NO 461
<211> LENGTH: 20
<212> TYPE: DNA
<213> ORGANISM: Artificial Sequence
<220> FEATURE:
<223> OTHER INFORMATION: Synthetic

<400> SEQUENCE: 461
actcacccac ttgccaccgc 20

<210> SEQ ID NO 462
<211> LENGTH: 20
<212> TYPE: DNA

<213> ORGANISM: Artificial Sequence
<220> FEATURE:
<223> OTHER INFORMATION: Synthetic

<400> SEQUENCE: 462
actcacccac tcgccacugc 20

<210> SEQ ID NO 463
<211> LENGTH: 20
<212> TYPE: DNA
<213> ORGANISM: Artificial Sequence
<220> FEATURE:
<223> OTHER INFORMATION: Synthetic

<400> SEQUENCE: 463
actcacccac ttgccacugc 20

<210> SEQ ID NO 464
<211> LENGTH: 20
<212> TYPE: DNA
<213> ORGANISM: Artificial Sequence
<220> FEATURE:
<223> OTHER INFORMATION: Synthetic

<400> SEQUENCE: 464
actcacccac ttgccaccgc 20

<210> SEQ ID NO 465
<211> LENGTH: 20
<212> TYPE: DNA
<213> ORGANISM: Artificial Sequence
<220> FEATURE:
<223> OTHER INFORMATION: Synthetic

<400> SEQUENCE: 465
actcacccac tcgccacugc 20

<210> SEQ ID NO 466
<211> LENGTH: 20
<212> TYPE: DNA
<213> ORGANISM: Artificial Sequence
<220> FEATURE:
<223> OTHER INFORMATION: Synthetic

<400> SEQUENCE: 466
actcacccac ttgccacugc 20

<210> SEQ ID NO 467
<211> LENGTH: 20
<212> TYPE: DNA
<213> ORGANISM: Artificial Sequence
<220> FEATURE:
<223> OTHER INFORMATION: Synthetic

<400> SEQUENCE: 467
actcacccac ttgccaccgc 20

<210> SEQ ID NO 468
<211> LENGTH: 20
<212> TYPE: DNA
<213> ORGANISM: Artificial Sequence
<220> FEATURE:
<223> OTHER INFORMATION: Synthetic

<400> SEQUENCE: 468
actcacccac ttgccaccgc 20

<210> SEQ ID NO 469
<211> LENGTH: 20
<212> TYPE: DNA
<213> ORGANISM: Artificial Sequence
<220> FEATURE:
<223> OTHER INFORMATION: Synthetic

<400> SEQUENCE: 469
actcacccac ttgccaccgc 20

<210> SEQ ID NO 470
<211> LENGTH: 20
<212> TYPE: DNA
<213> ORGANISM: Artificial Sequence
<220> FEATURE:
<223> OTHER INFORMATION: Synthetic

<400> SEQUENCE: 470
actcacccac ttgccaccgc 20

<210> SEQ ID NO 471
<211> LENGTH: 20
<212> TYPE: DNA
<213> ORGANISM: Artificial Sequence
<220> FEATURE:
<223> OTHER INFORMATION: Synthetic

<400> SEQUENCE: 471
actcacccac ttgccaccgc 20

<210> SEQ ID NO 472
<211> LENGTH: 20
<212> TYPE: DNA
<213> ORGANISM: Artificial Sequence
<220> FEATURE:
<223> OTHER INFORMATION: Synthetic

<400> SEQUENCE: 472
actcacccac ttgccaccgc 20

<210> SEQ ID NO 473
<211> LENGTH: 20
<212> TYPE: DNA
<213> ORGANISM: Artificial Sequence
<220> FEATURE:
<223> OTHER INFORMATION: Synthetic

<400> SEQUENCE: 473
cctcactcac ccactugcca 20

<210> SEQ ID NO 474
<211> LENGTH: 20
<212> TYPE: DNA
<213> ORGANISM: Artificial Sequence
<220> FEATURE:
<223> OTHER INFORMATION: Synthetic

<400> SEQUENCE: 474
cctcactcac ccactugcca 20

<210> SEQ ID NO 475
<211> LENGTH: 20
<212> TYPE: DNA
<213> ORGANISM: Artificial Sequence
<220> FEATURE:

<223> OTHER INFORMATION: Synthetic

<400> SEQUENCE: 475
cctcactcac ccactcgcua 20

<210> SEQ ID NO 476
<211> LENGTH: 20
<212> TYPE: DNA
<213> ORGANISM: Artificial Sequence
<220> FEATURE:
<223> OTHER INFORMATION: Synthetic

<400> SEQUENCE: 476
cctcactcac ccactugcua 20

<210> SEQ ID NO 477
<211> LENGTH: 20
<212> TYPE: DNA
<213> ORGANISM: Artificial Sequence
<220> FEATURE:
<223> OTHER INFORMATION: Synthetic

<400> SEQUENCE: 477
cctcactcac ccactcgccg 20

<210> SEQ ID NO 478
<211> LENGTH: 19
<212> TYPE: DNA
<213> ORGANISM: Artificial Sequence
<220> FEATURE:
<223> OTHER INFORMATION: Synthetic

<400> SEQUENCE: 478
cctcactcac ccactcgcc 19

<210> SEQ ID NO 479
<211> LENGTH: 19
<212> TYPE: DNA
<213> ORGANISM: Artificial Sequence
<220> FEATURE:
<223> OTHER INFORMATION: Synthetic

<400> SEQUENCE: 479
cctcactcac ccactcgcc 19

<210> SEQ ID NO 480
<211> LENGTH: 20
<212> TYPE: DNA
<213> ORGANISM: Artificial Sequence
<220> FEATURE:
<223> OTHER INFORMATION: Synthetic

<400> SEQUENCE: 480
cctcactcac ccactugcug 20

<210> SEQ ID NO 481
<211> LENGTH: 20
<212> TYPE: DNA
<213> ORGANISM: Artificial Sequence
<220> FEATURE:
<223> OTHER INFORMATION: Synthetic

<400> SEQUENCE: 481
cctcactcac ccactcgcca 20

-continued

<210> SEQ ID NO 482
<211> LENGTH: 20
<212> TYPE: DNA
<213> ORGANISM: Artificial Sequence
<220> FEATURE:
<223> OTHER INFORMATION: Synthetic

<400> SEQUENCE: 482
cctcactcac ccactcgccg 20

<210> SEQ ID NO 483
<211> LENGTH: 20
<212> TYPE: DNA
<213> ORGANISM: Artificial Sequence
<220> FEATURE:
<223> OTHER INFORMATION: Synthetic

<400> SEQUENCE: 483
cctcactcac ccactcgcca 20

<210> SEQ ID NO 484
<211> LENGTH: 20
<212> TYPE: DNA
<213> ORGANISM: Artificial Sequence
<220> FEATURE:
<223> OTHER INFORMATION: Synthetic

<400> SEQUENCE: 484
cctcactcac ccactcgccg 20

<210> SEQ ID NO 485
<211> LENGTH: 20
<212> TYPE: DNA
<213> ORGANISM: Artificial Sequence
<220> FEATURE:
<223> OTHER INFORMATION: Synthetic

<400> SEQUENCE: 485
cctcactcac ccactcgcca 20

<210> SEQ ID NO 486
<211> LENGTH: 20
<212> TYPE: DNA
<213> ORGANISM: Artificial Sequence
<220> FEATURE:
<223> OTHER INFORMATION: Synthetic

<400> SEQUENCE: 486
cctcactcac ccactcgccg 20

<210> SEQ ID NO 487
<211> LENGTH: 20
<212> TYPE: DNA
<213> ORGANISM: Artificial Sequence
<220> FEATURE:
<223> OTHER INFORMATION: Synthetic

<400> SEQUENCE: 487
actcacccac tcgccaccgc 20

<210> SEQ ID NO 488
<211> LENGTH: 20
<212> TYPE: DNA
<213> ORGANISM: Artificial Sequence
<220> FEATURE:
<223> OTHER INFORMATION: Synthetic -continued

<400> SEQUENCE: 488
actcacccac tcgccaccgc 20

<210> SEQ ID NO 489
<211> LENGTH: 20
<212> TYPE: DNA
<213> ORGANISM: Artificial Sequence
<220> FEATURE:
<223> OTHER INFORMATION: Synthetic

<400> SEQUENCE: 489
actcacccac tcgccaccgc 20

<210> SEQ ID NO 490
<211> LENGTH: 20
<212> TYPE: DNA
<213> ORGANISM: Artificial Sequence
<220> FEATURE:
<223> OTHER INFORMATION: Synthetic

<400> SEQUENCE: 490
actcacccac tcgccaccgc 20

<210> SEQ ID NO 491
<211> LENGTH: 20
<212> TYPE: DNA
<213> ORGANISM: Artificial Sequence
<220> FEATURE:
<223> OTHER INFORMATION: Synthetic

<400> SEQUENCE: 491
actcacccac tcgccaccgc 20

<210> SEQ ID NO 492
<211> LENGTH: 20
<212> TYPE: DNA
<213> ORGANISM: Artificial Sequence
<220> FEATURE:
<223> OTHER INFORMATION: Synthetic

<400> SEQUENCE: 492
actcacccac tcgccaccgc 20

<210> SEQ ID NO 493
<211> LENGTH: 20
<212> TYPE: DNA
<213> ORGANISM: Artificial Sequence
<220> FEATURE:
<223> OTHER INFORMATION: Synthetic

<400> SEQUENCE: 493
actcacccac tcgccaccgc 20

<210> SEQ ID NO 494
<211> LENGTH: 20
<212> TYPE: DNA
<213> ORGANISM: Artificial Sequence
<220> FEATURE:
<223> OTHER INFORMATION: Synthetic

<400> SEQUENCE: 494
actcacccac tcgccacugc 20

<210> SEQ ID NO 495
<211> LENGTH: 20

-continued

<212> TYPE: DNA
<213> ORGANISM: Artificial Sequence
<220> FEATURE:
<223> OTHER INFORMATION: Synthetic

<400> SEQUENCE: 495
actcacccac tcgccacugc 20

<210> SEQ ID NO 496
<211> LENGTH: 20
<212> TYPE: DNA
<213> ORGANISM: Artificial Sequence
<220> FEATURE:
<223> OTHER INFORMATION: Synthetic

<400> SEQUENCE: 496
actcacccac tcgccacugc 20

<210> SEQ ID NO 497
<211> LENGTH: 20
<212> TYPE: DNA
<213> ORGANISM: Artificial Sequence
<220> FEATURE:
<223> OTHER INFORMATION: Synthetic

<400> SEQUENCE: 497
actcacccac tcgccacugc 20

<210> SEQ ID NO 498
<211> LENGTH: 20
<212> TYPE: DNA
<213> ORGANISM: Artificial Sequence
<220> FEATURE:
<223> OTHER INFORMATION: Synthetic

<400> SEQUENCE: 498
actcacccac tcgccacugc 20

<210> SEQ ID NO 499
<211> LENGTH: 20
<212> TYPE: DNA
<213> ORGANISM: Artificial Sequence
<220> FEATURE:
<223> OTHER INFORMATION: Synthetic

<400> SEQUENCE: 499
cctcactcac ccactcgccg 20

<210> SEQ ID NO 500
<211> LENGTH: 20
<212> TYPE: DNA
<213> ORGANISM: Artificial Sequence
<220> FEATURE:
<223> OTHER INFORMATION: Synthetic

<400> SEQUENCE: 500
cctcactcac ccactcgccg 20

<210> SEQ ID NO 501
<211> LENGTH: 20
<212> TYPE: DNA
<213> ORGANISM: Artificial Sequence
<220> FEATURE:
<223> OTHER INFORMATION: Synthetic

<400> SEQUENCE: 501
cctcactcac ccactcgccg 20

<210> SEQ ID NO 502
<211> LENGTH: 20
<212> TYPE: DNA
<213> ORGANISM: Artificial Sequence
<220> FEATURE:
<223> OTHER INFORMATION: Synthetic

<400> SEQUENCE: 502
cctcactcac ccactcgccg 20

<210> SEQ ID NO 503
<211> LENGTH: 20
<212> TYPE: DNA
<213> ORGANISM: Artificial Sequence
<220> FEATURE:
<223> OTHER INFORMATION: Synthetic

<400> SEQUENCE: 503
cctcactcac ccactcgccg 20

<210> SEQ ID NO 504
<211> LENGTH: 20
<212> TYPE: DNA
<213> ORGANISM: Artificial Sequence
<220> FEATURE:
<223> OTHER INFORMATION: Synthetic

<400> SEQUENCE: 504
cctcactcac ccactcgccg 20

<210> SEQ ID NO 505
<211> LENGTH: 20
<212> TYPE: DNA
<213> ORGANISM: Artificial Sequence
<220> FEATURE:
<223> OTHER INFORMATION: Synthetic

<400> SEQUENCE: 505
cctcactcac ccactcgccg 20

<210> SEQ ID NO 506
<211> LENGTH: 20
<212> TYPE: DNA
<213> ORGANISM: Artificial Sequence
<220> FEATURE:
<223> OTHER INFORMATION: Synthetic

<400> SEQUENCE: 506
cctcactcac ccactugcug 20

<210> SEQ ID NO 507
<211> LENGTH: 20
<212> TYPE: DNA
<213> ORGANISM: Artificial Sequence
<220> FEATURE:
<223> OTHER INFORMATION: Synthetic

<400> SEQUENCE: 507
ccucactcac ccacttgctg 20

<210> SEQ ID NO 508
<211> LENGTH: 20
<212> TYPE: DNA
<213> ORGANISM: Artificial Sequence
<220> FEATURE:
<223> OTHER INFORMATION: Synthetic

<400> SEQUENCE: 508
cctcactcac ccacttgctg 20

<210> SEQ ID NO 509
<211> LENGTH: 20
<212> TYPE: DNA
<213> ORGANISM: Artificial Sequence
<220> FEATURE:
<223> OTHER INFORMATION: Synthetic

<400> SEQUENCE: 509
cctcactcac ccactugcug 20

<210> SEQ ID NO 510
<211> LENGTH: 20
<212> TYPE: DNA
<213> ORGANISM: Artificial Sequence
<220> FEATURE:
<223> OTHER INFORMATION: Synthetic

<400> SEQUENCE: 510
ccucactcac ccacttgctg 20

<210> SEQ ID NO 511
<211> LENGTH: 20
<212> TYPE: DNA
<213> ORGANISM: Artificial Sequence
<220> FEATURE:
<223> OTHER INFORMATION: Synthetic

<400> SEQUENCE: 511
cctcactcac ccacttgctg 20

<210> SEQ ID NO 512
<211> LENGTH: 20
<212> TYPE: DNA
<213> ORGANISM: Artificial Sequence
<220> FEATURE:
<223> OTHER INFORMATION: Synthetic

<400> SEQUENCE: 512
cctcactcac ccacttgctg 20

<210> SEQ ID NO 513
<211> LENGTH: 20
<212> TYPE: DNA
<213> ORGANISM: Artificial Sequence
<220> FEATURE:
<223> OTHER INFORMATION: Synthetic

<400> SEQUENCE: 513
actcacccac tcgccacugc 20

<210> SEQ ID NO 514
<211> LENGTH: 20
<212> TYPE: DNA
<213> ORGANISM: Artificial Sequence
<220> FEATURE:
<223> OTHER INFORMATION: Synthetic

<400> SEQUENCE: 514
cctcactcac ccacttgcca 20

<210> SEQ ID NO 515
<211> LENGTH: 19
<212> TYPE: DNA
<213> ORGANISM: Artificial Sequence
<220> FEATURE:
<223> OTHER INFORMATION: Synthetic

<400> SEQUENCE: 515
cctcactcac ccacttgcc 19

<210> SEQ ID NO 516
<211> LENGTH: 20
<212> TYPE: DNA
<213> ORGANISM: Artificial Sequence
<220> FEATURE:
<223> OTHER INFORMATION: Synthetic

<400> SEQUENCE: 516
actcacccac tcgccactgc 20

<210> SEQ ID NO 517
<211> LENGTH: 20
<212> TYPE: DNA
<213> ORGANISM: Artificial Sequence
<220> FEATURE:
<223> OTHER INFORMATION: Synthetic

<400> SEQUENCE: 517
actcacccac tcgccaccgc 20

<210> SEQ ID NO 518
<211> LENGTH: 20
<212> TYPE: DNA
<213> ORGANISM: Artificial Sequence
<220> FEATURE:
<223> OTHER INFORMATION: Synthetic

<400> SEQUENCE: 518
actcacccac tcgccaccgc 20

<210> SEQ ID NO 519
<211> LENGTH: 20
<212> TYPE: DNA
<213> ORGANISM: Artificial Sequence
<220> FEATURE:
<223> OTHER INFORMATION: Synthetic

<400> SEQUENCE: 519
actcacccac tcgccaccgc 20

<210> SEQ ID NO 520
<211> LENGTH: 20
<212> TYPE: DNA
<213> ORGANISM: Artificial Sequence
<220> FEATURE:
<223> OTHER INFORMATION: Synthetic

<400> SEQUENCE: 520
actcacccac tcgccaccgc 20

<210> SEQ ID NO 521
<211> LENGTH: 20
<212> TYPE: DNA
<213> ORGANISM: Artificial Sequence
<220> FEATURE:
<223> OTHER INFORMATION: Synthetic

<400> SEQUENCE: 521
actcacccac tcgccaccgc 20

<210> SEQ ID NO 522
<211> LENGTH: 20
<212> TYPE: DNA
<213> ORGANISM: Artificial Sequence
<220> FEATURE:
<223> OTHER INFORMATION: Synthetic

<400> SEQUENCE: 522
actcacccac tcgccaccgc 20

<210> SEQ ID NO 523
<211> LENGTH: 20
<212> TYPE: DNA
<213> ORGANISM: Artificial Sequence
<220> FEATURE:
<223> OTHER INFORMATION: Synthetic

<400> SEQUENCE: 523
actcacccac tcgccaccgc 20

<210> SEQ ID NO 524
<211> LENGTH: 20
<212> TYPE: DNA
<213> ORGANISM: Artificial Sequence
<220> FEATURE:
<223> OTHER INFORMATION: Synthetic

<400> SEQUENCE: 524
actcacccac tcgccaccgc 20

<210> SEQ ID NO 525
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is inosine
<220> FEATURE:
<221> NAME/KEY: misc_feature
<222> LOCATION: (5)..(5)
<223> OTHER INFORMATION: n is inosine

<400> SEQUENCE: 525
nctcncccac tcgccaccgc 20

<210> SEQ ID NO 526
<211> LENGTH: 51
<212> TYPE: PRT
<213> ORGANISM: Artificial Sequence
<220> FEATURE:
<223> OTHER INFORMATION: Synthetic

<400> SEQUENCE: 526

```
Gly Ala Gly Ala Gly Ala Gly Ala Gly Ala Gly Ala Gly Ala Gly Ala
1               5                   10                  15

Gly Ala Gly Ala Trp Ser Gly Arg Ala Arg Gly Arg Ala Arg Gly Gly
            20                  25                  30

Ala Ala Val Ala Val Pro Ala Pro Ala Ala Ala Glu Ala Gln Ala Val
        35                  40                  45
```

Ala Ser Gly
50

<210> SEQ ID NO 527
<211> LENGTH: 52
<212> TYPE: PRT
<213> ORGANISM: Artificial Sequence
<220> FEATURE:
<223> OTHER INFORMATION: Synthetic

<400> SEQUENCE: 527

Gly Pro Gly Pro Gly Pro Gly Pro Gly Pro Gly Pro Gly Pro Gly Pro
1 5 10 15

Gly Pro Gly Arg Gly Arg Gly Gly Pro Gly Gly Gly Pro Gly Ala Gly
20 25 30

Leu Arg Leu Arg Cys Leu Arg Pro Arg Arg Arg Arg Arg Arg Arg Trp
35 40 45

Arg Val Gly Glu
50

<210> SEQ ID NO 528
<211> LENGTH: 72
<212> TYPE: PRT
<213> ORGANISM: Artificial Sequence
<220> FEATURE:
<223> OTHER INFORMATION: Synthetic

<400> SEQUENCE: 528

Gly Arg Gly Arg Gly Arg Gly Arg Gly Arg Gly Arg Gly Arg Gly Arg
1 5 10 15

Gly Arg Gly Val Val Gly Ala Gly Pro Gly Ala Gly Pro Gly Arg Gly
20 25 30

Cys Gly Cys Gly Ala Cys Ala Arg Gly Gly Gly Gly Ala Gly Gly Gly
35 40 45

Glu Trp Val Ser Glu Glu Ala Ala Ser Trp Arg Val Ala Val Trp Gly
50 55 60

Ser Ala Ala Gly Lys Arg Arg Gly
65 70

<210> SEQ ID NO 529
<211> LENGTH: 24
<212> TYPE: PRT
<213> ORGANISM: Artificial Sequence
<220> FEATURE:
<223> OTHER INFORMATION: Synthetic

<400> SEQUENCE: 529

Pro Arg Pro Arg Pro Arg Pro Arg Pro Arg Pro Arg Pro Arg Pro Arg
1 5 10 15

Pro Arg Pro Leu Ala Arg Asp Ser
20

<210> SEQ ID NO 530
<211> LENGTH: 18
<212> TYPE: PRT
<213> ORGANISM: Artificial Sequence
<220> FEATURE:
<223> OTHER INFORMATION: Synthetic

<400> SEQUENCE: 530

Gly Pro Gly Pro Gly Pro Gly Pro Gly Pro Gly Pro Gly Pro Gly Pro
1 5 10 15

Gly Pro

<210> SEQ ID NO 531
<211> LENGTH: 42
<212> TYPE: PRT
<213> ORGANISM: Artificial Sequence
<220> FEATURE:
<223> OTHER INFORMATION: Synthetic

<400> SEQUENCE: 531

Pro Ala Pro Ala Pro Ala Pro Ala Pro Ala Pro Ala Pro Ala Pro Ala
1 5 10 15

Pro Ala Pro Ser Ala Arg Leu Leu Ser Ser Arg Ala Cys Tyr Arg Leu
20 25 30

Arg Leu Phe Pro Ser Leu Phe Ser Ser Gly
35 40

<210> SEQ ID NO 532
<211> LENGTH: 20
<212> TYPE: DNA
<213> ORGANISM: Artificial Sequence
<220> FEATURE:
<223> OTHER INFORMATION: Synthetic

<400> SEQUENCE: 532
actcacccac tcgccaccgc 20

<210> SEQ ID NO 533
<211> LENGTH: 6000
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: In some embodiments, “GGGGCC” repeats 30 times or more. The remaining “GGGGCC” may or may not be present.
<220> FEATURE:
<221> NAME/KEY: misc_feature
<223> OTHER INFORMATION: In some embodiments, “GGGGCC” repeats 50 times or more. The remaining “GGGGCC” may or may not be present.
<220> FEATURE:
<221> NAME/KEY: misc_feature
<223> OTHER INFORMATION: In some embodiments, “GGGGCC” repeats 100 times or more. The remaining “GGGGCC” may or may not be present.
<220> FEATURE:
<221> NAME/KEY: misc_feature
<223> OTHER INFORMATION: In some embodiments, “GGGGCC” repeats 150 times or more. The remaining “GGGGCC” may or may not be present.
<220> FEATURE:
<221> NAME/KEY: misc_feature
<223> OTHER INFORMATION: In some embodiments, “GGGGCC” repeats 200 times or more. The remaining “GGGGCC” may or may not be present.
<220> FEATURE:
<221> NAME/KEY: misc_feature
<223> OTHER INFORMATION: In some embodiments, “GGGGCC” repeats 300 times or more. The remaining “GGGGCC” may or may not be present.
<220> FEATURE:
<221> NAME/KEY: misc_feature
<223> OTHER INFORMATION: In some embodiments, “GGGGCC” repeats 400 times or more. The remaining “GGGGCC” may or may not be present.
<220> FEATURE:
<221> NAME/KEY: misc_feature
<223> OTHER INFORMATION: In some embodiments, “GGGGCC” repeats 500 times or more. The remaining “GGGGCC” may or may not be present.
<220> FEATURE:
<221> NAME/KEY: misc_feature
<223> OTHER INFORMATION: In some embodiments, “GGGGCC” repeats 600 times or more. The remaining “GGGGCC” may or may not be present.
<220> FEATURE:
<221> NAME/KEY: misc_feature
<223> OTHER INFORMATION: In some embodiments, "GGGGCC" repeats 700 times or more. The remaining "GGGGCC" may or may not be present.
<220> FEATURE:
<221> NAME/KEY: misc_feature
<223> OTHER INFORMATION: In some embodiments, "GGGGCC" repeats 800 times or more. The remaining "GGGGCC" may or may not be present.
<220> FEATURE:
<221> NAME/KEY: misc_feature
<223> OTHER INFORMATION: In some embodiments, "GGGGCC" repeats 900 times or more. The remaining "GGGGCC" may or may not be present.
<220> FEATURE:
<221> NAME/KEY: misc_feature
<223> OTHER INFORMATION: In some embodiments, "GGGGCC" repeats 1000 times or more.

<400> SEQUENCE: 533
ggggccgggg ccggggccgg ggccggggcc ggggccgggg ccggggccgg ggccggggcc 60
ggggccgggg ccggggccgg ggccggggcc ggggccgggg ccggggccgg ggccggggcc 120
ggggccgggg ccggggccgg ggccggggcc ggggccgggg ccggggccgg ggccggggcc 180
ggggccgggg ccggggccgg ggccggggcc ggggccgggg ccggggccgg ggccggggcc 240
ggggccgggg ccggggccgg ggccggggcc ggggccgggg ccggggccgg ggccggggcc 300
ggggccgggg ccggggccgg ggccggggcc ggggccgggg ccggggccgg ggccggggcc 360
ggggccgggg ccggggccgg ggccggggcc ggggccgggg ccggggccgg ggccggggcc 420
ggggccgggg ccggggccgg ggccggggcc ggggccgggg ccggggccgg ggccggggcc 480
ggggccgggg ccggggccgg ggccggggcc ggggccgggg ccggggccgg ggccggggcc 540
ggggccgggg ccggggccgg ggccggggcc ggggccgggg ccggggccgg ggccggggcc 600
ggggccgggg ccggggccgg ggccggggcc ggggccgggg ccggggccgg ggccggggcc 660
ggggccgggg ccggggccgg ggccggggcc ggggccgggg ccggggccgg ggccggggcc 720
ggggccgggg ccggggccgg ggccggggcc ggggccgggg ccggggccgg ggccggggcc 780
ggggccgggg ccggggccgg ggccggggcc ggggccgggg ccggggccgg ggccggggcc 840
ggggccgggg ccggggccgg ggccggggcc ggggccgggg ccggggccgg ggccggggcc 900
ggggccgggg ccggggccgg ggccggggcc ggggccgggg ccggggccgg ggccggggcc 960
ggggccgggg ccggggccgg ggccggggcc ggggccgggg ccggggccgg ggccggggcc 1020
ggggccgggg ccggggccgg ggccggggcc ggggccgggg ccggggccgg ggccggggcc 1080
ggggccgggg ccggggccgg ggccggggcc ggggccgggg ccggggccgg ggccggggcc 1140
ggggccgggg ccggggccgg ggccggggcc ggggccgggg ccggggccgg ggccggggcc 1200
ggggccgggg ccggggccgg ggccggggcc ggggccgggg ccggggccgg ggccggggcc 1260
ggggccgggg ccggggccgg ggccggggcc ggggccgggg ccggggccgg ggccggggcc 1320
ggggccgggg ccggggccgg ggccggggcc ggggccgggg ccggggccgg ggccggggcc 1380
ggggccgggg ccggggccgg ggccggggcc ggggccgggg ccggggccgg ggccggggcc 1440
ggggccgggg ccggggccgg ggccggggcc ggggccgggg ccggggccgg ggccggggcc 1500
ggggccgggg ccggggccgg ggccggggcc ggggccgggg ccggggccgg ggccggggcc 1560
ggggccgggg ccggggccgg ggccggggcc ggggccgggg ccggggccgg ggccggggcc 1620
ggggccgggg ccggggccgg ggccggggcc ggggccgggg ccggggccgg ggccggggcc 1680
ggggccgggg ccggggccgg ggccggggcc ggggccgggg ccggggccgg ggccggggcc 1740
ggggccgggg ccggggccgg ggccggggcc ggggccgggg ccggggccgg ggccggggcc 1800
ggggccgggg ccggggccgg ggccggggcc ggggccgggg ccggggccgg ggccggggcc 1860

-continued ggggccgggg ccggggccgg ggccggggcc ggggccgggg ccggggccgg ggccggggcc 1920
ggggccgggg ccggggccgg ggccggggcc ggggccgggg ccggggccgg ggccggggcc 1980
ggggccgggg ccggggccgg ggccggggcc ggggccgggg ccggggccgg ggccggggcc 2040
ggggccgggg ccggggccgg ggccggggcc ggggccgggg ccggggccgg ggccggggcc 2100
ggggccgggg ccggggccgg ggccggggcc ggggccgggg ccggggccgg ggccggggcc 2160
ggggccgggg ccggggccgg ggccggggcc ggggccgggg ccggggccgg ggccggggcc 2220
ggggccgggg ccggggccgg ggccggggcc ggggccgggg ccggggccgg ggccggggcc 2280
ggggccgggg ccggggccgg ggccggggcc ggggccgggg ccggggccgg ggccggggcc 2340
ggggccgggg ccggggccgg ggccggggcc ggggccgggg ccggggccgg ggccggggcc 2400
ggggccgggg ccggggccgg ggccggggcc ggggccgggg ccggggccgg ggccggggcc 2460
ggggccgggg ccggggccgg ggccggggcc ggggccgggg ccggggccgg ggccggggcc 2520
ggggccgggg ccggggccgg ggccggggcc ggggccgggg ccggggccgg ggccggggcc 2580
ggggccgggg ccggggccgg ggccggggcc ggggccgggg ccggggccgg ggccggggcc 2640
ggggccgggg ccggggccgg ggccggggcc ggggccgggg ccggggccgg ggccggggcc 2700
ggggccgggg ccggggccgg ggccggggcc ggggccgggg ccggggccgg ggccggggcc 2760
ggggccgggg ccggggccgg ggccggggcc ggggccgggg ccggggccgg ggccggggcc 2820
ggggccgggg ccggggccgg ggccggggcc ggggccgggg ccggggccgg ggccggggcc 2880
ggggccgggg ccggggccgg ggccggggcc ggggccgggg ccggggccgg ggccggggcc 2940
ggggccgggg ccggggccgg ggccggggcc ggggccgggg ccggggccgg ggccggggcc 3000
ggggccgggg ccggggccgg ggccggggcc ggggccgggg ccggggccgg ggccggggcc 3060
ggggccgggg ccggggccgg ggccggggcc ggggccgggg ccggggccgg ggccggggcc 3120
ggggccgggg ccggggccgg ggccggggcc ggggccgggg ccggggccgg ggccggggcc 3180
ggggccgggg ccggggccgg ggccggggcc ggggccgggg ccggggccgg ggccggggcc 3240
ggggccgggg ccggggccgg ggccggggcc ggggccgggg ccggggccgg ggccggggcc 3300
ggggccgggg ccggggccgg ggccggggcc ggggccgggg ccggggccgg ggccggggcc 3360
ggggccgggg ccggggccgg ggccggggcc ggggccgggg ccggggccgg ggccggggcc 3420
ggggccgggg ccggggccgg ggccggggcc ggggccgggg ccggggccgg ggccggggcc 3480
ggggccgggg ccggggccgg ggccggggcc ggggccgggg ccggggccgg ggccggggcc 3540
ggggccgggg ccggggccgg ggccggggcc ggggccgggg ccggggccgg ggccggggcc 3600
ggggccgggg ccggggccgg ggccggggcc ggggccgggg ccggggccgg ggccggggcc 3660
ggggccgggg ccggggccgg ggccggggcc ggggccgggg ccggggccgg ggccggggcc 3720
ggggccgggg ccggggccgg ggccggggcc ggggccgggg ccggggccgg ggccggggcc 3780
ggggccgggg ccggggccgg ggccggggcc ggggccgggg ccggggccgg ggccggggcc 3840
ggggccgggg ccggggccgg ggccggggcc ggggccgggg ccggggccgg ggccggggcc 3900
ggggccgggg ccggggccgg ggccggggcc ggggccgggg ccggggccgg ggccggggcc 3960
ggggccgggg ccggggccgg ggccggggcc ggggccgggg ccggggccgg ggccggggcc 4020
ggggccgggg ccggggccgg ggccggggcc ggggccgggg ccggggccgg ggccggggcc 4080
ggggccgggg ccggggccgg ggccggggcc ggggccgggg ccggggccgg ggccggggcc 4140
ggggccgggg ccggggccgg ggccggggcc ggggccgggg ccggggccgg ggccggggcc 4200
ggggccgggg ccggggccgg ggccggggcc ggggccgggg ccggggccgg ggccggggcc 4260

-continued gggggccgggg ccggggccgg ggccggggcc ggggccgggg ccggggccgg ggccggggcc 4320
ggggccgggg ccggggccgg ggccggggcc ggggccgggg ccggggccgg ggccggggcc 4380
ggggccgggg ccggggccgg ggccggggcc ggggccgggg ccggggccgg ggccggggcc 4440
ggggccgggg ccggggccgg ggccggggcc ggggccgggg ccggggccgg ggccggggcc 4500
ggggccgggg ccggggccgg ggccggggcc ggggccgggg ccggggccgg ggccggggcc 4560
ggggccgggg ccggggccgg ggccggggcc ggggccgggg ccggggccgg ggccggggcc 4620
ggggccgggg ccggggccgg ggccggggcc ggggccgggg ccggggccgg ggccggggcc 4680
ggggccgggg ccggggccgg ggccggggcc ggggccgggg ccggggccgg ggccggggcc 4740
ggggccgggg ccggggccgg ggccggggcc ggggccgggg ccggggccgg ggccggggcc 4800
ggggccgggg ccggggccgg ggccggggcc ggggccgggg ccggggccgg ggccggggcc 4860
ggggccgggg ccggggccgg ggccggggcc ggggccgggg ccggggccgg ggccggggcc 4920
ggggccgggg ccggggccgg ggccggggcc ggggccgggg ccggggccgg ggccggggcc 4980
ggggccgggg ccggggccgg ggccggggcc ggggccgggg ccggggccgg ggccggggcc 5040
ggggccgggg ccggggccgg ggccggggcc ggggccgggg ccggggccgg ggccggggcc 5100
ggggccgggg ccggggccgg ggccggggcc ggggccgggg ccggggccgg ggccggggcc 5160
ggggccgggg ccggggccgg ggccggggcc ggggccgggg ccggggccgg ggccggggcc 5220
ggggccgggg ccggggccgg ggccggggcc ggggccgggg ccggggccgg ggccggggcc 5280
ggggccgggg ccggggccgg ggccggggcc ggggccgggg ccggggccgg ggccggggcc 5340
ggggccgggg ccggggccgg ggccggggcc ggggccgggg ccggggccgg ggccggggcc 5400
ggggccgggg ccggggccgg ggccggggcc ggggccgggg ccggggccgg ggccggggcc 5460
ggggccgggg ccggggccgg ggccggggcc ggggccgggg ccggggccgg ggccggggcc 5520
ggggccgggg ccggggccgg ggccggggcc ggggccgggg ccggggccgg ggccggggcc 5580
ggggccgggg ccggggccgg ggccggggcc ggggccgggg ccggggccgg ggccggggcc 5640
ggggccgggg ccggggccgg ggccggggcc ggggccgggg ccggggccgg ggccggggcc 5700
ggggccgggg ccggggccgg ggccggggcc ggggccgggg ccggggccgg ggccggggcc 5760
ggggccgggg ccggggccgg ggccggggcc ggggccgggg ccggggccgg ggccggggcc 5820
ggggccgggg ccggggccgg ggccggggcc ggggccgggg ccggggccgg ggccggggcc 5880
ggggccgggg ccggggccgg ggccggggcc ggggccgggg ccggggccgg ggccggggcc 5940
ggggccgggg ccggggccgg ggccggggcc ggggccgggg ccggggccgg ggccggggcc 6000

<210> SEQ ID NO 534
<211> LENGTH: 3000
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: In some embodiments, "GGGGCC" repeats 30 times or more. The remaining "GGGGCC" may or may not be present.
<220> FEATURE:
<221> NAME/KEY: misc_feature
<223> OTHER INFORMATION: In some embodiments, "GGGGCC" repeats 50 times or more. The remaining "GGGGCC" may or may not be present.
<220> FEATURE:
<221> NAME/KEY: misc_feature
<223> OTHER INFORMATION: In some embodiments, "GGGGCC" repeats 100 times or more. The remaining "GGGGCC" may or may not be present.
<220> FEATURE:

-continued

<221> NAME/KEY: misc_feature
<223> OTHER INFORMATION: In some embodiments, "GGGGCC" repeats 200 times
or more. The remaining "GGGGCC" may or may not be present.
<220> FEATURE:
<221> NAME/KEY: misc_feature
<223> OTHER INFORMATION: In some embodiments, "GGGGCC" repeats 300 times
or more. The remaining "GGGGCC" may or may not be present.
<220> FEATURE:
<221> NAME/KEY: misc_feature
<223> OTHER INFORMATION: In some embodiments, "GGGGCC" repeats 400 times
or more. The remaining "GGGGCC" may or may not be present.
<220> FEATURE:
<221> NAME/KEY: misc_feature
<223> OTHER INFORMATION: In some embodiments, "GGGGCC" repeats 500 times
or more.

<400> SEQUENCE: 534
ggggccgggg ccggggccgg ggccggggcc ggggccgggg ccggggccgg ggccggggcc 60
ggggccgggg ccggggccgg ggccggggcc ggggccgggg ccggggccgg ggccggggcc 120
ggggccgggg ccggggccgg ggccggggcc ggggccgggg ccggggccgg ggccggggcc 180
ggggccgggg ccggggccgg ggccggggcc ggggccgggg ccggggccgg ggccggggcc 240
ggggccgggg ccggggccgg ggccggggcc ggggccgggg ccggggccgg ggccggggcc 300
ggggccgggg ccggggccgg ggccggggcc ggggccgggg ccggggccgg ggccggggcc 360
ggggccgggg ccggggccgg ggccggggcc ggggccgggg ccggggccgg ggccggggcc 420
ggggccgggg ccggggccgg ggccggggcc ggggccgggg ccggggccgg ggccggggcc 480
ggggccgggg ccggggccgg ggccggggcc ggggccgggg ccggggccgg ggccggggcc 540
ggggccgggg ccggggccgg ggccggggcc ggggccgggg ccggggccgg ggccggggcc 600
ggggccgggg ccggggccgg ggccggggcc ggggccgggg ccggggccgg ggccggggcc 660
ggggccgggg ccggggccgg ggccggggcc ggggccgggg ccggggccgg ggccggggcc 720
ggggccgggg ccggggccgg ggccggggcc ggggccgggg ccggggccgg ggccggggcc 780
ggggccgggg ccggggccgg ggccggggcc ggggccgggg ccggggccgg ggccggggcc 840
ggggccgggg ccggggccgg ggccggggcc ggggccgggg ccggggccgg ggccggggcc 900
ggggccgggg ccggggccgg ggccggggcc ggggccgggg ccggggccgg ggccggggcc 960
ggggccgggg ccggggccgg ggccggggcc ggggccgggg ccggggccgg ggccggggcc 1020
ggggccgggg ccggggccgg ggccggggcc ggggccgggg ccggggccgg ggccggggcc 1080
ggggccgggg ccggggccgg ggccggggcc ggggccgggg ccggggccgg ggccggggcc 1140
ggggccgggg ccggggccgg ggccggggcc ggggccgggg ccggggccgg ggccggggcc 1200
ggggccgggg ccggggccgg ggccggggcc ggggccgggg ccggggccgg ggccggggcc 1260
ggggccgggg ccggggccgg ggccggggcc ggggccgggg ccggggccgg ggccggggcc 1320
ggggccgggg ccggggccgg ggccggggcc ggggccgggg ccggggccgg ggccggggcc 1380
ggggccgggg ccggggccgg ggccggggcc ggggccgggg ccggggccgg ggccggggcc 1440
ggggccgggg ccggggccgg ggccggggcc ggggccgggg ccggggccgg ggccggggcc 1500
ggggccgggg ccggggccgg ggccggggcc ggggccgggg ccggggccgg ggccggggcc 1560
ggggccgggg ccggggccgg ggccggggcc ggggccgggg ccggggccgg ggccggggcc 1620
ggggccgggg ccggggccgg ggccggggcc ggggccgggg ccggggccgg ggccggggcc 1680
ggggccgggg ccggggccgg ggccggggcc ggggccgggg ccggggccgg ggccggggcc 1740
ggggccgggg ccggggccgg ggccggggcc ggggccgggg ccggggccgg ggccggggcc 1800
ggggccgggg ccggggccgg ggccggggcc ggggccgggg ccggggccgg ggccggggcc 1860

```
ggggccgggg ccggggccgg ggccggggcc ggggccgggg ccggggccgg ggccggggcc   1920
ggggccgggg ccggggccgg ggccggggcc ggggccgggg ccggggccgg ggccggggcc   1980
ggggccgggg ccggggccgg ggccggggcc ggggccgggg ccggggccgg ggccggggcc   2040
ggggccgggg ccggggccgg ggccggggcc ggggccgggg ccggggccgg ggccggggcc   2100
ggggccgggg ccggggccgg ggccggggcc ggggccgggg ccggggccgg ggccggggcc   2160
ggggccgggg ccggggccgg ggccggggcc ggggccgggg ccggggccgg ggccggggcc   2220
ggggccgggg ccggggccgg ggccggggcc ggggccgggg ccggggccgg ggccggggcc   2280
ggggccgggg ccggggccgg ggccggggcc ggggccgggg ccggggccgg ggccggggcc   2340
ggggccgggg ccggggccgg ggccggggcc ggggccgggg ccggggccgg ggccggggcc   2400
ggggccgggg ccggggccgg ggccggggcc ggggccgggg ccggggccgg ggccggggcc   2460
ggggccgggg ccggggccgg ggccggggcc ggggccgggg ccggggccgg ggccggggcc   2520
ggggccgggg ccggggccgg ggccggggcc ggggccgggg ccggggccgg ggccggggcc   2580
ggggccgggg ccggggccgg ggccggggcc ggggccgggg ccggggccgg ggccggggcc   2640
ggggccgggg ccggggccgg ggccggggcc ggggccgggg ccggggccgg ggccggggcc   2700
ggggccgggg ccggggccgg ggccggggcc ggggccgggg ccggggccgg ggccggggcc   2760
ggggccgggg ccggggccgg ggccggggcc ggggccgggg ccggggccgg ggccggggcc   2820
ggggccgggg ccggggccgg ggccggggcc ggggccgggg ccggggccgg ggccggggcc   2880
ggggccgggg ccggggccgg ggccggggcc ggggccgggg ccggggccgg ggccggggcc   2940
ggggccgggg ccggggccgg ggccggggcc ggggccgggg ccggggccgg ggccggggcc   3000
```

<210> SEQ ID NO 535
<211> LENGTH: 20
<212> TYPE: DNA
<213> ORGANISM: Artificial Sequence
<220> FEATURE:
<223> OTHER INFORMATION: Synthetic

<400> SEQUENCE: 535
ccttccctga aggttccucc 20

<210> SEQ ID NO 536
<211> LENGTH: 19
<212> TYPE: DNA
<213> ORGANISM: Artificial Sequence
<220> FEATURE:
<223> OTHER INFORMATION: Synthetic

<400> SEQUENCE: 536
agatgacgct tggtgtgtc 19

<210> SEQ ID NO 537
<211> LENGTH: 20
<212> TYPE: DNA
<213> ORGANISM: Artificial Sequence
<220> FEATURE:
<223> OTHER INFORMATION: Synthetic

<400> SEQUENCE: 537
taaacccaca cctgctcttg 20

<210> SEQ ID NO 538
<211> LENGTH: 23
<212> TYPE: DNA

<213> ORGANISM: Artificial Sequence
<220> FEATURE:
<223> OTHER INFORMATION: Synthetic

<400> SEQUENCE: 538
ctgctgcccg gttgcttctc ttt 23

<210> SEQ ID NO 539
<211> LENGTH: 23
<212> TYPE: DNA
<213> ORGANISM: Artificial Sequence
<220> FEATURE:
<223> OTHER INFORMATION: Synthetic

<400> SEQUENCE: 539
ggtcagagaa atgagaggga aag 23

<210> SEQ ID NO 540
<211> LENGTH: 18
<212> TYPE: DNA
<213> ORGANISM: Artificial Sequence
<220> FEATURE:
<223> OTHER INFORMATION: Synthetic

<400> SEQUENCE: 540
cgagtgggtg agtgagga 18

<210> SEQ ID NO 541
<211> LENGTH: 24
<212> TYPE: DNA
<213> ORGANISM: Artificial Sequence
<220> FEATURE:
<223> OTHER INFORMATION: Synthetic

<400> SEQUENCE: 541
aaatgcgtcg agctctgagg agag 24

<210> SEQ ID NO 542
<211> LENGTH: 6000
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: "GGGGCC" repeats at least 100 times and up to 1000 times.
<220> FEATURE:
<221> NAME/KEY: misc_feature
<222> LOCATION: (101)..(6000)
<223> OTHER INFORMATION: "GGGGCC" may or may not be present

<400> SEQUENCE: 542
ggggccgggg ccggggccgg ggccggggcc ggggccgggg ccggggccgg ggccggggcc 60
ggggccgggg ccggggccgg ggccggggcc ggggccgggg ccggggccgg ggccggggcc 120
ggggccgggg ccggggccgg ggccggggcc ggggccgggg ccggggccgg ggccggggcc 180
ggggccgggg ccggggccgg ggccggggcc ggggccgggg ccggggccgg ggccggggcc 240
ggggccgggg ccggggccgg ggccggggcc ggggccgggg ccggggccgg ggccggggcc 300
ggggccgggg ccggggccgg ggccggggcc ggggccgggg ccggggccgg ggccggggcc 360
ggggccgggg ccggggccgg ggccggggcc ggggccgggg ccggggccgg ggccggggcc 420
ggggccgggg ccggggccgg ggccggggcc ggggccgggg ccggggccgg ggccggggcc 480
ggggccgggg ccggggccgg ggccggggcc ggggccgggg ccggggccgg ggccggggcc 540

-continued

```
gggcccgggg ccggggccgg ggccggggcc ggggccgggg ccggggccgg ggccggggcc    600
ggggccgggg ccggggccgg ggccggggcc ggggccgggg ccggggccgg ggccggggcc    660
ggggccgggg ccggggccgg ggccggggcc ggggccgggg ccggggccgg ggccggggcc    720
ggggccgggg ccggggccgg ggccggggcc ggggccgggg ccggggccgg ggccggggcc    780
ggggccgggg ccggggccgg ggccggggcc ggggccgggg ccggggccgg ggccggggcc    840
ggggccgggg ccggggccgg ggccggggcc ggggccgggg ccggggccgg ggccggggcc    900
ggggccgggg ccggggccgg ggccggggcc ggggccgggg ccggggccgg ggccggggcc    960
ggggccgggg ccggggccgg ggccggggcc ggggccgggg ccggggccgg ggccggggcc   1020
ggggccgggg ccggggccgg ggccggggcc ggggccgggg ccggggccgg ggccggggcc   1080
ggggccgggg ccggggccgg ggccggggcc ggggccgggg ccggggccgg ggccggggcc   1140
ggggccgggg ccggggccgg ggccggggcc ggggccgggg ccggggccgg ggccggggcc   1200
ggggccgggg ccggggccgg ggccggggcc ggggccgggg ccggggccgg ggccggggcc   1260
ggggccgggg ccggggccgg ggccggggcc ggggccgggg ccggggccgg ggccggggcc   1320
ggggccgggg ccggggccgg ggccggggcc ggggccgggg ccggggccgg ggccggggcc   1380
ggggccgggg ccggggccgg ggccggggcc ggggccgggg ccggggccgg ggccggggcc   1440
ggggccgggg ccggggccgg ggccggggcc ggggccgggg ccggggccgg ggccggggcc   1500
ggggccgggg ccggggccgg ggccggggcc ggggccgggg ccggggccgg ggccggggcc   1560
ggggccgggg ccggggccgg ggccggggcc ggggccgggg ccggggccgg ggccggggcc   1620
ggggccgggg ccggggccgg ggccggggcc ggggccgggg ccggggccgg ggccggggcc   1680
ggggccgggg ccggggccgg ggccggggcc ggggccgggg ccggggccgg ggccggggcc   1740
ggggccgggg ccggggccgg ggccggggcc ggggccgggg ccggggccgg ggccggggcc   1800
ggggccgggg ccggggccgg ggccggggcc ggggccgggg ccggggccgg ggccggggcc   1860
ggggccgggg ccggggccgg ggccggggcc ggggccgggg ccggggccgg ggccggggcc   1920
ggggccgggg ccggggccgg ggccggggcc ggggccgggg ccggggccgg ggccggggcc   1980
ggggccgggg ccggggccgg ggccggggcc ggggccgggg ccggggccgg ggccggggcc   2040
ggggccgggg ccggggccgg ggccggggcc ggggccgggg ccggggccgg ggccggggcc   2100
ggggccgggg ccggggccgg ggccggggcc ggggccgggg ccggggccgg ggccggggcc   2160
ggggccgggg ccggggccgg ggccggggcc ggggccgggg ccggggccgg ggccggggcc   2220
ggggccgggg ccggggccgg ggccggggcc ggggccgggg ccggggccgg ggccggggcc   2280
ggggccgggg ccggggccgg ggccggggcc ggggccgggg ccggggccgg ggccggggcc   2340
ggggccgggg ccggggccgg ggccggggcc ggggccgggg ccggggccgg ggccggggcc   2400
ggggccgggg ccggggccgg ggccggggcc ggggccgggg ccggggccgg ggccggggcc   2460
ggggccgggg ccggggccgg ggccggggcc ggggccgggg ccggggccgg ggccggggcc   2520
ggggccgggg ccggggccgg ggccggggcc ggggccgggg ccggggccgg ggccggggcc   2580
ggggccgggg ccggggccgg ggccggggcc ggggccgggg ccggggccgg ggccggggcc   2640
ggggccgggg ccggggccgg ggccggggcc ggggccgggg ccggggccgg ggccggggcc   2700
ggggccgggg ccggggccgg ggccggggcc ggggccgggg ccggggccgg ggccggggcc   2760
ggggccgggg ccggggccgg ggccggggcc ggggccgggg ccggggccgg ggccggggcc   2820
ggggccgggg ccggggccgg ggccggggcc ggggccgggg ccggggccgg ggccggggcc   2880
```

-continued

```
ggggccgggg ccggggccgg ggccggggcc ggggccgggg ccggggccgg ggccggggcc   2940
ggggccgggg ccggggccgg ggccggggcc ggggccgggg ccggggccgg ggccggggcc   3000
ggggccgggg ccggggccgg ggccggggcc ggggccgggg ccggggccgg ggccggggcc   3060
ggggccgggg ccggggccgg ggccggggcc ggggccgggg ccggggccgg ggccggggcc   3120
ggggccgggg ccggggccgg ggccggggcc ggggccgggg ccggggccgg ggccggggcc   3180
ggggccgggg ccggggccgg ggccggggcc ggggccgggg ccggggccgg ggccggggcc   3240
ggggccgggg ccggggccgg ggccggggcc ggggccgggg ccggggccgg ggccggggcc   3300
ggggccgggg ccggggccgg ggccggggcc ggggccgggg ccggggccgg ggccggggcc   3360
ggggccgggg ccggggccgg ggccggggcc ggggccgggg ccggggccgg ggccggggcc   3420
ggggccgggg ccggggccgg ggccggggcc ggggccgggg ccggggccgg ggccggggcc   3480
ggggccgggg ccggggccgg ggccggggcc ggggccgggg ccggggccgg ggccggggcc   3540
ggggccgggg ccggggccgg ggccggggcc ggggccgggg ccggggccgg ggccggggcc   3600
ggggccgggg ccggggccgg ggccggggcc ggggccgggg ccggggccgg ggccggggcc   3660
ggggccgggg ccggggccgg ggccggggcc ggggccgggg ccggggccgg ggccggggcc   3720
ggggccgggg ccggggccgg ggccggggcc ggggccgggg ccggggccgg ggccggggcc   3780
ggggccgggg ccggggccgg ggccggggcc ggggccgggg ccggggccgg ggccggggcc   3840
ggggccgggg ccggggccgg ggccggggcc ggggccgggg ccggggccgg ggccggggcc   3900
ggggccgggg ccggggccgg ggccggggcc ggggccgggg ccggggccgg ggccggggcc   3960
ggggccgggg ccggggccgg ggccggggcc ggggccgggg ccggggccgg ggccggggcc   4020
ggggccgggg ccggggccgg ggccggggcc ggggccgggg ccggggccgg ggccggggcc   4080
ggggccgggg ccggggccgg ggccggggcc ggggccgggg ccggggccgg ggccggggcc   4140
ggggccgggg ccggggccgg ggccggggcc ggggccgggg ccggggccgg ggccggggcc   4200
ggggccgggg ccggggccgg ggccggggcc ggggccgggg ccggggccgg ggccggggcc   4260
ggggccgggg ccggggccgg ggccggggcc ggggccgggg ccggggccgg ggccggggcc   4320
ggggccgggg ccggggccgg ggccggggcc ggggccgggg ccggggccgg ggccggggcc   4380
ggggccgggg ccggggccgg ggccggggcc ggggccgggg ccggggccgg ggccggggcc   4440
ggggccgggg ccggggccgg ggccggggcc ggggccgggg ccggggccgg ggccggggcc   4500
ggggccgggg ccggggccgg ggccggggcc ggggccgggg ccggggccgg ggccggggcc   4560
ggggccgggg ccggggccgg ggccggggcc ggggccgggg ccggggccgg ggccggggcc   4620
ggggccgggg ccggggccgg ggccggggcc ggggccgggg ccggggccgg ggccggggcc   4680
ggggccgggg ccggggccgg ggccggggcc ggggccgggg ccggggccgg ggccggggcc   4740
ggggccgggg ccggggccgg ggccggggcc ggggccgggg ccggggccgg ggccggggcc   4800
ggggccgggg ccggggccgg ggccggggcc ggggccgggg ccggggccgg ggccggggcc   4860
ggggccgggg ccggggccgg ggccggggcc ggggccgggg ccggggccgg ggccggggcc   4920
ggggccgggg ccggggccgg ggccggggcc ggggccgggg ccggggccgg ggccggggcc   4980
ggggccgggg ccggggccgg ggccggggcc ggggccgggg ccggggccgg ggccggggcc   5040
ggggccgggg ccggggccgg ggccggggcc ggggccgggg ccggggccgg ggccggggcc   5100
ggggccgggg ccggggccgg ggccggggcc ggggccgggg ccggggccgg ggccggggcc   5160
ggggccgggg ccggggccgg ggccggggcc ggggccgggg ccggggccgg ggccggggcc   5220
ggggccgggg ccggggccgg ggccggggcc ggggccgggg ccggggccgg ggccggggcc   5280
```

ggggccgggg ccggggccgg ggccggggcc ggggccgggg ccggggccgg ggccggggcc 5340
ggggccgggg ccggggccgg ggccggggcc ggggccgggg ccggggccgg ggccggggcc 5400
ggggccgggg ccggggccgg ggccggggcc ggggccgggg ccggggccgg ggccggggcc 5460
ggggccgggg ccggggccgg ggccggggcc ggggccgggg ccggggccgg ggccggggcc 5520
ggggccgggg ccggggccgg ggccggggcc ggggccgggg ccggggccgg ggccggggcc 5580
ggggccgggg ccggggccgg ggccggggcc ggggccgggg ccggggccgg ggccggggcc 5640
ggggccgggg ccggggccgg ggccggggcc ggggccgggg ccggggccgg ggccggggcc 5700
ggggccgggg ccggggccgg ggccggggcc ggggccgggg ccggggccgg ggccggggcc 5760
ggggccgggg ccggggccgg ggccggggcc ggggccgggg ccggggccgg ggccggggcc 5820
ggggccgggg ccggggccgg ggccggggcc ggggccgggg ccggggccgg ggccggggcc 5880
ggggccgggg ccggggccgg ggccggggcc ggggccgggg ccggggccgg ggccggggcc 5940
ggggccgggg ccggggccgg ggccggggcc ggggccgggg ccggggccgg ggccggggcc 6000

<210> SEQ ID NO 543
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 5AmMC12 on 5' end

<400> SEQUENCE: 543
tggcgagtgg 10

<210> SEQ ID NO 544
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 3BioTEG on 3' end

<400> SEQUENCE: 544
gtgagtgagg 10

<210> SEQ ID NO 545
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Cy3 marker on 5' end

<400> SEQUENCE: 545
ggccccggcc ccggcccc 18

<210> SEQ ID NO 546
<211> LENGTH: 24
<212> TYPE: RNA
<213> ORGANISM: Artificial Sequence
<220> FEATURE:
<223> OTHER INFORMATION: Synthetic

<400> SEQUENCE: 546 ggugcgagu gggugaguga ggag 24

<210> SEQ ID NO 547
<211> LENGTH: 12
<212> TYPE: RNA
<213> ORGANISM: Artificial Sequence
<220> FEATURE:
<223> OTHER INFORMATION: Synthetic

<400> SEQUENCE: 547
auacuuaccu gg 12

<210> SEQ ID NO 548
<211> LENGTH: 21
<212> TYPE: DNA
<213> ORGANISM: Artificial Sequence
<220> FEATURE:
<223> OTHER INFORMATION: Synthetic

<400> SEQUENCE: 548
caaactttgc tttccctggt t 21

<210> SEQ ID NO 549
<211> LENGTH: 20
<212> TYPE: DNA
<213> ORGANISM: Artificial Sequence
<220> FEATURE:
<223> OTHER INFORMATION: Synthetic

<400> SEQUENCE: 549
tggcctgtat ccaacacttc 20

<210> SEQ ID NO 550
<211> LENGTH: 27
<212> TYPE: DNA
<213> ORGANISM: Artificial Sequence
<220> FEATURE:
<223> OTHER INFORMATION: Synthetic

<400> SEQUENCE: 550
gcgtttgctc ttcttcuugc gttttuu 27

<210> SEQ ID NO 551
<211> LENGTH: 20
<212> TYPE: DNA
<213> ORGANISM: Artificial Sequence
<220> FEATURE:
<223> OTHER INFORMATION: Synthetic

<400> SEQUENCE: 551
actcacccac tcgccaccgc 20

<210> SEQ ID NO 552
<211> LENGTH: 20
<212> TYPE: DNA
<213> ORGANISM: Artificial Sequence
<220> FEATURE:
<223> OTHER INFORMATION: Synthetic

<400> SEQUENCE: 552
actcacccac tcgccaccgc 20

<210> SEQ ID NO 553
<211> LENGTH: 20
<212> TYPE: DNA

<213> ORGANISM: Artificial Sequence
<220> FEATURE:
<223> OTHER INFORMATION: Synthetic

<400> SEQUENCE: 553
actcacccac tcgccaccgc 20

<210> SEQ ID NO 554
<211> LENGTH: 20
<212> TYPE: DNA
<213> ORGANISM: Artificial Sequence
<220> FEATURE:
<223> OTHER INFORMATION: Synthetic

<400> SEQUENCE: 554
actcacccac tcgccaccgc 20

<210> SEQ ID NO 555
<211> LENGTH: 20
<212> TYPE: DNA
<213> ORGANISM: Artificial Sequence
<220> FEATURE:
<223> OTHER INFORMATION: Synthetic

<400> SEQUENCE: 555
actcacccac tcgccaccgc 20

<210> SEQ ID NO 556
<211> LENGTH: 20
<212> TYPE: DNA
<213> ORGANISM: Artificial Sequence
<220> FEATURE:
<223> OTHER INFORMATION: Synthetic

<400> SEQUENCE: 556
actcacccac tcgccaccgc 20

<210> SEQ ID NO 557
<211> LENGTH: 20
<212> TYPE: DNA
<213> ORGANISM: Artificial Sequence
<220> FEATURE:
<223> OTHER INFORMATION: Synthetic

<400> SEQUENCE: 557
actcacccac tcgccaccgc 20

<210> SEQ ID NO 558
<211> LENGTH: 20
<212> TYPE: DNA
<213> ORGANISM: Artificial Sequence
<220> FEATURE:
<223> OTHER INFORMATION: Synthetic

<400> SEQUENCE: 558
actcacccac tcgccaccgc 20

<210> SEQ ID NO 559
<211> LENGTH: 20
<212> TYPE: DNA
<213> ORGANISM: Artificial Sequence
<220> FEATURE:
<223> OTHER INFORMATION: Synthetic

<400> SEQUENCE: 559
actcacccac tcgccaccgc 20

<210> SEQ ID NO 560
<211> LENGTH: 20
<212> TYPE: DNA
<213> ORGANISM: Artificial Sequence
<220> FEATURE:
<223> OTHER INFORMATION: Synthetic

<400> SEQUENCE: 560
actcacccac tcgccaccgc 20

<210> SEQ ID NO 561
<211> LENGTH: 20
<212> TYPE: DNA
<213> ORGANISM: Artificial Sequence
<220> FEATURE:
<223> OTHER INFORMATION: Synthetic

<400> SEQUENCE: 561
actcacccac tcgccaccgc 20

<210> SEQ ID NO 562
<211> LENGTH: 20
<212> TYPE: DNA
<213> ORGANISM: Artificial Sequence
<220> FEATURE:
<223> OTHER INFORMATION: Synthetic

<400> SEQUENCE: 562
actcacccac tcgccaccgc 20

<210> SEQ ID NO 563
<211> LENGTH: 20
<212> TYPE: DNA
<213> ORGANISM: Artificial Sequence
<220> FEATURE:
<223> OTHER INFORMATION: Synthetic

<400> SEQUENCE: 563
actcacccac tcgccaccgc 20

<210> SEQ ID NO 564
<211> LENGTH: 20
<212> TYPE: DNA
<213> ORGANISM: Artificial Sequence
<220> FEATURE:
<223> OTHER INFORMATION: Synthetic

<400> SEQUENCE: 564
actcacccac tcgccaccgc 20

<210> SEQ ID NO 565
<211> LENGTH: 20
<212> TYPE: DNA
<213> ORGANISM: Artificial Sequence
<220> FEATURE:
<223> OTHER INFORMATION: Synthetic

<400> SEQUENCE: 565
ccttccctga aggttccucc 20

<210> SEQ ID NO 566
<211> LENGTH: 9600
<212> TYPE: DNA
<213> ORGANISM: Artificial Sequence
<220> FEATURE:

-continued

<223> OTHER INFORMATION: Synthetic
<220> FEATURE:
<221> NAME/KEY: misc_feature
<223> OTHER INFORMATION: In some embodiments, "GGGGCC" repeats about or at least about 30, 40, 50, 60, 70, 80, 90, 100, 150, 200, 300, 400, 500, 600, 700, 800, 900, 1000, 1100, 1200, 1300, 1400, 1500, or 1600 repeats. The remaining "GGGGCC" may or may not be present.

<400> SEQUENCE: 566
ggggccgggg ccggggccgg ggccggggcc ggggccgggg ccggggccgg ggccggggcc 60
ggggccgggg ccggggccgg ggccggggcc ggggccgggg ccggggccgg ggccggggcc 120
ggggccgggg ccggggccgg ggccggggcc ggggccgggg ccggggccgg ggccggggcc 180
ggggccgggg ccggggccgg ggccggggcc ggggccgggg ccggggccgg ggccggggcc 240
ggggccgggg ccggggccgg ggccggggcc ggggccgggg ccggggccgg ggccggggcc 300
ggggccgggg ccggggccgg ggccggggcc ggggccgggg ccggggccgg ggccggggcc 360
ggggccgggg ccggggccgg ggccggggcc ggggccgggg ccggggccgg ggccggggcc 420
ggggccgggg ccggggccgg ggccggggcc ggggccgggg ccggggccgg ggccggggcc 480
ggggccgggg ccggggccgg ggccggggcc ggggccgggg ccggggccgg ggccggggcc 540
ggggccgggg ccggggccgg ggccggggcc ggggccgggg ccggggccgg ggccggggcc 600
ggggccgggg ccggggccgg ggccggggcc ggggccgggg ccggggccgg ggccggggcc 660
ggggccgggg ccggggccgg ggccggggcc ggggccgggg ccggggccgg ggccggggcc 720
ggggccgggg ccggggccgg ggccggggcc ggggccgggg ccggggccgg ggccggggcc 780
ggggccgggg ccggggccgg ggccggggcc ggggccgggg ccggggccgg ggccggggcc 840
ggggccgggg ccggggccgg ggccggggcc ggggccgggg ccggggccgg ggccggggcc 900
ggggccgggg ccggggccgg ggccggggcc ggggccgggg ccggggccgg ggccggggcc 960
ggggccgggg ccggggccgg ggccggggcc ggggccgggg ccggggccgg ggccggggcc 1020
ggggccgggg ccggggccgg ggccggggcc ggggccgggg ccggggccgg ggccggggcc 1080
ggggccgggg ccggggccgg ggccggggcc ggggccgggg ccggggccgg ggccggggcc 1140
ggggccgggg ccggggccgg ggccggggcc ggggccgggg ccggggccgg ggccggggcc 1200
ggggccgggg ccggggccgg ggccggggcc ggggccgggg ccggggccgg ggccggggcc 1260
ggggccgggg ccggggccgg ggccggggcc ggggccgggg ccggggccgg ggccggggcc 1320
ggggccgggg ccggggccgg ggccggggcc ggggccgggg ccggggccgg ggccggggcc 1380
ggggccgggg ccggggccgg ggccggggcc ggggccgggg ccggggccgg ggccggggcc 1440
ggggccgggg ccggggccgg ggccggggcc ggggccgggg ccggggccgg ggccggggcc 1500
ggggccgggg ccggggccgg ggccggggcc ggggccgggg ccggggccgg ggccggggcc 1560
ggggccgggg ccggggccgg ggccggggcc ggggccgggg ccggggccgg ggccggggcc 1620
ggggccgggg ccggggccgg ggccggggcc ggggccgggg ccggggccgg ggccggggcc 1680
ggggccgggg ccggggccgg ggccggggcc ggggccgggg ccggggccgg ggccggggcc 1740
ggggccgggg ccggggccgg ggccggggcc ggggccgggg ccggggccgg ggccggggcc 1800
ggggccgggg ccggggccgg ggccggggcc ggggccgggg ccggggccgg ggccggggcc 1860
ggggccgggg ccggggccgg ggccggggcc ggggccgggg ccggggccgg ggccggggcc 1920
ggggccgggg ccggggccgg ggccggggcc ggggccgggg ccggggccgg ggccggggcc 1980
ggggccgggg ccggggccgg ggccggggcc ggggccgggg ccggggccgg ggccggggcc 2040
ggggccgggg ccggggccgg ggccggggcc ggggccgggg ccggggccgg ggccggggcc 2100

-continued

```
ggggccgggg ccggggccgg ggccggggcc ggggccgggg ccggggccgg ggccggggcc   2160
ggggccgggg ccggggccgg ggccggggcc ggggccgggg ccggggccgg ggccggggcc   2220
ggggccgggg ccggggccgg ggccggggcc ggggccgggg ccggggccgg ggccggggcc   2280
ggggccgggg ccggggccgg ggccggggcc ggggccgggg ccggggccgg ggccggggcc   2340
ggggccgggg ccggggccgg ggccggggcc ggggccgggg ccggggccgg ggccggggcc   2400
ggggccgggg ccggggccgg ggccggggcc ggggccgggg ccggggccgg ggccggggcc   2460
ggggccgggg ccggggccgg ggccggggcc ggggccgggg ccggggccgg ggccggggcc   2520
ggggccgggg ccggggccgg ggccggggcc ggggccgggg ccggggccgg ggccggggcc   2580
ggggccgggg ccggggccgg ggccggggcc ggggccgggg ccggggccgg ggccggggcc   2640
ggggccgggg ccggggccgg ggccggggcc ggggccgggg ccggggccgg ggccggggcc   2700
ggggccgggg ccggggccgg ggccggggcc ggggccgggg ccggggccgg ggccggggcc   2760
ggggccgggg ccggggccgg ggccggggcc ggggccgggg ccggggccgg ggccggggcc   2820
ggggccgggg ccggggccgg ggccggggcc ggggccgggg ccggggccgg ggccggggcc   2880
ggggccgggg ccggggccgg ggccggggcc ggggccgggg ccggggccgg ggccggggcc   2940
ggggccgggg ccggggccgg ggccggggcc ggggccgggg ccggggccgg ggccggggcc   3000
ggggccgggg ccggggccgg ggccggggcc ggggccgggg ccggggccgg ggccggggcc   3060
ggggccgggg ccggggccgg ggccggggcc ggggccgggg ccggggccgg ggccggggcc   3120
ggggccgggg ccggggccgg ggccggggcc ggggccgggg ccggggccgg ggccggggcc   3180
ggggccgggg ccggggccgg ggccggggcc ggggccgggg ccggggccgg ggccggggcc   3240
ggggccgggg ccggggccgg ggccggggcc ggggccgggg ccggggccgg ggccggggcc   3300
ggggccgggg ccggggccgg ggccggggcc ggggccgggg ccggggccgg ggccggggcc   3360
ggggccgggg ccggggccgg ggccggggcc ggggccgggg ccggggccgg ggccggggcc   3420
ggggccgggg ccggggccgg ggccggggcc ggggccgggg ccggggccgg ggccggggcc   3480
ggggccgggg ccggggccgg ggccggggcc ggggccgggg ccggggccgg ggccggggcc   3540
ggggccgggg ccggggccgg ggccggggcc ggggccgggg ccggggccgg ggccggggcc   3600
ggggccgggg ccggggccgg ggccggggcc ggggccgggg ccggggccgg ggccggggcc   3660
ggggccgggg ccggggccgg ggccggggcc ggggccgggg ccggggccgg ggccggggcc   3720
ggggccgggg ccggggccgg ggccggggcc ggggccgggg ccggggccgg ggccggggcc   3780
ggggccgggg ccggggccgg ggccggggcc ggggccgggg ccggggccgg ggccggggcc   3840
ggggccgggg ccggggccgg ggccggggcc ggggccgggg ccggggccgg ggccggggcc   3900
ggggccgggg ccggggccgg ggccggggcc ggggccgggg ccggggccgg ggccggggcc   3960
ggggccgggg ccggggccgg ggccggggcc ggggccgggg ccggggccgg ggccggggcc   4020
ggggccgggg ccggggccgg ggccggggcc ggggccgggg ccggggccgg ggccggggcc   4080
ggggccgggg ccggggccgg ggccggggcc ggggccgggg ccggggccgg ggccggggcc   4140
ggggccgggg ccggggccgg ggccggggcc ggggccgggg ccggggccgg ggccggggcc   4200
ggggccgggg ccggggccgg ggccggggcc ggggccgggg ccggggccgg ggccggggcc   4260
ggggccgggg ccggggccgg ggccggggcc ggggccgggg ccggggccgg ggccggggcc   4320
ggggccgggg ccggggccgg ggccggggcc ggggccgggg ccggggccgg ggccggggcc   4380
ggggccgggg ccggggccgg ggccggggcc ggggccgggg ccggggccgg ggccggggcc   4440
```

-continued gggggccgggg ccggggccgg ggccggggcc ggggccgggg ccggggccgg ggccggggcc 4500
gggggccgggg ccggggccgg ggccggggcc ggggccgggg ccggggccgg ggccggggcc 4560
gggggccgggg ccggggccgg ggccggggcc ggggccgggg ccggggccgg ggccggggcc 4620
gggggccgggg ccggggccgg ggccggggcc ggggccgggg ccggggccgg ggccggggcc 4680
gggggccgggg ccggggccgg ggccggggcc ggggccgggg ccggggccgg ggccggggcc 4740
gggggccgggg ccggggccgg ggccggggcc ggggccgggg ccggggccgg ggccggggcc 4800
gggggccgggg ccggggccgg ggccggggcc ggggccgggg ccggggccgg ggccggggcc 4860
gggggccgggg ccggggccgg ggccggggcc ggggccgggg ccggggccgg ggccggggcc 4920
gggggccgggg ccggggccgg ggccggggcc ggggccgggg ccggggccgg ggccggggcc 4980
gggggccgggg ccggggccgg ggccggggcc ggggccgggg ccggggccgg ggccggggcc 5040
gggggccgggg ccggggccgg ggccggggcc ggggccgggg ccggggccgg ggccggggcc 5100
gggggccgggg ccggggccgg ggccggggcc ggggccgggg ccggggccgg ggccggggcc 5160
gggggccgggg ccggggccgg ggccggggcc ggggccgggg ccggggccgg ggccggggcc 5220
gggggccgggg ccggggccgg ggccggggcc ggggccgggg ccggggccgg ggccggggcc 5280
gggggccgggg ccggggccgg ggccggggcc ggggccgggg ccggggccgg ggccggggcc 5340
gggggccgggg ccggggccgg ggccggggcc ggggccgggg ccggggccgg ggccggggcc 5400
gggggccgggg ccggggccgg ggccggggcc ggggccgggg ccggggccgg ggccggggcc 5460
gggggccgggg ccggggccgg ggccggggcc ggggccgggg ccggggccgg ggccggggcc 5520
gggggccgggg ccggggccgg ggccggggcc ggggccgggg ccggggccgg ggccggggcc 5580
gggggccgggg ccggggccgg ggccggggcc ggggccgggg ccggggccgg ggccggggcc 5640
gggggccgggg ccggggccgg ggccggggcc ggggccgggg ccggggccgg ggccggggcc 5700
gggggccgggg ccggggccgg ggccggggcc ggggccgggg ccggggccgg ggccggggcc 5760
gggggccgggg ccggggccgg ggccggggcc ggggccgggg ccggggccgg ggccggggcc 5820
gggggccgggg ccggggccgg ggccggggcc ggggccgggg ccggggccgg ggccggggcc 5880
gggggccgggg ccggggccgg ggccggggcc ggggccgggg ccggggccgg ggccggggcc 5940
gggggccgggg ccggggccgg ggccggggcc ggggccgggg ccggggccgg ggccggggcc 6000
gggggccgggg ccggggccgg ggccggggcc ggggccgggg ccggggccgg ggccggggcc 6060
gggggccgggg ccggggccgg ggccggggcc ggggccgggg ccggggccgg ggccggggcc 6120
gggggccgggg ccggggccgg ggccggggcc ggggccgggg ccggggccgg ggccggggcc 6180
gggggccgggg ccggggccgg ggccggggcc ggggccgggg ccggggccgg ggccggggcc 6240
gggggccgggg ccggggccgg ggccggggcc ggggccgggg ccggggccgg ggccggggcc 6300
gggggccgggg ccggggccgg ggccggggcc ggggccgggg ccggggccgg ggccggggcc 6360
gggggccgggg ccggggccgg ggccggggcc ggggccgggg ccggggccgg ggccggggcc 6420
gggggccgggg ccggggccgg ggccggggcc ggggccgggg ccggggccgg ggccggggcc 6480
gggggccgggg ccggggccgg ggccggggcc ggggccgggg ccggggccgg ggccggggcc 6540
gggggccgggg ccggggccgg ggccggggcc ggggccgggg ccggggccgg ggccggggcc 6600
gggggccgggg ccggggccgg ggccggggcc ggggccgggg ccggggccgg ggccggggcc 6660
gggggccgggg ccggggccgg ggccggggcc ggggccgggg ccggggccgg ggccggggcc 6720
gggggccgggg ccggggccgg ggccggggcc ggggccgggg ccggggccgg ggccggggcc 6780
gggggccgggg ccggggccgg ggccggggcc ggggccgggg ccggggccgg ggccggggcc 6840

-continued

```
ggggccgggg ccggggccgg ggccggggcc ggggccgggg ccggggccgg ggccggggcc   6900
ggggccgggg ccggggccgg ggccggggcc ggggccgggg ccggggccgg ggccggggcc   6960
ggggccgggg ccggggccgg ggccggggcc ggggccgggg ccggggccgg ggccggggcc   7020
ggggccgggg ccggggccgg ggccggggcc ggggccgggg ccggggccgg ggccggggcc   7080
ggggccgggg ccggggccgg ggccggggcc ggggccgggg ccggggccgg ggccggggcc   7140
ggggccgggg ccggggccgg ggccggggcc ggggccgggg ccggggccgg ggccggggcc   7200
ggggccgggg ccggggccgg ggccggggcc ggggccgggg ccggggccgg ggccggggcc   7260
ggggccgggg ccggggccgg ggccggggcc ggggccgggg ccggggccgg ggccggggcc   7320
ggggccgggg ccggggccgg ggccggggcc ggggccgggg ccggggccgg ggccggggcc   7380
ggggccgggg ccggggccgg ggccggggcc ggggccgggg ccggggccgg ggccggggcc   7440
ggggccgggg ccggggccgg ggccggggcc ggggccgggg ccggggccgg ggccggggcc   7500
ggggccgggg ccggggccgg ggccggggcc ggggccgggg ccggggccgg ggccggggcc   7560
ggggccgggg ccggggccgg ggccggggcc ggggccgggg ccggggccgg ggccggggcc   7620
ggggccgggg ccggggccgg ggccggggcc ggggccgggg ccggggccgg ggccggggcc   7680
ggggccgggg ccggggccgg ggccggggcc ggggccgggg ccggggccgg ggccggggcc   7740
ggggccgggg ccggggccgg ggccggggcc ggggccgggg ccggggccgg ggccggggcc   7800
ggggccgggg ccggggccgg ggccggggcc ggggccgggg ccggggccgg ggccggggcc   7860
ggggccgggg ccggggccgg ggccggggcc ggggccgggg ccggggccgg ggccggggcc   7920
ggggccgggg ccggggccgg ggccggggcc ggggccgggg ccggggccgg ggccggggcc   7980
ggggccgggg ccggggccgg ggccggggcc ggggccgggg ccggggccgg ggccggggcc   8040
ggggccgggg ccggggccgg ggccggggcc ggggccgggg ccggggccgg ggccggggcc   8100
ggggccgggg ccggggccgg ggccggggcc ggggccgggg ccggggccgg ggccggggcc   8160
ggggccgggg ccggggccgg ggccggggcc ggggccgggg ccggggccgg ggccggggcc   8220
ggggccgggg ccggggccgg ggccggggcc ggggccgggg ccggggccgg ggccggggcc   8280
ggggccgggg ccggggccgg ggccggggcc ggggccgggg ccggggccgg ggccggggcc   8340
ggggccgggg ccggggccgg ggccggggcc ggggccgggg ccggggccgg ggccggggcc   8400
ggggccgggg ccggggccgg ggccggggcc ggggccgggg ccggggccgg ggccggggcc   8460
ggggccgggg ccggggccgg ggccggggcc ggggccgggg ccggggccgg ggccggggcc   8520
ggggccgggg ccggggccgg ggccggggcc ggggccgggg ccggggccgg ggccggggcc   8580
ggggccgggg ccggggccgg ggccggggcc ggggccgggg ccggggccgg ggccggggcc   8640
ggggccgggg ccggggccgg ggccggggcc ggggccgggg ccggggccgg ggccggggcc   8700
ggggccgggg ccggggccgg ggccggggcc ggggccgggg ccggggccgg ggccggggcc   8760
ggggccgggg ccggggccgg ggccggggcc ggggccgggg ccggggccgg ggccggggcc   8820
ggggccgggg ccggggccgg ggccggggcc ggggccgggg ccggggccgg ggccggggcc   8880
ggggccgggg ccggggccgg ggccggggcc ggggccgggg ccggggccgg ggccggggcc   8940
ggggccgggg ccggggccgg ggccggggcc ggggccgggg ccggggccgg ggccggggcc   9000
ggggccgggg ccggggccgg ggccggggcc ggggccgggg ccggggccgg ggccggggcc   9060
ggggccgggg ccggggccgg ggccggggcc ggggccgggg ccggggccgg ggccggggcc   9120
ggggccgggg ccggggccgg ggccggggcc ggggccgggg ccggggccgg ggccggggcc   9180
```

-continued gggggccgggg ccggggccgg ggccggggcc ggggccgggg ccggggccgg ggccggggcc 9240
ggggccgggg ccggggccgg ggccggggcc ggggccgggg ccggggccgg ggccggggcc 9300
ggggccgggg ccggggccgg ggccggggcc ggggccgggg ccggggccgg ggccggggcc 9360
ggggccgggg ccggggccgg ggccggggcc ggggccgggg ccggggccgg ggccggggcc 9420
ggggccgggg ccggggccgg ggccggggcc ggggccgggg ccggggccgg ggccggggcc 9480
ggggccgggg ccggggccgg ggccggggcc ggggccgggg ccggggccgg ggccggggcc 9540
ggggccgggg ccggggccgg ggccggggcc ggggccgggg ccggggccgg ggccggggcc 9600

<210> SEQ ID NO 567
<211> LENGTH: 180
<212> TYPE: DNA
<213> ORGANISM: Artificial Sequence
<220> FEATURE:
<223> OTHER INFORMATION: Synthetic

<400> SEQUENCE: 567
ggggccgggg ccggggccgg ggccggggcc ggggccgggg ccggggccgg ggccggggcc 60
ggggccgggg ccggggccgg ggccggggcc ggggccgggg ccggggccgg ggccggggcc 120
ggggccgggg ccggggccgg ggccggggcc ggggccgggg ccggggccgg ggccggggcc 180

<210> SEQ ID NO 568
<211> LENGTH: 300
<212> TYPE: DNA
<213> ORGANISM: Artificial Sequence
<220> FEATURE:
<223> OTHER INFORMATION: Synthetic

<400> SEQUENCE: 568
ggggccgggg ccggggccgg ggccggggcc ggggccgggg ccggggccgg ggccggggcc 60
ggggccgggg ccggggccgg ggccggggcc ggggccgggg ccggggccgg ggccggggcc 120
ggggccgggg ccggggccgg ggccggggcc ggggccgggg ccggggccgg ggccggggcc 180
ggggccgggg ccggggccgg ggccggggcc ggggccgggg ccggggccgg ggccggggcc 240
ggggccgggg ccggggccgg ggccggggcc ggggccgggg ccggggccgg ggccggggcc 300

<210> SEQ ID NO 569
<211> LENGTH: 600
<212> TYPE: DNA
<213> ORGANISM: Artificial Sequence
<220> FEATURE:
<223> OTHER INFORMATION: Synthetic

<400> SEQUENCE: 569
ggggccgggg ccggggccgg ggccggggcc ggggccgggg ccggggccgg ggccggggcc 60
ggggccgggg ccggggccgg ggccggggcc ggggccgggg ccggggccgg ggccggggcc 120
ggggccgggg ccggggccgg ggccggggcc ggggccgggg ccggggccgg ggccggggcc 180
ggggccgggg ccggggccgg ggccggggcc ggggccgggg ccggggccgg ggccggggcc 240
ggggccgggg ccggggccgg ggccggggcc ggggccgggg ccggggccgg ggccggggcc 300
ggggccgggg ccggggccgg ggccggggcc ggggccgggg ccggggccgg ggccggggcc 360
ggggccgggg ccggggccgg ggccggggcc ggggccgggg ccggggccgg ggccggggcc 420
ggggccgggg ccggggccgg ggccggggcc ggggccgggg ccggggccgg ggccggggcc 480
ggggccgggg ccggggccgg ggccggggcc ggggccgggg ccggggccgg ggccggggcc 540
ggggccgggg ccggggccgg ggccggggcc ggggccgggg ccggggccgg ggccggggcc 600

<210> SEQ ID NO 570
<211> LENGTH: 900
<212> TYPE: DNA
<213> ORGANISM: Artificial Sequence
<220> FEATURE:
<223> OTHER INFORMATION: Synthetic

<400> SEQUENCE: 570
ggggccgggg ccggggccgg ggccggggcc ggggccgggg ccggggccgg ggccggggcc 60
ggggccgggg ccggggccgg ggccggggcc ggggccgggg ccggggccgg ggccggggcc 120
ggggccgggg ccggggccgg ggccggggcc ggggccgggg ccggggccgg ggccggggcc 180
ggggccgggg ccggggccgg ggccggggcc ggggccgggg ccggggccgg ggccggggcc 240
ggggccgggg ccggggccgg ggccggggcc ggggccgggg ccggggccgg ggccggggcc 300
ggggccgggg ccggggccgg ggccggggcc ggggccgggg ccggggccgg ggccggggcc 360
ggggccgggg ccggggccgg ggccggggcc ggggccgggg ccggggccgg ggccggggcc 420
ggggccgggg ccggggccgg ggccggggcc ggggccgggg ccggggccgg ggccggggcc 480
ggggccgggg ccggggccgg ggccggggcc ggggccgggg ccggggccgg ggccggggcc 540
ggggccgggg ccggggccgg ggccggggcc ggggccgggg ccggggccgg ggccggggcc 600
ggggccgggg ccggggccgg ggccggggcc ggggccgggg ccggggccgg ggccggggcc 660
ggggccgggg ccggggccgg ggccggggcc ggggccgggg ccggggccgg ggccggggcc 720
ggggccgggg ccggggccgg ggccggggcc ggggccgggg ccggggccgg ggccggggcc 780
ggggccgggg ccggggccgg ggccggggcc ggggccgggg ccggggccgg ggccggggcc 840
ggggccgggg ccggggccgg ggccggggcc ggggccgggg ccggggccgg ggccggggcc 900

<210> SEQ ID NO 571
<211> LENGTH: 1200
<212> TYPE: DNA
<213> ORGANISM: Artificial Sequence
<220> FEATURE:
<223> OTHER INFORMATION: Synthetic

<400> SEQUENCE: 571
ggggccgggg ccggggccgg ggccggggcc ggggccgggg ccggggccgg ggccggggcc 60
ggggccgggg ccggggccgg ggccggggcc ggggccgggg ccggggccgg ggccggggcc 120
ggggccgggg ccggggccgg ggccggggcc ggggccgggg ccggggccgg ggccggggcc 180
ggggccgggg ccggggccgg ggccggggcc ggggccgggg ccggggccgg ggccggggcc 240
ggggccgggg ccggggccgg ggccggggcc ggggccgggg ccggggccgg ggccggggcc 300
ggggccgggg ccggggccgg ggccggggcc ggggccgggg ccggggccgg ggccggggcc 360
ggggccgggg ccggggccgg ggccggggcc ggggccgggg ccggggccgg ggccggggcc 420
ggggccgggg ccggggccgg ggccggggcc ggggccgggg ccggggccgg ggccggggcc 480
ggggccgggg ccggggccgg ggccggggcc ggggccgggg ccggggccgg ggccggggcc 540
ggggccgggg ccggggccgg ggccggggcc ggggccgggg ccggggccgg ggccggggcc 600
ggggccgggg ccggggccgg ggccggggcc ggggccgggg ccggggccgg ggccggggcc 660
ggggccgggg ccggggccgg ggccggggcc ggggccgggg ccggggccgg ggccggggcc 720
ggggccgggg ccggggccgg ggccggggcc ggggccgggg ccggggccgg ggccggggcc 780
ggggccgggg ccggggccgg ggccggggcc ggggccgggg ccggggccgg ggccggggcc 840

-continued gggggccgggg ccggggccgg ggccggggcc ggggccgggg ccggggccgg ggccggggcc 900 gggggccgggg ccggggccgg ggccggggcc ggggccgggg ccggggccgg ggccggggcc 960 gggggccgggg ccggggccgg ggccggggcc ggggccgggg ccggggccgg ggccggggcc 1020 gggggccgggg ccggggccgg ggccggggcc ggggccgggg ccggggccgg ggccggggcc 1080 gggggccgggg ccggggccgg ggccggggcc ggggccgggg ccggggccgg ggccggggcc 1140 gggggccgggg ccggggccgg ggccggggcc ggggccgggg ccggggccgg ggccggggcc 1200

<210> SEQ ID NO 572
<211> LENGTH: 1800
<212> TYPE: DNA
<213> ORGANISM: Artificial Sequence
<220> FEATURE:
<223> OTHER INFORMATION: Synthetic

<400> SEQUENCE: 572
ggggccgggg ccggggccgg ggccggggcc ggggccgggg ccggggccgg ggccggggcc 60
ggggccgggg ccggggccgg ggccggggcc ggggccgggg ccggggccgg ggccggggcc 120
ggggccgggg ccggggccgg ggccggggcc ggggccgggg ccggggccgg ggccggggcc 180
ggggccgggg ccggggccgg ggccggggcc ggggccgggg ccggggccgg ggccggggcc 240
ggggccgggg ccggggccgg ggccggggcc ggggccgggg ccggggccgg ggccggggcc 300
ggggccgggg ccggggccgg ggccggggcc ggggccgggg ccggggccgg ggccggggcc 360
ggggccgggg ccggggccgg ggccggggcc ggggccgggg ccggggccgg ggccggggcc 420
ggggccgggg ccggggccgg ggccggggcc ggggccgggg ccggggccgg ggccggggcc 480
ggggccgggg ccggggccgg ggccggggcc ggggccgggg ccggggccgg ggccggggcc 540
ggggccgggg ccggggccgg ggccggggcc ggggccgggg ccggggccgg ggccggggcc 600
ggggccgggg ccggggccgg ggccggggcc ggggccgggg ccggggccgg ggccggggcc 660
ggggccgggg ccggggccgg ggccggggcc ggggccgggg ccggggccgg ggccggggcc 720
ggggccgggg ccggggccgg ggccggggcc ggggccgggg ccggggccgg ggccggggcc 780
ggggccgggg ccggggccgg ggccggggcc ggggccgggg ccggggccgg ggccggggcc 840
ggggccgggg ccggggccgg ggccggggcc ggggccgggg ccggggccgg ggccggggcc 900
ggggccgggg ccggggccgg ggccggggcc ggggccgggg ccggggccgg ggccggggcc 960
ggggccgggg ccggggccgg ggccggggcc ggggccgggg ccggggccgg ggccggggcc 1020
ggggccgggg ccggggccgg ggccggggcc ggggccgggg ccggggccgg ggccggggcc 1080
ggggccgggg ccggggccgg ggccggggcc ggggccgggg ccggggccgg ggccggggcc 1140
ggggccgggg ccggggccgg ggccggggcc ggggccgggg ccggggccgg ggccggggcc 1200
ggggccgggg ccggggccgg ggccggggcc ggggccgggg ccggggccgg ggccggggcc 1260
ggggccgggg ccggggccgg ggccggggcc ggggccgggg ccggggccgg ggccggggcc 1320
ggggccgggg ccggggccgg ggccggggcc ggggccgggg ccggggccgg ggccggggcc 1380
ggggccgggg ccggggccgg ggccggggcc ggggccgggg ccggggccgg ggccggggcc 1440
ggggccgggg ccggggccgg ggccggggcc ggggccgggg ccggggccgg ggccggggcc 1500
ggggccgggg ccggggccgg ggccggggcc ggggccgggg ccggggccgg ggccggggcc 1560
ggggccgggg ccggggccgg ggccggggcc ggggccgggg ccggggccgg ggccggggcc 1620
ggggccgggg ccggggccgg ggccggggcc ggggccgggg ccggggccgg ggccggggcc 1680
ggggccgggg ccggggccgg ggccggggcc ggggccgggg ccggggccgg ggccggggcc 1740 gggggccgggg ccggggccgg ggccggggcc ggggccgggg ccggggccgg ggccggggcc 1800

<210> SEQ ID NO 573
<211> LENGTH: 3000
<212> TYPE: DNA
<213> ORGANISM: Artificial Sequence
<220> FEATURE:
<223> OTHER INFORMATION: Synthetic

<400> SEQUENCE: 573
ggggccgggg ccggggccgg ggccggggcc ggggccgggg ccggggccgg ggccggggcc 60
ggggccgggg ccggggccgg ggccggggcc ggggccgggg ccggggccgg ggccggggcc 120
ggggccgggg ccggggccgg ggccggggcc ggggccgggg ccggggccgg ggccggggcc 180
ggggccgggg ccggggccgg ggccggggcc ggggccgggg ccggggccgg ggccggggcc 240
ggggccgggg ccggggccgg ggccggggcc ggggccgggg ccggggccgg ggccggggcc 300
ggggccgggg ccggggccgg ggccggggcc ggggccgggg ccggggccgg ggccggggcc 360
ggggccgggg ccggggccgg ggccggggcc ggggccgggg ccggggccgg ggccggggcc 420
ggggccgggg ccggggccgg ggccggggcc ggggccgggg ccggggccgg ggccggggcc 480
ggggccgggg ccggggccgg ggccggggcc ggggccgggg ccggggccgg ggccggggcc 540
ggggccgggg ccggggccgg ggccggggcc ggggccgggg ccggggccgg ggccggggcc 600
ggggccgggg ccggggccgg ggccggggcc ggggccgggg ccggggccgg ggccggggcc 660
ggggccgggg ccggggccgg ggccggggcc ggggccgggg ccggggccgg ggccggggcc 720
ggggccgggg ccggggccgg ggccggggcc ggggccgggg ccggggccgg ggccggggcc 780
ggggccgggg ccggggccgg ggccggggcc ggggccgggg ccggggccgg ggccggggcc 840
ggggccgggg ccggggccgg ggccggggcc ggggccgggg ccggggccgg ggccggggcc 900
ggggccgggg ccggggccgg ggccggggcc ggggccgggg ccggggccgg ggccggggcc 960
ggggccgggg ccggggccgg ggccggggcc ggggccgggg ccggggccgg ggccggggcc 1020
ggggccgggg ccggggccgg ggccggggcc ggggccgggg ccggggccgg ggccggggcc 1080
ggggccgggg ccggggccgg ggccggggcc ggggccgggg ccggggccgg ggccggggcc 1140
ggggccgggg ccggggccgg ggccggggcc ggggccgggg ccggggccgg ggccggggcc 1200
ggggccgggg ccggggccgg ggccggggcc ggggccgggg ccggggccgg ggccggggcc 1260
ggggccgggg ccggggccgg ggccggggcc ggggccgggg ccggggccgg ggccggggcc 1320
ggggccgggg ccggggccgg ggccggggcc ggggccgggg ccggggccgg ggccggggcc 1380
ggggccgggg ccggggccgg ggccggggcc ggggccgggg ccggggccgg ggccggggcc 1440
ggggccgggg ccggggccgg ggccggggcc ggggccgggg ccggggccgg ggccggggcc 1500
ggggccgggg ccggggccgg ggccggggcc ggggccgggg ccggggccgg ggccggggcc 1560
ggggccgggg ccggggccgg ggccggggcc ggggccgggg ccggggccgg ggccggggcc 1620
ggggccgggg ccggggccgg ggccggggcc ggggccgggg ccggggccgg ggccggggcc 1680
ggggccgggg ccggggccgg ggccggggcc ggggccgggg ccggggccgg ggccggggcc 1740
ggggccgggg ccggggccgg ggccggggcc ggggccgggg ccggggccgg ggccggggcc 1800
ggggccgggg ccggggccgg ggccggggcc ggggccgggg ccggggccgg ggccggggcc 1860
ggggccgggg ccggggccgg ggccggggcc ggggccgggg ccggggccgg ggccggggcc 1920
ggggccgggg ccggggccgg ggccggggcc ggggccgggg ccggggccgg ggccggggcc 1980

-continued gggg ccgggg ccgggg ccgg ggccggggcc ggggccgggg ccggggccgg ggccggggcc 2040
ggggccgggg ccggggccgg ggccggggcc ggggccgggg ccggggccgg ggccggggcc 2100
ggggccgggg ccggggccgg ggccggggcc ggggccgggg ccggggccgg ggccggggcc 2160
ggggccgggg ccggggccgg ggccggggcc ggggccgggg ccggggccgg ggccggggcc 2220
ggggccgggg ccggggccgg ggccggggcc ggggccgggg ccggggccgg ggccggggcc 2280
ggggccgggg ccggggccgg ggccggggcc ggggccgggg ccggggccgg ggccggggcc 2340
ggggccgggg ccggggccgg ggccggggcc ggggccgggg ccggggccgg ggccggggcc 2400
ggggccgggg ccggggccgg ggccggggcc ggggccgggg ccggggccgg ggccggggcc 2460
ggggccgggg ccggggccgg ggccggggcc ggggccgggg ccggggccgg ggccggggcc 2520
ggggccgggg ccggggccgg ggccggggcc ggggccgggg ccggggccgg ggccggggcc 2580
ggggccgggg ccggggccgg ggccggggcc ggggccgggg ccggggccgg ggccggggcc 2640
ggggccgggg ccggggccgg ggccggggcc ggggccgggg ccggggccgg ggccggggcc 2700
ggggccgggg ccggggccgg ggccggggcc ggggccgggg ccggggccgg ggccggggcc 2760
ggggccgggg ccggggccgg ggccggggcc ggggccgggg ccggggccgg ggccggggcc 2820
ggggccgggg ccggggccgg ggccggggcc ggggccgggg ccggggccgg ggccggggcc 2880
ggggccgggg ccggggccgg ggccggggcc ggggccgggg ccggggccgg ggccggggcc 2940
ggggccgggg ccggggccgg ggccggggcc ggggccgggg ccggggccgg ggccggggcc 3000

<210> SEQ ID NO 574
<211> LENGTH: 6000
<212> TYPE: DNA
<213> ORGANISM: Artificial Sequence
<220> FEATURE:
<223> OTHER INFORMATION: Synthetic

<400> SEQUENCE: 574
ggggccgggg ccggggccgg ggccggggcc ggggccgggg ccggggccgg ggccggggcc 60
ggggccgggg ccggggccgg ggccggggcc ggggccgggg ccggggccgg ggccggggcc 120
ggggccgggg ccggggccgg ggccggggcc ggggccgggg ccggggccgg ggccggggcc 180
ggggccgggg ccggggccgg ggccggggcc ggggccgggg ccggggccgg ggccggggcc 240
ggggccgggg ccggggccgg ggccggggcc ggggccgggg ccggggccgg ggccggggcc 300
ggggccgggg ccggggccgg ggccggggcc ggggccgggg ccggggccgg ggccggggcc 360
ggggccgggg ccggggccgg ggccggggcc ggggccgggg ccggggccgg ggccggggcc 420
ggggccgggg ccggggccgg ggccggggcc ggggccgggg ccggggccgg ggccggggcc 480
ggggccgggg ccggggccgg ggccggggcc ggggccgggg ccggggccgg ggccggggcc 540
ggggccgggg ccggggccgg ggccggggcc ggggccgggg ccggggccgg ggccggggcc 600
ggggccgggg ccggggccgg ggccggggcc ggggccgggg ccggggccgg ggccggggcc 660
ggggccgggg ccggggccgg ggccggggcc ggggccgggg ccggggccgg ggccggggcc 720
ggggccgggg ccggggccgg ggccggggcc ggggccgggg ccggggccgg ggccggggcc 780
ggggccgggg ccggggccgg ggccggggcc ggggccgggg ccggggccgg ggccggggcc 840
ggggccgggg ccggggccgg ggccggggcc ggggccgggg ccggggccgg ggccggggcc 900
ggggccgggg ccggggccgg ggccggggcc ggggccgggg ccggggccgg ggccggggcc 960
ggggccgggg ccggggccgg ggccggggcc ggggccgggg ccggggccgg ggccggggcc 1020
ggggccgggg ccggggccgg ggccggggcc ggggccgggg ccggggccgg ggccggggcc 1080

```
ggggccgggg ccggggccgg ggccggggcc ggggccgggg ccggggccgg ggccggggcc   1140
ggggccgggg ccggggccgg ggccggggcc ggggccgggg ccggggccgg ggccggggcc   1200
ggggccgggg ccggggccgg ggccggggcc ggggccgggg ccggggccgg ggccggggcc   1260
ggggccgggg ccggggccgg ggccggggcc ggggccgggg ccggggccgg ggccggggcc   1320
ggggccgggg ccggggccgg ggccggggcc ggggccgggg ccggggccgg ggccggggcc   1380
ggggccgggg ccggggccgg ggccggggcc ggggccgggg ccggggccgg ggccggggcc   1440
ggggccgggg ccggggccgg ggccggggcc ggggccgggg ccggggccgg ggccggggcc   1500
ggggccgggg ccggggccgg ggccggggcc ggggccgggg ccggggccgg ggccggggcc   1560
ggggccgggg ccggggccgg ggccggggcc ggggccgggg ccggggccgg ggccggggcc   1620
ggggccgggg ccggggccgg ggccggggcc ggggccgggg ccggggccgg ggccggggcc   1680
ggggccgggg ccggggccgg ggccggggcc ggggccgggg ccggggccgg ggccggggcc   1740
ggggccgggg ccggggccgg ggccggggcc ggggccgggg ccggggccgg ggccggggcc   1800
ggggccgggg ccggggccgg ggccggggcc ggggccgggg ccggggccgg ggccggggcc   1860
ggggccgggg ccggggccgg ggccggggcc ggggccgggg ccggggccgg ggccggggcc   1920
ggggccgggg ccggggccgg ggccggggcc ggggccgggg ccggggccgg ggccggggcc   1980
ggggccgggg ccggggccgg ggccggggcc ggggccgggg ccggggccgg ggccggggcc   2040
ggggccgggg ccggggccgg ggccggggcc ggggccgggg ccggggccgg ggccggggcc   2100
ggggccgggg ccggggccgg ggccggggcc ggggccgggg ccggggccgg ggccggggcc   2160
ggggccgggg ccggggccgg ggccggggcc ggggccgggg ccggggccgg ggccggggcc   2220
ggggccgggg ccggggccgg ggccggggcc ggggccgggg ccggggccgg ggccggggcc   2280
ggggccgggg ccggggccgg ggccggggcc ggggccgggg ccggggccgg ggccggggcc   2340
ggggccgggg ccggggccgg ggccggggcc ggggccgggg ccggggccgg ggccggggcc   2400
ggggccgggg ccggggccgg ggccggggcc ggggccgggg ccggggccgg ggccggggcc   2460
ggggccgggg ccggggccgg ggccggggcc ggggccgggg ccggggccgg ggccggggcc   2520
ggggccgggg ccggggccgg ggccggggcc ggggccgggg ccggggccgg ggccggggcc   2580
ggggccgggg ccggggccgg ggccggggcc ggggccgggg ccggggccgg ggccggggcc   2640
ggggccgggg ccggggccgg ggccggggcc ggggccgggg ccggggccgg ggccggggcc   2700
ggggccgggg ccggggccgg ggccggggcc ggggccgggg ccggggccgg ggccggggcc   2760
ggggccgggg ccggggccgg ggccggggcc ggggccgggg ccggggccgg ggccggggcc   2820
ggggccgggg ccggggccgg ggccggggcc ggggccgggg ccggggccgg ggccggggcc   2880
ggggccgggg ccggggccgg ggccggggcc ggggccgggg ccggggccgg ggccggggcc   2940
ggggccgggg ccggggccgg ggccggggcc ggggccgggg ccggggccgg ggccggggcc   3000
ggggccgggg ccggggccgg ggccggggcc ggggccgggg ccggggccgg ggccggggcc   3060
ggggccgggg ccggggccgg ggccggggcc ggggccgggg ccggggccgg ggccggggcc   3120
ggggccgggg ccggggccgg ggccggggcc ggggccgggg ccggggccgg ggccggggcc   3180
ggggccgggg ccggggccgg ggccggggcc ggggccgggg ccggggccgg ggccggggcc   3240
ggggccgggg ccggggccgg ggccggggcc ggggccgggg ccggggccgg ggccggggcc   3300
ggggccgggg ccggggccgg ggccggggcc ggggccgggg ccggggccgg ggccggggcc   3360
ggggccgggg ccggggccgg ggccggggcc ggggccgggg ccggggccgg ggccggggcc   3420
```

-continued ggggccgggg ccggggccgg ggccggggcc ggggccgggg ccggggccgg ggccggggcc 3480
ggggccgggg ccggggccgg ggccggggcc ggggccgggg ccggggccgg ggccggggcc 3540
ggggccgggg ccggggccgg ggccggggcc ggggccgggg ccggggccgg ggccggggcc 3600
ggggccgggg ccggggccgg ggccggggcc ggggccgggg ccggggccgg ggccggggcc 3660
ggggccgggg ccggggccgg ggccggggcc ggggccgggg ccggggccgg ggccggggcc 3720
ggggccgggg ccggggccgg ggccggggcc ggggccgggg ccggggccgg ggccggggcc 3780
ggggccgggg ccggggccgg ggccggggcc ggggccgggg ccggggccgg ggccggggcc 3840
ggggccgggg ccggggccgg ggccggggcc ggggccgggg ccggggccgg ggccggggcc 3900
ggggccgggg ccggggccgg ggccggggcc ggggccgggg ccggggccgg ggccggggcc 3960
ggggccgggg ccggggccgg ggccggggcc ggggccgggg ccggggccgg ggccggggcc 4020
ggggccgggg ccggggccgg ggccggggcc ggggccgggg ccggggccgg ggccggggcc 4080
ggggccgggg ccggggccgg ggccggggcc ggggccgggg ccggggccgg ggccggggcc 4140
ggggccgggg ccggggccgg ggccggggcc ggggccgggg ccggggccgg ggccggggcc 4200
ggggccgggg ccggggccgg ggccggggcc ggggccgggg ccggggccgg ggccggggcc 4260
ggggccgggg ccggggccgg ggccggggcc ggggccgggg ccggggccgg ggccggggcc 4320
ggggccgggg ccggggccgg ggccggggcc ggggccgggg ccggggccgg ggccggggcc 4380
ggggccgggg ccggggccgg ggccggggcc ggggccgggg ccggggccgg ggccggggcc 4440
ggggccgggg ccggggccgg ggccggggcc ggggccgggg ccggggccgg ggccggggcc 4500
ggggccgggg ccggggccgg ggccggggcc ggggccgggg ccggggccgg ggccggggcc 4560
ggggccgggg ccggggccgg ggccggggcc ggggccgggg ccggggccgg ggccggggcc 4620
ggggccgggg ccggggccgg ggccggggcc ggggccgggg ccggggccgg ggccggggcc 4680
ggggccgggg ccggggccgg ggccggggcc ggggccgggg ccggggccgg ggccggggcc 4740
ggggccgggg ccggggccgg ggccggggcc ggggccgggg ccggggccgg ggccggggcc 4800
ggggccgggg ccggggccgg ggccggggcc ggggccgggg ccggggccgg ggccggggcc 4860
ggggccgggg ccggggccgg ggccggggcc ggggccgggg ccggggccgg ggccggggcc 4920
ggggccgggg ccggggccgg ggccggggcc ggggccgggg ccggggccgg ggccggggcc 4980
ggggccgggg ccggggccgg ggccggggcc ggggccgggg ccggggccgg ggccggggcc 5040
ggggccgggg ccggggccgg ggccggggcc ggggccgggg ccggggccgg ggccggggcc 5100
ggggccgggg ccggggccgg ggccggggcc ggggccgggg ccggggccgg ggccggggcc 5160
ggggccgggg ccggggccgg ggccggggcc ggggccgggg ccggggccgg ggccggggcc 5220
ggggccgggg ccggggccgg ggccggggcc ggggccgggg ccggggccgg ggccggggcc 5280
ggggccgggg ccggggccgg ggccggggcc ggggccgggg ccggggccgg ggccggggcc 5340
ggggccgggg ccggggccgg ggccggggcc ggggccgggg ccggggccgg ggccggggcc 5400
ggggccgggg ccggggccgg ggccggggcc ggggccgggg ccggggccgg ggccggggcc 5460
ggggccgggg ccggggccgg ggccggggcc ggggccgggg ccggggccgg ggccggggcc 5520
ggggccgggg ccggggccgg ggccggggcc ggggccgggg ccggggccgg ggccggggcc 5580
ggggccgggg ccggggccgg ggccggggcc ggggccgggg ccggggccgg ggccggggcc 5640
ggggccgggg ccggggccgg ggccggggcc ggggccgggg ccggggccgg ggccggggcc 5700
ggggccgggg ccggggccgg ggccggggcc ggggccgggg ccggggccgg ggccggggcc 5760
ggggccgggg ccggggccgg ggccggggcc ggggccgggg ccggggccgg ggccggggcc 5820 gggccgggg ccggggccgg ggccggggcc ggggccgggg ccggggccgg ggccggggcc 5880
ggggccgggg ccggggccgg ggccggggcc ggggccgggg ccggggccgg ggccggggcc 5940
ggggccgggg ccggggccgg ggccggggcc ggggccgggg ccggggccgg ggccggggcc 6000

<210> SEQ ID NO 575
<211> LENGTH: 9000
<212> TYPE: DNA
<213> ORGANISM: Artificial Sequence
<220> FEATURE:
<223> OTHER INFORMATION: Synthetic

<400> SEQUENCE: 575
ggggccgggg ccggggccgg ggccggggcc ggggccgggg ccggggccgg ggccggggcc 60
ggggccgggg ccggggccgg ggccggggcc ggggccgggg ccggggccgg ggccggggcc 120
ggggccgggg ccggggccgg ggccggggcc ggggccgggg ccggggccgg ggccggggcc 180
ggggccgggg ccggggccgg ggccggggcc ggggccgggg ccggggccgg ggccggggcc 240
ggggccgggg ccggggccgg ggccggggcc ggggccgggg ccggggccgg ggccggggcc 300
ggggccgggg ccggggccgg ggccggggcc ggggccgggg ccggggccgg ggccggggcc 360
ggggccgggg ccggggccgg ggccggggcc ggggccgggg ccggggccgg ggccggggcc 420
ggggccgggg ccggggccgg ggccggggcc ggggccgggg ccggggccgg ggccggggcc 480
ggggccgggg ccggggccgg ggccggggcc ggggccgggg ccggggccgg ggccggggcc 540
ggggccgggg ccggggccgg ggccggggcc ggggccgggg ccggggccgg ggccggggcc 600
ggggccgggg ccggggccgg ggccggggcc ggggccgggg ccggggccgg ggccggggcc 660
ggggccgggg ccggggccgg ggccggggcc ggggccgggg ccggggccgg ggccggggcc 720
ggggccgggg ccggggccgg ggccggggcc ggggccgggg ccggggccgg ggccggggcc 780
ggggccgggg ccggggccgg ggccggggcc ggggccgggg ccggggccgg ggccggggcc 840
ggggccgggg ccggggccgg ggccggggcc ggggccgggg ccggggccgg ggccggggcc 900
ggggccgggg ccggggccgg ggccggggcc ggggccgggg ccggggccgg ggccggggcc 960
ggggccgggg ccggggccgg ggccggggcc ggggccgggg ccggggccgg ggccggggcc 1020
ggggccgggg ccggggccgg ggccggggcc ggggccgggg ccggggccgg ggccggggcc 1080
ggggccgggg ccggggccgg ggccggggcc ggggccgggg ccggggccgg ggccggggcc 1140
ggggccgggg ccggggccgg ggccggggcc ggggccgggg ccggggccgg ggccggggcc 1200
ggggccgggg ccggggccgg ggccggggcc ggggccgggg ccggggccgg ggccggggcc 1260
ggggccgggg ccggggccgg ggccggggcc ggggccgggg ccggggccgg ggccggggcc 1320
ggggccgggg ccggggccgg ggccggggcc ggggccgggg ccggggccgg ggccggggcc 1380
ggggccgggg ccggggccgg ggccggggcc ggggccgggg ccggggccgg ggccggggcc 1440
ggggccgggg ccggggccgg ggccggggcc ggggccgggg ccggggccgg ggccggggcc 1500
ggggccgggg ccggggccgg ggccggggcc ggggccgggg ccggggccgg ggccggggcc 1560
ggggccgggg ccggggccgg ggccggggcc ggggccgggg ccggggccgg ggccggggcc 1620
ggggccgggg ccggggccgg ggccggggcc ggggccgggg ccggggccgg ggccggggcc 1680
ggggccgggg ccggggccgg ggccggggcc ggggccgggg ccggggccgg ggccggggcc 1740
ggggccgggg ccggggccgg ggccggggcc ggggccgggg ccggggccgg ggccggggcc 1800
ggggccgggg ccggggccgg ggccggggcc ggggccgggg ccggggccgg ggccggggcc 1860

-continued

```
ggggccgggg ccggggccgg ggccggggcc ggggccgggg ccggggccgg ggccggggcc   1920
ggggccgggg ccggggccgg ggccggggcc ggggccgggg ccggggccgg ggccggggcc   1980
ggggccgggg ccggggccgg ggccggggcc ggggccgggg ccggggccgg ggccggggcc   2040
ggggccgggg ccggggccgg ggccggggcc ggggccgggg ccggggccgg ggccggggcc   2100
ggggccgggg ccggggccgg ggccggggcc ggggccgggg ccggggccgg ggccggggcc   2160
ggggccgggg ccggggccgg ggccggggcc ggggccgggg ccggggccgg ggccggggcc   2220
ggggccgggg ccggggccgg ggccggggcc ggggccgggg ccggggccgg ggccggggcc   2280
ggggccgggg ccggggccgg ggccggggcc ggggccgggg ccggggccgg ggccggggcc   2340
ggggccgggg ccggggccgg ggccggggcc ggggccgggg ccggggccgg ggccggggcc   2400
ggggccgggg ccggggccgg ggccggggcc ggggccgggg ccggggccgg ggccggggcc   2460
ggggccgggg ccggggccgg ggccggggcc ggggccgggg ccggggccgg ggccggggcc   2520
ggggccgggg ccggggccgg ggccggggcc ggggccgggg ccggggccgg ggccggggcc   2580
ggggccgggg ccggggccgg ggccggggcc ggggccgggg ccggggccgg ggccggggcc   2640
ggggccgggg ccggggccgg ggccggggcc ggggccgggg ccggggccgg ggccggggcc   2700
ggggccgggg ccggggccgg ggccggggcc ggggccgggg ccggggccgg ggccggggcc   2760
ggggccgggg ccggggccgg ggccggggcc ggggccgggg ccggggccgg ggccggggcc   2820
ggggccgggg ccggggccgg ggccggggcc ggggccgggg ccggggccgg ggccggggcc   2880
ggggccgggg ccggggccgg ggccggggcc ggggccgggg ccggggccgg ggccggggcc   2940
ggggccgggg ccggggccgg ggccggggcc ggggccgggg ccggggccgg ggccggggcc   3000
ggggccgggg ccggggccgg ggccggggcc ggggccgggg ccggggccgg ggccggggcc   3060
ggggccgggg ccggggccgg ggccggggcc ggggccgggg ccggggccgg ggccggggcc   3120
ggggccgggg ccggggccgg ggccggggcc ggggccgggg ccggggccgg ggccggggcc   3180
ggggccgggg ccggggccgg ggccggggcc ggggccgggg ccggggccgg ggccggggcc   3240
ggggccgggg ccggggccgg ggccggggcc ggggccgggg ccggggccgg ggccggggcc   3300
ggggccgggg ccggggccgg ggccggggcc ggggccgggg ccggggccgg ggccggggcc   3360
ggggccgggg ccggggccgg ggccggggcc ggggccgggg ccggggccgg ggccggggcc   3420
ggggccgggg ccggggccgg ggccggggcc ggggccgggg ccggggccgg ggccggggcc   3480
ggggccgggg ccggggccgg ggccggggcc ggggccgggg ccggggccgg ggccggggcc   3540
ggggccgggg ccggggccgg ggccggggcc ggggccgggg ccggggccgg ggccggggcc   3600
ggggccgggg ccggggccgg ggccggggcc ggggccgggg ccggggccgg ggccggggcc   3660
ggggccgggg ccggggccgg ggccggggcc ggggccgggg ccggggccgg ggccggggcc   3720
ggggccgggg ccggggccgg ggccggggcc ggggccgggg ccggggccgg ggccggggcc   3780
ggggccgggg ccggggccgg ggccggggcc ggggccgggg ccggggccgg ggccggggcc   3840
ggggccgggg ccggggccgg ggccggggcc ggggccgggg ccggggccgg ggccggggcc   3900
ggggccgggg ccggggccgg ggccggggcc ggggccgggg ccggggccgg ggccggggcc   3960
ggggccgggg ccggggccgg ggccggggcc ggggccgggg ccggggccgg ggccggggcc   4020
ggggccgggg ccggggccgg ggccggggcc ggggccgggg ccggggccgg ggccggggcc   4080
ggggccgggg ccggggccgg ggccggggcc ggggccgggg ccggggccgg ggccggggcc   4140
ggggccgggg ccggggccgg ggccggggcc ggggccgggg ccggggccgg ggccggggcc   4200
ggggccgggg ccggggccgg ggccggggcc ggggccgggg ccggggccgg ggccggggcc   4260
```

-continued

```
ggggccgggg ccggggccgg ggccggggcc ggggccgggg ccggggccgg ggccggggcc   4320
ggggccgggg ccggggccgg ggccggggcc ggggccgggg ccggggccgg ggccggggcc   4380
ggggccgggg ccggggccgg ggccggggcc ggggccgggg ccggggccgg ggccggggcc   4440
ggggccgggg ccggggccgg ggccggggcc ggggccgggg ccggggccgg ggccggggcc   4500
ggggccgggg ccggggccgg ggccggggcc ggggccgggg ccggggccgg ggccggggcc   4560
ggggccgggg ccggggccgg ggccggggcc ggggccgggg ccggggccgg ggccggggcc   4620
ggggccgggg ccggggccgg ggccggggcc ggggccgggg ccggggccgg ggccggggcc   4680
ggggccgggg ccggggccgg ggccggggcc ggggccgggg ccggggccgg ggccggggcc   4740
ggggccgggg ccggggccgg ggccggggcc ggggccgggg ccggggccgg ggccggggcc   4800
ggggccgggg ccggggccgg ggccggggcc ggggccgggg ccggggccgg ggccggggcc   4860
ggggccgggg ccggggccgg ggccggggcc ggggccgggg ccggggccgg ggccggggcc   4920
ggggccgggg ccggggccgg ggccggggcc ggggccgggg ccggggccgg ggccggggcc   4980
ggggccgggg ccggggccgg ggccggggcc ggggccgggg ccggggccgg ggccggggcc   5040
ggggccgggg ccggggccgg ggccggggcc ggggccgggg ccggggccgg ggccggggcc   5100
ggggccgggg ccggggccgg ggccggggcc ggggccgggg ccggggccgg ggccggggcc   5160
ggggccgggg ccggggccgg ggccggggcc ggggccgggg ccggggccgg ggccggggcc   5220
ggggccgggg ccggggccgg ggccggggcc ggggccgggg ccggggccgg ggccggggcc   5280
ggggccgggg ccggggccgg ggccggggcc ggggccgggg ccggggccgg ggccggggcc   5340
ggggccgggg ccggggccgg ggccggggcc ggggccgggg ccggggccgg ggccggggcc   5400
ggggccgggg ccggggccgg ggccggggcc ggggccgggg ccggggccgg ggccggggcc   5460
ggggccgggg ccggggccgg ggccggggcc ggggccgggg ccggggccgg ggccggggcc   5520
ggggccgggg ccggggccgg ggccggggcc ggggccgggg ccggggccgg ggccggggcc   5580
ggggccgggg ccggggccgg ggccggggcc ggggccgggg ccggggccgg ggccggggcc   5640
ggggccgggg ccggggccgg ggccggggcc ggggccgggg ccggggccgg ggccggggcc   5700
ggggccgggg ccggggccgg ggccggggcc ggggccgggg ccggggccgg ggccggggcc   5760
ggggccgggg ccggggccgg ggccggggcc ggggccgggg ccggggccgg ggccggggcc   5820
ggggccgggg ccggggccgg ggccggggcc ggggccgggg ccggggccgg ggccggggcc   5880
ggggccgggg ccggggccgg ggccggggcc ggggccgggg ccggggccgg ggccggggcc   5940
ggggccgggg ccggggccgg ggccggggcc ggggccgggg ccggggccgg ggccggggcc   6000
ggggccgggg ccggggccgg ggccggggcc ggggccgggg ccggggccgg ggccggggcc   6060
ggggccgggg ccggggccgg ggccggggcc ggggccgggg ccggggccgg ggccggggcc   6120
ggggccgggg ccggggccgg ggccggggcc ggggccgggg ccggggccgg ggccggggcc   6180
ggggccgggg ccggggccgg ggccggggcc ggggccgggg ccggggccgg ggccggggcc   6240
ggggccgggg ccggggccgg ggccggggcc ggggccgggg ccggggccgg ggccggggcc   6300
ggggccgggg ccggggccgg ggccggggcc ggggccgggg ccggggccgg ggccggggcc   6360
ggggccgggg ccggggccgg ggccggggcc ggggccgggg ccggggccgg ggccggggcc   6420
ggggccgggg ccggggccgg ggccggggcc ggggccgggg ccggggccgg ggccggggcc   6480
ggggccgggg ccggggccgg ggccggggcc ggggccgggg ccggggccgg ggccggggcc   6540
ggggccgggg ccggggccgg ggccggggcc ggggccgggg ccggggccgg ggccggggcc   6600
```

-continued gggg ccgggg ccggggccgg ggccggggcc ggggccgggg ccggggccgg ggccggggcc 6660
ggggccgggg ccggggccgg ggccggggcc ggggccgggg ccggggccgg ggccggggcc 6720
ggggccgggg ccggggccgg ggccggggcc ggggccgggg ccggggccgg ggccggggcc 6780
ggggccgggg ccggggccgg ggccggggcc ggggccgggg ccggggccgg ggccggggcc 6840
ggggccgggg ccggggccgg ggccggggcc ggggccgggg ccggggccgg ggccggggcc 6900
ggggccgggg ccggggccgg ggccggggcc ggggccgggg ccggggccgg ggccggggcc 6960
ggggccgggg ccggggccgg ggccggggcc ggggccgggg ccggggccgg ggccggggcc 7020
ggggccgggg ccggggccgg ggccggggcc ggggccgggg ccggggccgg ggccggggcc 7080
ggggccgggg ccggggccgg ggccggggcc ggggccgggg ccggggccgg ggccggggcc 7140
ggggccgggg ccggggccgg ggccggggcc ggggccgggg ccggggccgg ggccggggcc 7200
ggggccgggg ccggggccgg ggccggggcc ggggccgggg ccggggccgg ggccggggcc 7260
ggggccgggg ccggggccgg ggccggggcc ggggccgggg ccggggccgg ggccggggcc 7320
ggggccgggg ccggggccgg ggccggggcc ggggccgggg ccggggccgg ggccggggcc 7380
ggggccgggg ccggggccgg ggccggggcc ggggccgggg ccggggccgg ggccggggcc 7440
ggggccgggg ccggggccgg ggccggggcc ggggccgggg ccggggccgg ggccggggcc 7500
ggggccgggg ccggggccgg ggccggggcc ggggccgggg ccggggccgg ggccggggcc 7560
ggggccgggg ccggggccgg ggccggggcc ggggccgggg ccggggccgg ggccggggcc 7620
ggggccgggg ccggggccgg ggccggggcc ggggccgggg ccggggccgg ggccggggcc 7680
ggggccgggg ccggggccgg ggccggggcc ggggccgggg ccggggccgg ggccggggcc 7740
ggggccgggg ccggggccgg ggccggggcc ggggccgggg ccggggccgg ggccggggcc 7800
ggggccgggg ccggggccgg ggccggggcc ggggccgggg ccggggccgg ggccggggcc 7860
ggggccgggg ccggggccgg ggccggggcc ggggccgggg ccggggccgg ggccggggcc 7920
ggggccgggg ccggggccgg ggccggggcc ggggccgggg ccggggccgg ggccggggcc 7980
ggggccgggg ccggggccgg ggccggggcc ggggccgggg ccggggccgg ggccggggcc 8040
ggggccgggg ccggggccgg ggccggggcc ggggccgggg ccggggccgg ggccggggcc 8100
ggggccgggg ccggggccgg ggccggggcc ggggccgggg ccggggccgg ggccggggcc 8160
ggggccgggg ccggggccgg ggccggggcc ggggccgggg ccggggccgg ggccggggcc 8220
ggggccgggg ccggggccgg ggccggggcc ggggccgggg ccggggccgg ggccggggcc 8280
ggggccgggg ccggggccgg ggccggggcc ggggccgggg ccggggccgg ggccggggcc 8340
ggggccgggg ccggggccgg ggccggggcc ggggccgggg ccggggccgg ggccggggcc 8400
ggggccgggg ccggggccgg ggccggggcc ggggccgggg ccggggccgg ggccggggcc 8460
ggggccgggg ccggggccgg ggccggggcc ggggccgggg ccggggccgg ggccggggcc 8520
ggggccgggg ccggggccgg ggccggggcc ggggccgggg ccggggccgg ggccggggcc 8580
ggggccgggg ccggggccgg ggccggggcc ggggccgggg ccggggccgg ggccggggcc 8640
ggggccgggg ccggggccgg ggccggggcc ggggccgggg ccggggccgg ggccggggcc 8700
ggggccgggg ccggggccgg ggccggggcc ggggccgggg ccggggccgg ggccggggcc 8760
ggggccgggg ccggggccgg ggccggggcc ggggccgggg ccggggccgg ggccggggcc 8820
ggggccgggg ccggggccgg ggccggggcc ggggccgggg ccggggccgg ggccggggcc 8880
ggggccgggg ccggggccgg ggccggggcc ggggccgggg ccggggccgg ggccggggcc 8940
ggggccgggg ccggggccgg ggccggggcc ggggccgggg ccggggccgg ggccggggcc 9000

-continued

```
<210> SEQ ID NO 576
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Cy3 marker on 5' end

<400> SEQUENCE: 576

ggggccgggg ccggggcc                                   18
```